US011834460B2

(12) United States Patent
Crews et al.

(10) Patent No.: US 11,834,460 B2
(45) Date of Patent: Dec. 5, 2023

(54) IMIDE-BASED MODULATORS OF PROTEOLYSIS AND ASSOCIATED METHODS OF USE

(71) Applicant: YALE UNIVERSITY, New Haven, CT (US)

(72) Inventors: Craig M. Crews, New Haven, CT (US); George Burslem, Sandwich (GB); Philipp M. Cromm, New Haven, CT (US); Saul Jaime-Figueroa, Morris Plains, NJ (US); Momar Toure, Billerica, MA (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 17/554,831

(22) Filed: Dec. 17, 2021

(65) Prior Publication Data

US 2022/0112211 A1 Apr. 14, 2022

Related U.S. Application Data

(62) Division of application No. 16/258,563, filed on Jan. 26, 2019, now Pat. No. 11,220,515.

(60) Provisional application No. 62/622,596, filed on Jan. 26, 2018.

(51) Int. Cl.

| | |
|---|---|
| *C07D 495/14* | (2006.01) |
| *C07D 261/08* | (2006.01) |
| *C07D 413/14* | (2006.01) |
| *C07D 417/14* | (2006.01) |
| *A61P 35/00* | (2006.01) |

(52) U.S. Cl.

CPC ............ *C07D 495/14* (2013.01); *A61P 35/00* (2018.01); *C07D 261/08* (2013.01)

(58) Field of Classification Search

CPC .. C07D 495/14; C07D 261/08; C07D 413/14; C07D 417/14; A61P 35/00

See application file for complete search history.

(56) References Cited

U.S. PATENT DOCUMENTS

| | | | |
|---|---|---|---|
| 5,492,922 | A | 2/1996 | Palkowitz |
| 6,306,663 | B1 | 10/2001 | Kenten et al. |
| 6,670,348 | B1 | 12/2003 | Rosen et al. |
| 7,041,298 | B2 | 5/2006 | Deshaies et al. |
| 7,208,157 | B2 | 4/2007 | Sakamoto et al. |
| 9,500,653 | B2 | 11/2016 | Crews et al. |
| 9,632,089 | B2 | 4/2017 | Crews et al. |
| 2008/0051432 | A1 | 2/2008 | Zhang |
| 2008/0214501 | A1 | 9/2008 | Pan et al. |
| 2008/0219929 | A1 | 9/2008 | Wischik et al. |
| 2010/0286127 | A1 | 11/2010 | Miyoshi et al. |
| 2011/0269793 | A1 | 11/2011 | Maccioni |
| 2012/0270800 | A1 | 10/2012 | Verdine et al. |
| 2012/0322073 | A1 | 12/2012 | Lopez-Girona et al. |
| 2014/0088143 | A1 | 3/2014 | Jain |
| 2014/0256700 | A1 | 9/2014 | Poss et al. |
| 2014/0302523 | A1 | 10/2014 | Crews et al. |
| 2014/0356322 | A1 | 12/2014 | Crews et al. |
| 2014/0371206 | A1 | 12/2014 | Albrecht et al. |
| 2015/0119435 | A1 | 4/2015 | Crews et al. |
| 2015/0141470 | A1 | 5/2015 | Garraway et al. |
| 2015/0148342 | A1 | 5/2015 | Yue et al. |
| 2015/0259288 | A1 | 9/2015 | Nam et al. |
| 2015/0291562 | A1 | 10/2015 | Crew et al. |
| 2015/0344473 | A1 | 12/2015 | Du et al. |
| 2016/0022642 | A1 | 1/2016 | Crews et al. |
| 2016/0045607 | A1 | 2/2016 | Crew et al. |
| 2016/0058872 | A1 | 3/2016 | Crew et al. |
| 2016/0136230 | A1 | 5/2016 | Campos et al. |
| 2016/0176864 | A1 | 6/2016 | Norris et al. |
| 2016/0214972 | A1 | 7/2016 | Jin et al. |
| 2016/0243247 | A1 | 8/2016 | Bradner et al. |
| 2016/0272635 | A1 | 9/2016 | Schmees et al. |
| 2016/0272639 | A1 | 9/2016 | Crew et al. |
| 2016/0368911 | A1 | 12/2016 | Campos et al. |
| 2017/0008904 | A1 | 1/2017 | Crew et al. |

(Continued)

FOREIGN PATENT DOCUMENTS

| | | | |
|---|---|---|---|
| CN | 102477033 | A | 5/2012 |
| EP | 2985285 | A1 | 2/2016 |

(Continued)

OTHER PUBLICATIONS

CAS 155180-53-3 published 1994.

CAS 155255-73-5 published 1995.

International Search Report and Written Opinion for PCT International Application PCT/US2019/015313 dated May 15, 2019.

Medline Plus Trusted Health Information for You, www.nlm.nih.gov/medlineplus/cancer.html, 2007, 1-10.

(Continued)

*Primary Examiner* — John M Mauro

(74) *Attorney, Agent, or Firm* — Saul Ewing LLP; Kathryn Doyle; Domingos J. Silva

(57) ABSTRACT

The description relates to imide-based compounds, including bifunctional compounds comprising the same, which find utility as modulators of targeted ubiquitination, especially inhibitors of a variety of polypeptides and other proteins which are degraded and/or otherwise inhibited by bifunctional compounds according to the present invention. In particular, the description provides compounds, which contain on one end a ligand which binds to the cereblon E3 ubiquitin ligase and on the other end a moiety which binds a target protein such that the target protein is placed in proximity to the ubiquitin ligase to effect degradation (and inhibition) of that protein. Compounds can be synthesized that exhibit a broad range of pharmacological activities consistent with the degradation/inhibition of targeted polypeptides of nearly any type.

20 Claims, 24 Drawing Sheets

Specification includes a Sequence Listing.

(56) References Cited

U.S. PATENT DOCUMENTS

| | | | |
|---|---|---|---|
| 2017/0037004 | A1 | 2/2017 | Crew et al. |
| 2017/0065719 | A1 | 3/2017 | Qian et al. |
| 2017/0121321 | A1 | 5/2017 | Crews et al. |
| 2017/0281784 | A1 | 10/2017 | Wang et al. |
| 2017/0307614 | A1 | 10/2017 | Crews et al. |
| 2017/0327469 | A1 | 11/2017 | Crew et al. |
| 2018/0015087 | A1 | 1/2018 | Liu et al. |
| 2018/0072711 | A1 | 3/2018 | Crew et al. |
| 2018/0099940 | A1 | 4/2018 | Crew et al. |
| 2018/0125821 | A1 | 5/2018 | Crew et al. |
| 2018/0147202 | A1 | 5/2018 | Crew et al. |
| 2018/0155322 | A1 | 6/2018 | Crew et al. |
| 2018/0177750 | A1 | 6/2018 | Crew et al. |
| 2018/0179183 | A1 | 6/2018 | Crew et al. |
| 2018/0193470 | A1 | 7/2018 | Crew et al. |
| 2018/0215731 | A1 | 8/2018 | Crew et al. |
| 2018/0228907 | A1 | 8/2018 | Crew et al. |
| 2018/0237418 | A1 | 8/2018 | Crew et al. |
| 2018/0256586 | A1 | 9/2018 | Crew et al. |

FOREIGN PATENT DOCUMENTS

| | | | |
|---|---|---|---|
| WO | 9730034 | A1 | 8/1997 |
| WO | 9803502 | A1 | 1/1998 |
| WO | 9915521 | A1 | 4/1999 |
| WO | 0200617 | A2 | 1/2002 |
| WO | 02059106 | A1 | 8/2002 |
| WO | 02066512 | A1 | 8/2002 |
| WO | 2006113942 | A2 | 10/2006 |
| WO | 2007027527 | A2 | 3/2007 |
| WO | 2007106670 | A2 | 9/2007 |
| WO | 2008027542 | A2 | 3/2008 |
| WO | 2010053732 | A1 | 5/2010 |
| WO | 2011008260 | A2 | 1/2011 |
| WO | 2011100380 | A1 | 8/2011 |
| WO | 2011119565 | A1 | 9/2011 |
| WO | 2011143660 | A2 | 11/2011 |
| WO | 2011143669 | A2 | 11/2011 |
| WO | 2012003281 | A2 | 1/2012 |
| WO | 2012040389 | A2 | 3/2012 |
| WO | 2012040527 | A2 | 3/2012 |
| WO | 2012078559 | A2 | 6/2012 |
| WO | 2012090104 | A1 | 7/2012 |
| WO | 2013106643 | A2 | 7/2013 |
| WO | 2013106646 | A2 | 7/2013 |
| WO | 2013170147 | A1 | 11/2013 |
| WO | 2014001356 | A1 | 1/2014 |
| WO | 2014108452 | A1 | 7/2014 |
| WO | 2014123418 | A1 | 8/2014 |
| WO | 2014128111 | A1 | 8/2014 |
| WO | 2015000868 | A1 | 1/2015 |
| WO | 2015015318 | A2 | 2/2015 |
| WO | 2015022332 | A1 | 2/2015 |
| WO | 2015067770 | A1 | 5/2015 |
| WO | 2015074064 | A2 | 5/2015 |
| WO | 2015160845 | A2 | 10/2015 |
| WO | 2015195863 | A1 | 12/2015 |
| WO | 2016050821 | A1 | 4/2016 |
| WO | 2016069578 | A1 | 5/2016 |
| WO | 2016118666 | A1 | 7/2016 |
| WO | 2016146985 | A1 | 9/2016 |
| WO | 2016169989 | A1 | 10/2016 |
| WO | 2016172134 | A2 | 10/2016 |
| WO | 2016201328 | A1 | 12/2016 |
| WO | 2017011590 | A1 | 1/2017 |
| WO | 2017030814 | A1 | 2/2017 |
| WO | 2017079267 | A1 | 5/2017 |

OTHER PUBLICATIONS

"Compounds containing sulfur Chromophores v. Complex cyanines", STN transcript excerpt Nov. 24, 2017.

Albrecht , et al., "Identification of a benzoisoxazoloazepine inhibitor (CPI-0610) of the bromodomain and extra-terminal (BETA) family as a candidate for human clinical trials", Journal Med. Chem. 59 2016, 2016, 1330-1339.

Allan , et al., "Therapeutic androgen receptor ligands", Nucl Recept Signal. 1, 2003, e009.

Ariza , "Tau positron emission tomography (PET) imaging: past, present, and future", Journal of Medicinal Chemistry 58, 2015, 4365-4382.

Asangani , et al., "Therapeutic targeting of BET bromodomain proteins in castration-resistant prostate cancer", Nature. 510(7504), Jun. 2014, 278-282.

Baratta , et al., "An in-tumor genetic screen reveals that the BET bromodomain protein, BRD4, is a potential therapeutic target in ovarian carcinonoma", PNAS, 112, 2015, 232-237.

Bargagna-Mohan , et al., "Use of PROTACS as molecular probes of angiogenesis", Bioorg Med Chem Lett. 15(11), 2005, 2724-2727.

Battista , et al., "Fulvestrant for the treatment of endometrial cancer", Expert Opin Investig Drugs 25, 2016, 475-483.

Belkina , et al., "BET domain co-regulators in obesity, inflammation and cancer", Nat Rev Cancer. 12(7), Jun. 2012, 465-477.

Boi , et al., "The BET Bromodomain inhibitor OTX015 Affects pathogenetic Pathways in Preclinical B-cell Tumor Models and synergizes with Targeted Drugs", Clin. Cancer Res. 21(7), 2015, 1628-1638.

Boitano , et al., "Aryl Hydrocarbon Receptor Antagonists Promote the Expansion of Human Hematopoietic Stem Cells", Science 329, Sep. 10, 2010, 1345-1348.

Bondeson , et al., "Catalytic in vivo protein knockdown by small-molecule PROTACs", Nat Chem Biol. 1(8), Aug. 2015, 611-617.

Bondeson , et al., "Lessons in PROTAC Design from Selective Degradation with a Promiscuous Warhead", Cell Chem Biol 25(1), 2018, 78-87 e75.

Bondeson , et al., "Targeted Protein Degradation by Small Molecules", Annu Rev Pharmacol Toxicol. 57, Jan. 2017, 107-123.

Bradbury , et al., "Small-molecule androgen receptor downregulators as an approach to treatment of advanced prostate cancer", Bioorg Med Chem Lett. 21(18), Sep. 2011, 5442-5445.

Brough , et al., "4,5-Diarylisoxazole HSP90 Chaperone Inhibitors: Potential Therapeutic Agents for the Treatment of Cancer", J Med Chem. 51(2), Jan. 24, 2008, 196-218.

Buckley , et al., "HaloPROTACS: Use of Small Molecule PROTACs to Induce Degradation of HaloTag Fusion Proteins", ACS Chem Biol.10(8), 2015, 1831-1837.

Burslem , et al., "Small-Molecule Modulation of Protein Homeostasis", Chem Rev. 117(17), 2017, 11269-11301.

Burslem , et al., "The Advantages of Targeted Protein Degradation Over Inhibition: An RTK Case Study", Cell Chem Biol. 25(1), 2018, 67-77.

Capitosti , et al., "Thalidomide analogues demonstrate dual inhibition of both angiogenesis and prostate cancer", Bioorg Med Chem. 12(2), 2004, 327-336.

Carmony , et al., "PROTAC-induced proteolytic targeting", Methods Mol Biol. 832, 2012, 627-638.

Ceribelli , et al., "Blockade of oncogenic IκB kinase activity in diffuse large B-cell lymphoma by bromodomain and extraterminal domain protein inhibitors", Proc Natl Acad Sci U S A. 111(31), Aug. 2014, 11365-11370.

Chan , et al., "Impact of Target Warhead and Linkage Vector on Inducing Protein Degradation: Comparison of Bromodomain and Extra-Terminal (BET) Degraders Derived from Triazolodiazepine (JQ1) and Tetrahydroquinoline (I-BET726) BET Inhibitor Scaffolds", J Med Chem. 61(2), 2018, 504-513.

Chang , et al., "Structural basis for G9a-like protein lysine methyltransferase inhibition by BIX-01294", Nat Struct Mol Biol. 16(3), Mar. 2009, 312-317.

Chapuy , et al., "Discovery and characterization of super-enhancer-associated dependencies in diffuse large B cell lymphoma.", Cancer Cell. 24(6), Dec. 2013, 777-790.

Chung , et al., "Discovery and Characterization of Small Molecule Inhibitors of the BET Family Bromodomains", J Med Chem. 54(11), Jun. 9, 2011, 3827-3838.

Churcher , "Protac-Induced Protein Degradation in Drug Discovery: Breaking the Rules or Just Making New Ones?", J Med Chem. 61(2), 2018, 444-452.

(56) References Cited

OTHER PUBLICATIONS

Contino-Pepin , et al., "Preliminary biological evaluations of new thalidomide analogues for multiple sclerosis application", Bioorganic & Medicinal Chemistry Letter 19, 2009, 878-881.
Corson , et al., "Design and applications of bifunctional small molecules: why two heads are better than one", ACS Chemical Biology 3(11), 2008, 677-692.
Crew , et al., "Identification and Characterization of Von Hippel-Lindau-Recruiting Proteolysis Targeting Chimeras (PROTACs) of TANK-Binding Kinase 1", J Med Chem. 61(2), 2018, 583-598.
Crews , et al., "Targeting the undruggable proteome: the small molecules of my dreams", Chem Biol. 17(6), 2010, 551-555.
Cromm , et al., "Targeted Protein Degradation: from Chemical Biology to Drug Discovery", Cell Chem Biol. 24(9), 2017, 1181-1190.
Cyrus , et al., "Impact of linker length on the activity of PROTACs", Mol Biosyst. 7(2), 2011, 359-364.
Cyrus , et al., "Jostling for position: optimizing linker location in the design of estrogen receptor-targeting PROTACs", ChemMedChem. 5(7), Jul. 5, 2010, 979-985.
Cyrus , et al., "Two-headed PROTAC: an effective new tool for targeted protein degradation", Chembiochem. 11(11), 2010, 1531-1534.
Dawson , et al., "Inhibition of BET recruitment to chromatin as an effective treatment for MLL-fusion leukaemia", Nature 478, Oct. 2, 2011, 529-533.
Delmore , et al., "BET bromodomain inhibition as a therapeutic strategy to target c-Myc", Cell. 146(6), Sep. 2011, 904-917.
Deroo , et al., "Estrogen receptors and human disease", Journal of Clinical Investigation 116(3), 2006, 561-570.
Di, et al., "Reactivation of p53 by inhibiting Mdm2 E3 ligase: a novel antitumor approach", Curr Cancer Drug Targets. 11(8), Oct. 2011, 987-994.
Dixon , et al., "Identifying druggable disease-modifying gene products", Curr Opin Chem Biol. 13(5-6), Dec. 2009, 549-555.
Filippakopoulos , et al., "Selective inhibition of BET bromodomains", Nature 468, Dec. 23, 2010, 1067-1073.
Finnin , et al., "Structures of a histone deacetylase homologue bound to the TSA and SAHA inhibitors", Nature 401, Sep. 9, 1999, 188-193.
Fischer , "Structure of the DDB1-CRBN E3 ubiquitin ligase in complex with thalidomide", Nature. 512(7512), Aug. 2014, 49-53.
Gadd , et al., "Structural basis of PROTAC cooperative recognition for selective protein degradation", Nat Chem Biol. 13, 2017, 514-521.
Gangjee , et al., "The contribution of a 2-amino group on receptor tyrosine kinase inhibition and antiangiogenic activity in 4-anilinosubstituted pyrrolo[2,3-d]pyrimidines", Bioorg Med Chem Lett. 20(10), May 2010, 3177-3181.
Golub , et al., "Molecular classification of cancer: class discovery and class prediction by gene expression monitoring", Science. 286(5439), Oct. 1999, 531-537.
Gosink , et al., "Redirecting the specificity of ubiquitination by modifying ubiquitin-conjugating enzymes", Proc Natl Acad Sci U S A. 92(20), 1995, 9117-9121.
Guo , et al., "Design of oxobenzimidazoles and oxindoles as novel androgen receptor antagonists", Bioorganic & Medicinal Chemistry Letters 22, 2012, 2572-2578.
Guo , et al., "Discovery of Aryloxy Tetramethylcyclobutanes as Novel Androgen Receptor Antagonists", J. Med. Chem. 54, 2011, 7693-7704.
Gustafson , et al., "Small-Molecule-Mediated Degradation of the Androgen Receptor through Hydrophobic Lagging", Agnew Chem Int Ed. 54, 2015, 9659-9662.
Hewings , et al., "3,5-Dimethylisoxazoles Act As Acetyllysine-mimetic Bromodomain", J Med Chem. 54(19), Oct. 13, 2011, 6761-6770.
Hines , et al., "Posttranslational protein knockdown coupled to receptor tyrosine kinase activation with phosphoPROTACs", Proc Natl Acad Sci U S A. 110(22), 2013, 8942-8947.
Hoffmann , et al., "Characterization of new estrogen receptor destabilizing compounds: effects on estrogen-sensitive and tamoxifen-resistant breast cancer", J Natl Cancer Inst 96(3), Feb. 2004, 210-218.
Huang , et al., "A Chemoproteomic Approach to Query the Degradable Kinome Using a Multi-kinase Degrader", Cell Chem Biol. 25(1), 2018, 88-99.
Huang , et al., "Drugging the undruggables: exploring the ubiquitin system fordrug development", Cell Res 26(4), 2016, 484-498.
Hughes , et al., "Molecular recognition of ternary complexes: a new dimension in the structure-guided design of chemical degraders", Essays Biochem. 61(5), Nov. 2017, 505-516.
Ishikawa, et al., "Design and synthesis of novel human epidermal growth factor receptor 2 (HER2)/epidermal growth factor receptor (EGFR) dual inhibitors bearing a pyrrolo[3,2-d]pyrimidine scaffold", J Med Chem. 54(23), Dec. 2011, 8030-8050.
Jang , et al., "Targeted Degradation of Proteins by PROTACs", Curr Protoc Chem Biol. 2(2), 2010, 71-87.
Jung , et al., "Structure-activity relationship for thiohydantoin androgen receptor antagonists for castration-resistant prostate cancer (CRPC)", J Med Chem. 53(7), Apr. 2010, 2779-2796.
Kim , et al., "Heat shock protein as molecular targets for breast cancer therapeutics", J Breast Cancer. 14(3), Sep. 2011, 167-174.
Knott , et al., "ompounds containing sulphur chromophores. Part I. The action of bases on heterocyclic sulphide quarternary salts", Journal of The Chemical Society (resumed). 10.1039/jr9550000916. (USPTO summary attached), 1955, 949-954.
Konecny , et al., "Activity of the dual kinase inhibitor lapatinib (GW572016) against HER-2-overexpressing and trastuzumab-treated breast cancer cells", Cancer Res. 66(3), Feb. 2006, 1630-1639.
Kronke , et al., "Lenalidomide Causes Selective Degradation of IKZF1 and IKZF3 in Multiple Myeloma Cells", Science 343, 2014, 301-305.
Kurimchak , et al., "Resistance to BET Bromodomain Inhibitors Is Mediated by Kinome Reprogramming in Ovarian Cancer", Cell Reports 16, 2016, 1273-1286.
Lai , et al., "Induced protein degradation: an emerging drug discovery paradigm", Nat Rev Drug Discov. 16(2), 2017, 101-114.
Lai , et al., "Modular PROTAC Design for the Degradation of Oncogenic BCR-ABL", Angew Chem Int Ed Engl. 55(2), 2016, 807-810.
Lala , et al., "Role of nitric oxide in tumor progression: Lessons from experimental tumors", Cancer and Metastasis Reviews 17, 1998, 91-106.
Lebraud , et al., "Protein Degradation by In-Cell Self-Assembly of Proteolysis Targeting Chimeras", ACS Cent Sci. 2(12), Dec. 2016, 927-934.
Lee , et al., "Targeted Degradation of the Aryl Hydrocarbon Receptor by the PROTAC Approach: A Useful Chemical Genetic Tool", ChemBioChem. 8(17), Nov. 23, 2007, 2058-2062.
Lelais , et al., "Discovery of (R,E)-N-(7-Chloro-1-(1-[4-(dimethylamino)but-2-enoyl]azepan-3-yl)-1H-benzo[d] imidazol-2-yl)-2-methylisonicotinamide (EGF816), a Novel, Potent, and WT Sparing Covalent Inhibitor of Oncogenic (L858R, ex19del) and Resistant (T790M) EGFR Mutants f", J Med Chem. 59(14), Jul. 2016, 6671-6689.
Levine , et al., "Targeting the androgen receptor with steroid conjugates", J Med Chem. 57(20), Oct. 2014, 3224-8237.
Li , et al., "Single polymer-drug conjugate carrying two drugs for fixed-dose co-delivery", Medicinal Chemistry vol. 4 (10), 2014, 676-683.
Liu , et al., "Bioactivation of the selective estrogen receptor modulator desmethylated arzoxifene to quinoids: 4'-fluoro substitution prevents quinoid formation", Chem. Res. Toxicol. 18, 2005, 162-173.
Liu , et al., "Design and biological characterization of hybrid compounds of curcumin and thalidomide for multiple myeloma", Org Biomol Chem. 11(29), Aug. 2013, 4757-4763.
Liu , et al., "Discovery of a 2,4-diamino-7-aminoalkoxyquinazoline as a potent and selective inhibitor of histone lysine methyltransferase G9a", J Med Chem. 52(24), Dec. 24, 2009, 7950-7953.

(56) References Cited

OTHER PUBLICATIONS

Llinàs-Brunet, et al., "Discovery of a potent and selective noncovalent linear inhibitor of the hepatitis C virus NS3 protease (BI 201335)", J Med Chem. 53(17), Sep. 9, 2010, 6466-6476.
Lopez-Girona , et al., "Cereblon is a direct protein target for immunomodulatory and antiproliferative activities of lenalidomide and pomalidomide", Leukemia. 26(11), Nov. 2012, 2326-2335.
Lountos , et al., "Structural Characterization of Inhibitor Complexes with Checkpoint Kinase 2 (Chk2), a Drug Target for Cancer Therapy", J Struct Biol.176(3), Dec. 2011, 292-301.
Lovén , et al., "Selective inhibition of tumor oncogenes by disruption of super-enhancers", Cell. 153(2), Apr. 2013, 320-334.
Lu , et al., "Hijacking the E3 Ubiquitin Ligase Cereblon to Efficiently Target BRD4", Chem Biol. 22(6), 2015, 755-763.
Lu , et al., "The myeloma drug lenalidomide promotes the cereblon-dependent destruction of ikaros proteins", Science 343, 2014, 305-309.
Maniaci, et al., "Homo-PROTACs: bivalent small-molecule dimerizers of the VHL E3 ubiquitin ligase to induce self-degradation", Nat Commun. 8:830, 2017, 1-13.
Martin-Kohler , et al., "Furo[2,3-d]pyrimidines and Oxazolo[5,4-d]pyrimidines as Inhibitors of Receptor Tyrosine Kinases (RTK)", Helvetica Chimica Acta 87, 2004, 956-975.
Mehellou , et al., "Twenty-six years of anti-HIV drug discovery: where do we stand and where do we go?", J Med Chem. 53(2), Jan. 28, 2010, 521-538.
Mertz , et al., "Targeting MYC dependence in cancer by inhibiting BET bromodomains", PNAS. 108, 2011, 16669-16674.
Millan , et al., "Design and Synthesis of Inhaled p38 Inhibitors for the Treatment of Chronic Obstructive Pulmonary Disease", J Med Chem.54(22), Nov. 24, 2011, 7797-7814.
Mohler , et al., "Androgen receptor antagonists: a patent review (2008-2011)", Expert Opin Ther Pat. 22(5), May 2012, 541-565.
Muller , et al., "Amino-substituted thalidomide analogs: potent inhibitors of TNF-alpha production", Bioorg Med Chem Lett. 9(11), Jun. 1999, 1625-1630.
Mathan , et al., "A Review of Fulvestrant in Breast Cancer", Oncol Ther. 5, 2017, 17-29.
Neklesa, et al., "Chemical biology: Greasy tags for protein removal", Nature 487, 2012, 308-309.
Neklesa , et al., "Targeted protein degradation by PROTACs", Pharmacology & Therapeutics 174, 2017, 138-144.
Nicodeme , et al., "Suppression of inflammation by a synthetic histone mimic", Nature 468, Dec. 23, 2010, 1119-1123.
Noel , et al., "Abstract C244: Development of the BET bromodomain inhibitor OTX015", Mol Cancer Ther; 12(11 Suppl): Abstract C244., 2013, Abstract Only.
Noguchi-yachide , "BET Bromodomain as a Target of Epigenetic Therapy", Chem Pharm Bull (Tokyo). 64(6), 2016, 540-547.
Ohoka , et al., "SNIPER(TACC3) induces cytoplasmic vacuolization and sensitizes cancer cells to Bortezomib", Cancer Sci. 108, 2017, 1032-1041.
Ottis , "Assessing Different E3 Ligases for Small Molecule Induced Protein Ubiquitination and Degradation", ACS Chem Biol. 12(10), 2017, 2570-2578.
Ottis , et al., "Proteolysis-Targeting Chimeras: Induced Protein Degradation as a Therapeutic Strategy", ACS Chem Biol. 12(4), 2017, 892-898.
Pepe , et al., "Synthesis and structure-activity relationship studies of novel dihydropyridones as androgen receptor modulators", J. Med. Chem. 56, 2013, 8280-8297.
Poutiainen , et al., "Design, synthesis, and biological evaluation of nonsteroidal cycloalkane[d]isoxazole-containing androgen receptor modulators", J. Med. Chem. 55, 2012, 6316-6327.
Powell , et al., "Chemically Induced Degradation of Anaplastic Lymphoma Kinase (ALK)", J. Med. Chem. 61, 2018, 4249-4255.
Puissant , et al., "Targeting MYCN in neuroblastoma by BET bromodomain inhibition", Cancer Discov. 3(3), Mar. 2013, 308-323.
Puppala, et al., "Development of an aryl hydrocarbon receptor antagonist using the proteolysis-targeting chimeric molecules approach: a potential tool for chemoprevention", Mol Pharmacol. 73(4), 2008, 1064-1071.
Qin , et al., "Benzothiophene selective estrogen receptor modulators with modulated oxidative activity and receptor affinity", J. Med Chem. 50, 2007, 2682-2692.
Raina , et al., "PROTAC-induced BET protein degradation as a therapy for castration-resistant prostate cancer", Proc Natl Acad Sci U S A. 113(26), 2016, 7124-7129.
Raina , et al., "Targeted protein knockdown using small molecule degraders", Curr Opin Chem Biol. 39, 2017, 46-53.
Remillard , et al., "Degradation of the BAF Complex Factor BRD9 by Heterobifunctional Ligands", Angew Chem Int Ed Engl. 56(21), 2017, 5738-5743.
Robertson , "Fulvestrant (Faslodex)—How to Make a Good Drug Better", The Oncologist 12, 2007, 774-784.
Rodriguez-Gonzalez , et al., "Targeting steroid hormone receptors for ubiquitination and degradation in breast and prostate cancer", Oncogene. 27(57), Dec. 4, 2008, 7201-7211.
Rotili, et al., "Photoactivable peptides for identifying enzyme-substrate and protein-protein interactions", Chem Commun (Camb). 47(5), 2011, 1488-1490.
Ruchelman , et al., "Isosteric analogs of lenalidomide and pomalidomide: synthesis and biological activity", Bioorg Med Chem Lett. 23(1), Janaury 2013, 360-365.
Rusch , et al., "Identification of acyl protein thioesterases 1 and 2 as the cellular targets of the Ras-signaling modulators palmostatin B and M", Angew Chem Int Ed Engl.50(42), Oct. 10, 2011, 9838-9842.
Sakamoto , et al., "Development of Protacs to target cancer-promoting proteins for ubiquitination and degradation", Mol Cell Proteomics. 2(12), Dec. 2003, 1350-1358.
Sakamoto , et al., "Protacs: chimeric molecules that target proteins to the Skp1-Cullin-F box complex for ubiquitination and degradation", Proc Natl Acad Sci U S A. 98(15), Jul. 17, 2001, 8554 8559.
Salami, et al., "Waste disposal—An attractive strategy for cancer therapy", Science 355, 2017, 1163-1167.
Scagliotti, et al., "Phase III Multinational, Randomized, Double-Blind, Placebo-Controlled Study of Tivantinib (ARQ 197) Plus Erlotinib Versus Erlotinib Alone in Previously Treated Patients With Locally Advanced or Metastatic Nonsquamous Non-Small-Cell Lung Cancer", J Clin Oncol. Aug. 20, 2015;33(24), Aug. 2015, 2667-2674.
Schenkel , et al., "Discovery of Potent and Highly Selective Thienopyridine Janus Kinase 2 Inhibitors", J Med Chem.54(24), Dec. 22, 2011, 8440-8450.
Schiedel , et al., "Chemically Induced Degradation of Sirtuin 2 (Sirt2) by a Proteolysis Targeting Chimera (PROTAC) Based on Sirtuin Rearranging Ligands (SirReals)", J Med Chem. 61, 2017, 482-491.
Schneekloth , et al., "Chemical genetic control of protein levels: selective in vivo targeted degradation", J Am Chem Soc. 126(12), Mar. 31, 2004, 3748-3754.
Schneekloth , et al., "Targeted intracellular protein degradation induced by a small molecule: En route to chemical proteomics", Bioorg Med Chem Lett. 18(22), Nov. 2008, 5904-5908.
Sequist , et al., "Randomized phase II study of erlotinib plus tivantinib versus erlotinib plus placebo in previously treated non-small-cell lung cancer", J Clin Oncol. 29(24), Aug. 2011, 3307-3315.
Smith , et al., "Targeted Intracellular Protein Degradation Induced by a Small Molecule: En Route to Ghemical Proteomics", Bioorg Med Chem Lett. 18(22), Nov. 15, 2008, 5904-5908.
Stanton , et al., "Chemically induced proximity in biology and medicine", Science 359(6380), 2018.
Stewart , et al., "Efforts toward elucidating Thalidomide's molecular target: an expedient synthesis of the first Thalidomide biotin analogue", Org Biomol Chem. 8(18), Sep. 2010, 4059-4062.
Stoppler , "Endometriosis Definition and Facts", Endometriosis [online] URL http://www.medicinenet.com/endometriosis/article.htm, retrieved on Apr. 5, 2017.

(56) References Cited

OTHER PUBLICATIONS

Stoppler , "What about surgery for Endometriosis?", Endometriosis [online], URL http://www.medicinenet.com/endometriosis/article.htm, retrieved on Apr. 5, 2017.
Stuhlmiller , et al., "Inhibition of Lapatinib-Induced Kinome Reprogramming in ERBB2-Positive Breast Cancer by Targeting BET Family Bromodomains", Cell Rep. 11(3), Apr. 2015, 390-404.
Suh , et al., "Arzoxifene, a new selective estrogen receptor modulator for chemoprevention of experimental breast Cancer", Cancer Res 61, 2001, 8412-8415.
Sun , et al., "BET protein proteolysis targeting chimera (PROTAC) exerts potent lethal activity against mantle cell lymphoma cells", Leukemia 32, 2018, 343-352.
Toure , "Small-Molecule PROTACS: New Approaches to Protein Degradation", Angew Chem Int Ed Engl 55(6), 2016, 1966-1973.
Turk , et al., "Binding of thalidomide to alpha1-acid glycoprotein may be involved in its inhibition of tumor necrosis factor alpha production", Proc Natl Acad Sci USA. 93(15), Jul. 1996, 7552-7556.
Vallée , et al., "Tricyclic Series of Heat Shock Protein 90 (HSP90) Inhibitors Part I: Discovery of Tricyclic Imidazo [4,5-c] Pyridines as Potent Inhibitors of the Hsp90 Molecular Chaperone", J Med Chem. 54(20), Oct. 2011, 7206-7219.
Van Eis , et al., "2,6-Naphthyridines as potent and selective inhibitors of the novel protein kinase C isozymes", Bioorg Med Chem Lett.21(24), Dec. 15, 2011, 7367-7372.
Vassilev , et al., "In vivo activation of the p53 pathway by small-molecule antagonists of MDM2", Science 303, Feb. 6, 2004, 844-848.
Vu , et al., "Discovery of RG7112: a small-molecule MDM2 inhibitor in clinical development", ACS Med. Chem. Lett. 4, 2013, 466-469.
Wang , et al., "Estrogen induces c-myc gene expression via an upstream enhancer activated by the estrogen receptor and the AP-1 transcription factor", Mol Endocrinol. 25, 2011, 1527-1538.
Wang , et al., "Small-molecule inhibitors of the MDM2-p53 protein-protein interaction (MDM2 inhibitors) in clinical trials for cancer treatment", J. Med. Chem. 58, 2015, 1038-1052.
Wang , et al., "Temporal activation of p53 by a specific MDM2 inhibitor is selectively toxic to tumors and leads to complete tumor growth inhabitation", PNAS USA 105, 2008, 3933-3938.
Willson , et al., "3-[4-(1,2-Diphenylbut-1-Enyl)Phenyl] Acrylic Acid: A non-steroidal estrogen with functional selectivity for bone over uterus in rats", Journal of Medicinal Chemistry 37(11), May 1994, 1550-1552.
Winter , et al., "Phthalimide Conjugation as a strategy for in vivo target protein degradation", Science 348(6241), 2015, 1376-1381.
Wright , et al., "Structure-Activity Relationships in Purine-Based Inhibitor Binding to HSP90 Isoforms", Chem Biol. 11(6), Jun. 2004, 775-785.
Zengerle , et al., "Selective Small Molecule Induced Degradation of the BET Bromodomain Protein BRD4", ACS Chem Biol. 10(8), 2015, 1770-1777.
Zhang , et al., "Small-molecule MDM2-p53 inhibitors: recent advances", Future Med. Chem. 7, 2015, 631-645.
Zhang , et al., "Targeted degradation of proteins by small molecules: a novel tool for functional proteomics", Comb Chem High Throughput Screen. 7(7), 2004, 689-697.
Zhou , et al., "Discovery of a Small-Molecule Degrader of Bromodomain and Extra-Terminal (BET) Proteins with Picomolar Cellular Potencies and Capable of Achieving Tumor Regression", J Med Chem. 61(2), 2018, 462-481.
Zillhardt , et al., "Foretinib (GSK1363089), an orally available multikinase inhibitor of c-Met and VEGFR-2, blocks proliferation, induces anoikis, and impairs ovarian cancer metastasis", Clin Cancer Res 17(12), Jun. 2011, 4042-4051.
grant "Hackh's chemical dictionar." (1969) p. 148.

Namalwa

Ramos

CA-46

Daudi

IMIDE-BASED MODULATORS OF PROTEOLYSIS AND ASSOCIATED METHODS OF USE

CROSS-REFERENCE TO RELATED APPLICATIONS

The present application is a divisional of, and claims priority under 35 U.S.C. § 121 to, U.S. application Ser. No. 16/258,563, filed Jan. 26, 2019, now allowed, which claims priority under 35 U.S.C. § 119(e) to U.S. Provisional Application No. 62/622,596, filed Jan. 26, 2018, which applications are hereby incorporated by reference in their entireties herein.

SEQUENCE LISTING

The instant application contains a Sequence Listing which has been submitted in ASCII format via EFS-Web and is hereby incorporated by reference in its entirety. Said ASCII copy, created on Dec. 15, 2021, is named 047162-7199US2_Sequence_Listing.txt and is 2.22 kilobytes in size

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and thus are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands that bind to these ligases. For example, since the discovery of nutlins, the first small molecule E3 ligase inhibitors, additional compounds that target E3 ligases have been reported but the field remains underdeveloped.

One E3 ligase with therapeutic potential is the von Hippel-Lindau (VHL) tumor suppressor. VHL comprises the substrate recognition subunit/E3 ligase complex VCB, which includes elongins B and C, and a complex including Cullin-2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. The first small molecule ligands of Von Hippel Lindau (VHL) to the substrate recognition subunit of the E3 ligase, VCB, an important target in cancer, chronic anemia and ischemia, has been identified and crystal structures thereof confirm that the compound mimics the binding mode of the transcription factor HIF-1α, the major substrate of VHL.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism not been completely elucidated, cereblon ubiquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Thalidomide, which has been approved for the treatment of a number of immunological indications, has also been approved for the treatment of certain neoplastic diseases, including multiple myeloma. In addition to multiple myeloma, thalidomide and several of its analogs are also currently under investigation for treating a variety of other types of cancer. While the precise mechanism of thalidomide's anti-tumor activity is still emerging, it is known to inhibit angiogenesis. Recent literature discussing the biology of the imides includes Lu, et al., Science 343, 305 (2014) and Kronke, et al., Science 343, 301 (2014).

Significantly, thalidomide and its analogs, e.g. pomolinamiode and lenalinomide, are known to bind cereblon. These agents bind to cereblon, altering the specificity of the complex to induce the ubiquitination and degradation of Ikaros (IKZF1) and Aiolos (IKZF3), transcription factors essential for multiple myeloma growth. Indeed, higher expression of cereblon has been linked to an increase in efficacy of imide drugs in the treatment of multiple myeloma.

BRD4 has captured considerable attention from academia and pharmaceutical industry alike due to its great potential as a novel target in multiple disease settings, particularly in cancer. BRD4 belongs to the bromodomain and extra-terminal domain (BET) family, which is characterized by two bromodomains (BD domain) at the N-terminus and an extraterminal domain (ET domain) at the C-terminus (J. Shi, et al., Molecular cell, 54 (2014) 728-736 and A. C. Belkina, et al., Nat. Rev. Cancer, 12 (2012) 465-477). The two BD domains recognize and interact with acetylated-lysine residues at the N-terminal tail of histone protein; the ET domain is not yet fully characterized, and is largely considered to serve a scaffolding function in recruiting diverse transcriptional regulators. Thus, BRD4 plays a key role in regulating gene expression by recruiting relevant transcription modulators to specific genomic loci. Several studies have establish that BRD4 is preferentially located at super-enhancer regions, which often reside upstream of important oncogenes, such as c-MYC, Bcl-xL and BCL-6, and play a key role in regulating their expressions (J. Loven, et al., Cell, 153 (2013) 320-334 and B. Chapuy, et al., Cancer Cell, 24 (2013) 777-790). Owing to its pivotal role in modulating the expression of essential oncogenes, BRD4 emerges as a promising therapeutic target in multiple cancer types, including midline carcinoma, AML, MM, BL, and prostate cancer (J. Loven, et al., Cell, 153 (2013) 320-334; J. Zuber, et al., Nature, 478 (2011) 524-528; J. E. Delmore, et al., Cell, 146 (2011) 904-917; J. A. Mertz, et al., PNAS, 108 (2011) 16669-16674; A. Wyce, et al., Oncotarget, 4 (2013) 2419-2429; I. A. Asangani, et al., Nature, 510 (2014) 278-282; and C. A. French, et al., Oncogene, 27 (2008) 2237-2242).

BRD4's distinct high occupancy of genomic loci proximal to specific oncogenes provides a potential therapeutic window that will allow specific targeting of tumor cells while sparing normal tissues. Particularly, BRD4 may serve as an alternative strategy of targeting c-MYC, which contributes to the development and maintenance of a majority of human cancers but has remained undruggable (J. E. Delmore, et al., Cell, 146 (2011) 904-917; J. A. Mertz, et al., PNAS, 108 (2011) 16669-16674; M. G. Baratta, et al., PNAS, 112 (2015) 232-237; and M. Gabay, et al., Cold Spring Harb Perspect Med. (2014) 4:a014241).

The development of small molecule BRD4 inhibitors, such as JQ1, iBET and OTX15, has demonstrated promising therapeutic potential in preclinical models of various cancers, including BL (J. Loven, et al., Cell, 153 (2013) 320-334; B. Chapuy, et al., Cancer Cell, 24 (2013) 777-790; J. E. Delmore, et al., Cell, 146 (2011) 904-917; J. A. Mertz, et al., PNAS, 108 (2011) 16669-16674; I. A. Asangani, et al., Nature, 510 (2014) 278-282; M. G. Baratta, et al., PNAS, 112 (2015) 232-237; M. Boi, et al., Clin. Cancer Res., (2015) 21(7):1628-38; and A. Puissant, et al., Cancer discovery, 3 (2013) 308-323). Indeed, BRD4 inhibitors have shown various anti-tumor activities with good tolerability in different mouse tumor models and, not surprisingly, high sensitivity to BRD4 inhibitors such as JQ1, has been associated with high level of either c-MYC and N-MYC in different tumor types, including c-MYC driven BL. Almost all BL cases contain c-myc gene translocation that places it under control of a super-enhancer located upstream of IgH, thus driving an abnormally high level of c-MYC expression, tumor development and maintenance (K. Klapproth, et al., British journal of haematology, 149 (2010) 484-497).

Currently, four BET Bromodomain inhibitors are in phase I clinical trial with focus largely on midline carcinoma and hematological malignancies (CPI-0610, NCT01949883; GSK525762, NCT01587703; OTX015, NCT01713582; TEN-010, NCT01987362). Preclinical studies with BRD4 inhibitors demonstrate their value in suppressing c-MYC and proliferation in BL cell lines, albeit with $IC_{50}$ values often in the range of 100 nM to 1 uM (J. A. Mertz, et al., PNAS, 108 (2011) 16669-16674 and M. Ceribelli, et al., PNAS, 111 (2014) 11365-11370). Thus, despite the rapid progress of BRD4 inhibitors, the effect of BRD4 inhibition has been encouraging, but less than ideal, as the effect is mostly cytostatic and requires relatively high concentration of inhibitors.

There is a need in the art for effective treatments for disease, especially hyperplasias and cancers, such as multiple myeloma. However, non-specific effects, and the inability to target and modulate certain classes of proteins altogether, such as transcription factors, remain as obstacles to the development of effective anti-cancer agents. As such, small molecule therapeutic agents that leverage or potentiate cereblon's substrate specificity and, at the same time, are "tunable" such that a wide range of protein classes can be targeted and modulated with specificity would be very useful as a therapeutic.

SUMMARY

The present disclosure describes bifunctional compounds that function to recruit endogenous proteins to an E3 Ubiquitin Ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds as described herein. A non-limiting advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer, e.g., multiple myeloma.

As such, in one aspect the disclosure provides novel imide-based compounds as described herein. In an additional aspect, the disclosure provides bifunctional or PROTAC compounds, which comprise an E3 Ubiquitin Ligase binding moiety (i.e., a ligand for an E3 Ubiquitin Ligase or "ULM" group), and a moiety that binds a target protein (i.e., a protein/polypeptide targeting ligand or "PTM" group) such that the target protein/polypeptide is placed in proximity to the ubiquitin ligase to effect degradation (and inhibition) of that protein. In certain embodiments, the target protein/polypeptide is intracellular.

In a non-limiting embodiment, the ULM is a cereblon E3 Ubiquitin Ligase binding moiety (i.e., a "CLM"). For example, the structure of the bifunctional compound can be depicted as: PTM-CLM. The respective positions of the PTM and CLM moieties as well as their number as illustrated herein is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as: PTM-L-CLM, where PTM is a protein/polypeptide targeting moiety, L is a linker, and CLM is a cereblon E3 ubiquitin ligase binding moiety.

In certain non-limiting embodiments, the E3 Ubiquitin Ligase is cereblon. As such, in certain additional embodiments, the CLM of the bifunctional compound comprises chemistries such as imide, amide, thioamide, thioimide derived moieties. In additional embodiments, the CLM comprises a phthalimido group or an analog or derivative thereof. In still additional embodiments, the CLM comprises a phthalimido-glutarimide group or an analog or derivative thereof. In still other embodiments, the CLM comprises a member of the group consisting of thalidomide, lenalidomide, pomalidomide, and analogs or derivatives thereof.

In certain embodiments, the compounds as described herein comprise multiple CLMs, multiple PTMs, multiple chemical linkers or a combination thereof.

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer. In yet another aspect, the present invention provides a method of ubiquitinating/degrading a target protein in a cell. In certain embodiments, the method comprises administering a bifunctional compound as described herein comprising a CLM and a PTM, preferably linked through a linker moiety, as otherwise described herein, wherein the CLM is coupled to the PTM and wherein the CLM recognizes a ubiquitin pathway protein (e.g., an ubiquitin ligase, preferably an E3 ubiquitin ligase such as, e.g., cereblon) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present invention provides treatment of a disease state or condition, which is modulated through the target protein by lowering the level of that protein in the cells of a patient.

In an additional aspect, the description provides a method for assessing (i.e., determining and/or measuring) a CLM's binding affinity. In certain embodiments, the method comprises providing a test agent or compound of interest, for example, an agent or compound having an imide moiety, e.g., a phthalimido group, phthalimido-glutarimide group, derivatized thalidomide, derivatized lenalidomide or derivatized pomalidomide, and comparing the cereblon binding affinity and/or inhibitory activity of the test agent or compound as compared to an agent or compound known to bind and/or inhibit the activity of cereblon.

In still another aspect, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the degradation of proteins of interest in a biological system using compounds according to the present invention.

The present invention comprises the following non-limiting embodiments:

Embodiment 1: A compound comprising the chemical structure: PTM-L-CLM, wherein: L is a bond or a chemical linker coupling the PTM to the CLM; PTM is a protein target moiety that binds to a target protein or polypeptide; CLM is a cereblon E3 ubiquitin ligase binding moiety comprising a structure selected from the group consisting of:

(a)

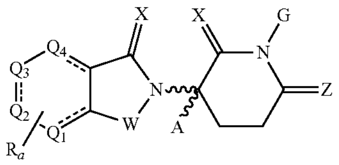

(b)

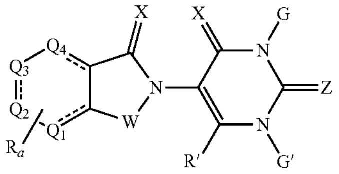

(c)

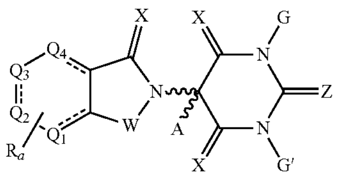

-continued (d)

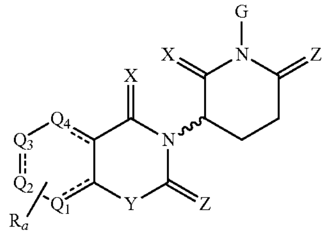

(e)

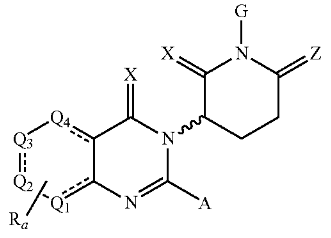

(f)

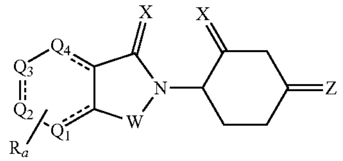

(g)

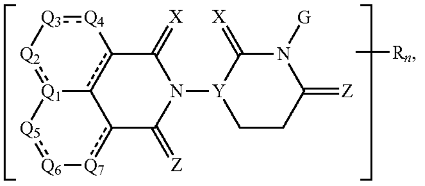

wherein: each occurrence of W is independently selected from the group consisting of $CH_2$, CHR, C═O, $S(═O)_2$, NH, and N-alkyl; each occurrence of X is independently selected from the group consisting of O, S and $H_2$; each occurrence of Y is independently selected from the group consisting of NH, N-alkyl, N-aryl, N-heteroaryl, N-cycloalkyl, N-heterocyclyl, O, and S; each occurrence of Z is independently selected from the group consisting of O, S, and $H_2$, with the proviso that both X and Z cannot be simultaneously $H_2$; each occurrence of G or G' is independently selected from the group consisting of H, alkyl, OH, $CH_2$-heterocyclyl optionally substituted with R', and benzyl optionally substituted with R'; each of $Q_1$-$Q_7$ is independently selected from the group consisting of N, N-oxide, and a carbon substituted with at least one independently selected from the group consisting of R', $NH_2$, OH, halo, $C_1$-$C_6$ alkyl, $C_1$-$C_6$ alkyl bound to another $Q_1$-$Q_7$ group within the same ring, acetyl, and carboxyl, with the proviso that (a) each ring has 0-2 $Q_1$-$Q_7$ selected from the group corresponding to N and N-oxide; (b) when one $Q_1$-$Q_7$ group is a carbon substituted with a $C_1$-$C_6$ alkyl bound to a non-contiguous $Q_1$-$Q_7$ group within the same given ring, the given ring has 0-2 unsaturated bonds; each occurrence of A is independently selected from the group consisting of H, alkyl, cycloalkyl, Cl, and F; each occurrence of R is independently selected from the group consisting of —C(═O)NR'R", —OR', —NR'R", —SR', —S(═O)$_2$R', —S(═O)$_2$NR'R", —CR'R"—, —CR'NR'R"—, aryl, heteroaryl, alkyl, cycloalkyl, heterocyclyl, —P(═O)(OR')R", —P(═O)R'R", —OP(═O)(OR')R", —OP(═O)R'R", —Cl, —F, —Br, —I, —$CF_3$, —CN, —NR'S(═O)$_2$NR'R", —NR'C(═O)NR'R", —C(═O)NR'C(═O)R", —NR'C(═N—CN)NR'R", —C(═N—CN)NR'R", —NR'C(═N—CN)R", —NR'C(═C—$NO_2$)NR'R", —S(═O)$_2$NR'C(═O)R", —$NO_2$, —$CO_2$R', —C(C═N—OR')R", —CR'═CR'R", —CCR', —S(C═O)(C═N—R')R", —$SF_5$, and —$OCF_3$; each occurrence of R' and R" is independently selected from the group consisting of a bond, H, alkyl, cycloalkyl, aryl, heteroaryl, and heterocyclyl; each occurrence of n is independently selected from the group consisting of 1, 2, 3, and 4; ∿∿∿ represents a bond that may be stereospecific ((R) or (S)) or non-stereospecific; and or a salt, solvate, polymorph, and/or deuterated form thereof.

Embodiment 2: The compound of Embodiment 1, wherein one R is modified to be covalently linked to at least one selected from the group consisting of the PTM, the L, an ULM, another independently selected CLM (or CLM'), or any combinations thereof.

Embodiment 3: The compound of any of Embodiments 1-2, wherein each occurrence of W is C═O.

Embodiment 4: The compound of any of Embodiments 1-3, wherein each occurrence of X and Z is O.

Embodiment 5: The compound of any of Embodiments 1-4, wherein each occurrence of A is H.

Embodiment 6: The compound of any of Embodiments 1-5, wherein each occurrence of G is H.

Embodiment 7: The compound of any of Embodiments 1-5, wherein each of $Q_1$-$Q_4$ is independently ra carbon substituted with a group independently selected from the group consisting of R', $NH_2$, OH, halo, $C_1$-$C_6$ alkyl, acetyl, and carboxyl.

Embodiment 8: The compound of any of Embodiments 1-7, wherein the ring comprising $Q_1$-$Q_4$ and the ring comprising $Q_1$, $Q_5$-$Q_7$ are independently mono-, di-, or tri-unsaturated (such as for example phenyl or pyridinyl).

Embodiment 9: The compound of any of Embodiments 1-8, wherein the CLM is selected from the group consisting of:

1

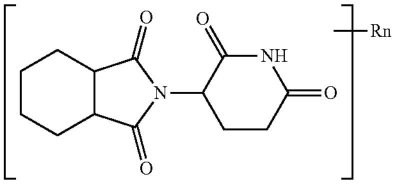

2

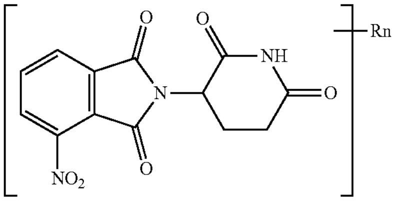

3

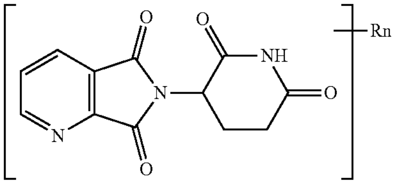

-continued

4

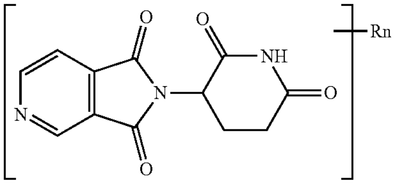

5

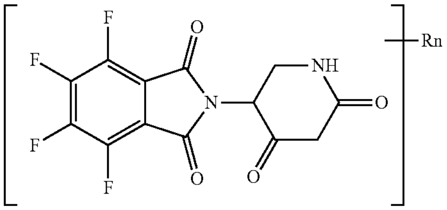

6

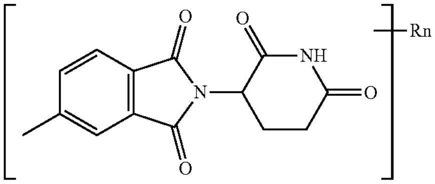

7

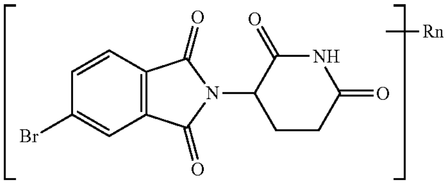

8

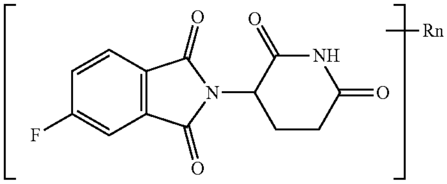

9

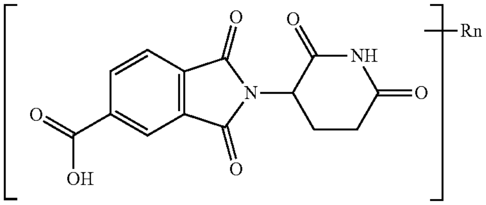

10

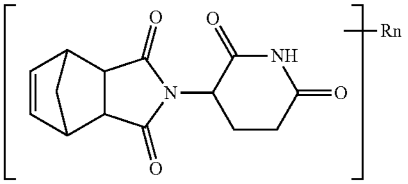

11

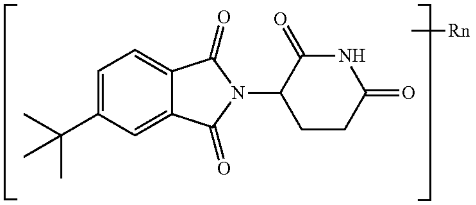

-continued

12

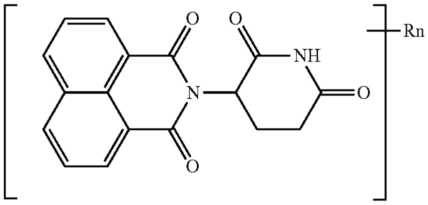

13

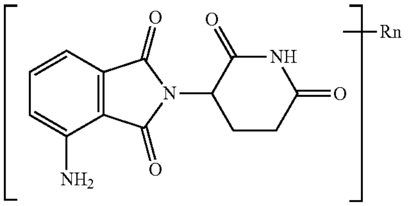

14

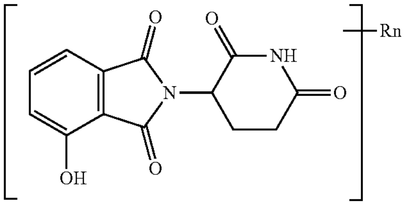

15

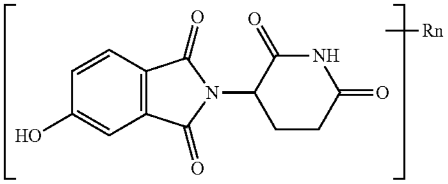

16

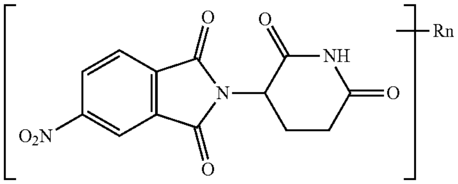

17

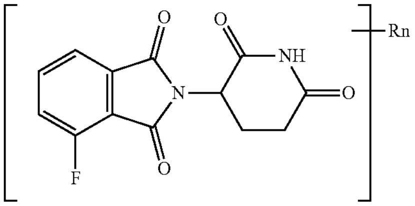

18

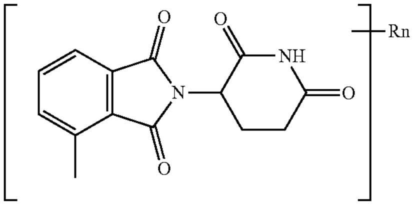

-continued

19

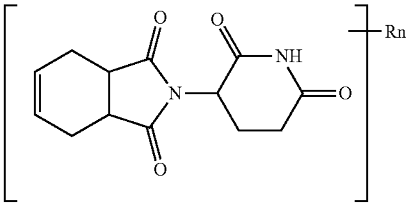

20

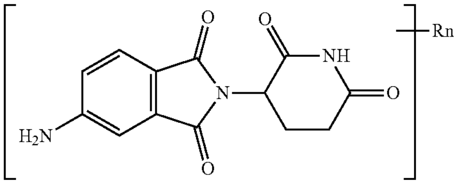

21

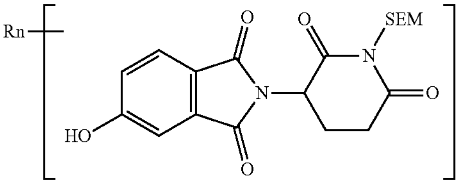

or

22

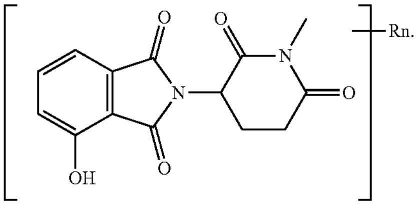

Embodiment 10: The compound of any of Embodiments 1-9, wherein the PTM is a small molecule.

Embodiment 11: The compound of any of Embodiments 1-10, wherein the small molecule PTM targets an intracellular protein or polypeptide.

Embodiment 12: The compound of any of Embodiments 1-11, wherein the L is $-(A^L)_q-$, wherein: q is an integer greater than or equal to 1; each $A^L_q$ is independently selected from the group consisting of, a bond, $CR^{L1}R^{L2}$, O, S, S(═O), $S(═O)_2$, $NR^{L3}$, $S(═O)_2NR^{L3}$, $S(═O)NR^{L3}$, $C(═O)NR^{L3}$, $NR^{L3}C(═O)NR^{L4}$, $NR^{L3}S(═O)_2NR^{L4}$, C(═O), $CR^{L1}═CR^{L2}$, C≡C, $SiR^{L1}R^{L2}$, $P(═O)R^{L1}$, $P(═O)OR^{L1}$, $NR^{L3}C(═NCN)NR^{L4}$, $NR^{L3}C(═NCN)$, $NR^{L3}C(═CNO_2)NR^{L4}$, $C_{3-11}$cycloalkyl optionally substituted with 0-6 $R^{L1}$ and/or $R^{L2}$ groups, $C_{5-13}$ spirocycloalkyl optionally substituted with 0-9 $R^{L1}$ and/or $R^{L2}$ groups, $C_{3-11}$heterocyclyl optionally substituted with 0-6 $R^{L1}$ and/or $R^{L2}$ groups, $C_{5-13}$ spiroheterocycloalkyl optionally substituted with 0-8 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and $R^{L1}$, $R^{L2}$, $R^{L3}$, $R^{L4}$ and $R^{L5}$ are each independently selected from the group consisting of H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}cycloalkyl)_2$, $N(C_{1-8}cycloalkyl)(C_{1-8}alkyl)$, OH, $NH_2$, SH, $S(═O)_2C_{1-8}$alkyl, $P(═O)(OC_{1-8}alkyl)(C_{1-8}alkyl)$, $P(═O)(OC_{1-8}alkyl)_2$, C≡C—$C_{1-8}$alkyl, C≡CH, $CH{=}CH(C_{1\text{-}8}alkyl)$, $C(C_{1\text{-}8}alkyl){=}CH(C_{1\text{-}8}alkyl)$, $C(C_{1\text{-}8}alkyl){=}C(C_{1\text{-}8}alkyl)_2$, $Si(OH)_3$, $Si(C_{1\text{-}8}alkyl)_3$, $Si(OH)(C_{1\text{-}8}alkyl)_2$, $C({=}O)C_{1\text{-}8}alkyl$, $CO_2H$, halogen, CN, $CF_3$, $CHF_2$, $CH_2F$, $NO_2$, $SF_5$, $SO_2NHC_{1\text{-}8}alkyl$, $S({=}O)_2N(C_{1\text{-}8}alkyl)_2$, $S({=}O)NHC_{1\text{-}8}alkyl$, $S({=}O)N(C_{1\text{-}8}alkyl)_2$, $C({=}O)NHC_{1\text{-}8}alkyl$, $C({=}O)N(C_{1\text{-}8}alkyl)_2$, $N(C_{1\text{-}8}alkyl)C({=}O)NH(C_{1\text{-}8}alkyl)$, $N(C_{1\text{-}8}alkyl)C({=}O)N(C_{1\text{-}8}alkyl)_2$, $NHC({=}O)NH(C_{1\text{-}8}alkyl)$, $NHC({=}O)N(C_{1\text{-}8}alkyl)_2$, $NHC({=}O)NH_2$, $N(C_{1\text{-}8}alkyl)S({=}O)_2NH(C_{1\text{-}8}alkyl)$, $N(C_{1\text{-}8}alkyl)\ S({=}O)_2N(C_{1\text{-}8}alkyl)_2$, $NHS({=}O)_2NH(C_{1\text{-}8}alkyl)$, $NHS({=}O)_2N(C_{1\text{-}8}alkyl)_2$, and $NHS({=}O)_2NH_2$.

Embodiment 13: The compound of any of Embodiments 1-11, wherein the L comprises a group selected from the group consisting of: $-NR(CH_2)_n$-(lower alkyl)-, $-NR(CH_2)_n$-(lower alkoxyl)-, $-NR(CH_2)_n$-(lower alkoxyl)-$OCH_2-$, $-NR(CH_2)_n$-(lower alkoxyl)-(lower alkyl)-$OCH_2-$, $-NR(CH_2)_n$-(cycloalkyl)-(lower alkyl)-$OCH_2-$, $-NR(CH_2)_n$-(heterocycloalkyl)-, $-NR(CH_2CH_2O)_n$-(lower alkyl)-O$-CH_2-$, $-NR(CH_2CH_2O)_n$-(heterocycloalkyl)-O$-CH_2-$, $-NR(CH_2CH_2O)_n$-Aryl-O$-CH_2-$, $-NR(CH_2CH_2O)_n$-(heteroaryl)-O$-CH_2-$, $-NR(CH_2CH_2O)_n$-(cycloalkyl)-O-(heteroaryl)-O$-CH_2-$, $-NR(CH_2CH_2O)_n$-(cycloalkyl)-O-Aryl-O$-CH_2-$, $-NR(CH_2CH_2O)_n$-(lower alkyl)-NH-Aryl-O$-CH_2-$, $-NR(CH_2CH_2O)_n$-(lower alkyl)-O-Aryl-$CH_2$, $-NR(CH_2CH_2O)_n$-cycloalkyl-O-Aryl-, $-NR(CH_2CH_2O)_n$-cycloalkyl-O-(heteroaryl)l-, $-NR(CH_2CH_2)_n$-(cycloalkyl)-O-(heterocycle)-$CH_2$, $-NR(CH_2CH_2)_n$-(heterocycle)-(heterocycle)-$CH_2$, $-N(R_1R_2)$-(heterocycle)-$CH_2$; wherein: each n of each linker is 0, 1, 2, 3, 4, 5, 6, 7, 8, 9, or 10; each R is independently H or lower alkyl; and each $R_1$ and $R_2$ of each linker can independently form a ring with the connecting N.

Embodiment 14: The compound of any of Embodiments 1-11, wherein the L is selected from the group consisting of:

$-N(R)-(CH_2)_m-O(CH_2)_n-O(CH_2)_o-O(CH_2)_p-O(CH_2)_q-O(CH_2)_r-OCH_2-$, $-O-(CH_2)_m-O(CH_2)_n-O(CH_2)_o-O(CH_2)_p-O(CH_2)_q-O(CH_2)_r-OCH_2-$, $-O-(CH_2)_m-O(CH_2)_n-O(CH_2)_o-O(CH_2)_p-O(CH_2)_q-O(CH_2)_r-O-$;

$-N(R)-(CH_2)_m-O(CH_2)_n-O(CH_2)_o-O(CH_2)_p-O(CH_2)_q-O(CH_2)_r-O-$;

$-(CH_2)_m-O(CH_2)_n-O(CH_2)_o-O(CH_2)_p-O(CH_2)_q-O(CH_2)_r-O-$;

$-(CH_2)_m-O(CH_2)_n-O(CH_2)_o-O(CH_2)_p-O(CH_2)_q-O(CH_2)_r-OCH_2-$;

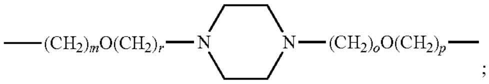
;

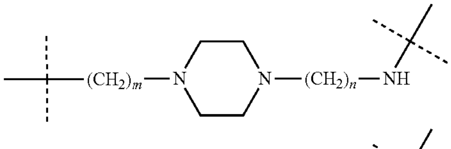
;

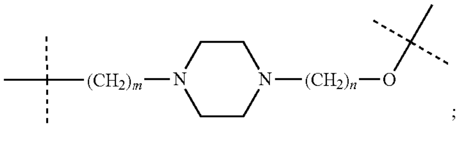
;

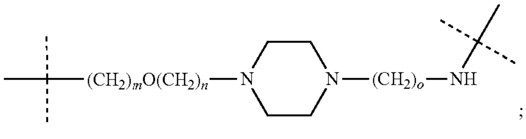
;

-continued

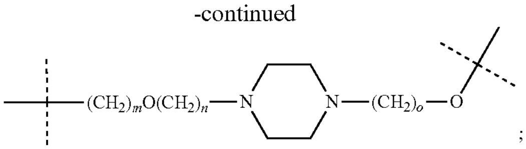
;

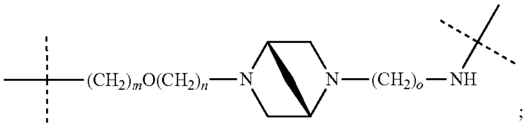
;

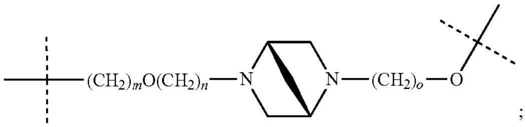
;

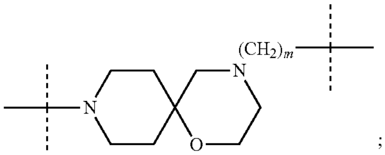
;

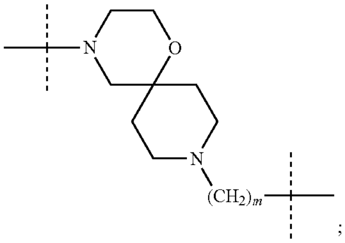
;

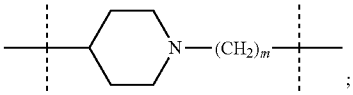
;

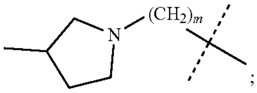
;

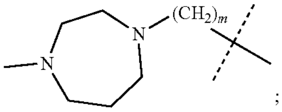
;

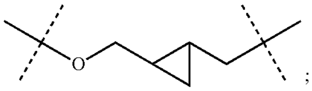
;

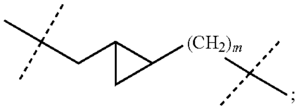
;

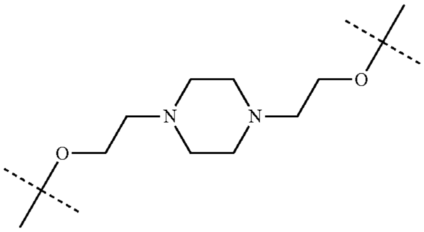

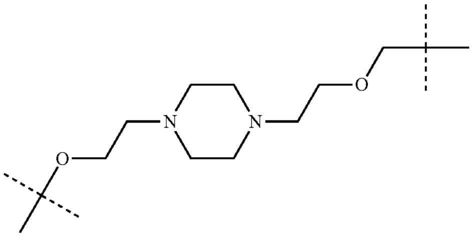

-continued
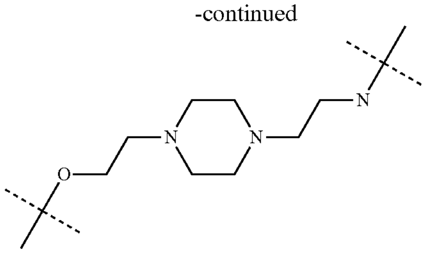
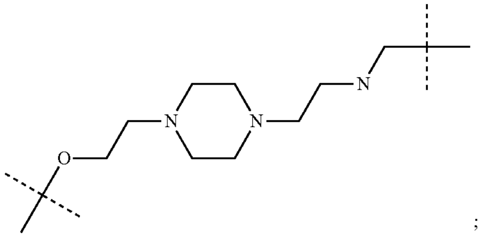
;
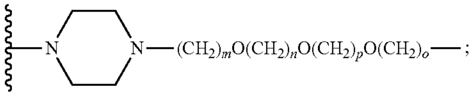
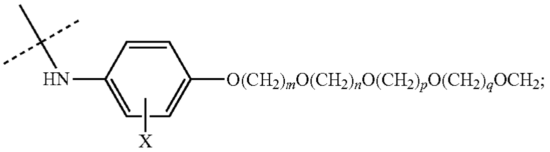
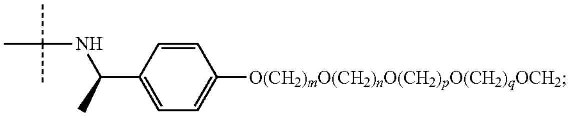
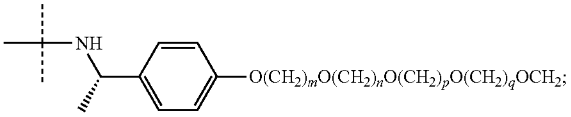
-continued
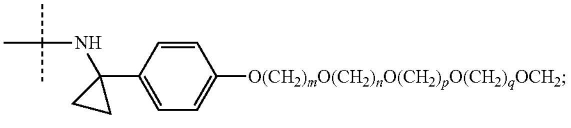
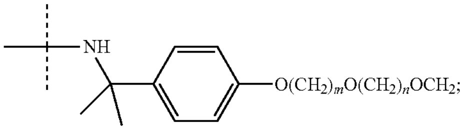
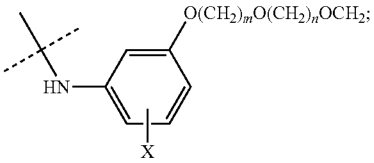
and
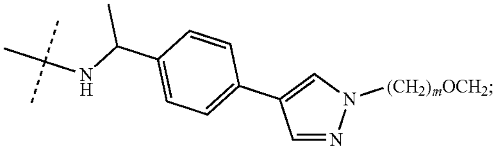
wherein each m, n, o, p, q, and r of each linker is independently 0, 1, 2, 3, 4, 5, 6, 7, 8, 9, 10, 11, 12, 13, 14, 15, 16, 17, 18, 19, or 20, with the proviso that, if n=0, there is no N—O or O—O bond; each R of each linker is independently H, methyl, or ethyl; and each X of each linker is independently H or F.
Embodiment 15: The compound of any of Embodiments 1-14, which is selected from the group consisting of:
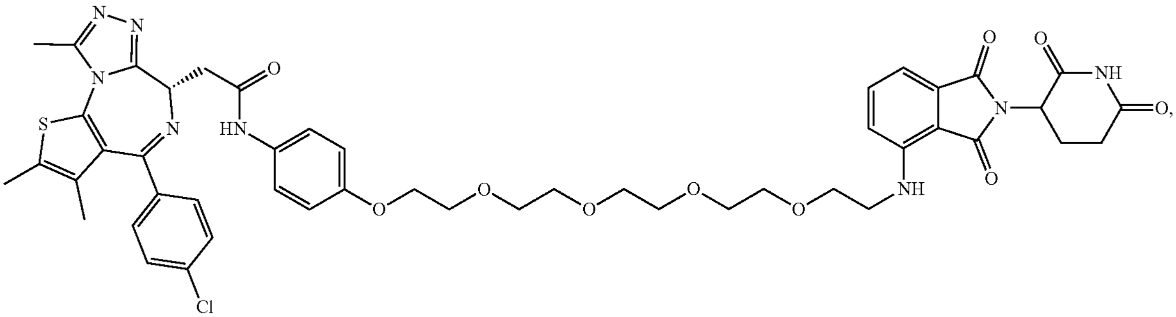
,
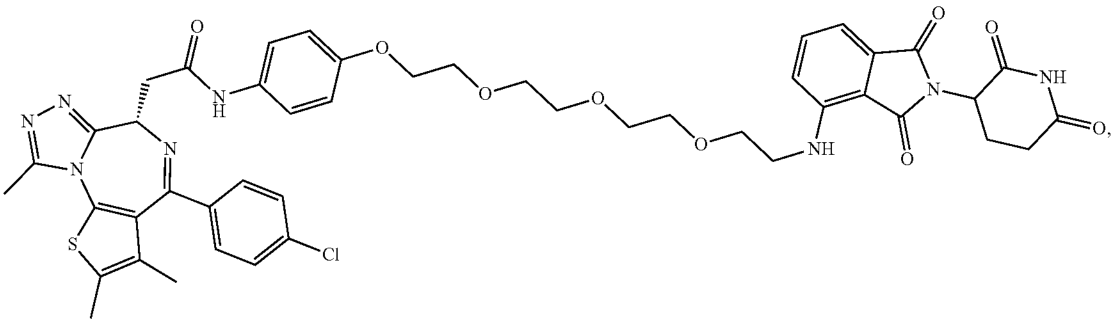
, -continued
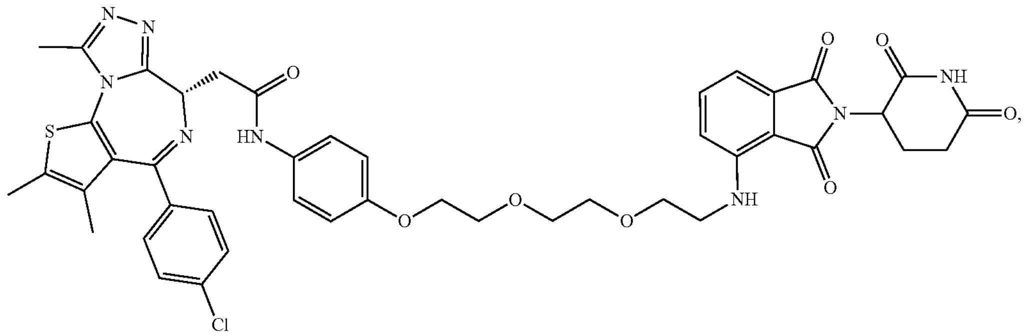
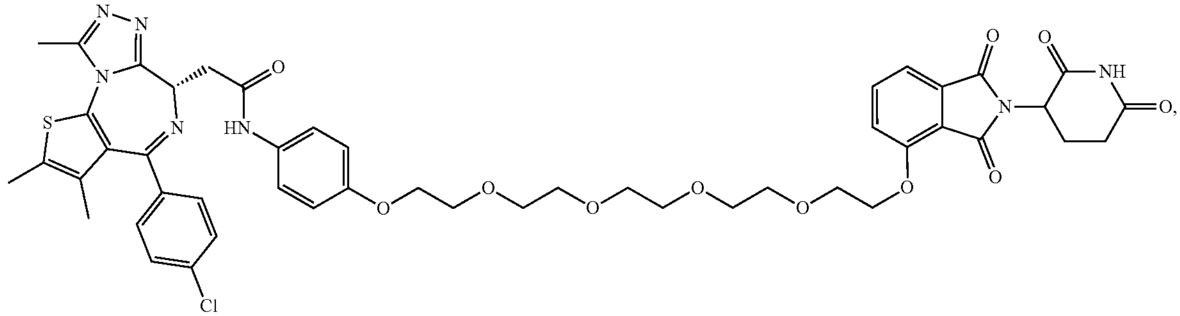
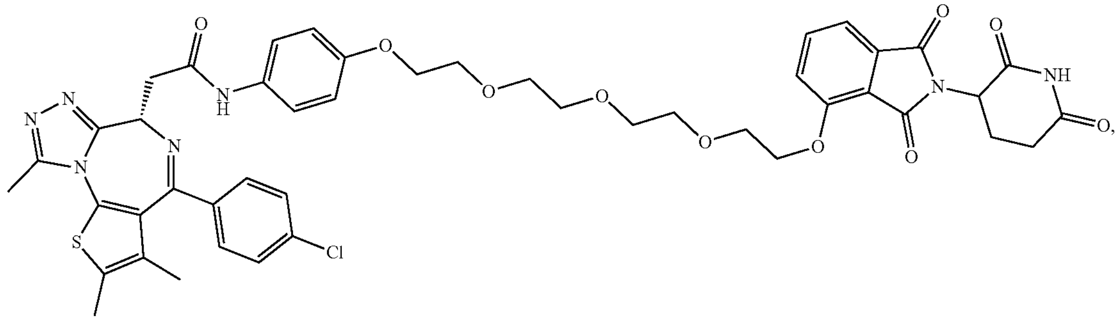
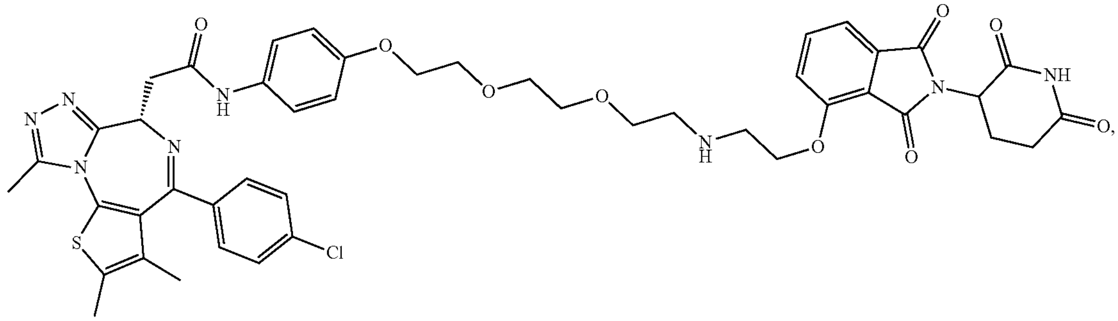
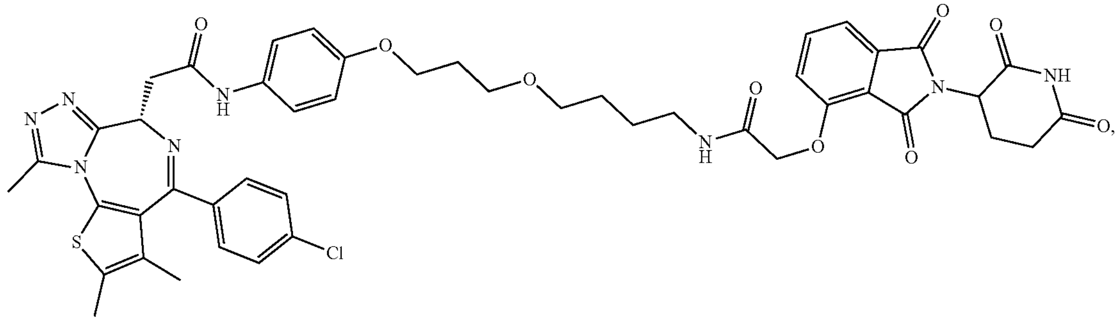

-continued
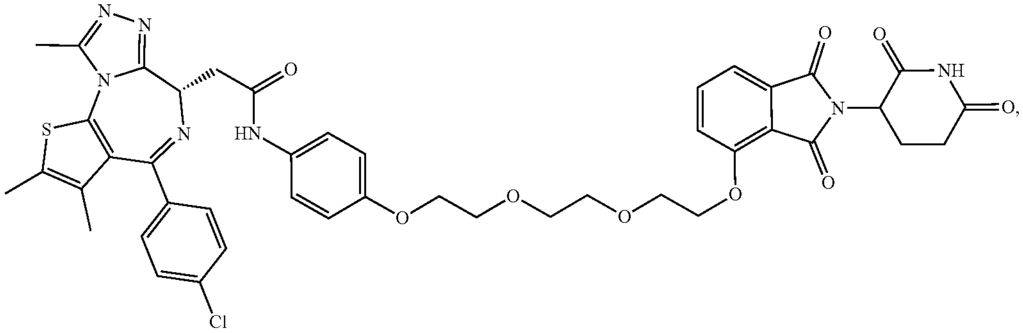
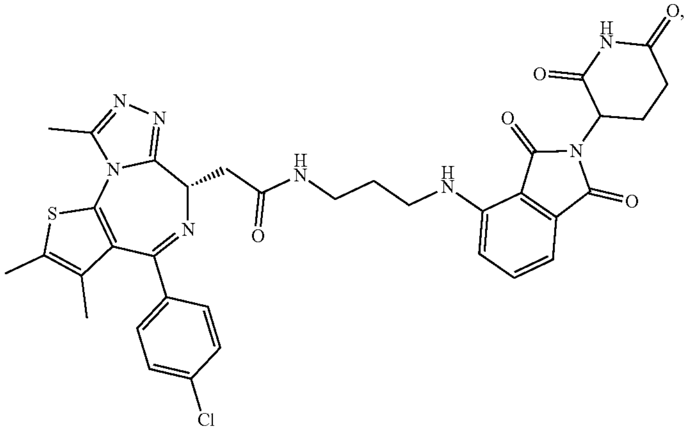
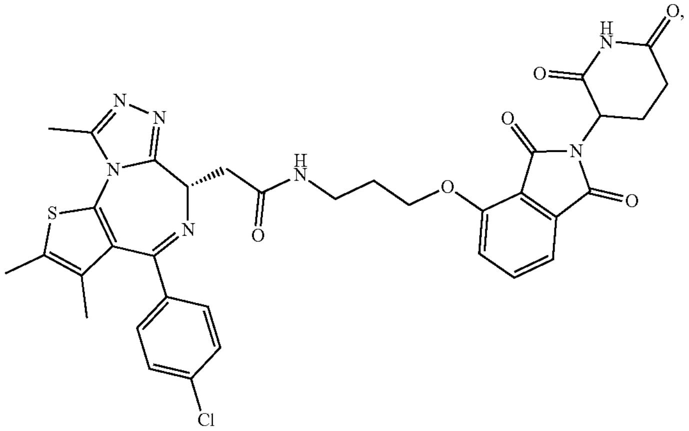
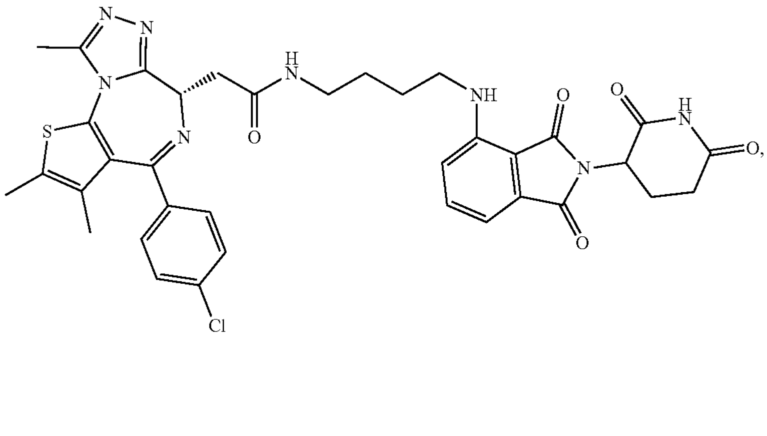

-continued
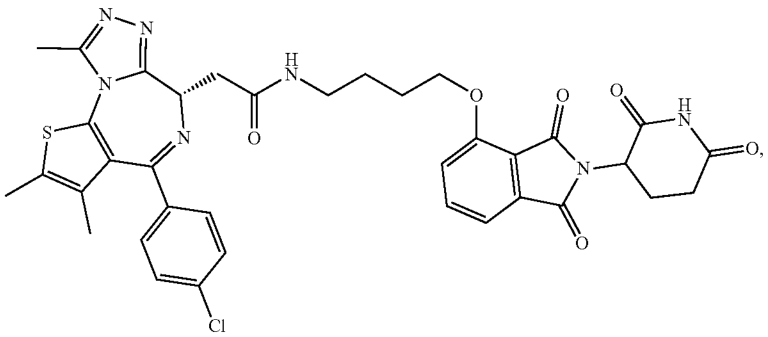
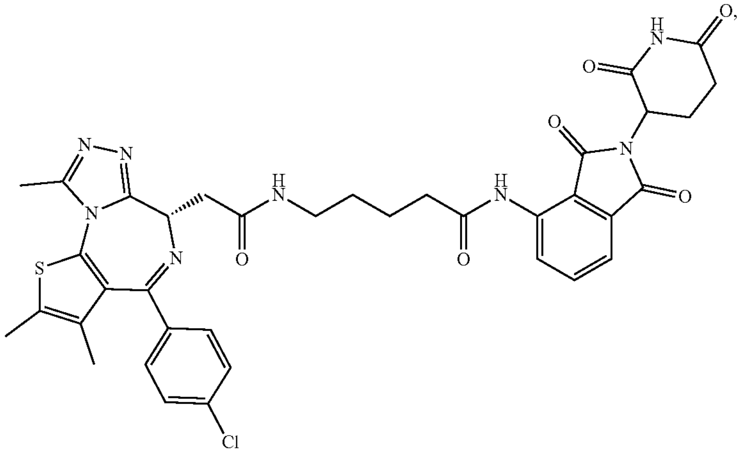
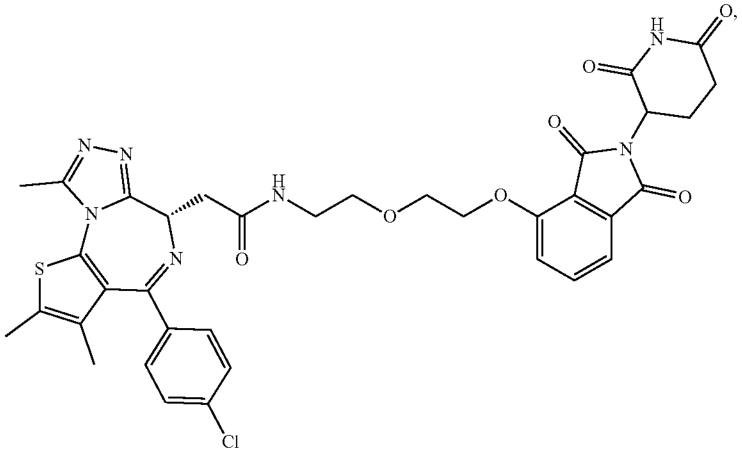
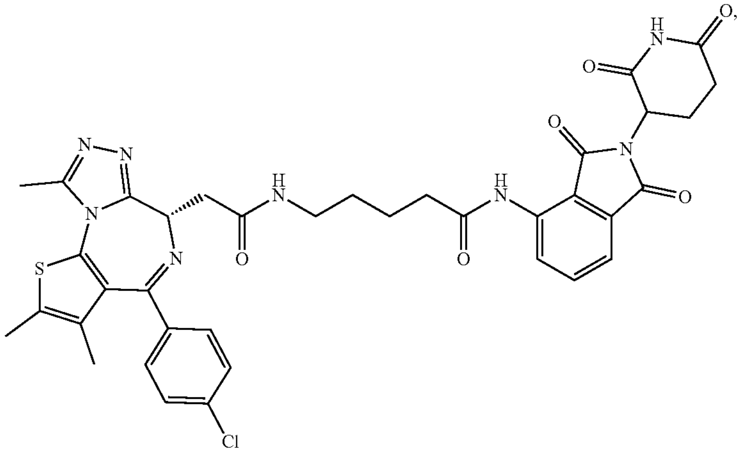

-continued
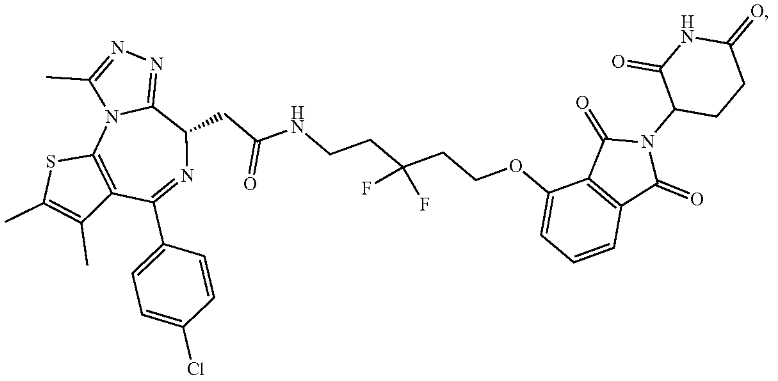
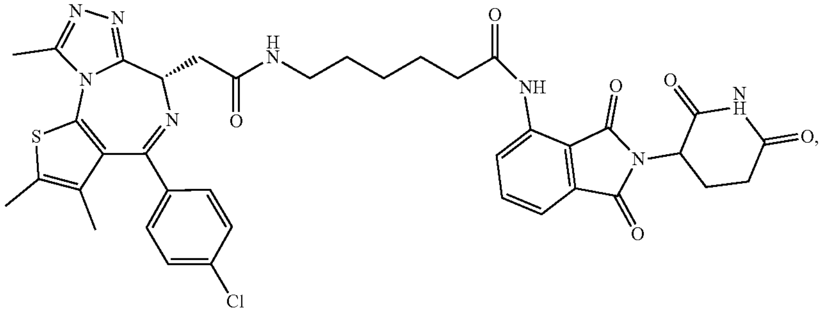
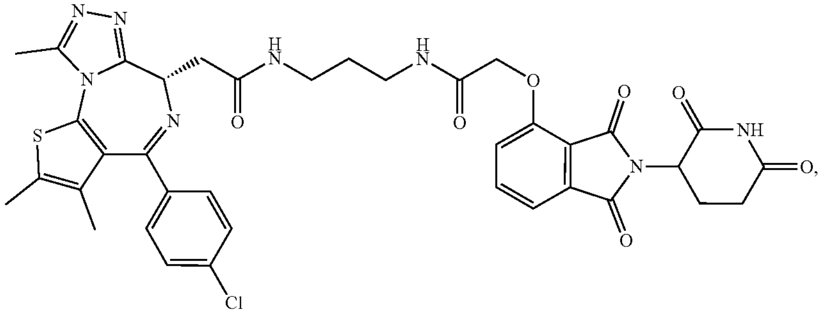
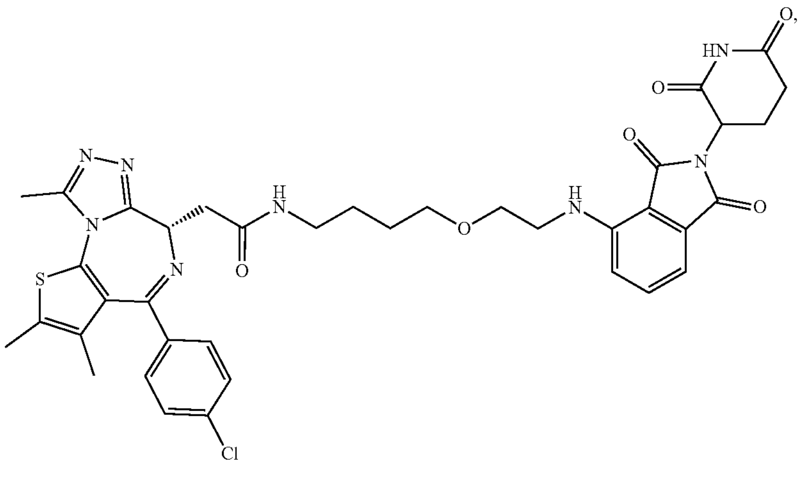

-continued
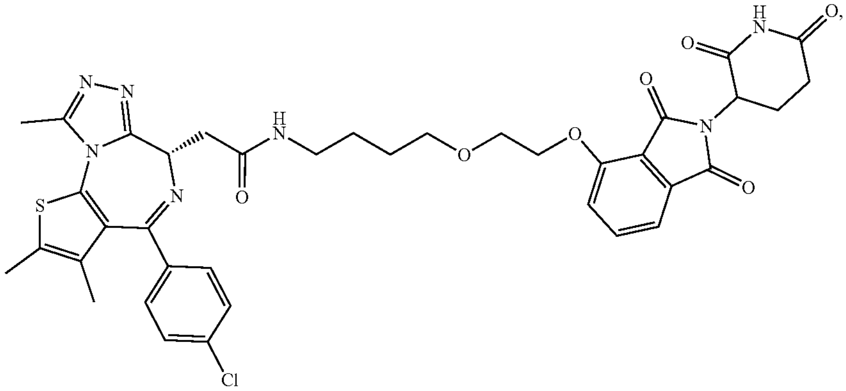
,
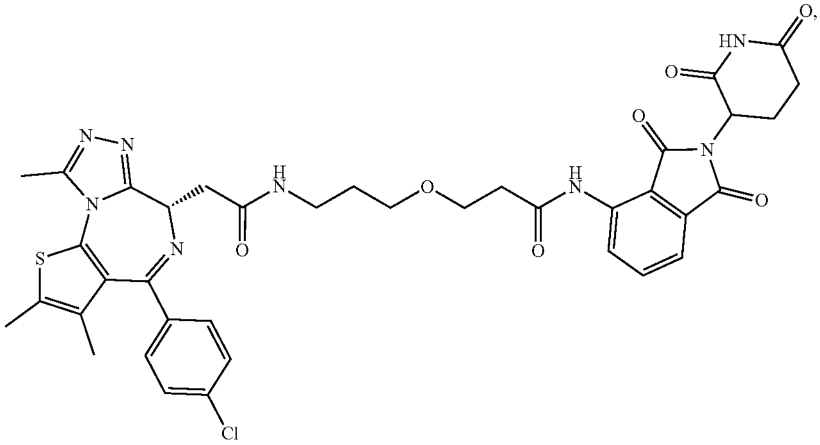
,
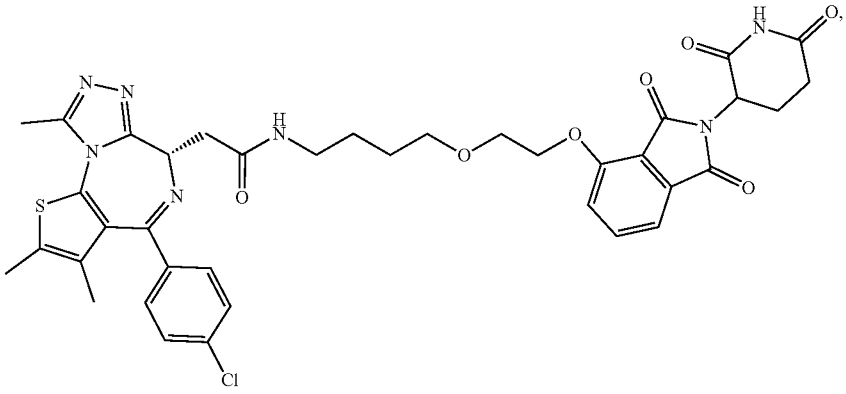
,
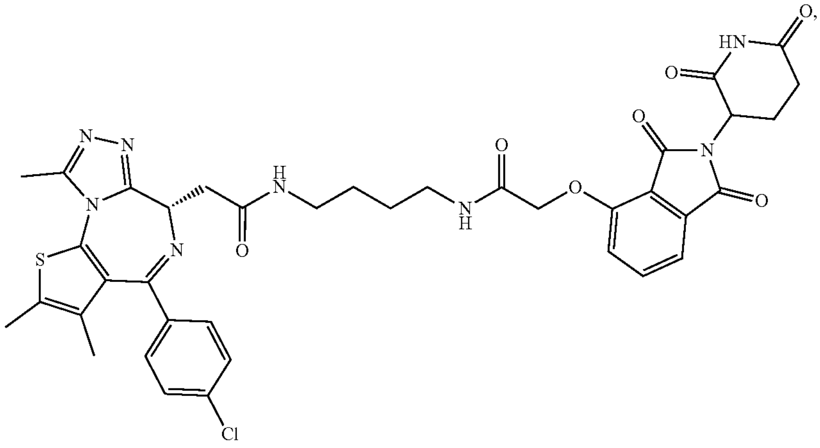
,

-continued
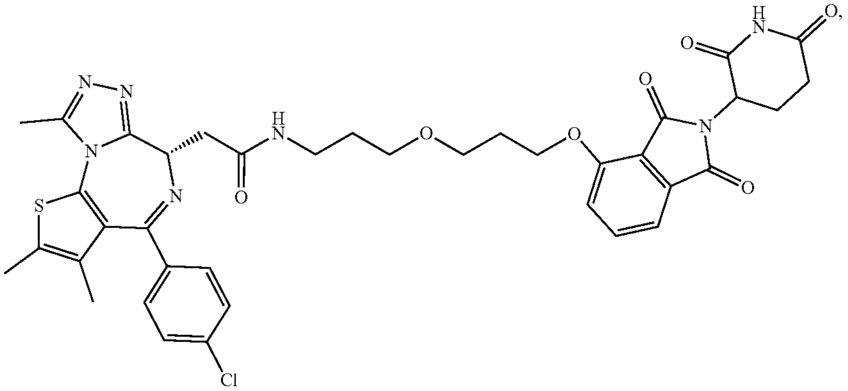
,
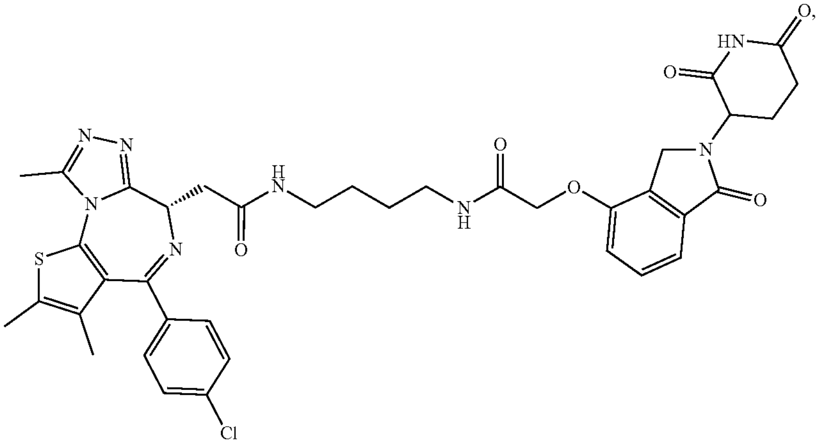
,
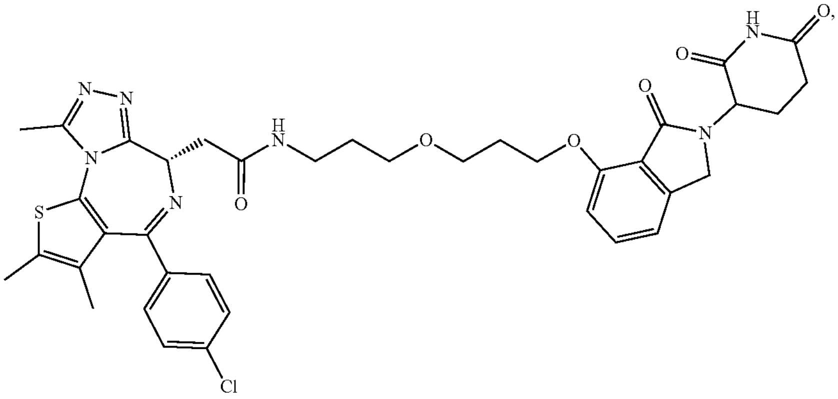
,
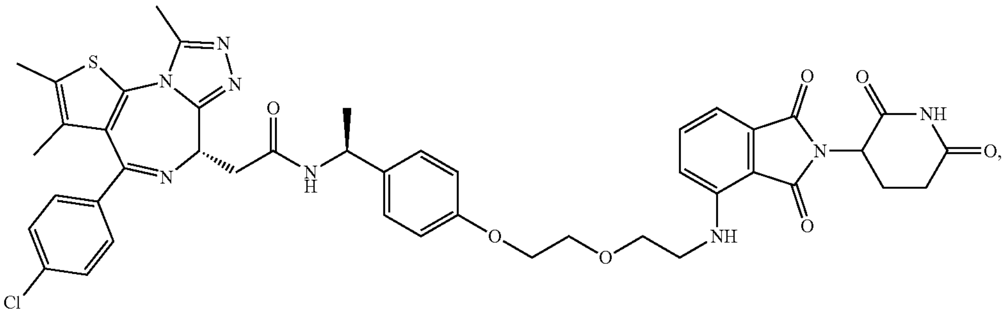
,

-continued

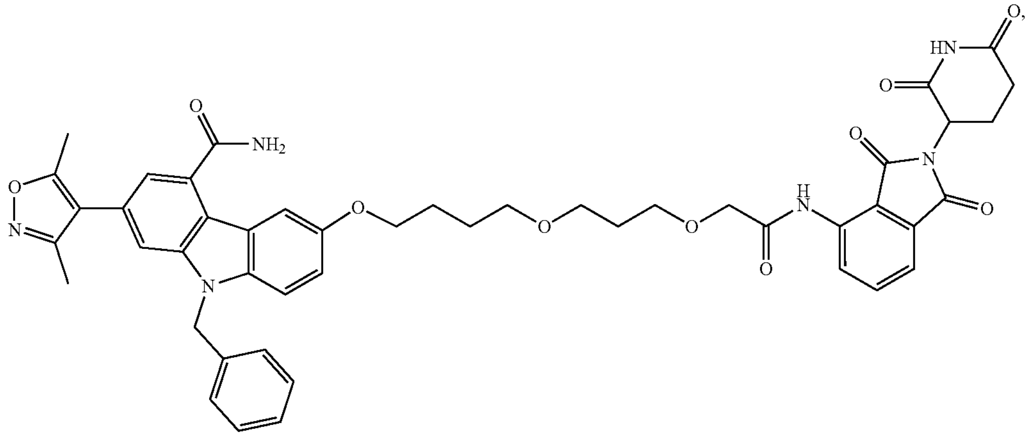

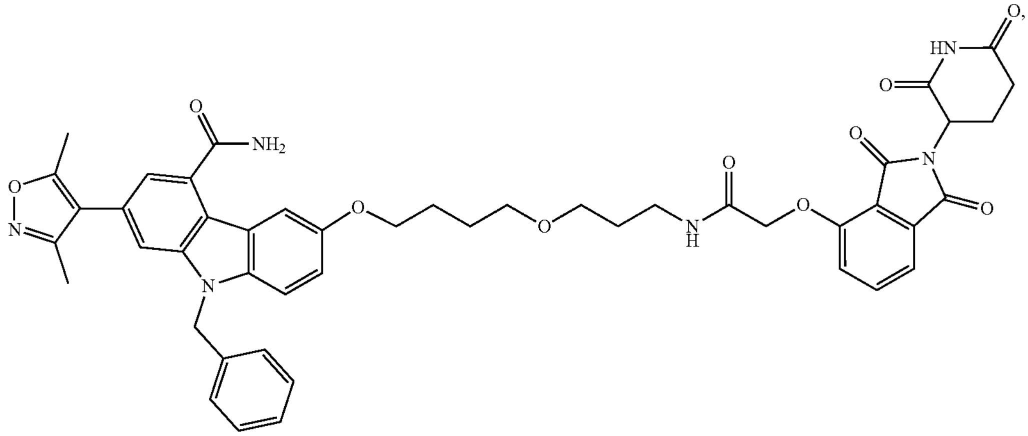

and

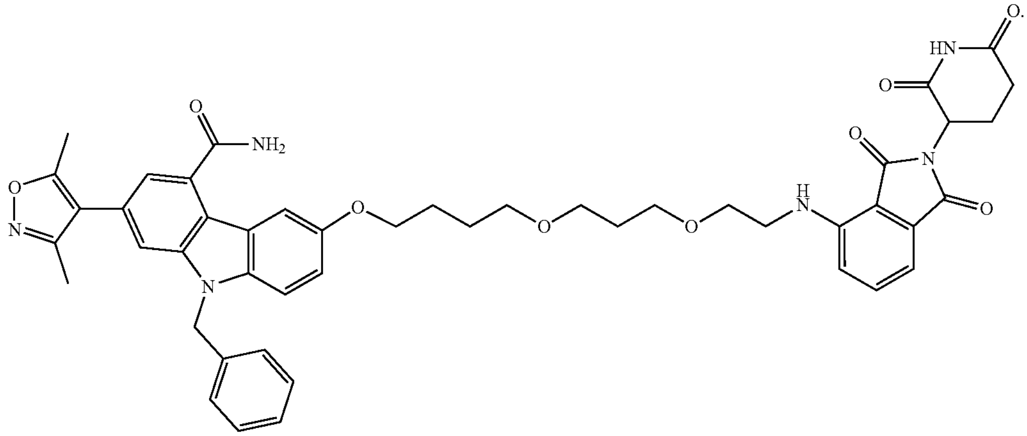

Embodiment 16: A composition comprising the compound of any of Embodiments 1-154.

Embodiment 17: The pharmaceutical composition comprising the compound of any of Embodiments 1-15, and a pharmaceutically acceptable carrier, additive, and/or excipient.

Embodiment 18: A method for inducing degradation of a target protein in a cell, the method comprising contacting the cell with an effective amount of the compound of any of Embodiments 1-15 or composition of any of Embodiments 16-17, wherein the compound or composition is effective in degrading the target protein in the cell.

Embodiment 19: A method for treating a disease state or condition in a subject, wherein dysregulated protein activity is responsible for the disease state or condition, the method comprising administering to the subject a therapeutically effective amount of the compound of any of Embodiments 1-15 or composition of any of Embodiments 16-17, whereby the compound or composition promotes protein degradation or inhibition.

Embodiment 20: The method of Embodiment 19, wherein the disease state or condition is cancer.

Embodiment 21: The method of any of Embodiments 19-20, wherein the cancer is at least one selected from the group consisting of squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; multiple myeloma, sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor, and teratocarcinomas.

Embodiment 22: The method of any of Embodiments 19-21, wherein the cancer is at least one selected from the group consisting of T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL, and Philadelphia chromosome positive CML.

Embodiment 23: The method of any of Embodiments 19-22, wherein the subject is in need of being treated for the disease state or condition.

This application incorporates by reference the disclosure of U.S. Nonprovisional Application Publication No. US20160058872A1, which corresponds to U.S. Nonprovisional application Ser. No. 14/686,640, filed Apr. 14, 2015, which claims priority to U.S. Provisional Application Ser. No. 61/979,351, filed Apr. 14, 2014, and U.S. Provisional Application Ser. No. 62/171,090, filed Jun. 4, 2015, both titled "IMIDE-BASED MODULATORS OF PROTEOLYSIS AND ASSOCIATED METHODS OF USE."

The preceding general areas of utility are given by way of example only and are not intended to be limiting on the scope of the present disclosure and appended claims. Additional objects and advantages associated with the compositions, methods, and processes of the present invention will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present invention. The publications and other materials used herein to illuminate the background of the invention, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which:

(FIG. 1A) Exemplary PROTACs comprise a protein targeting moiety (PTM; darkly shaded rectangle), a ubiquitin ligase binding moiety (ULM; lightly shaded triangle), and optionally a linker moiety (L; black line) coupling or tethering the PTM to the ULM. (FIG. 1B) Illustrates the functional use of the PROTACs as described herein. Briefly, the ULM recognizes and binds to a specific E3 Ubiquitin Ligase, and the PTM binds and recruits a target protein bringing it into close proximity to the E3 Ubiquitin Ligase. Typically, the E3 Ubiquitin Ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degration by the proteosomal machinery of the cell.

(FIG. 3G) The c-Myc suppression effect by JQ1 is reversible: Small molecule BRD4 inhibitors lead to downstream MYC suppression, but not efficiently, with both JQ-1 and OTX leading to MYC suppression; however higher dose does not induce a further downregulation of MYC (Namalwa cells were treated overnight with increasing doses of JQ1 and OTX15, lysates were collected and analyzed by immunoblot with antibodies for c-MYC and Actin). The c-Myc suppression effect by JQ1 and OTX-15 in NAMALWA cells (FIG. 3H) and Ramos cells (FIG. 3I) is reversible. Loss of c-MYC suppression was observed shortly after BRD4 inhibitors withdrawal (FIG. 3H: Namalwa cells were treated with JQ1 (1.0 uM) for 24 hours, followed by three washes to remove compound. Cells were re-seeded for lysates collection at various time points, c-MYC level was determined by immunoblot with Actin serving as loading control. FIG. 3I: Ramos cells were treated with JQ1 (1.0 uM) or OTX15 (1.0 uM) for 24 hours, followed by compounds removal and re-seeding in fresh medium for 4 hours; lysates were subjected for immunoblot with c-MYC and Actin antibodies).

(FIG. 4C) and (FIG. 4D) BRD4 degradation by A825 occurs rapidly (Namalwa and Ramos cells were treated with A825 (0.1 uM) for indicated time points, lysates were collected and subjected to immunoblot analysis with antibodies for BRD4 and Actin). (FIG. 4E) and (FIG. 4F) BRD4 degradation induced by A825 treatment is dependent on Cereblon (Namalwa and Ramos cells were treated overnight with various concentrations of A825 or Pomalidomide (10 uM), or combinations of A825 and Pomalidomide; lysates were analyzed by immunoblot for BRD4 and Actin). (FIG. 4G) BRD4 degradation by A825 is mediated by the proteasome (Namalwa cells were treated overnight with A825 (10 nM and 100 nM) alone, MG132 (5 uM) or Carfizomib (5 uM) alone, or combination of A825 with MG132 or with Carfizomib; lysates were collected and analyzed by immunoblot for BRD4 and Actin).

(FIG. 5A) and (FIG. 5B) c-Myc suppression by A825 is more significant than JQ1 and OTX-15 (Namalwa and Ramos cells were treated overnight with increasing doses of A825 (up to 1.0 uM), or JQ1 (up to 10.0 uM), or OTX15 (up to 10.0 uM); lysates were analyzed by immunoblot for BRD4, c-MYC and Actin). (FIG. 5C) c-Myc protein levels are suppressed longer following treatment with A825 compared to JQ1 and OTX-15 (Namalwa cells were treated for 24 hours with A825 (0.1 uM), JQ1 (1.0 uM) and OTX15 (1.0 uM), followed by three washes to remove compounds, and re-seeded in fresh medium for various time points. Lysates were collected and analyzed by immunoblot for BRD4, c-MYC and Actin; Protein samples subjected to immunoblot analysis of BRD4, MYC; RNA samples subjected to RT-QPCR analysis of MYC downstream gene). (FIG. 5D), (FIG. 5E) and (FIG. 5F) c-Myc protein function (as evaluated by SLC19A1 gene expression) is suppressed longer following treatment with A825 compared to JQ1 and OTX-15 (Namalwa cells were treated as in FIG. 5B, RNA was extracted at 0, 6 and 24 hours post compounds removal, reverse-transcribed into cDNA and quantified by QPCR with SLC19A1 specific primers with GAPDH as internal control).

(FIGS. 6A-6D) A825 has superior anti-proliferation effect on in BL lines compared to JQ1 and OTX-15 (Different BL cell lines were seeded at 50000 cells/100 ul in 96-well plates, treated with increasing doses of A825, JQ1 and OTX15; relative proliferation was determined by CTG assay 72 hours later). (FIG. 6E) A825 leads to longer lasting proliferation suppression compared to JQ1 and OTX-15 (Namalwa cells were treated for 24 hours with A825 (0.1 uM), JQ1 (1.0 uM) and OTX15 (1.0 uM), followed by three washes to remove compounds, and re-seeded in fresh medium in 96-well plate, relative proliferation was determined by CTG assay at 24 hours and 48 hours after re-seeding). (FIG. 6F) Pomalidomide rescues cells from the anti-proliferation effects of low-does A825 treatment. (FIG. 6G) Pomalidomide partially rescues cells from the anti-proliferation effects of high-dose A825 treatment. Different BL cell lines were treated with A825 (10 nM or 100 nM) alone, or together with Pomalidomide (1.0 uM or 10.0 uM) for 72 hours, relative cell proliferation was determined by CTG assay. (FIG. 6H) Pomalidomide alone does not have significant effect on BL cell proliferation (Different BL cell lines were treated with increasing doses of Pomalidomide (up to 10.0 uM) for 72 hours, relative proliferation was determined by CTG assay).

(FIG. 7A) A825 leads to more significant apoptosis induction in BL cells (as monitored by casepase activity) compared to JQ1 and OTX-15 (caspase assay; 24 hour treatment). (FIG. 7B) A825 leads to more significant apoptosis induction in BL cells (as monitored by PARP cleavage) compared to JQ1 and OTX-15 (24 h treatment).

(FIG. 8A) Cells treated with low concentrations of A825 effectively bind to BRD4 and Cereblon forming a "BRD4-A825-Cereblon" trimer complex, which drives efficient BDR4 degradation in the cell. (FIG. 8B) Cells treated with high concentrations of A825 form "BRD4-A825" and "A825-Cereblon" dimers and which hinder optimal trimer formation and BRD4 degradation. A825 leads to efficient degradation of BRD4 through formation of a BRD4-A825-Cereblon trimer FIGS. 9A-9B. Cellular evaluation of selected compounds.

DETAILED DESCRIPTION

The following is a detailed description provided to aid those skilled in the art in practicing the present invention. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

The description provides imide-based compounds, including bifunctional compounds comprising the same, and associated methods of use. The bifunctional compounds are useful as modulators of targeted ubiquitination, especially with respect to a variety of polypeptides and other proteins, which are degraded and/or otherwise inhibited by bifunctional compounds according to the present invention.

Figure 1A:
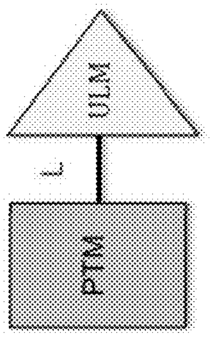
FIGS. 1A-1B: Illustration of general principle for PROTAC function.
Figure 1B:
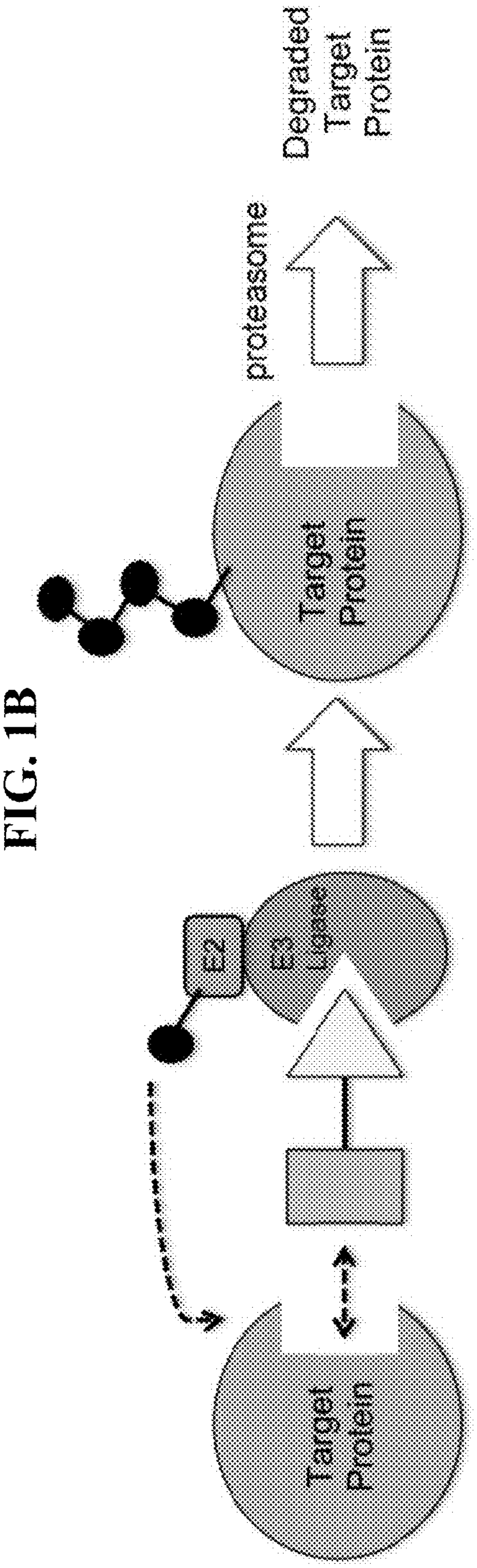

Presently described are compositions and methods that relate to the surprising and unexpected discovery that an E3 Ubiquitin Ligase protein, e.g., cereblon, ubiquitinates a target protein once it and the target protein are placed in proximity by a bifunctional or chimeric construct that binds the E3 Ubiquitin Ligase protein and the target protein. Accordingly the present invention provides such compounds and compositions comprising an E3 Ubiquintin Ligase binding moiety ("ULM") coupled to a protein target binding moiety ("PTM"), which result in the ubiquitination of a chosen target protein, which leads to degradation of the target protein by the proteasome (see FIGS. 1A-1B). The present invention also provides a library of compositions and methods using the same.

Unless otherwise defined, all technical and scientific terms used herein have the same meaning as commonly understood by one of ordinary skill in the art to which this invention belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain non-limiting aspects, one or more of the present compounds described herein, are coadministered in combination with at least one additional bioactive agent, especially including an anticancer agent. In particularly non-limiting aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented within the context of the compound shown.

The term "Ubiquitin Ligase" refers to a family of proteins that facilitate the transfer of ubiquitin to a specific substrate protein, targeting the substrate protein for degradation. For example, cereblon is an E3 Ubiquitin Ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "patient" or "subject" is used throughout the specification to describe an animal, preferably a human or a domesticated animal, to whom treatment, including prophylactic treatment, with the compositions according to the present invention is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present invention, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

Compounds and Compositions

In one aspect, the description provides compounds comprising an E3 Ubiquitin Ligase binding moiety ("ULM") that is a cereblon E3 Ubiquitin Ligase binding moiety ("CLM"). In one embodiment, the CLM is coupled to a chemical linker (L) according to the structure:

L-CLM (I)

wherein L is a chemical linker group and CLM is a cereblon E3 Ubiquitin Ligase binding moiety. The number and/or relative positions of the moieties in the compounds illustrated herein is provided by way of example only. As would be understood by the skilled artisan, compounds as described herein can be synthesized with any desired number and/or relative position of the respective functional moieties.

The terms ULM and CLM are used in their inclusive sense unless the context indicates otherwise. For example, the term ULM is inclusive of all ULMs, including those that bind cereblon (i.e., CLMs). Further, the term CLM is inclusive of all possible cereblon E3 Ubiquitin Ligase binding moieties.

In another aspect, the present invention provides bifunctional or multifunctional PROTAC compounds useful for regulating protein activity by inducing the degradation of a target protein. In certain embodiments, the compound comprises a CLM coupled, e.g., linked covalently, directly or indirectly, to a moiety that binds a target protein (i.e., protein targeting moiety or "PTM"). In certain embodiments, the CLM and PTM are joined or coupled via a chemical linker (L). The CLM recognizes the cereblon E3 ubiquitin ligase and the PTM recognizes a target protein and the interaction of the respective moieties with their targets facilitates the degradation of the target protein by placing the target protein in proximity to the ubiquitin ligase protein. An exemplary bifunctional compound can be depicted as:

PTM-CLM (II)

In certain embodiments, the bifunctional compound further comprises a chemical linker ("L"). For example, the bifunctional compound can be depicted as:

PTM-L-CLM (III)

wherein PTM is a protein/polypeptide targeting moiety, L is a linker, and CLM is a cereblon E3 ligase binding moiety.

In certain embodiments, the compounds as described herein comprise multiple PTMs (targeting the same or different protein targets), multiple CLMs, one or more ULMs (i.e., moieties that bind specifically to another E3 Ubiquitin Ligase, e.g., VHL) or a combination thereof. In any of the aspects of embodiments described herein, the PTMs, CLMs, and ULMs can be coupled directly or via one or more chemical linkers or a combination thereof. In additional embodiments, where a compound has multiple ULMs, the ULMs can be for the same E3 Ubiquintin Ligase or each respective ULM can bind specifically to a different E3 Ubiquitin Ligase. In still further embodiments, where a compound has multiple PTMs, the PTMs can bind the same target protein or each respective PTM can bind specifically to a different target protein.

In another embodiment, the description provides a compound which comprises a plurality of CLMs coupled directly or via a chemical linker moiety (L). For example, a compound having two CLMs can be depicted as:

CLM-CLM, or (IV)

CLM-L-CLM (V)

In certain embodiments, where the compound comprises multiple CLMs, the CLMs are identical. In additional embodiments, the compound comprising a plurality of CLMs further comprises at least one PTM coupled to a CLM directly or via a chemical linker (L) or both. In certain additional embodiments, the compound comprising a plurality of CLMs further comprises multiple PTMs. In still additional embodiments, the PTMs are the same or, optionally, different. In still further embodiments, wherein the PTMs are different the respective PTMs may bind the same protein target or bind specifically to a different protein target.

In additional embodiments, the description provides a compound comprising at least two different CLMs coupled directly or via a chemical linker (L) or both. For example, such a compound having two different CLMs can be depicted as:

CLM-CLM' or (VI)

CLM-L-CLM' (VII)

wherein CLM' indicates a cereblon E3 Ubiquitin Ligase binding moiety that is structurally different from CLM. In certain embodiments, the compound may comprise a plurality of CLMs and/or a plurality of CLM's. In further embodiments, the compound comprising at least two different CLMs, a plurality of CLMs, and/or a plurality of CLM's further comprises at least one PTM coupled to a CLM or a CLM' directly or via a chemical linker or both. In any of the embodiments described herein, a compound comprising at least two different CLMs can further comprise multiple PTMs. In still additional embodiments, the PTMs are the same or, optionally, different. In still further embodiments, wherein the PTMs are different the respective PTMs may bind the same protein target or bind specifically to a different protein target. In still further embodiments, the PTM itself is a ULM or CLM (or ULM' or CLM').

In a non-limiting embodiment, the CLM comprises a moiety that is a ligand of the cereblon E3 Ubiquitin Ligase (CRBN). In certain embodiments, the CLM comprises a chemotype from the "imide" class of molecules. In certain additional embodiments, the CLM comprises a phthalimido group or an analog or derivative thereof. In still additional embodiments, the CLM comprises a phthalimido-glutarimide group or an analog or derivative thereof. In still other embodiments, the CLM comprises a member of the group consisting of thalidomide, lenalidomide, pomalidomide, and analogs or derivatives thereof.

In additional embodiments, the description provides the compounds as described herein including their enantiomers, diastereomers, solvates and polymorphs, including pharmaceutically acceptable salt forms thereof, e.g., acid and base salt forms.

Neo-Imide Compounds

In one aspect, the description provides compounds useful for binding and/or inhibiting cereblon. In certain embodiments, the compound is according to the structure:

(a)

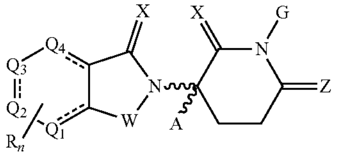

(b)

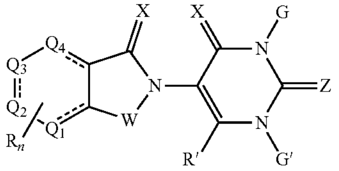

(c)

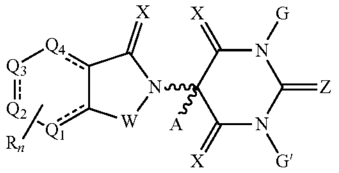

(d)

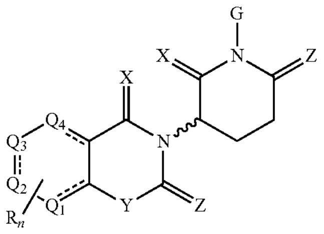

-continued (e)

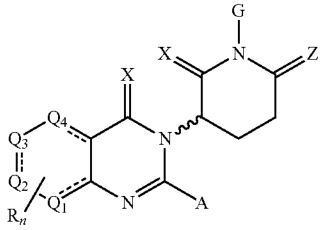

(f)

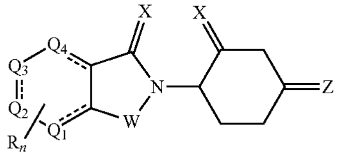

(g)

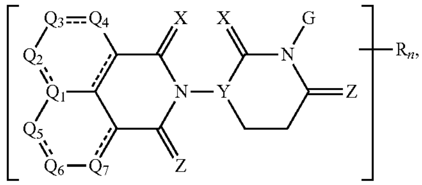

wherein each occurrence of W is independently selected from the group consisting of $CH_2$, CHR, C═O, $S(═O)_2$, NH, and N-alkyl;

each occurrence of X is independently selected from the group consisting of O, S and $H_2$;

each occurrence of Y is independently selected from the group consisting of NH, N-alkyl, N-aryl, N-heteroaryl, N-cycloalkyl, N-heterocyclyl, O, and S;

each occurrence of Z is independently selected from the group consisting of O, S, and $H_2$, with the proviso that both X and Z cannot be simultaneously $H_2$;

each occurrence of G or G' is independently selected from the group consisting of H, alkyl, OH, $CH_2$-heterocyclyl optionally substituted with R', and benzyl optionally substituted with R';

each of $Q_1$-$Q_7$ is independently selected from the group consisting of N, N-oxide, and a carbon substituted with at least one independently selected from the group consisting of R', $NH_2$, OH, halo, $C_1$-$C_6$ alkyl, $C_1$-$C_6$ alkyl bound to another $Q_1$-$Q_7$ group within the same ring, acetyl, and carboxyl, with the proviso that (a) each ring has 0-2 $Q_1$-$Q_7$ selected from the group corresponding to N and N-oxide; (b) when one $Q_1$-$Q_7$ group is a carbon substituted with a $C_1$-$C_6$ alkyl bound to a non-contiguous $Q_1$-$Q_7$ group within the same given ring, the given ring has 0-2 unsaturated bonds;

each occurrence of A is independently selected from the group consisting of H, alkyl, cycloalkyl, Cl, and F;

each occurrence of R is independently selected from the group consisting of —C(═O)NR'R", —OR', —NR'R", —SR', $—S(═O)_2R'$, $—S(═O)_2NR'R"$, —CR'R"—, —CR'NR'R"—, aryl, heteroaryl, alkyl, cycloalkyl, heterocyclyl, —P(═O)(OR')R", —P(═O)R'R", —OP(═O)(OR')R", —OP(═O)R'R", —Cl, —F, —Br, —I, $—CF_3$, —CN, $—NR'S(═O)_2NR'R"$, —NR'C(═O)NR'R", —C(═O)NR'C(═O)R", —NR'C(═N—CN)NR'R", —C(═N—CN)NR'R", —NR'C(═N—CN)R", $—NR'C(═C—NO_2)NR'R"$, $—S(═O)_2NR'C(═O)R"$, —$NO_2$, —$CO_2R'$, —C(C═N—OR')R", —CR'═CR'R", —CCR', —S(C═O)(C═N—R')R", —$SF_5$, and —$OCF_3$;

each occurrence of R' and R" is independently selected from the group consisting of a bond, H, alkyl, cycloalkyl, aryl, heteroaryl, and heterocyclyl;

each occurrence of n is independently selected from the group consisting of 1, 2, 3, and 4;

$R_n$ comprises n (n=1-4) independently selected R groups, represents a bond that may be stereospecific ((R) or (S)) or non-stereospecific; and or a salt, solvate, polymorph, and/or deuterated form thereof.

Exemplary CLMs

In any of the compounds described herein, the CLM comprises or is a chemical structure of:

(a)

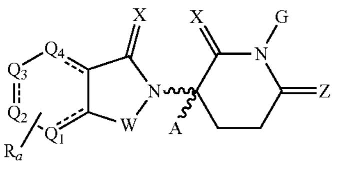

(b)

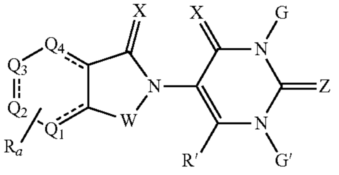

(c)

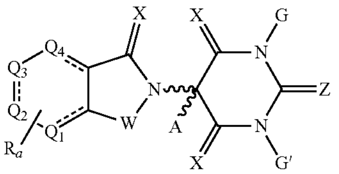

(d)

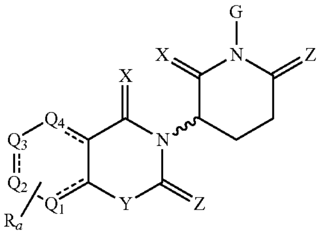

(e)

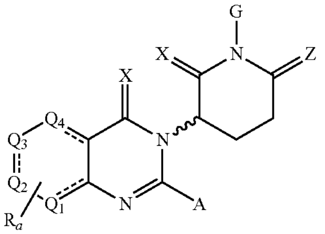

-continued (f)

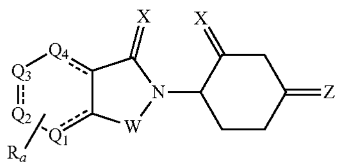

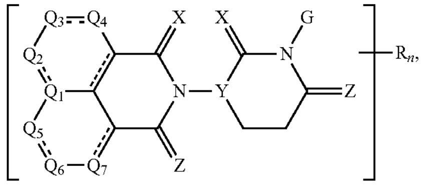

wherein:

each occurrence of W is independently selected from the group consisting of $CH_2$, CHR, C═O, S(═O)$_2$, NH, and N-alkyl;

each occurrence of X is independently selected from the group consisting of O, S and $H_2$;

each occurrence of Y is independently selected from the group consisting of NH, N-alkyl, N-aryl, N-heteroaryl, N-cycloalkyl, N-heterocyclyl, O, and S;

each occurrence of Z is independently selected from the group consisting of O, S, and $H_2$, with the proviso that both X and Z cannot be simultaneously $H_2$;

each occurrence of G or G' is independently selected from the group consisting of H, alkyl, OH, $CH_2$-heterocyclyl optionally substituted with R', and benzyl optionally substituted with R';

each of $Q_1$-$Q_7$ is independently selected from the group consisting of N, N-oxide, and a carbon substituted with at least one independently selected from the group consisting of R', $NH_2$, OH, halo, $C_1$-$C_6$ alkyl, $C_1$-$C_6$ alkyl bound to another $Q_1$-$Q_7$ group within the same ring, acetyl, and carboxyl, with the proviso that (a) each ring has 0-2 $Q_1$-$Q_7$ selected from the group corresponding to N and N-oxide; (b) when one $Q_1$-$Q_7$ group is a carbon substituted with a $C_1$-$C_6$ alkyl bound to a non-contiguous $Q_1$-$Q_7$ group within the same given ring, the given ring has 0-2 unsaturated bonds;

each occurrence of A is independently selected from the group consisting of H, alkyl, cycloalkyl, Cl, and F;

each occurrence of R is independently selected from the group consisting of —C(═O)NR'R", —OR', —NR'R", —SR', —S(═O)$_2$R', —S(═O)$_2$NR'R", —CR'R"—, —CR'NR'R"—, aryl, heteroaryl, alkyl, cycloalkyl, heterocyclyl, —P(═O)(OR')R", —P(═O)R'R", —OP(═O)(OR')R", —OP(═O)R'R", —Cl, —F, —Br, —I, —$CF_3$, —CN, —NR'S(═O)$_2$NR'R", —NR'C(═O)NR'R", —C(═O)NR'C(═O)R", —NR'C(═N—CN)NR'R", —C(═N—CN)NR'R", —NR'C(═N—CN)R", —NR'C(═C—$NO_2$)NR'R", —S(═O)$_2$NR'C(═O)R", —$NO_2$, —$CO_2R'$, —C(C═N—OR')R", —CR'═CR'R", —CCR', —S(C═O)(C═N—R')R", —$SF_5$, and —$OCF_3$;

each occurrence of R' and R" is independently selected from the group consisting of a bond, H, alkyl, cycloalkyl, aryl, heteroaryl, and heterocyclyl;

each occurrence of n is independently selected from the group consisting of 1, 2, 3, and 4;

$R_n$ comprises 1-4 independently selected R groups, optionally, one of which is modified to be covalently joined to a PTM, a chemical linker group (L), a ULM, CLM (or CLM') or combination thereof, ⁓ represents a bond that may be stereospecific ((R) or (S)) or non-stereospecific; and or a salt, solvate, polymorph, and/or deuterated form thereof.

The term "independently" is used herein to indicate that the variable, which is independently applied, varies independently from application to application.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain embodiments, the alkyl group is end-capped with a halogen group (At, Br, Cl, F, or I). In certain non-limiting embodiments, compounds according to the present invention which may be used to covalently bind to dehalogenase enzymes. These compounds generally contain a side chain (often linked through a polyethylene glycol group) which terminates in an alkyl group which has a halogen substituent (often chlorine or bromine) on its distal end which results in covalent binding of the compound containing such a moiety to the protein.

The term "alkenyl" refers to linear, branch-chained or cyclic $C_2$-$C_{10}$ (preferably $C_2$-$C_6$) hydrocarbon radicals containing at least one C═C bond.

The term "alkynyl" refers to linear, branch-chained or cyclic $C_2$-$C_{10}$ (preferably $C_2$-$C_6$) hydrocarbon radicals containing at least one C≡C bond.

The term "alkylene" when used, refers to a $—(CH_2)_n—$ group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than substituent occurs, each substituent is independent of another substituent) one or more substituents (independently up to five substitutents, preferably up to three substituents, often 1 or 2 substituents on a moiety in a compound according to the present invention and may include substituents which themselves may be further substituted) at a carbon (or nitrogen) position anywhere on a molecule within context, and includes as substituents hydroxyl, thiol, carboxyl, cyano (C—N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present invention may include, for example—$SiR_1R_2R_3$ groups where each of $R_1$ and $R_2$ is as otherwise described herein and $R_3$ is H or a $C_1$-$C_6$ alkyl group, preferably $R_1$, $R_2$, $R_3$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteraryl moiety) through an optionally substituted $—(CH_2)_m—$ or alternatively an optionally substituted $—(OCH_2)_m—$, $—(OCH_2CH_2)_m—$ or $—(CH_2CH_2O)_m—$ group, which may be substituted with any one or more of the above-described substituents. Alkylene groups $—(CH_2)_m—$ or $—(CH_2)_n—$ groups or other chains such as ethylene glycol chains, as identified above, may be substituted anywhere on the chain. Non-limiting substitutents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a sidechain of an amino acid as otherwise described herein and optionally substituted amide (preferably carboxamide substituted as described above) or urethane groups (often with one or two $C_0$-$C_6$ alkyl substitutents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present invention, a moiety in a molecule may be optionally substituted with up to five substituents, preferably up to three substituents. Most often, in the present invention moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane—O—C(═O)—$NR_1R_2$ or —N($R_1$)—C(═O)—O—$R_1$, nitro, cyano and amine (especially including a $C_1$-$C_6$ alkylene-$NR_1R_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, non-limiting substituents will include for example, —NH—, —NHC(═O)—, —O—, ═O, —$(CH_2)_m$— (here, m and n are in context, 1, 2, 3, 4, 5 or 6), —S—, —S(═O)—, $S(═O)_2$— or —NH—C(═O)—NH—, —$(CH_2)_n$OH, —$(CH_2)_n$SH, —$(CH_2)_n$COOH, $C_1$-$C_6$ alkyl, —$(CH_2)_n$O—($C_1$-$C_6$ alkyl), —$(CH_2)_n$C(═O)—($C_1$-$C_6$ alkyl), —$(CH_2)_n$OC(═O)—($C_1$-$C_6$ alkyl), —$(CH_2)_n$C(═O)O—($C_1$-$C_6$ alkyl), —$(CH_2)_n$NHC(═O)—$R_1$, —$(CH_2)_n$C(═O)—$NR_1R_2$, —$(OCH_2)_n$OH, —$(CH_2O)_n$COOH, $C_1$-$C_6$ alkyl, —$(OCH_2)_n$O—($C_1$-$C_6$ alkyl), —$(CH_2O)_n$C(═O)—($C_1$-$C_6$ alkyl), —$(OCH_2)_n$NHC(═O)—$R_1$, —$(CH_2O)_n$C(═O)—$NR_1R_2$, —$S(═O)_2$—$R_S$, —S(═O)—$R_S$ ($R_S$ is $C_1$-$C_6$ alkyl or a —$(CH_2)_m$—$NR_1R_2$ group), $NO_2$, CN or halogen (F, Cl, Br, I, preferably F or Cl), depending on the context of the use of the substituent. $R_1$ and $R_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(═O)—$NR_1R_2$ group where $R_1$ and $R_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present invention at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: —$(CH_2)_n$OH, —$(CH_2)_n$—O—($C_1$-$C_6$)alkyl, —$(CH_2)_n$—O—$(CH_2)_n$—($C_1$-$C_6$)alkyl, —$(CH_2)_n$—C(═O)($C_0$-$C_6$) alkyl, —$(CH_2)_n$—C(═O)O($C_0$-$C_6$)alkyl, —$(CH_2)_n$—OC(═O)($C_0$-$C_6$)alkyl, amine, mono- or di-($C_1$-$C_6$ alkyl) amine wherein the alkyl group on the amine is optionally substituted with 1 or 2 hydroxyl groups or up to three halo (preferably F, Cl) groups, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is preferably substituted with a linker group attached to a PTM group, including a ULM group), and/or at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group —C(═O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted $-(CH_2)_m-O-C_1$-$C_6$ alkyl group or an optionally substituted $-(CH_2)_m-C(=O)-O-C_1$-$C_6$ alkyl group), an optionally substituted pyridine (2-, 3, or 4-pyridine) or a group according to the chemical structure:

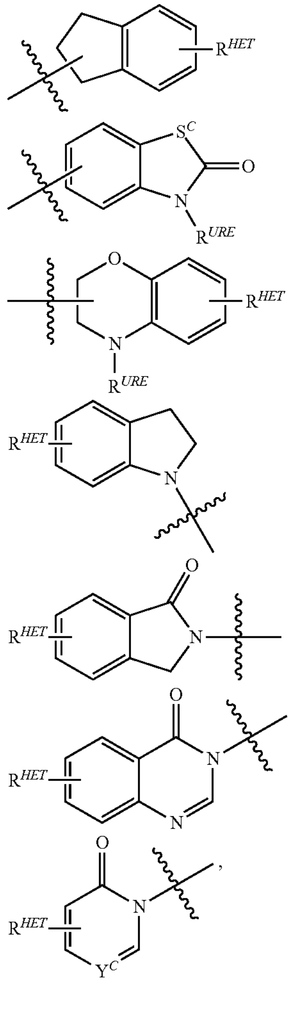

wherein $S^c$ is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group $-C{\equiv}C-R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted $O-(C_1$-$C_6$ alkyl) (preferably substituted with one or two hydroxyl groups or up to three halo groups) or an optionally substituted $-C(O)(C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a $-C(=O)(C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ is N or $C-R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group $-C{\equiv}C-R_a$ where $R_a$ is H or a $C_1$-$C_6$ alkyl group (preferably $C_1$-$C_3$ alkyl).

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —S(═O)-alkyl, —S(═O)-substituted alkyl, —S(═O)aryl, —S(═O)-heteroaryl, —S(═O)$_2$-alkyl, —S(═O)$_2$-substituted alkyl, —S(═O)$_2$-aryl, oxo (═O), and —S(═O)$_2$-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S or P. "Substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "hydrocarbyl" shall mean a compound which contains carbon and hydrogen and which may be fully saturated, partially unsaturated or aromatic and includes aryl groups, alkyl groups, alkenyl groups and alkynyl groups.

In any of the embodiments described herein, the W, X, Y, Z, G, G', R, R', R", Q1-Q4, A, and Rn can independently be covalently coupled to a linker and/or a linker to which is attached one or more PTM, ULM, CLM or CLM' groups.

More specifically, non-limiting examples of CLMs include those shown below as well as those 'hybrid' molecules that arise from the combination of 1 or more of the different features shown in the molecules below.

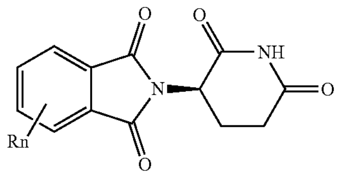

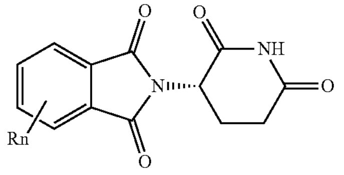

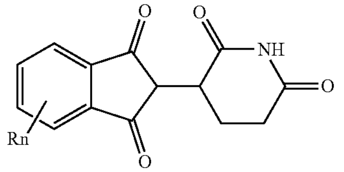

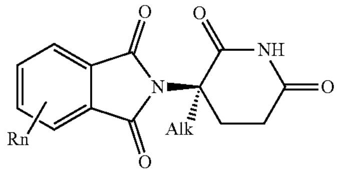

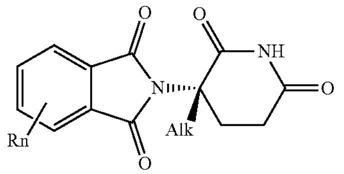

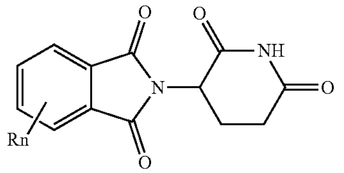

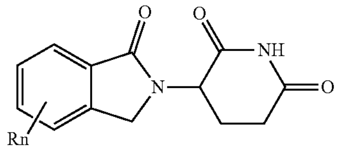

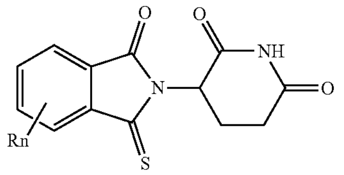

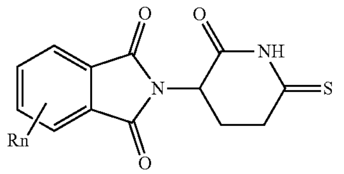

-continued
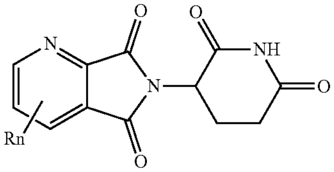
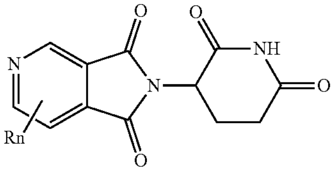
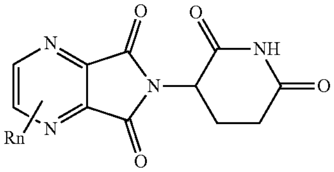
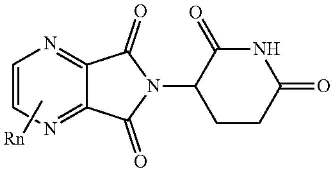
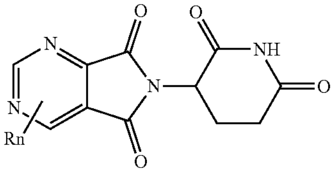
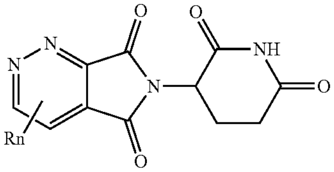
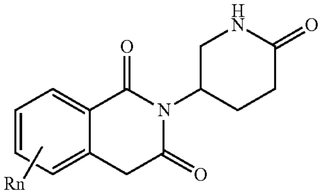
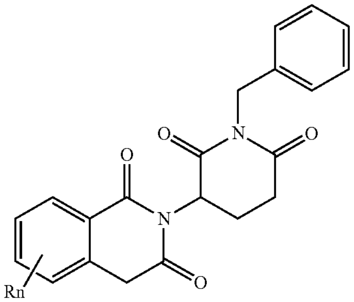
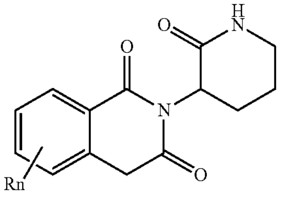
-continued
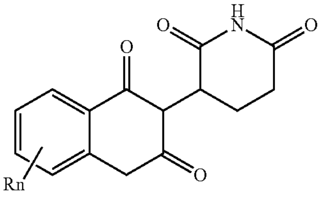
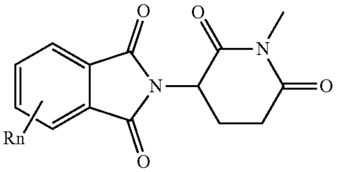
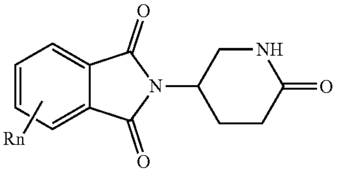
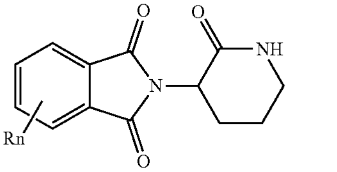
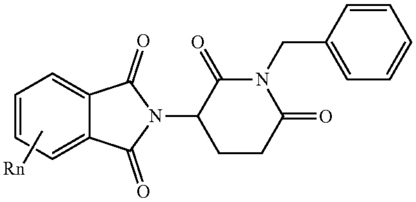
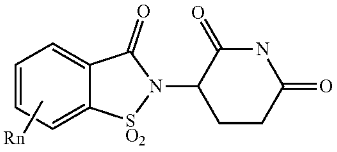
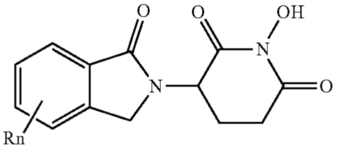
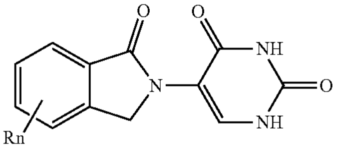
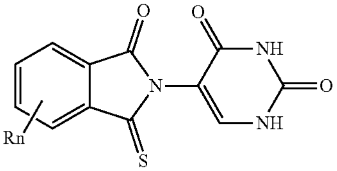
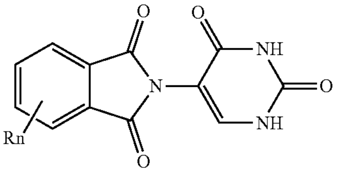

-continued
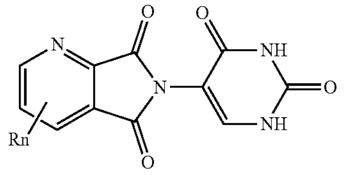
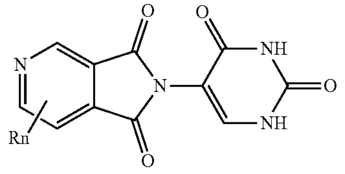
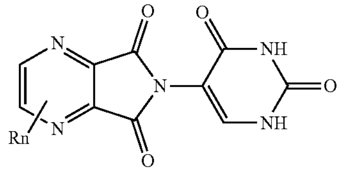
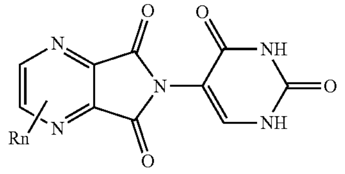
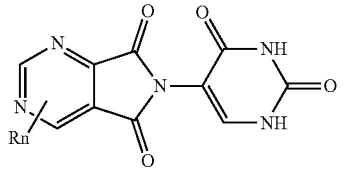
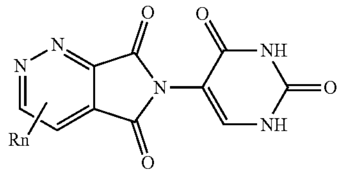
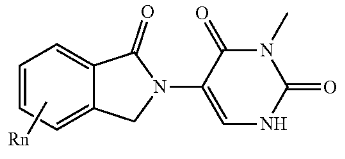
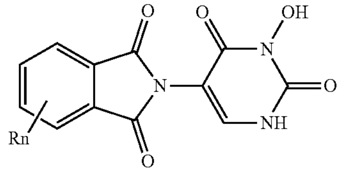
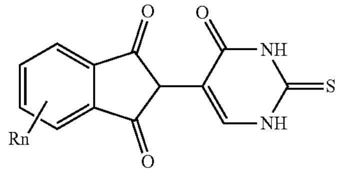
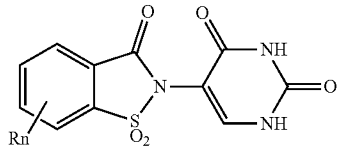
-continued
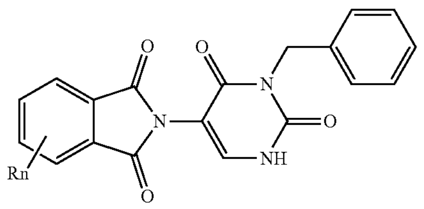
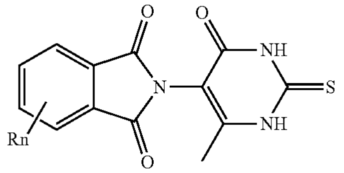
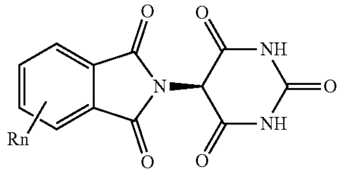
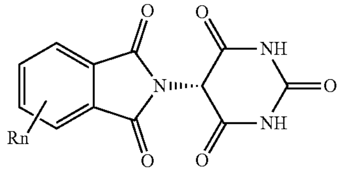
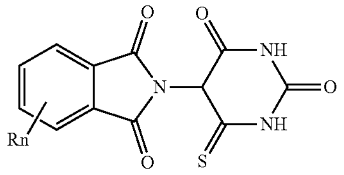
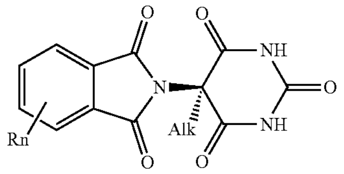
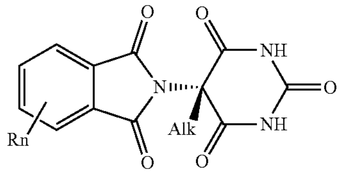
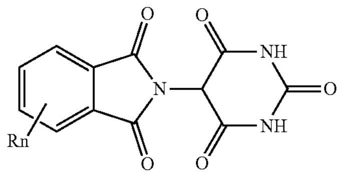
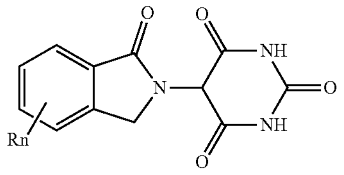

-continued
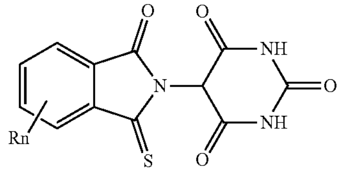
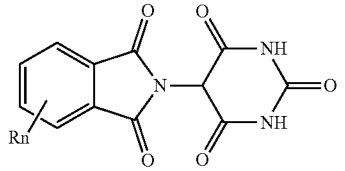
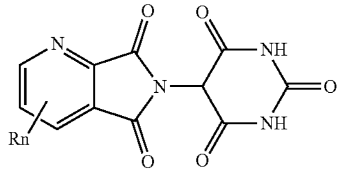
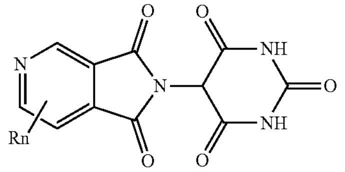
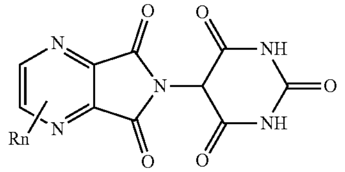
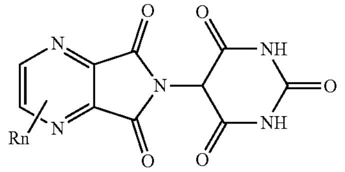
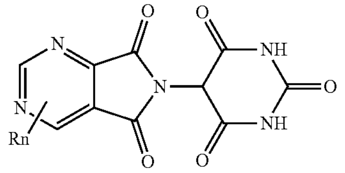
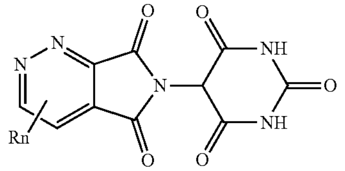
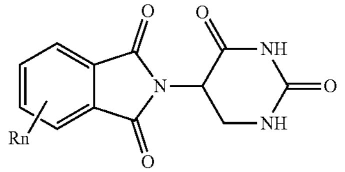
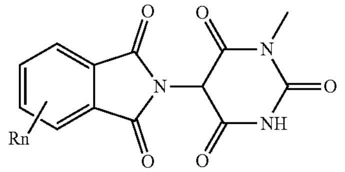
-continued
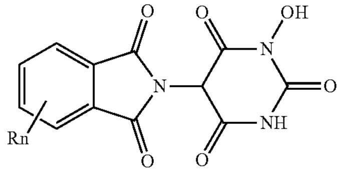
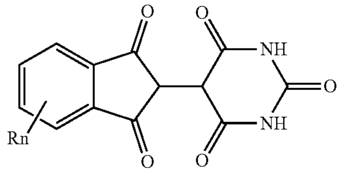
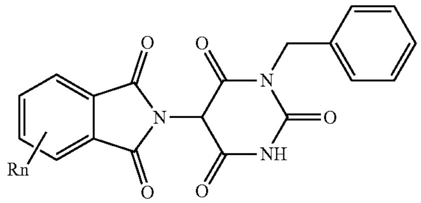
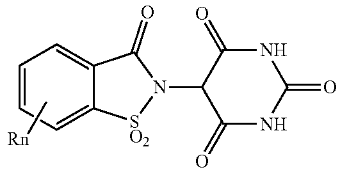
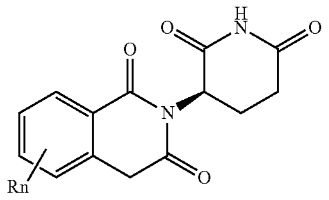
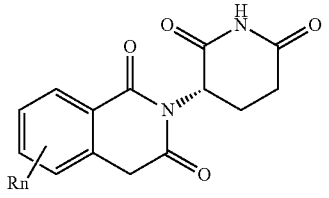
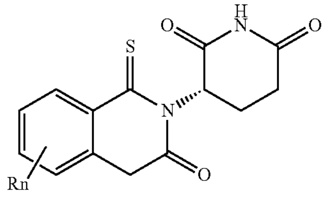
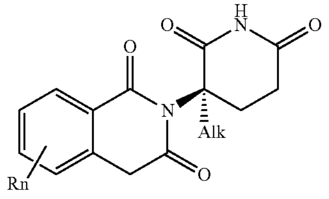
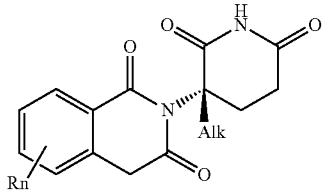

-continued
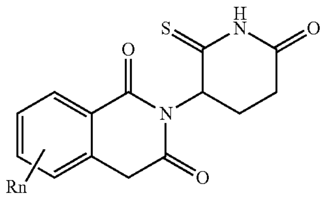
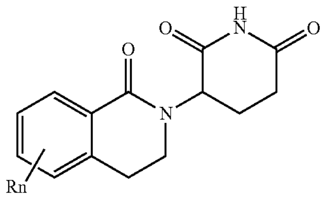
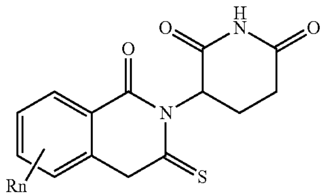
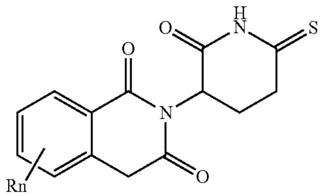
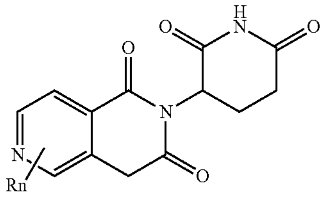
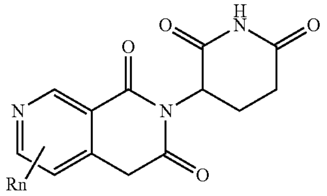
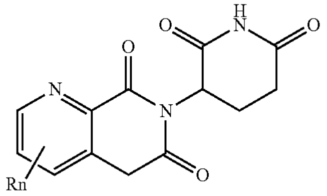
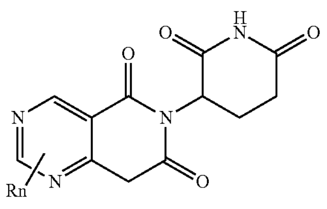
-continued
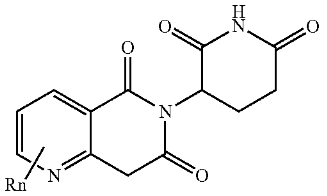
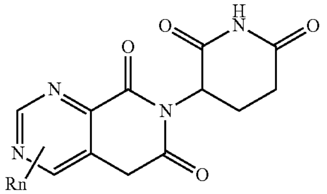
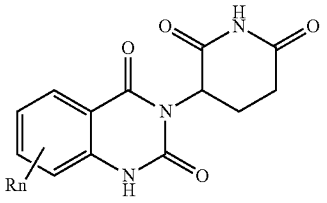
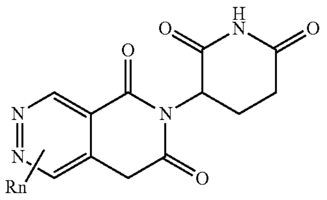
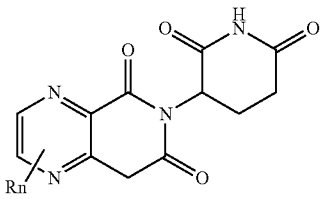
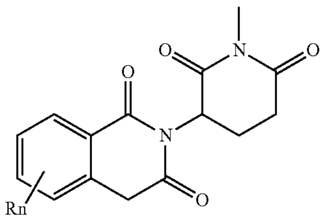
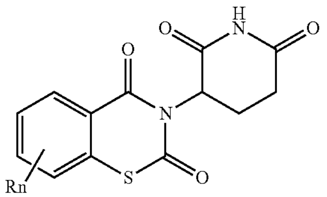
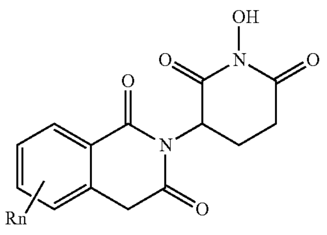

-continued
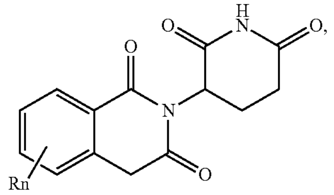
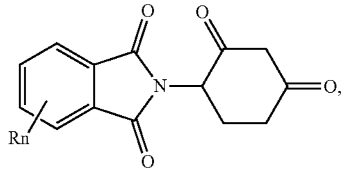
1
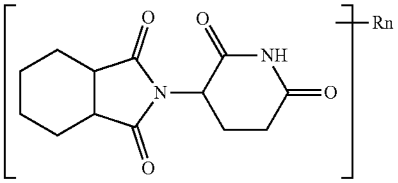
2
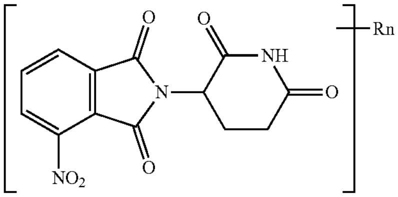
3
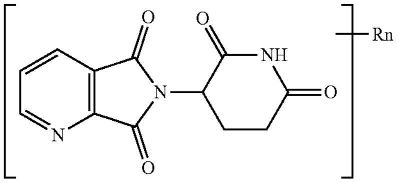
4
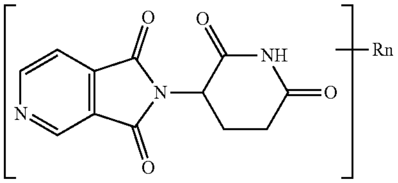
5
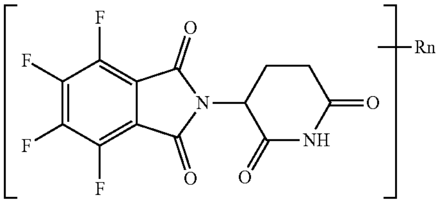
6
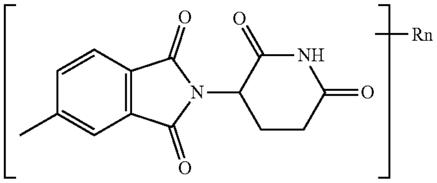
-continued
7
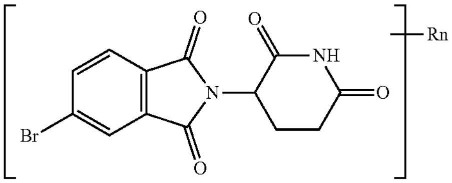
8
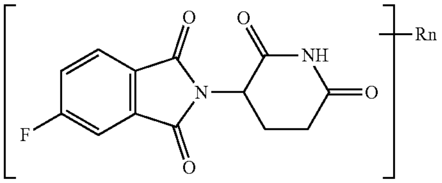
9
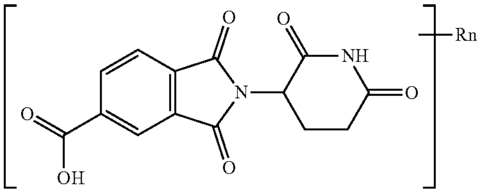
10
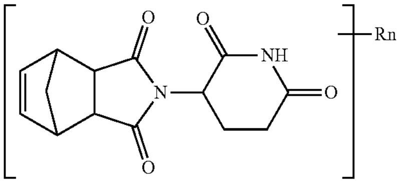
11
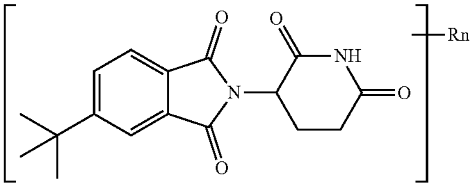
12
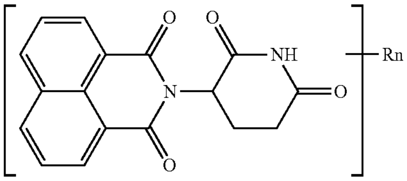
13
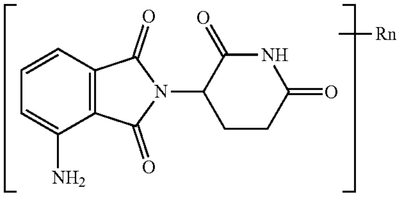
14
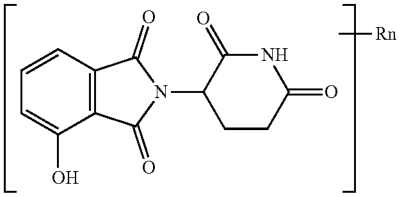

-continued
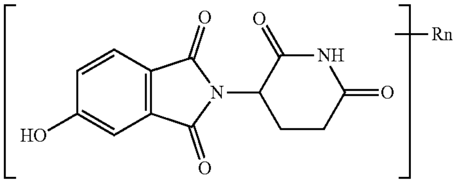
15
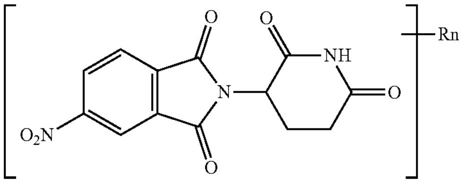
16
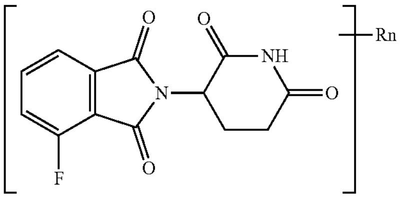
17
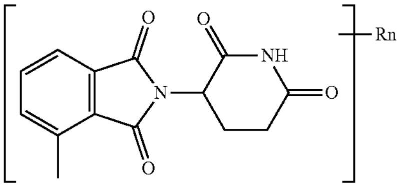
18
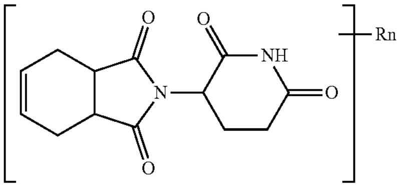
19
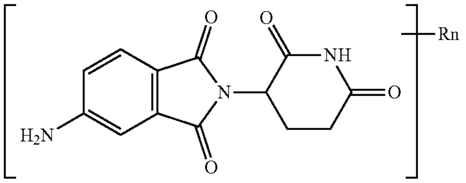
20
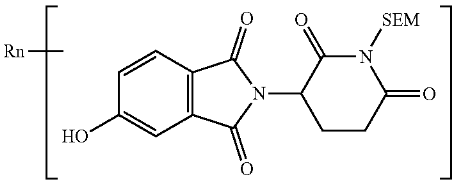
21
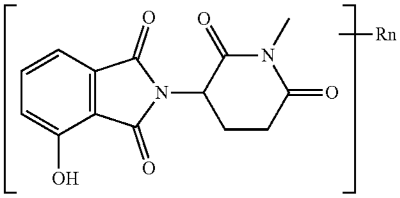
22
In certain cases, “CLM” can be imides that binding to cereblon E3 ligase. These imides and linker attachment point can be but not limited to the following structures:
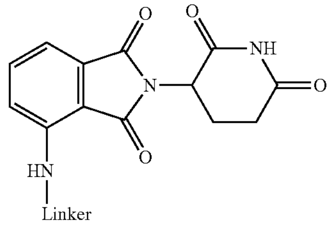
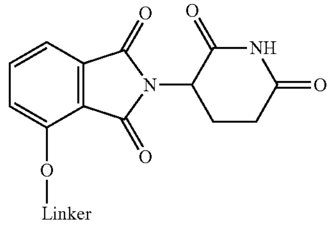
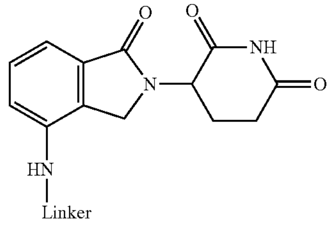
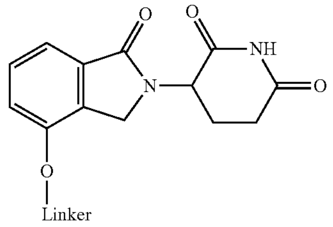
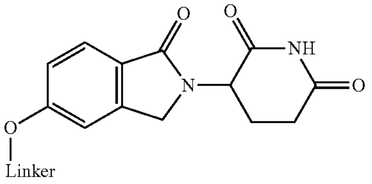
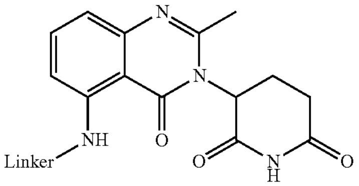
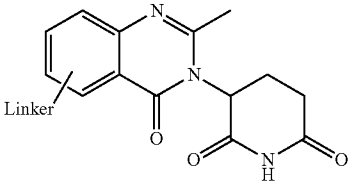

-continued

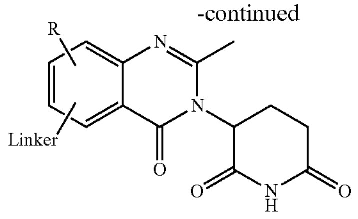

Exemplary Linkers

In certain embodiments, the compounds as described herein include one or more PTMs chemically linked or coupled to one or more ULMs (e.g., at least one of CLM, VLM, ML-M, ILM, or a combination thereof) via a chemical linker (L). In certain embodiments, the linker group L is a group comprising one or more covalently connected structural units (e.g., $-A^L_1 \ldots (A^L)_q-$ or $-(A^L)_q-$), wherein $A_1$ is a group coupled to PTM, and $(A^L)_q$ is a group coupled to ULM.

In certain embodiments, the linker group L is selected from $-(A^L)_q-$. $(A^L)_q$ is a group which is connected to at least one of a ULM, a PTM moiety, or a combination thereof; q of the linker is an integer greater than or equal to 1; each $A^L_q$ is independently selected from the group consisting of, a bond, $CR^{L1}R^{L2}$, O, S, S(═O), $S(═O)_2$, $NR^{L3}$, $S(═O)_2NR^{L3}$, $S(═O)NR^{L3}$, $C(═O)NR^{L3}$, $NR^{L3}C(═O)NR^{L4}$, $NR^{L3}S(═O)_2NR^{L4}$, C(═O), $CR_{L1}═CR^{L2}$, C≡C, $SiR^{L1}R^{L2}$, $P(═O)R^{L1}$, $P(═O)OR^{L1}$, $NR^{L3}C(═NCN)NR^{L4}$, $NR^{L3}C(═NCN)$, $NR^{L3}C(═CNO_2)NR^{L4}$, $C_{3-11}$cycloalkyl optionally substituted with 0-6 $R^{L1}$ and/or $R^{L2}$ groups, $C_{5-13}$ spirocycloalkyl optionally substituted with 0-9 $R^{L1}$ and/or $R^{L2}$ groups, $C_{3-11}$heterocyclyl optionally substituted with 0-6 $R^{L1}$ and/or $R^{L2}$ groups, $C_{5-13}$ spiroheterocycloalkyl optionally substituted with 0-8 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}cycloalkyl)_2$, $N(C_{1-8}cycloalkyl)(C_{1-8}alkyl)$, OH, $NH_2$, SH, $SO_2C_{1-8}$alkyl, $P(═O)(OC_{1-8}alkyl)(C_{1-8}alkyl)$, $P(═O)(OC_{1-8}alkyl)_2$, C≡C—$C_{1-8}$alkyl, C≡CH, CH═CH($C_{1-8}$alkyl), $C(C_{1-8}alkyl)═CH(C_{1-8}alkyl)$, $C(C_{1-8}alkyl)═C(C_{1-8}alkyl)_2$, $Si(OH)_3$, $Si(C_{1-8}alkyl)_3$, $Si(OH)(C_{1-8}alkyl)_2$, $C(═O)C_{1-8}$alkyl, $CO_2H$, halogen, CN, $CF_3$, $CHF_2$, $CH_2F$, $NO_2$, $SF_5$, $SO_2NHC_{1-8}$alkyl, $S(═O)_2N(C_{1-8}alkyl)_2$, $S(═O)NHC_{1-8}$alkyl, $S(═O)N(C_{1-8}alkyl)_2$, $C(═O)NHC_{1-8}$alkyl, $C(═O)N(C_{1-8}alkyl)_2$, $N(C_{1-8}alkyl)C(═O)NH(C_{1-8}alkyl)$, $N(C_{1-8}alkyl)C(═O)N(C_{1-8}alkyl)_2$, $NHC(═O)NH(C_{1-8}alkyl)$, $NHC(═O)N(C_{1-8}alkyl)_2$, $NHC(═O)NH_2$, $N(C_{1-8}alkyl)S(═O)_2NH(C_{1-8}alkyl)$, $N(C_{1-8}alkyl)\ S(═O)_2N(C_{1-8}alkyl)_2$, $NHS(═O)_2NH(C_{1-8}alkyl)$, $NHS(═O)_2N(C_{1-8}alkyl)_2$, NH $S(═O)_2NH_2$.

In certain embodiments, q of the linker is an integer greater than or equal to 0. In certain embodiments, q is an integer greater than or equal to 1.

In certain embodiments, e.g., where q of the linker is greater than 2, $(A^L)_q$ is a group which is connected to ULM, and $A^L_1$ and $(A^L)_q$ are connected via structural units of the linker (L).

In certain embodiments, e.g., where q of the linker is 2, $(A^L)_q$ is a group which is connected to $A^L_1$ and to a ULM.

In certain embodiments, e.g., where q of the linker is 1, the structure of the linker group L is $-A^L_1-$, and $A^L_1$ is a group which is connected to a ULM moiety and a PTM moiety.

In certain embodiments, the linker (L) comprises a group represented by a general structure selected from the group consisting of: $—NR(CH_2)_n$-(lower alkyl)-, $—NR(CH_2)_n$-(lower alkoxyl)-, $—NR(CH_2)_n$-(lower alkoxyl)-$OCH_2$—, $—NR(CH_2)_n$-(lower alkoxyl)-(lower alkyl)-$OCH_2$—, $—NR(CH_2)_n$-(cycloalkyl)-(lower alkyl)-$OCH_2$—, $—NR(CH_2)_n$-(heterocycloalkyl)-, $—NR(CH_2CH_2O)_n$— (lower alkyl)-O—$CH_2$—, $—NR(CH_2CH_2O)_n$-(heterocycloalkyl)-O—$CH_2$—, $—NR(CH_2CH_2O)_n$-Aryl-O—$CH_2$—, $—NR(CH_2CH_2O)_n$-(heteroaryl)-O—$CH_2$—, $—NR(CH_2CH_2O)_n$-(cycloalkyl)-O-(heteroaryl)-O—$CH_2$—, $—NR(CH_2CH_2O)_n$-(cycloalkyl)-O-Aryl-O—$CH_2$—, $—NR(CH_2CH_2O)_n$-(lower alkyl)-NH-Aryl-O—$CH_2$—, $—NR(CH_2CH_2O)_n$-(lower alkyl)-O-Aryl-$CH_2$, $—NR(CH_2CH_2O)_n$-cycloalkyl-O-Aryl-, $—NR(CH_2CH_2O)_n$-cycloalkyl-O-(heteroaryl)l-, $—NR(CH_2CH_2)_n$-(cycloalkyl)-O-(heterocycle)-$CH_2$, $—NR(CH_2CH_2)_n$-(heterocycle)-(heterocycle)-$CH_2$, $—N(R_1R_2)$-(heterocycle)-$CH_2$; wherein: each n of each linker can be independently 0 to 10; each R of the linker can be independently H or lower alkyl; each $R_1$ and $R_2$ of each linker can independently form a ring with the connecting N.

In certain embodiments, the linker (L) comprises a group represented by a general structure selected from the group consisting of:

$—N(R)—(CH_2)_m—O(CH_2)_n—O(CH_2)_o—O(CH_2)_p—O(CH_2)_q—O(CH_2)_r—OCH_2—$, $—O—(CH_2)_m—O(CH_2)_n—O(CH_2)_o—O(CH_2)_p—O(CH_2)_q—O(CH_2)_r—OCH_2—$, $—O—(CH_2)_m—O(CH_2)_n—O(CH_2)_o—O(CH_2)_p—O(CH_2)_q—O(CH_2)_r—O—$;

$—N(R)—(CH_2)_m—O(CH_2)_n—O(CH_2)_o—O(CH_2)_p—O(CH_2)_q—O(CH_2)_r—O—$;

$—(CH_2)_m—O(CH_2)_n—O(CH_2)_o—O(CH_2)_p—O(CH_2)_q—O(CH_2)_r—O—$;

$—(CH_2)_m—O(CH_2)_n—O(CH_2)_o—O(CH_2)_p—O(CH_2)_q—O(CH_2)_r—OCH_2—$;

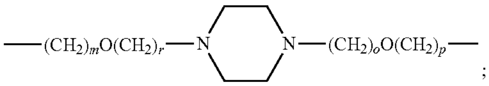
;

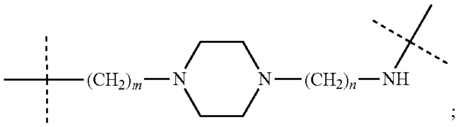
;

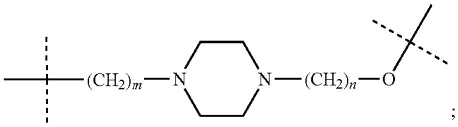
;

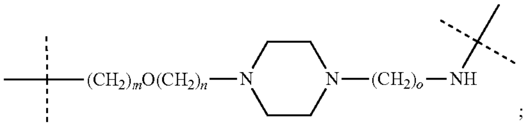
;

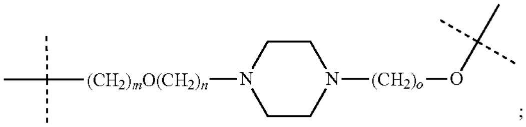
;

-continued
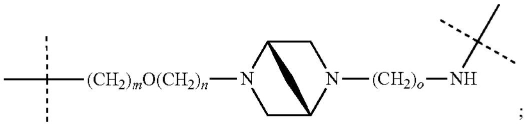
;
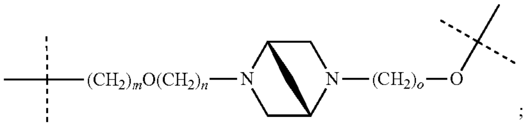
;
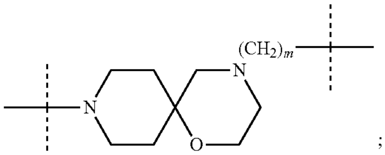
;
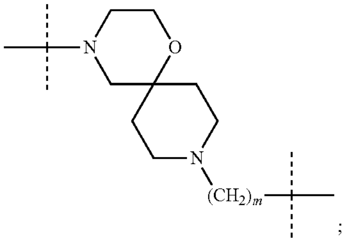
;
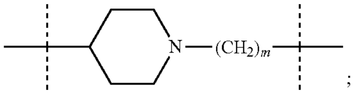
;
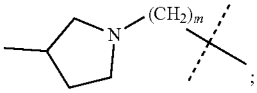
;
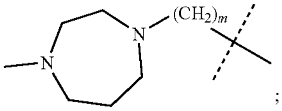
;
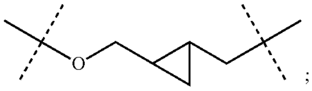
;
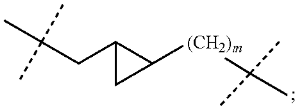
;
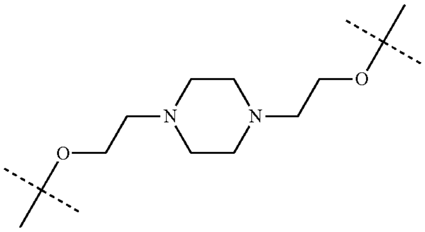
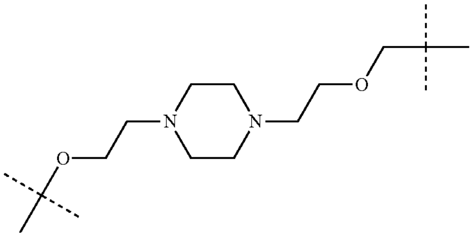
-continued
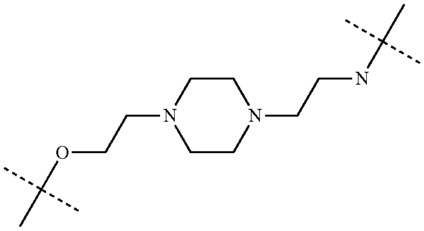
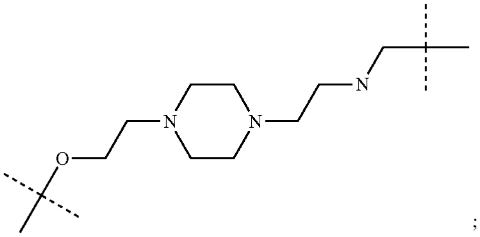
;
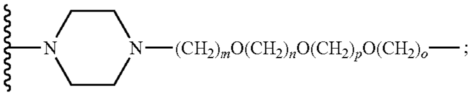
;
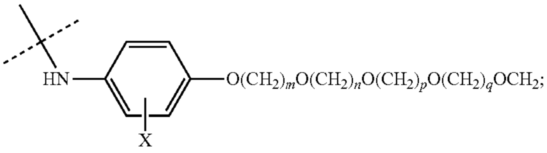
;
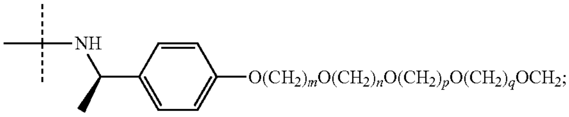
;
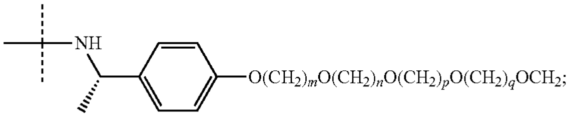
;
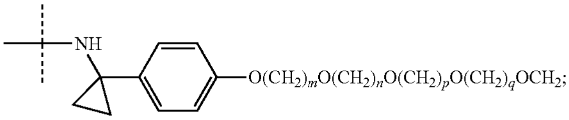
;
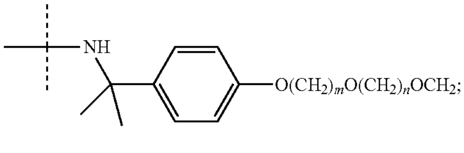
;
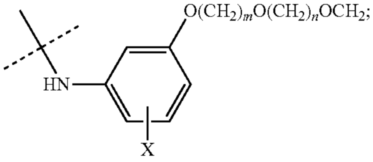
; and -continued
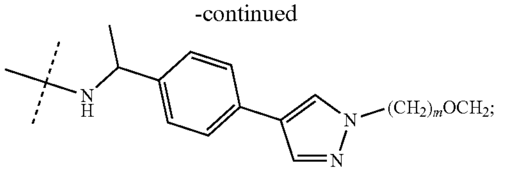
wherein
each m, n, o, p, q, and r of each linker are independently 0, 1, 2, 3, 4, 5, 6, 7, 8, 9, 10, 11, 12, 13, 14, 15, 16, 17, 18, 19, or 20, wherein, if n=0, there is no N—O or O—O bond;
each R of each linker is independently H, methyl, or ethyl;
each X of each linker is independently H or F;
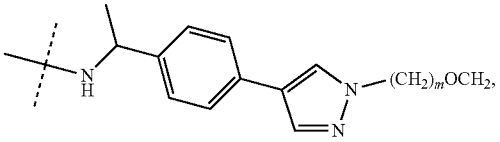
where m is 2, 3, 4, or 5;
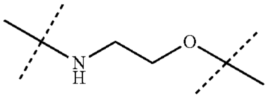
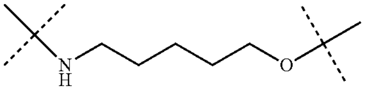
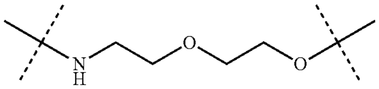
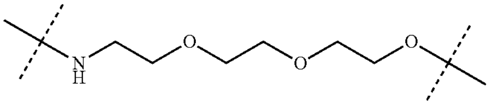
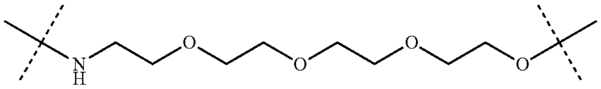
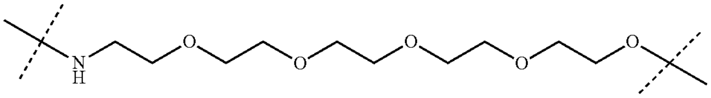
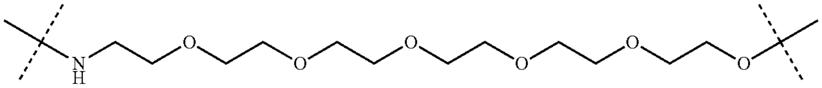
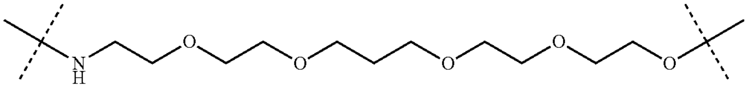
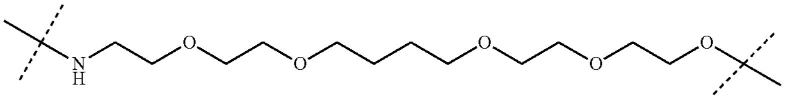
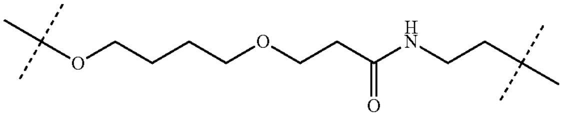
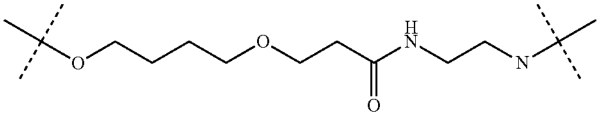
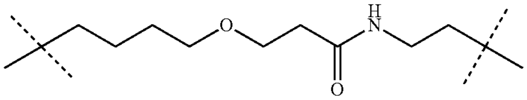
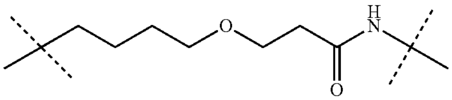
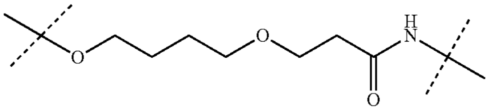
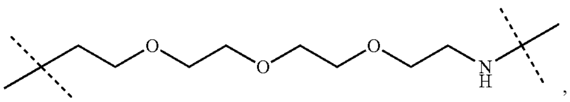,
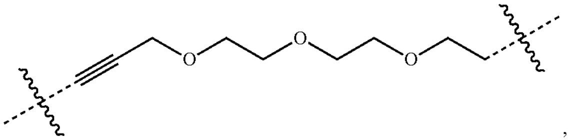,
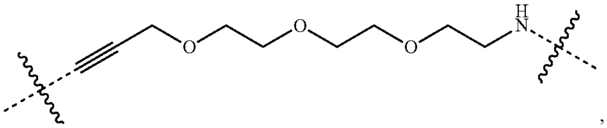,
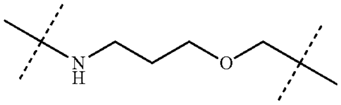
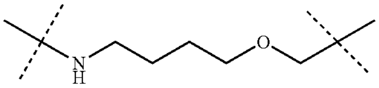
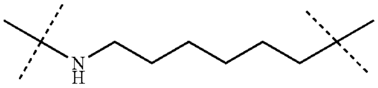
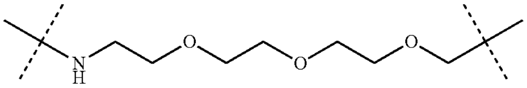
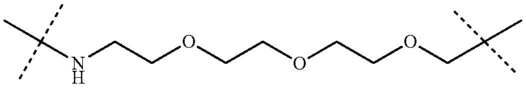

-continued
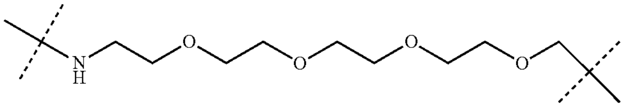
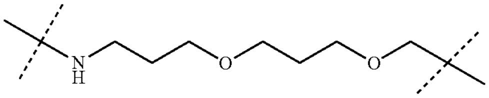
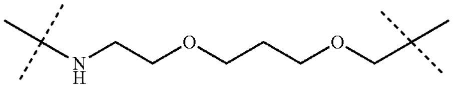
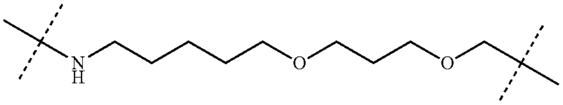
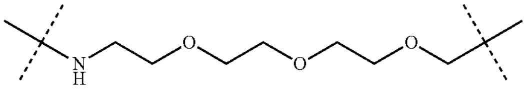
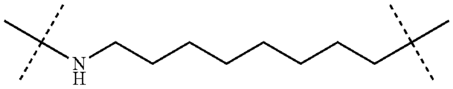
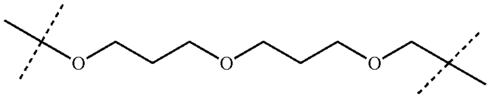
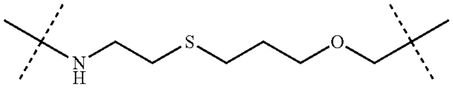
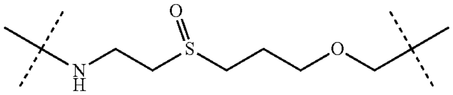
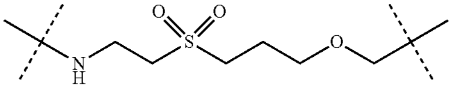
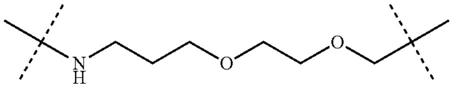
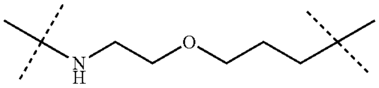
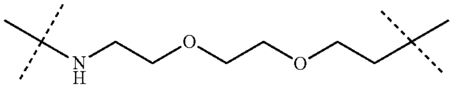
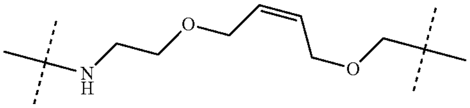
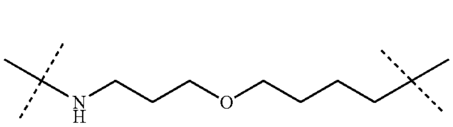
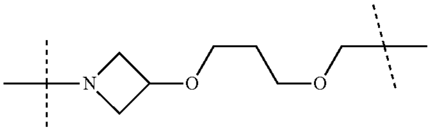
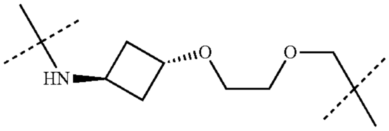
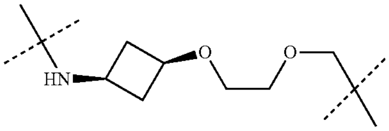
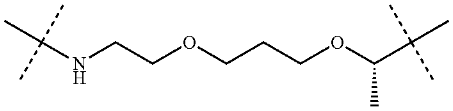
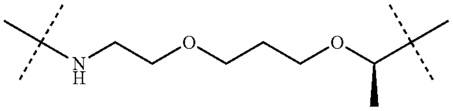
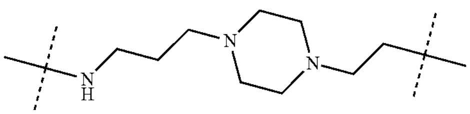
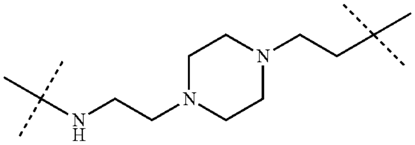
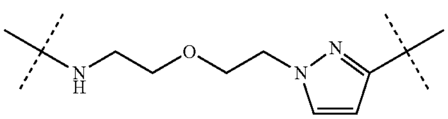
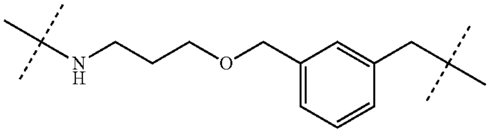
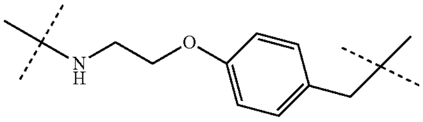
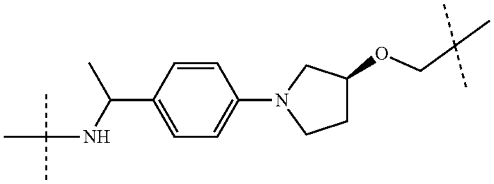

-continued
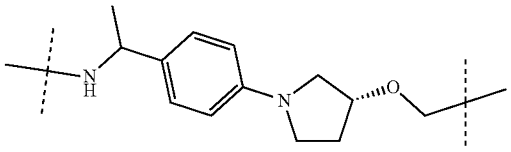
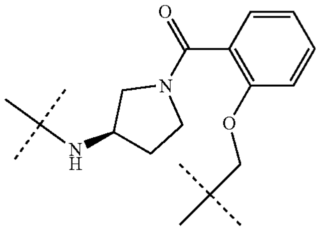
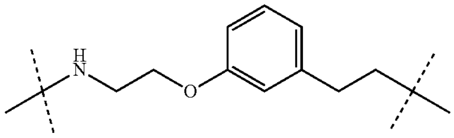
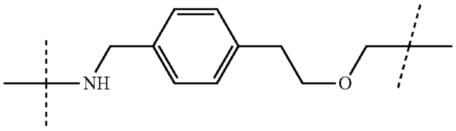
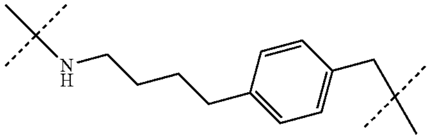
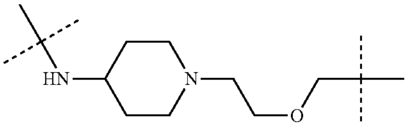
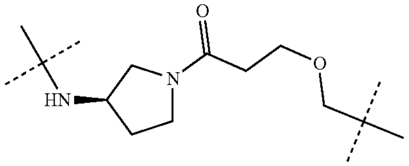
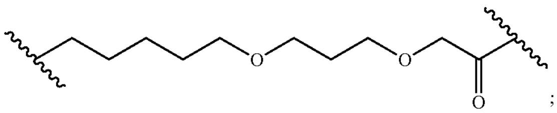
;
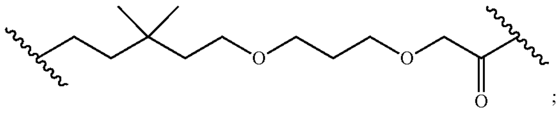
;
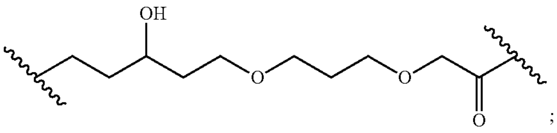
;
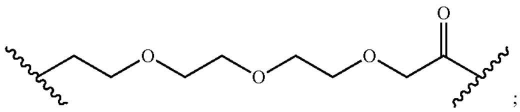
;
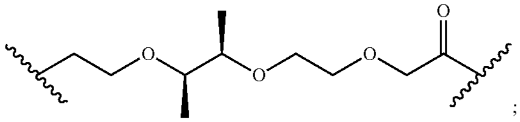
;
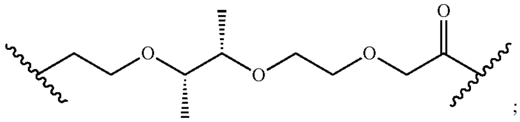
;
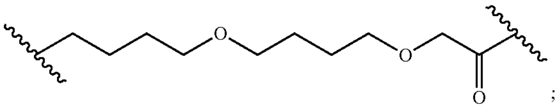
;
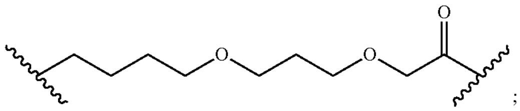
;
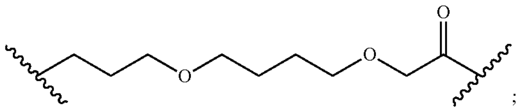
;
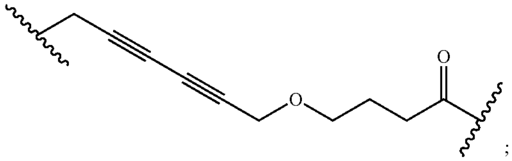
;
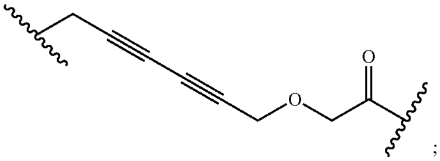
;
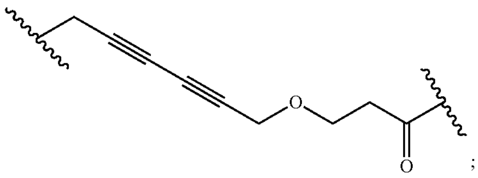
;
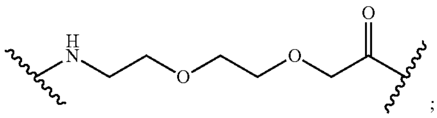
;
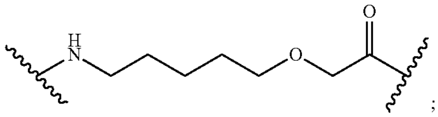
;
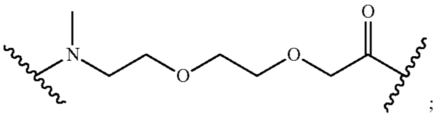
;
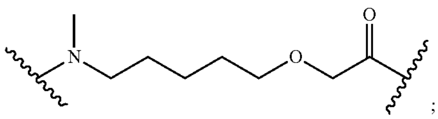
;
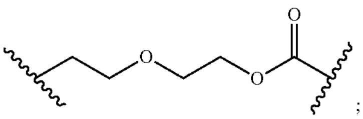
;

-continued
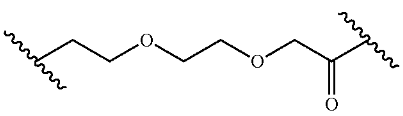
;
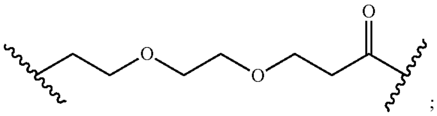
;
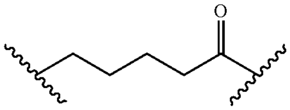
;
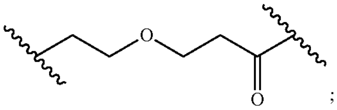
;
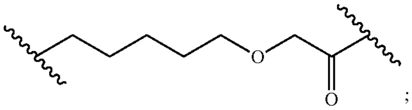
;
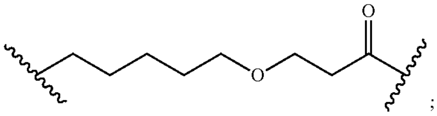
;
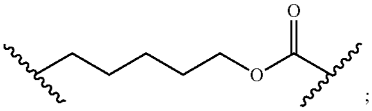
;
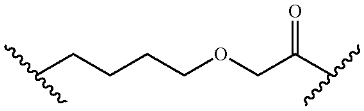
;
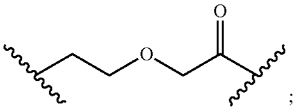
;
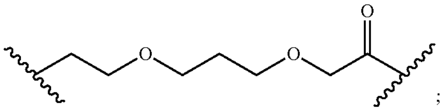
;
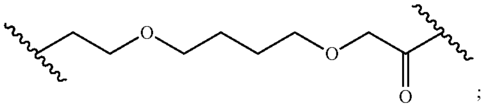
;
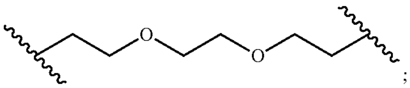
;
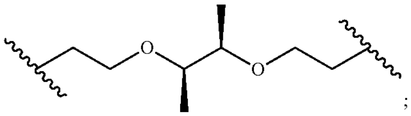
;
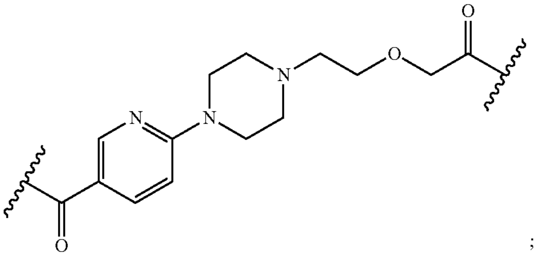
;
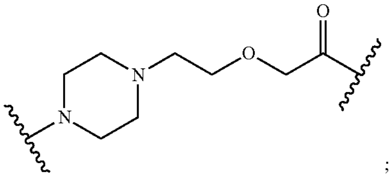
;
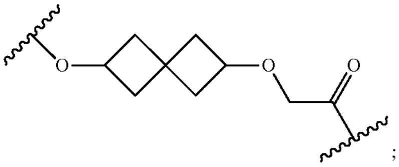
;
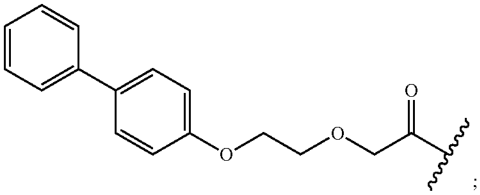
;
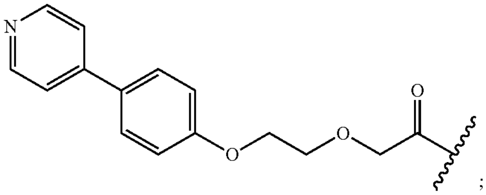
;
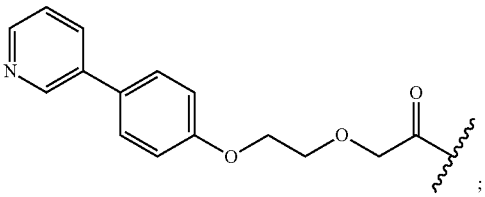
;
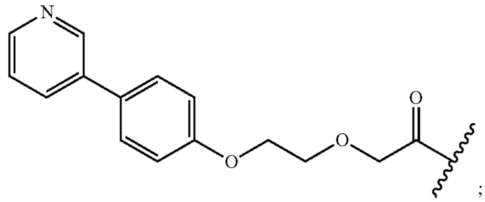
;
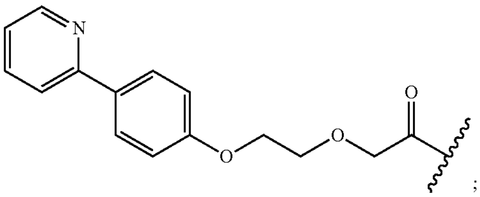
;
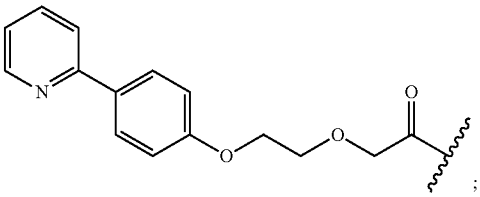
;

-continued
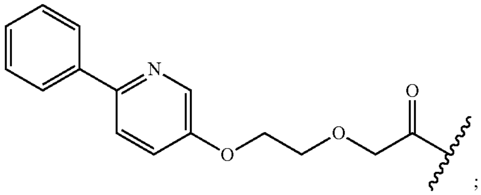
;
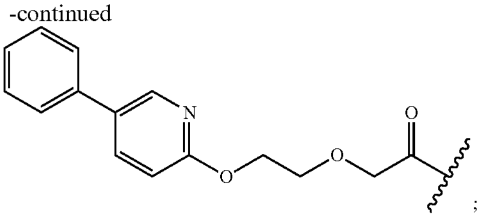
;
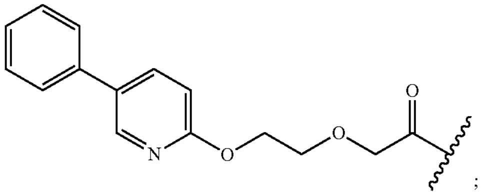
;
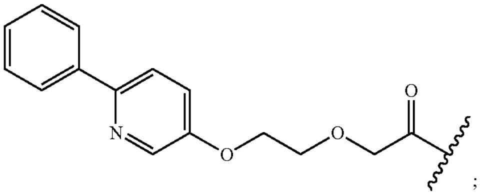
;
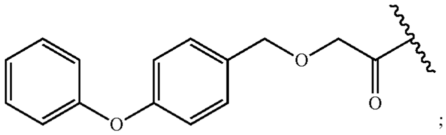
;
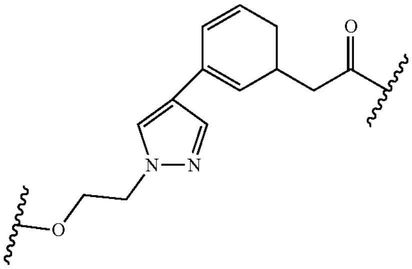
;
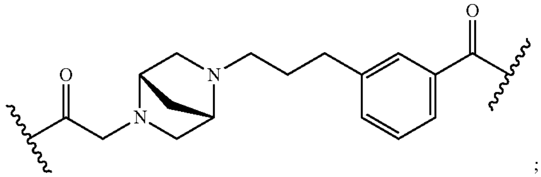
;
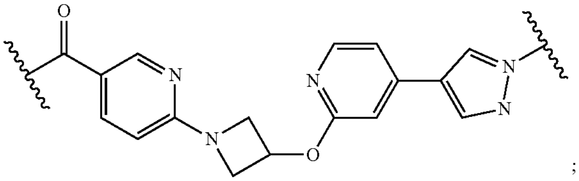
;
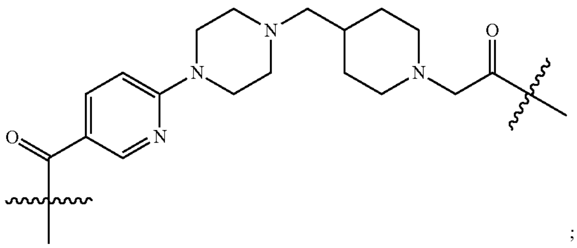
;
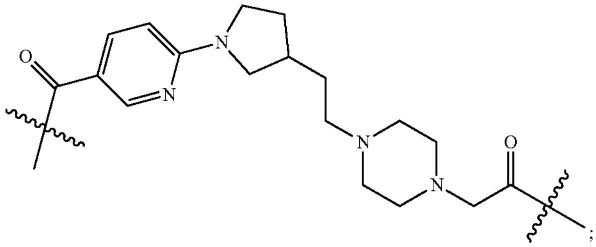
;
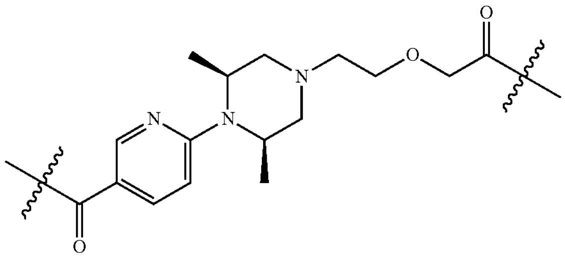
;
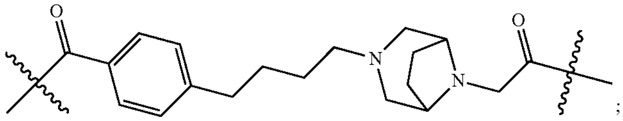
;

-continued
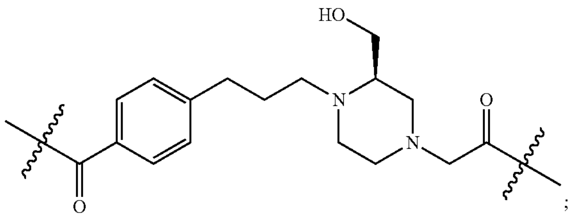 ; 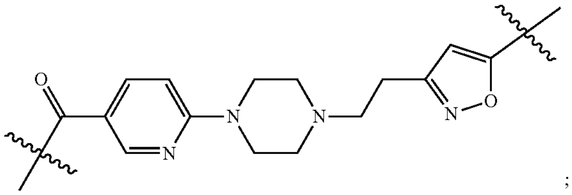 ;
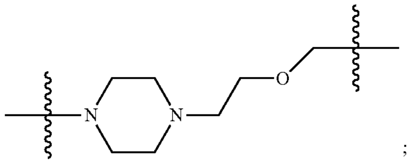 ; 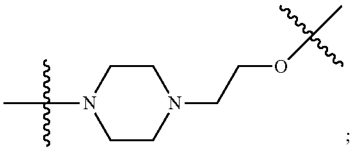 ;
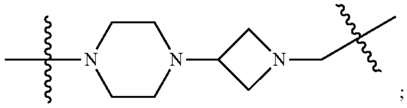 ; 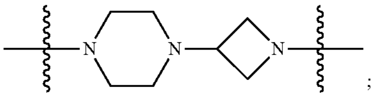 ;
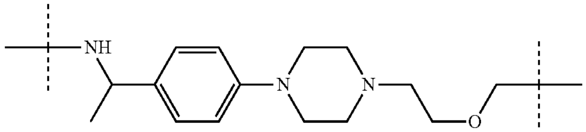
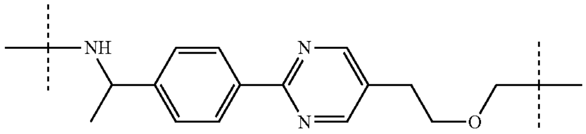
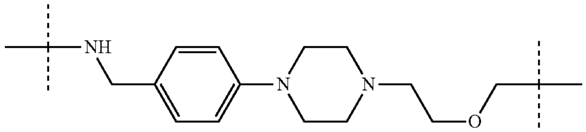
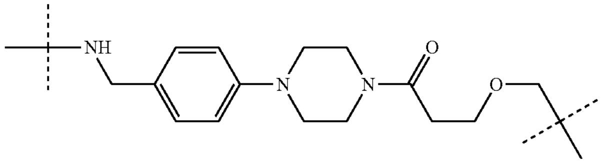
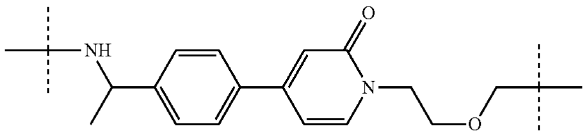
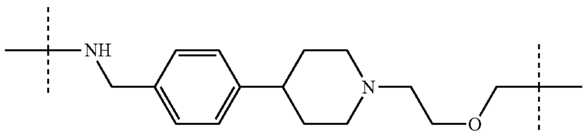 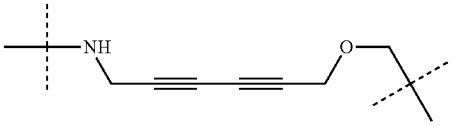
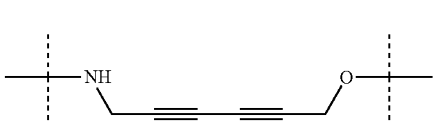 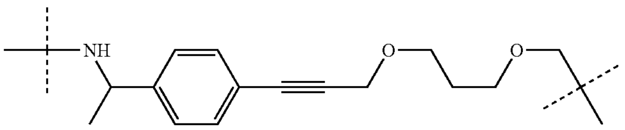
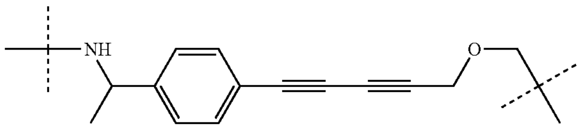 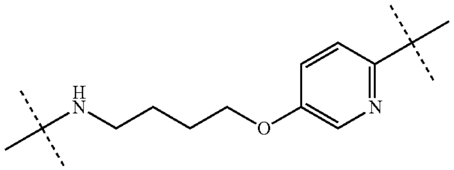

-continued
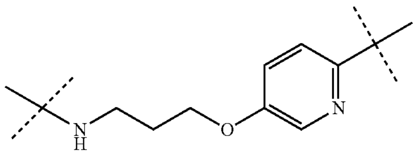
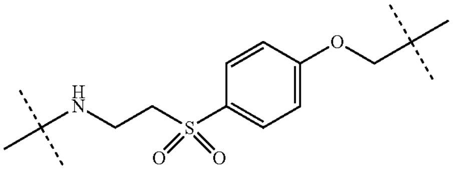
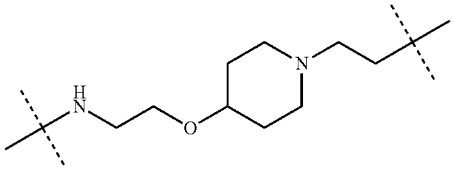
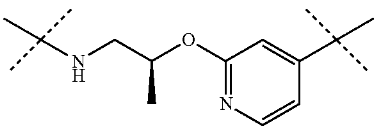
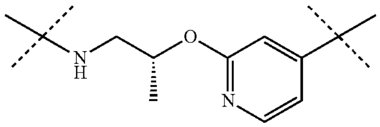
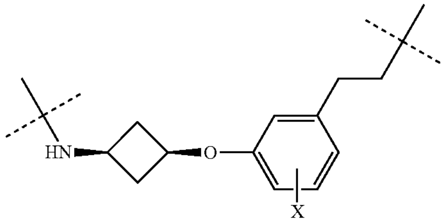
X = H, F
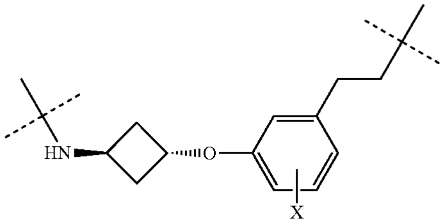
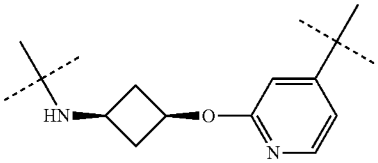
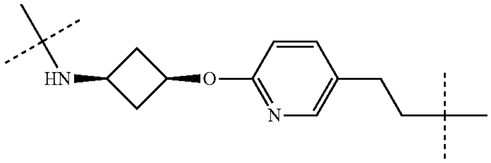
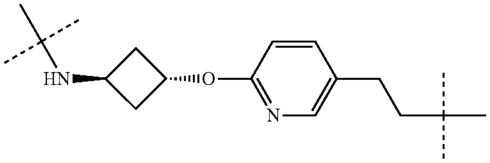
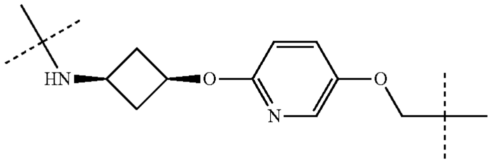
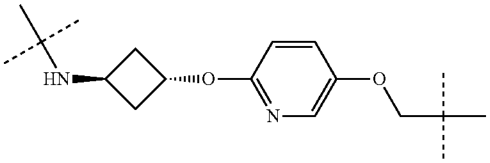
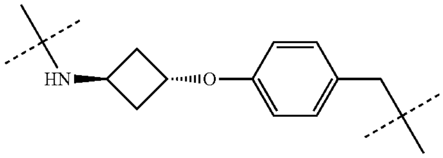
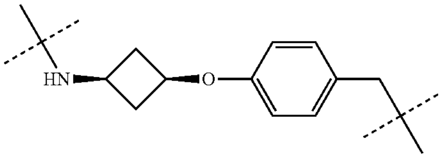
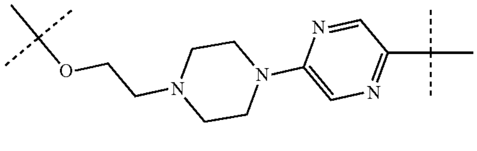
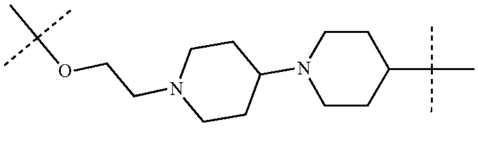
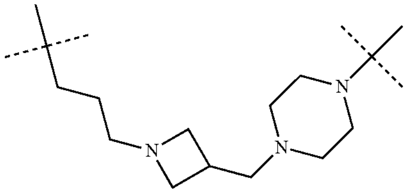
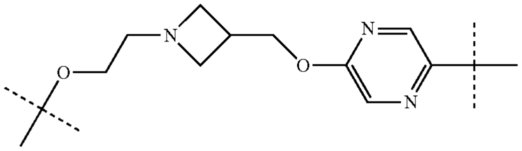

-continued
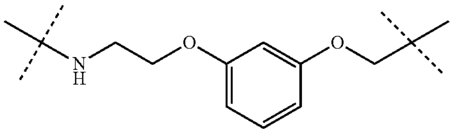
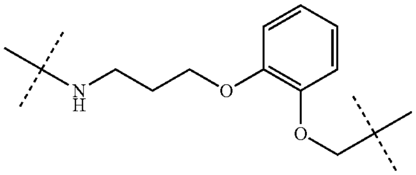
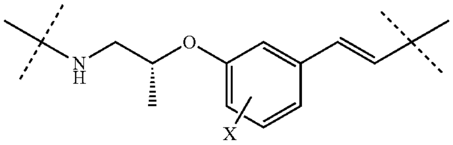
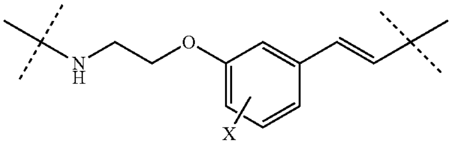
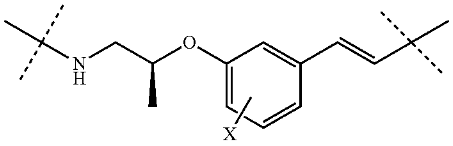
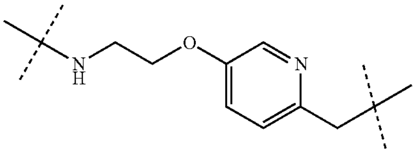
X = H, F
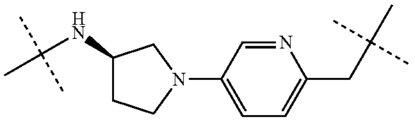
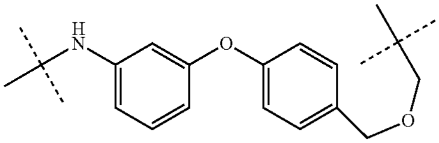
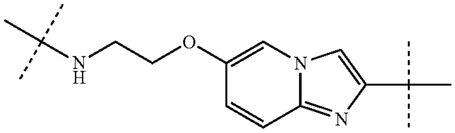
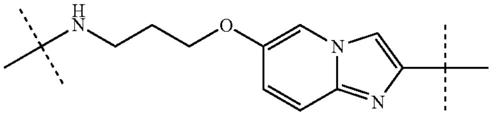
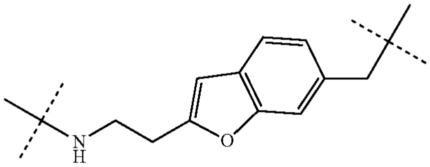
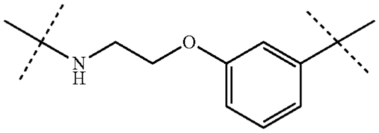
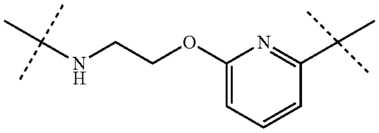
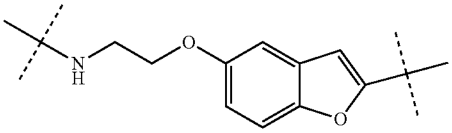
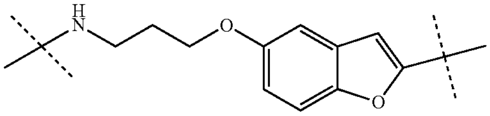
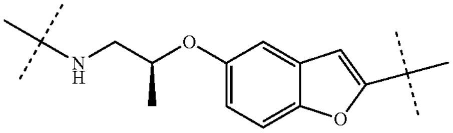
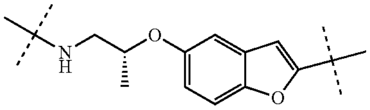
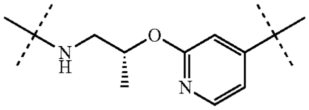
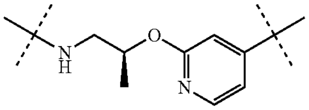
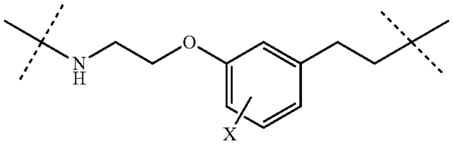
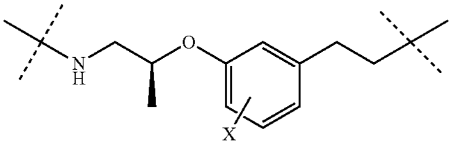
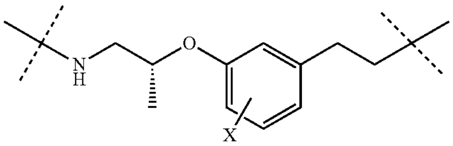
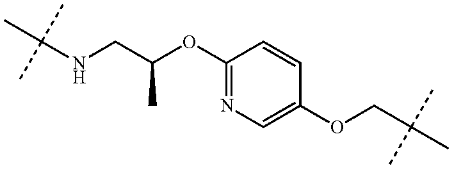

-continued
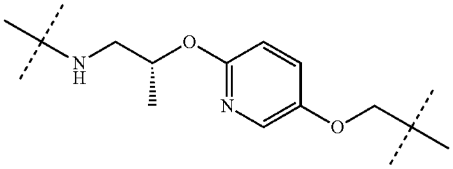
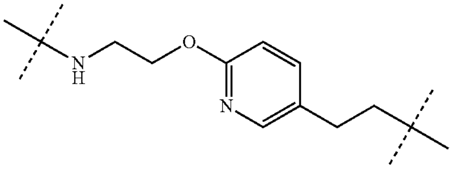
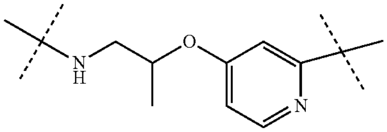
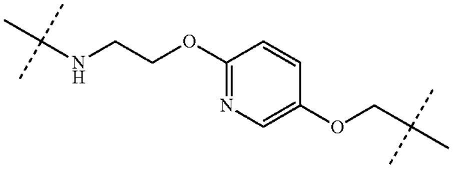
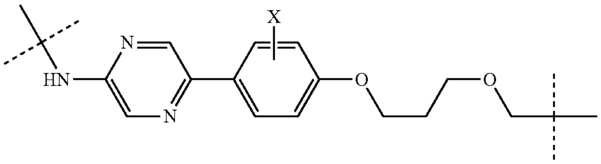
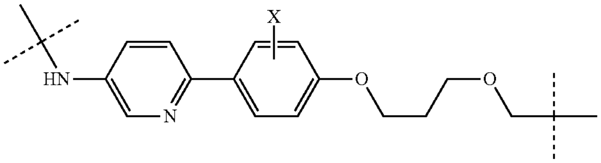
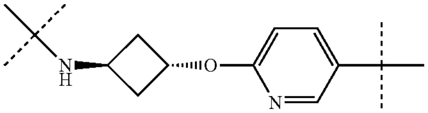
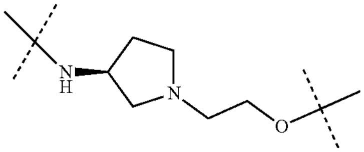
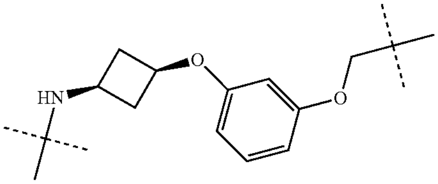
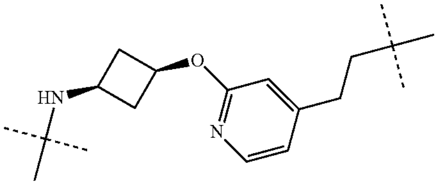
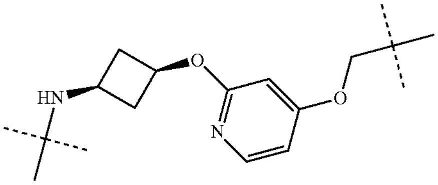
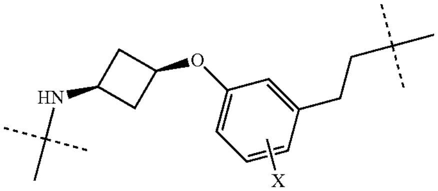
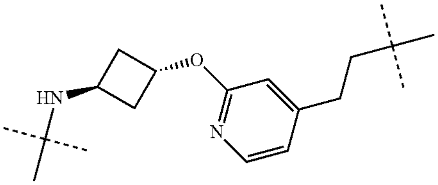
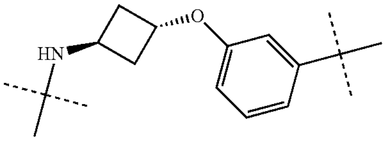
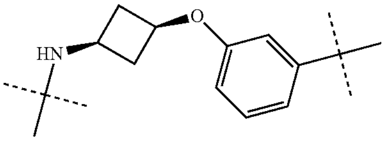
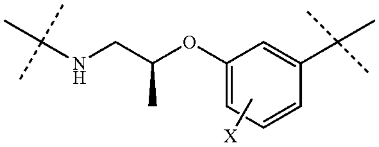
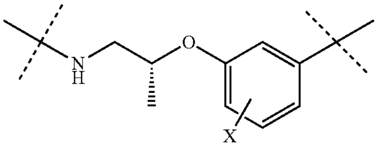
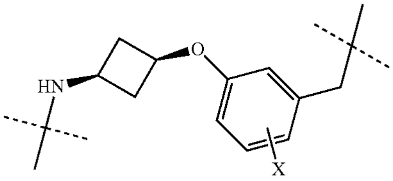
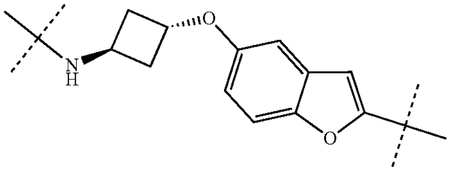

-continued
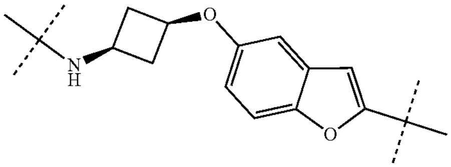
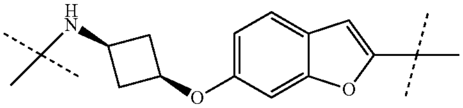
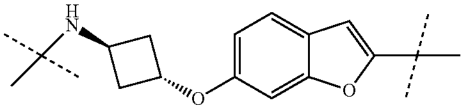
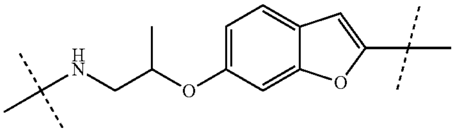
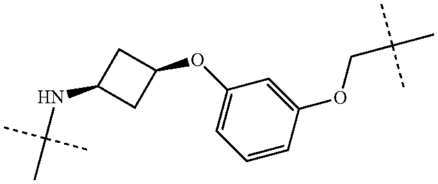
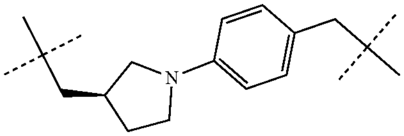
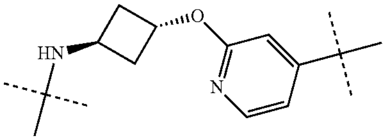
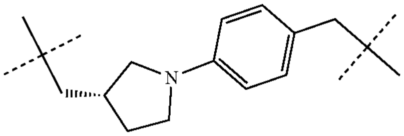
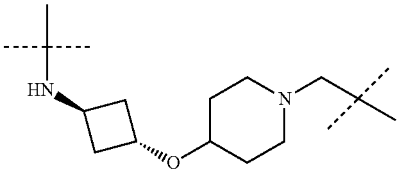
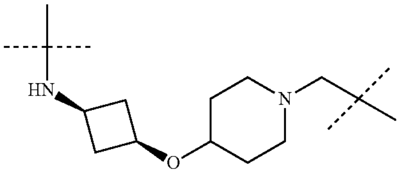
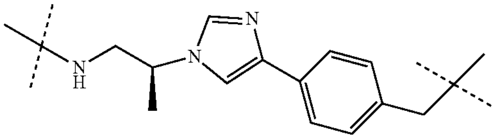
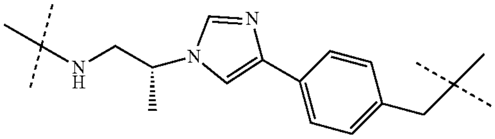
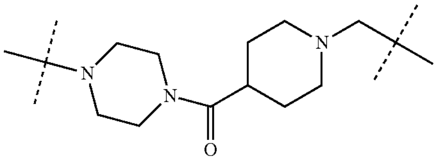
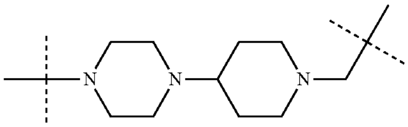
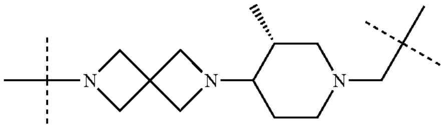
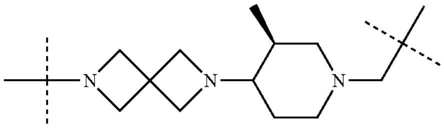
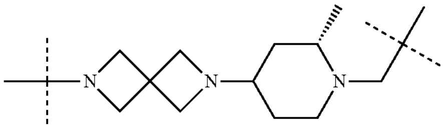
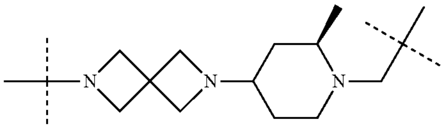
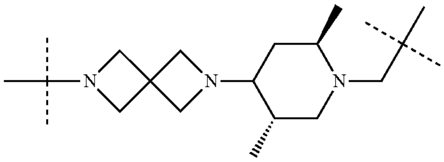
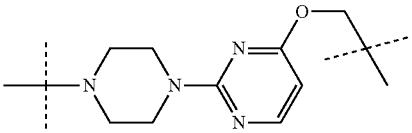
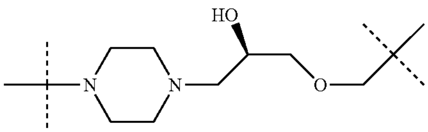
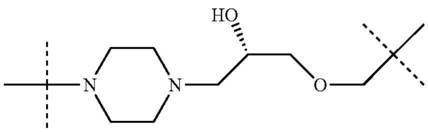

-continued
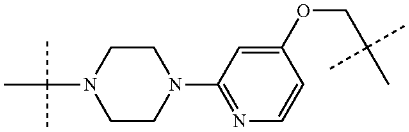
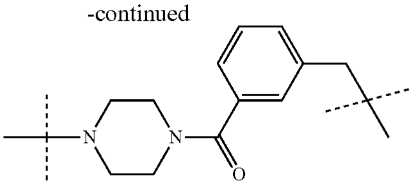
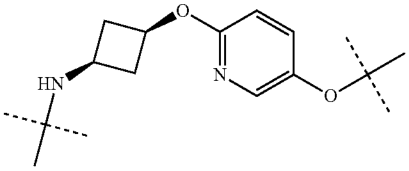
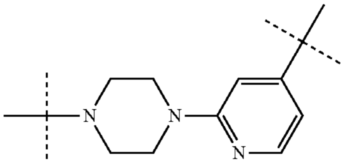
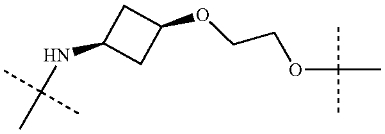
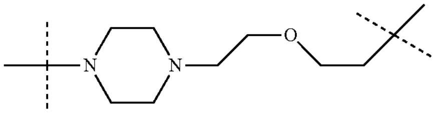
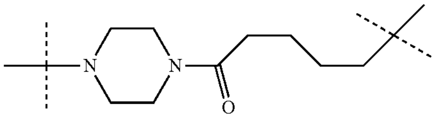
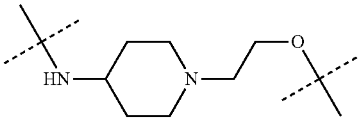
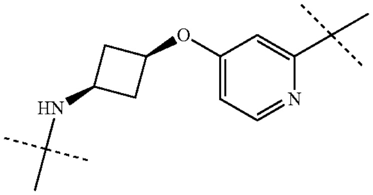
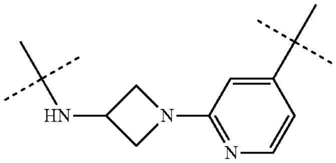
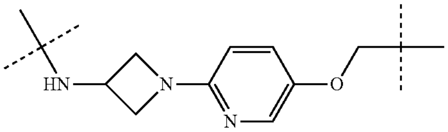
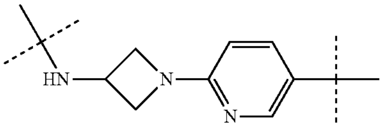
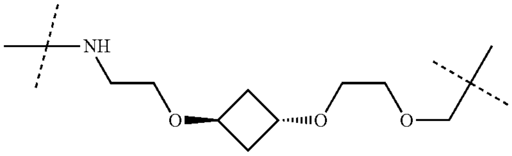
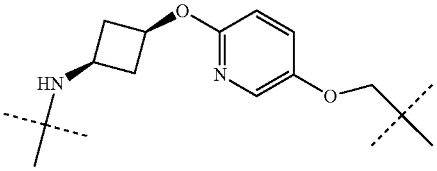
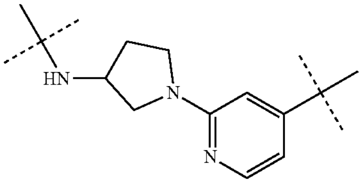
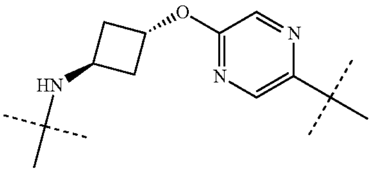
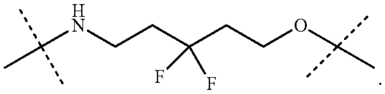
.
In any aspect or embodiment described herein, the linker (L) is selected from the group consisting of:
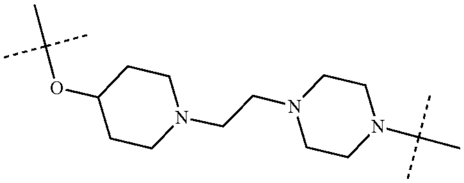
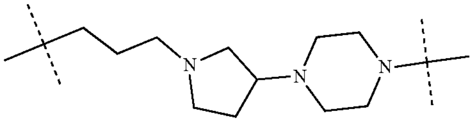
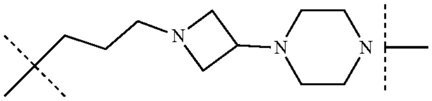
-continued
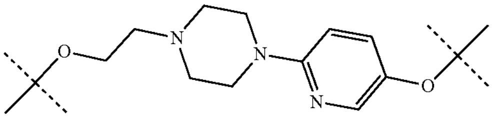
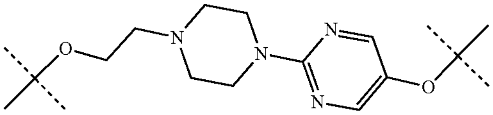
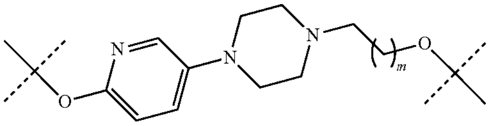

-continued
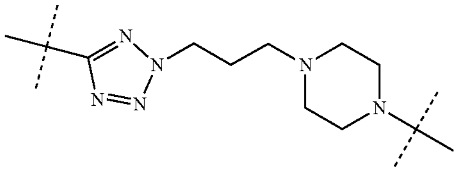
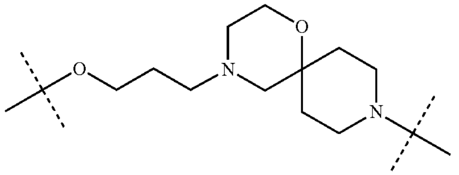
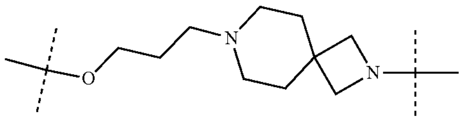
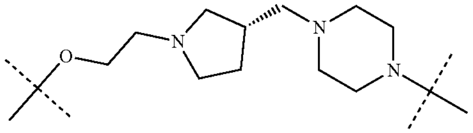
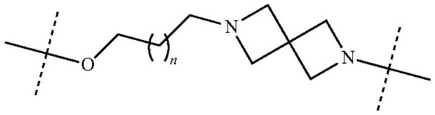
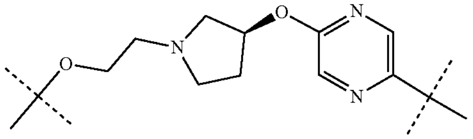
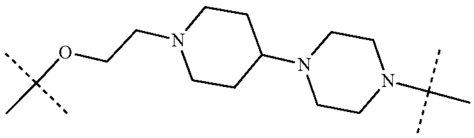
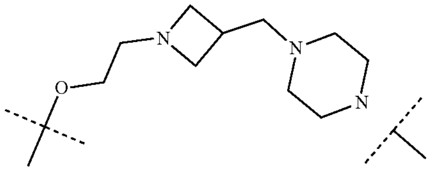
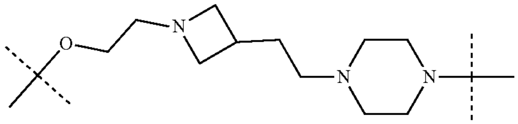
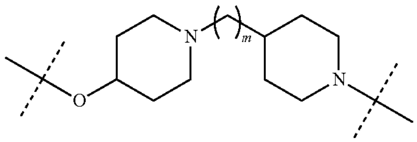
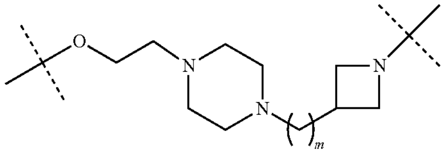
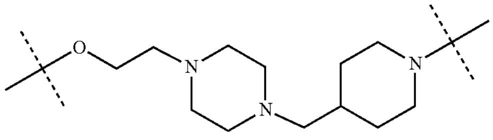
-continued
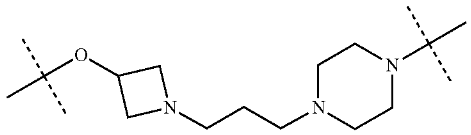
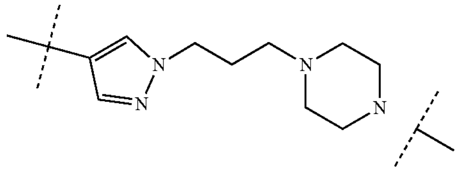
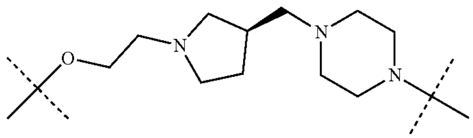
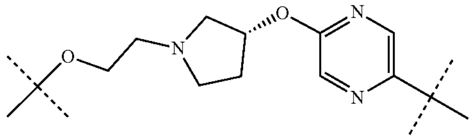
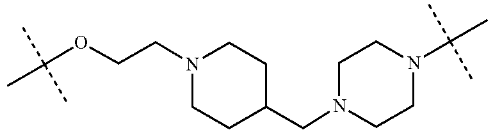
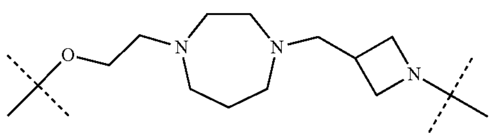
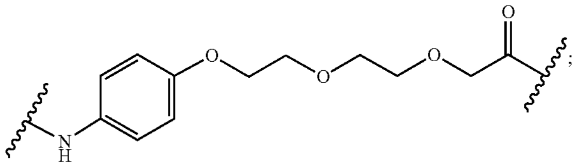
;
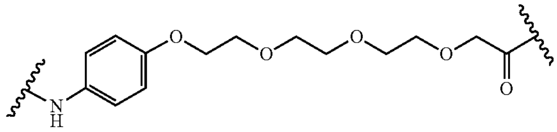
;
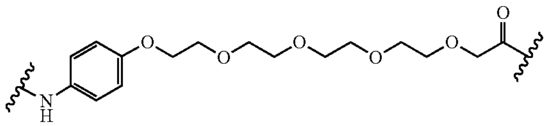
;
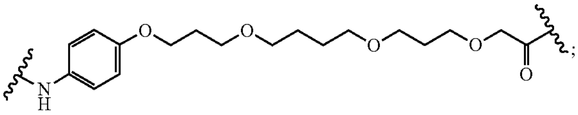
;
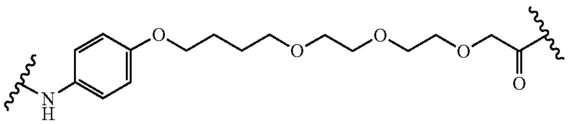
;
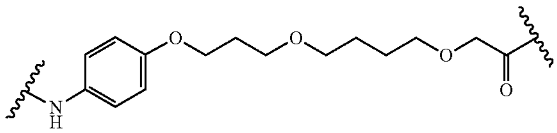
;

-continued
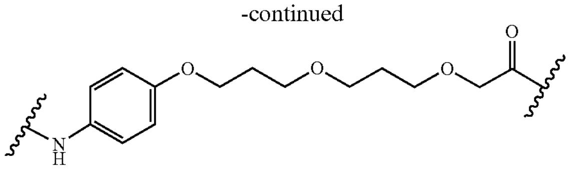
;
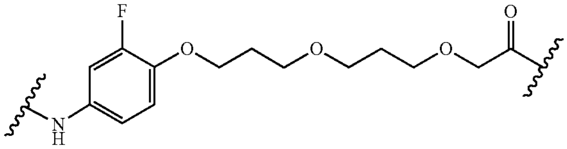
;
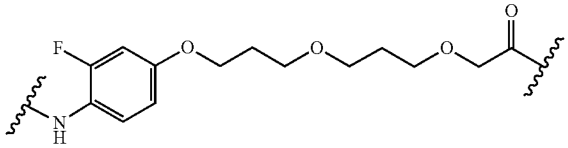
;
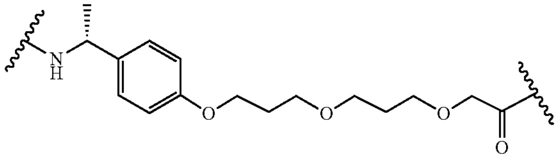
;
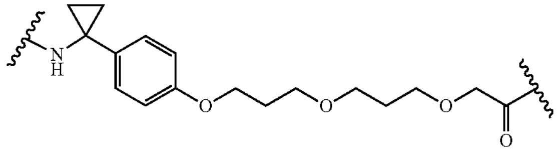
;
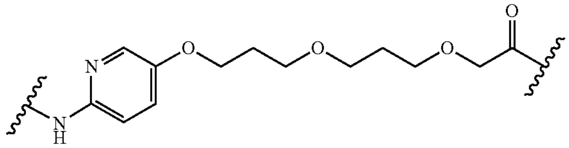
;
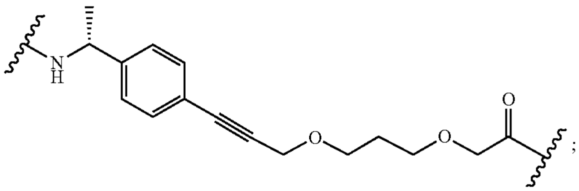
;
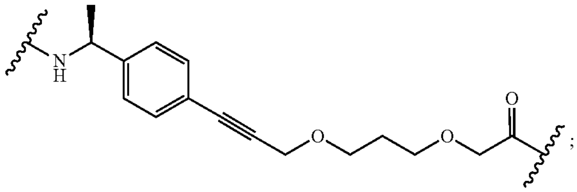
;
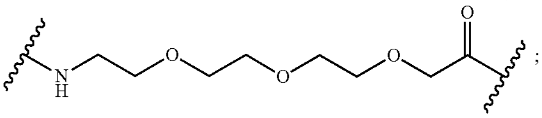
;
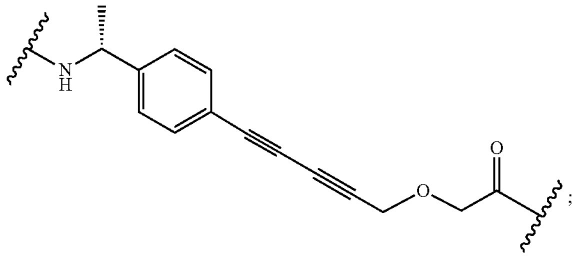
;
-continued
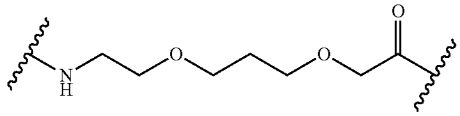
;
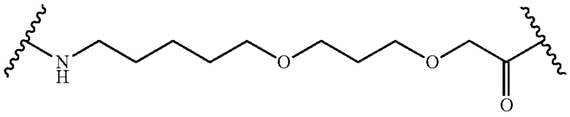
;
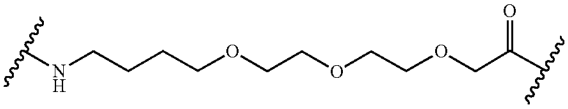
;
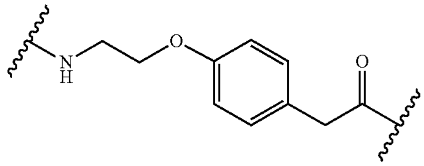
;
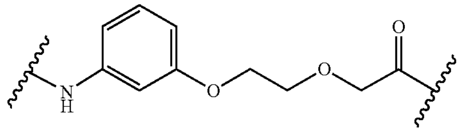
;
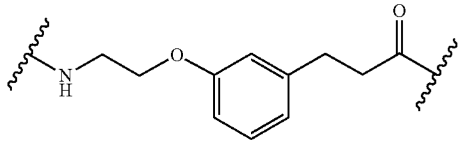
;
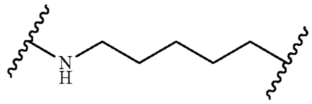
;
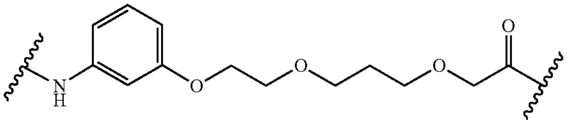
;
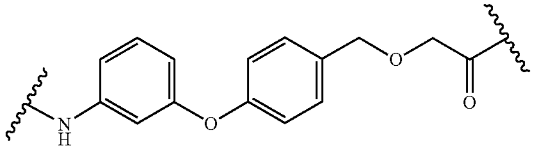
;
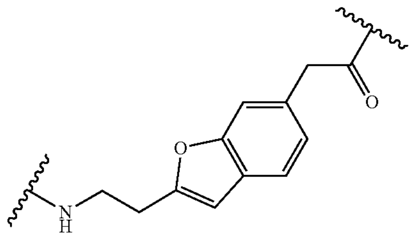
;
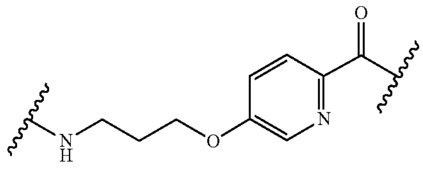
;

-continued
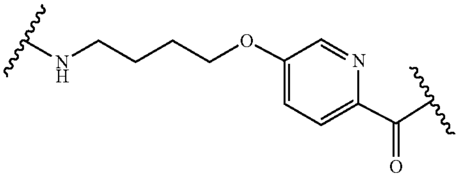
;
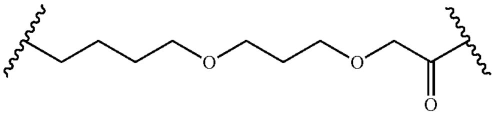
;
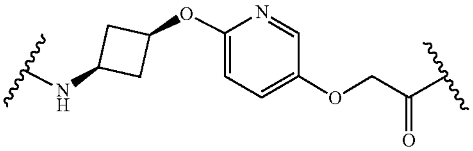
;
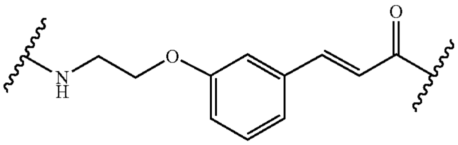
;
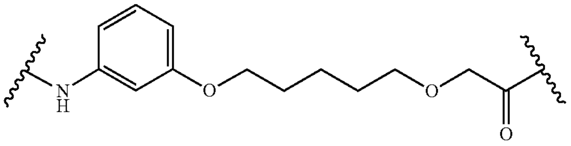
;
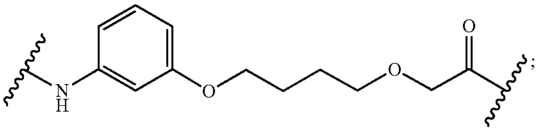
;
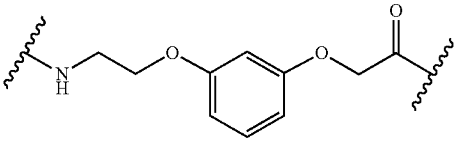
;
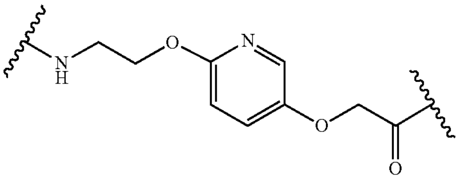
;
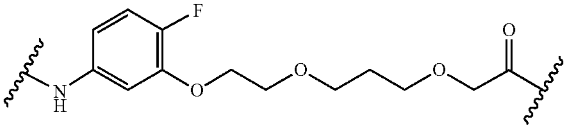
;
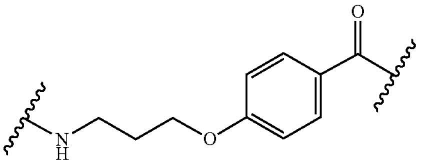
;
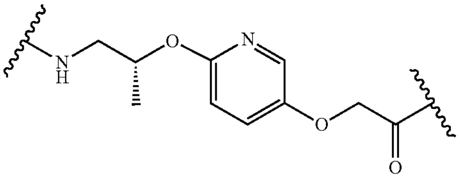
;
-continued
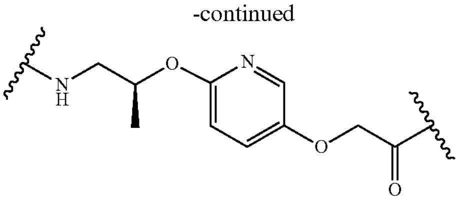
;
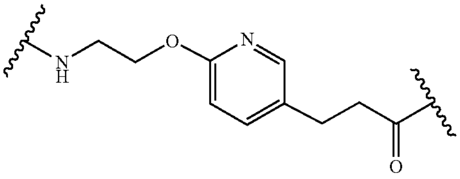
;
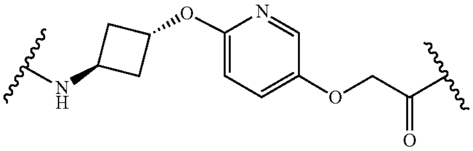
;
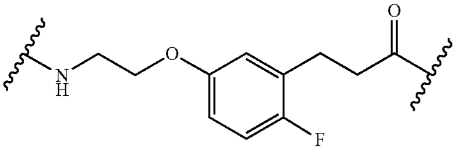
;
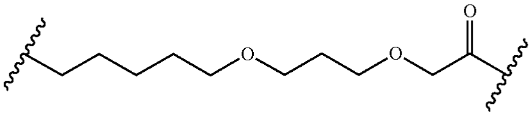
;
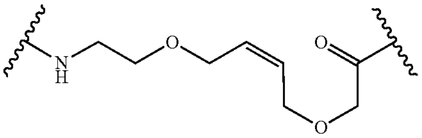
;
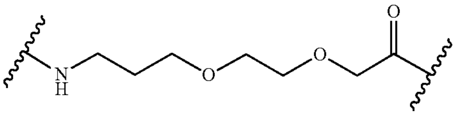
;
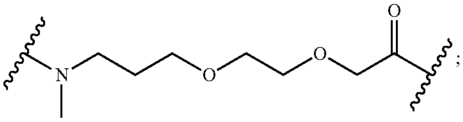
;
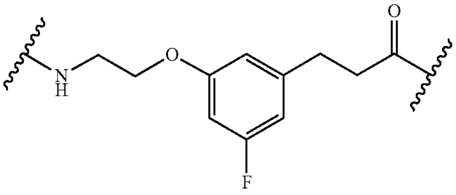
;
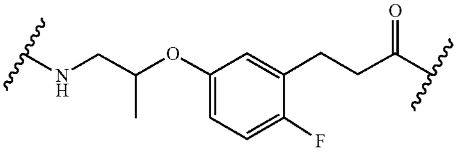
;
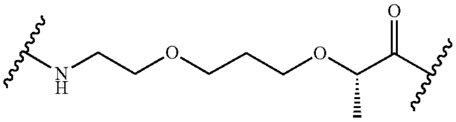
;
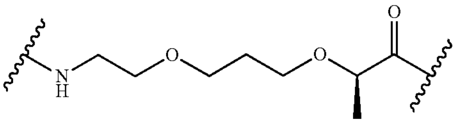
;

-continued
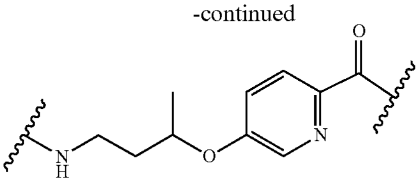
;
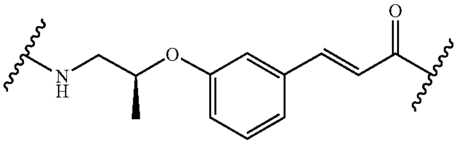
;
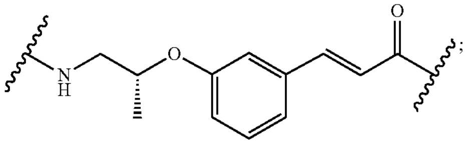
;
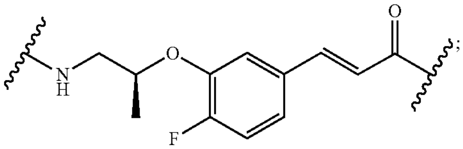
;
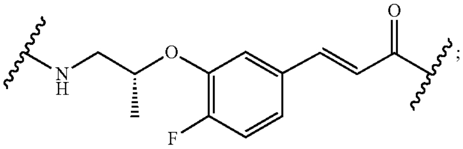
;
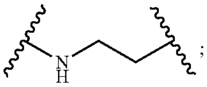
;
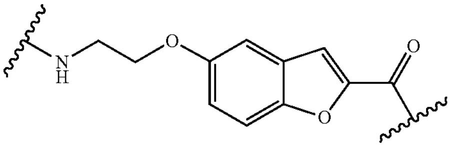
;
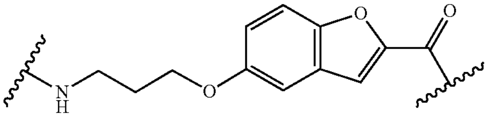
;
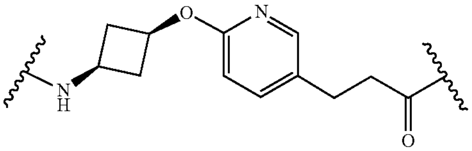
;
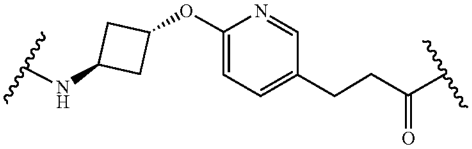
;
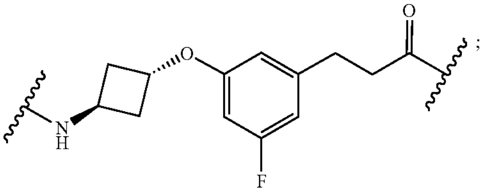
;
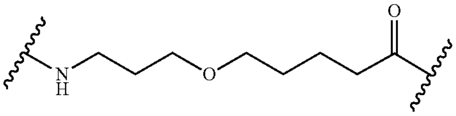
;
-continued
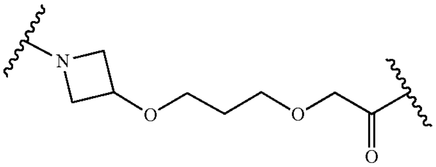
;
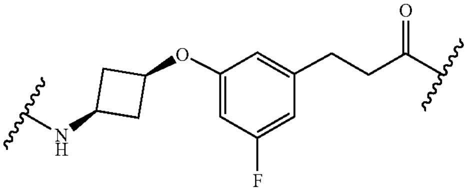
;
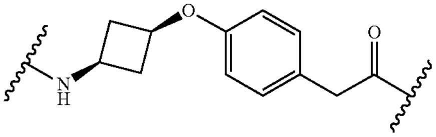
;
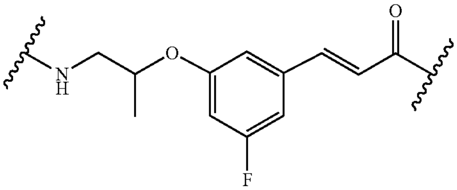
;
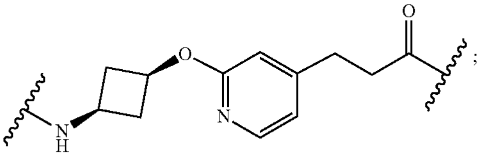
;
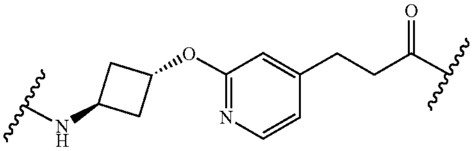
;
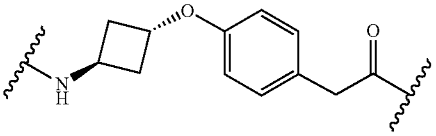
;
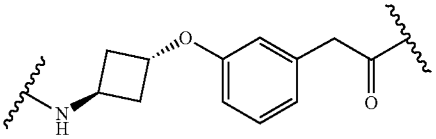
;
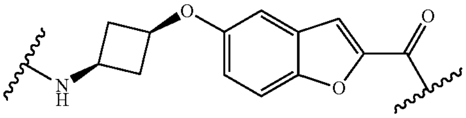
;
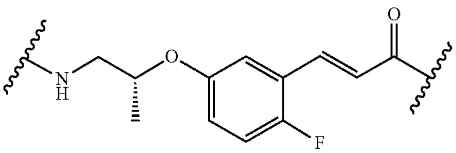
;
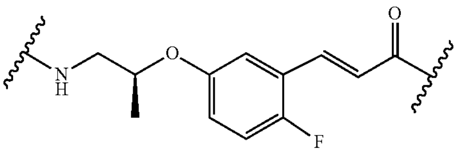
;

-continued
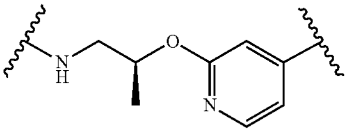
;
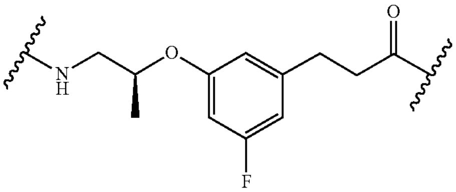
;
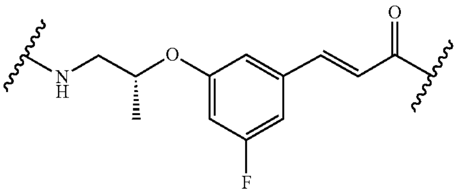
;
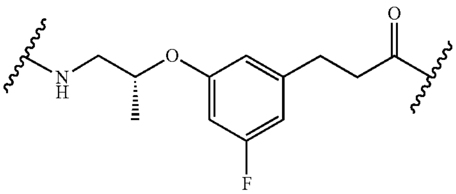
;
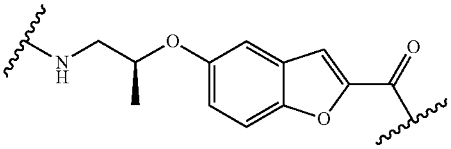
;
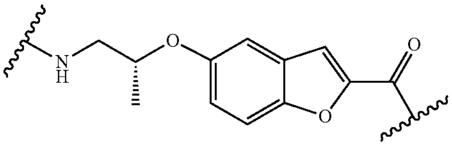
;
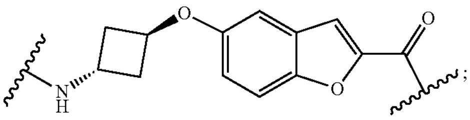
;
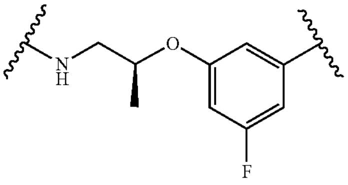
;
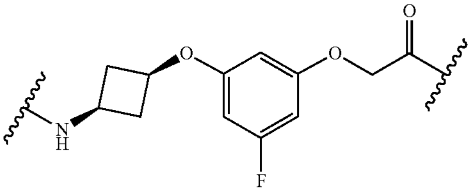
;
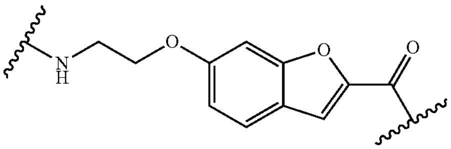
;
-continued
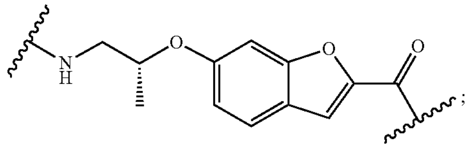
;
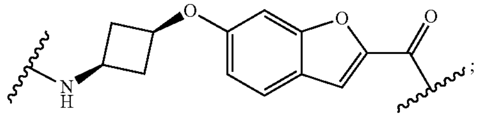
;
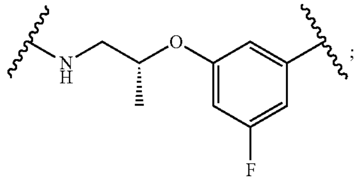
;
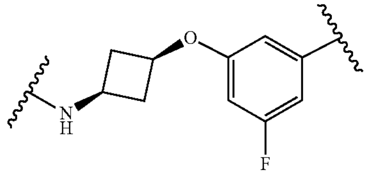
;
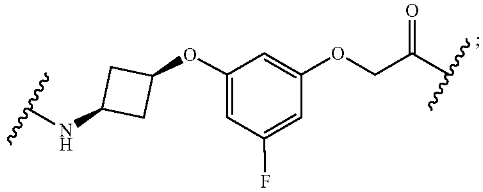
;
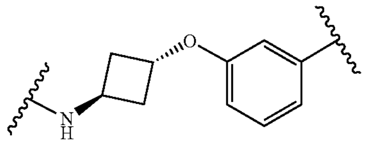
;
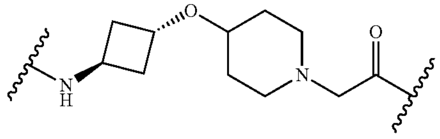
;
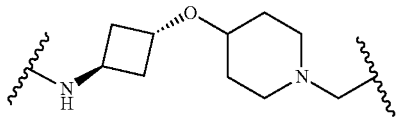
and
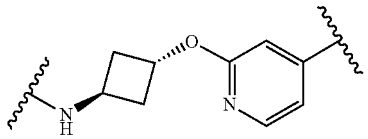
,
wherein each occurrence of m and n is independently selected from the group consisting of 0, 1, 2, 3, 4, 5, and 6.
In any aspect or embodiment described herein, the linker (L) is selected from the group consisting of:
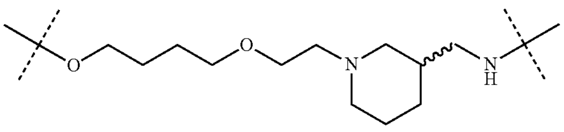
;

-continued
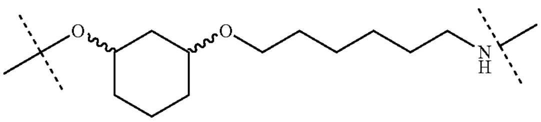
;
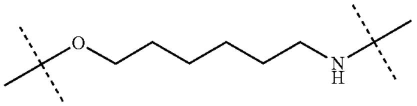
;
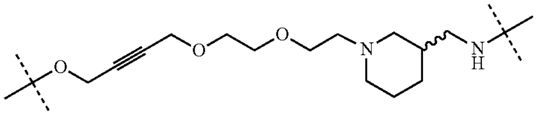
;
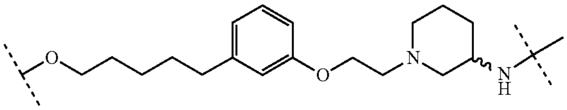
;
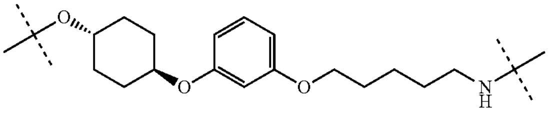
;
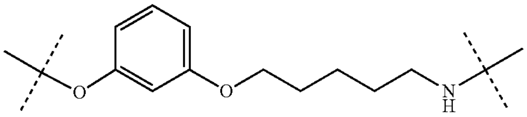
;
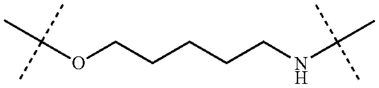
;
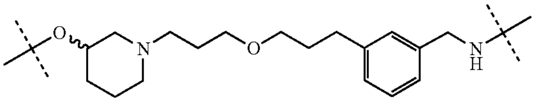
;
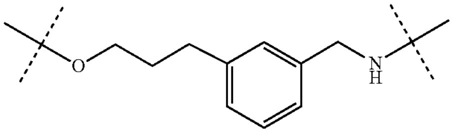
;
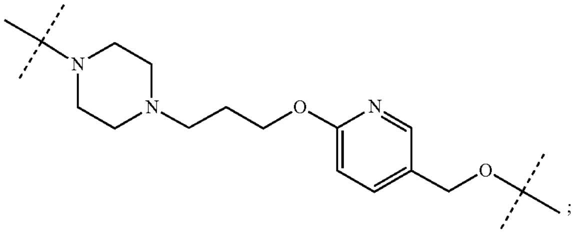
;
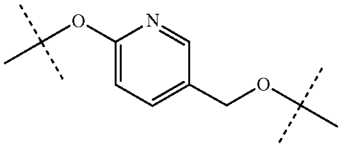
;
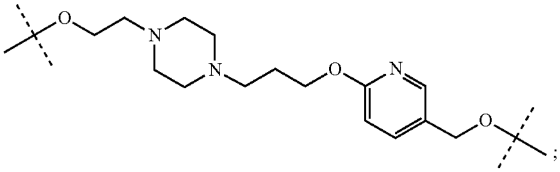
;
-continued
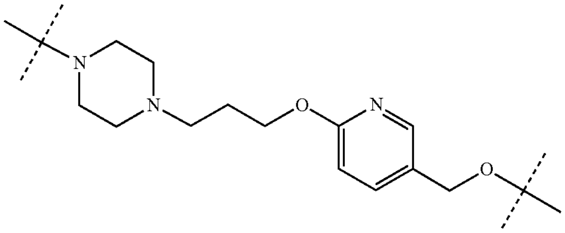
;
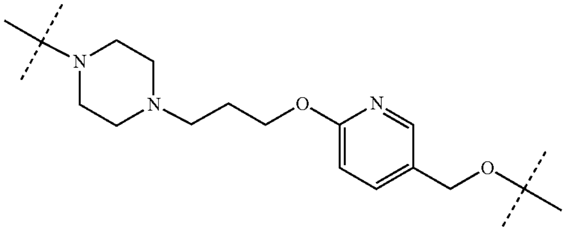
;
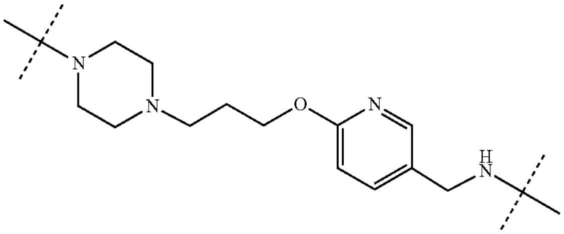
;
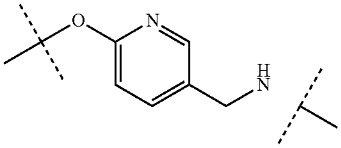
;
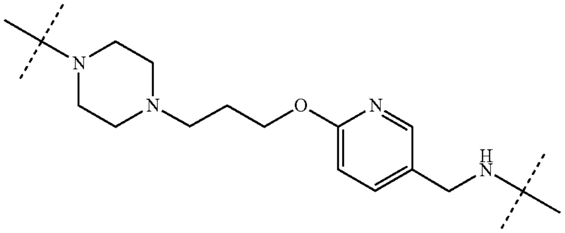
;
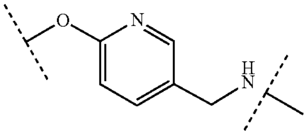
;
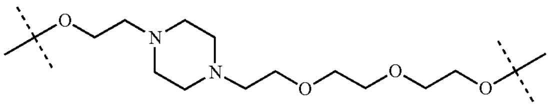
;
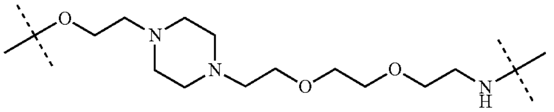
;
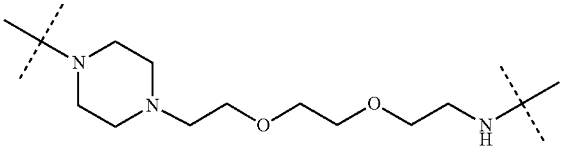
;
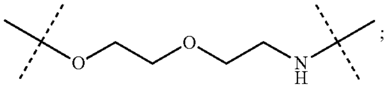
;

-continued
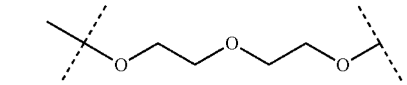
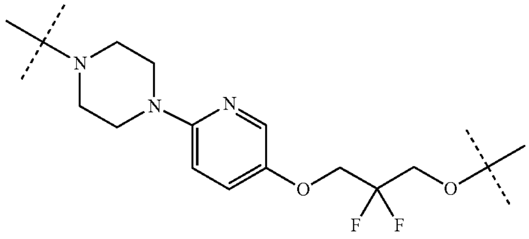
;
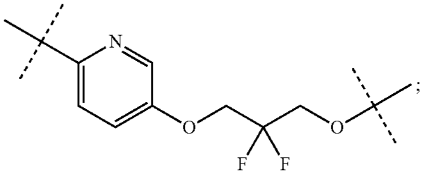
;
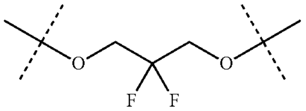
;
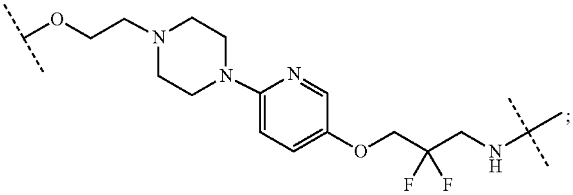
;
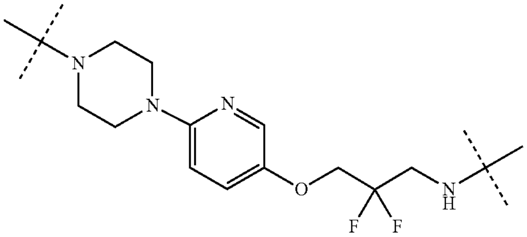
;
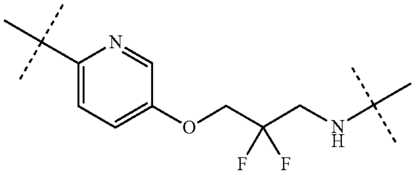
;
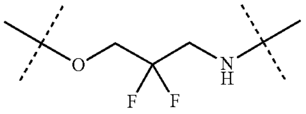
;
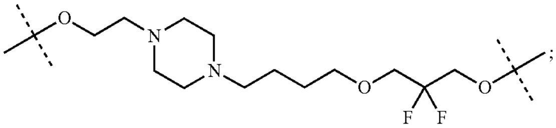
;
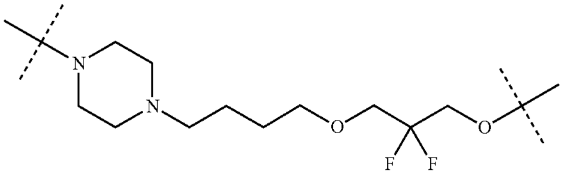
;
-continued
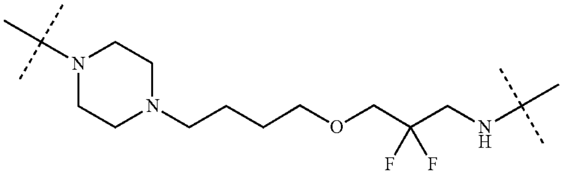
;
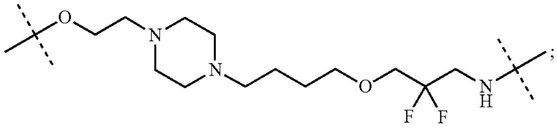
;
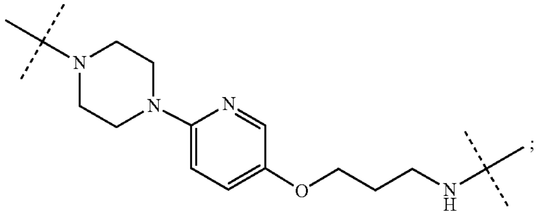
;
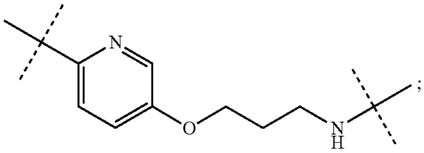
;
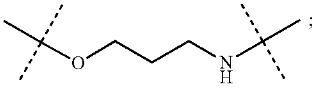
;
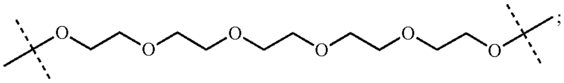
;
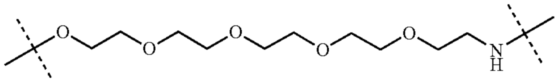
;
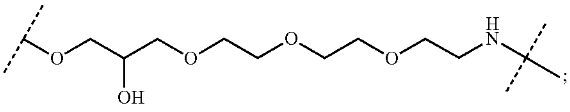
;
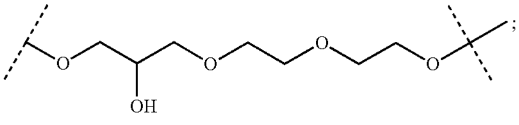
;
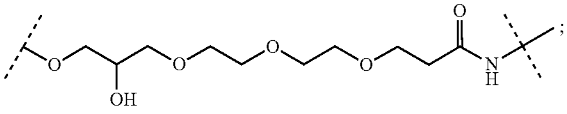
;
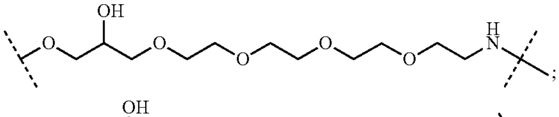
;
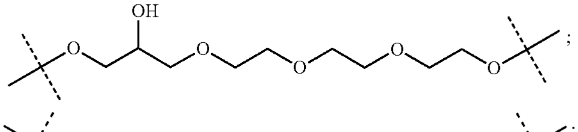
;
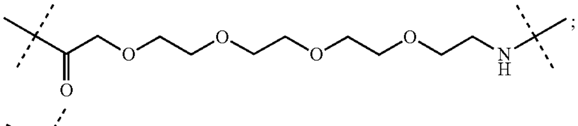
;
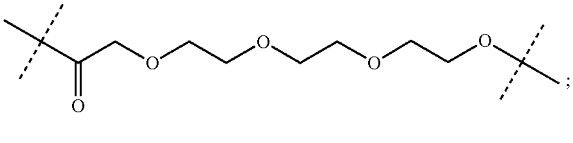
;

-continued
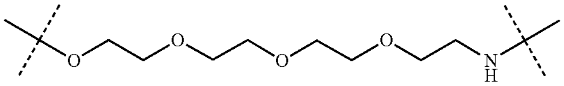
;
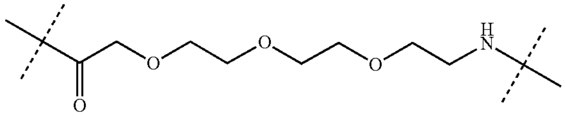
;
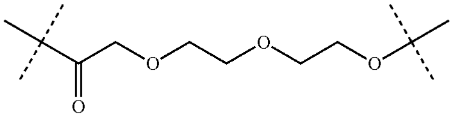
;
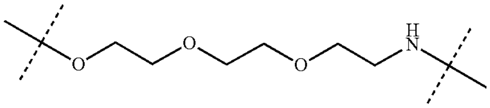
;
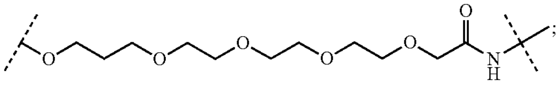
;
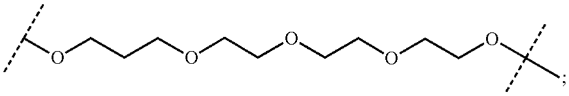
;
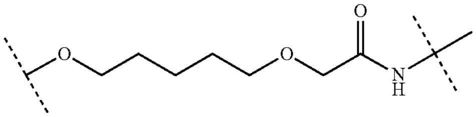
;
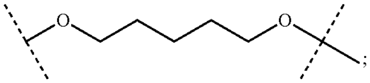
;
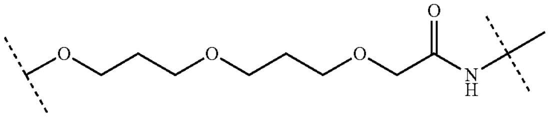
;
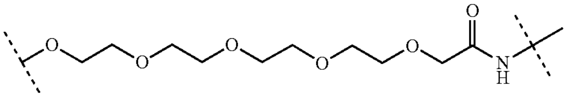
;
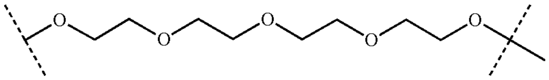
;
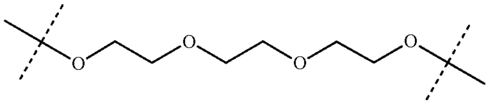
;
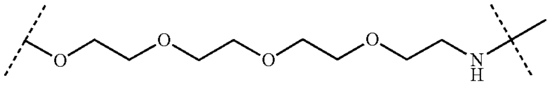
;
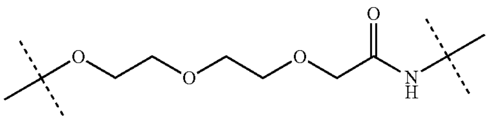
;
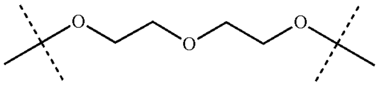
;
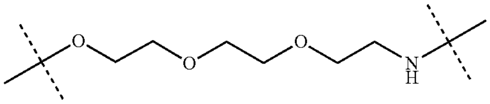
;
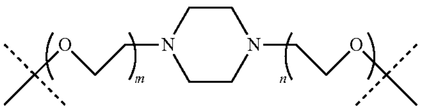
-continued
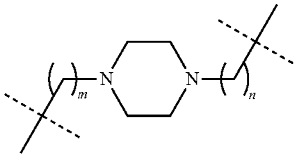
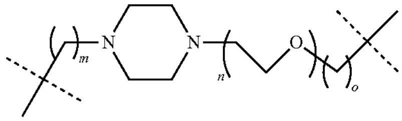
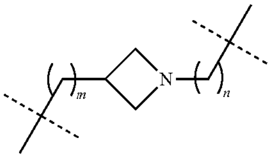
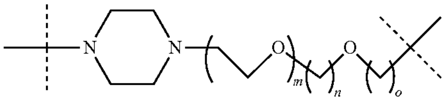
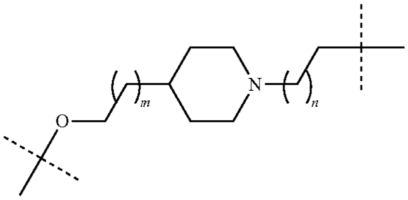
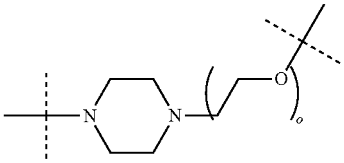
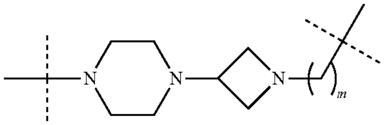
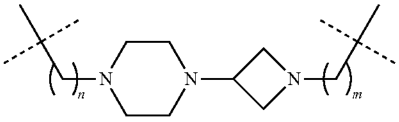
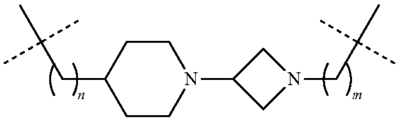
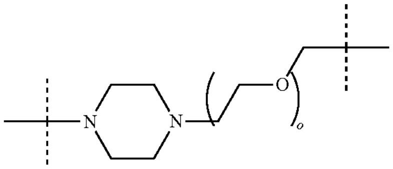
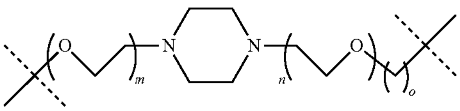
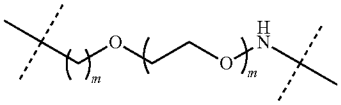

-continued
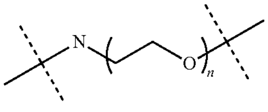
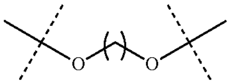
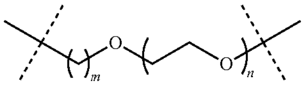
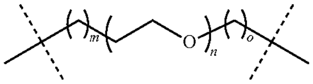
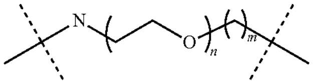
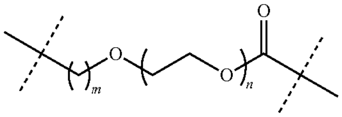
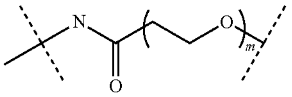
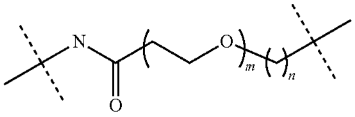
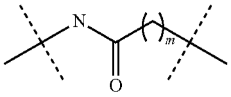
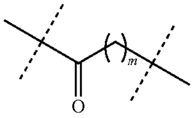
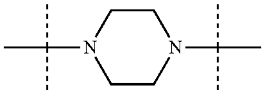
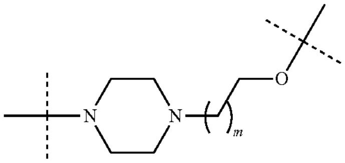
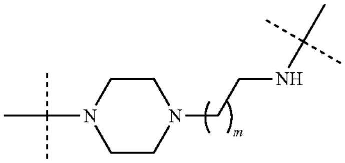
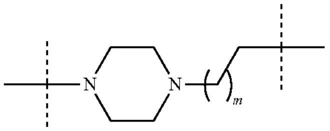
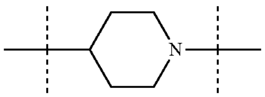
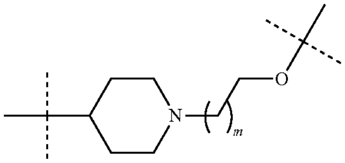
-continued
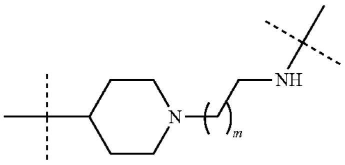
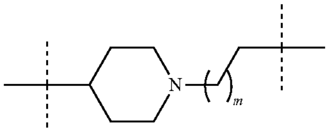
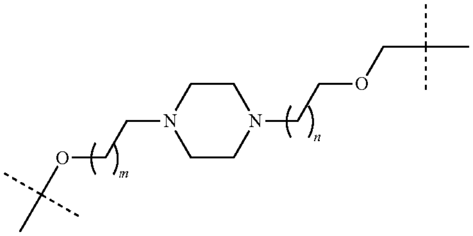
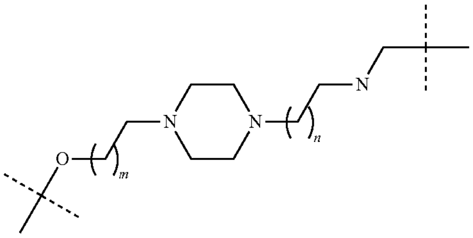
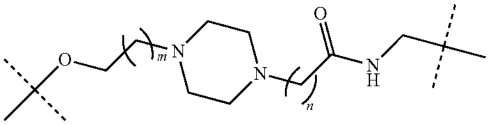
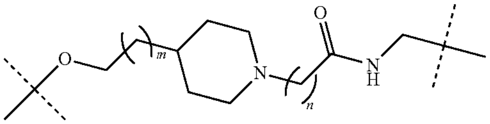
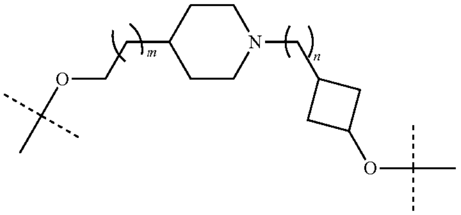
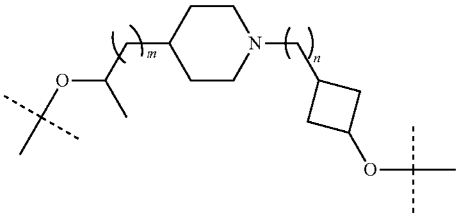
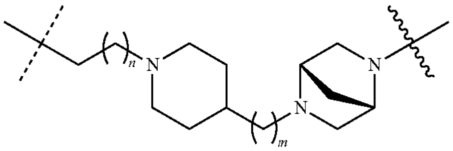

-continued
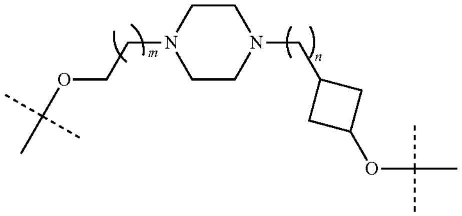
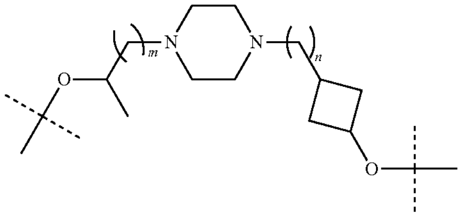
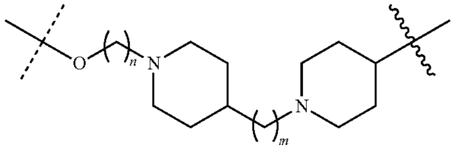
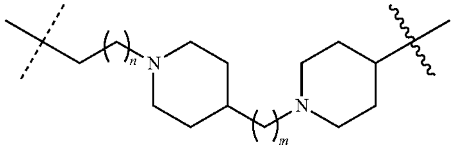
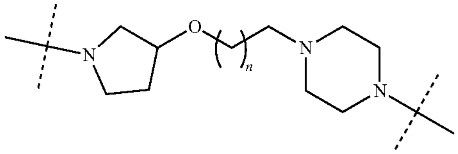
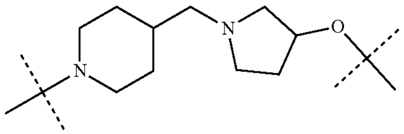
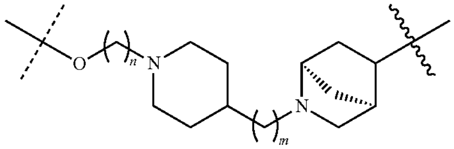
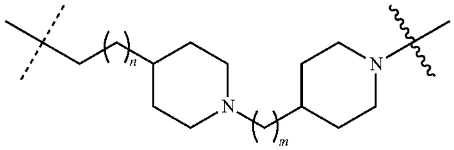
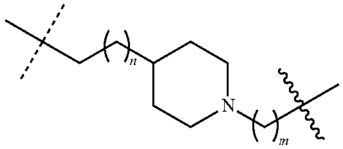
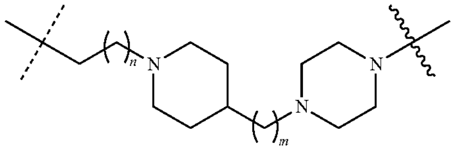
-continued
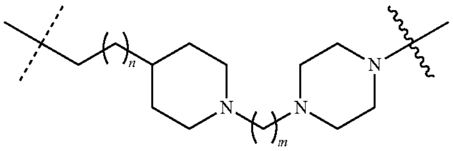
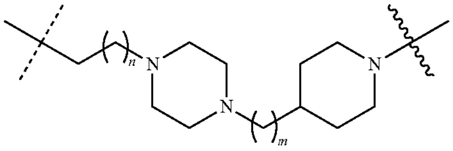
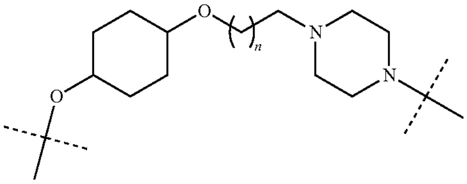
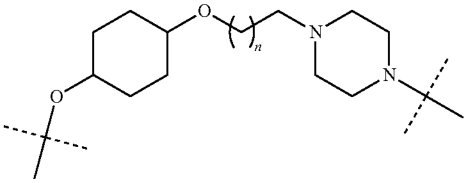
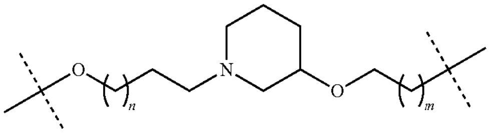
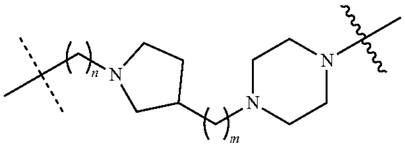
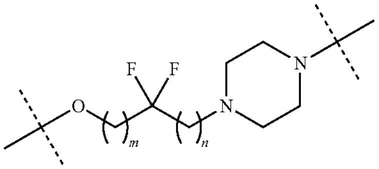
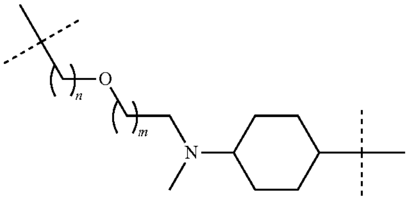
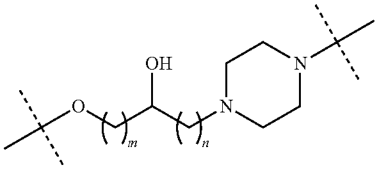
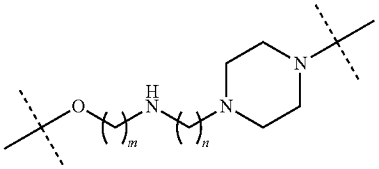

-continued
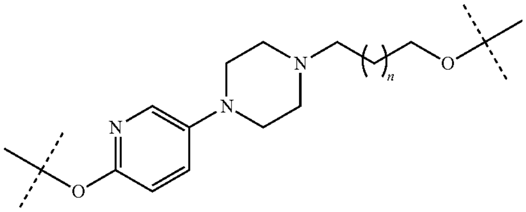
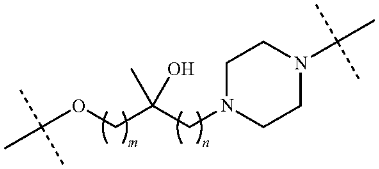
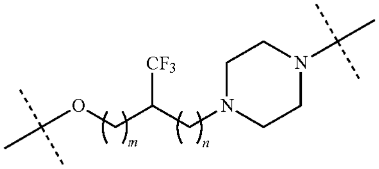
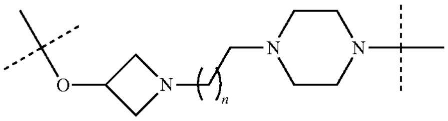
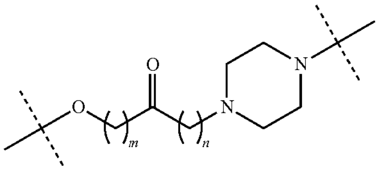
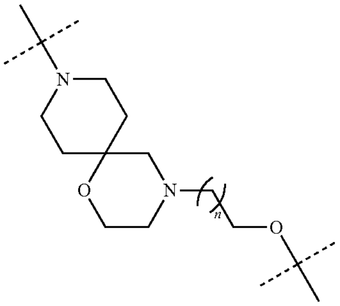
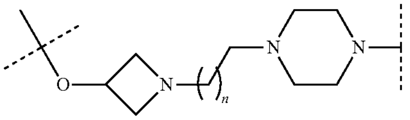
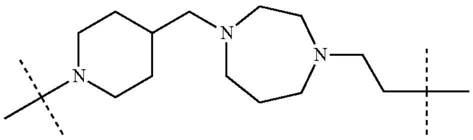
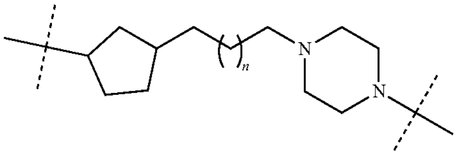
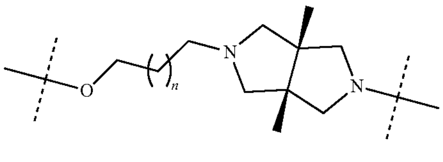
-continued
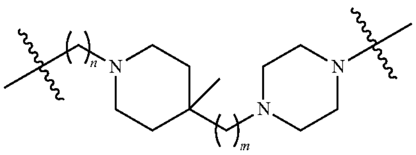
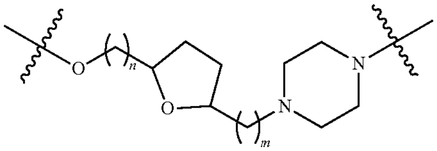
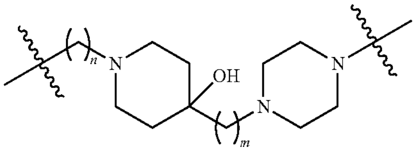
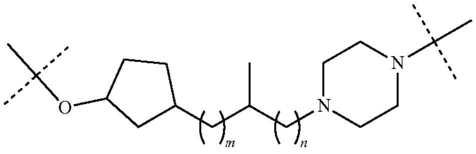
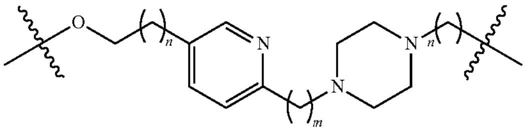
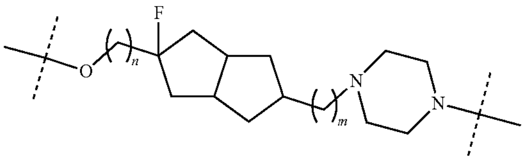
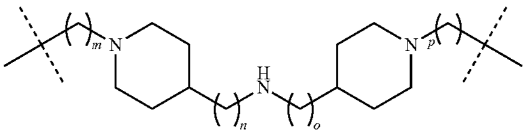
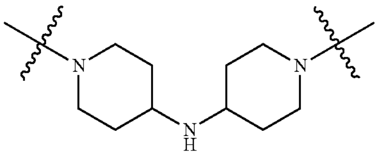
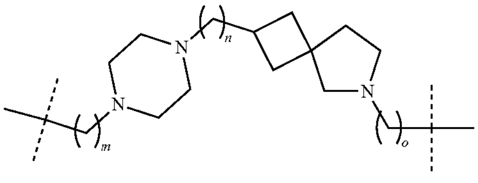
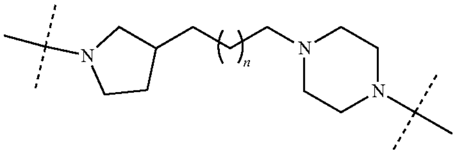
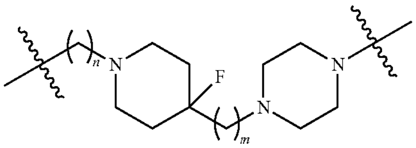

-continued
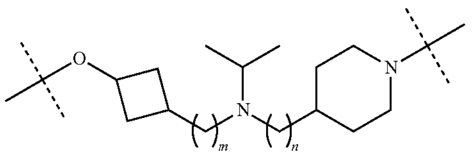
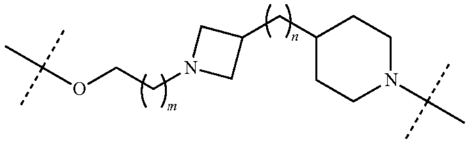
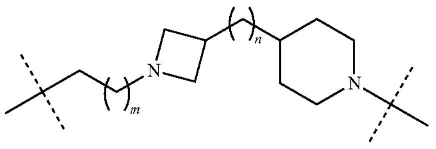
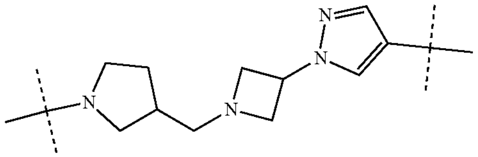
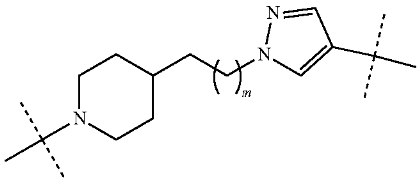
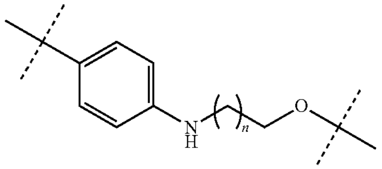
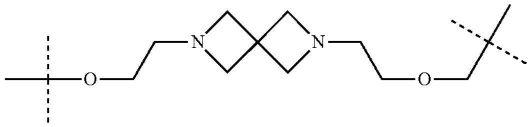
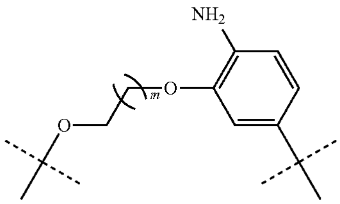
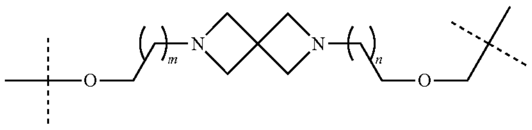
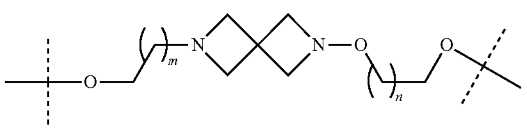
-continued
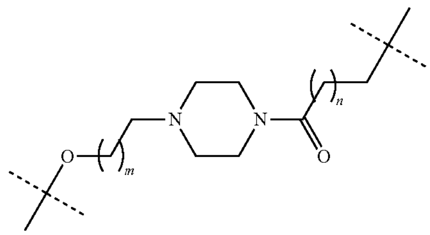
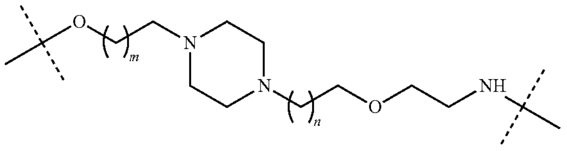
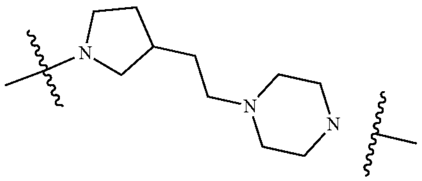
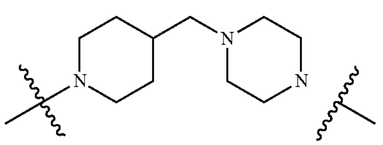
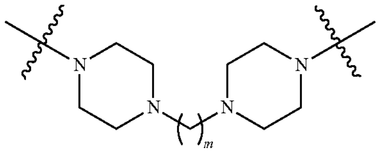
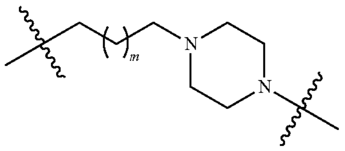
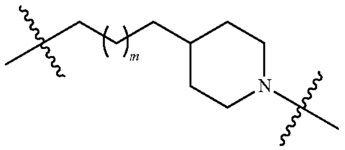
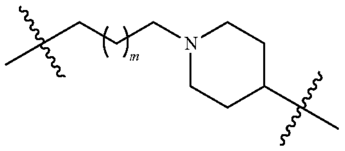
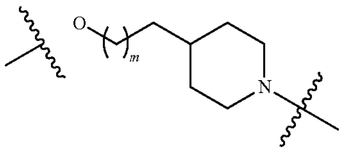
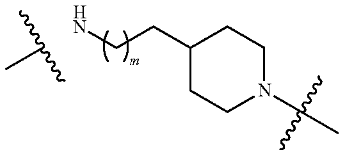

-continued
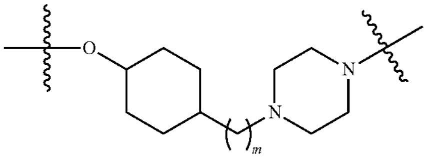
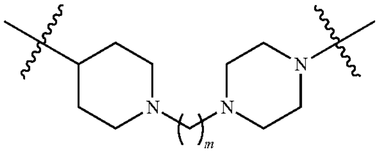
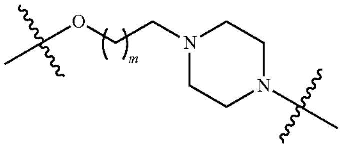
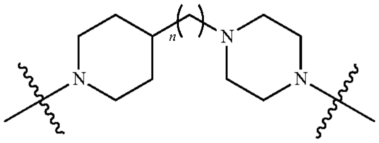
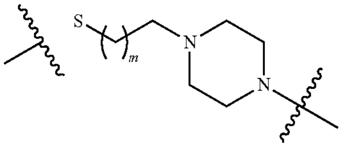
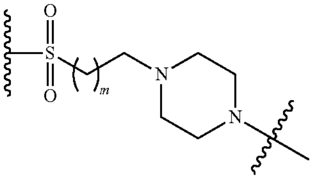
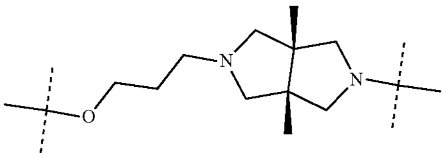
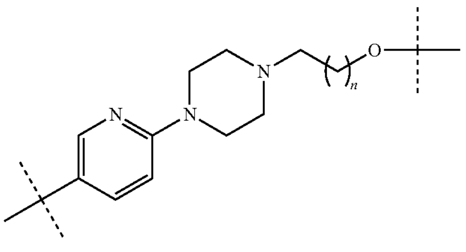
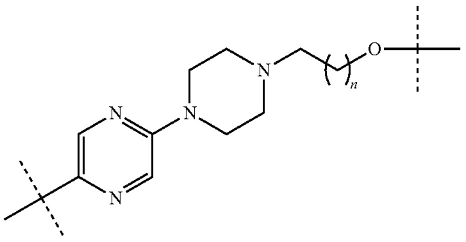
-continued
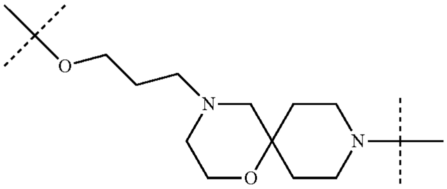
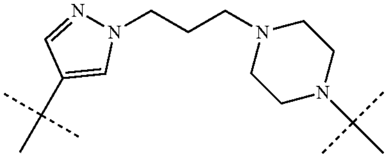
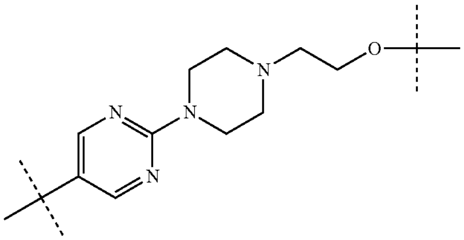
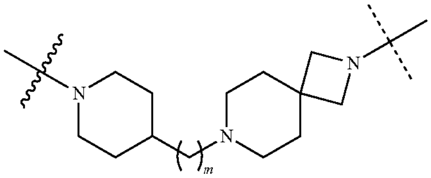
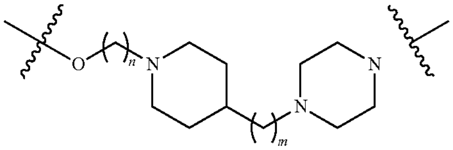
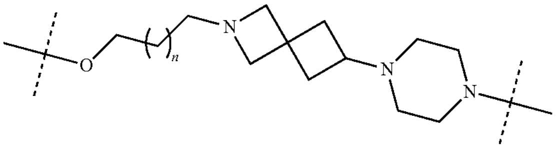
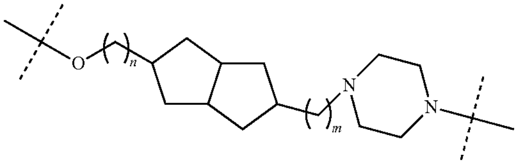
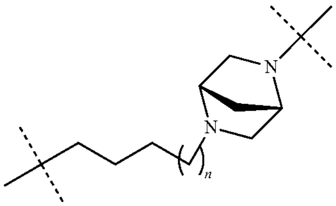
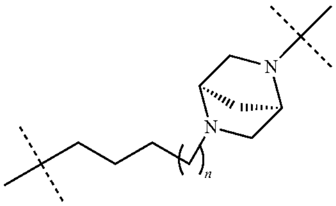

-continued
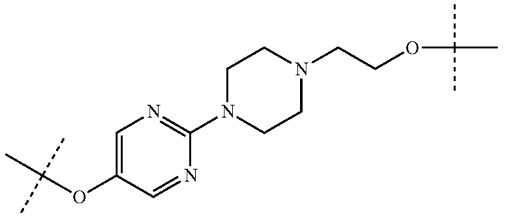
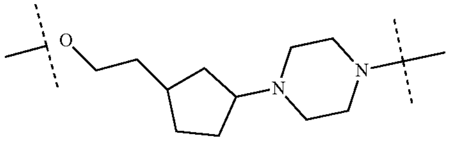
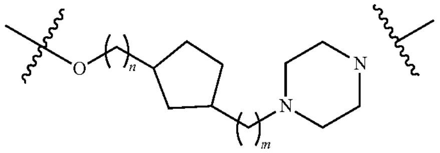
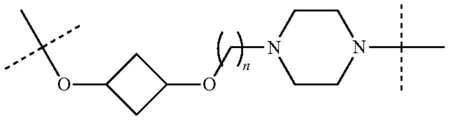
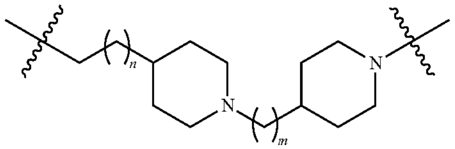
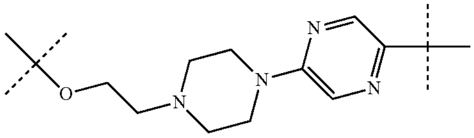
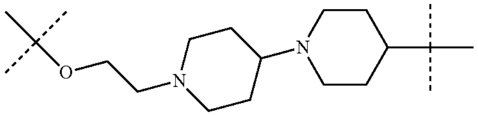
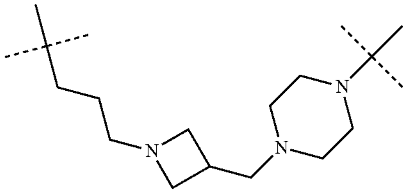
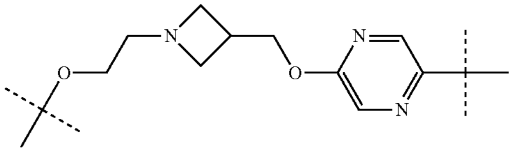
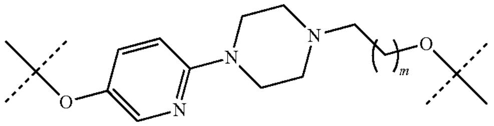
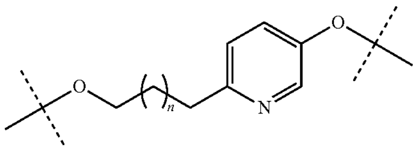
-continued
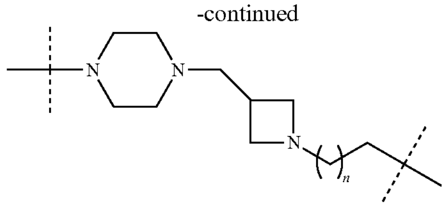
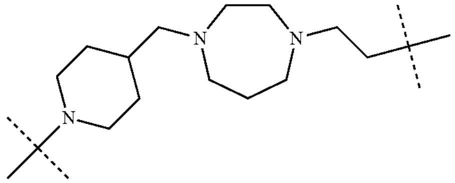
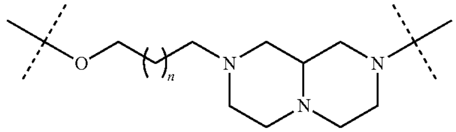
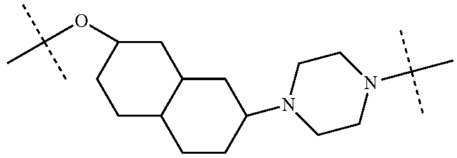
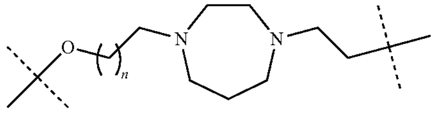
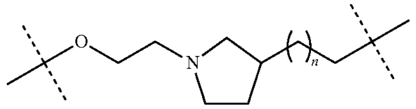
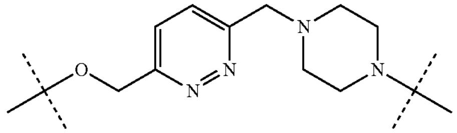
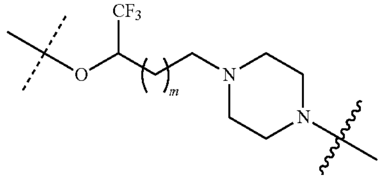
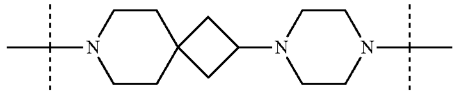
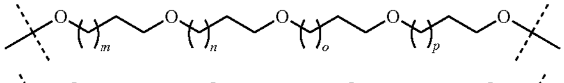
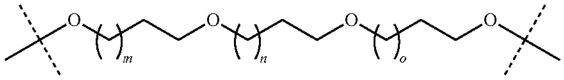
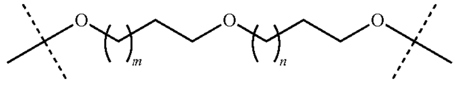
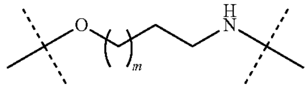
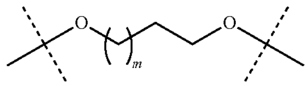

-continued
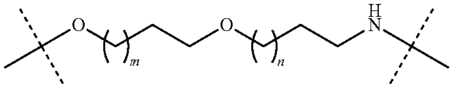
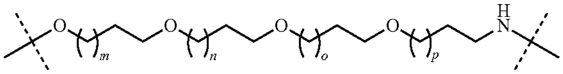
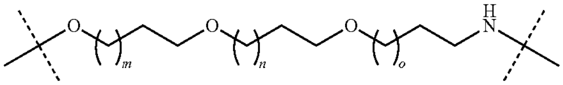
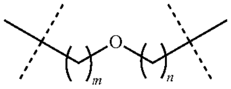
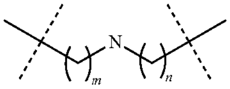
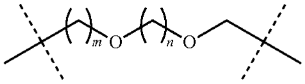
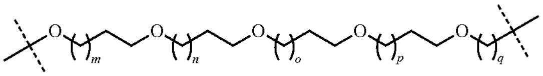
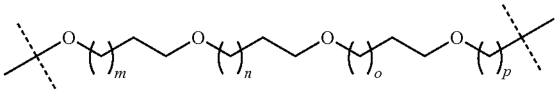
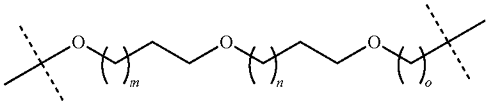
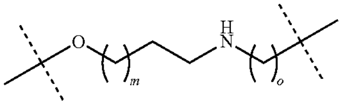
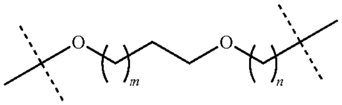
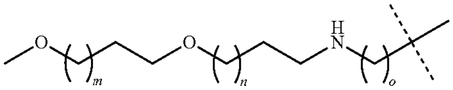
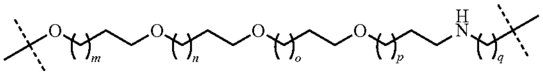
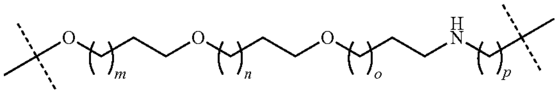
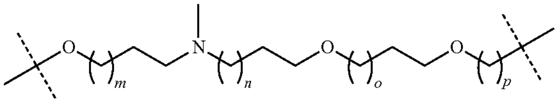
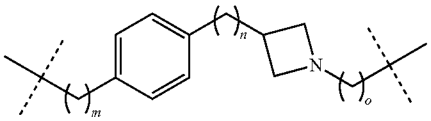
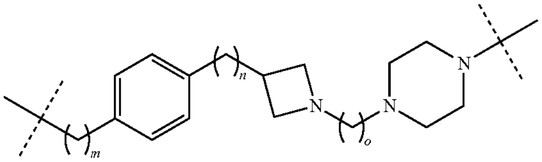
-continued
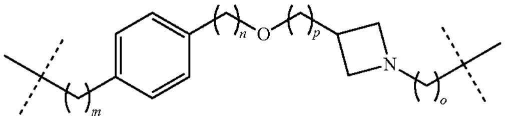
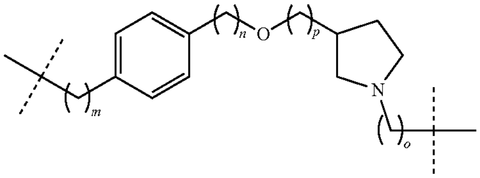
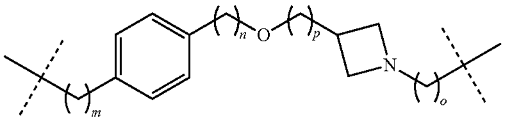
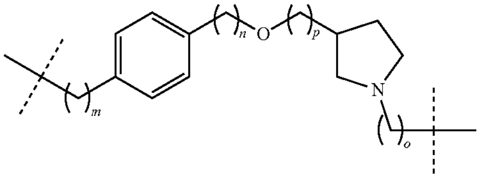
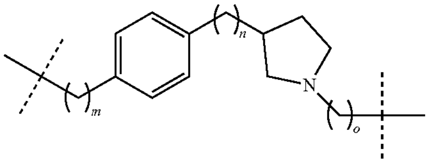
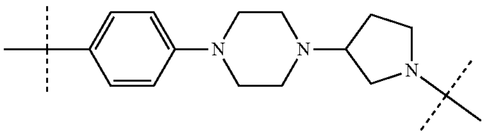
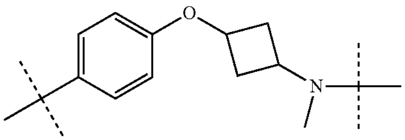
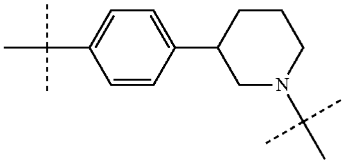
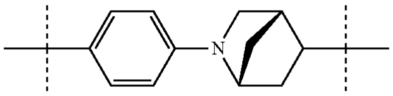
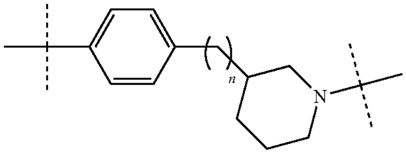
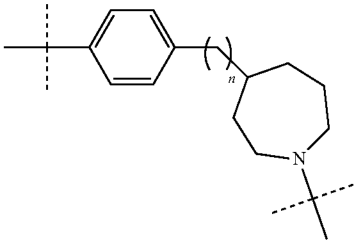

-continued
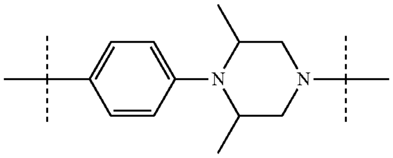
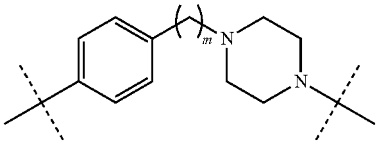
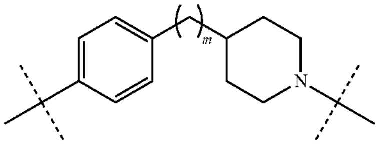
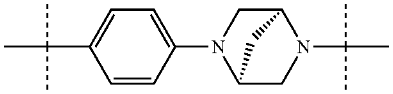
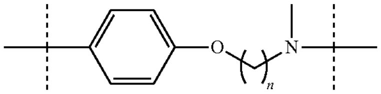
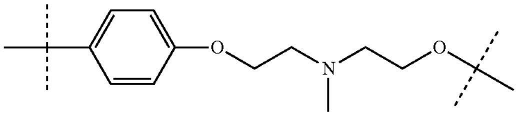
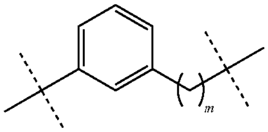
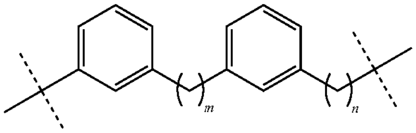
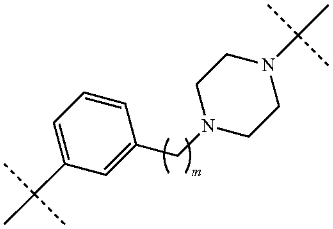
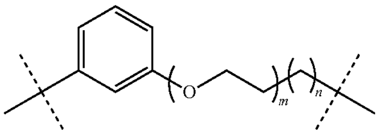
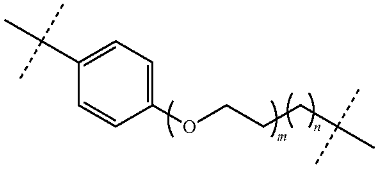
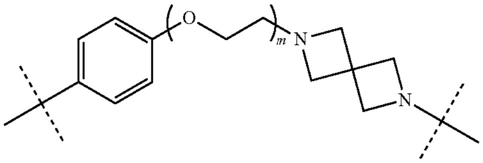
-continued
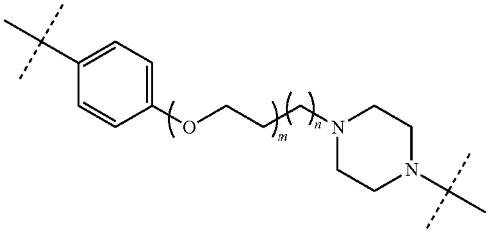
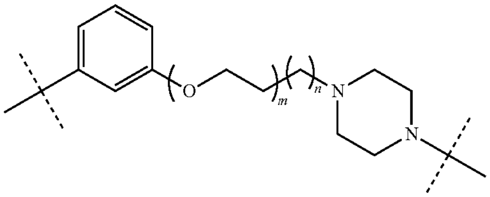
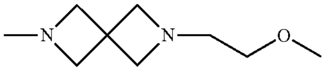
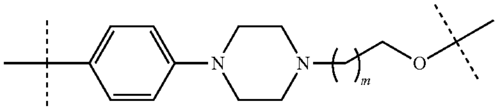
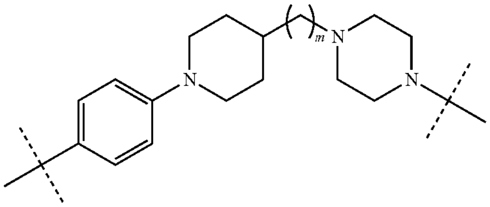
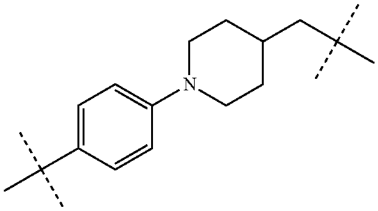
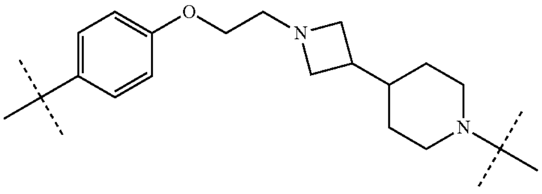
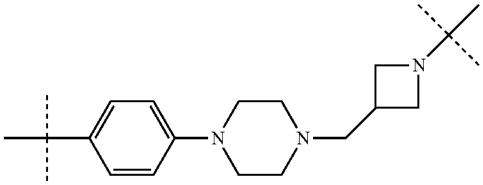
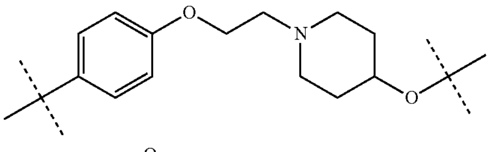
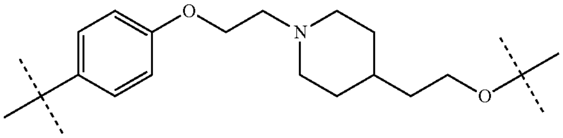

-continued
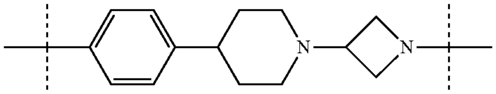
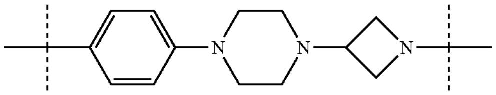
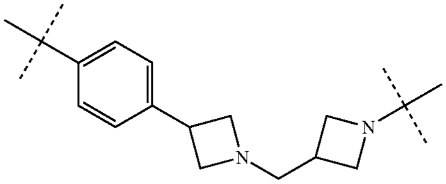
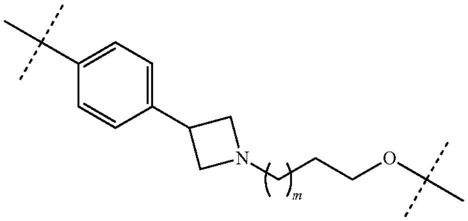
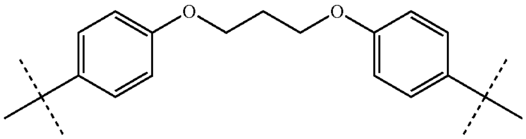
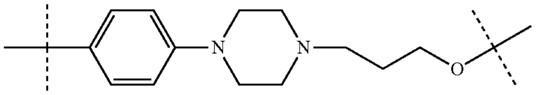
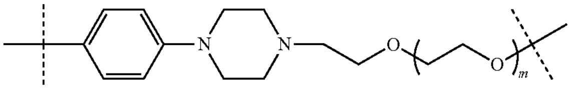
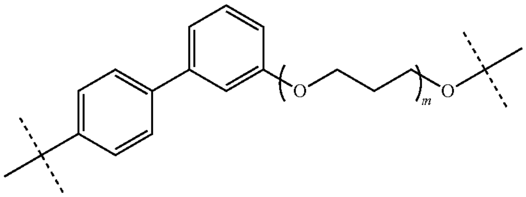
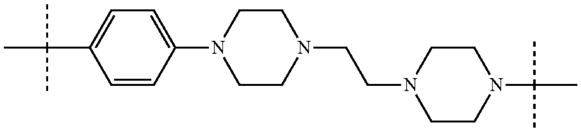
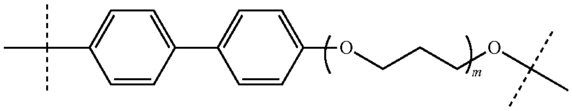
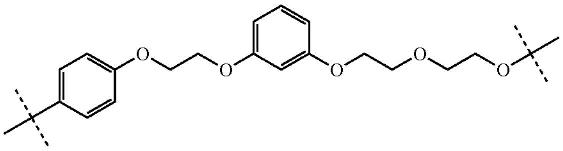
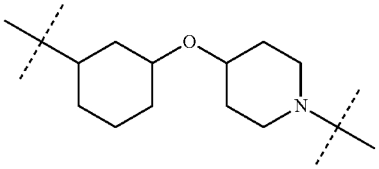
-continued
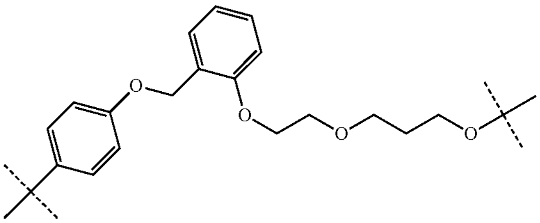
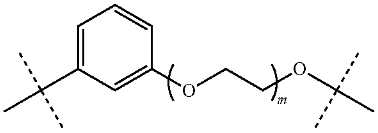
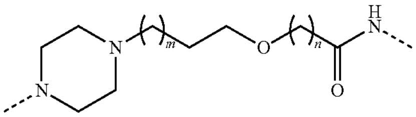
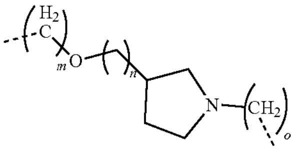
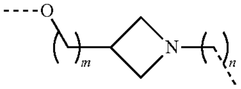
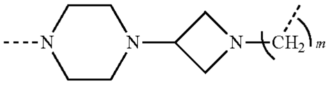
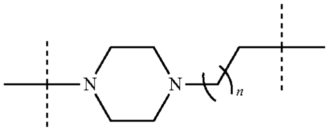
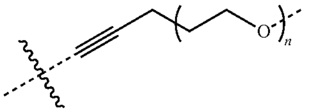
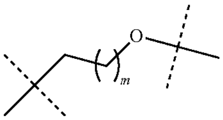
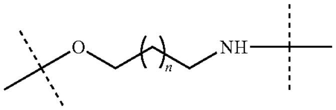
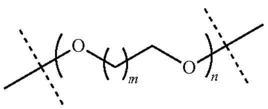
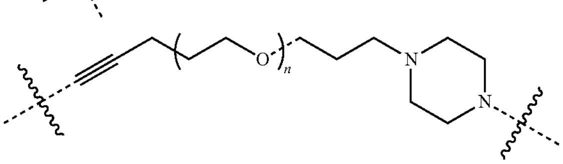
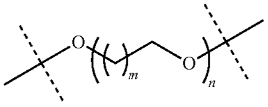

-continued
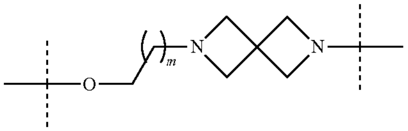
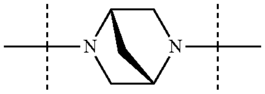
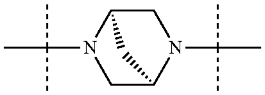
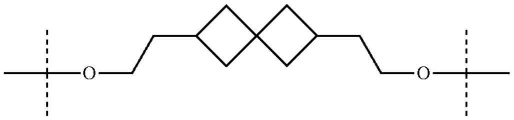
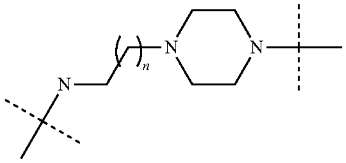
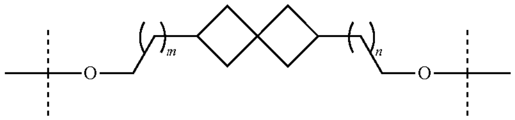
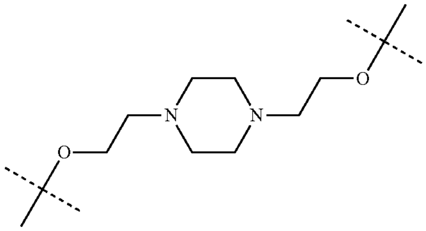
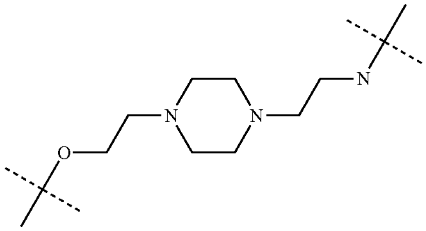
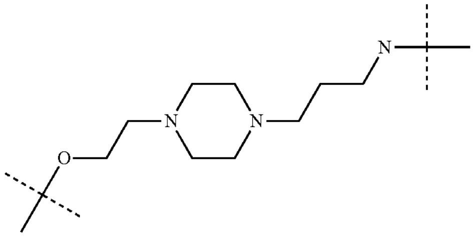
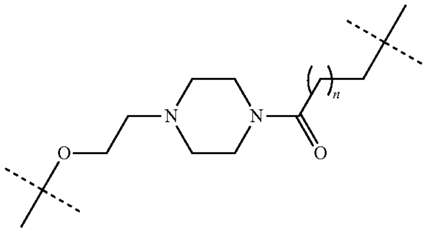
-continued
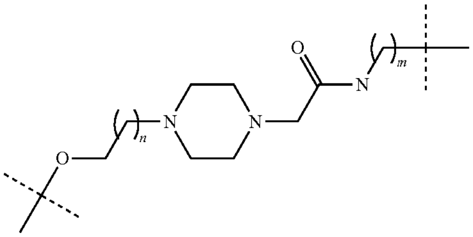
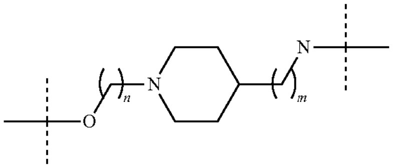
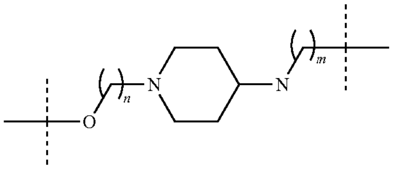
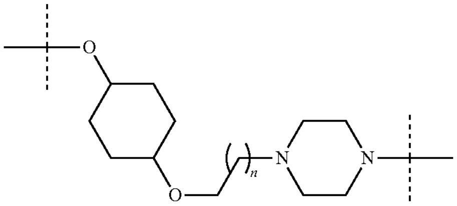
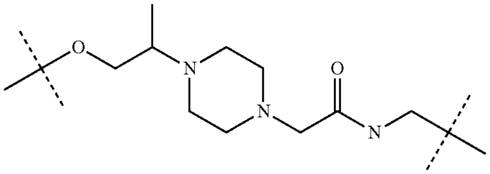
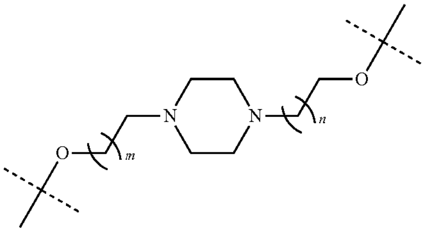
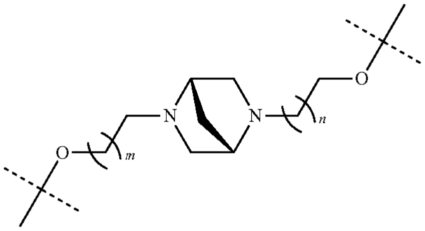
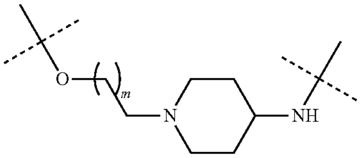

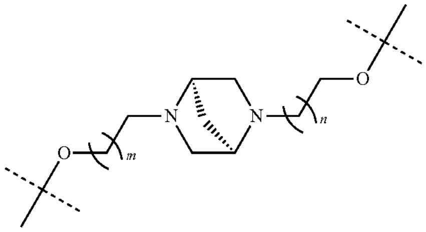
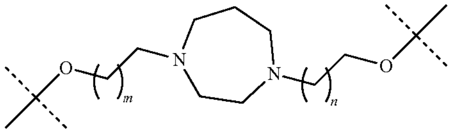
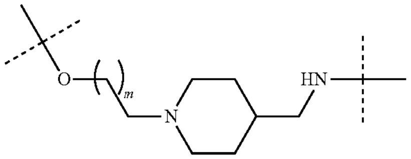
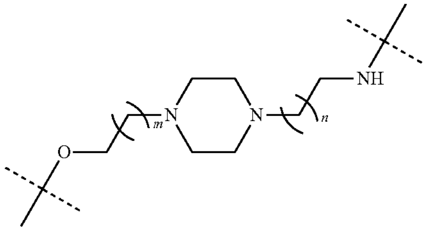
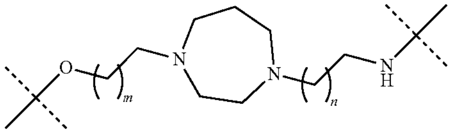
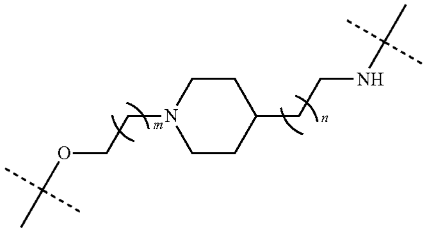
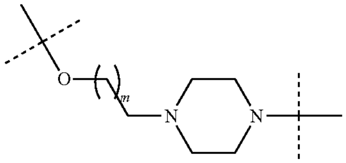
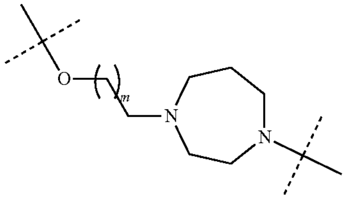
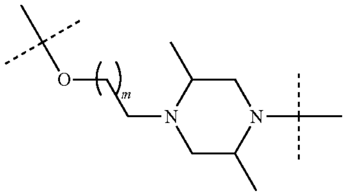
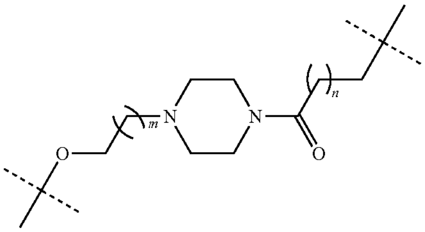
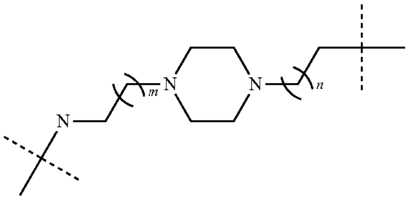
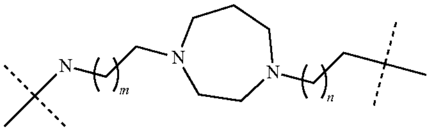
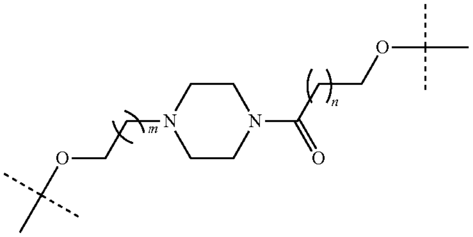
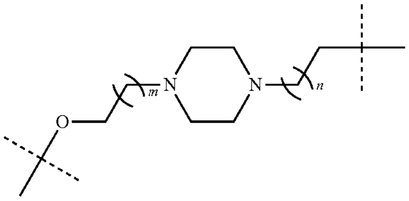
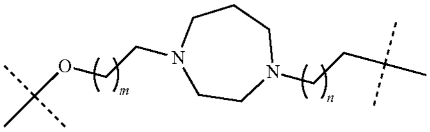
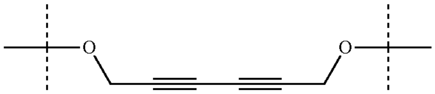
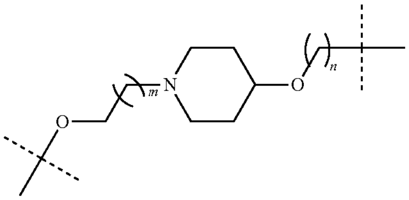
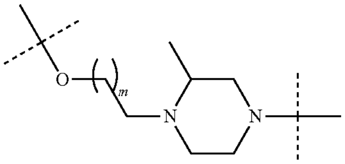

-continued
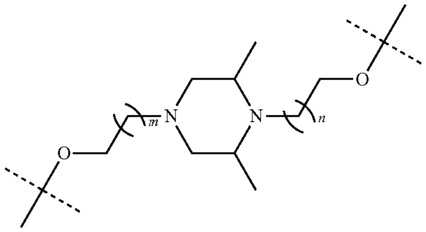
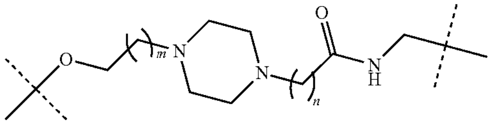
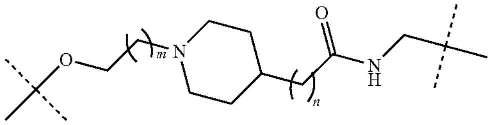
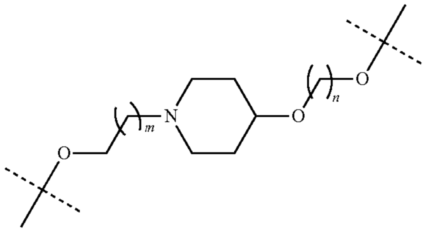
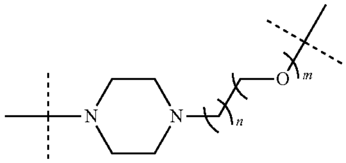
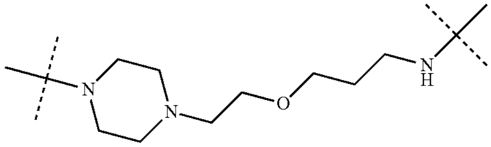
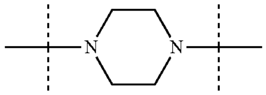
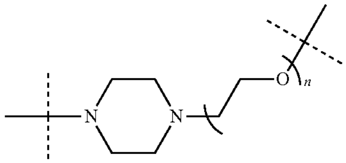
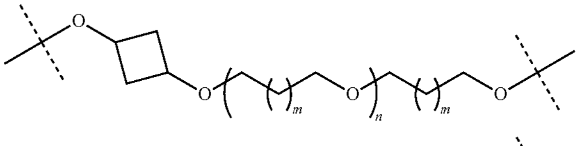
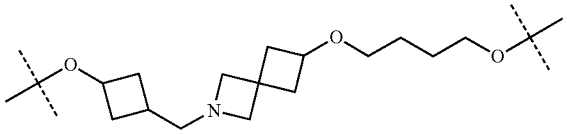
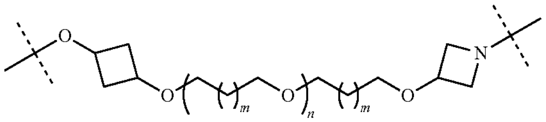
-continued
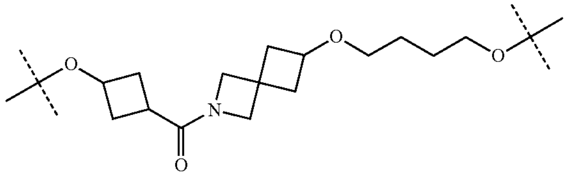
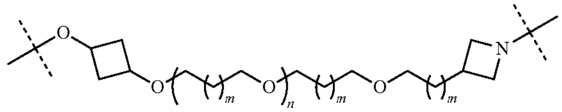
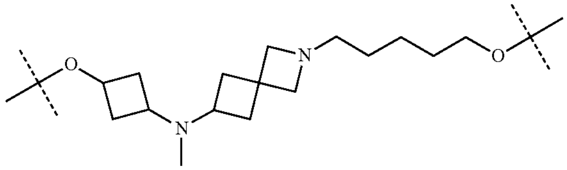
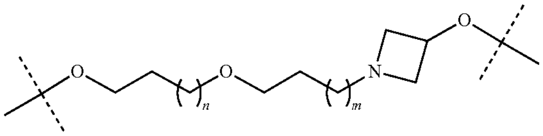
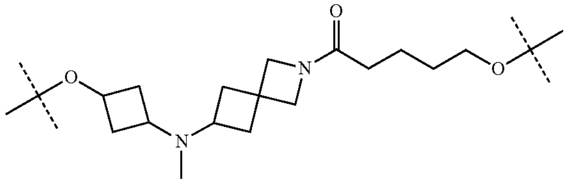
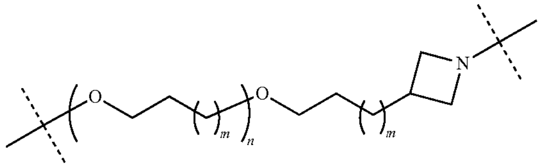
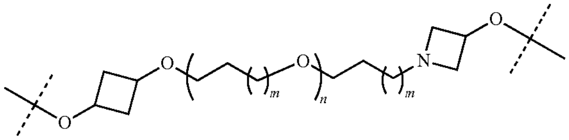
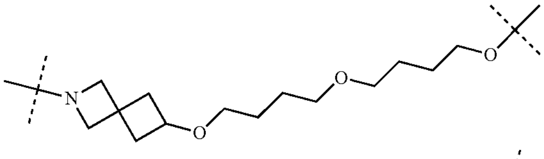
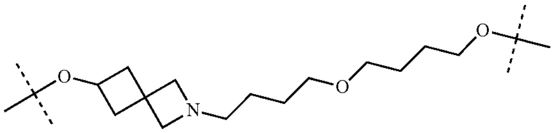
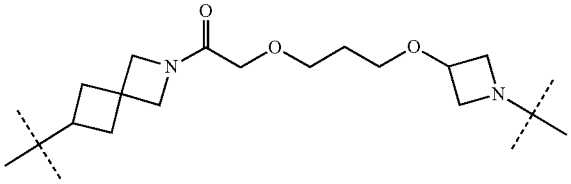
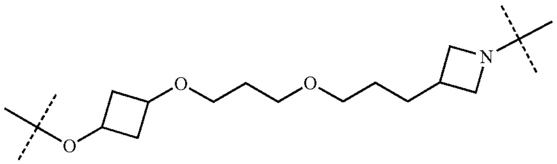

-continued
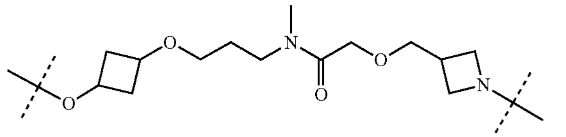
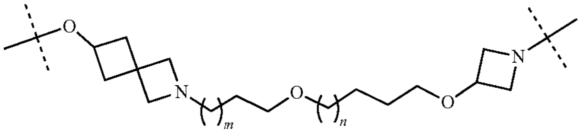
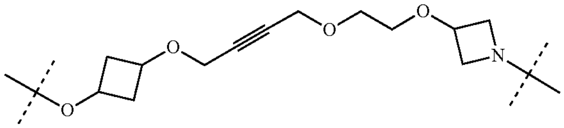
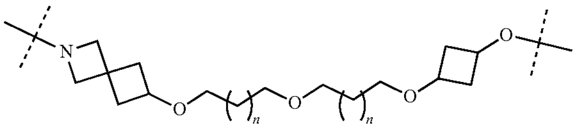
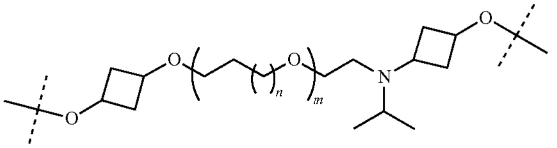
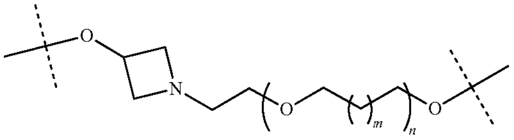
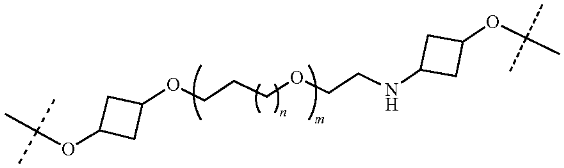
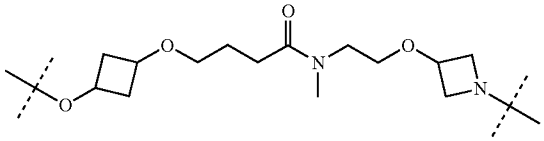
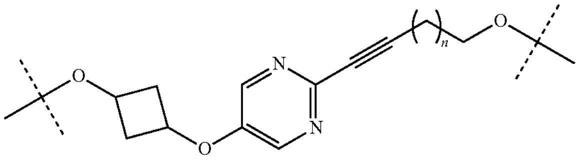
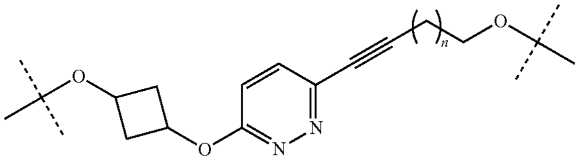
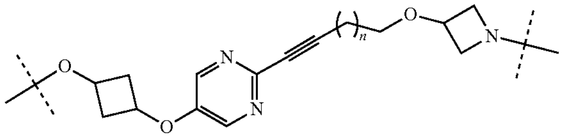
-continued
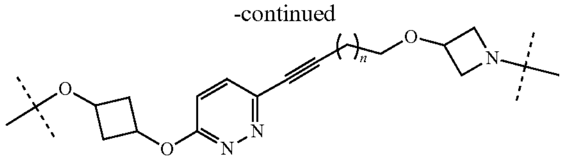
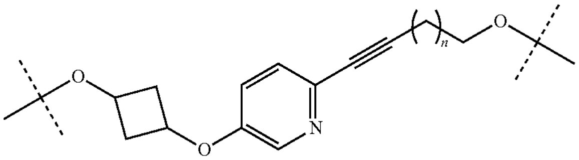
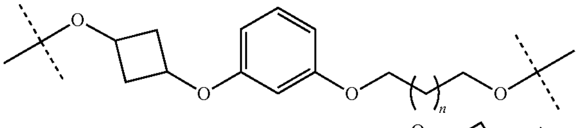
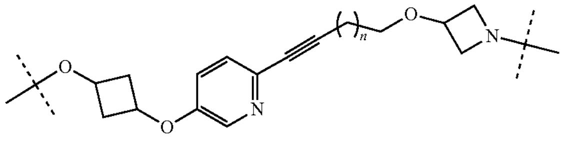
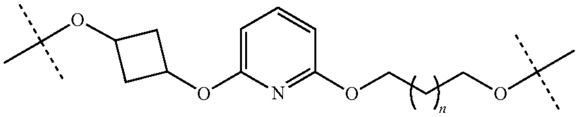
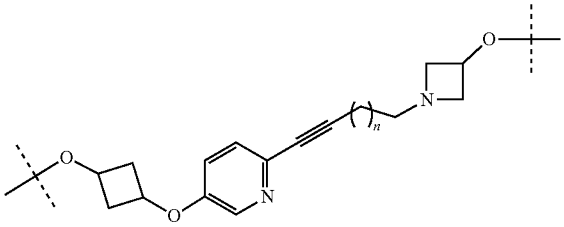
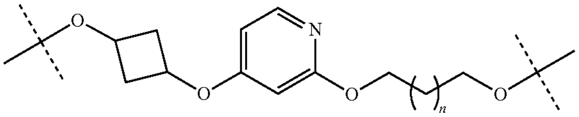
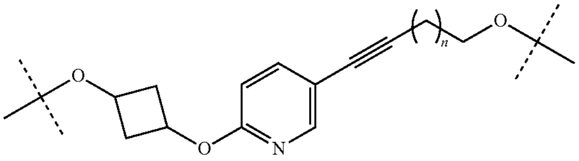
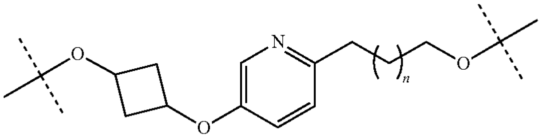
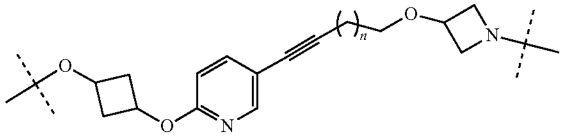
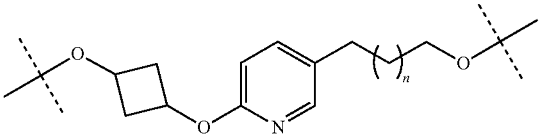
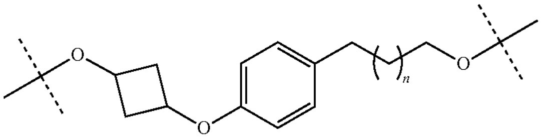

-continued
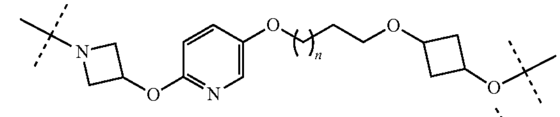
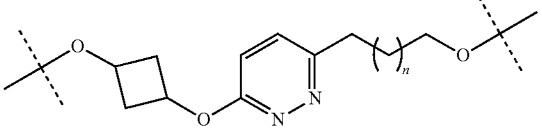
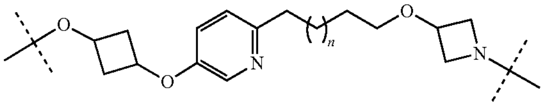
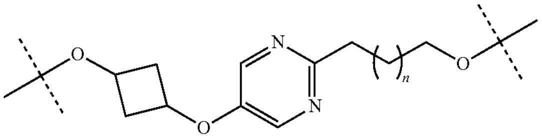
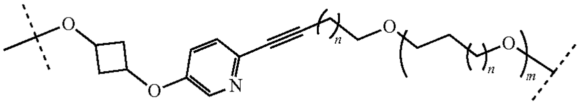
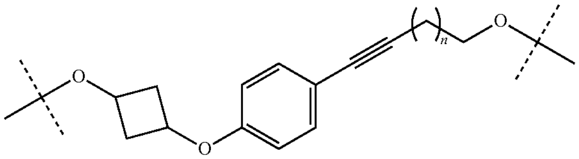
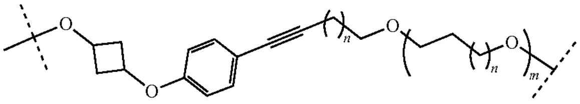
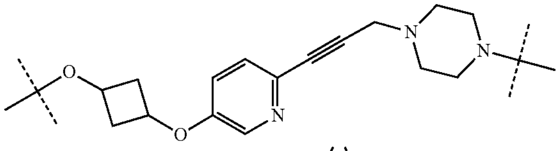
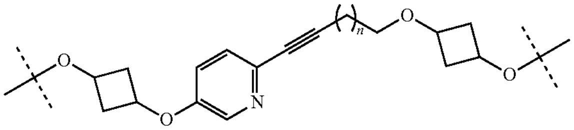
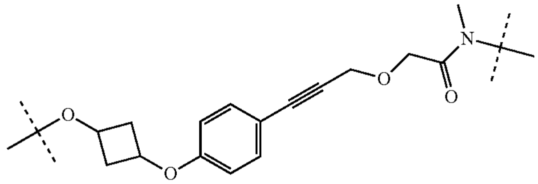
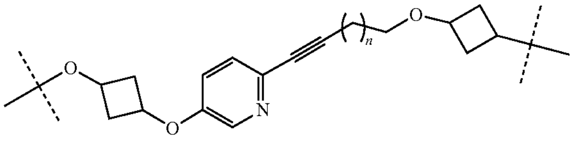
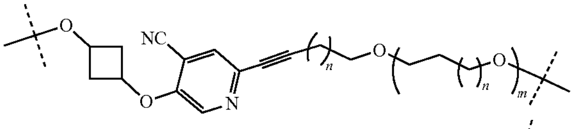
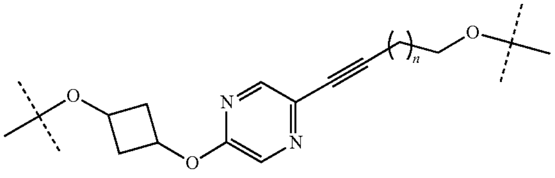
-continued
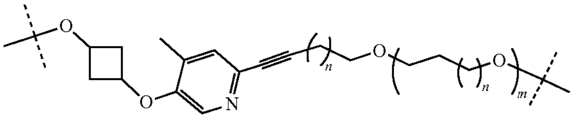
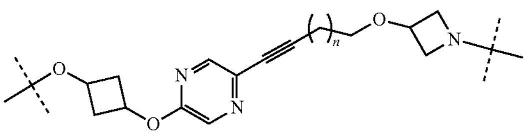
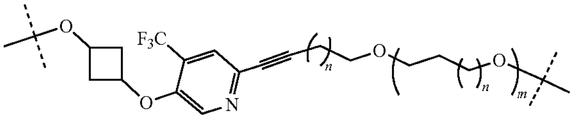
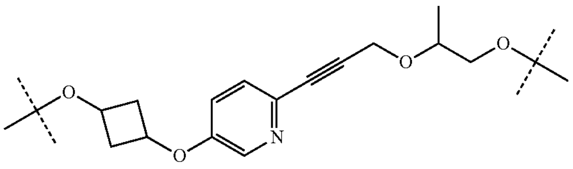
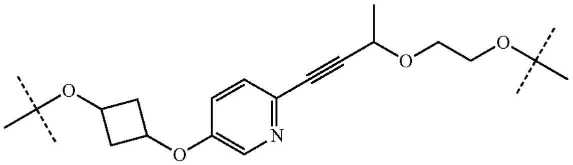
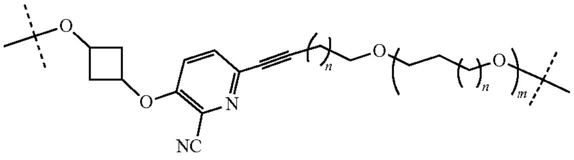
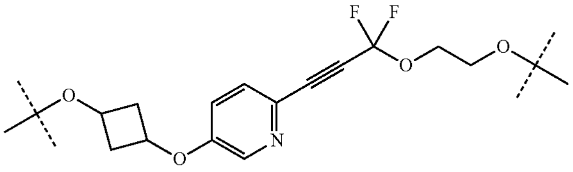
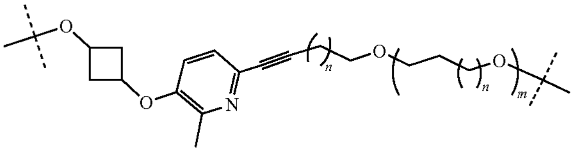
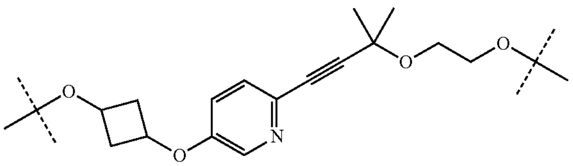
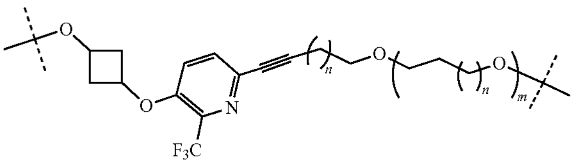
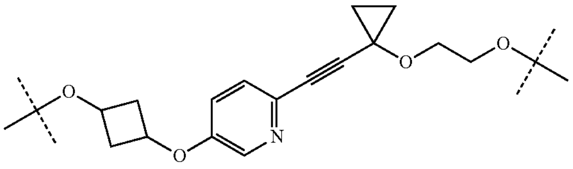

-continued
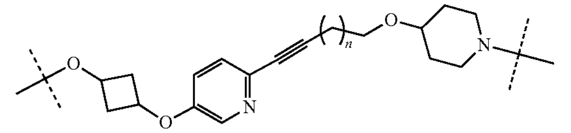
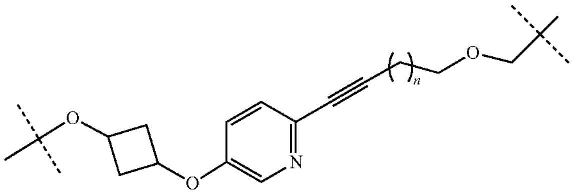
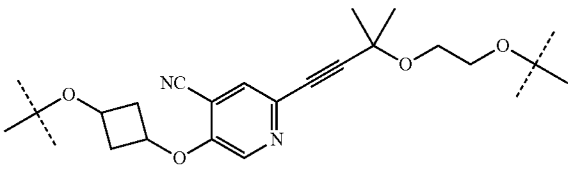
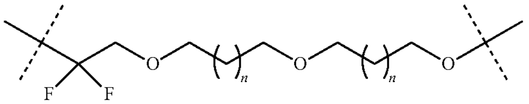
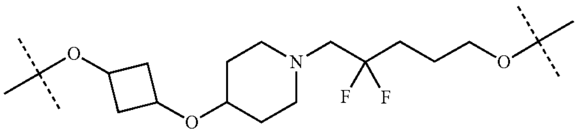
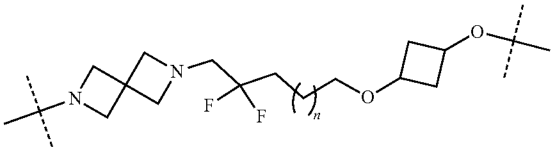
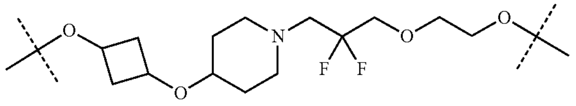
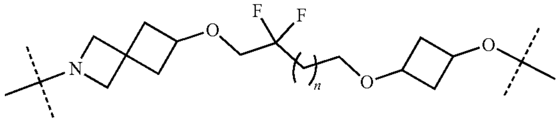
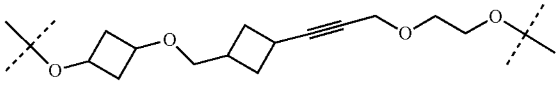
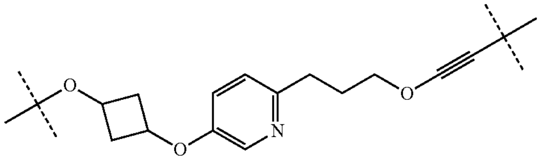
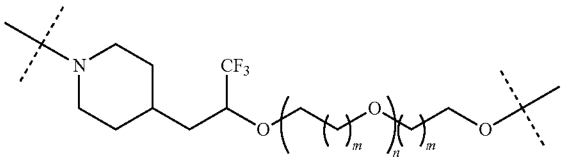
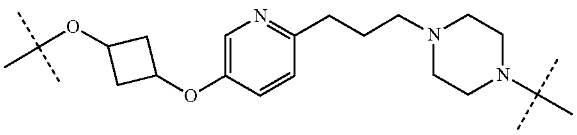
-continued
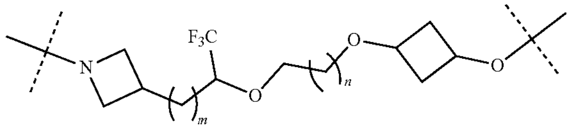
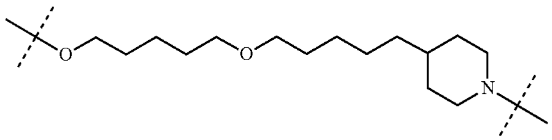
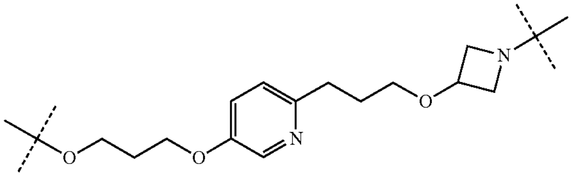
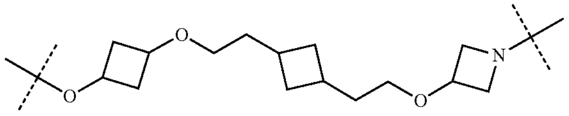
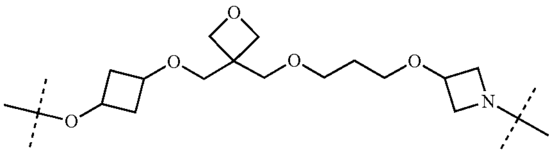
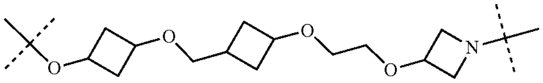
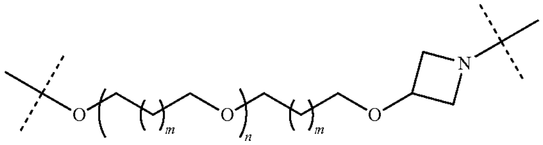
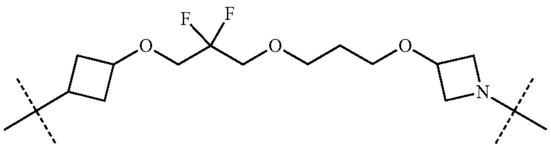
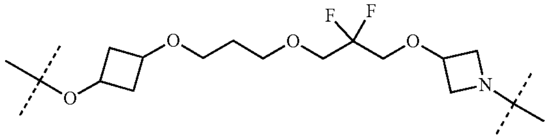
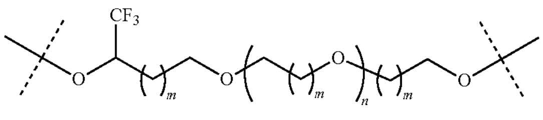
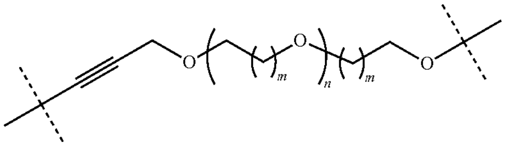
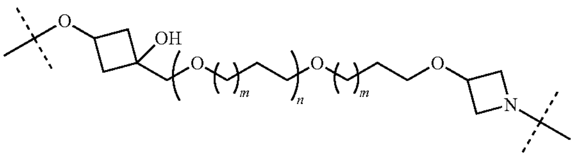

-continued
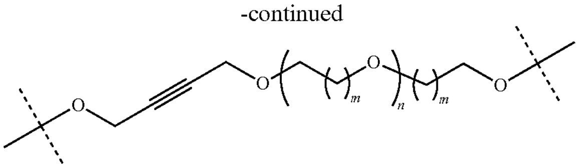
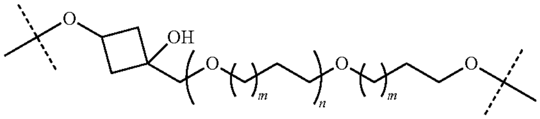
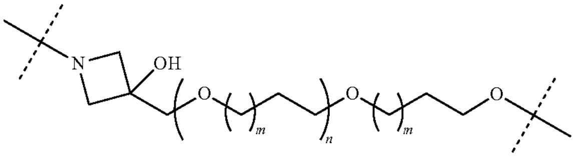
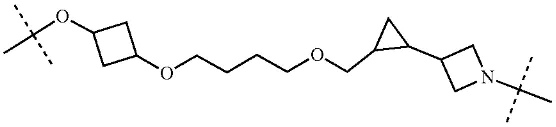
-continued
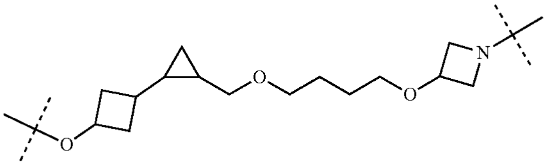
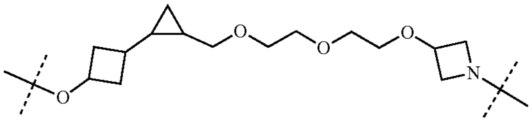
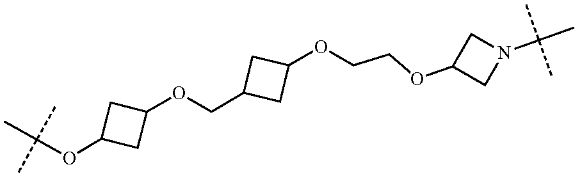
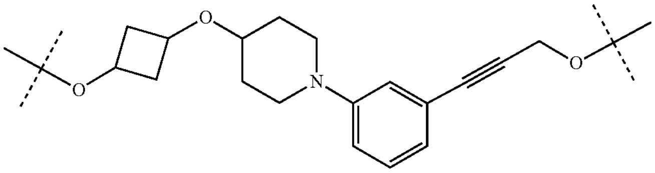
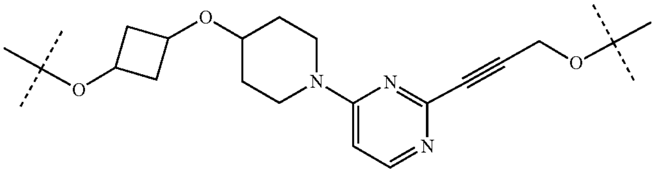
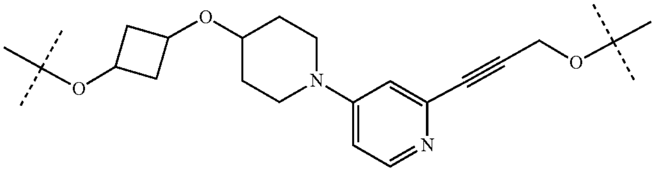
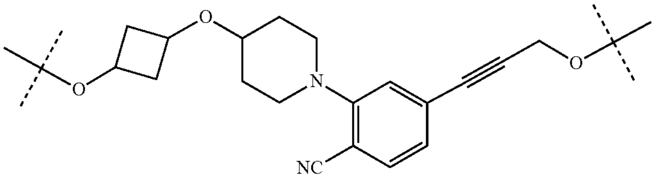
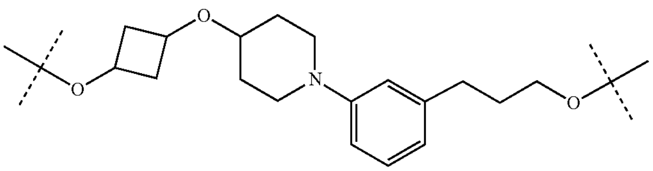
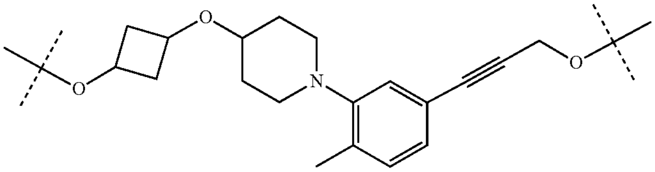

-continued
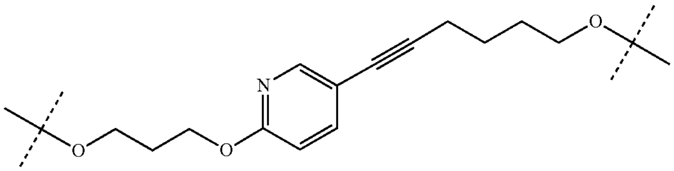
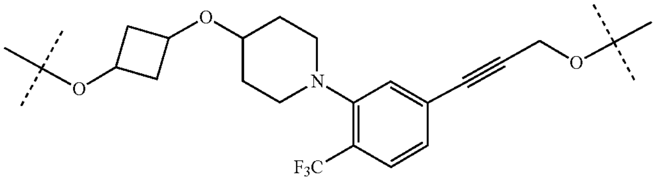
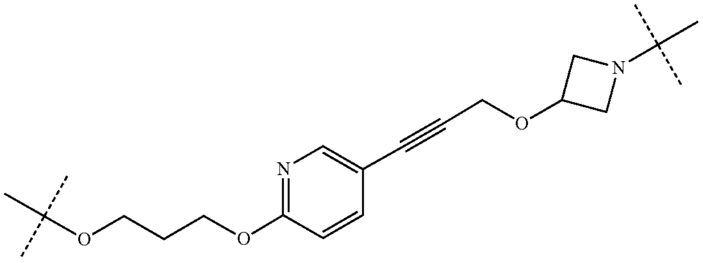
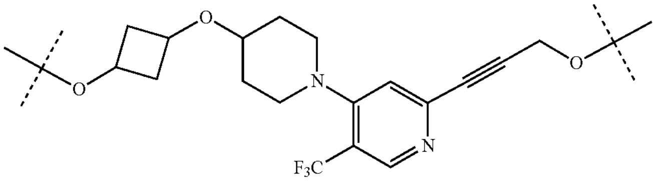
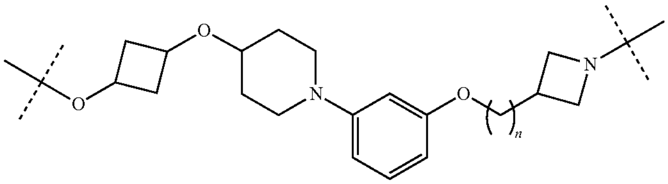
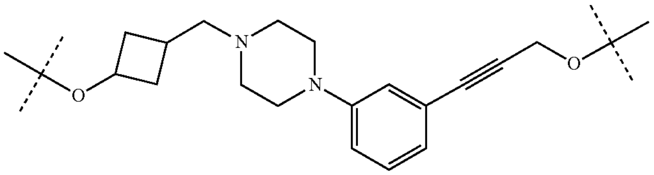
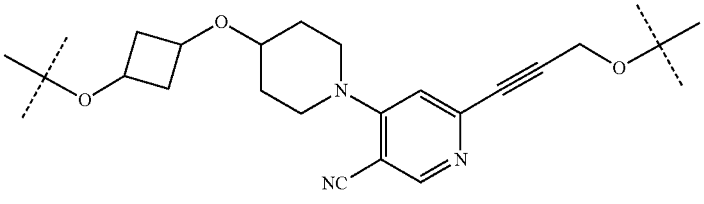
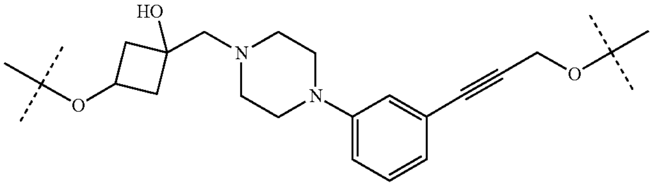

-continued
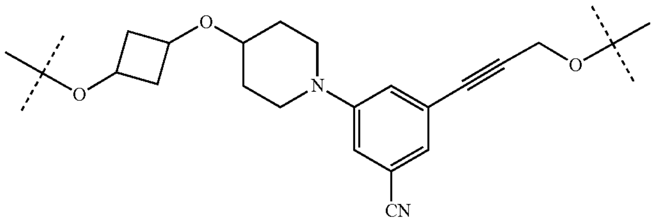
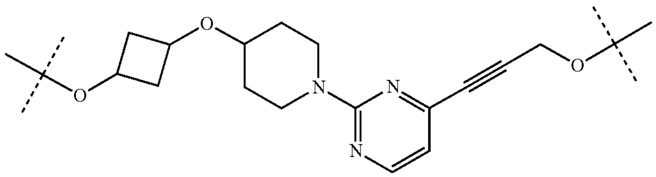
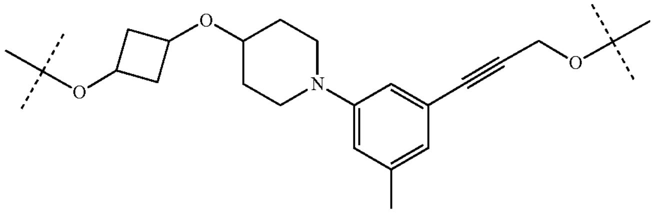
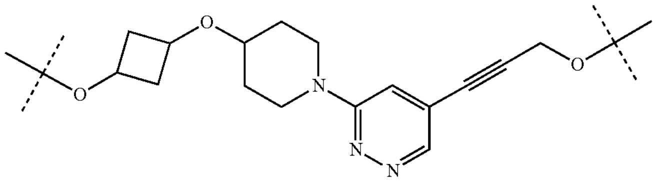
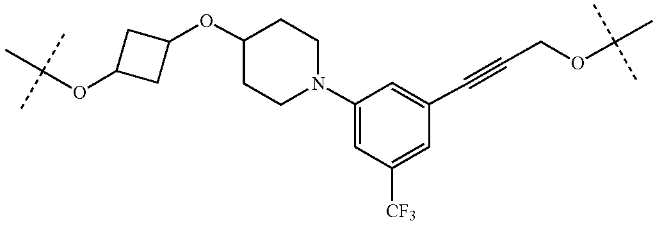
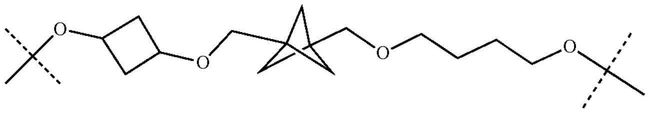
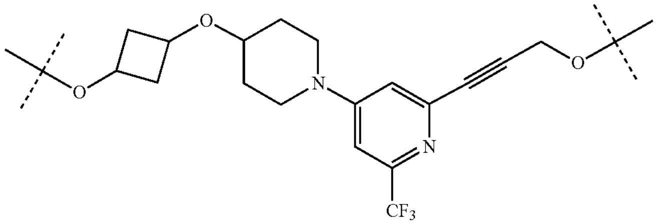
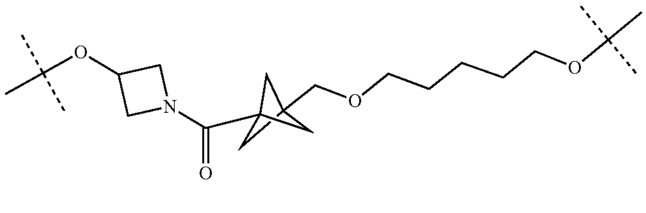

-continued
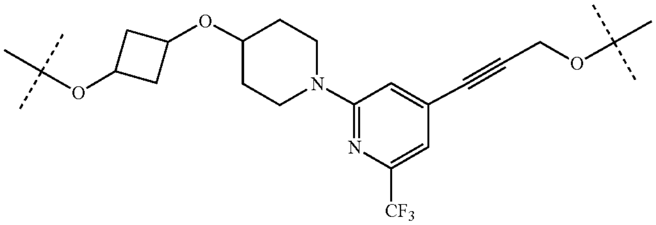
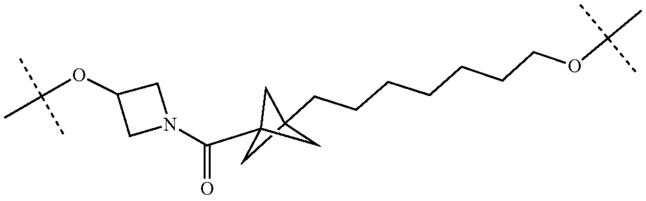
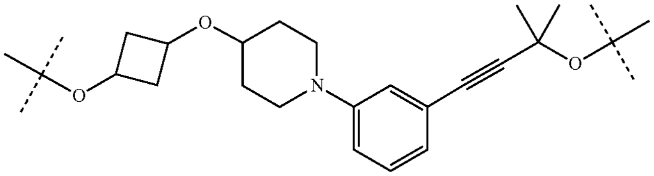
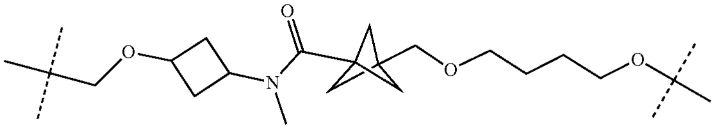
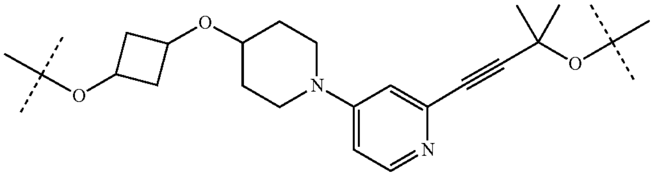
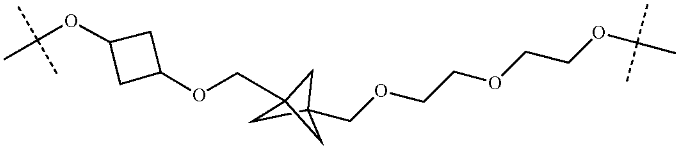
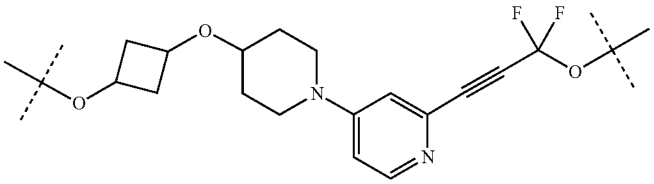
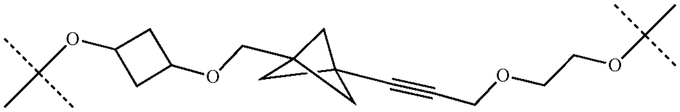
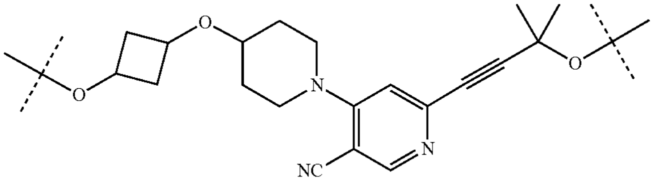
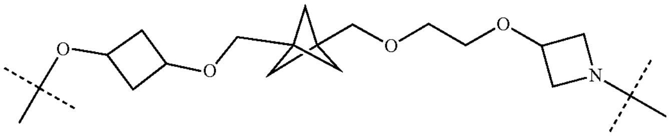

-continued
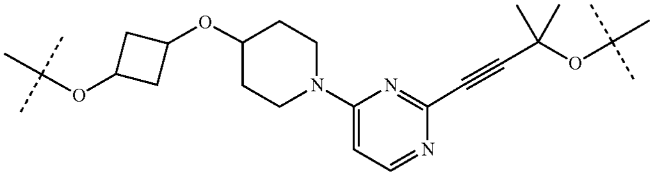
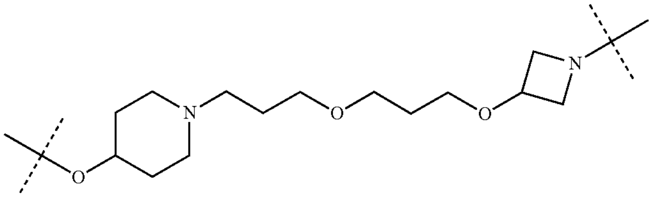
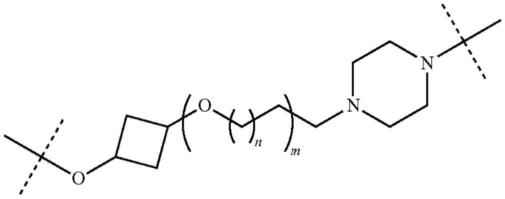
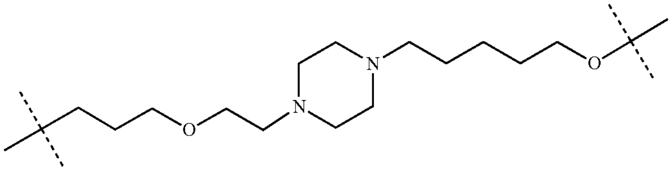
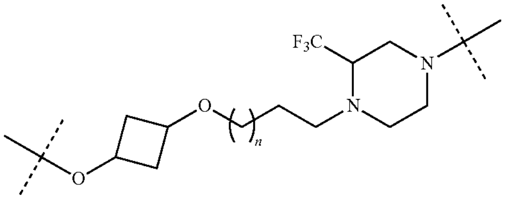
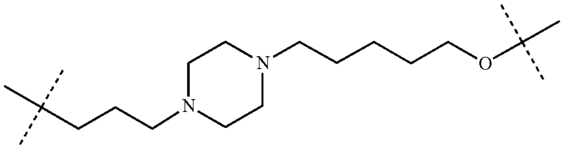
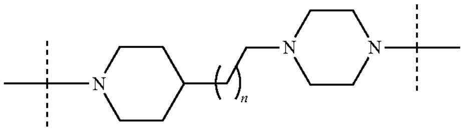
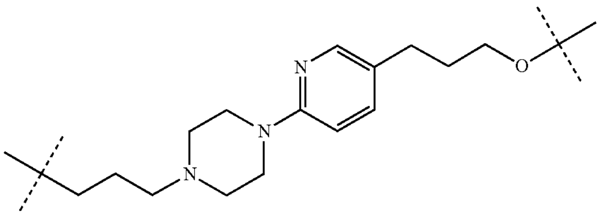
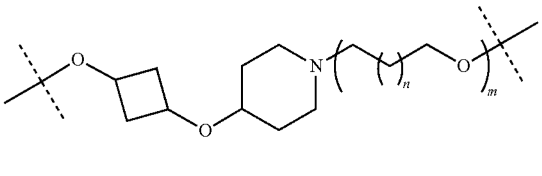

-continued
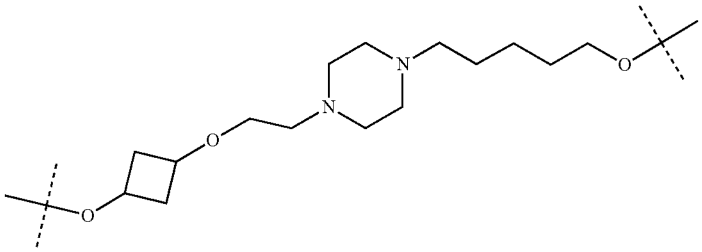
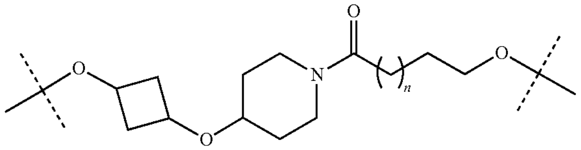
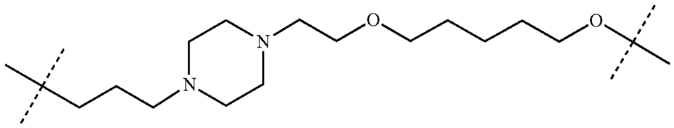
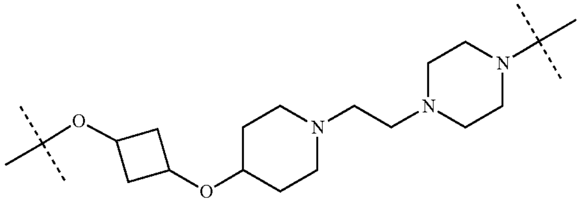
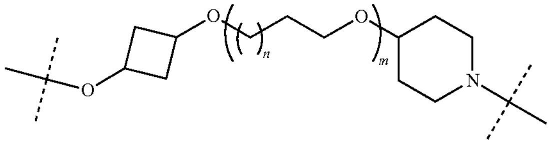
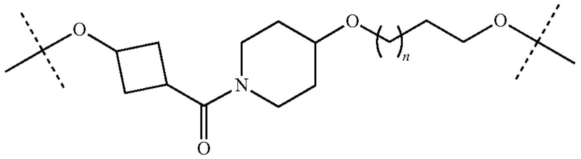
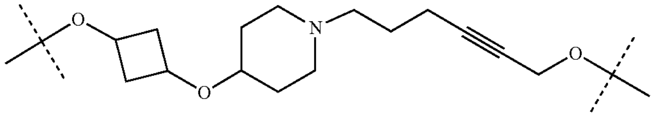
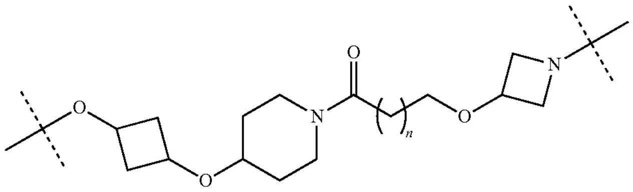
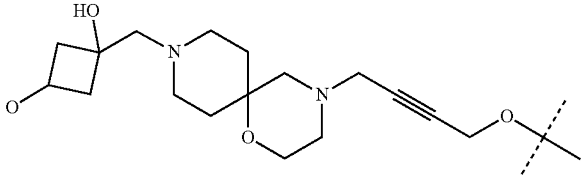
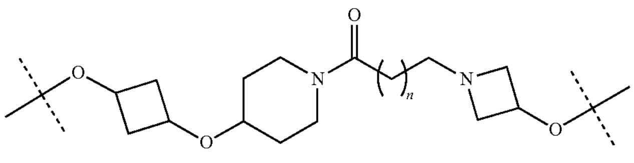

-continued
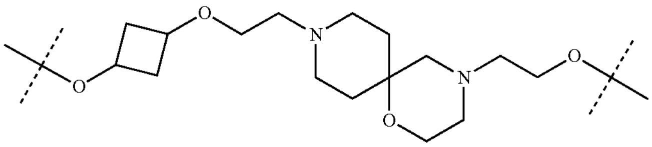
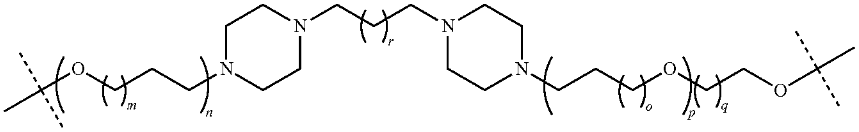
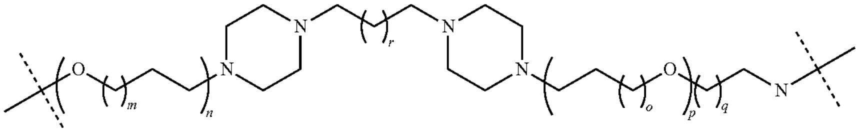
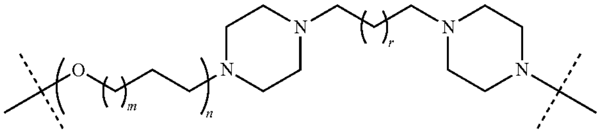
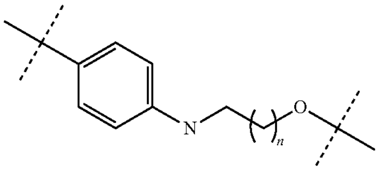
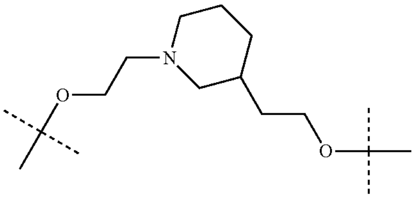
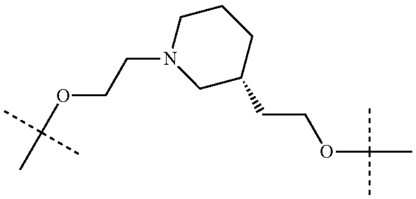
;
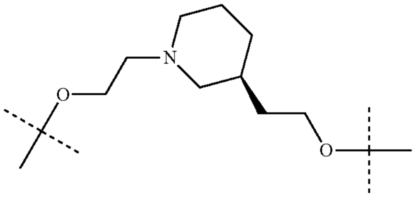
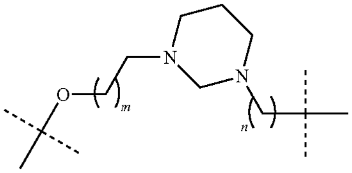
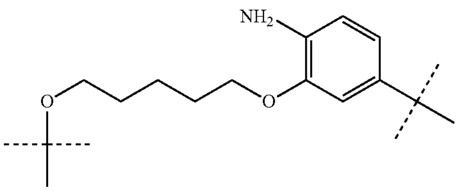
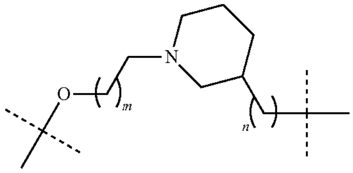
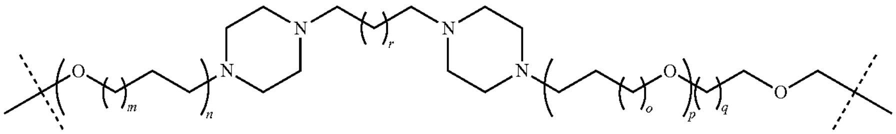

-continued
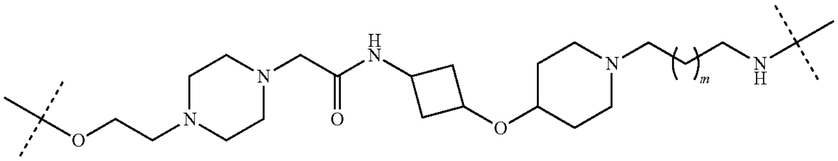
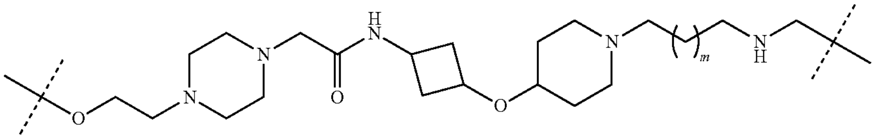
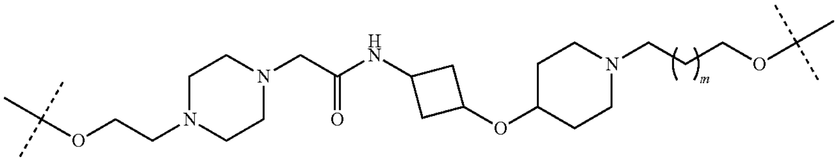
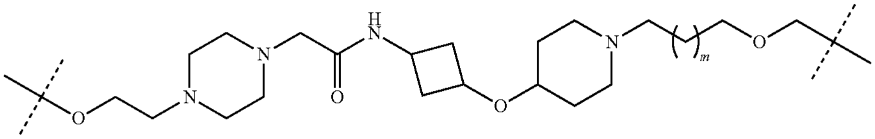
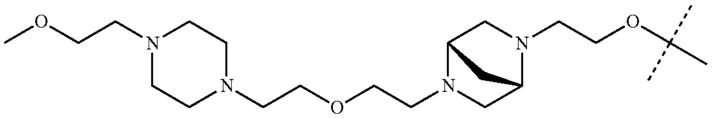
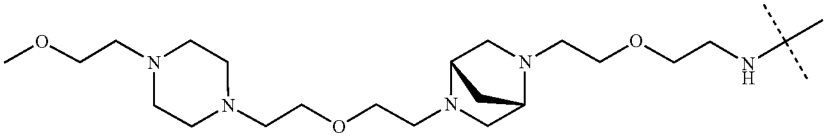
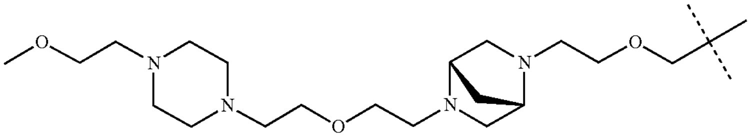
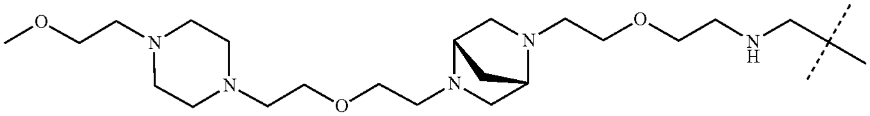
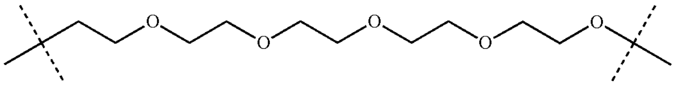
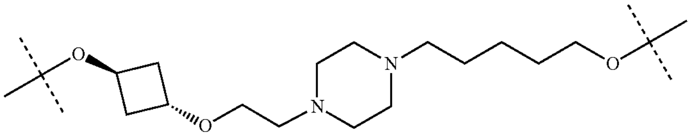
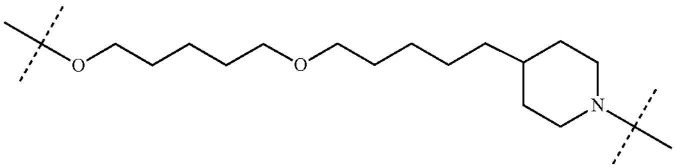
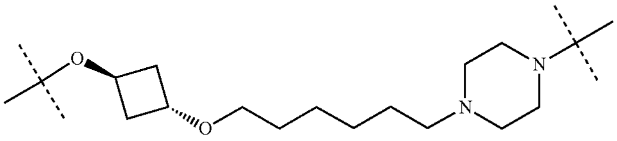

-continued
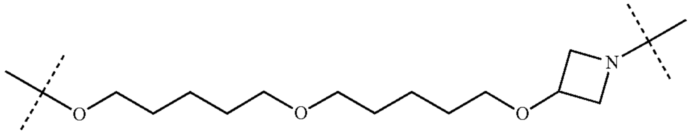
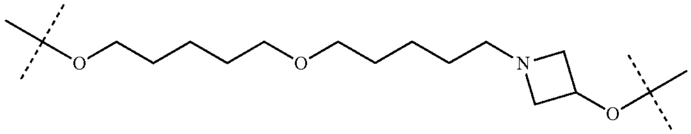
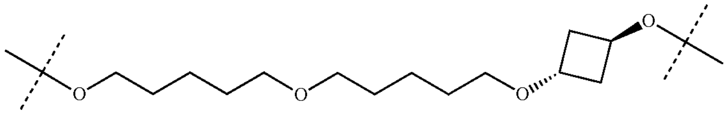
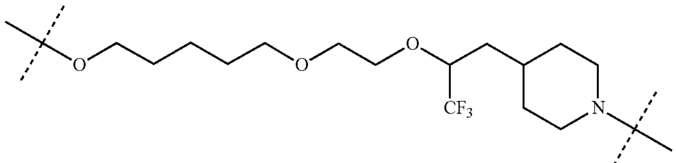
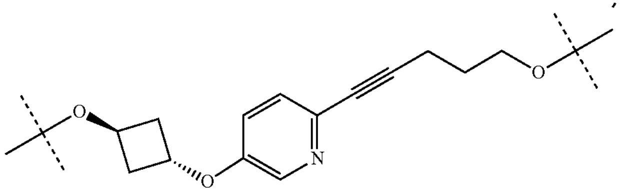
,
wherein each occurrence of m, n, o, p, q, and r is independently 0, 1, 2, 3, 4, 5, 6, 7, 8, 9, 10, 11, 12, 13, 14, 15, 16, 17, 18, 19, or 20.
In any aspect or embodiment described herein, L is selected from the group consisting of:
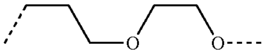
;
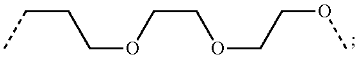
;
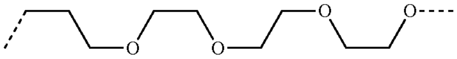
;
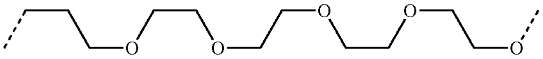
;
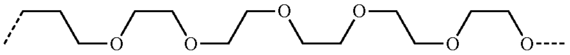
;
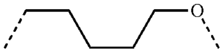
;
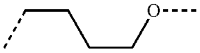
;
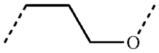
;
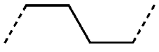
;
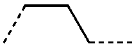
;
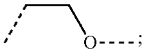
;
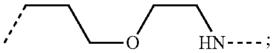
;
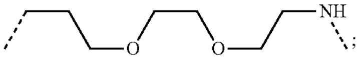
;
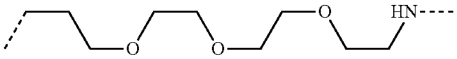
;
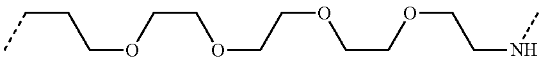
;
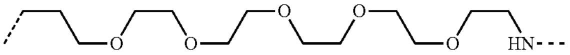
;
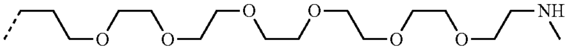
;
-continued
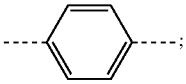
;
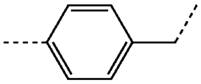
;
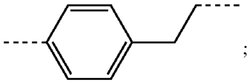
;
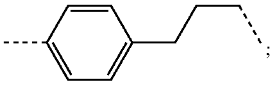
;
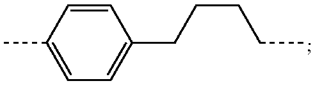
;
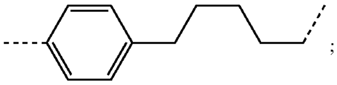
;
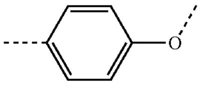
;
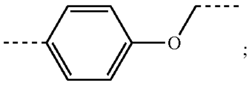
;
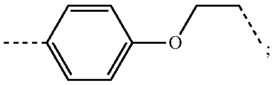
;
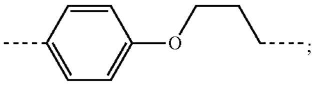
;
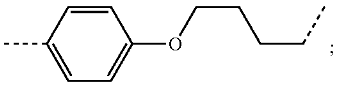
;
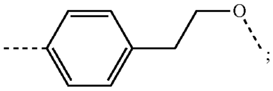
;

-continued
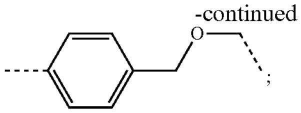
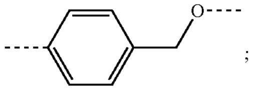
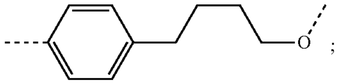
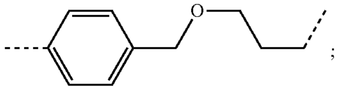
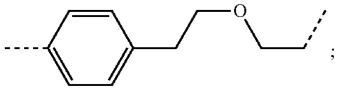
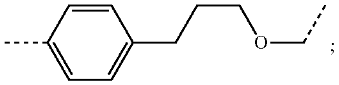
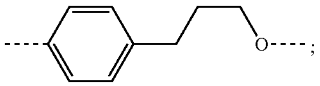
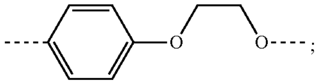
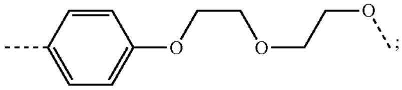
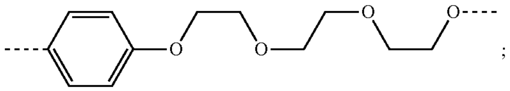
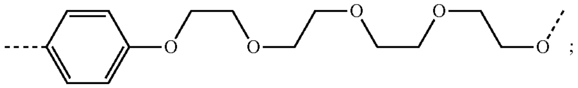
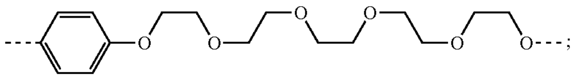
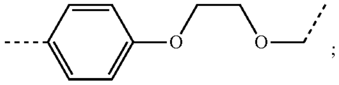
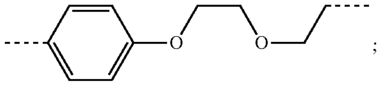
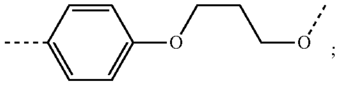
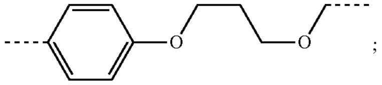
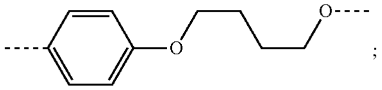
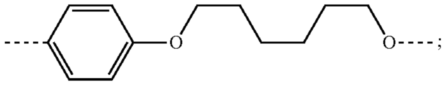
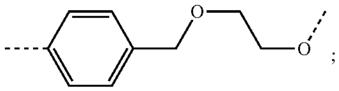
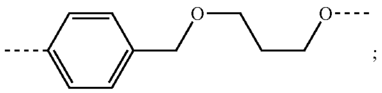
-continued
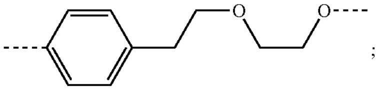
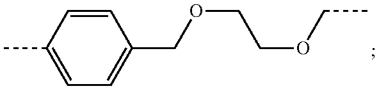
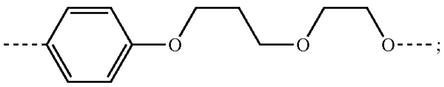
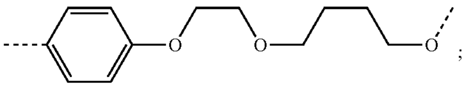
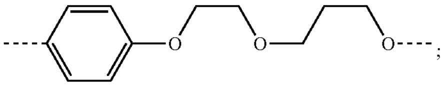
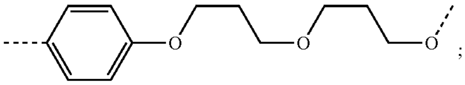
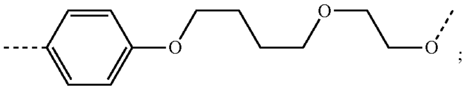
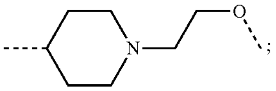
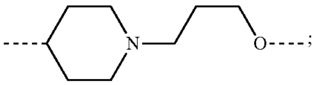
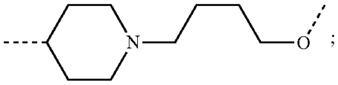
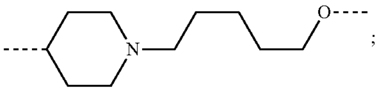
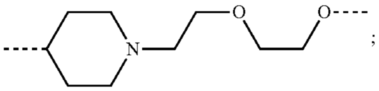
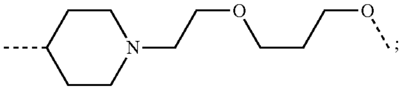
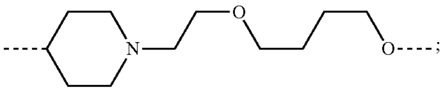
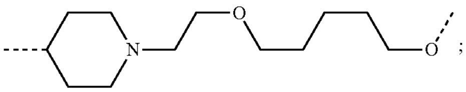
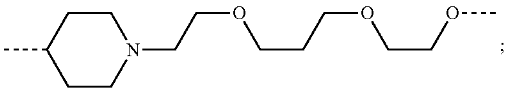
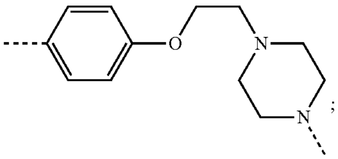
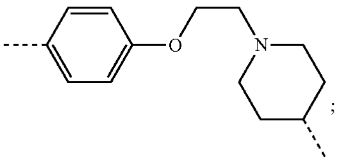

-continued
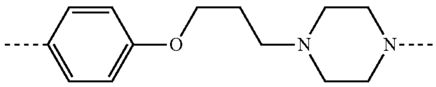;
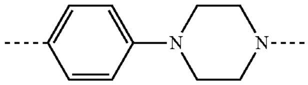;
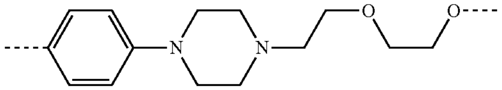;
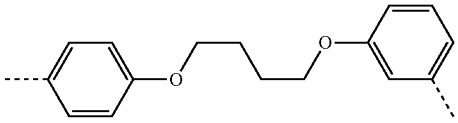;
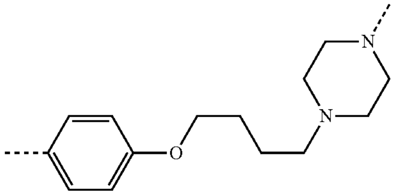;
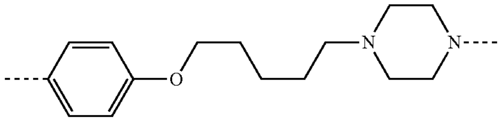;
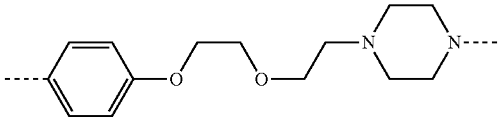;
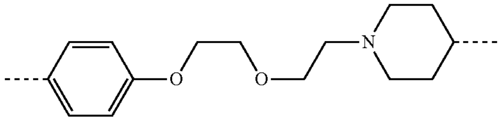;
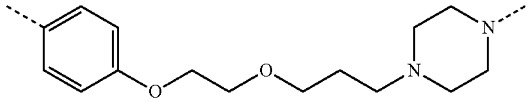;
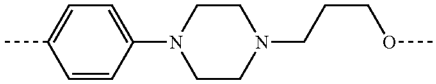;
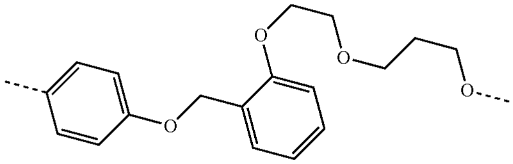;
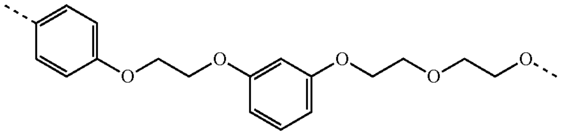;
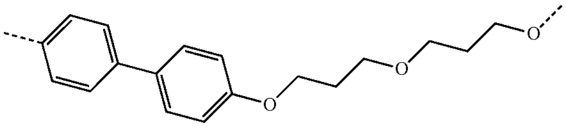;
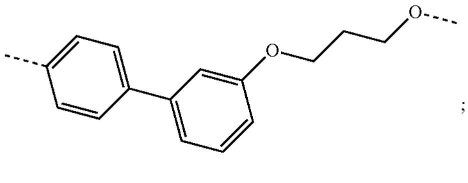;
-continued
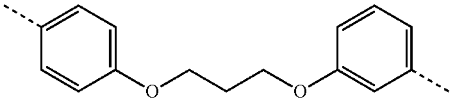;
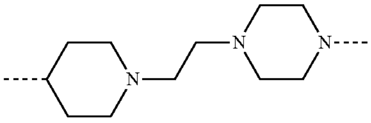;
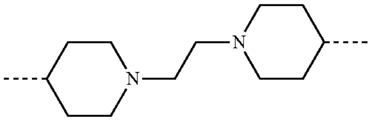;
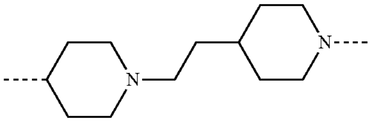;
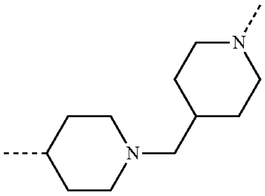;
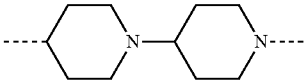;
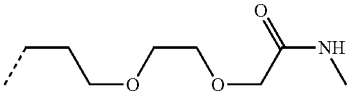;
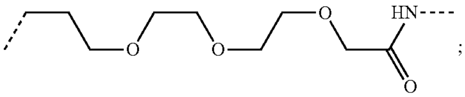;
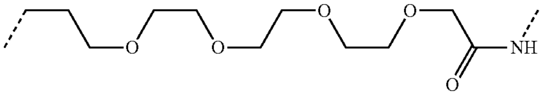;
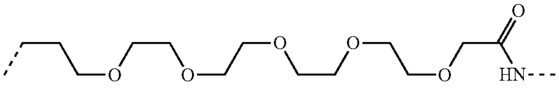;
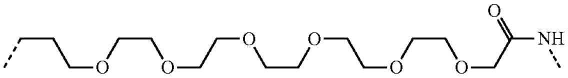;
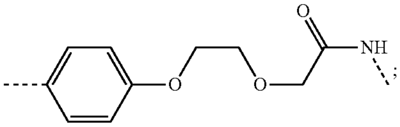;
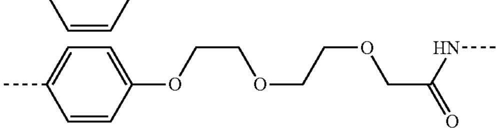;
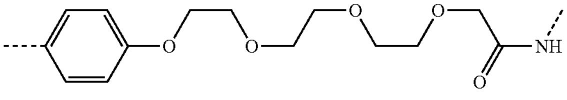;
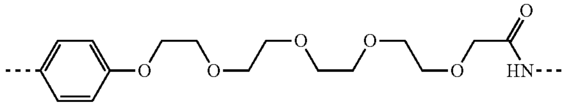;
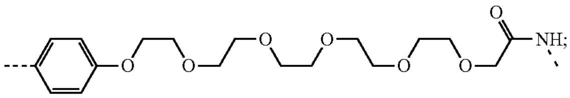;

-continued
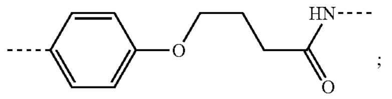
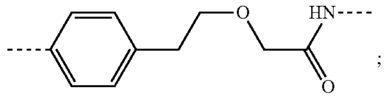
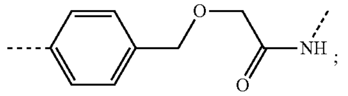
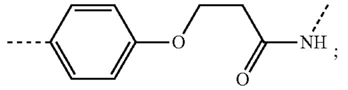
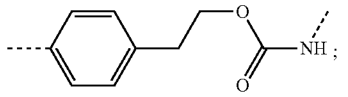
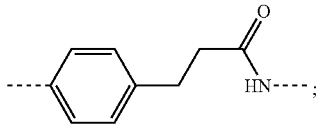
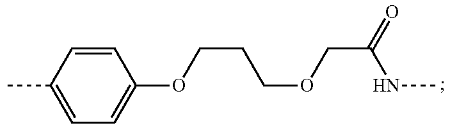
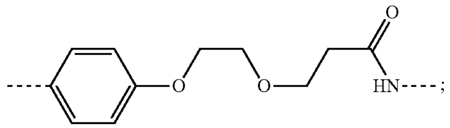
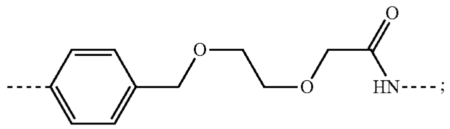
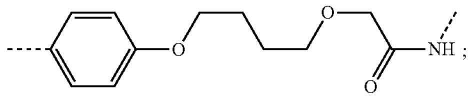
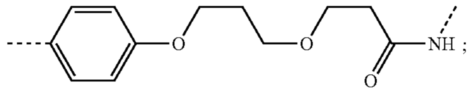
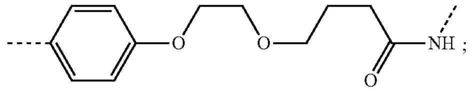
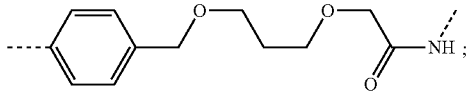
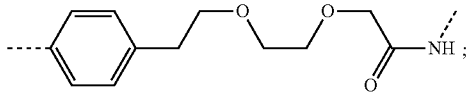
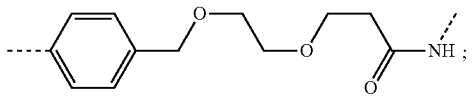
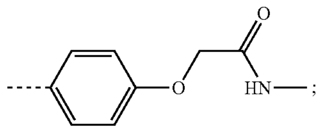
-continued
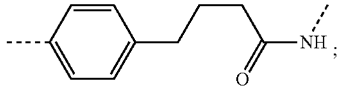
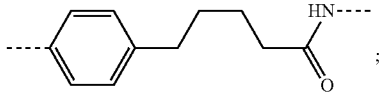
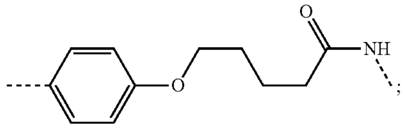
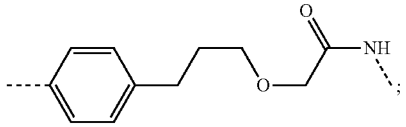
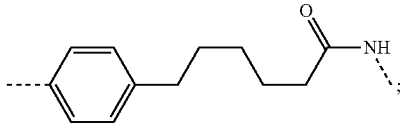
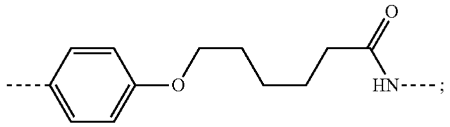
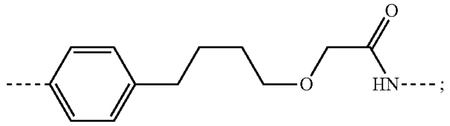
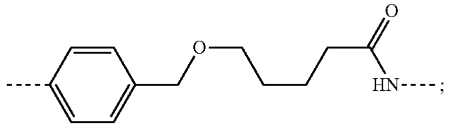
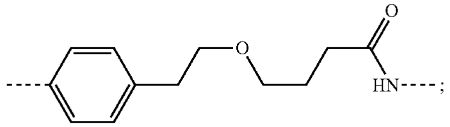
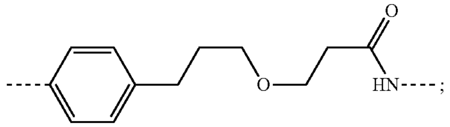
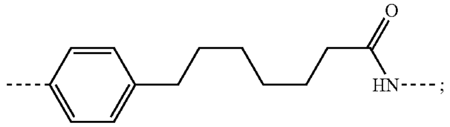
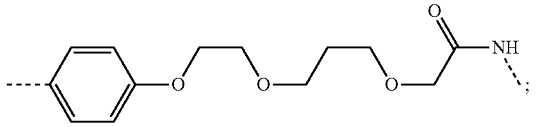
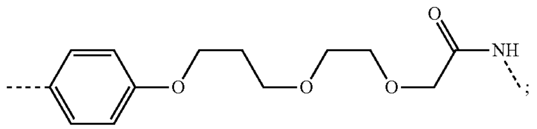
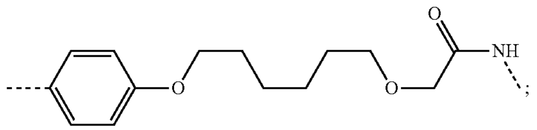

-continued
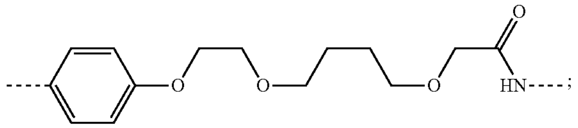
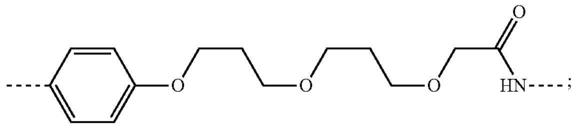
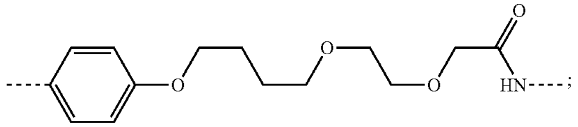
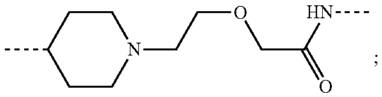
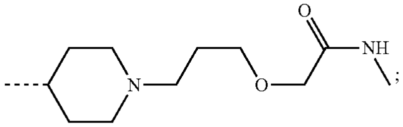
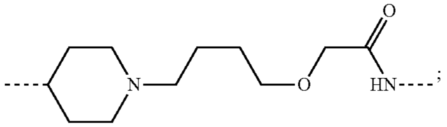
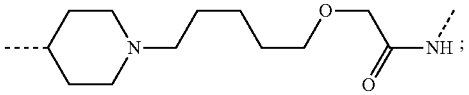
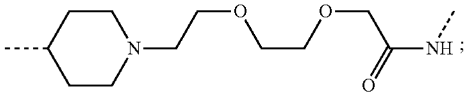
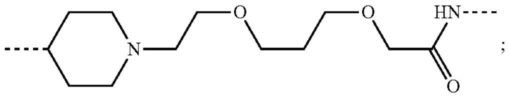
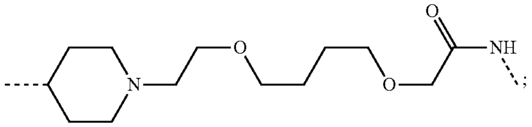
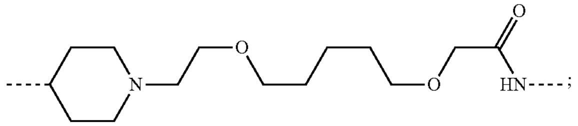
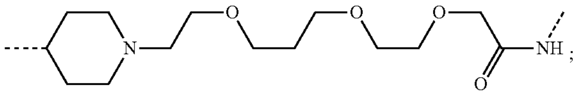
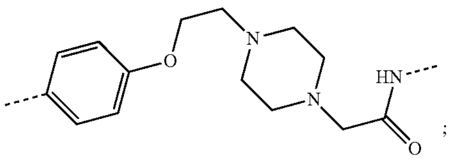
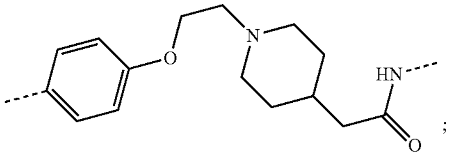
-continued
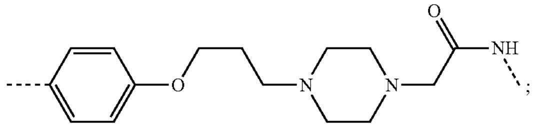
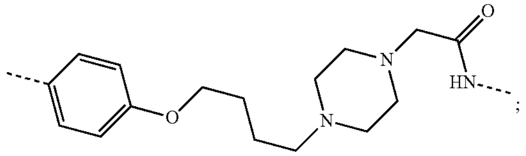
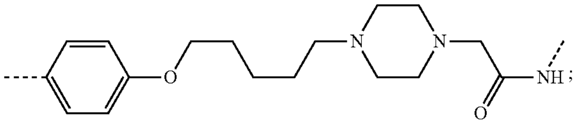
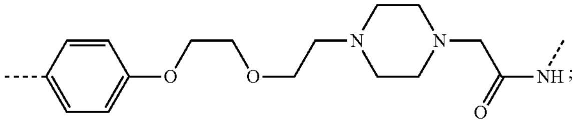
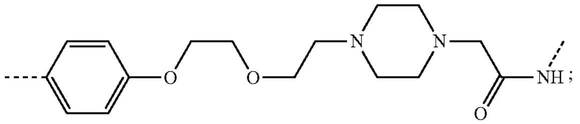
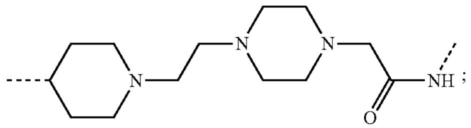
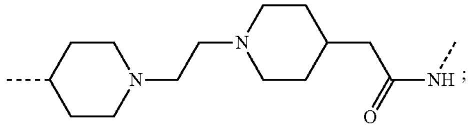
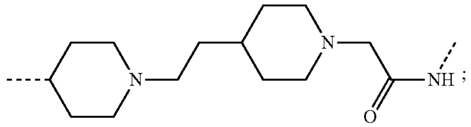
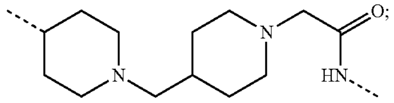
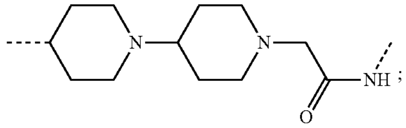
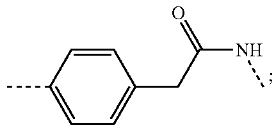
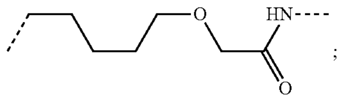
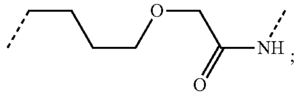
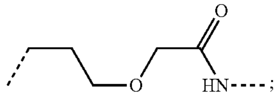

-continued
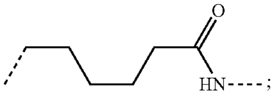;
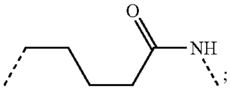;
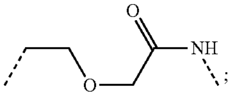;
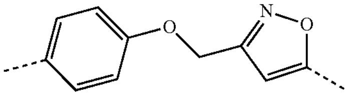;
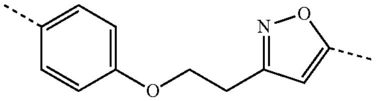;
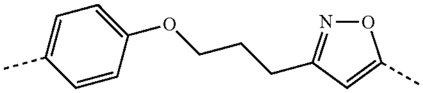;
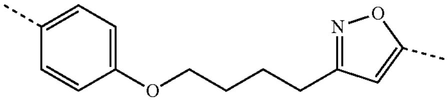;
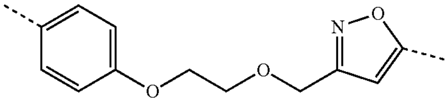;
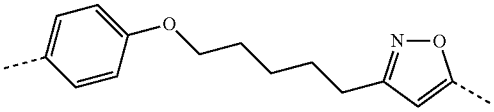;
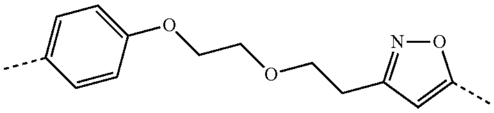;
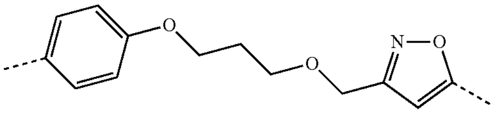;
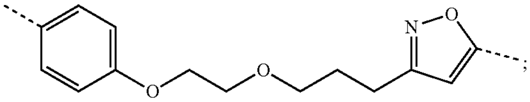;
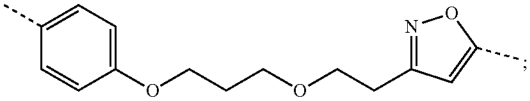;
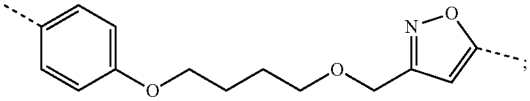;
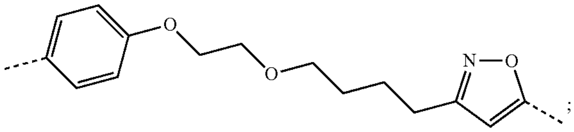;
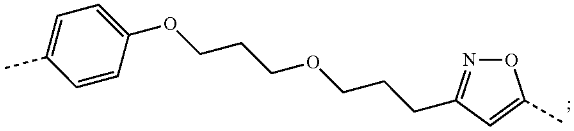;
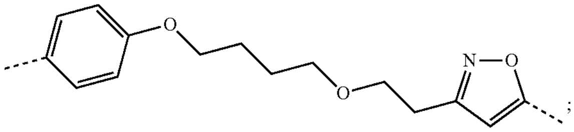;
-continued
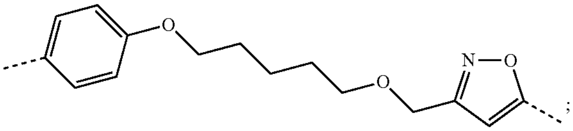;
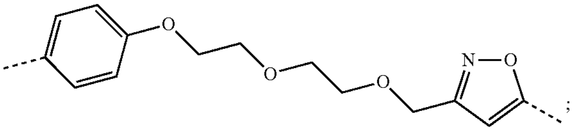;
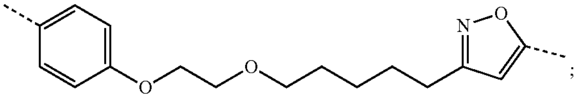;
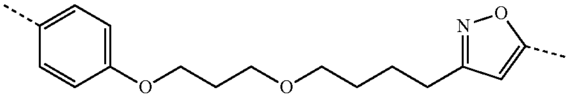;
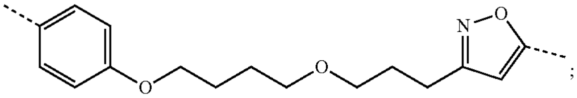;
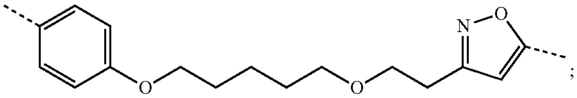;
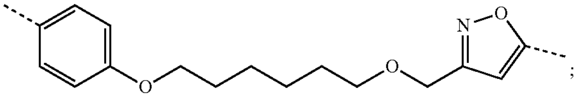;
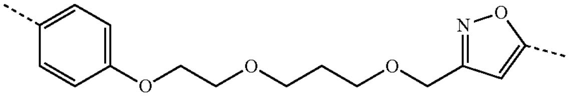;
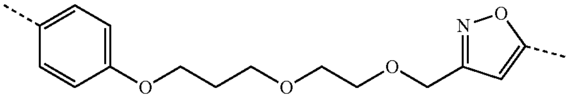;
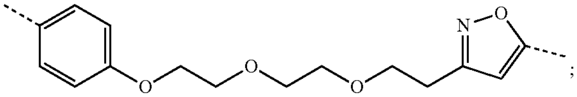;
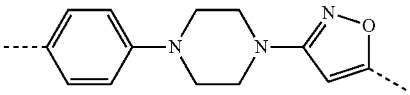;
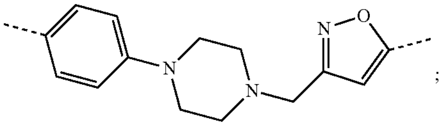;
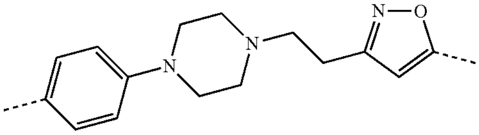;
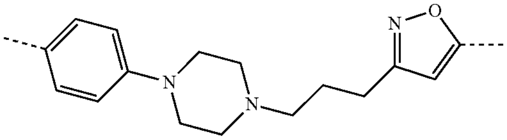;
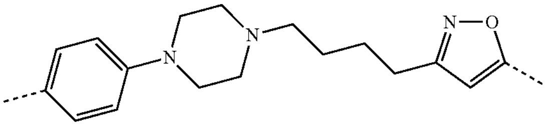;

-continued
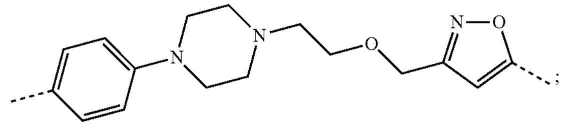;
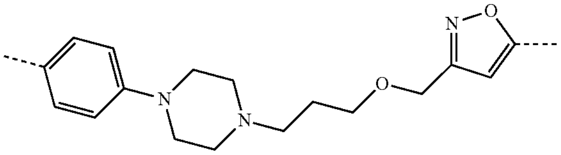;
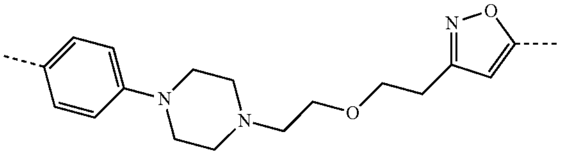;
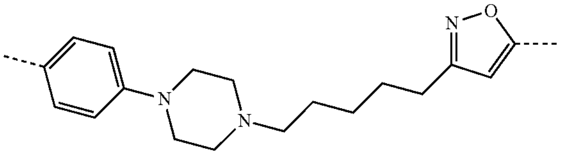;
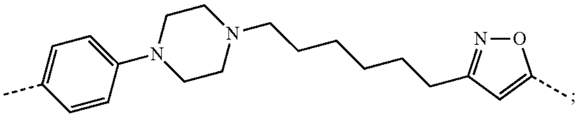;
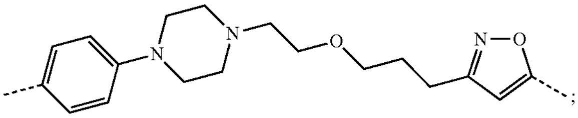;
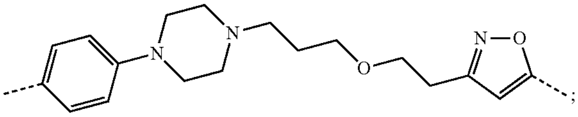;
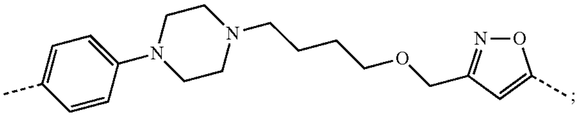;
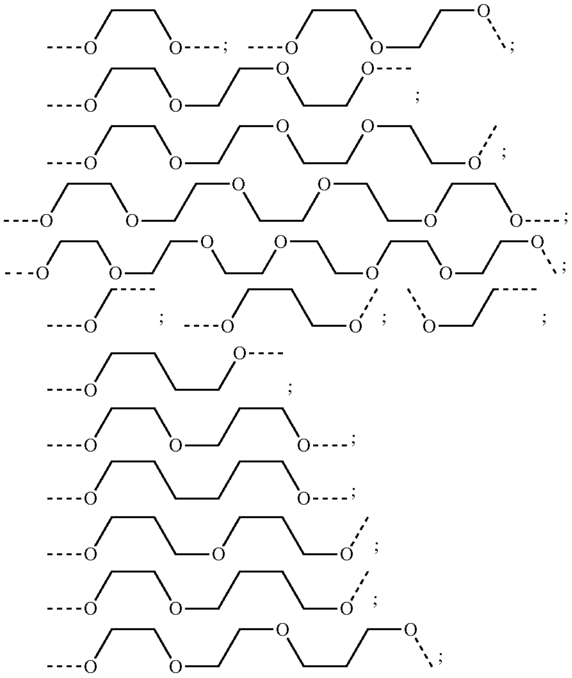
-continued
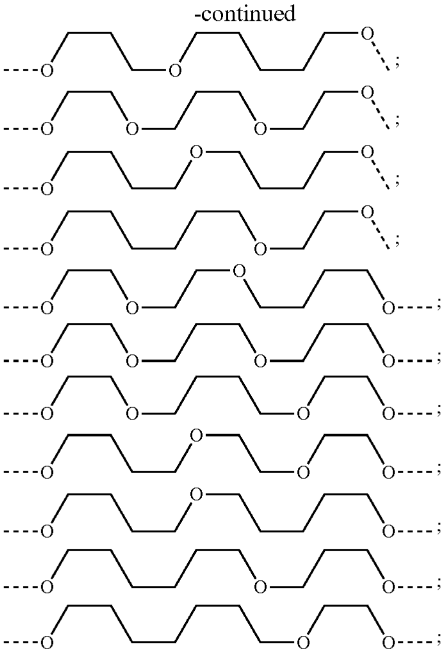
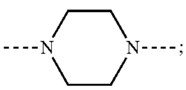; 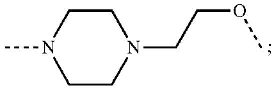;
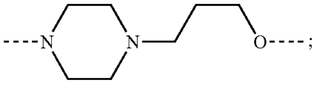;
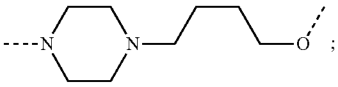;
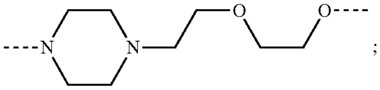;
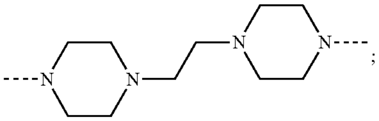;
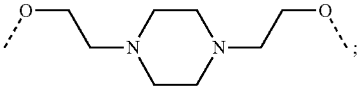;
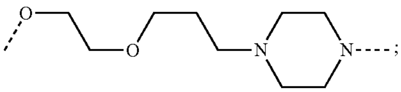;
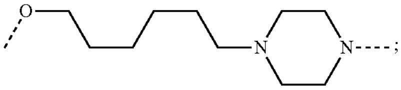;
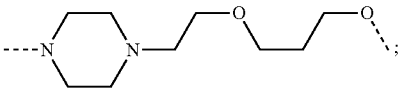;
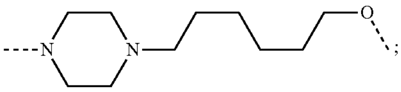;
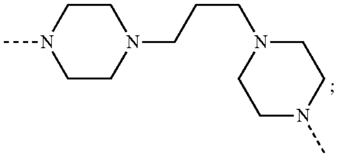;

-continued
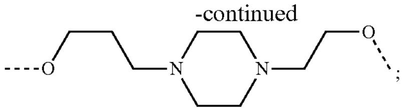
;
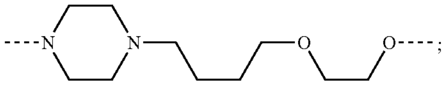
;
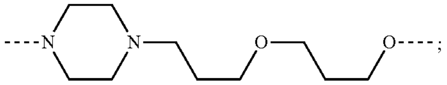
;
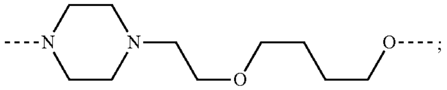
;
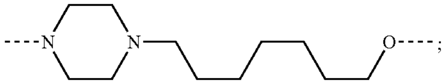
;
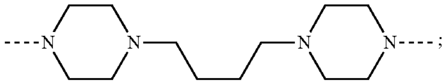
;
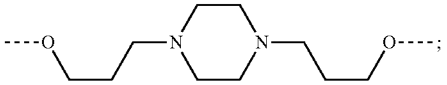
;
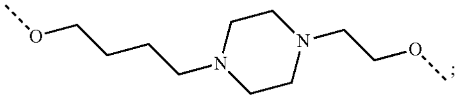
;
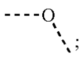
;
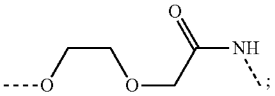
;
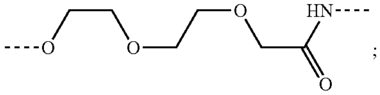
;
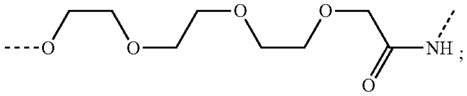
;
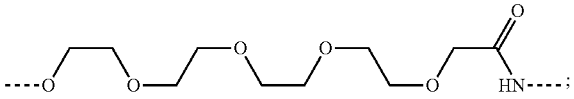
;
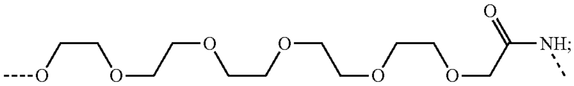
;
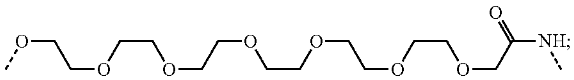
;
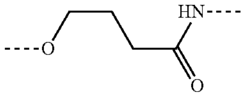
;
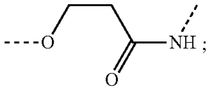
;
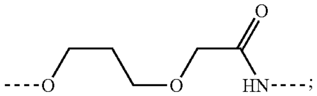
;
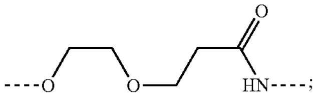
;
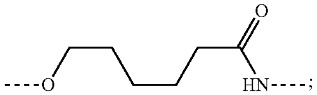
;
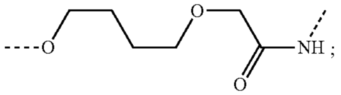
;
-continued
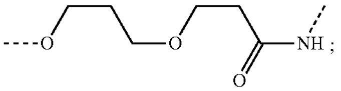
;
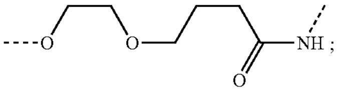
;
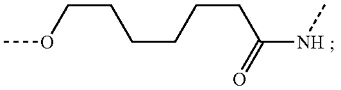
;
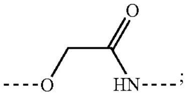
;
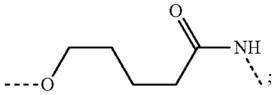
;
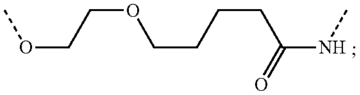
;
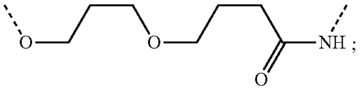
;
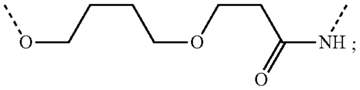
;
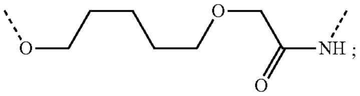
;
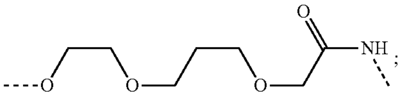
;
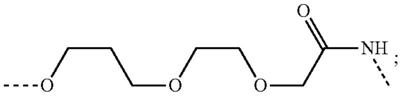
;
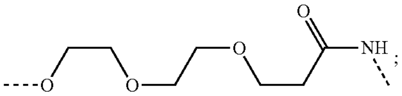
;
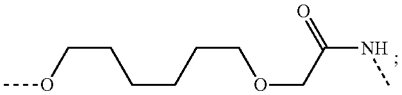
;
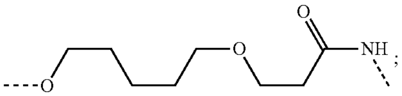
;
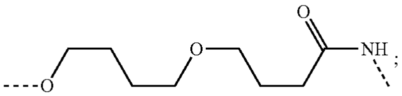
;
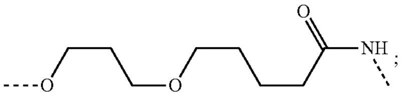
;
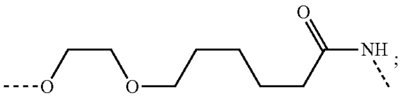
;
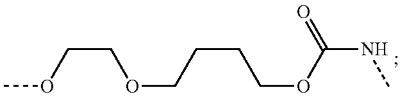
;
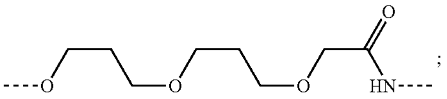
;

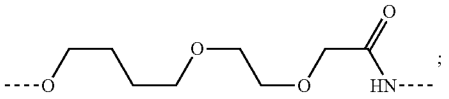
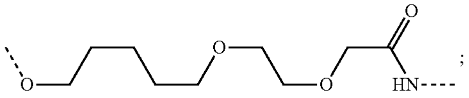
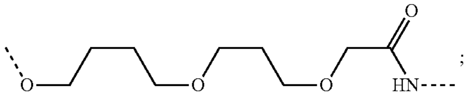
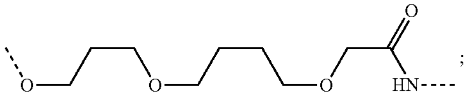
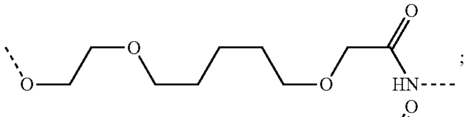
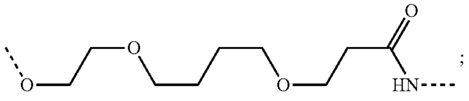
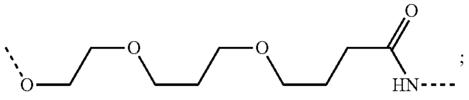
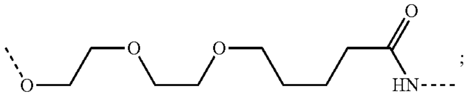
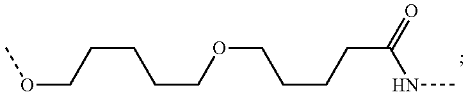
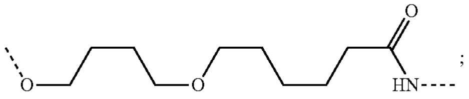
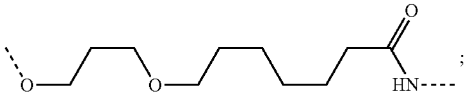
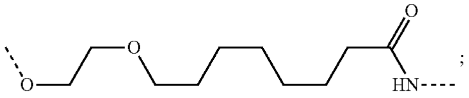
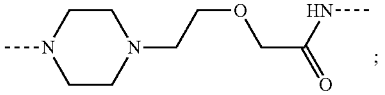
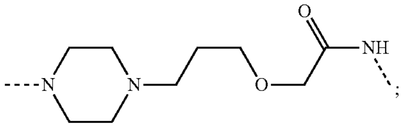
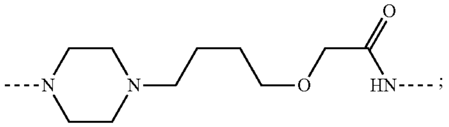
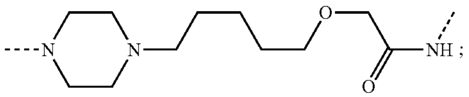
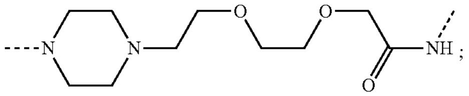
-continued
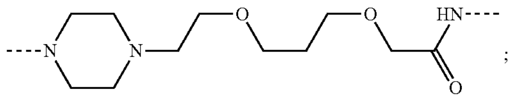
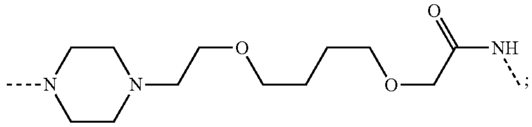
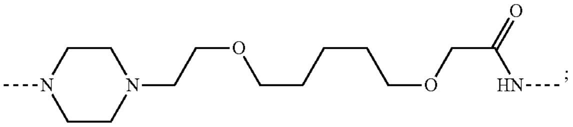
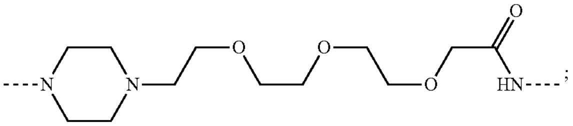
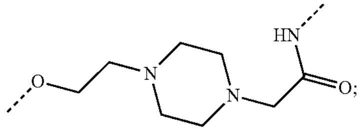
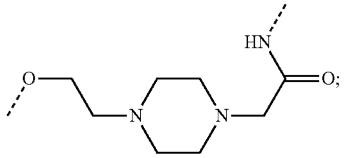
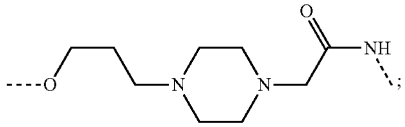
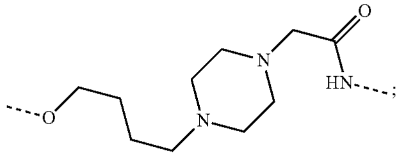
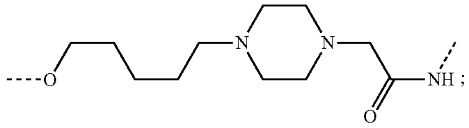
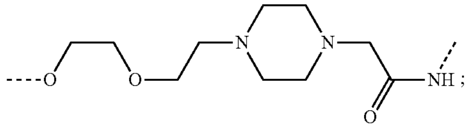
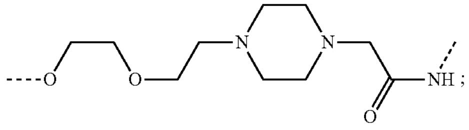
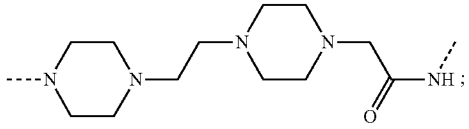
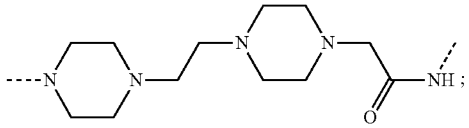

-continued
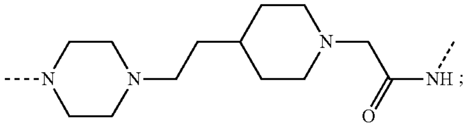
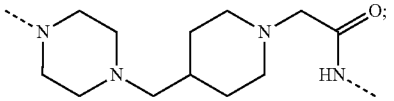
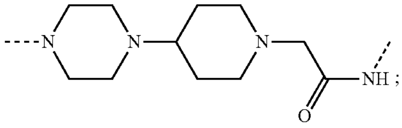
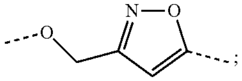
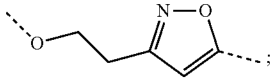
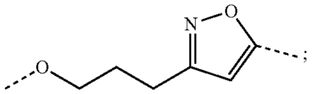
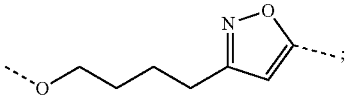
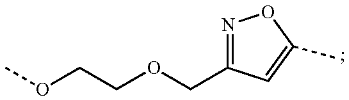
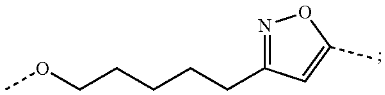
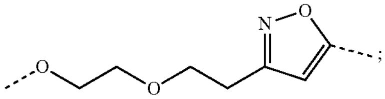
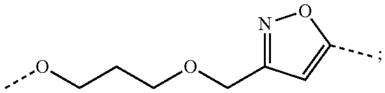
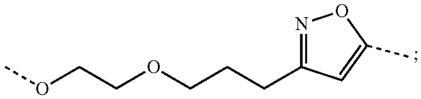
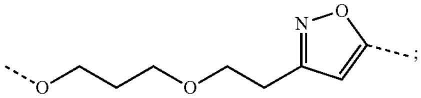
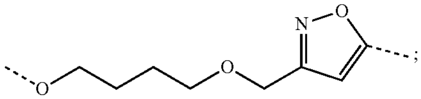
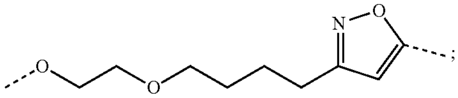
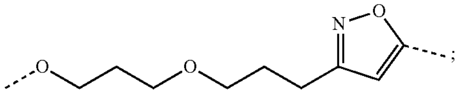
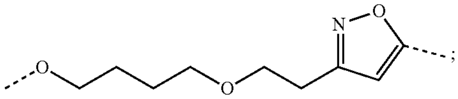
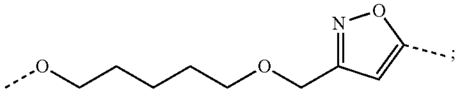
-continued
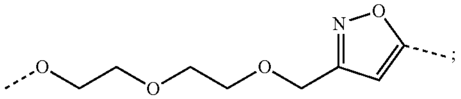
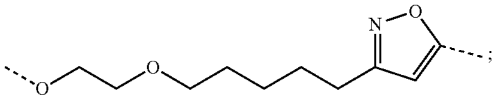
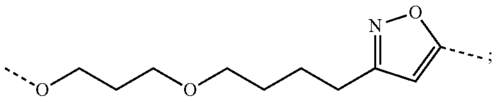
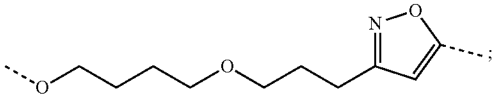
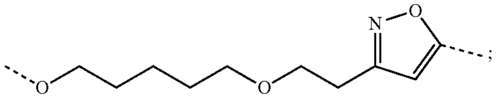
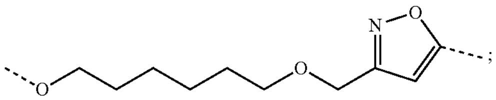
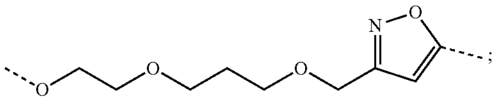
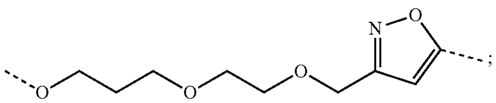
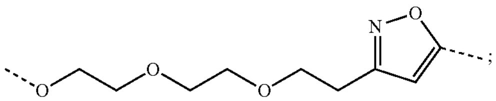
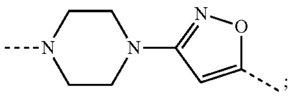
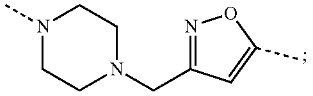
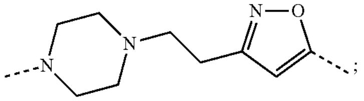
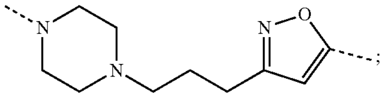
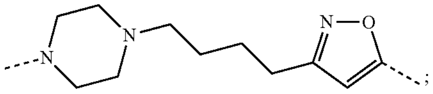
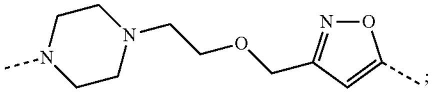
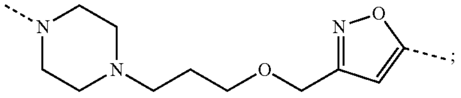
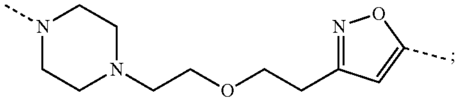

-continued

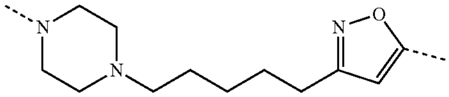

;

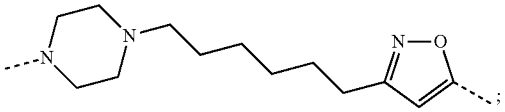

;

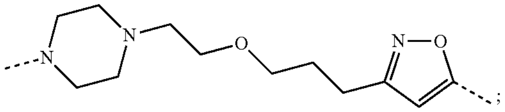

;

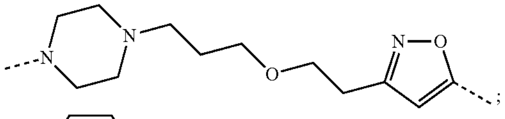

;

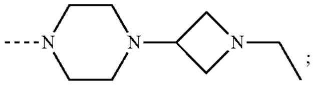

; and

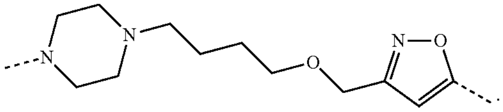

.

In additional embodiments, the linker (L) comprises a structure selected from, but not limited to the structure shown below, where a dashed line indicates the attachment point to the PTM or ULM moieties:

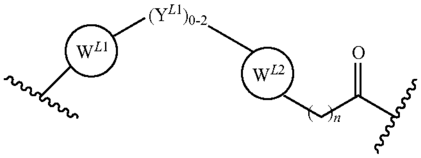

or

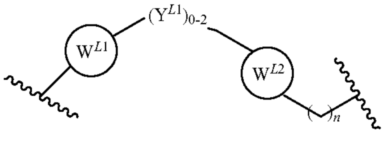

, wherein:

$W^{L1}$ and $W^{L2}$ are each independently a 4-8 membered ring with 0-4 heteroatoms, optionally substituted with $R^Q$, each $R^Q$ is independently a H, halo, OH, CN, $CF_3$, $C_1$-$C_6$ alkyl (linear, branched, optionally substituted), $C_1$-$C_6$ alkoxy (linear, branched, optionally substituted), or 2 $R^Q$ groups taken together with the atom they are attached to, form a 4-8 membered ring system containing 0-4 heteroatoms;

$Y^{L1}$ is each independently a bond, $C_1$-$C_6$ alkyl (linear, branched, optionally substituted) and optionally one or more C atoms are replaced with O; or $C_1$-$C_6$ alkoxy (linear, branched, optionally substituted);

each occurrence of n is independently 0-10; and a dashed line indicates the attachment point to the PTM or ULM moieties.

In additional embodiments, the linker (L) comprises a structure selected from, but not limited to the structure shown below, where a dashed line indicates the attachment point to the PTM or ULM moieties:

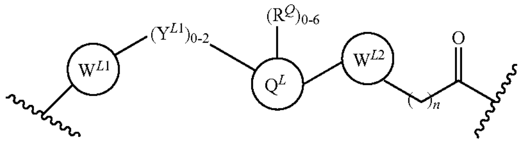

or

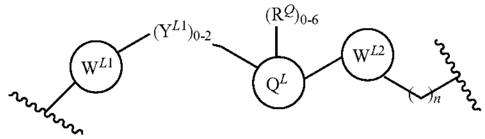

, wherein:

$W^{L1}$ and $W^{L2}$ are each independently aryl, heteroaryl, cyclic, heterocyclic, $C_{1-6}$ alkyl, bicyclic, biaryl, biheteroaryl, or biheterocyclic, each optionally substituted with $R^Q$, each $R^Q$ is independently a H, halo, OH, CN, $CF_3$, hydroxyl, nitro, C≡CH, $C_{2-6}$ alkenyl, $C_{2-6}$ alkynyl, $C_1$-$C_6$ alkyl (linear, branched, optionally substituted), $C_1$-$C_6$ alkoxy (linear, branched, optionally substituted), $OC_{1-3}$alkyl (optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;

$Y^{L1}$ is each independently a bond, $NR^{YL1}$, O, S, $NR^{YL2}$, $CR^{YL1}R^{YL2}$, C═O, C═S, SO, $SO_2$, $C_1$-$C_6$ alkyl (linear, branched, optionally substituted) and optionally one or more C atoms are replaced with O; $C_1$-$C_6$ alkoxy (linear, branched, optionally substituted);

$Q^L$ is a 3-6 membered alicyclic or aromatic ring with 0-4 heteroatoms, optionally bridged, optionally substituted with 0-6 $R^Q$, each $R^Q$ is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^{YL1}$, $R^{YL2}$ are each independently H, OH, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms);

each occurrence of n is independently 0-10; and a dashed line indicates the attachment point to the PTM or ULM moieties.

In additional embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In another embodiment, the present disclosure is directed to a compound which comprises a PTM group as described herein, which binds to a target protein, e.g., EGFR or polypeptide derived therefrom, which is ubiquitinated by an ubiquitin ligase and is chemically linked directly to the ULM group or through a linker moiety L, or PTM is alternatively a ULM' group which is also a ubiquitin ligase binding moiety, which may be the same or different than the ULM group as described above and is linked directly to the ULM group directly or through the linker moiety; and L is a linker moiety as described above which may be present or absent and which chemically (covalently) links ULM to PTM, or a pharmaceutically acceptable salt, enantiomer, stereoisomer, solvate or polymorph thereof.

In certain embodiments, the linker group L is a group comprising one or more covalently connected structural units independently selected from the group consisting of:

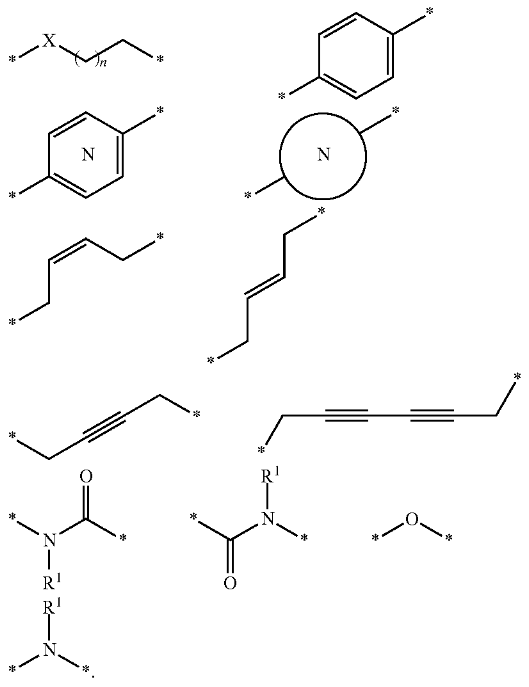

The X is selected from the group consisting of O, N, S, S(O) and $SO_2$; n is integer from 1-5, 5; $R^{L1}$ is hydrogen or alkyl,

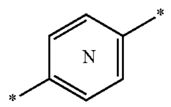

is a mono- or bicyclic aryl or heteroaryl optionally substituted with 1-3 substituents selected from alkyl, halogen, haloalkyl, hydroxy, alkoxy or cyano;

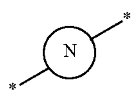

is a mono- or bicyclic cycloalkyl or a heterocycloalkyl optionally substituted with 1-3 substituents selected from alkyl, halogen, haloalkyl, hydroxy, alkoxy or cyano; and the phenyl ring fragment can be optionally substituted with 1, 2 or 3 substituents selected from the group consisting of alkyl, halogen, haloalkyl, hydroxy, alkoxy and cyano. In an embodiment, the linker group L comprises up to 10 covalently connected structural units, as described above.

Without being limited by any particular theory, the inventors believe that the composition and structure of the linker, although unlimited in principal, can have significant effects on the efficacy and potency of the bifunctional compound as described herein; perhaps due to modulation of the interaction between the ULM and the PTM. However, the linker can be optimized according to the present teachings without undue experimentation.

Although the ULM group and PTM group may be covalently linked to the linker group through any group which is appropriate and stable to the chemistry of the linker, in non-limiting aspects of the present disclosure, the linker is independently covalently bonded to the ULM group and the PTM group preferably through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. (It is noted that in certain aspects where the PTM group is a ULM group, the target protein for degradation may be the ubiquitin ligase itself). In certain non-limiting aspects, the linker may be linked to an optionally substituted alkyl, alkylene, alkene or alkyne group, an aryl group or a heterocyclic group on the ULM and/or PTM groups.

Exemplary PTMs

In non-limiting aspects of the invention, the PTM group is a group, which binds to target proteins. Targets of the PTM group are numerous in kind and are selected from proteins that are expressed in a cell such that at least a portion of the sequences is found in the cell and may bind to a PTM group. The term "protein" includes oligopeptides and polypeptide sequences of sufficient length that they can bind to a PTM group according to the present invention. Any protein in a eukaryotic system or a microbial system, including a virus, bacteria or fungus, as otherwise described herein, are targets for ubiquitination mediated by the compounds according to the present invention. Preferably, the target protein is a eukaryotic protein. In certain aspects, the protein binding moiety is a haloalkane (preferably a $C_1$-$C_{10}$ alkyl group which is substituted with at least one halo group, preferably a halo group at the distal end of the alkyl group (i.e., away from the linker or CLM group), which may covalently bind to a dehalogenase enzyme in a patient or subject or in a diagnostic assay.

PTM groups according to the present invention include, for example, include any moiety which binds to a protein specifically (binds to a target protein) and includes the following non-limiting examples of small molecule target protein moieties: Hsp90 inhibitors, kinase inhibitors, HDM2 & MDM2 inhibitors, compounds targeting Human BET Bromodomain-containing proteins, HDAC inhibitors, human lysine methyltransferase inhibitors, angiogenesis inhibitors, nuclear hormone receptor compounds, immunosuppressive compounds, and compounds targeting the aryl hydrocarbon receptor (AHR), among numerous others. The compositions described below exemplify some of the members of these nine types of small molecule target protein binding moieties. Such small molecule target protein binding moieties also include pharmaceutically acceptable salts, enantiomers, solvates and polymorphs of these compositions, as well as other small molecules that may target a protein of interest. These binding moieties are linked to the ubiquitin ligase binding moiety preferably through a linker in order to present a target protein (to which the protein target moiety is bound) in proximity to the ubiquitin ligase for ubiquitination and degradation.

Any protein, which can bind to a protein target moiety or PTM group and acted on or degraded by an ubiquitin ligase is a target protein according to the present invention. In general, target proteins may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catrabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eurkaryotes and prokaryotes including humans as targets for drug therapy, other animals, including domesticated animals, microbials for the determination of targets for antibiotics and other antimicrobials and plants, and even viruses, among numerous others.

In still other embodiments, the PTM group is a haloalkyl group, wherein said alkyl group generally ranges in size from about 1 or 2 carbons to about 12 carbons in length, often about 2 to 10 carbons in length, often about 3 carbons to about 8 carbons in length, more often about 4 carbons to about 6 carbons in length. The haloalkyl groups are generally linear alkyl groups (although branched-chain alkyl groups may also be used) and are end-capped with at least one halogen group, preferably a single halogen group, often a single chloride group. Haloalkyl PT, groups for use in the present invention are preferably represented by the chemical structure—$(CH_2)_v$-Halo where v is any integer from 2 to about 12, often about 3 to about 8, more often about 4 to about 6. Halo may be any halogen, but is preferably Cl or Br, more often Cl.

In another embodiment, the present invention provides a library of compounds. The library comprises more than one compound wherein each composition has a formula of A-B, wherein A is a ubiquitin pathway protein binding moiety (preferably, an E3 ubiquitin ligase moiety as otherwise disclosed herein) and B is a protein binding member of a molecular library, wherein A is coupled (preferably, through a linker moiety) to B, and wherein the ubiquitin pathway protein binding moiety recognizes an ubiquitin pathway protein, in particular, an E3 ubiquitin ligase, such as cereblon. In a particular embodiment, the library contains a specific cereblon E3 ubiquitin ligase binding moiety bound to random target protein binding elements (e.g., a chemical compound library). As such, the target protein is not determined in advance and the method can be used to determine the activity of a putative protein binding element and its pharmacological value as a target upon degradation by ubiquitin ligase.

The present invention may be used to treat a number of disease states and/or conditions, including any disease state and/or condition in which proteins are dysregulated and where a patient would benefit from the degradation of proteins.

In an additional aspect, the description provides therapeutic compositions comprising an effective amount of a compound as described herein or salt form thereof, and a pharmaceutically acceptable carrier, additive or excipient, and optionally an additional bioactive agent. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer. In certain additional embodiments, the disease is multiple myeloma.

In alternative aspects, the present invention relates to a method for treating a disease state or ameliorating the symptoms of a disease or condition in a subject in need thereof by degrading a protein or polypeptide through which a disease state or condition is modulated comprising administering to said patient or subject an effective amount, e.g., a therapeutically effective amount, of at least one compound as described hereinabove, optionally in combination with a pharmaceutically acceptable carrier, additive or excipient, and optionally an additional bioactive agent, wherein the composition is effective for treating or ameliorating the disease or disorder or symptom thereof in the subject. The method according to the present invention may be used to treat a large number of disease states or conditions including cancer, by virtue of the administration of effective amounts of at least one compound described herein. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

In another aspect, the description provides methods for identifying the effects of the degradation of proteins of interest in a biological system using compounds according to the present invention.

The term "target protein" is used to describe a protein or polypeptide, which is a target for binding to a compound according to the present invention and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to CLM or ULM groups through linker groups L.

Target proteins which may be bound to the protein target moiety and degraded by the ligase to which the ubiquitin ligase binding moiety is bound include any protein or peptide, including fragments thereof, analogues thereof, and/or homologues thereof. Target proteins include proteins and peptides having any biological function or activity including structural, regulatory, hormonal, enzymatic, genetic, immunological, contractile, storage, transportation, and signal transduction. In certain embodiments, the target proteins include structural proteins, receptors, enzymes, cell surface proteins, proteins pertinent to the integrated function of a cell, including proteins involved in catalytic activity, aromatase activity, motor activity, helicase activity, metabolic processes (anabolism and catrabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eurkaryotes and prokaryotes, including microbes, viruses, fungi and parasites, including humans, microbes, viruses, fungi and parasites, among numerous others, as targets for drug therapy, other animals, including domesticated animals, microbials for the determination of targets for antibiotics and other antimicrobials and plants, and even viruses, among numerous others.

More specifically, a number of drug targets for human therapeutics represent protein targets to which protein target moiety may be bound and incorporated into compounds according to the present invention. These include proteins which may be used to restore function in numerous polygenic diseases, including for example B7.1 and B7, TINFR1m, TNFR2, NADPH oxidase, BclIBax and other partners in the apotosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, newokinins and receptors, inosine monophosphate dehydrogenase, p38 MAP Kinase, RaslRaflMEWERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), famesyltransferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further target proteins include Acetyl-CoA carboxylase, adenylosuccinate synthetase, protoporphyrinogen oxidase, and enolpyruvylshikimate-phosphate synthase.

Haloalkane dehalogenase enzymes are another target of specific compounds according to the present invention. Compounds according to the present invention which contain chloroalkane peptide binding moieties ($C_1$-$C_{12}$ often about $C_2$-$C_{10}$ alkyl halo groups) may be used to inhibit and/or degrade haloalkane dehalogenase enzymes which are used in fusion proteins or related diagnostic proteins as described in PCT/US2012/063401 filed Dec. 6, 2011 and published as WO 2012/078559 on Jun. 14, 2012, the contents of which is incorporated by reference herein.

These various protein targets may be used in screens that identify compound moieties which bind to the protein and by incorporation of the moiety into compounds according to the present invention, the level of activity of the protein may be altered for therapeutic end result.

The term "protein target moiety" or PTM is used to describe a small molecule which binds to a target protein or other protein or polypeptide of interest and places/presents that protein or polypeptide in proximity to an ubiquitin ligase such that degradation of the protein or polypeptide by ubiquitin ligase may occur. Non-limiting examples of small molecule target protein binding moieties include Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. The compositions described below exemplify some of the members of these nine types of small molecule target protein.

Exemplary protein target moieties according to the present disclosure include, haloalkane halogenase inhibitors, Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR).

The compositions described below exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest. References which are cited hereinbelow are incorporated by reference herein in their entirety.

I. Heat Shock Protein 90 (HSP90) Inhibitors:

HSP90 inhibitors as used herein include, but are not limited to:

1. The HSP90 inhibitors identified in Vallee, et al., "Tricyclic Series of Heat Shock Protein 90 (HSP90) Inhibitors Part I: Discovery of Tricyclic Imidazo[4,5-C]Pyridines as Potent Inhibitors of the HSP90 Molecular Chaperone (2011) J. Med. Chem. 54: 7206, including YKB (N-[4-(3H-imidazo [4,5-C]Pyridin-2-yl)-9H-Fluoren-9-yl]-succinamide):

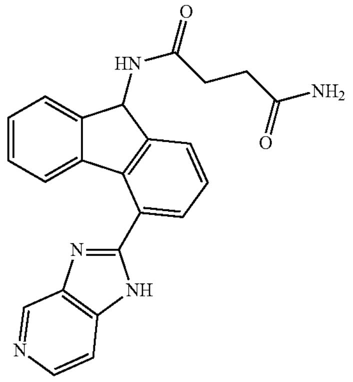 [SMILES: NC(=O)CCC(=O)NC1c2ccccc2-c2c(-c3nc4cnccc4[nH]3)cccc21]

derivatized where a linker group L or a -(L-CLM) group is attached, for example, via the terminal amide group;

2. The HSP90 inhibitor p54 (modified) (8-[(2,4-dimethylphenyl)sulfanyl]-3]pent-4-yn-1-yl-3H-purin-6-amine):

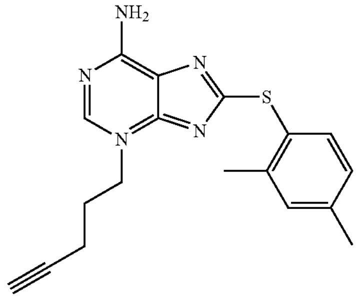

derivatized where a linker group L or a -(L-CLM) group is attached, for example, via the terminal acetylene group;

3. The HSP90 inhibitors (modified) identified in Brough, et al., "4,5-Diarylisoxazole HSP90 Chaperone Inhibitors: Potential Therapeutic Agents for the Treatment of Cancer", J. Med. Chem. vol: 51, pag: 196 (2008), including the compound 2GJ (5-[2,4-dihydroxy-5-(1-methylethyl)phenyl]-n-ethyl-4-[4-(morpholin-4-ylmethyl)phenyl]isoxazole-3-carboxamide) having the structure:

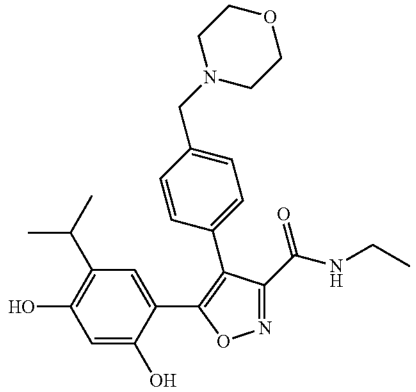 [SMILES: CCNC(=O)c1noc(-c2cc(C(C)C)c(O)cc2O)c1-c1ccc(CN2CCOCC2)cc1]

derivatized, where a linker group L or a -(L-CLM) group is attached, for example, via the amide group (at the amine or at the alkyl group on the amine);

4. The HSP90 inhibitors (modified) identified in Wright, et al., Structure-Activity Relationships in Purine-Based Inhibitor Binding to HSP90 Isoforms, Chem Biol. 2004 June; 11(6):775-85, including the HSP90 inhibitor PU3 having the structure:

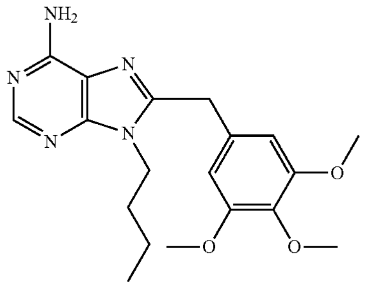 [SMILES: CCCCn1c(Cc2cc(OC)c(OC)c(OC)c2)nc2c(N)ncnc21]

derivatized where a linker group L or -(L-CLM) is attached, for example, via the butyl group; and 5. The HSP90 inhibitor geldanamycin ((4E,6Z,8S,9S,10E,12S,13R,14S,16R)-13-hydroxy-8,14,19-trimethoxy-4,10,12,16-tetramethyl-3,20,22-trioxo-2-azabicyclo[16.3.1] (derivatized) or any of its derivatives (e.g. 17-alkylamino-17-desmethoxygeldanamycin ("17-AAG") or 17-(2-dimethylaminoethyl)amino-17-desmethoxygeldanamycin ("17-DMAG")) (derivatized, where a linker group L or a -(L-CLM) group is attached, for example, via the amide group).

II. Kinase and Phosphatase Inhibitors:

Kinase inhibitors as used herein include, but are not limited to:

1. Erlotinib Derivative Tyrosine Kinase Inhibitor:

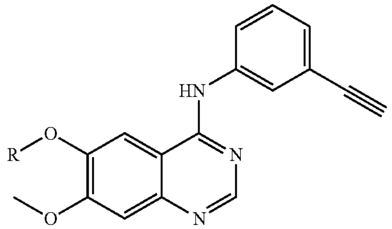

where R is a linker group L or a -(L-CLM) group attached, for example, via the ether group;

2. The kinase inhibitor sunitinib (derivatized):

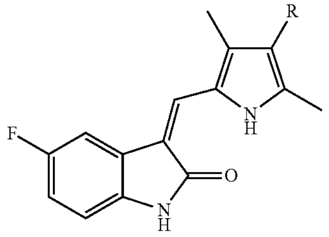

derivatized where R is a linker group L or a -(L-CLM) group attached, for example, to the pyrrole moiety;

3. Kinase Inhibitor sorafenib (derivatized):

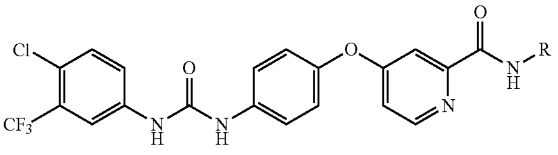

derivatized where R is a linker group L or a -(L-CLM) group attached, for example, to the amide moiety;

4. The kinase inhibitor desatinib (derivatized):

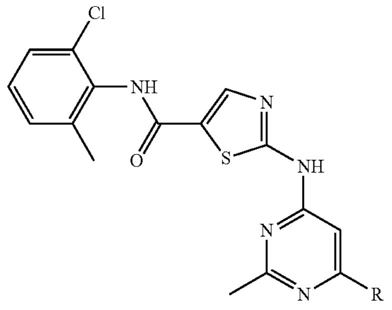

derivatized where R is a linker group L or a -(L-CLM) attached, for example, to the pyrimidine;

5. The kinase inhibitor lapatinib (derivatized):

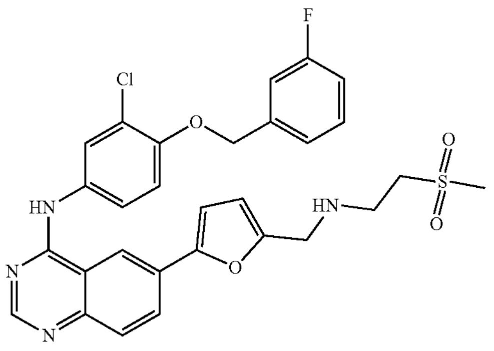 [SMILES: CS(=O)(=O)CCNCc1ccc(-c2ccc3ncnc(Nc4ccc(OCc5cccc(F)c5)c(Cl)c4)c3c2)o1]

derivatized where a linker group L or a -(L-CLM) group is attached, for example, via the terminal methyl of the sulfonyl methyl group;

6. The kinase inhibitor U09-CX-5279 (derivatized):

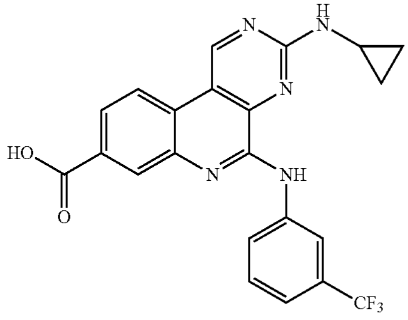 [SMILES: O=C(O)c1ccc2c(c1)nc(Nc1cccc(C(F)(F)F)c1)c1nc(NC3CC3)ncc12]

derivatized where a linker group L or a -(L-CLM) group is attached, for example, via the amine (aniline), carboxylic acid or amine alpha to cyclopropyl group, or cyclopropyl group;

7. The kinase inhibitors identified in Millan, et al., Design and Synthesis of Inhaled P38 Inhibitors for the Treatment of Chronic Obstructive Pulmonary Disease, J. Med. Chem. vol: 54, pag: 7797 (2011), including the kinase inhibitors Y1W and Y1X (Derivatized) having the structures:

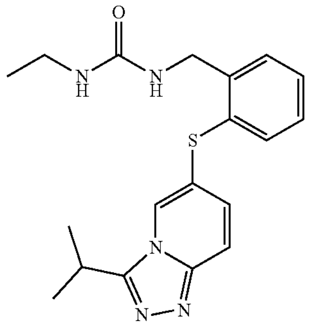 [SMILES: CCNC(=O)NCc1ccccc1Sc1ccc2nnc(C(C)C)n2c1]

YIX or 1-ethyl-3-(2-{[3-(1-methylethyl)[1,2,4] triazolo[4,3-a]pyridine-6-yl]sulfanyl}benzyl)urea, derivatized where a linker group L or a -(L-CLM) group is attached, for example, via the *i*propyl group;

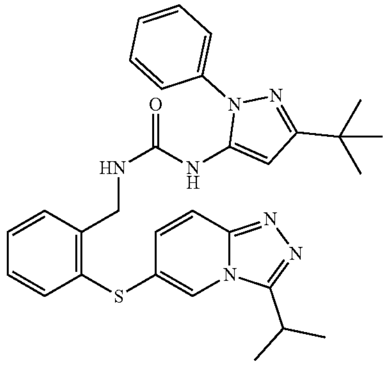 [SMILES: CC(C)c1nnc2ccc(Sc3ccccc3CNC(=O)Nc3cc(C(C)(C)C)nn3-c3ccccc3)cn12]

YIW or 1-(3-tert-butyl-1-phenyl-1H-pyrazol-5-yl)-3-(2-{[3-(1-methylethyl)[1,2,4]triazolo[4,3-a]pyridin-6-yl]sulfanyl}benzyl)urea derivatized where a linker group L or a -(L-CLM) group is attached, for example, preferably via either the i-propyl group or the t-butyl group;

8. The kinase inhibitors identified in Schenkel, et al., Discovery of Potent and Highly Selective Thienopyridine Janus Kinase 2 Inhibitors J. Med. Chem., 2011, 54 (24), pp 8440-8450, including the compounds 6TP and 0TP (Derivatized) having the structures:

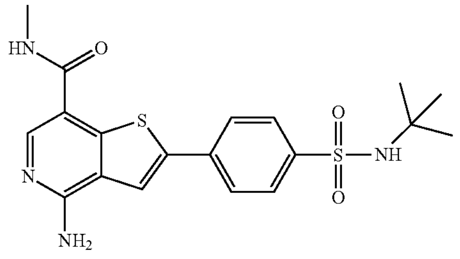 [SMILES: CNC(=O)c1cnc(N)c2cc(-c3ccc(S(=O)(=O)NC(C)(C)C)cc3)sc12]

6TP or 4-amino-2-[4-(tert-butylsulfamoyl)phenyl]-N-methylthieno[3,2-c]pyridine-7-carboxamide; derivatized where a linker group L or a -(L-CLM) group is attached, for example, via the terminal methyl group bound to amide moiety;

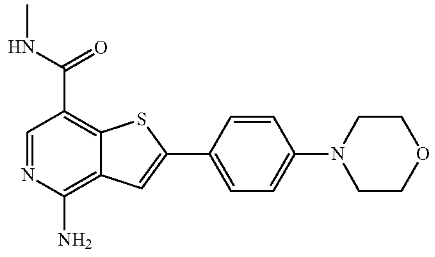 [SMILES: CNC(=O)c1cnc(N)c2cc(-c3ccc(N4CCOCC4)cc3)sc12]

0TP or 4-amino-N-methyl-2-[4-(morpholin-4-yl)phenyl]thieno[3,2-c]pyridine-7-carboxamide, derivatized where a linker group L or a -(L-CLM) group is attached, for example, via the terminal methyl group bound to the amide moiety;

9. The kinase inhibitors identified in Van Eis, et al., "2,6-Naphthyridines as potent and selective inhibitors of the novel protein kinase C isozymes", *Biorg. Med. Chem. Lett.* 2011 Dec. 15; 21(24):7367-72, including the kinase inhibitor 07U having the structure:

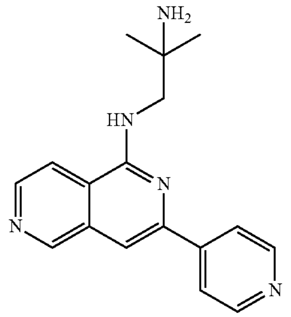 [SMILES: CC(C)(N)CNc1nc(-c2ccncc2)cc2cnccc12]

07U or 2-methyl-N-1-[3-(pyridine-4-yl)-2,6-naphthyridin-1-yl]propane-1,2-diamine derivatized where a linker group L or a -(L-CLM) group is attached, for example, via the secondary amine or terminal amino group;

10. The kinase inhibitors identified in Lountos, et al., "Structural Characterization of Inhibitor Complexes with Checkpoint Kinase 2 (Chk2), a Drug Target for Cancer Therapy", *J. STRUCT. BIOL. vol:* 176, pag: 292 (2011), including the kinase inhibitor YCF having the structure:

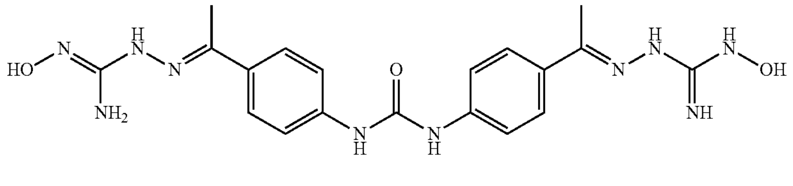 [SMILES: C/C(=N\NC(=N)NO)c1ccc(NC(=O)Nc2ccc(/C(C)=N/N/C(N)=N/O)cc2)cc1]

derivatized where a linker group L or a -(L-CLM) group is attached, for example, via either of the terminal hydroxyl groups;

11. The kinase inhibitors identified in Lountos, et al., "Structural Characterization of Inhibitor Complexes with Checkpoint Kinase 2 (Chk2), a Drug Target for Cancer Therapy", J. STRUCT. BIOL. vol: 176, pag: 292 (2011), including the kinase inhibitors XK9 and NXP (derivatized) having the structures:

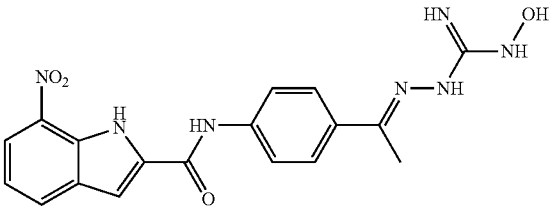 [SMILES: C/C(=N\NC(=N)NO)c1ccc(NC(=O)c2cc3cccc([N+](=O)[O-])c3[nH]2)cc1]

XK9 or N-{4-[(1E)-N—(N-hydroxycarbamimidoyl)ethanehydrazonoyl]phenyl}-7-nitro-1H-indole-2-carboxamide;

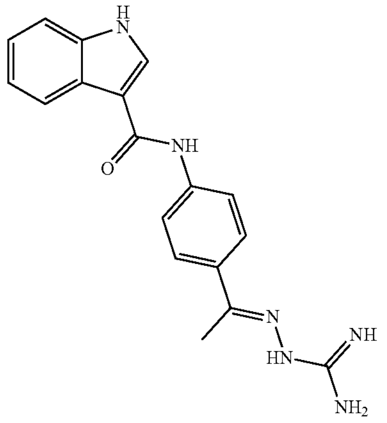 [SMILES: C/C(=N\NC(=N)N)c1ccc(NC(=O)c2c[nH]c3ccccc23)cc1]

NXP or N-{4-[(1E)-N-carbamimidoylethane hydrazonoyl] phenyl}-1H-indole-3-carboxamide derivatized where a linker group L or a -(L-CLM) group is attached, for example, via the terminal hydroxyl group (XK9) or the hydrazone group (NXP);

12. The kinase inhibitor afatinib (derivatized) (N-[4-[(3-chloro-4-fluorophenyl)amino]-7-[[(3S)-tetrahydro-3-furanyl]oxy]-6-quinazolinyl]-4(dimethylamino)-2-butenamide) (Derivatized where a linker group L or a -(L-CLM) group is attached, for example, via the aliphatic amine group);

13. The kinase inhibitor fostamatinib (derivatized) ([6-({5-fluoro-2-[(3,4,5-trimethoxyphenyl) amino]pyrimidin-4-yl}amino)-2,2-dimethyl-3-oxo-2,3-dihydro-4H-pyrido[3,2-b]-1,4-oxazin-4-yl]methyl disodium phosphate hexahydrate) (Derivatized where a linker group L or a -(L-CLM) group is attached, for example, via a methoxy group);

14. The kinase inhibitor gefitinib (derivatized) (N-(3-chloro-4-fluoro-phenyl)-7-methoxy-6-(3-morpholin-4-ylpropoxy) quinazolin-4-amine):

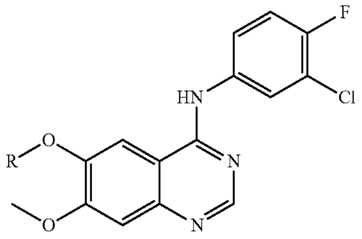

derivatized where a linker group L or a -(L-CLM) group is attached, for example, via a methoxy or ether group;

15. The kinase inhibitor lenvatinib (derivatized) (4-[3-chloro-4-(cyclopropylcarbamoylamino) phenoxy]-7-methoxy-quinoline-6-carboxamide) (derivatized where a linker group L or a -(L-CLM) group is attached, for example, via the cyclopropyl group);

16. The kinase inhibitor vandetanib (derivatized) (N-(4-bromo-2-fluorophenyl)-6-methoxy-7-[(1-methylpiperidin-4-yl)methoxy]quinazolin-4-amine) (derivatized where a linker group L or a -(L-CLM) group is attached, for example, via the methoxy or hydroxyl group);

17. The kinase inhibitor vemurafenib (derivatized) (propane-1-sulfonic acid {3-[5-(4-chlorophenyl)-1H-pyrrolo[2,3-b]pyridine-3-carbonyl]-2,4-difluoro-phenyl}-amide), derivatized where a linker group L or a -(L-CLM) group is attached, for example, via the sulfonyl propyl group;

18. The kinase inhibitor Gleevec (derivatized):

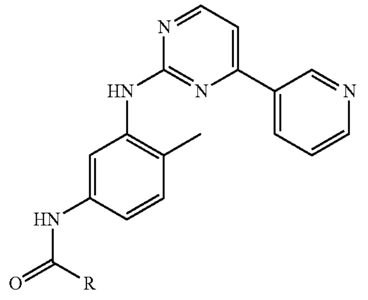

derivatized where R as a linker group L or a -(L-CLM) group is attached, for example, via the amide group or via the aniline amine group;

19. The kinase inhibitor pazopanib (derivatized) (VEGFR3 inhibitor):

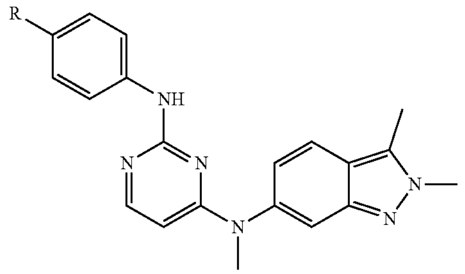

derivatized where R is a linker group L or a -(L-CLM) group attached, for example, to the phenyl moiety or via the aniline amine group;

20. The kinase inhibitor AT-9283 (Derivatized) Aurora Kinase Inhibitor

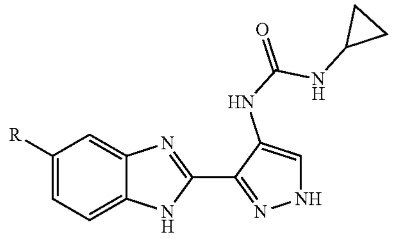

where R is a linker group L or a -(L-CLM) group attached, for example, to the phenyl moiety);

21. The kinase inhibitor TAE684 (derivatized) ALK inhibitor

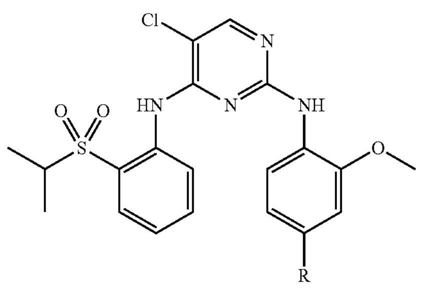

where R is a linker group L or a -(L-CLM) group attached, for example, to the phenyl moiety);

22. The kinase inhibitor nilotanib (derivatized) Abl inhibitor:

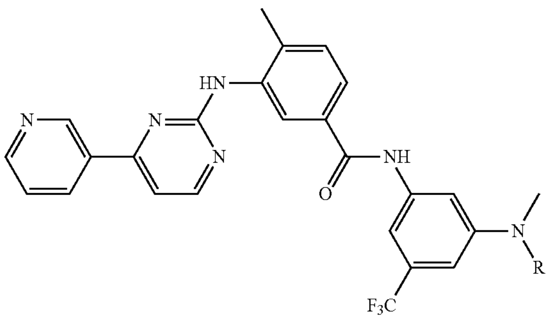

derivatized where R is a linker group L or a -(L-CLM) group attached, for example, to the phenyl moiety or the aniline amine group;

23. Kinase Inhibitor NVP-BSK805 (derivatized) JAK2 Inhibitor

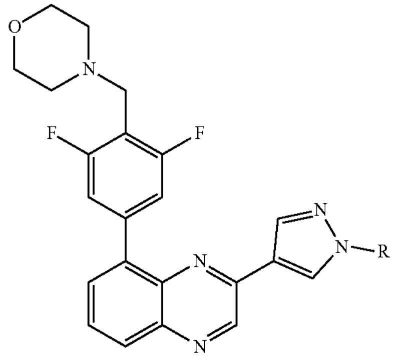

derivatized where R is a linker group L or a -(L-CLM) group attached, for example, to the phenyl moiety or the diazole group;

24. Kinase Inhibitor crizotinib Derivatized Alk Inhibitor

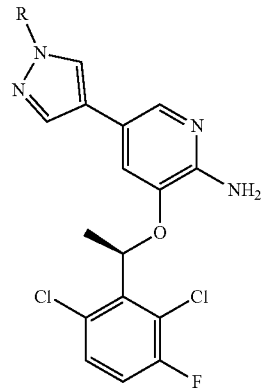

derivatized where R is a linker group L or a -(L-CLM) group attached, for example, to the phenyl moiety or the diazole group;

25. Kinase Inhibitor JNJ FMS (derivatized) Inhibitor

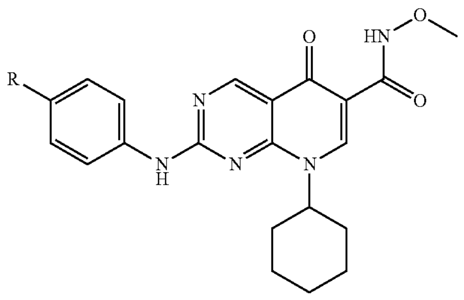

derivatized where R is a linker group L or a -(L-CLM) group attached, for example, to the phenyl moiety;

26. The kinase inhibitor foretinib (derivatized) Met Inhibitor

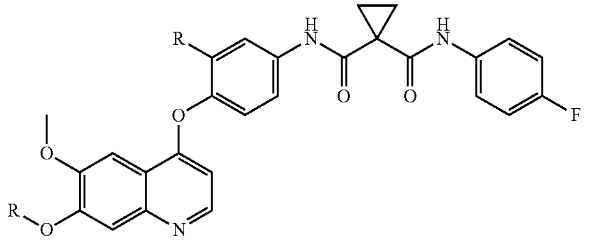

derivatized where R is a linker group L or a -(L-CLM) group attached, for example, to the phenyl moiety or a hydroxyl or ether group on the quinoline moiety;

27. The allosteric Protein Tyrosine Phosphatase Inhibitor PTP1B (derivatized):

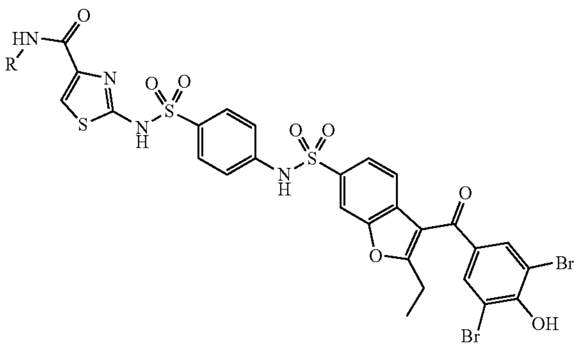

derivatized where a linker group L or a -(L-CLM) group is attached, for example, at R, as indicated;

28. The inhibitor of SHP-2 Domain of Tyrosine Phosphatase (derivatized):

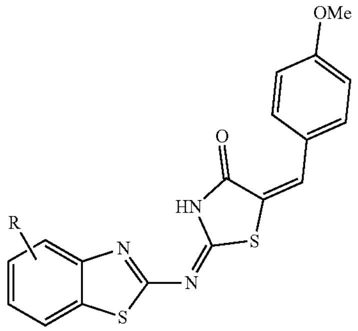

derivatized where a linker group L or a -(L-CLM) group is attached, for example, at R;

29. The inhibitor (derivatized of BRAF ($BRAF^{V600E}$)/MEK:

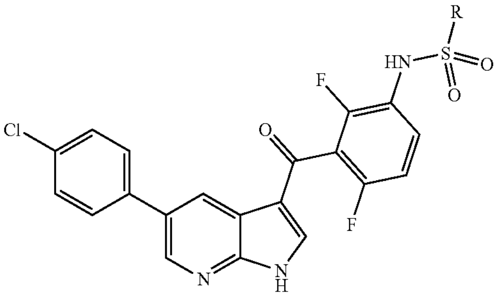

derivatized where a linker group L or a -(L-CLM) group is attached, for example, at R;

30. Inhibitor (derivatized) of Tyrosine Kinase ABL

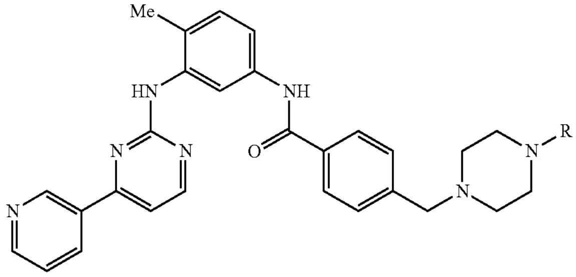

derivatized where a linker group L or a -(L-CLM) group is attached, for example, at R;

31. The kinase inhibitor OSI-027 (derivatized) mTORC1/2 inhibitor

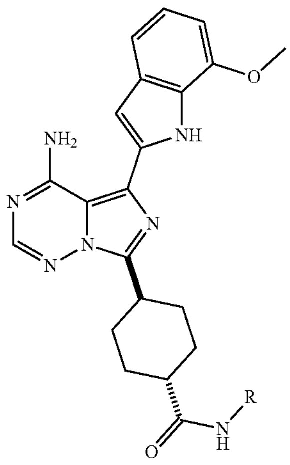

derivatized where a linker group L or a -(L-CLM) group is attached, for example, at R;

32. The kinase inhibitor OSI-930 (derivatized) c-Kit/KDR inhibitor

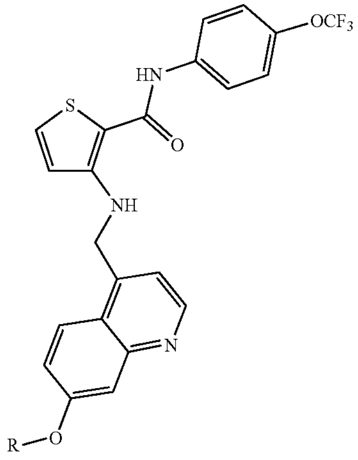

derivatized where a linker group L or a -(L-CLM) group is attached, for example, at R; and 33. The kinase inhibitor OSI-906 (derivatized) IGF1R/IR inhibitor

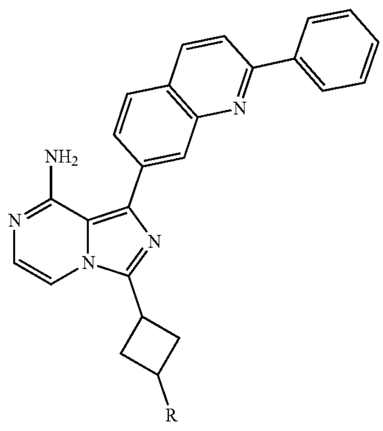

derivatized where a linker group L or a -(L-CLM) group is attached, for example, at R.

Wherein, in any of the embodiments described in sections I-XVII, "R" designates a site for attachment of a linker group L or a -(L-CLM) group on the piperazine moiety.

III. HDM2/MDM2 Inhibitors:

HDM2/MDM2 inhibitors as used herein include, but are not limited to:

1. The HDM2/MDM2 inhibitors identified in Vassilev, et al., In vivo activation of the p53 pathway by small-molecule antagonists of MDM2, SCIENCE vol: 303, pag: 844-848 (2004), and Schneekloth, et al., Targeted intracellular protein degradation induced by a small molecule: En route to chemical proteomics, Bioorg. Med. Chem. Lett. 18 (2008) 5904-5908, including (or additionally) the compounds nutlin-3, nutlin-2, and nutlin-1 (derivatized) as described below, as well as all derivatives and analogs thereof:

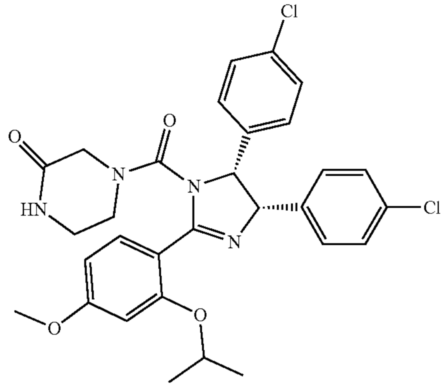 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

(derivatized where a linker group L or a -(L-CLM) group is attached, for example, at the methoxy group or as a hydroxyl group);

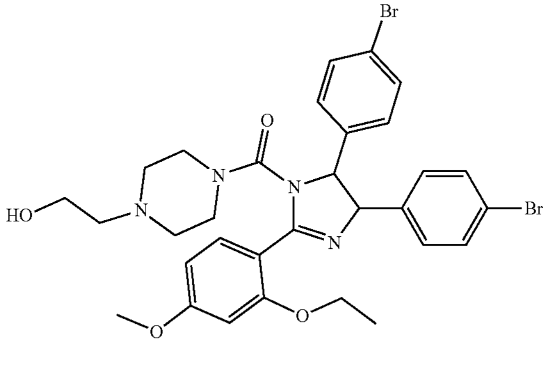 [SMILES: CCOc1cc(OC)ccc1C1=NC(c2ccc(Br)cc2)C(c2ccc(Br)cc2)N1C(=O)N1CCN(CCO)CC1]

(derivatized where a linker group L or a -(L-CLM) group is attached, for example, at the methoxy group or hydroxyl group);

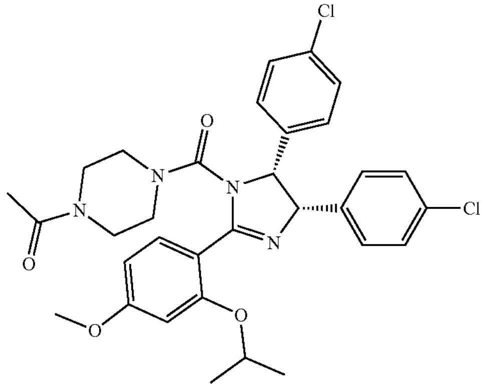 [SMILES: COc1ccc(C2=N[C@@H](c3ccc(Cl)cc3)[C@@H](c3ccc(Cl)cc3)N2C(=O)N2CCN(C(C)=O)CC2)c(OC(C)C)c1]

(derivatized where a linker group L or a -(L-CLM) group is attached, for example, via the methoxy group or as a hydroxyl group); and 2. Trans-4-Iodo-4'-Boranyl-Chalcone

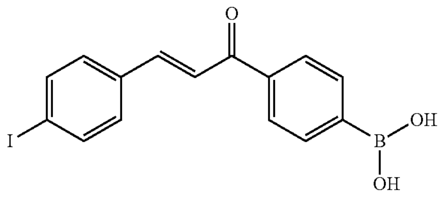 [SMILES: O=C(/C=C/c1ccc(I)cc1)c1ccc(B(O)O)cc1]

(derivatized where a linker group L or a linker group L or a -(L-CLM) group is attached, for example, via a hydroxy group).

IV. Compounds Targeting Human BET Bromodomain-Containing Proteins:

In certain embodiments, "PTM" can be ligands binding to Bromo- and Extra-terminal (BET) proteins BRD2, BRD3 and BRD4. Compounds targeting Human BET Bromodomain-containing proteins include, but are not limited to the compounds associated with the targets as described below, where "R" or "linker" designates a site for linker group L or a -(L-CLM) group attachment, for example:

1. JQ1, Filippakopoulos et al. Selective inhibition of BET bromodomains. Nature (2010):
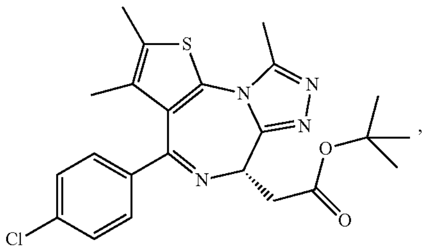
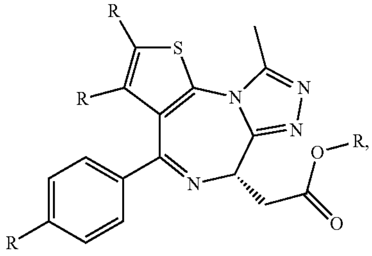
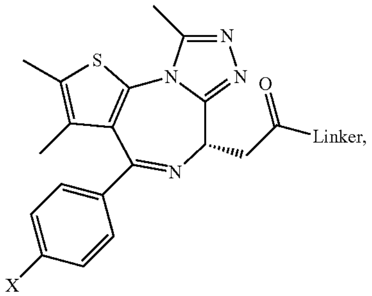
X = Cl, Br, F, H
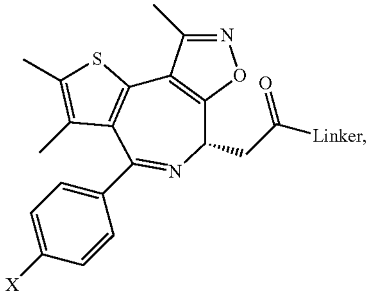
X = Cl, Br, F, H
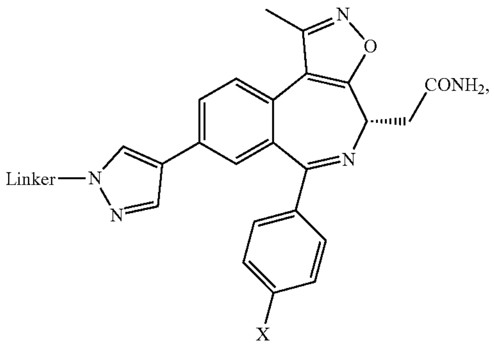
X = Cl, Br, F, H
-continued
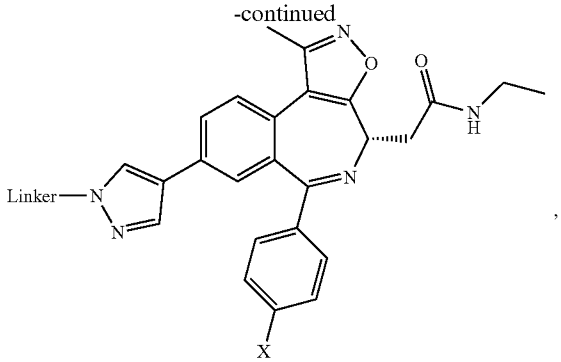
X = Cl, Br, F, H
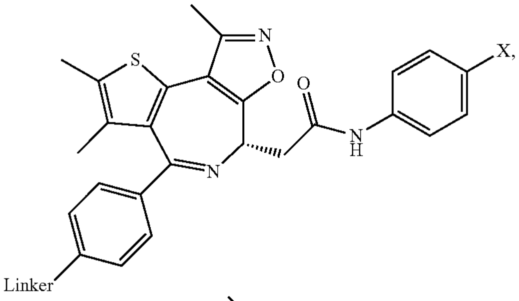
or
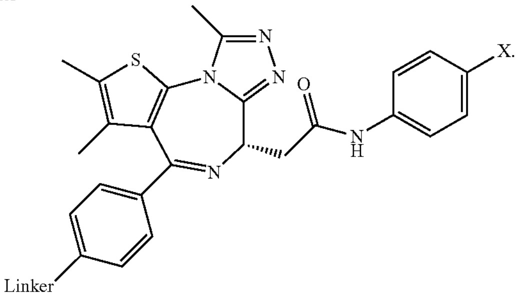
X = H, F
2. I-BET, Nicodeme et al. Supression of Inflammation by a Synthetic Histone Mimic. Nature (2010). Chung et al. Discovery and Characterization of Small Molecule Inhibitors of the BET Family Bromodomains. J. Med Chem. (2011):
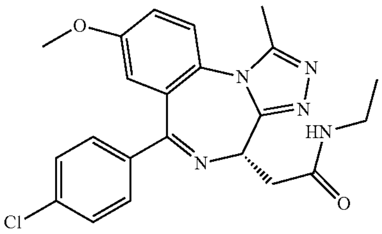
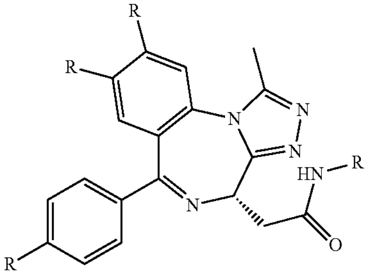

3. Compounds described in Hewings et al. 3,5-Dimethylisoxazoles Act as Acetyl-lysine Bromodomain Ligands. J. Med. Chem. (2011) 54 6761-6770.
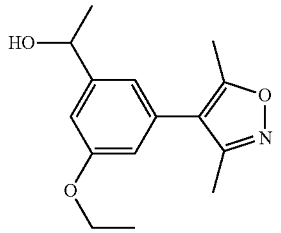
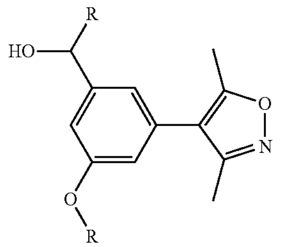
4. I-BET151, Dawson et al. Inhibition of BET Recruitment to Chromatin as an Effective Treatment for MLL-fusion Leukemia. Nature (2011):
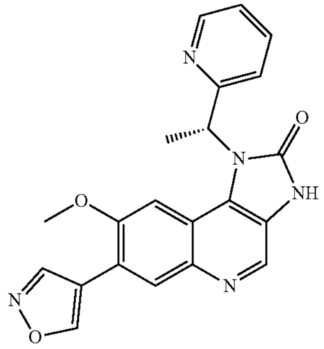
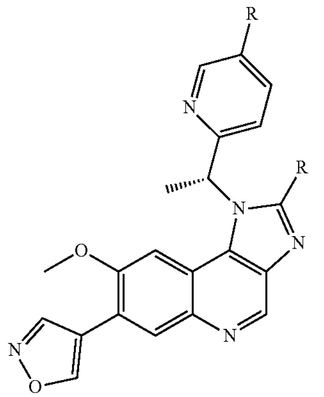
5. Carbazole type (US 2015/0256700)
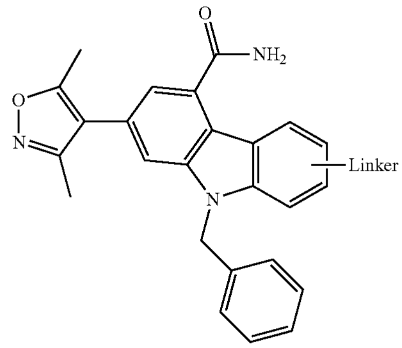
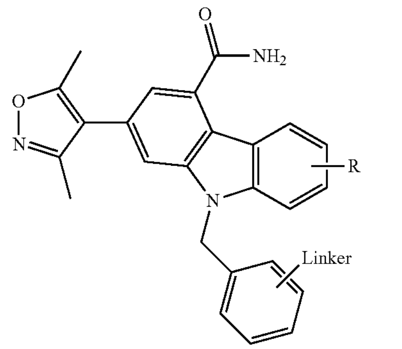
6. Pyrrolopyridone type (US 2015/0148342)
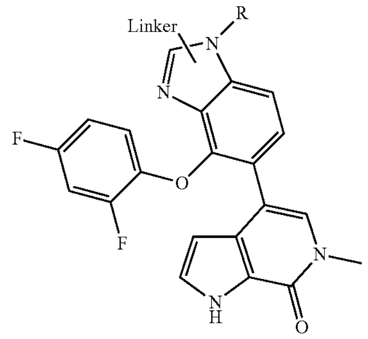
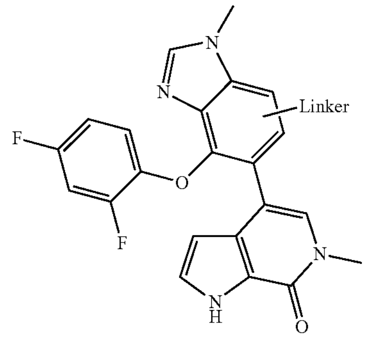

7. Tetrahydroquinoline type (WO 2015/074064)

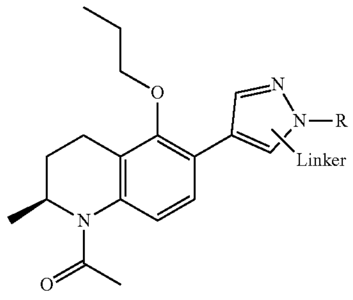

8. Triazolopyrazine type (WO 2015/067770)

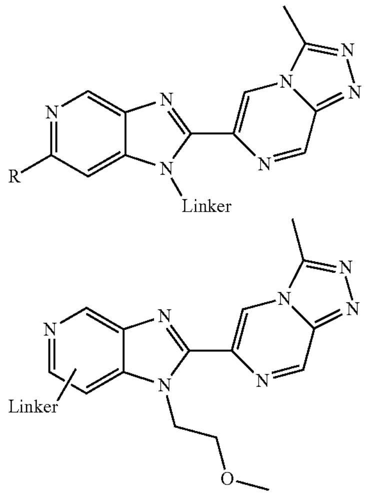

9. Pyridone type (WO 2015/022332)

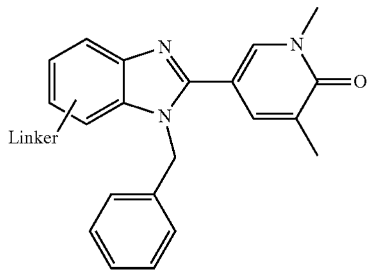

10. Quinazolinone type (WO 2015/015318)

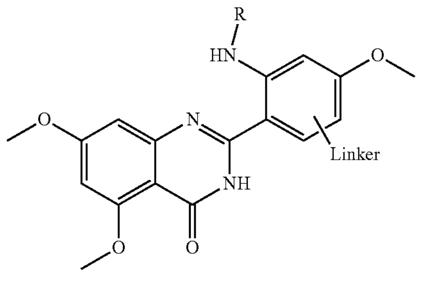

11. Dihydropyridopyrazinone type (WO 2015/011084)

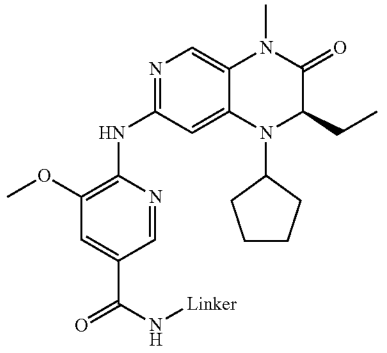

(Where R or L or linker, in each instance, designates a site for attachment, for example, of a linker group L or a -(L-CLM) group).

The following chimeric molecules using cereblon ligands are representatives of BET PROTAC. The methodology described in this invention is not limited to these examples.

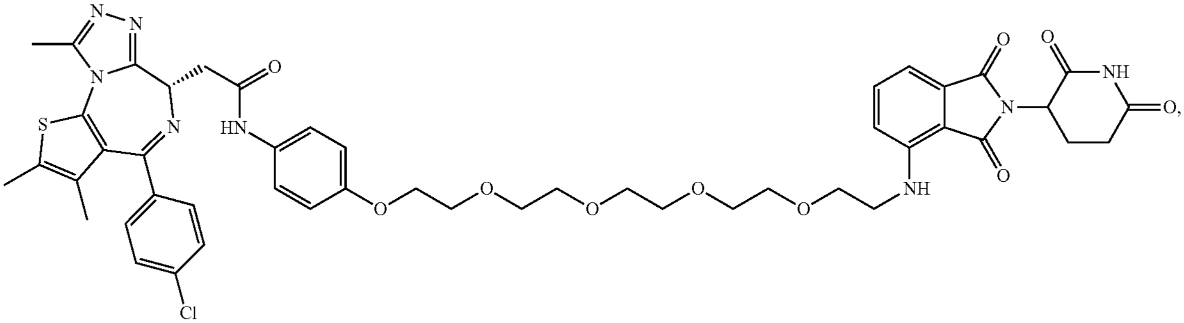,

-continued
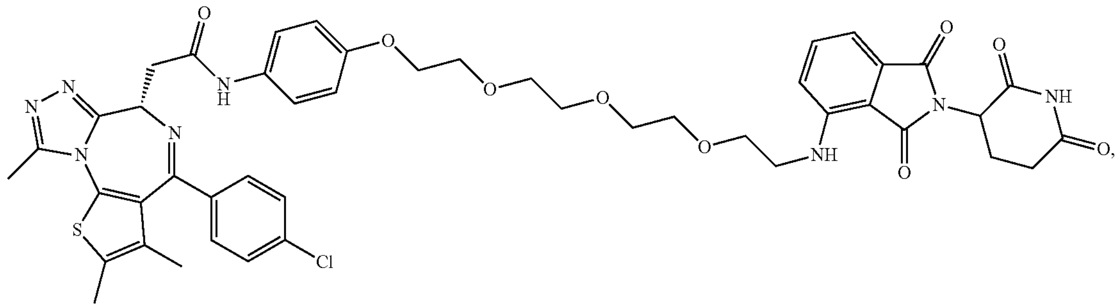
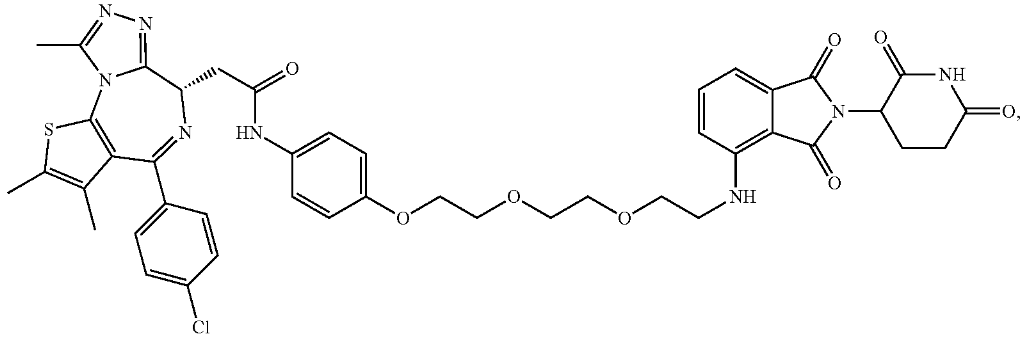
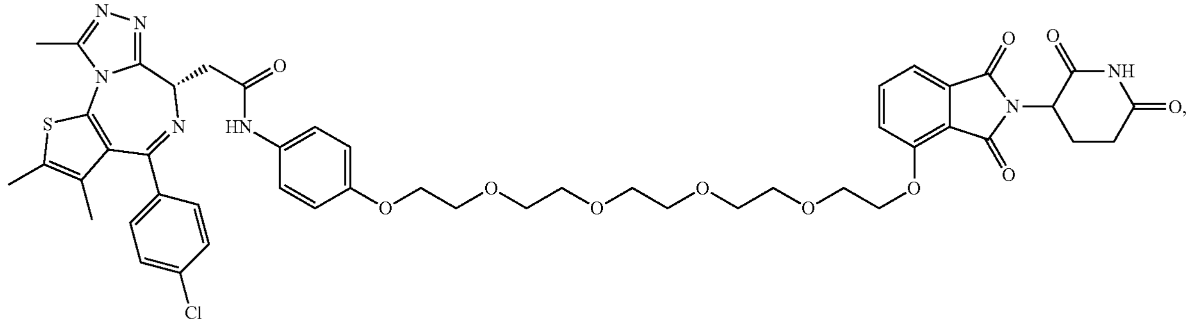
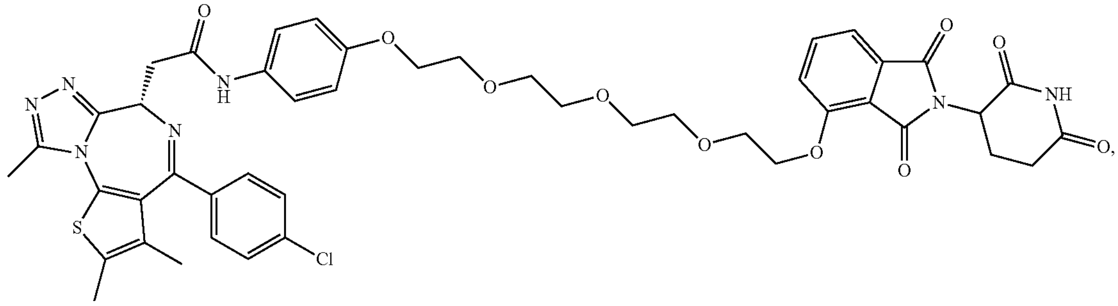
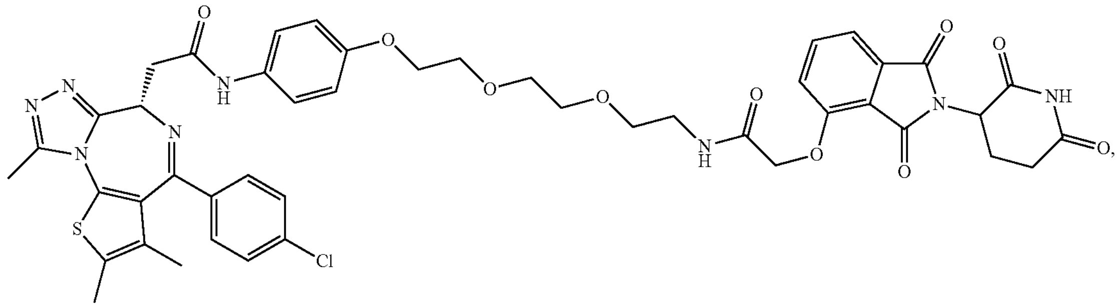

-continued
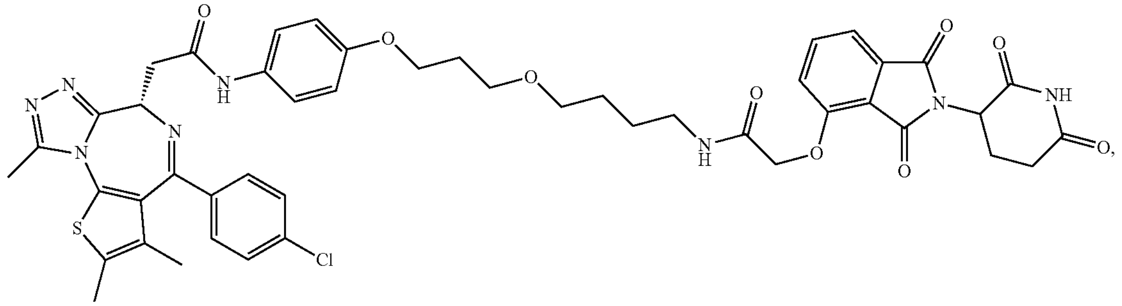
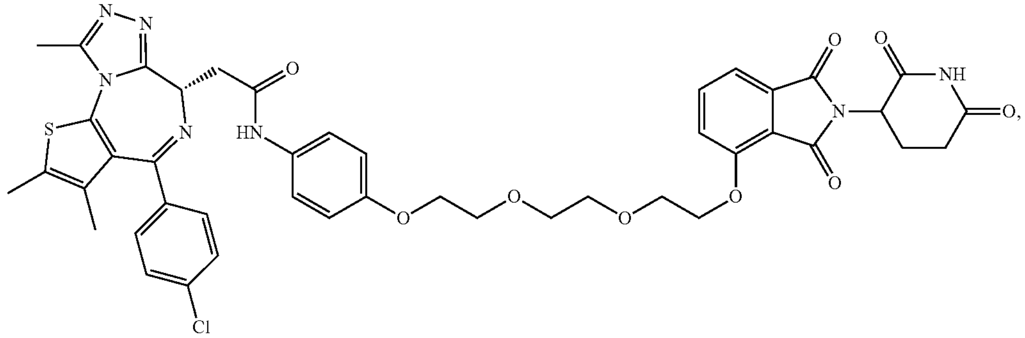
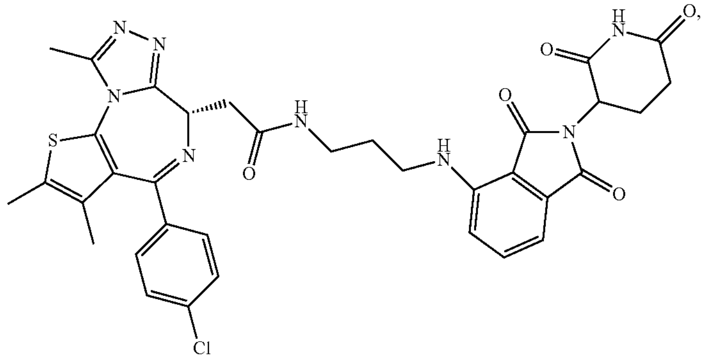
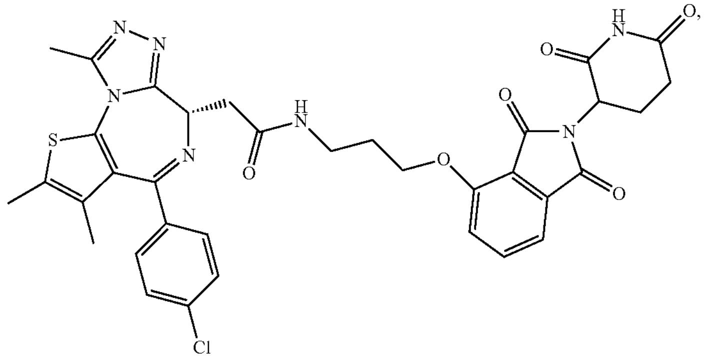
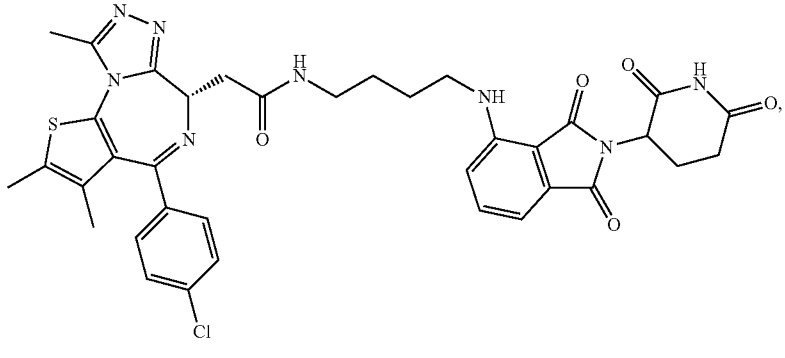

-continued
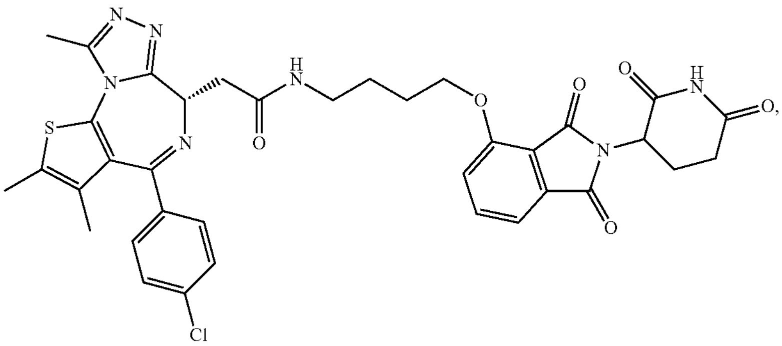
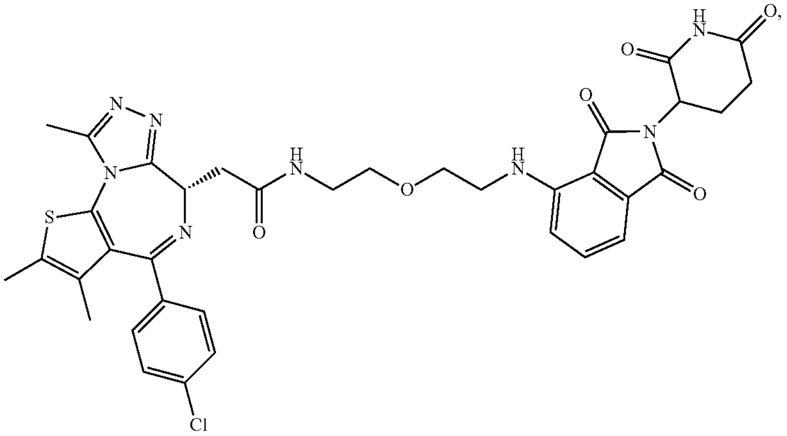
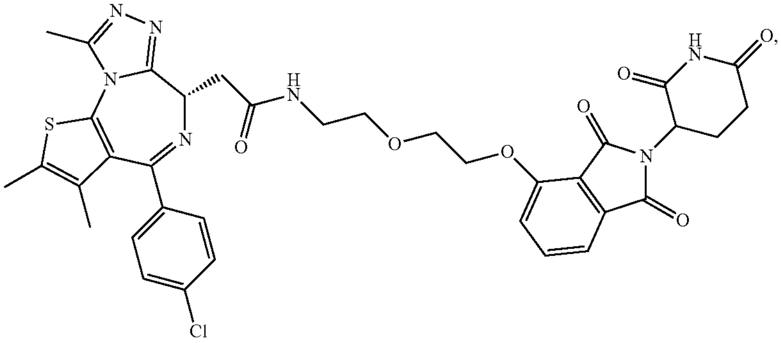
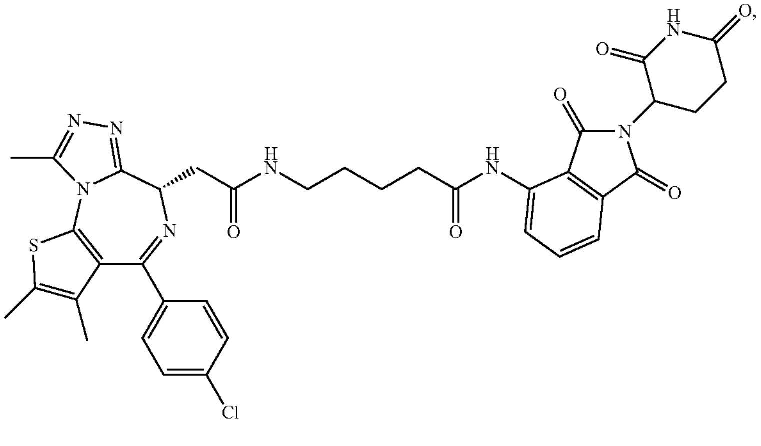

-continued
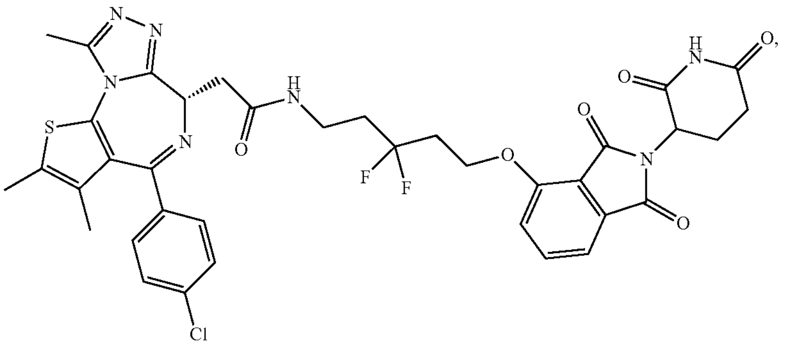
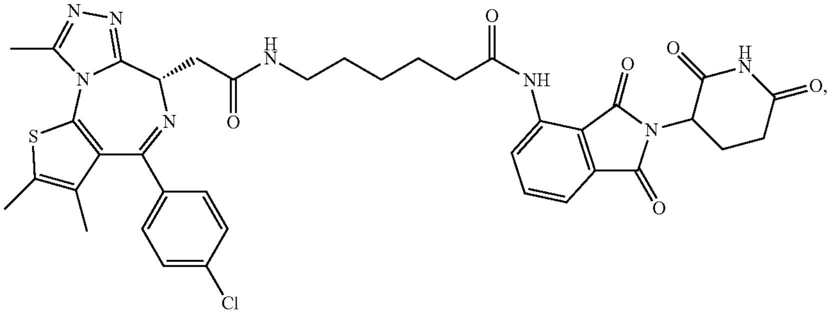
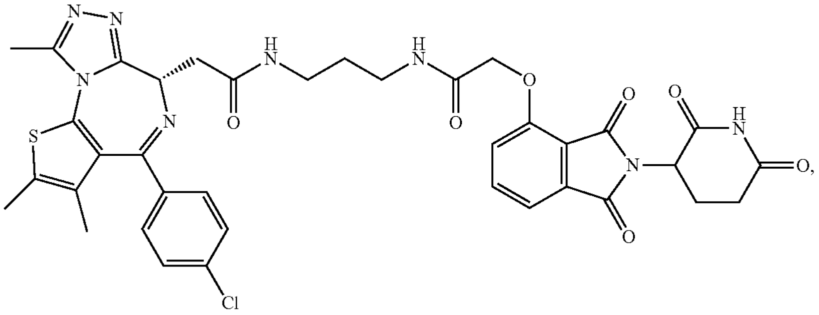
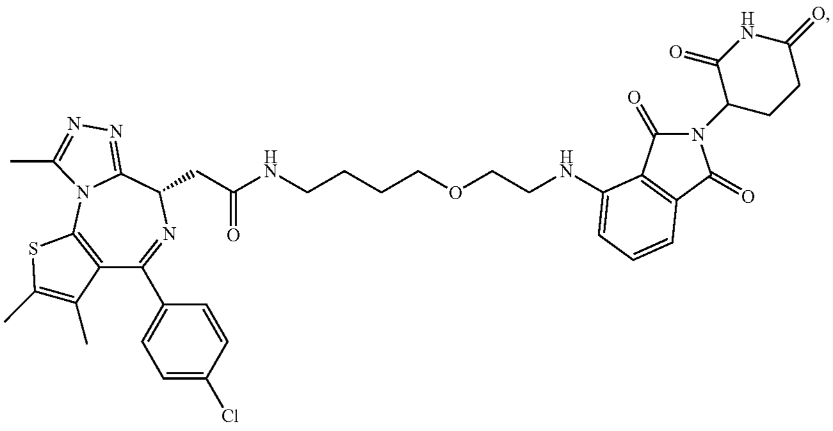

-continued
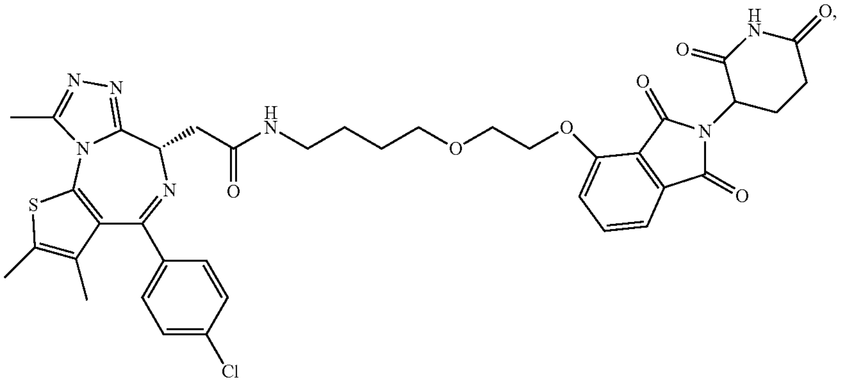
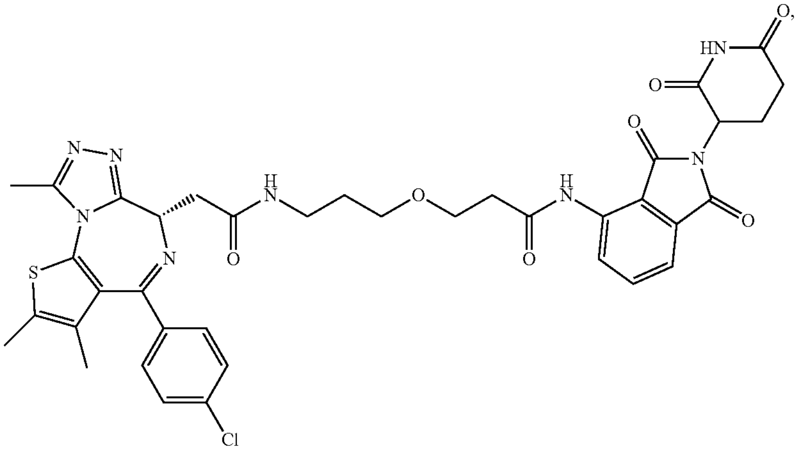
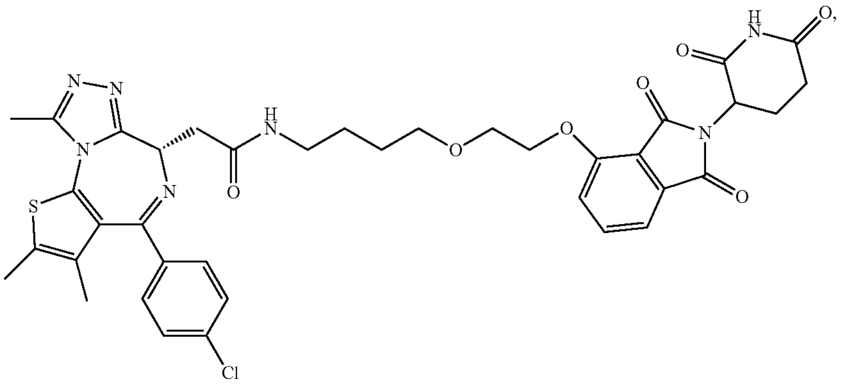
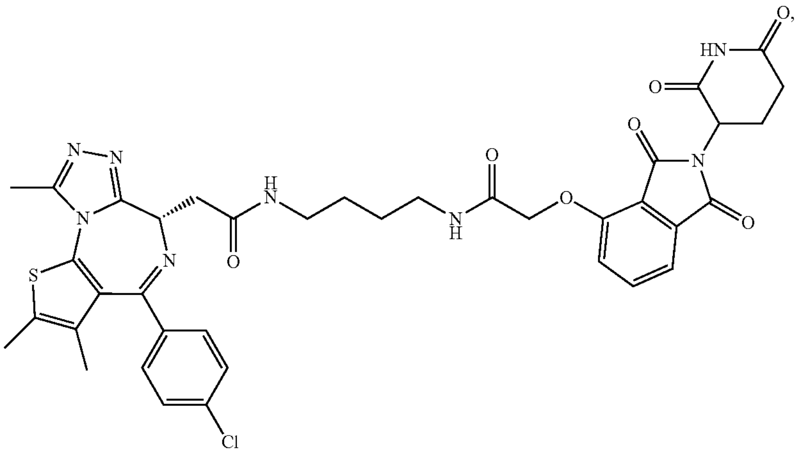

-continued
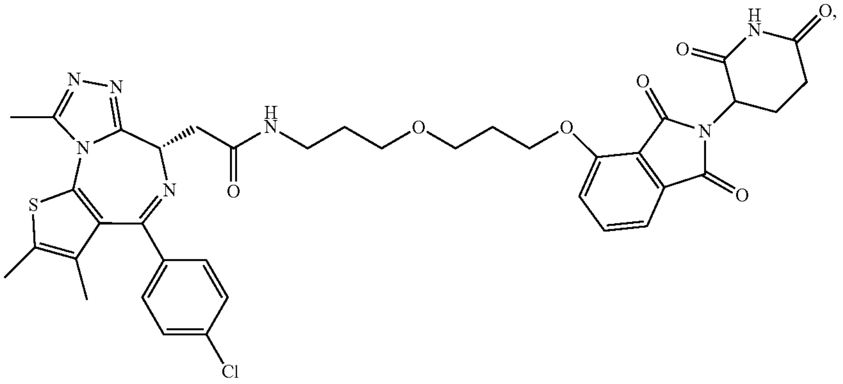
,
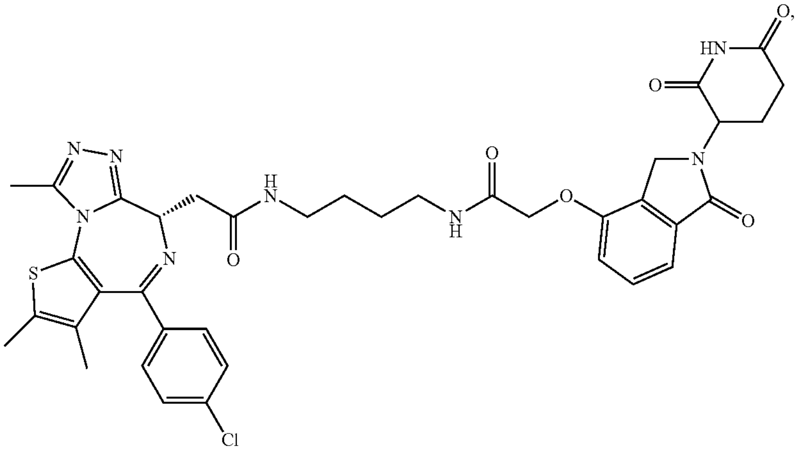
,
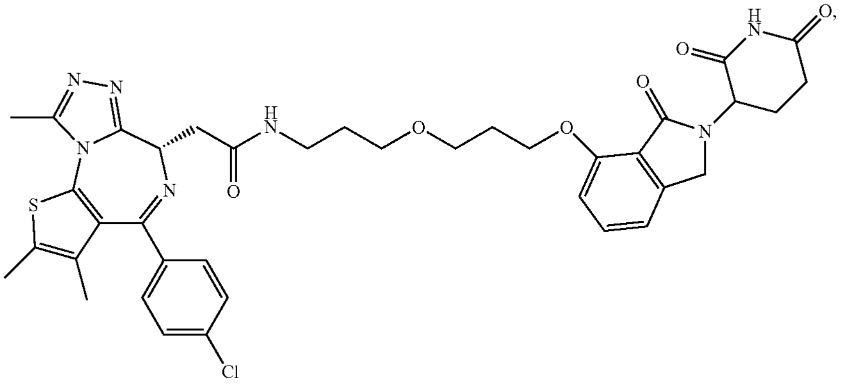
,
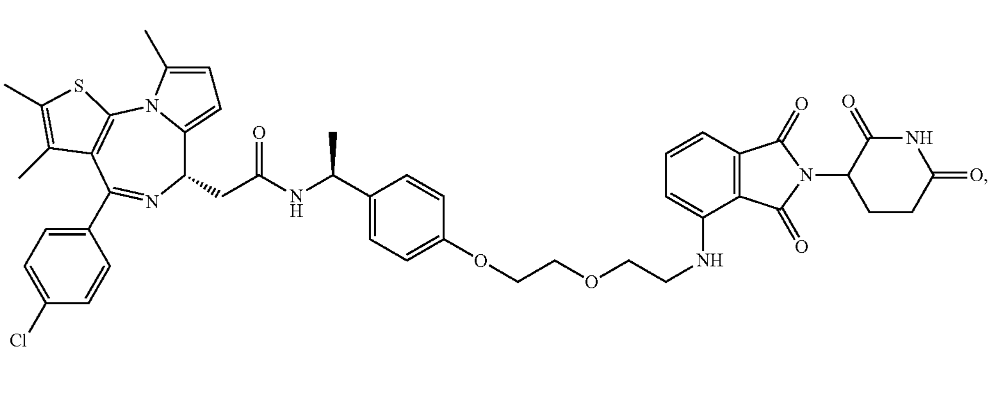
,

-continued
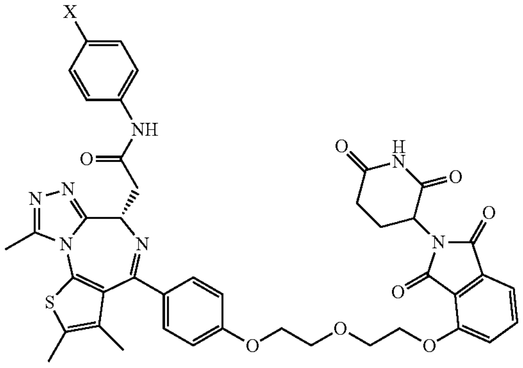,
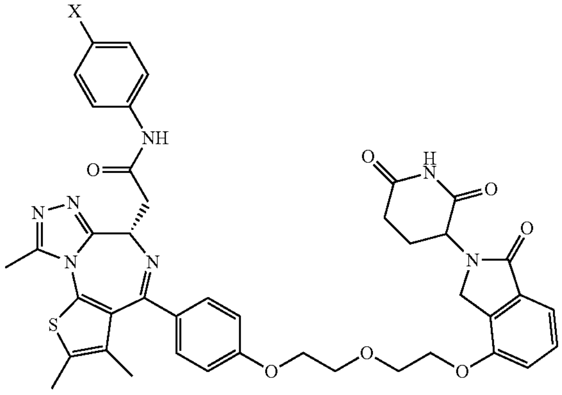,
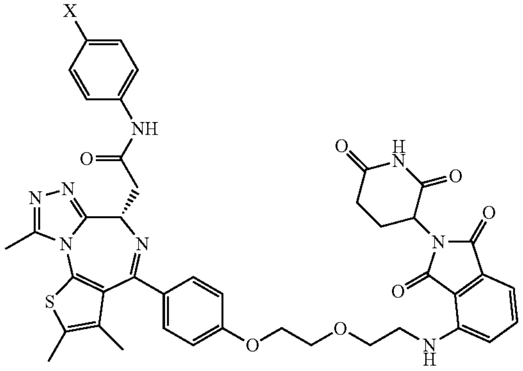,
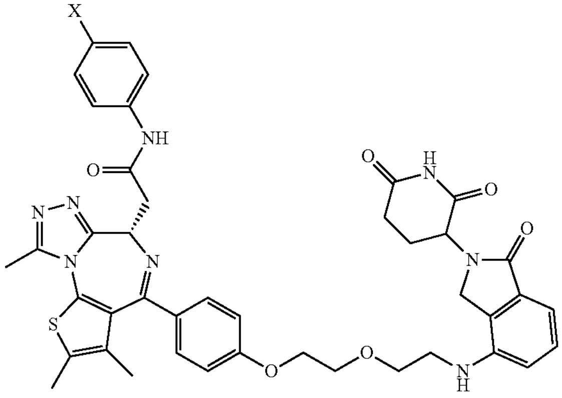,
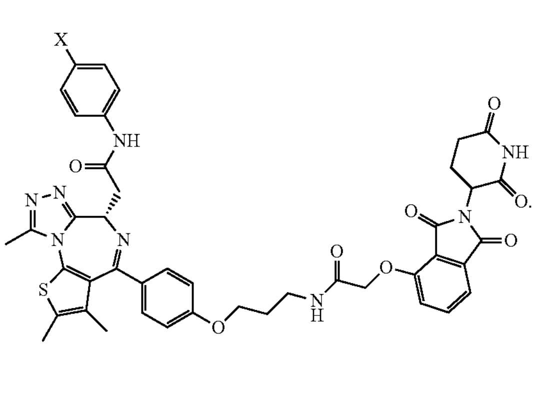.
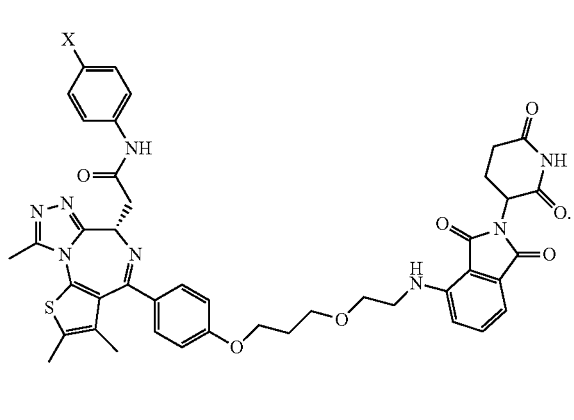.

-continued

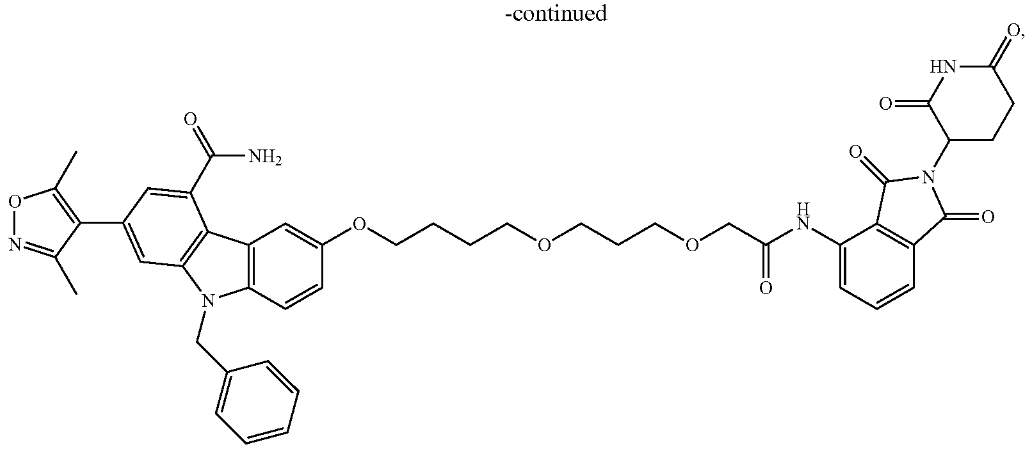

O,

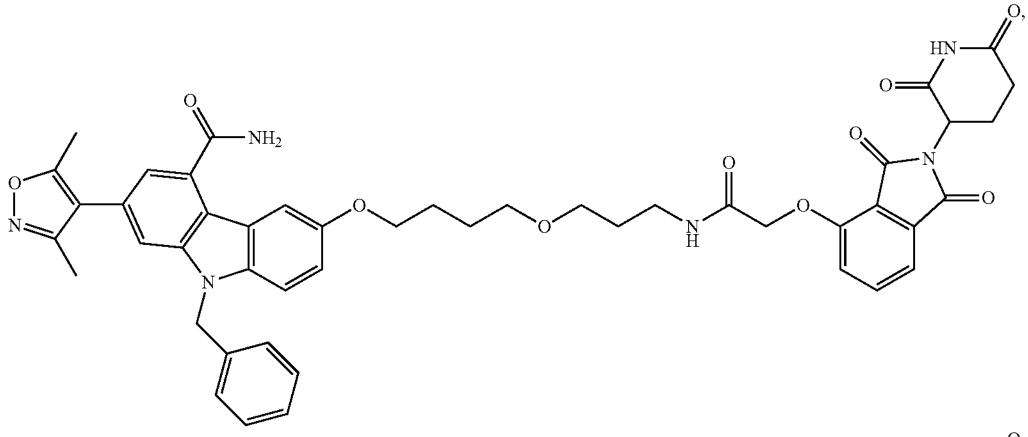

O, and

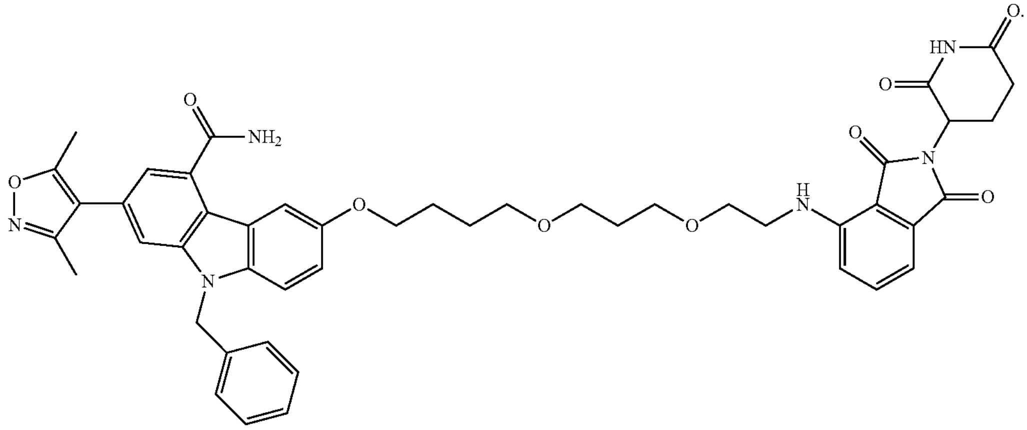

O.

In certain embodiments, each occurrence of X is independently selected from the group consisting of H, —C(═O)NR'R", —OR', —NR'R", —SR', —S(═O)$_2$R', —S(═O)$_2$NR'R", —CR'R"—, —CR'NR'R"—, aryl, heteroaryl, alkyl, cycloalkyl, heterocyclyl, —P(═O)(OR')R", —P(═O)R'R", —OP(═O)(OR')R", —OP(═O)R'R", —Cl, —F, —Br, —I, —CF$_3$, —CN, —NR'S(═O)$_2$NR'R", —NR'C(═O)NR'R", —C(═O)NR'C(═O)R", —NR'C(═N—CN)NR'R", —C(═N—CN)NR'R", —NR'C(═N—CN)R", —NR'C(═C—NO$_2$)NR'R", —S(═O)$_2$NR'C(═O)R", —NO$_2$, —CO$_2$R', —C(C═N—OR')R", —CR'═CR'R", —CCR', —S(C═O)(C═N—R')R", —SF$_5$, —OCF$_3$, a site for linker group L, and a site for another -(L-CLM) group attachment. In other embodiments, each occurrence of R' and R" is independently selected from the group consisting of a bond, H, alkyl, cycloalkyl, aryl, heteroaryl, and heterocyclyl.

V. HDAC Inhibitors:

HDAC Inhibitors (derivatized) include, but are not limited to:

1. Finnin, M. S. et al. Structures of Histone Deacetylase Homologue Bound to the TSA and SAHA Inhibitors. Nature 40, 188-193 (1999).

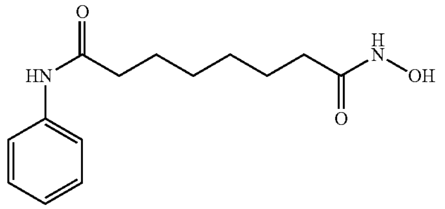

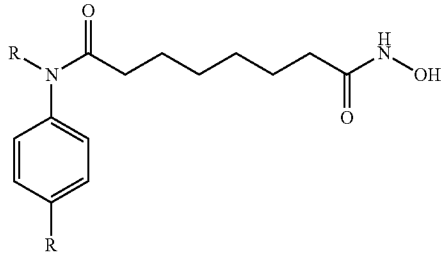

(Derivatized where "R" designates a site for attachment, for example, of a linker group L or a -(L-CLM) group); and 2. Compounds as defined by formula (I) of PCT WO0222577 ("DEACETYLASE INHIBITORS") (Derivatized where a linker group L or a -(L-CLM) group is attached, for example, via the hydroxyl group).

VI. Human Lysine Methyltransferase Inhibitors:

Human Lysine Methyltransferase inhibitors include, but are not limited to:

1. Chang et al. Structural Basis for G9a-Like protein Lysine Methyltransferase Inhibition by BIX-1294. Nat. Struct. Biol. (2009) 16(3) 312.

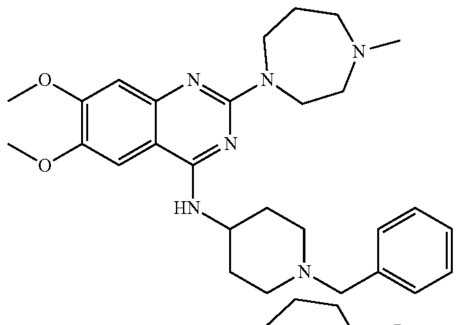

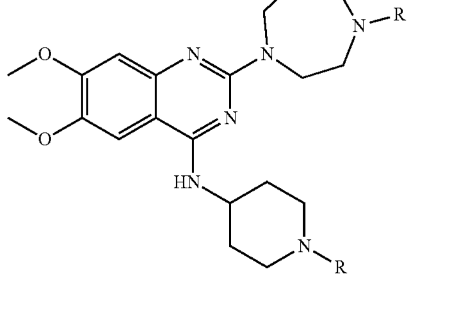

(Derivatized where "R" designates a site for attachment, for example, of a linker group L or a -(L-CLM) group);

2. Liu, F. et al Discovery of a 2,4-Diamino-7-aminoalkoxy-quinazoline as a Potent and Selective Inhibitor of Histone Methyltransferase G9a. J. Med. Chem. (2009) 52(24) 7950.

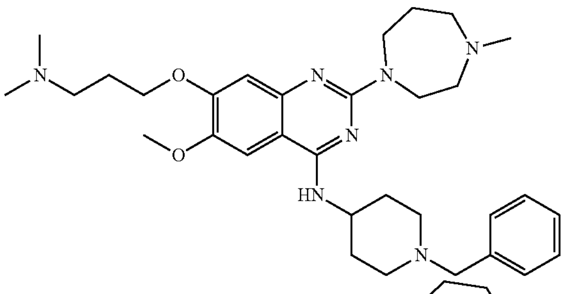

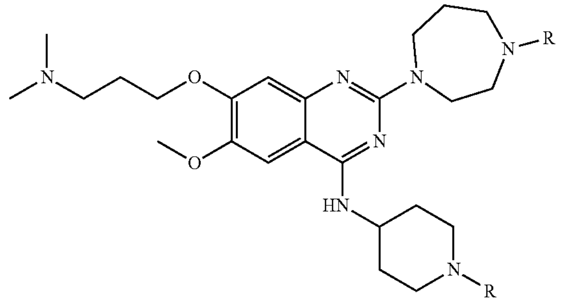

(Derivatized where "R" designates a potential site for attachment, for example, of a linker group L or a -(L-CLM) group);

3. Azacitidine (derivatized) (4-amino-1-β-D-ribofuranosyl-1,3,5-triazin-2(1H)-one) (Derivatized where a linker group L or a -(L-CLM) group is attached, for example, via the hydroxy or amino groups); and 4. Decitabine (derivatized) (4-amino-1-(2-deoxy-b-D-erythro-pentofuranosyl)-1, 3, 5-triazin-2(1H)-one) (Derivatized where a linker group L or a -(L-CLM) group is attached, for example, via either of the hydroxy groups or at the amino group).

VII. Angiogenesis Inhibitors:

Angiogenesis inhibitors include, but are not limited to:

1. GA-1 (derivatized) and derivatives and analogs thereof, having the structure(s) and binding to linkers as described in Sakamoto, et al., Development of Protacs to target cancer-promoting proteins for ubiquitination and degradation, *Mol Cell Proteomics* 2003 December; 2(12):1350-8;

2. Estradiol (derivatized), which may be bound to a linker group L or a -(L-CLM) group as is generally described in Rodriguez-Gonzalez, et al., Targeting steroid hormone receptors for ubiquitination and degradation in breast and prostate cancer, *Oncogene* (2008) 27, 7201-7211;

3. Estradiol, testosterone (derivatized) and related derivatives, including but not limited to DHT and derivatives and analogs thereof, having the structure(s) and binding to a linker group L or a -(L-CLM) group as generally described in Sakamoto, et al., Development of Protacs to target cancer-promoting proteins for ubiquitination and degradation, *Mol Cell Proteomics* 2003 December; 2(12):1350-8; and 4. Ovalicin, fumagillin (derivatized), and derivatives and analogs thereof, having the structure(s) and binding to a linker group L or a -(L-CLM) group as is generally described in Sakamoto, et al., Protacs: chimeric molecules that target proteins to the Skp1-Cullin-F box complex for ubiquitination and degradation *Proc Natl Acad Sci USA*. 2001 Jul. 17; 98(15):8554-9 and U.S. Pat. No. 7,208,157.

VIII. Immunosuppressive Compounds:

Immunosuppressive compounds include, but are not limited to:

1. AP21998 (derivatized), having the structure(s) and binding to a linker group L or a -(L-CLM) group as is generally described in Schneekloth, et al., Chemical Genetic Control of Protein Levels: Selective in Vivo Targeted Degradation, J. AM. CHEM. SOC. 2004, 126, 3748-3754;

2. Glucocorticoids (e.g., hydrocortisone, prednisone, prednisolone, and methylprednisolone) (Derivatized where a linker group L or a -(L-CLM) group is to bound, e.g. to any of the hydroxyls) and beclometasone dipropionate (Derivatized where a linker group or a -(L-CLM) is bound, e.g. to a proprionate);

3. Methotrexate (Derivatized where a linker group or a -(L-CLM) group can be bound, e.g. to either of the terminal hydroxyls);

4. Ciclosporin (Derivatized where a linker group or a -(L-CLM) group can be bound, e.g. at any of the butyl groups);

5. Tacrolimus (FK-506) and rapamycin (Derivatized where a linker group L or a -(L-CLM) group can be bound, e.g. at one of the methoxy groups); and 6. Actinomycins (Derivatized where a linker group L or a -(L-CLM) group can be bound, e.g. at one of the isopropyl groups).

IX. Compounds Targeting the Aryl Hydrocarbon Receptor (AHR):

Compounds targeting the aryl hydrocarbon receptor (AHR) include, but are not limited to:

1. Apigenin (Derivatized in a way which binds to a linker group L or a -(L-CLM) group as is generally illustrated in Lee, et al., Targeted Degradation of the Aryl Hydrocarbon Receptor by the PROTAC Approach: A Useful Chemical Genetic Tool, Chem Bio Chem Volume 8, Issue 17, pages 2058-2062, Nov. 23, 2007); and 2. SR1 and LGC006 (derivatized such that a linker group L or a -(L-CLM) is bound), as described in Boitano, et al., Aryl Hydrocarbon Receptor Antagonists Promote the Expansion of Human Hematopoietic Stem Cells, *Science* 10 Sep. 2010: Vol. 329 no. 5997 pp. 1345-1348.

X. Compounds Targeting RAF Receptor (Kinase):

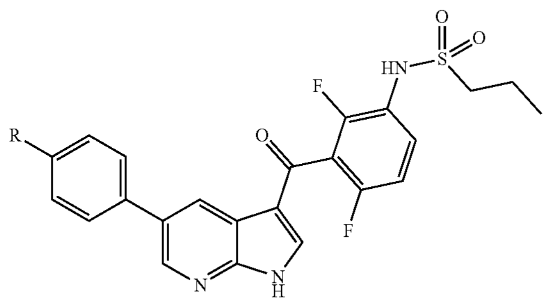

PLX4032 (Derivatized where "R" designates a site for linker group L or -(L-CLM) group attachment, for example).

XI. Compounds Targeting FKBP:

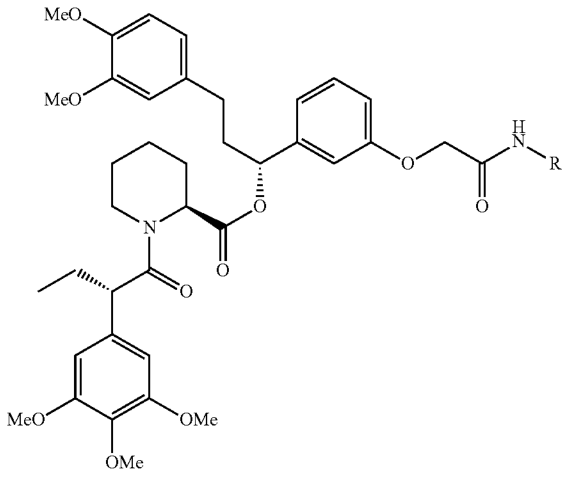

(Derivatized where "R" designates a site for a linker group L or a -(L-CLM) group attachment, for example).

XII. Compounds Targeting Androgen Receptor (AR)

1. RU59063 Ligand (derivatized) of Androgen Receptor

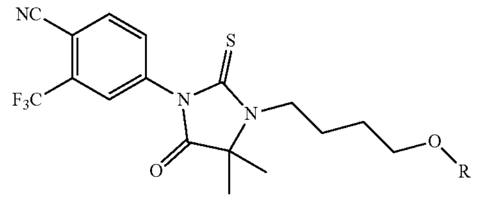

(Derivatized where "R" designates a site for a linker group L or a -(L-CLM) group attachment, for example).

2. SARM Ligand (derivatized) of Androgen Receptor

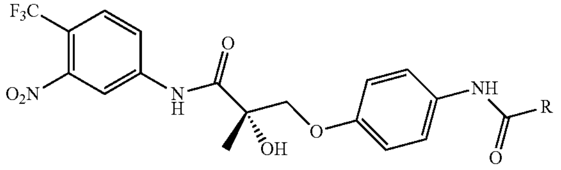

(Derivatized where "R" designates a site for a linker group L or a -(L-CLM) group attachment, for example).

3. Androgen Receptor Ligand DHT (derivatized)

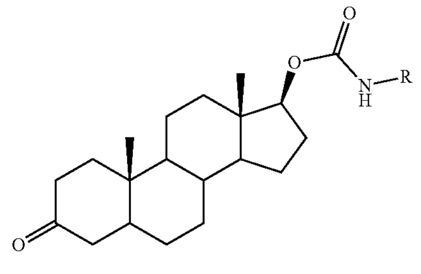

(Derivatized where "R" designates a site for a linker group L or -(L-CLM) group attachment, for example).

4. MDV3100 Ligand (derivatized)

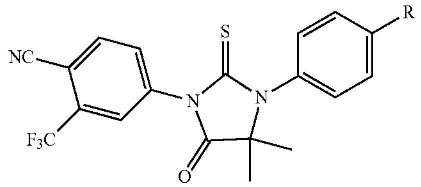

5. ARN-509 Ligand (derivatized)

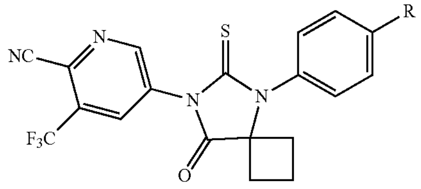

6. Hexahydrobenzisoxazoles

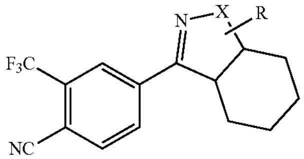

7. Tetramethylcyclobutanes

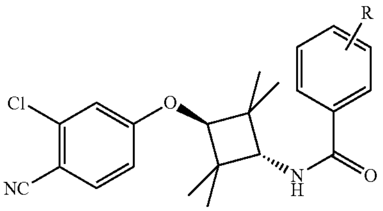

XIII. Compounds Targeting Estrogen Receptor (ER) ICI-182780

1. Estrogen Receptor Ligand

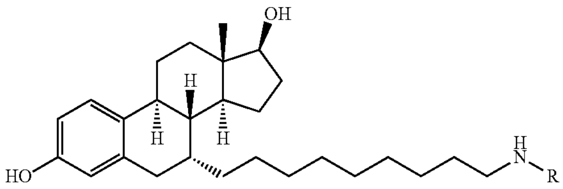

(Derivatized where "R" designates a site for linker group L or -(L-CLM) group attachment).

XIV. Compounds Targeting Thyroid Hormone Receptor (TR)

1. Thyroid Hormone Receptor Ligand (derivatized)

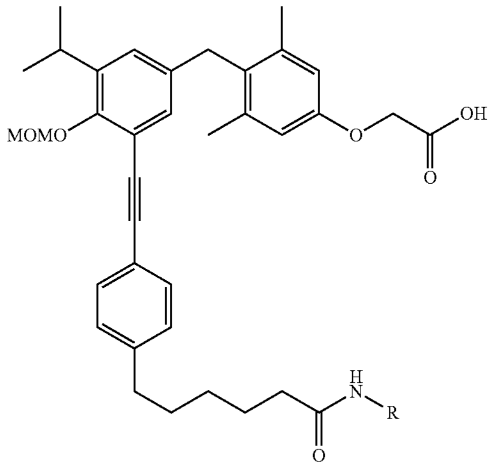

(Derivatized where "R" designates a site for linker group L or -(L-CLM) group attachment and MOMO indicates a methoxymethoxy group).

XV. Compounds Targeting HIV Protease

1. Inhibitor of HIV Protease (Derivatized)

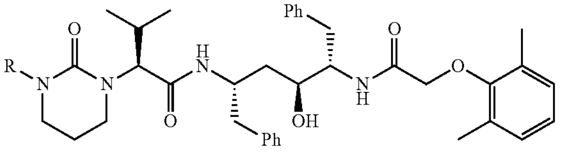

(Derivatized where "R" designates a site for linker group L or -(L-CLM) group attachment). See, J. Med. Chem. 2010, 53, 521-538.

2. Inhibitor of HIV Protease

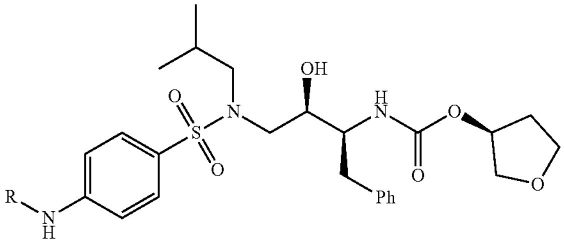

(Derivatized where "R" designates a potential site for linker group L or -(L-CLM) group attachment). See, *J. Med. Chem.* 2010, 53, 521-538.

XVI. Compounds Targeting HIV Integrase

1. Inhibitor of HIV Integrase (Derivatized)

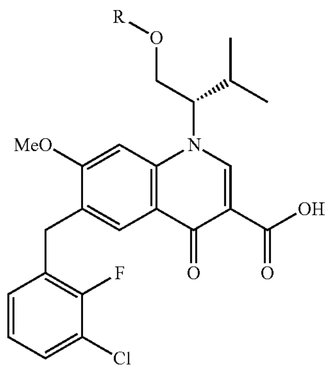

(Derivatized where "R" designates a site for linker group L or -(L CLM) group attachment). See, *J. Med. Chem.* 2010, 53, 6466.

2. Inhibitor of HIV Integrase (Derivatized)

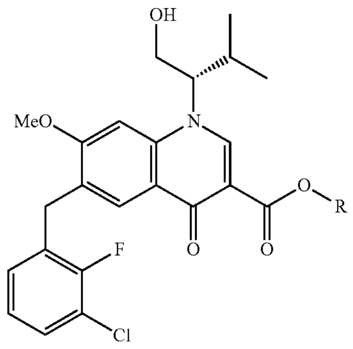

3. Inhibitor of HIV Integrase Isetntress (Derivatized)

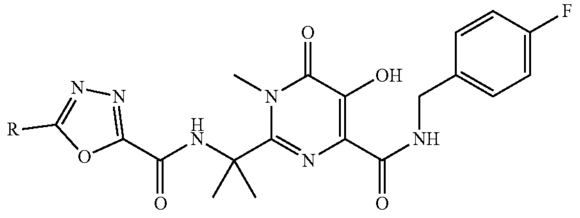

(Derivatized where "R" designates a site for linker group L or -(L-CLM) group attachment). See, *J. Med. Chem.* 2010, 53, 6466.

XVII. Compounds Targeting HCV Protease

1. Inhibitors of HCV Protease (Derivatized)

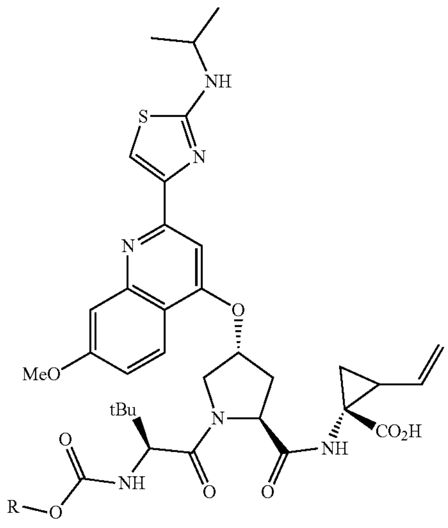

(Derivatized where "R" designates a site for linker group L or -(L-CLM) group attachment).

XVIII. Compounds Targeting Acyl-protein Thioesterase-1 and -2 (APT1 and APT2)

1. Inhibitor of APT1 and APT2 (Derivatized)

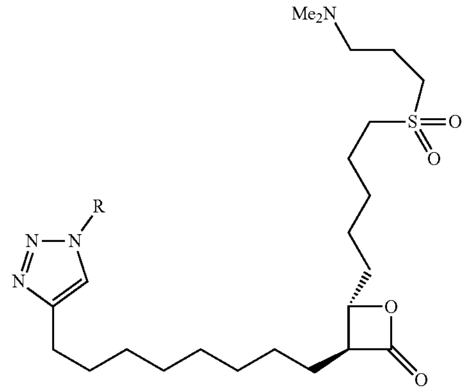

(Derivatized where "R" designates a site for linker group L or -(L-CLM) group attachment). See, Angew. Chem. Int. Ed. 2011, 50, 9838-9842, where L is a linker group as otherwise described herein and said CLM group is as otherwise described herein such that -(L-CLM) binds the CLM group to a PTM group as otherwise described herein.

Therapeutic Compositions

Pharmaceutical compositions comprising combinations of an effective amount of at least one bifunctional compound as described herein, and one or more of the compounds otherwise described herein, all in effective amounts, in combination with a pharmaceutically effective amount of a carrier, additive or excipient, represents a further aspect of the present disclosure.

The present disclosure includes, where applicable, the compositions comprising the pharmaceutically acceptable salts, in particular, acid or base addition salts of compounds as described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosure ion may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term “parenteral” as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer’s solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. In certain non-limiting aspects of the invention, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition as described herein that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present invention.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present invention including pharmaceutically acceptable salts, solvates or polymorphs, thereof optionally in a pharmaceutically acceptable carrier or diluent, either alone, or in combination with other known erythopoiesis stimulating agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A non-limiting dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as erythropoietin stimulating agents, including EPO and darbapoietin alfa, among others. In certain non-limiting aspects of the invention, one or more compounds according to the present invention are coadministered with another bioactive agent, such as an erythropoietin stimulating agent or a would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, non-limiting carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, which may be treated using compounds according to the present invention are set forth hereinabove.

The description provides therapeutic compositions as described herein for effectuating the degradation of proteins of interest for the treatment or amelioration of a disease, e.g., cancer. In certain additional embodiments, the disease is multiple myeloma. As such, in another aspect, the description provides a method of ubiquitinating/degrading a target protein in a cell. In certain embodiments, the method comprises administering a bifunctional compound as described herein comprising, e.g., a CLM and a PTM, preferably linked through a linker moiety, as otherwise described herein, wherein the CLM is coupled to the PTM and wherein the CLM recognizes a ubiquitin pathway protein (e.g., an ubiquitin ligase, preferably an E3 ubiquitin ligase such as, e.g., cereblon) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present invention provides treatment of a disease state or condition, which is modulated through the target protein by lowering the level of that protein in the cell, e.g., cell of a patient. In certain embodiments, the method comprises administering an effective amount of a compound as described herein, optionally including a pharmaceutically acceptable excipient, carrier, adjuvant, another bioactive agent or combination thereof.

In additional embodiments, the description provides methods for treating or emeliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another aspect, the description provides methods for identifying the effects of the degradation of proteins of interest in a biological system using compounds according to the present invention.

In another embodiment, the present invention is directed to a method of treating a human patient in need for a disease state or condition modulated through a protein where the degradation of that protein will produce a therapeutic effect in that patient, the method comprising administering to a patient in need an effective amount of a compound according to the present invention, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein, which leads to a disease state and/or condition The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Disease states of conditions which may be treated using compounds according to the present invention include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

Further disease states or conditions which may be treated by compounds according to the present invention include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barre syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by compounds according to the present invention include aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alstrom syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome #arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dube syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich's ataxia, familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysyl-hydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alstrom syndrome), Vrolik disease, Waardenburg syndrome, Warburg Sjo Fledelius Syndrome, Weissenbacher-Zweymuller syndrome, Wolf-Hirschhorn syndrome, Wolff Periodic disease, Weissenbacher-Zweymuller syndrome and Xeroderma pigmentosum, among others.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present invention include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

The term "bioactive agent" is used to describe an agent, other than a compound according to the present invention, which is used in combination with the present compounds as an agent with biological activity to assist in effecting an intended therapy, inhibition and/or prevention/prophylaxis for which the present compounds are used. Non-limiting bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The term "additional anti-cancer agent" is used to describe an anti-cancer agent, which may be combined with compounds according to the present invention to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdRi KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term “anti-HIV agent” or “additional anti-HIV agent” includes, for example, nucleoside reverse transcriptase inhibitors (NRTI), other non-nucloeoside reverse transcriptase inhibitors (i.e., those which are not representative of the present invention), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in coadministration with compounds according to the present invention include, for example, other NNRTI’s (i.e., other than the NNRTI’s according to the present invention) may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis (methoxycarbonyl)-6,6-diphenylhexenoate), Methyl 3-Bromo-5-(1-5-bromo-4-methoxy-3-(methoxycarbonyl) phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl] piperazine, 1-[3-(Ethylamino)-2-[pyridinyl]-4-[(5-hydroxy-2-indolyl)carbonyl]piperazine, 1-[(6-Formyl-2-indolyl) carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S(1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

The term “pharmaceutically acceptable salt” is used throughout the specification to describe, where applicable, a salt form of one or more of the compounds described herein which are presented to increase the solubility of the compound in the gastric juices of the patient’s gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly non-limiting as neutralization salts of the phosphates according to the present invention.

The term “pharmaceutically acceptable derivative” is used throughout the specification to describe any pharmaceutically acceptable prodrug form (such as an ester, amide other prodrug group), which, upon administration to a patient, provides directly or indirectly the present compound or an active metabolite of the present compound.

General Synthetic Approach

The synthetic realization and optimization of the bifunctional molecules as described herein may be approached in a step-wise or modular fashion. For example, identification of compounds that bind to the target molecules can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the linker chemistry previously referred to herein. Where crystallographic or NMR structural data are available, these can be used to focus such a synthetic effort.

In a very analogous way one can identify and optimize ligands for an E3 Ligase, i.e. ULMs/CLMs.

With PTMs and ULMs (e.g. CLMs) in hand one skilled in the art can use known synthetic methods for their combination with or without a linker moiety. Linker moieties can be synthesized with a range of compositions, lengths and flexibility and functionalized such that the PTM and ULM groups can be attached sequentially to distal ends of the linker. Thus a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

Some non-limiting exemplary methods to generate the CLMs as described herein are summarized as shown below.

1

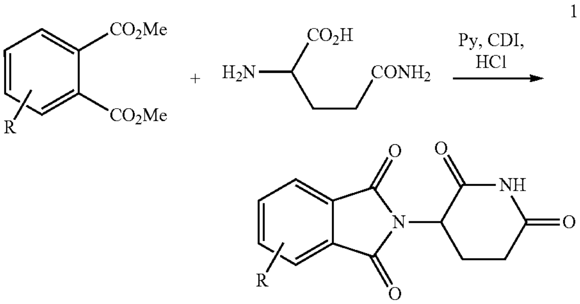

2

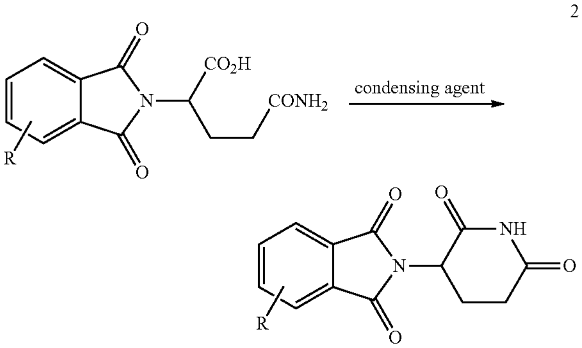

3

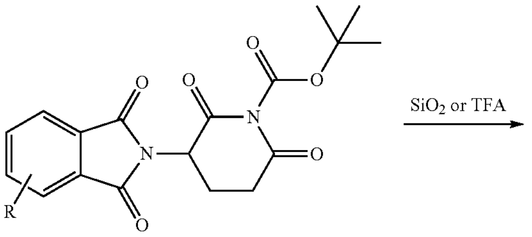

-continued

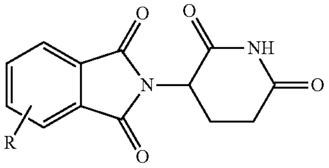

4

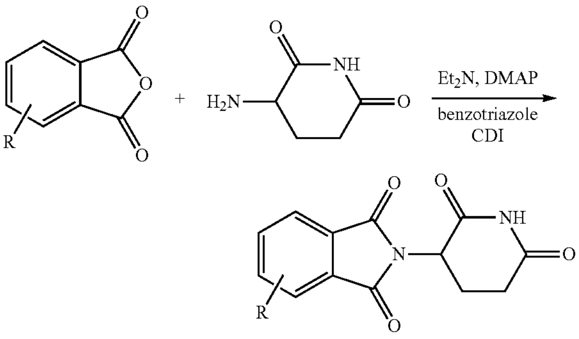

5

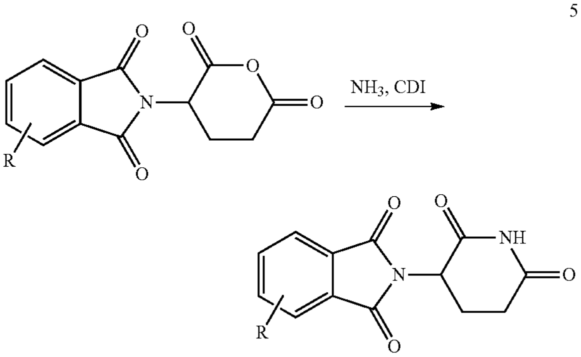

6

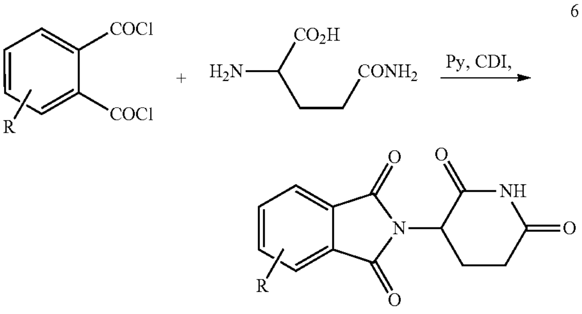

7

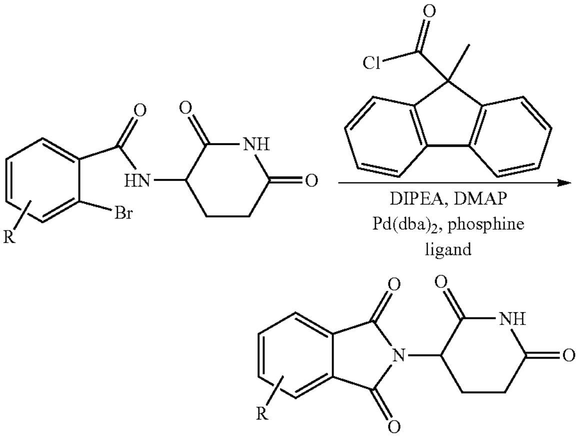

-continued
8
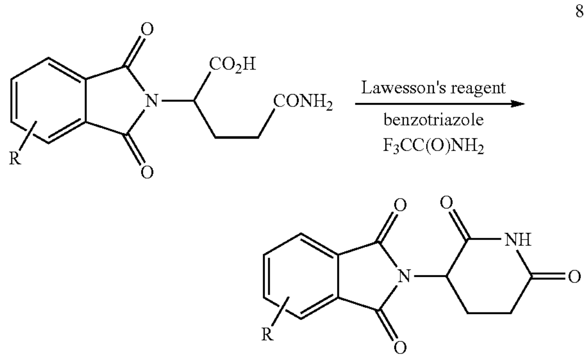
9
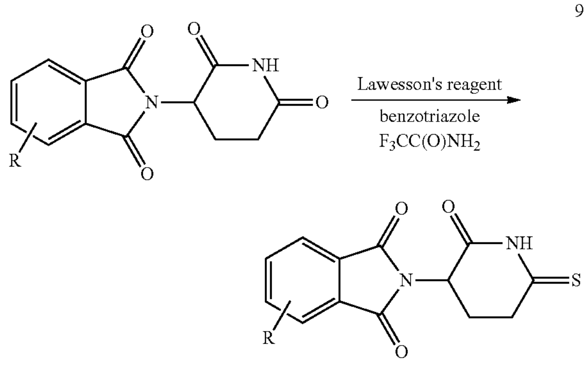
10
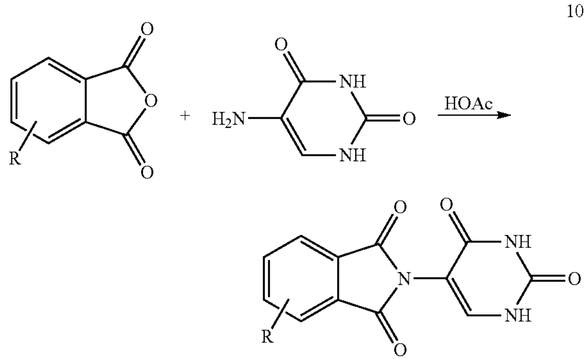
11
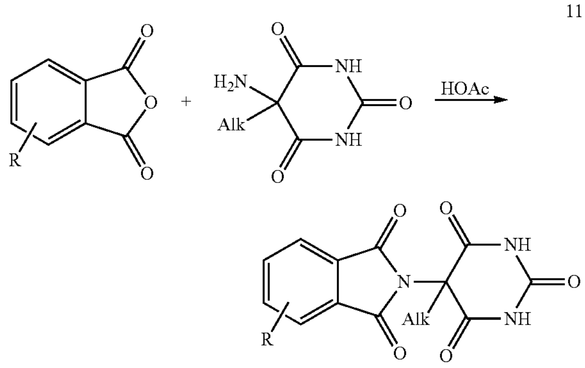
12
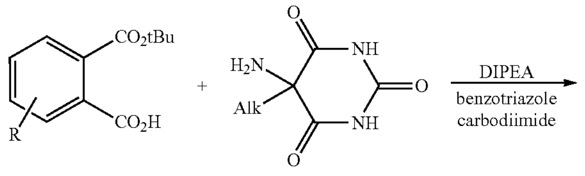
-continued
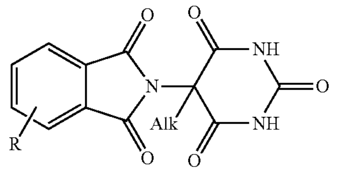
13
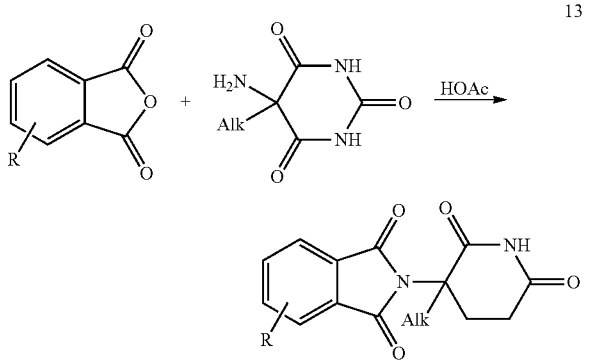
14
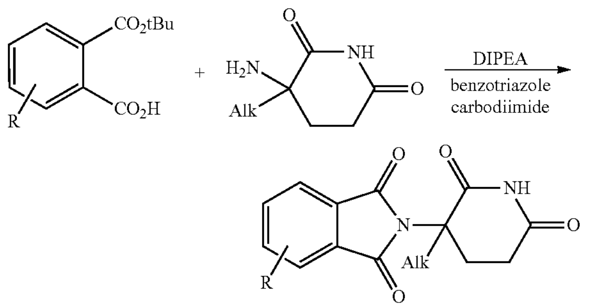
15
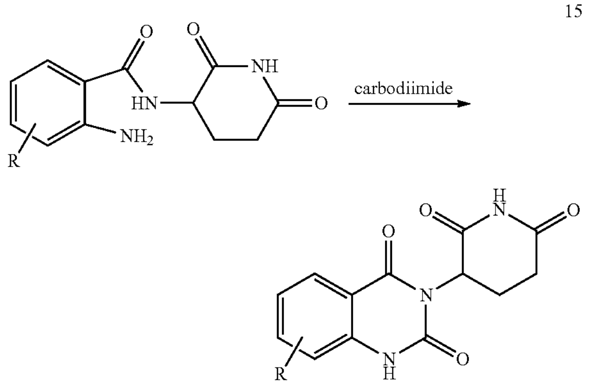
16
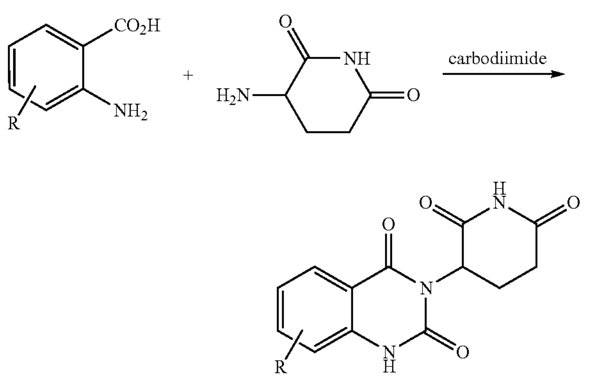

-continued
17
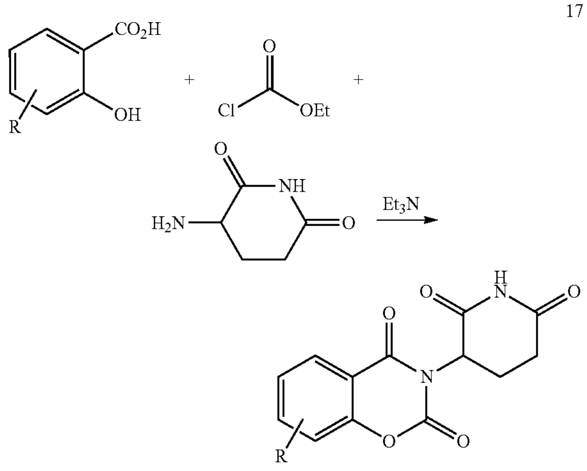
18
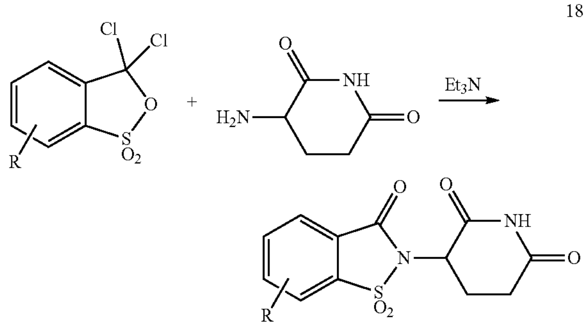
19
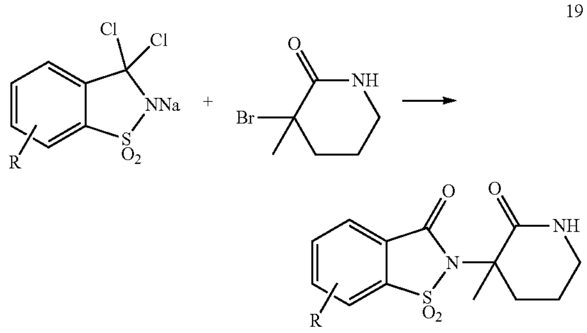
20
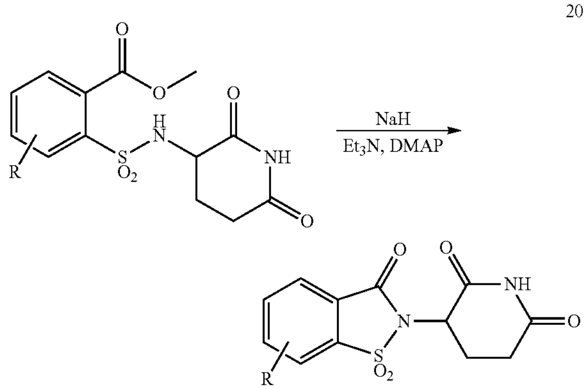
21
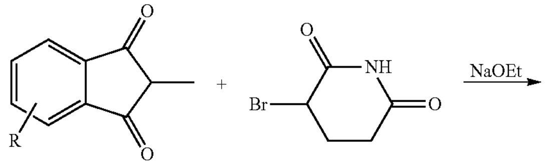
-continued
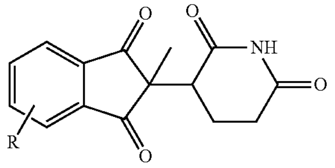
22
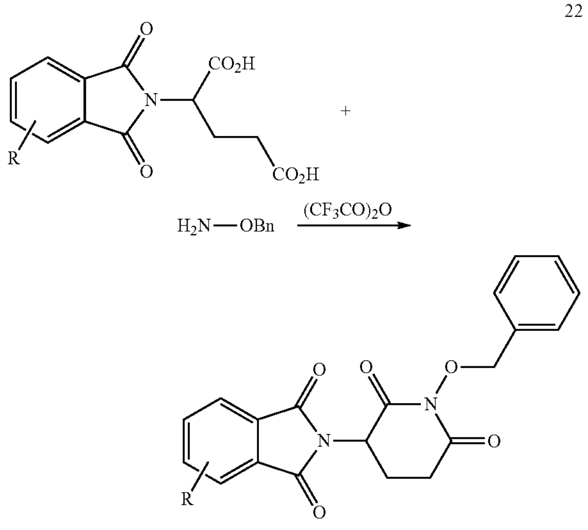
23
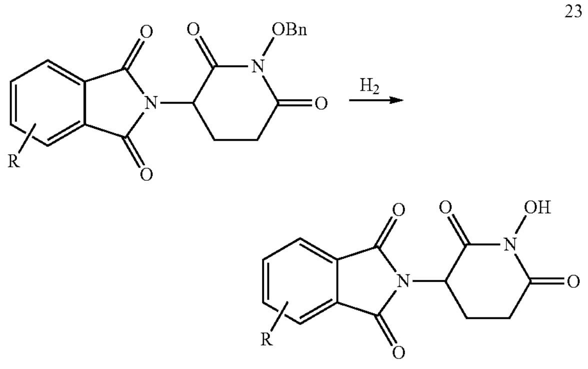
24
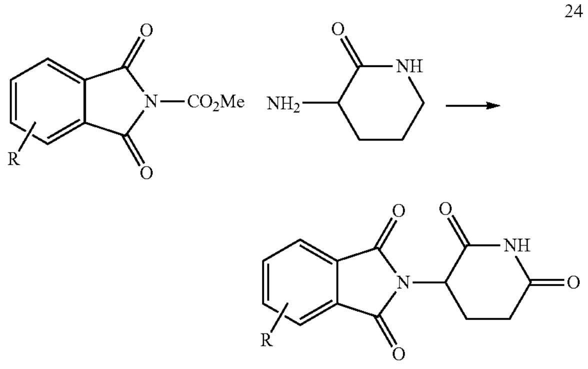
25
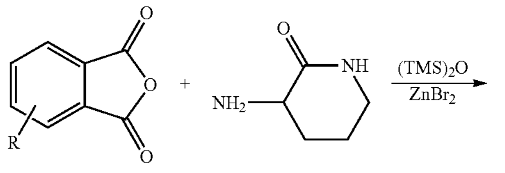

-continued

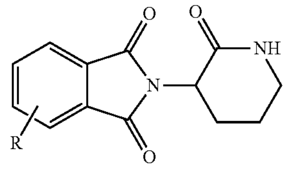

26

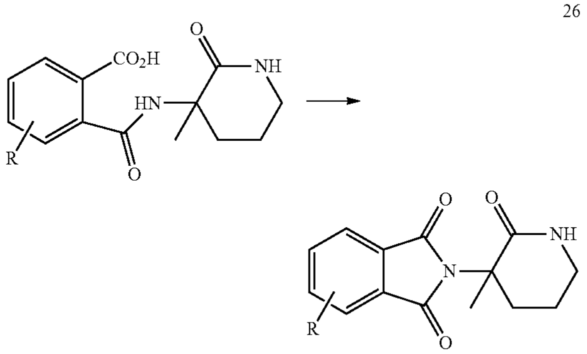

27

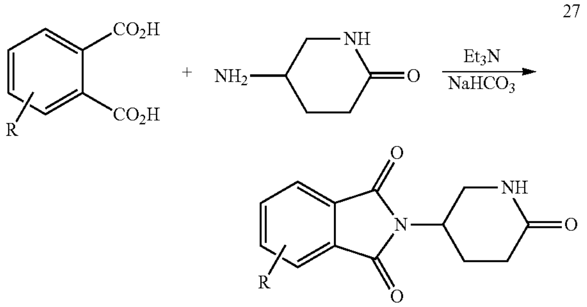

28

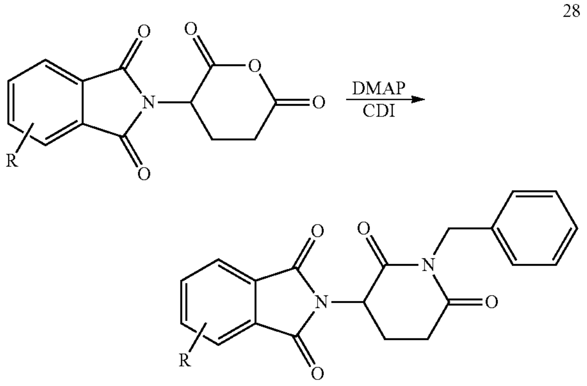

29

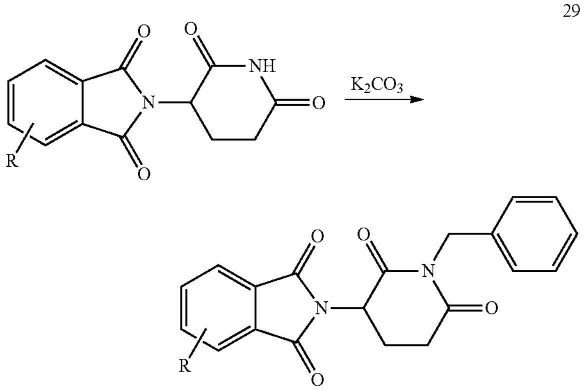

As shown in representative reaction 1, dimethyl phthalate derivatives can be condensed with glutamine (racemate or enantiomer) or glutamine analogs then further reacted with agents such as carbonyl diimidazole to form 2-(2,6-dioxopiperidin-3-yl)-2,3-dihydro-1H-isoindole-1,3-dione derivatives.

Alternatively as shown in representative reaction 2, the intermediate phthalimide produced in the initial condensation described above may be separately prepared and/or isolated and then reacted with dehydrating agents such as trifluoroacetamide, $POCl_3$ or acetic anhydride to form the desired 2-(2,6-dioxopiperidin-3-yl)-2,3-dihydro-1H-isoindole-1,3-dione derivatives. The same type of intermediate phthalimide can also be reacted with Lawesson's reagent prior to the dehydration step to provide thio analogs such as that shown in representative reactions 8 and 9.

Protected examples of 2-(2,6-dioxopiperidin-3-yl)-2,3-dihydro-1H-isoindole-1,3-dione derivatives such as the $N^1$-BOC species shown in representative example 3 can be deprotected to reveal the target 2-(2,6-dioxopiperidin-3-yl)-2,3-dihydro-1H-isoindole-1,3-dione derivatives by using, in this case, reagents such as TFA or silica.

Phthalic anhydrides such as that shown in representative example 4 can be ring-opened by reaction with amines such as 3-aminopiperidine-2,6-dione to form an intermediate carboxylate species, that on treatment with carbonyldiimidazole and benzotriazole will form the target 2-(2,6-dioxopiperidin-3-yl)-2,3-dihydro-1H-isoindole-1,3-dione derivatives. Alternatively, the two components may be combined in the presence of acetic acid to provide desired product as shown in representative reaction 13.

In an analogous reaction, anhydride derivatives like those shown in representative reaction 5 may be reacted with amines (ammonia in the example shown) then carbonyldiimidazoleto form the desired 2-(2,6-dioxopiperidin-3-yl)-2,3-dihydro-1H-isoindole-1,3-dione derivatives.

Where phthaloyl chlorides are available, direct condensation with glutamine (racemate or enantiomer) or glutamine analogs is possible, followed by further reaction with agents such as carbonyl diimidazole to form 2-(2,6-dioxopiperidin-3-yl)-2,3-dihydro-1H-isoindole-1,3-dione derivatives as shown in representative reaction 6.

o-Bromobenzamides can be reacted with a source of CO such as the acid chloride shown in representative reaction 7 in the presence of a palladium catalyst and associated phosphine ligand to produce the desired 2-(2,6-dioxopiperidin-3-yl)-2,3-dihydro-1H-isoindole-1,3-dione derivatives. Alternatively CO gas itself may be used in conjunction with rhodium (II) catalysts and silver carbonate to provide the desired products.

2-(2,4-dioxo-1,2,3,4-tetrahydropyrimidin-5-yl)-2,3-dihydro-1H-isoindole-1,3-dione, and 5-(1,3-dioxo-2,3-dihydro-1H-isoindol-2-yl)-1,3-diazinane-2,4,6-trione derivatives can be prepared by analogous means to some of the methods described above for 2-(2,6-dioxopiperidin-3-yl)-2,3-dihydro-1H-isoindole-1,3-dione derivatives. In representative reactions 20 and 21, a phthalic anhydride can be reacted with 5-amino-1,2,3,4-tetrahydropyrimidine-2,4-dione or 5-amino-1,3-diazinane-2,4,6-trione derivatives, respectively, in the presence of acetic acid to form the desired products.

Alternatively, 5-(1,3-dioxo-2,3-dihydro-1H-isoindol-2-yl)-1,3-diazinane-2,4,6-trione derivatives can be prepared by reaction of 5-amino-1,3-diazinane-2,4,6-trione derivatives with phthalic acid mono tert-butyl esters in the presence of Hünig's base, a carbodiimide and benzotriazole as shown in representative reaction 12. Similar conditions can be employed for the preparation of 2-(2,6-dioxopiperidin- 3-yl)-2,3-dihydro-1H-isoindole-1,3-dione derivatives from phthalic acid mono tert-butyl esters as shown in representative reaction 14.

Compounds such as 3-(2,6-dioxopiperidin-3-yl)-1,2,3,4-tetrahydroquinazoline-2,4-dione can be prepared from anthranilic acid derivatives by reaction of 3-aminopiperidine-2,6-diones with a carbodiimide as in representative reaction 16. The intermediate benzamide product may be isolated (or separately produced) and further reacted with a carbodiimide to produce 3-(2,6-dioxopiperidin-3-yl)-1,2,3,4-tetrahydroquinazoline-2,4-dione derivatives as shown in representative reaction 15.

3-(2,6-Dioxopiperidin-3-yl)-3,4-dihydro-2H-1,3-benzoxazine-2,4-dione analogs can be prepared by activation of salicylic acids with chloroformates then condensation with 3-aminopiperidine-2,6-diones as shown in representative reaction 17.

3,3-Dichloro-2,1$\lambda^6$-benzoxathiole-1,1-diones as shown in representative reaction 18 can be prepared by reaction of 2-sulfobenzoic acids with $POCl_3$ and $PCl_5$. These compounds can be reacted with amino derivatives to produce, for example, desired 2-(2,6-dioxopiperidin-3-yl)-2,3-dihydro-1$\lambda^6$,2-benzothiazole-1,1,3-trione derivatives.

As shown in representative reaction 19, anions of saccharin derivatives can be alkylated with electrophiles such as the 3-bromo-3-methylpiperidin-2-one to produce targeted 2-(3-methyl-2-oxopiperidin-3-yl)-2,3-dihydro-1$\lambda^6$,2-benzothiazole-1,1,3-trione derivatives.

Analogs of 2-(2,6-dioxopiperidin-3-yl)-2,3-dihydro-1$\lambda^6$,2-benzothiazole-1,1,3-trione may also be prepared by reaction of methyl 2-[(2,6-dioxopiperidin-3-yl)sulfamoyl]benzoate with strong bases such as sodium hydride (see representative reaction 20).

Deprotonation of 2-methyl-2,3-dihydro-1H-indene-1,3,dione derivatives with sodium ethoxide then reaction with electrophiles such as 3-bromopiperidin-2,6-dione affords 3-(2-methyl-1,3-dioxo-1H-inden-2-yl)piperidine-2,6-dione as shown in representative reaction 21.

Preparation of $N^1$-substituted compounds such as 2-[1-(benzyloxy)-2,6-dioxopiperidin-3-yl]-2,3-dihydro-1H-isoindole-1,4-dione (representative reaction 22) can be achieved by reaction of 2-(1,3-dioxo-2,3-dihydro-1H-isoindol-2-yl)pentanedioic acid with N-benzylhydroxylamine and with trifluoroacetic anhydride.

In turn molecules such as 2-[1-(benzyloxy)-2,6-dioxopiperidin-3-yl]-2,3-dihydro-1H-isoindole-1,4-dione (representative reaction 23) maybe subject to benzyl removal under hydrogenation conditions to yield $N^1$-hydroxy analogs such as 2-(1-hydroxy-2,6-dioxopiperidin-3-yl)-2,3-dihydro-1H-isoindole-1,3-dione.

In representative reaction 24, methyl 1,3-dioxo-2,3-dihydro-1H-isoindole-2-carboxylate (and analogs) is reacted with 3-aminopiperidin-2-one to provide 2-(2-oxopiperidin-3-yl)-2,3-dihydro-1H-isoindole-1,3-diones.

The same amine can also be reacted with phthalic anhydride derivatives in the presence of a Lewis acid such as zinc bromide and trimethylsilyl ether to yield the same type of product as shown in representative reaction 25. Intermediate products from this reaction if isolated or otherwise prepared (representative reaction 26) can be pushed to full cyclization through use of a dehydrating agent.

The isomeric derivatives such as 2-(6-oxopiperidin-3-yl)-2,3-dihydro-1H-isoindole-1,3-dione shown in representative reaction 27 are attainable through reaction of phthalic acid with 5-aminopiperidin-2-one.

Preparation of $N^1$-substituted compounds such as 2-(1-benzyl-2,6-dioxopiperidin-3-yl)-2,3-dihydro-1H-isoindole-1,4-dione (representative reactions 28 and 29) can be achieved through multiple routes. For example the anhydride (2-(2,6-dioxooxan-3-yl)-2,3-dihydro-1H-isoindole-1,3-dione) can be condensed with 3-aminopiperidine-2,6-dione in the presence of DMAP and carbonyldiimidazole (representative reaction 28), or 2-(2,6-dioxopiperidin-3-yl)-2,3-dihydro-1H-isoindole-1,3-dione derivatives can be alkylated with electrophiles such as benzyl bromide in the presence of base as shown in representative reaction 29.

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

Protein Level Control

This description also provides methods for the control of protein levels with a cell. This is based on the use of compounds as described herein, which are known to interact with a specific target protein such that degradation of a target protein in vivo will result in the control of the amount of protein in a biological system, preferably to a particular therapeutic benefit.

The following examples are used to assist in describing the present invention, but should not be seen as limiting the present invention in any way.

Example 1

A. Cloning & Analysis

1. Cloning, Expression and Purification of Human CRBN and DDB1.

The procedure is standard to one versed in the art, as typified by the description in Lopez-Girona et al. (Cereblon is a direct protein target for immunomodulatory and antiproliferative activities of lenalidomide and pomalidomide, A Lopez-Girona, D Mendy, T Ito, K Miller, A K Gandhi, J Kang, S Karasawa, G Carmel, P Jackson, M Abbasian, A Mahmoudi, B Cathers, E Rychak, S Gaidarova, R Chen, P H Schafer, H Handa, T O Daniel, J F Evans and R Chopra, Leukemia 26: 2326-2335, 2012).

The cDNAs for the CRBN and DDB1 genes can be amplified by PCR using Pfusion (NEB) as the polymerase and the following primer sequences:

| Primer | Sequence |
|---|---|
| CRBN-Forward | GTGCCGCGTGGCTCCATGGCCGGCGAAGGAGATCAGCAGGA (SEQ ID NO: 1) |
| CRBN-Rev | GCTTCCTTTCGGGCTTATTACAAGCAAAGTATTACTTTGTC (SEQ ID NO: 2) |
| DDB1-Forward | TCGGGCGCGGCTCTCGGTCCGAAAAGGATGTCGTACAACTACGTGGTAAC (SEQ ID NO: 3) |
| DDB1-Rev | GCTTCCTTTCGGGCTTATTTTTCGAACTGCGGGTGGCTCCAATGGATCCGAGTTAGCTCCT (SEQ ID NO: 4) |
| CRBN-Flag-Rev | GCTTCCTTTCGGGCTTACTTATCGTCATCGTCCTTGTAGTCCAAGCAAAGTATTACTTTGT (SEQ ID NO: 5) |

CRBN can be cloned into pBV-ZZ-HT-LIC, pBV-GST-LIC, pMA-HT-LIC, and DDB1 into pBV-notag-LIC, using ligation-independent cloning 26. For cloning into the mammalian vector pMA-HT-LIC, the CRBN-Flag-Reverse oligo adds a C-terminal FLAG tag for immunodetection. The DDB1-Rev adds a StrepTag 27. A ZZ-tag 28 is necessary to achieve high expression of soluble CRBN; without it, the His-CRBN expressed at low level, while a GST-CRBN results in aggregated protein. Recombinant baculovirus of ZZ-His-CRBN and DDB1-StrepTag (ST) are generated and amplified using Bac-to-Bac baculovirus expression system from Invitrogen in Sf9 insect cells. ZZ-His-CRBN and DDB1-ST are co-expressed in High Five (Tni) insect in 10 L wave bags at 27° C. using un-supplemented ESF921 media from Expression Systems. Cells are harvested 48 hours post infection by centrifugation and paste re-suspended in PBS plus 5× Protease Inhibitor cocktail (Roche, Indianapolis, IN).

All subsequent protein purification steps are carried out at 4° C. Frozen cells are thawed, resuspended in 5 volumes of lysis buffer (50 mM Tris HCl pH 8.0, 0.5 M NaCl, 10% glycerol, 2 mM DTT) plus 20 mM imidazole and protease inhibitors, lysed and centrifuged to yield a clear supernatant. The CRBN-DDB1 is purified on a ÄKTA-xpress system (GE Healthcare) using a Nickel-Sepharose and S200 Sephacryl chromatography. The complex is then further purified using anion exchange chromatography on an 8 ml MonoQ column and a second pass on a S-200 gel filtration. CRBN-DDB1 is identified by SDS-PAGE and the CRBN-DDB1 containing fractions were pooled and stored at −70° C.

2. Fluorescence Thermal Melt Assay to Measure Binding of Compounds to Recombinant CRBN The assay is standard to one versed in the art, as typified by the description in Lopez-Girona et al. (Cereblon is a direct protein target for immunomodulatory and antiproliferative activities of lenalidomide and pomalidomide, A Lopez-Girona, D Mendy, T Ito, K Miller, A K Gandhi, J Kang, S Karasawa, G Carmel, P Jackson, M Abbasian, A Mahmoudi, B Cathers, E Rychak, S Gaidarova, R Chen, P H Schafer, H Handa, T O Daniel, J F Evans and R Chopra, Leukemia 26: 2326-2335, 2012).

Thermal stabilities of CRBN-DDB1 in the presence or absence of test compounds are done in the presence of Sypro Orange in a microplate format according to Pantoliano et al. (Pantoliano M W, Petrella E C, Kwasnoski J D, Lobanov V S, Myslik J, Graf E et al. High-density miniaturized thermal shift assays as a general strategy for drug discovery. J Biomol Screen 2001; 6: 429-440.) Two mg of protein in 20 ml of assay buffer (25 mM Tris HCl, pH 8.0, 150 mM NaCl, 2 uM Sypro Orange) are subjected to stepwise increase of temperature from 20 to 70° C. and the fluorescence read at every 1° C. on an ABIPrism 7900HT (Applied Biosystems, Carlsbad, CA, USA). Compounds are dissolved in DMSO (1% final in assay) and tested in quadruplicate at a concentration range between 30 nM to 1000 uM; controls contained 1% DMSO only.

3. LCMS Method

The analysis is conducted on a Poroshell 120 EC C18 column (50 mm×3.0 mm internal diameter 2.7 m packing diameter) at 45° C.

The solvents employed are:

A=0.1% v/v solution of formic acid in water.

B=0.1% v/v solution of formic acid in acetonitrile.

The gradient employed are as follows:

| Time (minutes) | Flow Rate (mL/min) | % A | % B |
|---|---|---|---|
| 0 | 1 | 95 | 5 |
| 0.5 | 1 | 95 | 5 |
| 3.0 | 1 | 1 | 99 |
| 3.75 | 1 | 1 | 99 |
| 4.0 | 1 | 95 | 5 |

The UV detection is an averaged signal from wavelength of 210 nm to 350 nm and mass spectra are recorded on a mass spectrometer using positive mode electrospray ionization.

The following illustrates the mobile phases and gradients used when compounds undergo purification by preparative HPLC.

4. Preparative HPLC (Formic Acid Modifier)

The HPLC analysis is conducted on an X Bridge RP18 OBD column (150 mm×19 mm internal diameter, 5 m packing diameter) at ambient temperature. The solvents employed are:

A=0.1% v/v solution of formic acid in water.

B=acetonitrile.

5. Preparative HPLC (Ammonium Bicarbonate Modifier)

The HPLC analysis is conducted on an X Bridge RP18 OBD column (150 mm×19 mm internal diameter, 5 m packing diameter) at ambient temperature. The solvents employed are:

A=10 mM ammonium bicarbonate in water.

B=acetonitrile.

For each of the preparative purifications, irrespective of the modifier used, the gradient employed is dependent upon the retention time of the particular compound undergoing purification as recorded in the analytical LCMS. The flow rate is 20 mL/min.

The UV detection is a signal from wavelength of 254 nm or 220 nm.

While non-limiting embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

B. Synthesis

The synthetic details for the examples included below are representative of the general procedures that inform on the synthesis of the broader example set.

1. 2-(2,6-dioxopiperidin-3-yl)-4-fluoro-2,3-dihydro-1H-isoindole-1,3-dione

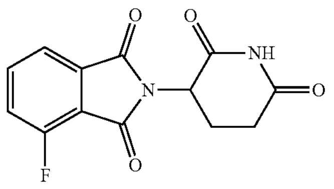 [SMILES: O=C1CCC(N2C(=O)c3cccc(F)c3C2=O)C(=O)N1]

Step 1: 4-fluoroisobenzofuran-1,3-dione

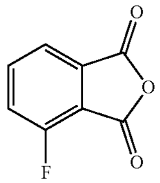 [SMILES: O=C1OC(=O)c2c(F)cccc21]

A mixture of 3-fluorophthalic acid (50 g, 271.7 mmol) in acetic anhydride (400 mL) was refluxed for 2 h. The volatiles were removed by vacuum, and the residues were crystallized in acetic anhydride to afford 4-fluoroisobenzofuran-1,3-dione (40 g, crude) as a brown solid. LC-MS: 167.1 [MH]+. $^{1}$H NMR (400 MHz, $CDCl_3$): δ 7.58 (t, J=8.0 Hz, 1H), 7.86 (d, J=7.2 Hz, 1H), 7.92-7.97 (m, 1H).

Step 2: 5-amino-2-(4-fluoro-1,3-dioxoisoindolin-2-yl)-5-oxopentanoic acid

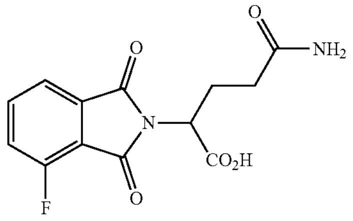 [SMILES: NC(=O)CCC(C(=O)O)N1C(=O)c2cccc(F)c2C1=O]

A mixture of the above 4-fluoroisobenzofuran-1,3-dione (40 g, crude) and L-glutamine (35 g, 239 mmol) in dry DMF (200 mL) was stirred at 90° C. for 8 h. The solvent was removed under reduced pressure. The residue was re-dissolved in 4N HCl (200 mL) and stirred for additional 8 h. The resulting precipitation was collected by filtration, washed with water, and dried to afford 5-amino-2-(4-fluoro-1,3-dioxoisoindolin-2-yl)-5-oxopentanoic acid (37 g, crude) as an off-white solid. LC-MS: 295.2 $[MH]^+$. $^{1}$H NMR (400 MHz, $CDCl_3$): δ 2.16-2.20 (m, 2H), 2.31-2.43 (m, 2H), 4.79-4.83 (m, 1H), 6.79 (br, 1H), 7.26 (br, 1H), 7.77-7.85 (m, 2H), 7.98-8.03 (m, 1H), 13.32 (br, 1H).

Step 3: 2-(2,6-dioxopiperidin-3-yl)-4-fluoro-2,3-dihydro-1H-isoindole-1,3-dione

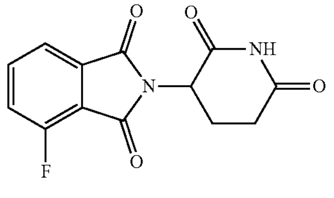 [SMILES: O=C1CCC(N2C(=O)c3cccc(F)c3C2=O)C(=O)N1]

A mixture of the above 5-amino-2-(4-fluoro-1,3-dioxoisoindolin-2-yl)-5-oxopentanoic acid (37 g, crude), 1,1'-carbonyldiimidazole (CDI) (24.2 g, 149.4 mmol) and 4-dimethylaminopyridine (DMAP) (1.3 g, 11.5 mmol) in acetonitrile (80 mL) was refluxed for 5 h. The reaction mixture was cooled to room temperature. The resulting solid was collected by filtration, and washed with acetonitrile (100 mL) to afford the crude product, which was purified by silica gel chromatography using 1-10% MeOH in DCM as eluent to afford 2-(2,6-dioxopiperidin-3-yl)-4-fluoroisoindoline-1,3-dione (9.0 g, 12% yield over three steps) as a light yellow solid. LC-MS: 277.2 $[MH]^+$. $^{1}$H NMR (400 MHz, $CDCl_3$): δ 2.14-2.19 (m, 1H), 2.75-2.95 (m, 3H), 4.97-5.01 (m, 1H), 7.43 (t, J=8.4 Hz, 1H), 7.10-7.81 (m, 2H), 8.08 (br, 1H).

2. N-(3-(5-bromo-2-chloropyrimidin-4-ylamino)propyl)-N-methylcyclobutane carboxamide

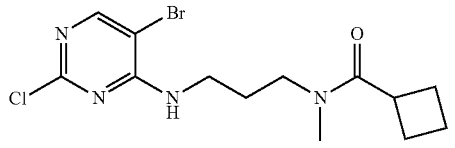 [SMILES: CN(CCCNc1nc(Cl)ncc1Br)C(=O)C1CCC1]

Step 1: tert-butyl N-{3-[(5-bromo-2-chloropyrimidin-4-yl)amino]propyl}-N-methylcarbamate

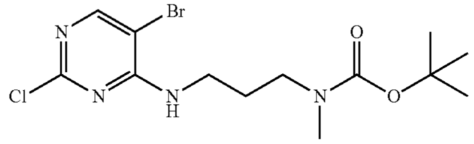 [SMILES: CN(CCCNc1nc(Cl)ncc1Br)C(=O)OC(C)(C)C]

A mixture of tert-butyl N-(3-aminopropyl)-N-methylcarbamate (826 mg, 4.40 mmol) and 5-bromo-2,4-dichloropyrimidine (400 mg, 1.76 mmol) in MeOH (10 mL) was stirred at rt for 1 h. The reaction mixture was then concentrated in vacuo, and the residue was purified using a Teledyne ISCO Chromatography [0→35% EtOAc/Heptanes] to afford tert-butyl N-{3-[(5-bromo-2-chloropyrimidin-4-yl)amino]propyl}-N-methylcarbamate (615 mg, 92% yield). LC-MS ($ES^+$): m/z=381.05/383.05 $[MH^+]$, $t_R$=2.55 min.

Step 2: {3-[(5-bromo-2-chloropyrimidin-4-yl)amino]propyl}(methyl)amine

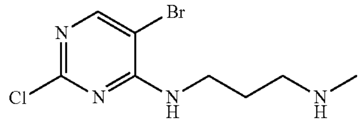

To a solution of tert-butyl N-{3-[(5-bromo-2-chloropyrimidin-4-yl)amino]propyl}-N-methylcarbamate (615 mg, 1.62 mmoL) in DCM (5 mL) was added trifluoroacetic acid (0.54 mL, 6.5 mmol) at rt. After the mixture was stirred for 1 h, it was concentrated in vacuo. The residue was purified using a Teledyne ISCO Chromatography [0→15% methanol in DCM] to afford {3-[(5-bromo-2-chloropyrimidin-4-yl)amino]propyl}(methyl)amine (371 mg, 82% yield). LC-MS ($ES^+$): m/z=280.99/282.99 [$MH^+$], $t_R$=1.13 min.

Step 3: N-{3-[(5-bromo-2-chloropyrimidin-4-yl)amino]propyl}-N-methylcyclobutanecarboxamide

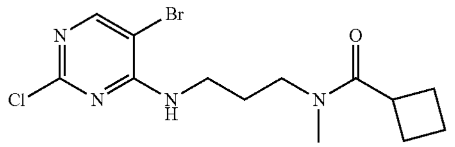 [SMILES: CN(CCCNc1nc(Cl)ncc1Br)C(=O)C1CCC1]

To a solution of {3-[(5-bromo-2-chloropyrimidin-4-yl)amino]propyl}(methyl)amine (371 mg, 1.33 mmol) and cyclobutanecarbonyl chloride (188 mg, 1.60 mmol) in DCM (10 mL) at rt was added triethyl amine (0.41 mL, 2.92 mmol). The reaction mixture was left to stir at rt for 16 h, then concentrated in vacuo. The residue was purified using a Teledyne ISCO Chromatography [0→100% EtOAc/Heptanes] to afford N-{3-[(5-bromo-2-chloropyrimidin-4-yl)amino]propyl}-N-methylcyclobutane carboxamide (268 mg, 56%). LC-MS ($ES^+$): m/z=363.04/365.04 [$MH^+$], $t_R$=2.18 min.

3. (S)-2-(4-(4-chlorophenyl)-2,3,9-trimethyl-6H-thieno [3,2-f] [1,2,4]triazolo[4,3-a][1,4]diazepin-6-yl)acetic acid

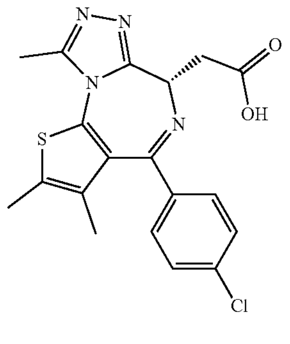 [SMILES: Cc1sc2c(c1C)C(c1ccc(Cl)cc1)=N[C@@H](CC(=O)O)c1nnc(C)n1-2]

The title compound was prepared according to the procedures described in WO2011/143660

4. (Z)-4-(4-((2,4-dioxothiazolidin-5-ylidene)methyl)-2-methoxyphenoxy)-3-(trifluoromethyl)benzonitrile

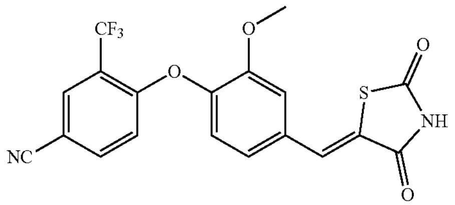 [SMILES: COc1cc(/C=C2\SC(=O)NC2=O)ccc1Oc1ccc(C#N)cc1C(F)(F)F]

The title compound was prepared according to the procedures described in Patch, R. J. et al *J. Med. Chem.* 2011, 54, 788-808.

5. 4-[3-(4-hydroxyphenyl)-4,4-dimethyl-5-oxo-2-sulfanylideneimidazolidin-1-yl]-2-(trifluoromethyl)benzonitrile

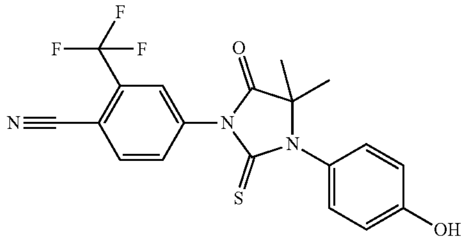 [SMILES: CC1(C)C(=O)N(c2ccc(C#N)c(C(F)(F)F)c2)C(=S)N1c1ccc(O)cc1]

The title compound was prepared according to the procedures described in Jung, M. E. et al *J.* Med. Chem. 2010, 53, 2779-2796.

6. 2-chloro-4-(trans-3-amino-2,2,4,4-tetramethylcyclobutoxy)benzonitrile hydrogen chloride salt

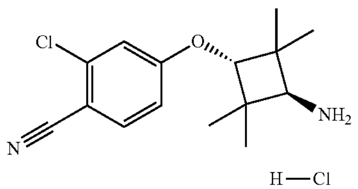

The title compound was prepared according to the procedures described in Guo, C. et al *J. Med. Chem.* 2011, 54, 7693-7704.

7. [N-(3-(5-bromo-2-(4-(2-(2-(2-(2-(2-(2,6-dioxopiperidin-3-yl)-1,3-dioxoisoindolin-4-ylamino)ethoxy)ethoxy)ethoxy)ethoxy)phenylamino)pyrimidin-4-ylamino)propyl)-N-methylcyclobutanecarboxamide]

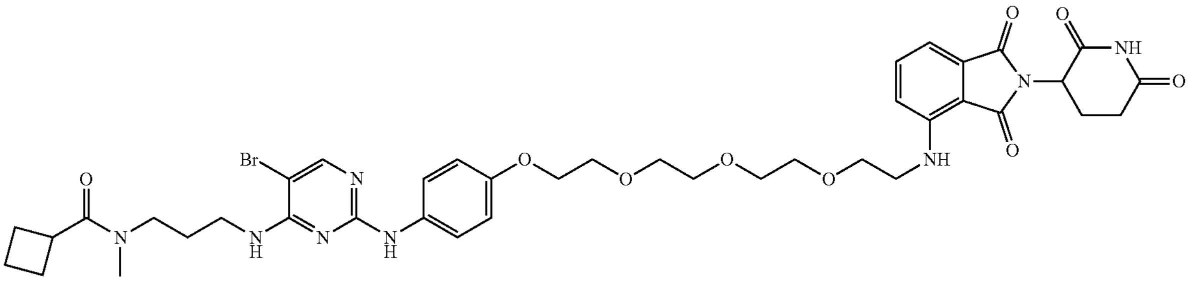 [SMILES: CN(CCCNc1nc(Nc2ccc(OCCOCCOCCOCCNc3cccc4c3C(=O)N(C3CCC(=O)NC3=O)C4=O)cc2)ncc1Br)C(=O)C1CCC1]

(Compound Structure #17 shown in Table 1)

Step 1: 2-(2-(2-(2-(4-nitrophenoxy)ethoxy)ethoxy)ethoxy)ethyl 4-methylbenzenesulfonate

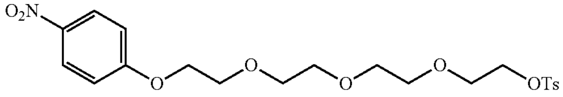 [SMILES: Cc1ccc(S(=O)(=O)OCCOCCOCCOCCOc2ccc([N+](=O)[O-])cc2)cc1]

A mixture of 2,2'-(2,2'-oxybis(ethane-2,1-diyl)bis(oxy))bis(ethane-2,1-diyl) bis(4-methylbenzenesulfonate) (3 g, 5.96 mmol), 4-nitrophenol (813 mg, 5.84 mmol) and potassium carbonate (1.65 g, 11.94 mmol) in dry N,N-dimethylformamide (20 mL) was stirred at 50° C. overnight. The mixture was cooled to room temperature and poured into water (60 mL), then extracted with ethyl acetate (80 mL×3). The combined organic phases were washed with water (50 mL) and brine (50 mL), dried over anhydrous sodium sulfate, and concentrated under reduced pressure. The residue was purified by silica gel flash column chromatography (eluted with 10-20% ethyl acetate in hexane) to afford 2-(2-(2-(2-(4-nitrophenoxy)ethoxy)ethoxy)ethoxy)ethyl 4-methylbenzenesulfonate (2.65 g, 95% yield) as a yellow oil. LC-MS ($ES^+$): m/z 470.2 [$MH^+$] ($t_R$=2.83 min)

Step 2: [1-(2-(2-(2-(2-azidoethoxy)ethoxy)ethoxy)ethoxy)-4-nitrobenzene]

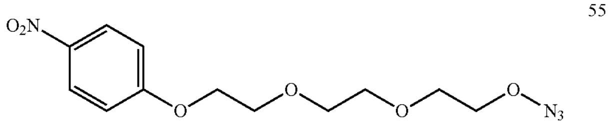

A mixture of 2-(2-(2-(2-(4-nitrophenoxy)ethoxy)ethoxy)ethoxy)ethyl 4-methylbenzenesulfonate (2.65 g, 5.64 mmol) and sodium azide (734 mg, 11.29 mmol) in ethanol (30 mL) was refluxed for 16 h. The mixture was cooled to room temperature, quenched with water (50 mL), and extracted with dichloromethane (50 mL×3). The combined organic phases were washed with water (50 mL) and brine (40 mL), dried over anhydrous sodium sulfate, and concentrated under reduced pressure to afford the crude 1-(2-(2-(2-(2-azidoethoxy)ethoxy)ethoxy)ethoxy)-4-nitrobenzene (865 mg) as a yellow oil.

Step 3: [2-(2-(2-(2-(4-nitrophenoxy)ethoxy)ethoxy)ethoxy)ethanamine]

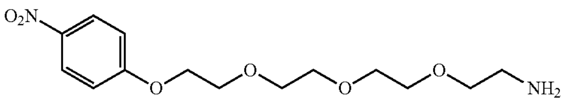

A mixture of the above 1-(2-(2-(2-(2-azidoethoxy)ethoxy)ethoxy)ethoxy)-4-nitrobenzene (865 mg, 2.54 mmol), triphenylphosphine (999 mg, 3.81 mmol) and water (69 mg, 3.83 mmol) in tetrahydrofuran (10 mL) was stirred at room temperature for 14 h under nitrogen atmosphere. The volatiles were removed under reduced pressure to afford a crude residue, which was purified by silica gel flash column chromatography (eluted with 3-5% methanol in dichloromethane) to afford 2-(2-(2-(2-(4-nitrophenoxy)ethoxy)ethoxy)ethoxy)ethanamine (661 mg, 83% yield) as a yellow oil. $^1H$ NMR (400 MHz, $CDCl_3$): δ 2.86 (t, J=5.2 Hz, 2H), 3.51 (t, J=5.6 Hz, 2H), 3.63-3.75 (m, 8H), 3.90 (t, J=4.4 Hz, 2H), 4.23 (t, J=4.8 Hz, 2H), 6.97-6.99 (m, 2H), 8.18-8.22 (m, 2H).

Step 4: tert-butyl 2-(2-(2-(2-(4-nitrophenoxy)ethoxy)ethoxy)ethoxy)ethylcarbamate

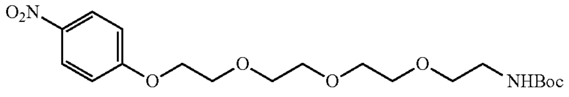 [SMILES: CC(C)(C)OC(=O)NCCOCCOCCOCCOc1ccc([N+](=O)[O-])cc1]

A mixture of 2-(2-(2-(2-(4-nitrophenoxy)ethoxy)ethoxy)ethoxy)ethanamine (661 mg, 2.1 mmol), triethylamine (449 mg, 4.43 mmol) and di-tert-butyl dicarbonate (505 mg, 2.31 mmol) in dichloromethane (25 mL) was stirred at room temperature for 2 h. The mixture was diluted with dichloromethane (100 mL), washed with water (30 mL×2) and brine (30 mL), dried over anhydrous sodium sulfate, and concentrated under reduced pressure. The residue was purified by silica gel flash column chromatography (eluted with 20-40% ethyl acetate in hexane) to afford tert-butyl 2-(2-(2-(2-(4-nitrophenoxy)ethoxy)ethoxy)ethoxy)ethylcarbamate (818 mg, 94% yield) as a yellow oil. $^1H$ NMR (400 MHz, $CDCl_3$): δ 1.44 (s, 9H), 3.37 (d, J=5.2 Hz, 2H), 3.54 (t, J=5.2

Hz, 2H), 3.62-3.70 (m, 6H), 3.73-3.76 (m, 2H), 3.90 (t, J=4.4 Hz, 2H), 4.23 (t, J=4.8 Hz, 2H), 5.01 (br, 1H), 6.96-7.00 (m, 2H), 8.18-8.22 (m, 2H).

Step 5: tert-butyl 2-(2-(2-(2-(4-aminophenoxy) ethoxy)ethoxy)ethoxy)ethylcarbamate

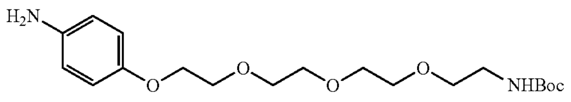

A mixture of 2-(2-(2-(2-(4-nitrophenoxy)ethoxy)ethoxy) ethoxy)ethylcarbamate (818 mg, 1.97 mmol), iron powder (1.1 g, 0.65 mmol), and ammonium chloride (528 mg, 9.87 mmol) in ethanol (20 mL) and water (5 mL) was stirred at 80° C. for 1 h. The mixture was cooled to room temperature, the solid precipitate was removed by filtration and washed with ethyl acetate (20 mL×2). The filtrate was partitioned between ethyl acetate (120 mL) and water (30 mL). The organic phase was washed with brine (30 mL), dried over anhydrous sodium sulfate, and concentrated under reduced pressure. The residue was purified by silica gel chromatography (eluted with 30-40% ethyl acetate in hexane) to afford tert-butyl 2-(2-(2-(2-(4-aminophenoxy)ethoxy)ethoxy) ethoxy)ethylcarbamate (512 mg, 67% yield) as a yellow oil.†

Step 6: tert-butyl 2-(2-(2-(2-(4-(5-bromo-4-(3-(N-methylcyclobutanecarboxamido) propylamino)pyrimidin-2-ylamino)phenoxy)ethoxy)ethoxy)ethoxy) ethylcarbamate

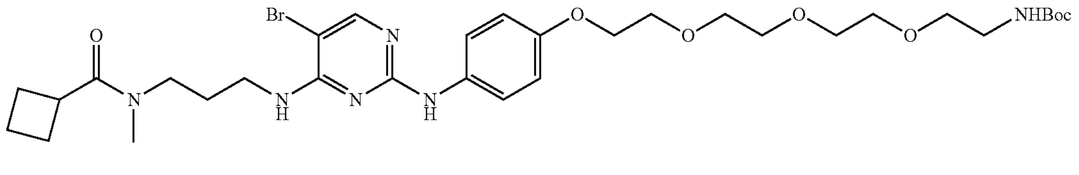 [SMILES: CN(CCCNc1nc(Nc2ccc(OCCOCCOCCOCCNC(=O)OC(C)(C)C)cc2)ncc1Br)C(=O)C1CCC1]

A mixture of tert-butyl 2-(2-(2-(2-(4-aminophenoxy) ethoxy)ethoxy)ethoxy)ethyl carbamate (130 mg, 0.34 mmol), N-(3-(5-bromo-2-chloropyrimidin-4-ylamino)propyl)-N-methylcyclobutanecarboxamide (24 mg, 0.06 mmol) and p-toluenesulfonic acid (11.6 mg, 0.07 mmol) in dioxane (1.5 mL) was refluxed for 16 h. The reaction mixture was cooled to room temperature, quenched with aqueous sodium bicarbonate solution (1.0 N, 30 mL), and extracted with ethyl acetate (30 mL×3). The combined organic phases were washed with water (30 mL) and brine (30 mL), dried over anhydrous sodium sulfate, and concentrated under reduced pressure. The crude residue was purified by silica gel flash column chromatography (eluted with 50% ethyl acetate in hexane) to afford tert-butyl 2-(2-(2-(2-(4-(5-bromo-4-(3-(N-methylcyclobutanecarboxamido)propylamino)pyrimidin-2-ylamino)phenoxy)ethoxy)ethoxy)ethoxy)ethylcarbamate (40 mg, 17% yield) as a yellow oil.

Step 7: N-(3-(2-(4-(2-(2-(2-(2-aminoethoxy)ethoxy) ethoxy)ethoxy)phenylamino)-5-bromopyrimidin-4-ylamino)propyl)-N-methylcyclobutanecarboxamide

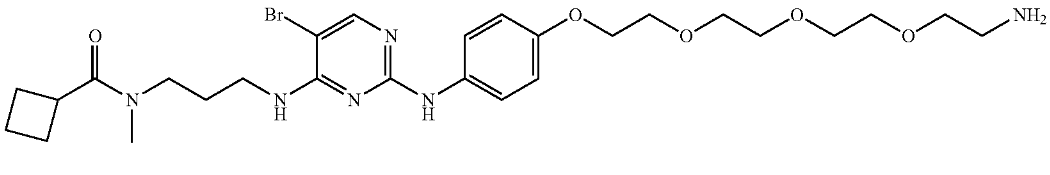 [SMILES: CN(CCCNc1nc(Nc2ccc(OCCOCCOCCOCCN)cc2)ncc1Br)C(=O)C1CCC1]

A mixture of tert-butyl 2-(2-(2-(2-(4-(5-bromo-4-(3-(N-methylcyclobutanecarboxamido) propylamino)pyrimidin-2-ylamino)phenoxy) ethoxy)ethoxy)ethoxy)ethylcarbamate (40 mg, 0.06 mmol) in 2,2,2-trifluoroacetic acid (1 mL) and dichloromethane (1 mL) was stirred at room temperature for 2 h. The volatiles were removed under reduced pressure. The residue was partitioned between dichloromethane (60 mL) and aqueous sodium bicarbonate solution (2.0 N, 30 mL). The organic layer was washed with brine (20 mL), dried over anhydrous sodium sulfate, and concentrated under reduced pressure to afford N-(3-(2-(4-(2-(2-(2-(2-aminoethoxy)ethoxy)ethoxy)ethoxy)phenylamino)-5-bromopyrimidin-4-ylamino)propyl)-N-methylcyclobutanecarboxamide (18 mg, 52% yield) as a yellow oil.

Step 8: N-(3-(5-bromo-2-(4-(2-(2-(2-(2-(2-(2,6-dioxopiperidin-3-yl)-1,3-dioxoisoindolin-4-ylamino) ethoxy)ethoxy)ethoxy)ethoxy)phenylamino)pyrimidin-4-ylamino)propyl)-N-methylcyclobutanecarboxamide

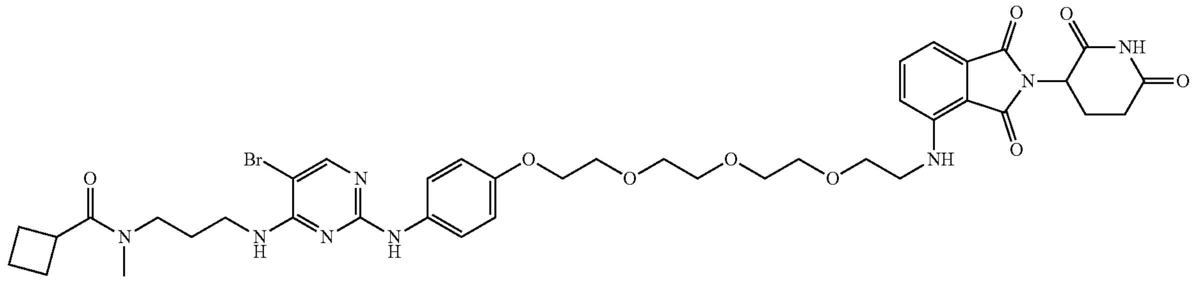 [SMILES: CN(CCCNc1nc(Nc2ccc(OCCOCCOCCOCCNc3cccc4c3C(=O)N(C3CCC(=O)NC3=O)C4=O)cc2)ncc1Br)C(=O)C1CCC1]

A mixture of N-(3-(2-(4-(2-(2-(2-(2-aminoethoxy) ethoxy)ethoxy)ethoxy) phenylamino)-5-bromopyrimidin-4-ylamino)propyl)-N-methylcyclobutane carboxamide (130 mg, 0.03 mmol), 2-(2,6-dioxopiperidin-3-yl)-4-fluoro-2,3-dihydro-1H-isoindole-1,3-dione (8.2 mg, 0.03 mmol) and N-ethyl-N-isopropylpropan-2-amine (7.6 mg, 0.06 mmol) in dry N,N-dimethylformamide (1 mL) was stirred at 90° C. for 12 h. The reaction mixture was cooled to room temperature, partitioned between ethyl acetate (100 mL) and water (30 mL). The organic phase was washed with brine (30 mL), dried over anhydrous sodium sulfate, and concentrated under reduced pressure. The residue was purified by prep-TLC to afford N-(3-(5-bromo-2-(4-(2-(2-(2-(2-(2-(2,6-dioxopiperidin-3-yl)-1,3-dioxoisoindolin-4-ylamino)ethoxy) ethoxy)ethoxy)ethoxy) phenylamino)pyrimidin-4-ylamino) propyl)-N-methylcyclobutanecarboxamide (10.2 mg, 40% yield) as a yellow solid. LC-MS ($ES^+$): m/z=865.27/867.27 (1:1) $[MH]^+$. $t_R$=2.06 min. $^1H$ NMR (400 MHz, $CD_3OD$): δ 1.68-1.77 (m, 3H), 1.89-1.92 (m, 3H), 2.08-2.15 (m, 3H), 2.60-2.79 (m, 7H), 3.28-3.35 (m, 6H), 3.55-3.61 (m, 10H), 3.69-3.72 (m, 2H), 3.96-3.99 (m, 2H), 4.91-4.95 (m, 1H), 6.75-6.78 (m, 2H), 6.91-6.94 (m, 2H), 7.34-7.42 (m, 3H), 7.76 (d, J=12.8 Hz, 1H).

8. 2-((S)-4-(4-chlorophenyl)-2,3,9-trimethyl-6H-thieno [3,2-f][1,2,4]triazolo[4,3-a][1,4]diazepin-6-yl)-N-(4-(2-(2-(2-(2-(2-(2,6-dioxopiperidin-3-yl)-1,3-dioxoisoindolin-4-ylamino)ethoxy)ethoxy)ethoxy) ethoxy)phenyl)acetamide

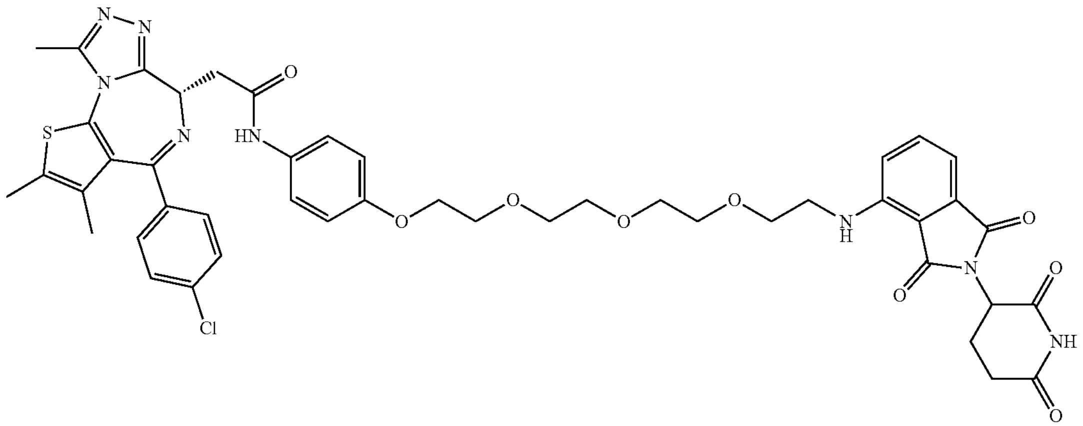 [SMILES: Cc1sc2c(c1C)C(c1ccc(Cl)cc1)=N[C@@H](CC(=O)Nc1ccc(OCCOCCOCCOCCNc3cccc4c3C(=O)N(C3CCC(=O)NC3=O)C4=O)cc1)c1nnc(C)n1-2]

(Structure #14 shown in Table 1)

Step 1: (2-(2,6-dioxopiperidin-3-yl)-4-(2-(2-(2-(2-(4-nitrophenoxy)ethoxy)ethoxy)ethoxy)ethylamino) isoindoline-1,3-dione

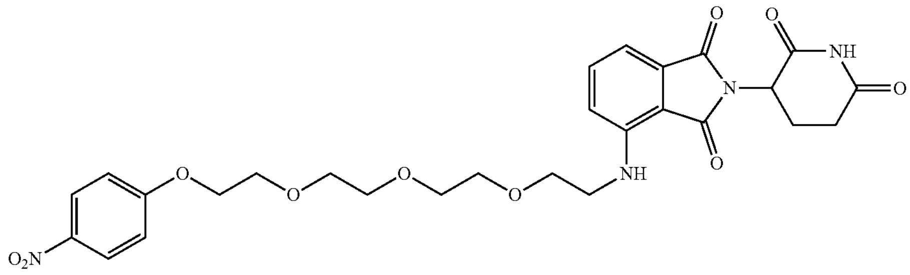 [SMILES: O=C1CCC(N2C(=O)c3cccc(NCCOCCOCCOCCOc4ccc([N+](=O)[O-])cc4)c3C2=O)C(=O)N1]

A mixture of 2-(2-(2-(2-(4-nitrophenoxy)ethoxy)ethoxy) ethoxy)ethanamine (128 mg, 0.41 mmol), 2-(2,6-dioxopiperidin-3-yl)-4-fluoro-2,3-dihydro-1H-isoindole-1,3-dione (112.5 mg, 0.41 mmol) and N-ethyl-N-isopropylpropan-2-amine (105 mg, 0.81 mmol) in dry N,N-dimethylformamide (2 mL) was stirred at 90° C. for 12 h. The mixture was cooled to room temperature, poured into water (20 mL) and extracted with ethyl acetate (35 mL×2). The combined organic phases were washed with water (30 mL) and brine (30 mL), dried over anhydrous sodium sulfate, and concentrated under reduced pressure. The crude residue was purified by pre-TLC to afford 2-(2,6-dioxopiperidin-3-yl)-4-(2-(2-(2-(2-(4-nitrophenoxy)ethoxy)ethoxy) ethoxy) ethylamino)isoindoline-1,3-dione (73 mg, 31% yield) as a yellow solid. LC-MS ($ES^+$): m/z 571.3 [$MH^+$], $t_R$=2.46 min.

Step 2: (4-(2-(2-(2-(2-(4-aminophenoxy)ethoxy) ethoxy)ethoxy)ethylamino)-2-(2,6-dioxopiperidin-3-yl)isoindoline-1,3-dione)

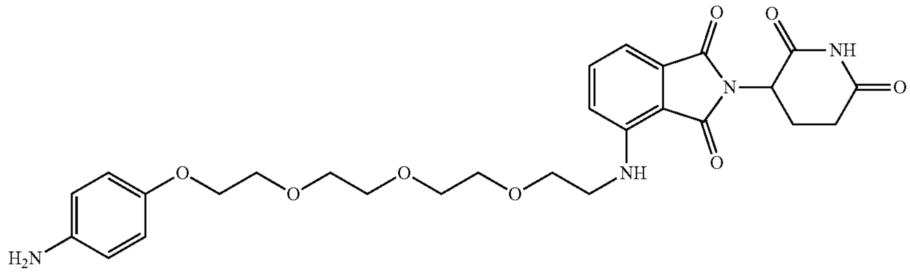

To a suspension of 2-(2,6-dioxopiperidin-3-yl)-4-(2-(2-(2-(2-(4-nitrophenoxy)ethoxy) ethoxy)ethoxy)ethylamino) isoindoline-1,3-dione (73 mg, 0.128 mmol) and iron powder (71.6 mg, 1.28 mmol) in ethanol (2 mL) was added a solution of ammonium chloride (68 mg, 1.26 mmol) in water (0.5 mL) at room temperature, the resulting mixture was stirred at 80° C. for 1 h. After the mixture was cooled to room temperature, the solid precipitate was filtered off and washed with ethyl acetate (10 mL×2). The filtrate was partitioned between ethyl acetate (60 mL) and water (30 mL). The organic layer was washed with brine (30 mL), dried over anhydrous sodium sulfate, and concentrated under reduced pressure to afford 4-(2-(2-(2-(2-(4-aminophenoxy)ethoxy)ethoxy)ethoxy)ethylamino)-2-(2,6-dioxopiperidin-3-yl)isoindoline-1,3-dione (66.5 mg, crude) as a yellow oil. LC-MS ($ES^+$): m/z 541.5 [$MH^+$], $t_R$=1.593 min.

Step 3: 2-((S)-4-(4-chlorophenyl)-2,3,9-trimethyl-6H-thieno [3,2-f][1,2,4]triazolo[4,3-a][1,4]diazepin-6-yl)-N-(4-(2-(2-(2-(2-(2-(2,6-dioxopiperidin-3-yl)-1,3-dioxoisoindolin-4-ylamino)ethoxy)ethoxy)ethoxy)ethoxy)phenyl)acetamide

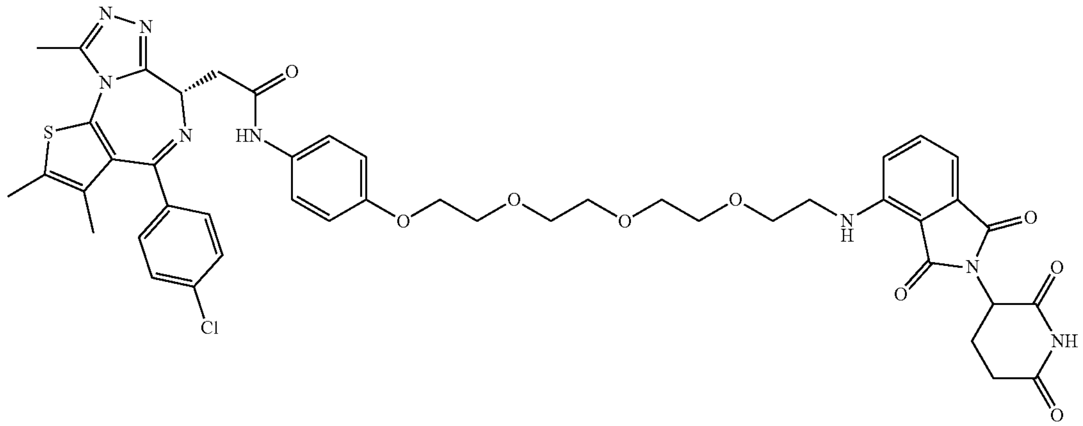 [SMILES: Cc1sc2c(c1C)C(c1ccc(Cl)cc1)=N[C@@H](CC(=O)Nc1ccc(OCCOCCOCCOCCNc3cccc4c3C(=O)N(C3CCC(=O)NC3=O)C4=O)cc1)c1nnc(C)n1-2]

To a stirred solution of 4-(2-(2-(2-(2-(4-aminophenoxy)ethoxy)ethoxy)ethoxy)ethylamino)-2-(2,6-dioxopiperidin-3-yl)isoindoline-1,3-dione (58.4 mg, 0.11 mmol), (S)-2-(4-(4-chlorophenyl)-2,3,9-trimethyl-6H-thieno[3,2-f][1,2,4]triazolo[4,3-a][1,4]diazepin-6-yl)acetic acid (43.3 mg, 0.11 mmol) and N-ethyl-N-isopropylpropan-2-amine (41.8 mg, 0.32 mmol) in dry N,N-dimethylformamide (1 mL) was added (2-(7-aza-1H-benzotriazole-1-yl)-1,1,3,3-tetramethyluroniumhexafluorophosphate) (82 mg, 0.21 mmol) at 0° C. The resulting mixture was allowed to warm up to room temperature and stirred at room temperature for 20 min. The mixture was poured into water (25 mL), extracted with ethyl acetate (35 ml×2). The combined organic phases were washed with water (20 mL) and brine (30 mL), dried over anhydrous sodium sulfate, and concentrated under reduced pressure. The crude residue was purified by prep-TLC to afford 2-((S)-4-(4-chlorophenyl)-2,3,9-trimethyl-6H-thieno[3,2-f][1,2,4]triazole [4,3-a][1,4]diazepin-6-yl)-N-(4-(2-(2-(2-(2-(2-(2,6-dioxopiperidin-3-yl)-1,3-dioxoisoindolin-4-ylamino)ethoxy)ethoxy)ethoxy)ethoxy)phenyl)acetamide (52 mg, 52% yield) as a yellow solid. LC-MS ($ES^+$): m/z 923.29/925.29 (3:1) [$MH^+$], $t_R$=2.689 min. $^1H$ NMR (400 MHz, $CDCl_3$): δ 1.67 (s, 3H), 2.05-2.12 (m, 1H), 2.40 (s, 3H), 2.65-2.85 (m, 6H), 3.41-3.54 (m, 4H), 3.65-3.74 (m, 10H), 3.81-3.85 (m, 2H), 4.06-4.11 (m, 2H), 4.63-4.69 (m, 1H), 4.85-4.93 (m, 1H), 6.38-6.55 (m, 1H), 6.83 (d, J=8.8 Hz, 2H), 6.92 (d, J=8.8 Hz, 1H), 7.09 (d, J=7.2 Hz, 1H), 7.33 (d, J=8.4 Hz, 2H), 7.39-7.51 (m, 5H), 8.59 (d, J=5.2 Hz, 1H), 8.77 (d, J=3.2 Hz, 1H).

9. (Z)-4-(4-((3-(2-(2-(2-(2-(2,6-dioxopiperidin-3-yl)-1,3-dioxoisoindolin-4-ylamino)ethoxy)ethoxy)ethyl)-2,4-dioxothiazolidin-5-ylidene)methyl)-2-methoxyphenoxy)-3-(trifluoromethyl)benzonitrile

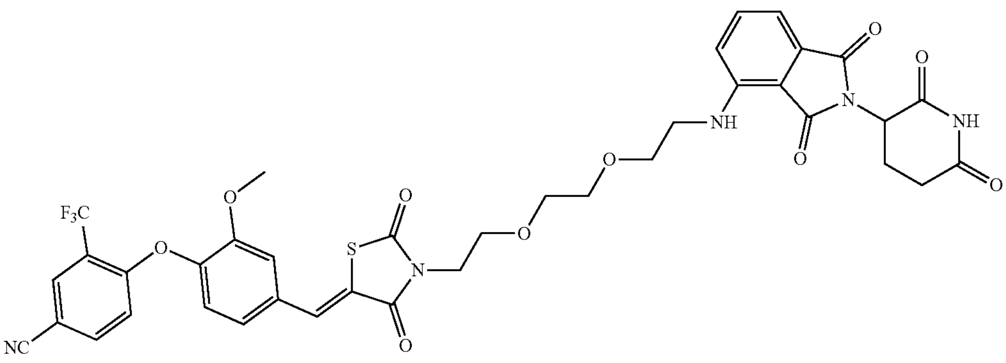 [SMILES: COc1cc(/C=C2\SC(=O)N(CCOCCOCCNc3cccc4c3C(=O)N(C3CCC(=O)NC3=O)C4=O)C2=O)ccc1Oc1ccc(C#N)cc1C(F)(F)F]

(Compound #22 shown in Table 1)

Step 1: (Z)-2-(2-(2-(5-(4-(4-cyano-2-(trifluoromethyl)phenoxy)-3-methoxybenzylidene)-2,4-dioxothiazolidin-3-yl)ethoxy)ethoxy)ethyl 4-methylbenzenesulfonate)

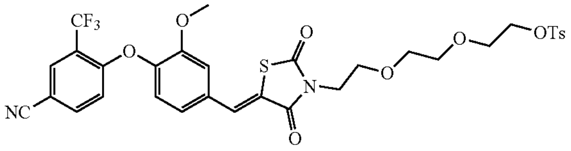 [SMILES: COc1cc(/C=C2\SC(=O)N(CCOCCOCCOS(=O)(=O)c3ccc(C)cc3)C2=O)ccc1Oc1ccc(C#N)cc1C(F)(F)F]

A mixture of (Z)-4-(4-((2,4-dioxothiazolidin-5-ylidene)methyl)-2-methoxyphenoxy)-3-(trifluoromethyl)benzonitrile (1.0 g, 2.3 mmol), potassium carbonate (1.0 g, 6.9 mmol) and 2,2'-(ethane-1,2-diylbis(oxy))bis(ethane-2,1-diyl) bis(4-methylbenzenesulfonate) (1.3 g, 2.7 mmol) in N,N-dimethylformamide (10 mL) was stirred at 80° C. for 16 h. The reaction mixture was cooled to room temperature, quenched with water (10 mL), and extracted with ethyl acetate (40 mL×3). The combined organic phases were washed with water (50 mL) and brine (50 mL), dried over sodium sulfate, and evaporated under reduced pressure. The crude residue was purified by silica gel flash column chromatography (eluted with 10-30% ethyl acetate in hexane) to afford (Z)-2-(2-(2-(5-(4-(4-cyano-2-(trifluoromethyl)phenoxy)-3-methoxybenzylidene)-2,4-dioxothiazolidin-3-yl)ethoxy)ethoxy)ethyl 4-methylbenzenesulfonate (1.0 g, 61% yield) as a light yellow solid.

Step 2: (Z)-4-(4-((3-(2-(2-(2-azidoethoxy)ethoxy)ethyl)-2,4-dioxothiazolidin-5-ylidene)methyl)-2-methoxyphenoxy)-3-(trifluoromethyl)benzonitrile

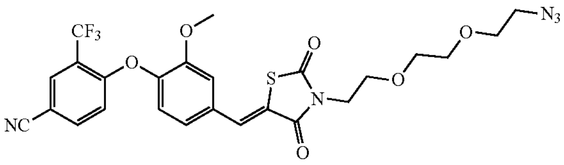 [SMILES: COc1cc(/C=C2\SC(=O)N(CCOCCOCCN=[N+]=[N-])C2=O)ccc1Oc1ccc(C#N)cc1C(F)(F)F]

A mixture of (Z)-2-(2-(2-(5-(4-(4-cyano-2-(trifluoromethyl)phenoxy)-3-methoxybenzylidene)-2,4-dioxothiazolidin-3-yl)ethoxy)ethoxy)ethyl 4-methylbenzenesulfonate (1.0 g, 1.4 mmol) and sodium azide (185 mg, 2.8 mmol) in ethanol (20 mL) was refluxed for 16 h. The reaction mixture was cooled to room temperature and partitioned between ethyl acetate (100 mL) and water (20 mL). The organic layer was washed with brine (30 ml), dried over anhydrous sodium sulfate and concentrated under reduced pressure to afford (Z)-4-(4-((3-(2-(2-(2-azidoethoxy)ethoxy)ethyl)-2,4-dioxothiazolidin-5-ylidene)methyl)-2-methoxyphenoxy)-3-(trifluoromethyl)benzonitrile (130 mg, crude) as a light yellow oil, which was used in next step without further purification.

Step 3: (Z)-4-(4-((3-(2-(2-(2-aminoethoxy)ethoxy)ethyl)-2,4-dioxothiazolidin-5-ylidene)methyl)-2-methoxyphenoxy)-3-(trifluoromethyl)benzonitrile

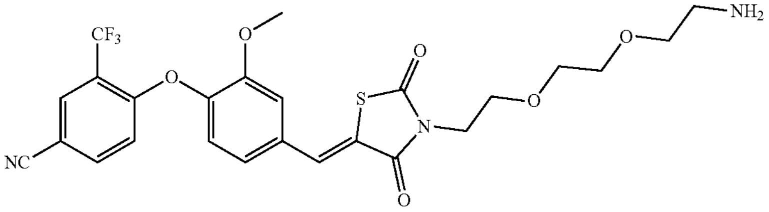 [SMILES: COc1cc(/C=C2\SC(=O)N(CCOCCOCCN)C2=O)ccc1Oc1ccc(C#N)cc1C(F)(F)F]

A mixture of the above (Z)-4-(4-((3-(2-(2-(2-azidoethoxy)ethoxy)ethyl)-2,4-dioxothiazolidin-5-ylidene)methyl)-2-methoxyphenoxy)-3-(trifluoromethyl)benzonitrile) (130 mg, crude), triphenylphosphine (100 mg, 0.34 mmol) in water (0.2 mL) and tetrahydrofuran (20 mL) was stirred at room temperature for 14 h. The mixture was concentrated under reduced pressure. The crude residue was purified by silica gel flash column chromatography (eluted with 3-5% methanol in dichloromethane) to give (Z)-4-(4-((3-(2-(2-(2-aminoethoxy) ethoxy)ethyl)-2,4-dioxothiazolidin-5-ylidene)methyl)-2-methoxyphenoxy)-3-(trifluoromethyl) benzonitrile (60 mg, 8% yield over two steps) as a yellow oil. LC-MS ($ES^+$): m/z 552.1 [$MH^+$], $t_R$=2.15 min.

Step 4: (Z)-4-(4-((3-(2-(2-(2-(2-(2,6-dioxopiperidin-3-yl)-1,3-dioxoisoindolin-4-ylamino)ethoxy)ethoxy) ethyl)-2,4-dioxothiazolidin-5-ylidene)methyl)-2-methoxyphenoxy)-3-(trifluoromethyl)benzonitrile

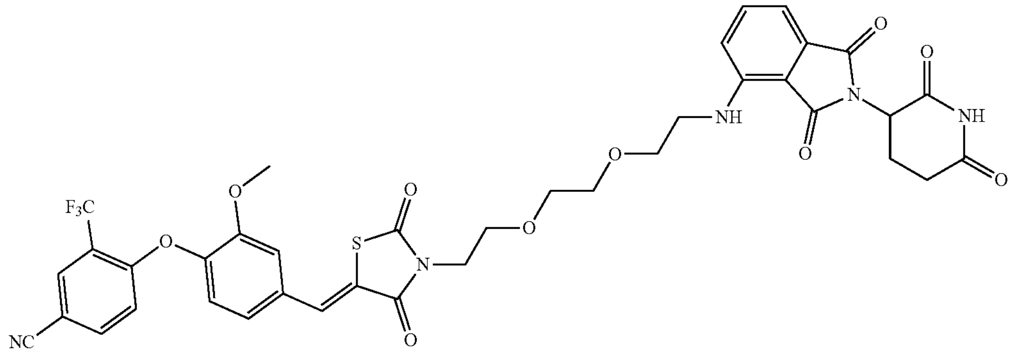 [SMILES: COc1cc(/C=C2\SC(=O)N(CCOCCOCCNc3cccc4c3C(=O)N(C3CCC(=O)NC3=O)C4=O)C2=O)ccc1Oc1ccc(C#N)cc1C(F)(F)F]

A mixture of (Z)-4-(4-((3-(2-(2-(2-aminoethoxy)ethoxy) ethyl)-2,4-dioxothiazolidin-5-ylidene) methyl)-2-methoxyphenoxy)-3-(trifluoromethyl)benzonitrile) (60 mg, 0.10 mmol), 2-(2,6-dioxopiperidin-3-yl)-4-fluoro-2,3-dihydro-1H-isoindole-1,3-dione (30 mg, 0.13 mmol) and N-ethyl-N-isopropylpropan-2-amine (50 mg, 0.39 mmol) in 1-methylpyrrolidin-2-one (1 mL) was stirred at 90° C. for 16 h. The reaction mixture was cooled to room temperature, quenched with water (5 mL), and extracted with ethyl acetate (20 mL×3). The combined organic layers were washed with water (10 mL×2) and brine (10 mL), dried over anhydrous sodium sulfate, and concentrated under reduced pressure. The crude residue was purified by prep-TLC to afford (Z)-4-(4-((3-(2-(2-(2-(2-(2,6-dioxopiperidin-3-yl)-1,3-dioxoisoindolin-4-ylamino)ethoxy)ethoxy) ethyl)-2,4-dioxothiazolidin-5-ylidene)methyl)-2-methoxyphenoxy)-3-(trifluoromethyl) benzonitrile (9.5 mg, 11.8% yield) as a yellow solid. LC-MS ($ES^+$): m/z 808.19 [$MH^+$], $t_R$=3.022 min. $^1H$ NMR (400 MHz, $CDCl_3$): δ 2.12-2.16 (m, 1H), 2.73-2.91 (m, 3H), 3.42 (s, 2H), 3.67-3.80 (m, 11H), 3.99 (s, 2H), 4.91-4.95 (m, 1H), 6.51 (s, 1H), 6.76-6.86 (m, 2H), 7.02-7.19 (m, 4H), 7.43 (t, J=7.6 Hz, 1H), 7.68 (d, J=8.0 Hz, 1H), 7.85-8.12 (m, 3H).

10. 4-(3-(4-(3-(2-(2-(2-((2-(2,6-dioxopiperidin-3-yl)-1,3-dioxoisoindolin-4-yl)amino) ethoxy)ethoxy) ethoxy)propoxy)phenyl)-4,4-dimethyl-5-oxo-2-thioxoimidazolidin-1-yl)-2-(trifluoromethyl)benzonitrile

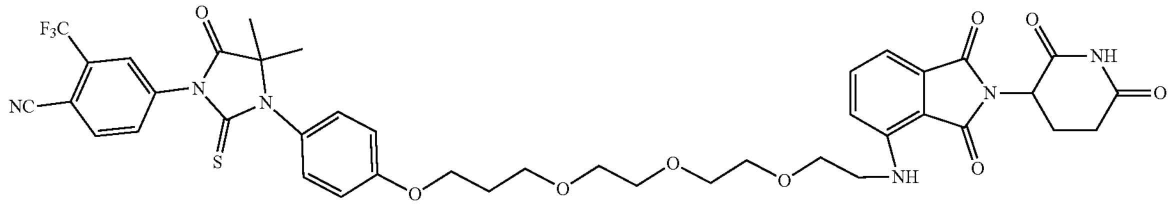 [SMILES: CC1(C)C(=O)N(c2ccc(C#N)c(C(F)(F)F)c2)C(=S)N1c1ccc(OCCCOCCOCCOCCNc2cccc3c2C(=O)N(C2CCC(=O)NC2=O)C3=O)cc1]

(Compound #1 shown in Table 1)

Step 1: 1,1,1,16-tetraphenyl-2,5,8,11,15-pentaoxahexadecane

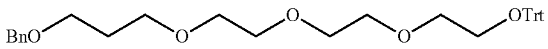

To a solution of 2-(2-(2-(trityloxy)ethoxy)ethoxy)ethanol (7 g, 17.7 mmol) in N,N-dimethylformamide (50 mL) was slowly added sodium hydride (60% in mineral oil, 707 mg, 17.7 mmol) at 0° C. After the mixture was stirred at rt for 30 min, 3-(benzyloxy)propyl 4-methylbenzenesulfonate (5.8 g 18.0 mmol) was added in one portion at 0° C., the resulting mixture was allowed to stir at 70° C. overnight. After the mixture was cooled to rt, it was carefully quenched with water (40 mL), extracted with ethyl acetate (60 mL×3). The combined organic phases were washed with brine (80 mL), dried over anhydrous sodium sulfate, and concentrated under reduced pressure. The crude residue was purified by silica gel flash chromatography (eluted with 5-10% ethyl acetate in hexane) to afford 1,1,1,16-tetraphenyl-2,5,8,11,15-pentaoxahexadecane (4.8 g, 50% yield) as a colorless oil. $^1H$ NMR (400 MHz, $CDCl_3$): δ 1.85-1.92 (m, 2H), 3.23 (t, J=5.2 Hz, 2H), 3.53-3.59 (m, 6H), 3.64-3.68 (m, 8H), 4.47 (s, 2H), 7.19-7.33 (m, 15H), 7.45-7.47 (m, 5H).

Step 2: 1-phenyl-2,6,9,12-tetraoxatetradecan-14-ol

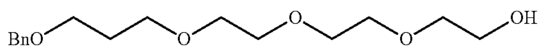 [SMILES: OCCOCCOCCOCCCOCc1ccccc1]

To a solution of 1,1,1,16-tetraphenyl-2,5,8,11,15-pentaoxahexadecane (4.8 g 8.8 mmol) in methylene dichloride (10 mL) and methanol (10 mL) was added aqueous hydrochloric acid (37%, 2.5 mL) at 0° C. The reaction mixture was stirred at rt for 2 h. The reaction mixture was poured into water (30 mL), and extracted with dichloromethane (20 mL×3). The combined organic phases were washed with aqueous sodium bicarbonate (1N, 50 mL), water (30 mL), brine, dried over anhydrous $Na_2SO_4$, and concentrated under reduced pressure. The crude residue was purified by silica gel flash column chromatography (eluted with 20-40% ethyl acetate in hexane) to afford 1-phenyl-2,6,9,12-tetraoxatetradecan-14-ol (1.9 g, 73% yield) as a colorless oil.

Step 3: 1-phenyl-2,6,9,12-tetraoxatetradecan-14-yl 4-methylbenzenesulfonate

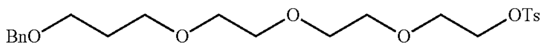 [SMILES: Cc1ccc(S(=O)(=O)OCCOCCOCCOCCCOCc2ccccc2)cc1]

A mixture of 1-phenyl-2,7,10,13-tetraoxapentadecan-15-ol (1.9 g, 6.3 mmol), triethylamine (1.3 mL, 9.5 mmol), N,N-dimethylpyridin-4-amine (75 mg, 0.63 mmol) and 4-methylbenzene-1-sulfonyl chloride (1.45 g, 7.65 mmol) in dichloromethane (20 mL) was stirred at rt for 3 h. Water (20 mL) was added to quench the reaction, and the product was extracted with dichloromethane (40 mL×3). The combined organic phases were washed with brine (50 mL), dried over sodium sulfate, and evaporated under reduced pressure. The crude residue was purified by silica gel flash column chromatography (eluted with 10-30% ethyl acetate in hexane) to afford 1-phenyl-2,6,9,12-tetraoxatetradecan-14-yl 4-methylbenzenesulfonate (2.2 g, 78% yield) as a colorless oil. $^1H$ NMR (400 MHz, $CDCl_3$): δ 1.87-1.92 (m, 2H), 2.43 (s, 3H), 3.54-3.60 (m, 12H), 3.67 (t, J=5.2 Hz, 2H), 4.15 (t, J=5.0 Hz, 2H), 4.48 (s, 2H), 7.27-7.33 (m, 7H), 7.79 (d, J=8.4 Hz, 2H).

Step 4: 14-azido-1-phenyl-2,6,9,12-tetraoxatetradecane

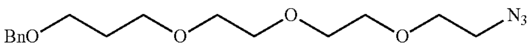 [SMILES: [N-]=[N+]=NCCOCCOCCOCCCOCc1ccccc1]

A mixture of 1-phenyl-2,6,9,12-tetraoxatetradecan-14-yl 4-methylbenzenesulfonate (2.2 g, 4.9 mmol) and sodium azide (420 mg, 6.3 mmol) in ethanol (10 mL) was refluxed for 5 h. The reaction mixture was cooled to rt, poured into water (10 mL), and extracted with dichloromethane (50 mL×3). The combined organic layers were washed with brine (50 mL), dried over anhydrous sodium sulfate, and concentrated under reduced pressure to give 14-azido-1-phenyl-2,6,9,12-tetraoxatetradecane (1.4 g, crude) as a colorless oil, which was used in next step without further purification.

Step 5: tert-butyl (1-phenyl-2,6,9,12-tetraoxatetradecan-14-yl)carbamate

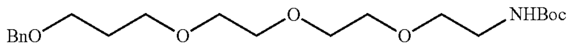 [SMILES: CC(C)(C)OC(=O)NCCOCCOCCOCCCOCc1ccccc1]

A mixture of the above 14-azido-1-phenyl-2,6,9,12-tetraoxatetradecane (1.4 g, crude) and triphenylphosphine (1.7 g, 6.5 mmol) in tetrahydrofuran (15 mL) and water (0.5 mL) was stirred at rt overnight under nitrogen atmosphere. To the reaction mixture were added triethylamine (0.9 mL, 6.5 mmol) and di-tert-butyl dicarbonate (1.1 g, 5.2 mmol) at 0° C. The resulting mixture was allowed to warm up to rt and stir at rt for 2 h. The volatiles were evaporated under reduced pressure, and the residue was partitioned between dichloromethane (100 mL) and water (50 mL). The organic phase was washed with brine (30 mL), dried over anhydrous sodium sulfate, and concentrated under reduced pressure. The crude residue was purified by silica gel flash chromatography (eluted with 30-50% ethyl acetate in hexane) to afford tert-butyl (1-phenyl-2,6,9,12-tetraoxatetradecan-14-yl)carbamate (1.2 g, 50% yield over two steps) as a colorless oil.

Step 6: tert-butyl 2-(2-(2-(3-hydroxypropoxy)ethoxy)ethoxy)ethylcarbamate

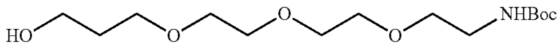 [SMILES: CC(C)(C)OC(=O)NCCOCCOCCOCCCO]

A mixture of tert-butyl (1-phenyl-2,6,9,12-tetraoxatetradecan-14-yl)carbamate (1.2 g, 3 mmol) and palladium on carbon (10%, 200 mg) in ethanol (50 mL) was stirred at rt under hydrogen atmosphere (hydrogen balloon). Palladium on carbon was removed by filtration and washed with ethanol (20 mL). The filtrate was concentrated under reduced pressure to afford tert-butyl 2-(2-(2-(3-hydroxy-propoxy)ethoxy)ethoxy)ethylcarbamate (900 mg, crude) as a colorless oil, which was used in next step without further purification.

Step 7: 2,2-dimethyl-4-oxo-3,8,11,14-tetraoxa-5-azaheptadecan-17-yl 4-methylbenzenesulfonate

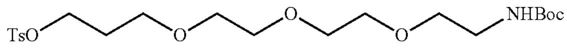 [SMILES: Cc1ccc(S(=O)(=O)OCCCOCCOCCOCCNC(=O)OC(C)(C)C)cc1]

A mixture of the above tert-butyl 2-(2-(2-(3-hydroxy-propoxy)ethoxy)ethoxy) ethylcarbamate (900 mg, crude), triethylamine (0.6 mL, 4.35 mmol), N,N-dimethylpyridin-4-amine (16 mg, 0.14 mmol) and 4-methylbenzene-1-sulfonyl chloride (660 mg, 3.5 mmol) in anhydrous dichloromethane (15 mL) was stirred at rt for 3 h. Water (20 mL) was added to quench the reaction and the product was extracted with dichloromethane (50 mL×3). The combined organic phases were washed with brine (50 mL), dried over anhydrous sodium sulfate, and evaporated under reduced pressure. The crude residue was purified by silica gel flash column chromatography (eluted with 20-30% ethyl acetate in hexane) to afford 2,2-dimethyl-4-oxo-3,8,11,14-tetraoxa-5-azaheptadecan-17-yl 4-methylbenzenesulfonate (650 mg, 77% yield) as a light yellow oil. $^1$H NMR (400 MHz, $CDCl_3$): δ 1.44 (s, 9H), 1.88-1.95 (m, 2H), 2.45 (s, 3H), 3.29-3.33 (m, 2H), 3.48-3.61 (m, 12H), 4.09-4.15 (m, 2H), 5.04 (brs, 1H), 7.34 (d, J=8.0 Hz, 2H), 7.79 (d, J=8.0 Hz, 2H).

Step 8: tert-butyl (2-(2-(2-(3-(4-(3-(4-cyano-3-(trifluoromethyl)phenyl)-5,5-dimethyl-4-oxo-2-thioxoimidazolidin-1-yl)phenoxy)propoxy)ethoxy)ethoxy) ethyl)carbamate

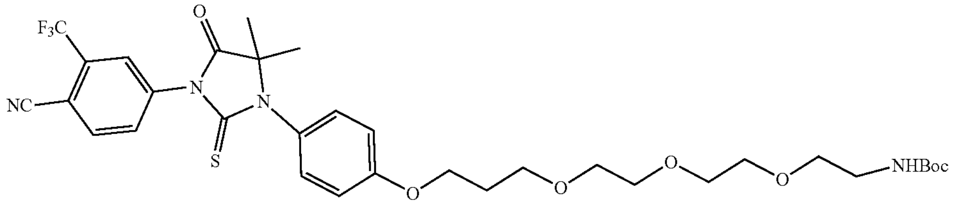 [SMILES: CC(C)(C)OC(=O)NCCOCCOCCOCCCOc1ccc(N2C(=S)N(c3ccc(C#N)c(C(F)(F)F)c3)C(=O)C2(C)C)cc1]

A mixture of 2,2-dimethyl-4-oxo-3,8,11,14-tetraoxa-5-azaheptadecan-17-yl 4-methylbenzenesulfonate (115 mg, 0.25 mmol), potassium carbonate (69 mg, 0.50 mmol) and 4-(3-(4-hydroxyphenyl)-4,4-dimethyl-5-oxo-2-thioxoimidazolidin-1-yl)-2-(trifluoromethyl)benzonitrile (100 mg, 0.25 mmol) in acetonitrile (5 mL) was stirred at 80° C. for 16 h. The reaction mixture was cooled to room temperature, quenched with water (30 mL), and extracted with ethyl acetate (30 mL×3). The combined organic phases were washed with water (30 mL) and brine (30 mL), dried over magnesium sulfate, and evaporated under reduced pressure. The crude residue was purified by silica gel flash column chromatograph (eluted with 10-30% ethyl acetate in hexane) to afford tert-butyl 2-(2-(2-(3-(4-(3-(4-cyano-3-(trifluoromethyl)phenyl)-5,5-dimethyl-4-oxo-2-thioxoimidazolidin-1-yl)phenoxy)propoxy)ethoxy)ethoxy) ethylcarbamate (150 mg, 82% yield) as a yellow oil. LC-MS ($ES^+$): m/z 695.40 [$MH^+$], $t_R$=2.79 min.

Step 9: 4-(3-(4-(3-(2-(2-(2-aminoethoxy)ethoxy) ethoxy)propoxy)phenyl)-4,4-dimethyl-5-oxo-2-thioxoimidazolidin-1-yl)-2-(trifluoromethyl)benzonitrile

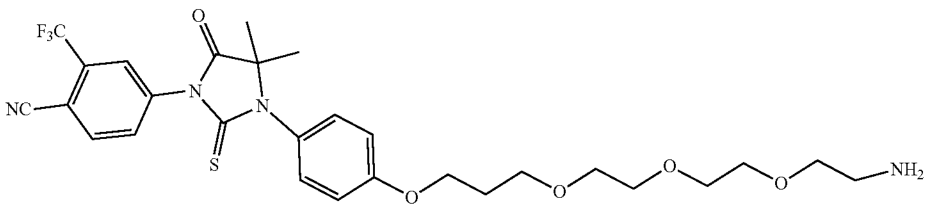 [SMILES: CC1(C)C(=O)N(c2ccc(C#N)c(C(F)(F)F)c2)C(=S)N1c1ccc(OCCCOCCOCCOCCN)cc1]

A mixture of tert-butyl 2-(2-(2-(3-(4-(3-(4-cyano-3-(trifluoromethyl)phenyl)-5,5-dimethyl-4-oxo-2-thioxoimidazolidin-1-yl)phenoxy)propoxy)ethoxy)ethoxy) ethylcarbamate (150 mg, 0.21 mmol) in anhydrous dichloromethane (2 mL) and 2,2,2-trifluoroacetic acid (1 mL) was stirred at rt for 1 h. The volatiles were evaporated under reduced pressure, the residue was poured into aqueous sodium bicarbonate (1N, 20 mL), and extracted with dichloromethane (50 mL×3). The combined organic phases were washed with brine (50 mL), dried over anhydrous sodium sulfate, and concentrated under reduced pressure to give 4-(3-(4-(3-(2-(2-(2-aminoethoxy)ethoxy)ethoxy)propoxy)phenyl)-4,4-dimethyl-5-oxo-2-thioxoimidazolidin-1-yl)-2-(trifluoromethyl)benzonitrile (115 mg, crude) as a brown oil, which was used in next step without further purification.

Step 10: 4-(3-(4-(3-(2-(2-(2-((2-(2,6-dioxopiperidin-3-yl)-1,3-dioxoisoindolin-4-yl)amino)ethoxy)ethoxy)ethoxy)propoxy)phenyl)-4,4-dimethyl-5-oxo-2-thioxoimidazolidin-1-yl)-2-(trifluoromethyl)benzonitrile

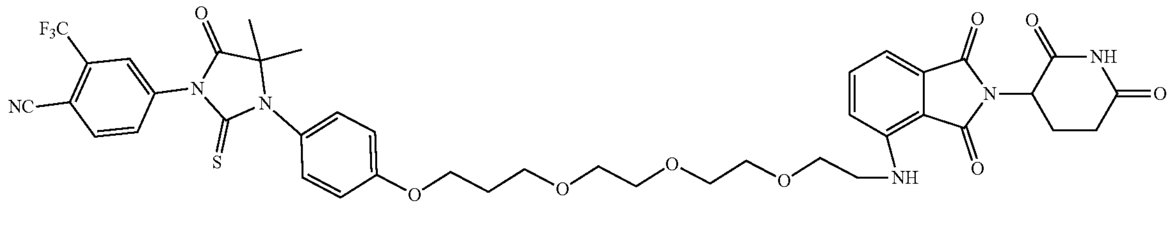 [SMILES: CC1(C)C(=O)N(c2ccc(C#N)c(C(F)(F)F)c2)C(=S)N1c1ccc(OCCCOCCOCCOCCNc2cccc3c2C(=O)N(C2CCC(=O)NC2=O)C3=O)cc1]

A solution of the above 4-(3-(4-(3-(2-(2-(2-aminoethoxy)ethoxy)ethoxy) propoxy)phenyl)-4,4-dimethyl-5-oxo-2-thioxoimidazolidin-1-yl)-2-(trifluoromethyl)benzonitrile (115 mg, crude), 2-(2,6-dioxopiperidin-3-yl)-4-fluoro-2,3-dihydro-1H-isoindole-1,3-dione (41 mg, 0.15 mmol) and N-ethyl-N-isopropylpropan-2-amine (58 mg, 0.44 mmol) in N,N-dimethylformamide (2 mL) was stirred at 90° C. for 16 h. The reaction mixture was cooled to rt, quenched with water (3 mL), and extracted with ethyl acetate (30 mL×3). The combined organic layers were washed with water (30 mL×2) and brine (20 mL), dried over anhydrous sodium sulfate, and concentrated under reduced pressure. The crude residue was purified by prep-TLC to afford 4-(3-(4-(3-(2-(2-(2-((2-(2,6-dioxopiperidin-3-yl)-1,3-dioxoisoindolin-4-yl)amino)ethoxy)ethoxy)ethoxy) propoxy)phenyl)-4,4-dimethyl-5-oxo-2-thioxoimidazolidin-1-yl)-2-(trifluoromethyl) benzonitrile (34.5 mg, 27% yield) as a yellow solid. LC-MS ($ES^+$): m/z 851.25 [$MH^+$], $t_R$=2.652 min. $^1$H NMR (400 MHz, $CD_3OD$): δ 1.57 (s, 6H), 2.07-2.11 (m, 3H), 2.70-2.90 (m, 3H), 3.46-3.72 (m, 14H), 4.10 (t, J=6.2 Hz, 2H), 4.88-4.92 (m, 1H), 6.48-6.49 (m, 1H), 6.91-7.26 (m, 6H), 7.49 (t, J=7.8 Hz, 1H), 7.83-7.85 (m, 1H), 7.97-8.02 (m, 3H).

11. 4-{[5-(3-{[2-(2,6-dioxopiperidin-3-yl)-1,3-dioxo-2,3-dihydro-1H-isoindol-4-yl]amino}propoxy)pentyl]oxy}-N-[trans-3-(3-chloro-4-cyanophenoxy)-2,2,4,4-tetramethylcyclobutyl]benzamide

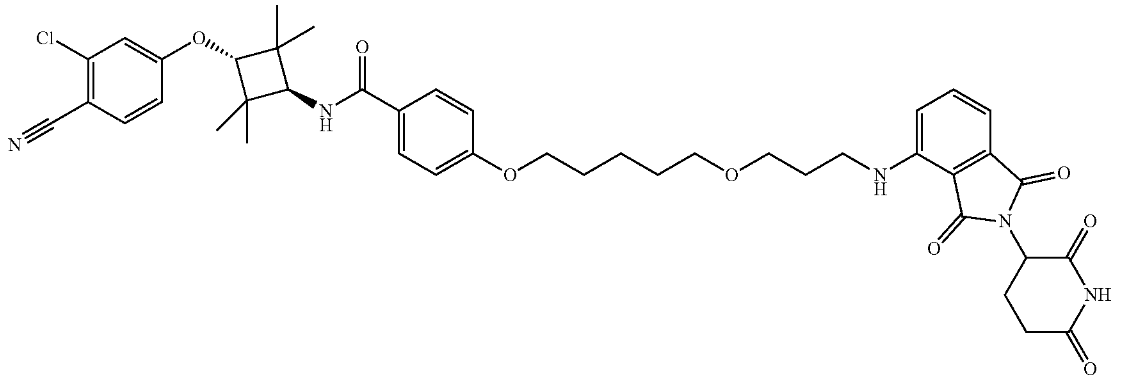 [SMILES: CC1(C)[C@H](NC(=O)c2ccc(OCCCCCOCCCNc3cccc4c3C(=O)N(C3CCC(=O)NC3=O)C4=O)cc2)C(C)(C)[C@H]1Oc1ccc(C#N)c(Cl)c1]

Step 1: 3-[(5-hydroxypentyl)oxy]propanenitrile

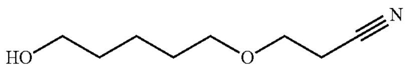 [SMILES: N#CCCOCCCCCO]

Pentane-1,5-diol (2.98 g, 28.6 mmol) was added to a suspension of sodium hydride (60% dispersion in mineral oil, 820 mg, 34.2 mmol) in THE (50 mL). After the mixture was stirred at rt for 20 min, it was cooled to 0° C., and acrylonitrile (1.20 g, 22.8 mmol) was added dropwise. The resulting mixture was stirred at rt for 10 h. Part of the solvent was removed under vacuum and the residue was poured into water. The mixture was extracted with DCM (3×). The organic layer was filtered through a Biotage Universal Phase Separator and concentrated in vacuo. The crude material was purified by silica gel chromatography on a Teledyne Combiflash ISCO eluting with MeOH/DCM (0:100 to 3:97) to yield 3-[(5-hydroxypentyl)oxy]propanenitrile (635 mg, 18% yield). $^1$H NMR (400 MHz, $CDCl_3$) δ 3.60-3.73 (m, 4H), 3.45-3.55 (m, 2H), 2.60 (dt, J=4.1, 6.4 Hz, 2H), 2.06 (d, J=3.9 Hz, 1H), 1.57-1.69 (m, 4H), 1.43-1.50 (m, 2H).

Step 2: tert-butyl N-{3-[(5-hydroxypentyl)oxy]propyl}carbamate

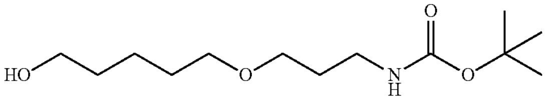 [SMILES: CC(C)(C)OC(=O)NCCCOCCCCCO]

To a solution of 3-[(5-hydroxypentyl)oxy]propanenitrile (400 mg, 2.54 mmol) in MeOH (12 mL) and $H_2O$ (2.0 mL) was added Nickel(II) chloride (393 mg, 3.04 mmol), followed by sodium borohydride (360 mg, 9.52 mmol) portionwise. The mixture was stirred at rt for 3 h, then quenched with MeOH (12 mL). The mixture was filtered through celite and washed with MeOH. The filtrate was concentrated in vacuo. To a solution of the above crude product in THE (5 mL) were added 6 M aq NaOH (0.5 mL) and di-tert-butyl dicarbonate (831 mg, 3.81 mmol), the resulting mixture was stirred at rt for 3 h, then concentrated in vacuo. The crude material was purified by silica gel chromatography on a Teledyne Combiflash ISCO eluting with MeOH/DCM (0:100 to 4:96) to yield tert-butyl N-{3-[(5-hydroxypentyl)oxy]propyl}carbamate (366 mg, 55% yield).

$^1$H NMR (400 MHz, $CDCl_3$) δ 4.91 (br. s., 1H), 3.66 (br. s., 2H), 3.49 (t, J=5.9 Hz, 2H), 3.43 (t, J=6.3 Hz, 2H), 3.24 (q, J=5.9 Hz, 2H), 1.75 (quin, J=6.2 Hz, 2H), 1.57-1.65 (m, 5H), 1.41-1.52 (m, 11H).

Step 3: tert-butyl N-[3-({5-[(4-methylbenzenesulfonyl)oxy]pentyl}oxy)propyl]carbamate

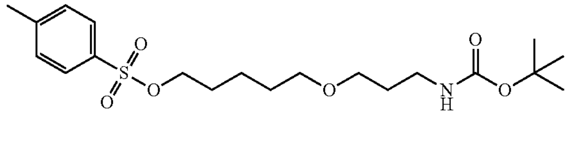 [SMILES: Cc1ccc(S(=O)(=O)OCCCCCOCCCNC(=O)OC(C)(C)C)cc1]

To a solution of tert-butyl (3-((5-hydroxypentyl)oxy)propyl)carbamate (300 mg, 3.88 mmol) in DCM (10 mL) were added DIPEA (599.3 μL, 3.44 mmol), tosyl chloride (262.3 mg, 1.38 mmol) and 4-dimethylaminopyridine (14.0 mg, 0.115 mmol). The resulting mixture was stirred at rt for 20 h. The reaction was quenched with a semi-saturated sodium bicarbonate, extracted with DCM (2×), filtered through a Biotage Universal Phase Separator, and concentrated in vacuo. The crude material was purified by silica gel chromatography on a Teledyne Combiflash ISCO eluting with EtOAc/Heptane (0:100 to 30:70) to yield tert-butyl N-[3-({5-[(4-methylbenzenesulfonyl)oxy]pentyl}oxy)propyl]carbamate (914 mg, 26% yield). $^1$H NMR (400 MHz, $CDCl_3$) δ 7.78 (d, J=8.2 Hz, 2H), 7.34 (d, J=8.2 Hz, 2H), 4.02 (t, J=6.5 Hz, 2H), 3.44 (t, J=6.1 Hz, 2H), 3.35 (t, J=6.3 Hz, 2H), 3.19 (q, J=5.9 Hz, 2H), 2.44 (s, 3H), 1.64-1.74 (m, 5H), 1.49-1.54 (m, 2H), 1.42 (s, 9H), 1.33-1.40 (m, 2H). LC-MS ($ES^+$): m/z 438.19 [$MNa^+$], $t_R$=2.65 min.

Step 4: methyl 4-{[5-(3-{[(tert-butoxy)carbonyl]amino}propoxy)pentyl]oxy}benzoate

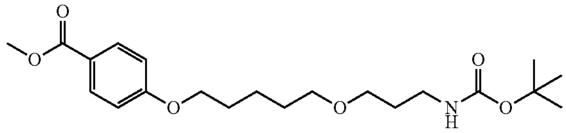 [SMILES: COC(=O)c1ccc(OCCCCCOCCCNC(=O)OC(C)(C)C)cc1]

A mixture of tert-butyl N-[3-({5-[(4-methylbenzenesulfonyl)oxy]pentyl}oxy)propyl]carbamate (340 mg, 0.82 mmol), methyl 4-hydroxybenzoate (117 mg, 0.77 mmol), potassium carbonate (203 mg, 1.47 mmol) in MeCN (10 mL) were stirred at 80° C. for 24 h. The reaction mixture was diluted with EtOAc, washed with semi-saturated sodium bicarbonate solution (1×), water (2×), brine (1×) and then filtered through a Biotage Universal Phase Separator. The filtrate was concentrated in vacuo, and the residue was purified by silica gel chromatography on a Teledyne Combiflash ISCO eluting with EtOAc/Heptane (0:100 to 50:50) to yield methyl 4-{[5-(3-{[(tert-butoxy)carbonyl]amino}propoxy)pentyl]oxy}benzoate (300 mg, 93% yield). LC-MS ($ES^+$): m/z 418.21 [$MNa^+$], $t_R$=2.74 min.

Step 5: 4-{[5-(3-{[(tert-butoxy)carbonyl]amino}propoxy)pentyl]oxy}benzoic acid

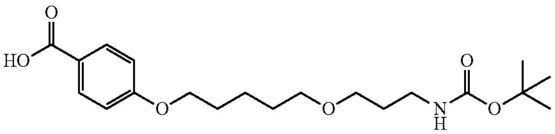 [SMILES: CC(C)(C)OC(=O)NCCCOCCCCCOc1ccc(C(=O)O)cc1]

To a solution of 4-{[5-(3-{[(tert-butoxy)carbonyl]amino}propoxy)pentyl]oxy}benzoate (150 mg, 0.38 mmol) in 1:1:1 THF/Water/MeOH (6.0 mL, v/v/v) was added lithium hydroxide (81.6 mg, 3.41 mmol). The resulting mixture was stirred overnight at rt, then acidified to a pH 2-3 with 6N aqueous HCl. The mixture was concentrated in vacuo to remove most solvents, then diluted with EtOAc, washed with water (2×), brine (2×), filtered through a Biotage Universal Phase Separator, and concentrated in vacuo. The crude product was carried onto next step without further purification (123 mg). LC-MS ($ES^+$): m/z 404.20 [$MNa^+$], $t_R$=2.40 min.

Step 6: tert-butyl N-(3-{[5-(4-{[trans-3-(3-chloro-4-cyanophenoxy)-2,2,4,4-tetramethylcyclobutyl]carbamoyl}phenoxy)pentyl]oxy}propyl)carbamate

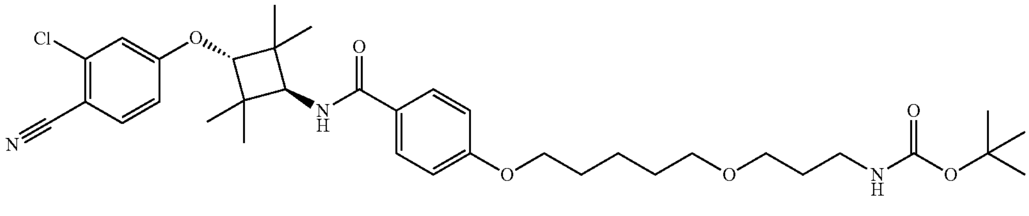 [SMILES: CC(C)(C)OC(=O)NCCCOCCCCCOc1ccc(C(=O)N[C@H]2C(C)(C)[C@H](Oc3ccc(C#N)c(Cl)c3)C2(C)C)cc1]

To a solution of 4-{[5-(3-{[(tert-butoxy)carbonyl]amino}propoxy)pentyl]oxy}benzoic acid (124 mg, 0.322 mmol), 2-chloro-4-(trans-3-amino-2,2,4,4-tetramethylcyclobutoxy)benzonitrile (89.8 mg, 0.322 mmol) in DMF (5 mL) were added DIPEA (112 μL, 0.65 mmol) and TBTU (155 mg, 0.48 mmol). The resulting mixture was stirred at rt for 1 h, then diluted with EtOAc, washed with water (3×), brine (1×), filtered through a Biotage Universal Phase Separator and concentrated in vacuo. The residue was purified by silica gel chromatography on a Teledyne Combiflash ISCO eluting with MeOH/DCM (0:100 to 5:95) to yield tert-butyl N-(3-{[5-(4-{[trans-3-(3-chloro-4-cyanophenoxy)-2,2,4,4-tetramethylcyclobutyl]carbamoyl}phenoxy) pentyl]oxy}propyl)carbamate (169 mg, 82% yield). LC-MS ($ES^+$): m/z 643.32/645.31 (3:1) [$MH^+$], $t_R$=3.04 min.

12. 4-{[5-(3-aminopropoxy)pentyl]oxy}-N-[trans-3-(3-chloro-4-cyanophenoxy)-2,2,4,4-tetramethylcyclobutyl]benzamide

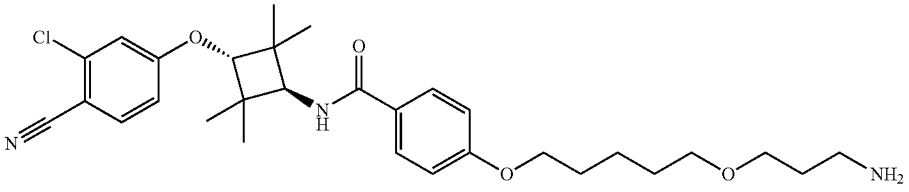 [SMILES: CC1(C)[C@H](NC(=O)c2ccc(OCCCCCOCCCN)cc2)C(C)(C)[C@H]1Oc1ccc(C#N)c(Cl)c1]

To a solution of tert-butyl N-(3-{[5-(4-{[trans-3-(3-chloro-4-cyanophenoxy)-2,2,4,4-tetramethylcyclobutyl]carbamoyl}phenoxy)pentyl]oxy}propyl)carbamate (124 mg, 0.192 mmol) in DCM (5 mL) was added trifluoroacetic acid (372 μL, 4.86 mmol) and heated at 45° C. for 1 h until completion. The reaction was then concentrated in vacuo to a solid and carried onto next step without further purification (104 mg, 99% yield). LC-MS ($ES^+$): m/z 543.27/545.26 (3:1) [$MH^+$], $t_R$=2.26 min.

13. 4-{[5-(3-{[2-(2,6-dioxopiperidin-3-yl)-1,3-dioxo-2,3-dihydro-1H-isoindol-4-yl]amino}propoxy)pentyl]oxy}-N-[trans-3-(3-chloro-4-cyanophenoxy)-2,2,4,4-tetramethylcyclobutyl]benzamide

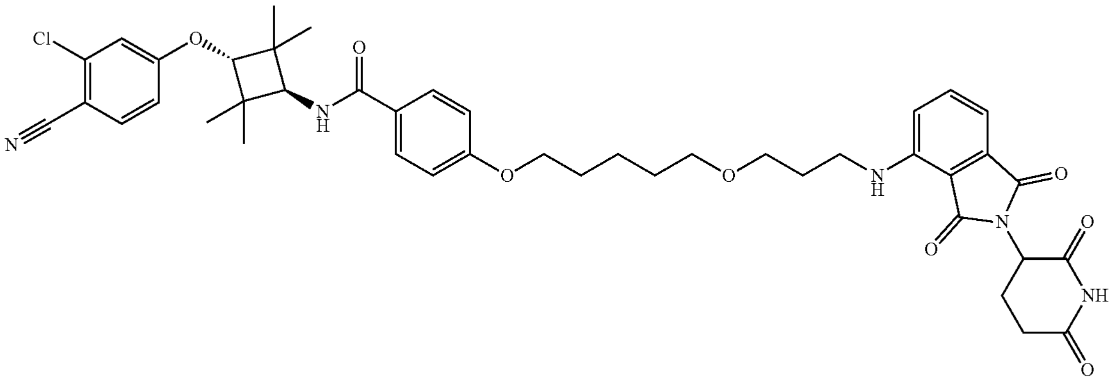 [SMILES: CC1(C)[C@H](NC(=O)c2ccc(OCCCCCOCCCNc3cccc4c3C(=O)N(C3CCC(=O)NC3=O)C4=O)cc2)C(C)(C)[C@H]1Oc1ccc(C#N)c(Cl)c1]

(Compound #11 shown in Table 1)

To a solution of 4-{[5-(3-aminopropoxy)pentyl]oxy}-N-[trans-3-(3-chloro-4-cyanophenoxy)-2,2,4,4-tetramethylcyclobutyl]benzamide (30.0 mg, 0.0553 mmol) in 1,4-dioxane (2 mL) were added diisopropylethylamine (384 μL, 2.21 mmol), 2-(2,6-dioxopiperidin-3-yl)-4-fluoro-2,3-dihydro-1H-isoindole-1,3-dione (18.3 mg, 0.0664 mmol). The resulting mixture was refluxed for 16 h, then diluted with EtOAc, washed with semi-saturated brine solution (2×), filtered through a Biotage Universal Phase Separator and concentrated in vacuo. The residue was purified by silica gel chromatography on a Teledyne Combiflash ISCO eluting with MeOH/DCM (0:100 to 7:93) to yield 4-{[5-(3-{[2-(2,6-dioxopiperidin-3-yl)-1,3-dioxo-2,3-dihydro-1H-isoindol-4-yl]amino}propoxy)pentyl]oxy}-N-[trans-3-(3-chloro-4-cyanophenoxy)-2,2,4,4-tetramethylcyclobutyl]benzamide (12 mg, 28% yield). LC-MS ($ES^+$): m/z 799.31/801.31 (3:1) [$MH^+$], $t_R$=2.97 min. $^1H$ NMR (400 MHz, $CDCl_3$) δ 8.03 (s, 1H), 7.72 (d, J=9.0 Hz, 2H), 7.58 (d, J=8.6 Hz, 1H), 7.48 (dd, J=7.2, 8.4 Hz, 1H), 7.07 (d, J=7.0 Hz, 1H), 6.98 (d, J=2.3 Hz, 1H), 6.89-6.96 (m, 3H), 6.82 (dd, J=2.5, 8.8 Hz, 1H), 6.18 (d, J=8.2 Hz, 1H), 4.89 (dd, J=5.1, 12.1 Hz, 1H), 4.16 (d, J=7.8 Hz, 1H), 4.06 (s, 1H), 4.02 (t, J=6.7 Hz, 2H), 3.56 (t, J=5.9 Hz, 2H), 3.50 (s, 2H), 3.46-3.48 (m, 1H), 3.41 (t, J=6.5 Hz, 2H), 2.82-2.90 (m, 1H), 2.76-2.81 (m, 1H), 2.67-2.75 (m, 1H), 2.07-2.14 (m, 1H), 1.94 (quin, J=6.1 Hz, 2H), 1.82-1.87 (m, 2H), 1.67-1.73 (m, 2H), 1.53-1.59 (m, 2H), 1.28 (s, 6H), 1.20-1.25 (m, 6H).

14. 2-((S)-4-(4-chlorophenyl)-2,3,9-trimethyl-6H-thieno[3,2-f][1,2,4]triazolo[4,3-a][1,4]diazepin-6-yl)-N-((1S)-1-(4-(5-(3-(2-(2,6-dioxopiperidin-3-yl)-1,3-dioxoisoindolin-4-ylamino)propoxy)pyrimidin-2-yl)phenyl)ethyl)acetamide a.k.a. 2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]-N-[(1S)-1-{4-[5-(3-{[2-(2,6-dioxopiperidin-3-yl)-1,3-dioxo-2,3-dihydro-1H-isoindol-4-yl]amino}propoxy)pyrimidin-2-yl]phenyl}ethyl]acetamide

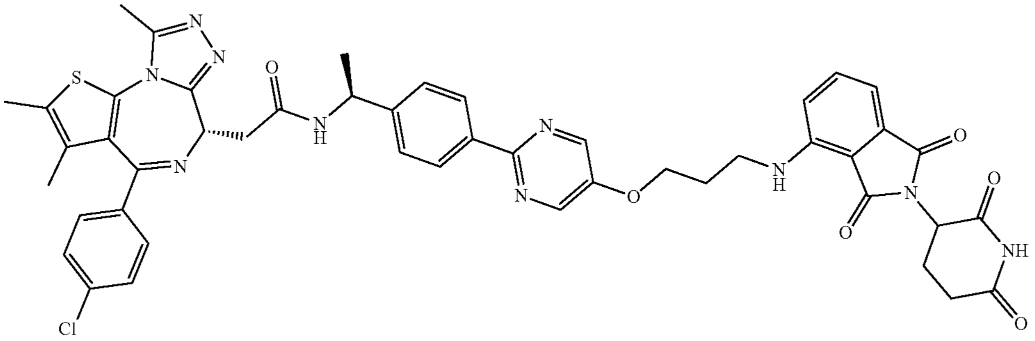 [SMILES: Cc1sc2c(c1C)C(c1ccc(Cl)cc1)=N[C@@H](CC(=O)N[C@@H](C)c1ccc(-c3ncc(OCCCNc4cccc5c4C(=O)N(C4CCC(=O)NC4=O)C5=O)cn3)cc1)c1nnc(C)n1-2]

(Compound #40, Table 1)

Compound 40 can be prepared by the following exemplary scheme:

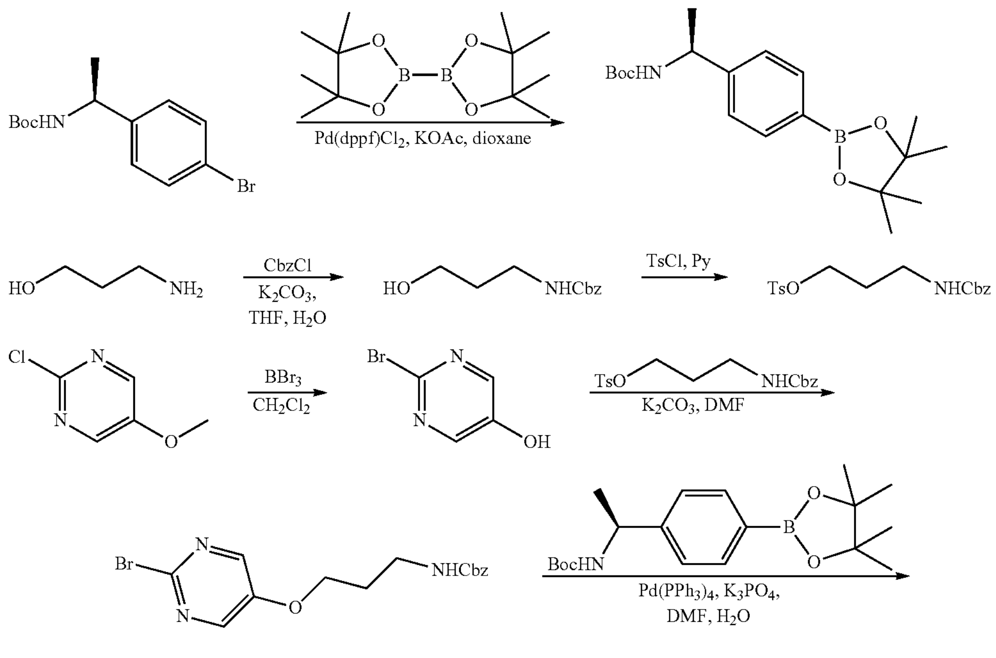

-continued

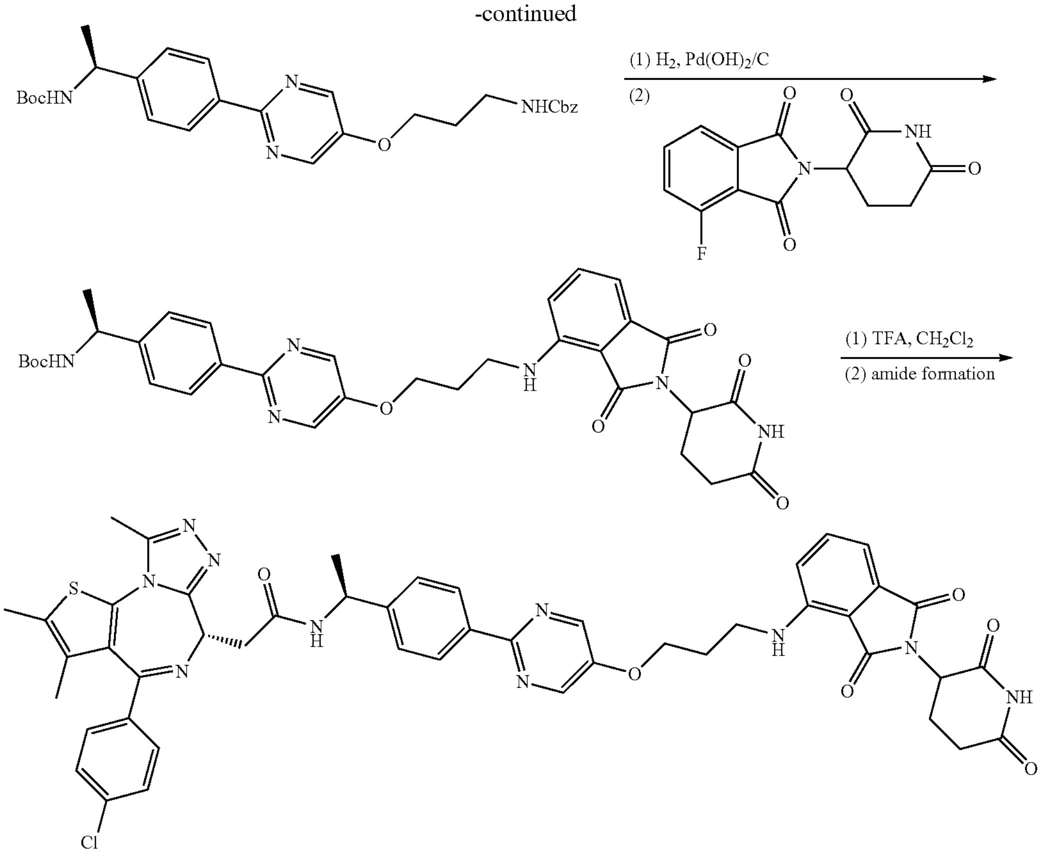

Compound 40

Step 1: Preparation of (S)-tert-butyl 1-(4-(4,4,5,5-tetramethyl-1,3,2-dioxaborolan-2-yl)phenyl)ethylcarbamate

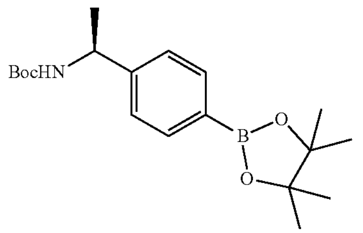 [SMILES: C[C@H](NC(=O)OC(C)(C)C)c1ccc(B2OC(C)(C)C(C)(C)O2)cc1]

To a stirred solution of (S)-tert-butyl 1-(4-bromophenyl) ethylcarbamate (6 g, 20.0 mmol), 4,4,4',4',5,5,5',5'-octamethyl-2,2'-bi(1,3,2-dioxaborolane) (7.6 g, 29.9 mmol) and potassium acetate (5.9 mg, 60.1 mmol) in dioxane (50 mL) was added [1,1'-bis(diphenylphosphino) ferrocene dichloropalladium(II) (440 mg, 0.60 mmol) at room temperature under nitrogen atmosphere. The mixture was degassed and refilled with nitrogen three times. The resulting mixture was stirred at 90° C. overnight. After cooling to room temperature, the reaction mixture was partitioned between ethyl acetate (100 mL) and water (50 mL). The aqueous layer was separated and extracted with ethyl acetate (50 mL×2). The combined organic layers were washed with brine (100 mL), dried over anhydrous sodium sulfate, and concentrated under reduced pressure to give a crude residue which was purified by silica gel flash column chromatography (eluted with 5-10% ethyl acetate in hexane) to afford (S)-tert-butyl 1-(4-(4,4,5,5-tetramethyl-1,3,2-dioxaborolan-2-yl)phenyl) ethylcarbamate (7.4 g, yield 98%) as a yellow oil. LC/MS ($ES^+$): m/z 370.0 [$M+Na^+$]; $t_R$=3.165 min; $^1$HNMR (400 MHz, $CDCl_3$): δ 1.26 (s, 12H), 1.34 (s, 12H), 4.78 (br, 1H), 7.30 (d, J=7.6 Hz, 2H), 7.78 (d, J=8.0 Hz, 2H); chemical formula: $C_{19}H_{30}BNO_4$; molecular weight: 347.26

Step 2: Preparation of benzyl 3-hydroxypropylcarbamate

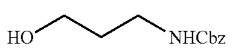

To a stirred solution of 3-aminopropan-1-ol (20 g, 266 mmol) and potassium carbonate (73 g, 529 mmol) in a mixture of water (50 mL) and tetrahydrofuran (100 mL) was added benzylchloroformate (68 g, 398 mmol) at 0° C. The mixture was allowed to warm up to room temperature and stirred at room temperature overnight. The reaction mixture was partitioned between ethyl acetate (200 mL) and water (100 mL). The organic layer was collected, washed with brine (100 mL), dried over anhydrous sodium sulfate, and concentrated under reduced pressure to give a crude residue which was purified by silica gel flash column chromatography (eluted with 20-50% ethyl acetate in hexane) to afford benzyl 3-hydroxypropylcarbamate (26.9 g, yield 52%) as a colorless oil. LC/MS ($ES^+$): m/z 232.1 [$M+Na^+$]; $t_R$=1.697 min; $^1$HNMR (400 MHz, $CDCl_3$): δ 1.67-1.73 (m, 2H), 2.56 (t, J=5.8 Hz, 1H), 3.33-3.38 (m, 2H), 3.65-3.70 (m, 2H), 5.06 (br, 1H), 5.11 (s, 2H), 7.29-7.36 (m, 5H); chemical formula: $C_{11}H_{15}NO_3$; molecular weight: 209.24

Step 3: Preparation of 3-(benzyloxycarbonylamino)propyl 4-methylbenzenesulfonate

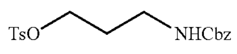

To a stirred solution of benzyl 3-hydroxypropylcarbamate (26.9 g, 128.6 mmol) in pyridine (40 mL) was added 4-toluenesulfonyl chloride (73 g, 384 mmol) at 0° C. The mixture was allowed to warm up to room temperature and stirred at room temperature for 2 hours. The reaction mixture was partitioned between ethyl acetate (120 mL) and water (80 mL). The organic layer was collected, washed with hydrochloric acid (1N, 480 mL) and brine (100 mL), dried over anhydrous sodium sulfate, and concentrated under reduced pressure to give a crude residue which was purified by silica gel flash column chromatography (eluted with 10-20% ethyl acetate in hexane) to afford 3-(benzyloxycarbonylamino)propyl 4-methylbenzenesulfonate (38.5 g, yield 82%) as a yellow oil. LC/MS ($ES^+$): m/z 386.2 [$M+Na^+$]; $t_R$=2.582 min; $^1$HNMR (400 MHz, $CDCl_3$): δ 1.85-1.91 (m, 2H), 2.43 (s, 3H), 3.25 (m, 2H), 4.09 (t, J=6.0 Hz, 2H), 4.83 (br, 1H), 5.07 (s, 2H), 7.26-7.39 (m, 7H), 7.78 (d, J=8.4 Hz, 2H); chemical formula: $C18H_{21}NO_5S$; molecular weight: 363.43

Step 4: Preparation of 2-bromopyrimidin-5-ol

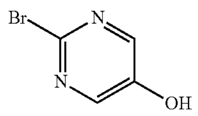

To a stirred solution of 2-chloro-5-methoxypyrimidine (10 g, 69.1 mmol) in anhydrous dichloromethane (60 mL) was added a solution of boron tribromide (34.7 g, 138.5 mmol) in dichloromethane (100 mL) at −78° C. The mixture was allowed to warm up to room temperature and stirred at room temperature overnight. The reaction was quenched by addition of methanol (80 mL) dropwise at −78° C. Solvent was removed under reduced pressure to give a crude residue which was purified by silica gel flash column chromatography (eluted with 2-5% methanol in anhydrous dichloromethane) to afford 2-bromopyrimidin-5-ol (6.5 g, yield 54%) as a yellow solid. $^1$HNMR (400 MHz, DMSO-d6): δ 8.26 (s, 2H), 8.49 (s, 1H); chemical formula: $C_4H_3BrN_2O$; molecular weight: 174.98

Step 5: Preparation of benzyl 3-(2-bromopyrimidin-5-yloxy)propylcarbamate

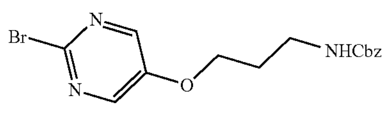 [SMILES: O=C(NCCCOc1cnc(Br)nc1)OCc1ccccc1]

A mixture of 2-bromopyrimidin-5-ol (5 g, 38.3 mmol), 3-(benzyloxycarbonylamino)propyl 4-methylbenzenesulfonate (13.9 g, 38.2 mmol) and potassium carbonate (10.6 g, 76.8 mmol) in N,N-dimethylformamide (30 mL) was stirred at 80° C. overnight. After cooling to room temperature, the reaction mixture was partitioned between ethyl acetate (50 mL) and water (30 mL). The aqueous layer was separated and extracted with ethyl acetate (50 mL×2). The combined organic layers were washed with brine (80 mL), dried over anhydrous sodium sulfate, and concentrated under reduced pressure to give a crude residue which was purified by silica gel flash column chromatography (eluted with 20-40% ethyl acetate in hexane) to afford benzyl 3-(2-bromopyrimidin-5-yloxy)propylcarbamate (2.4 g, yield 23%) as a colorless oil. LC/MS ($ES^+$): m/z 367.9 [M+1] for $Br^{81}$; $t_R$=2.375 min; $^1$HNMR (400 MHz, $CDCl_3$): δ 2.04-2.08 (m, 2H), 3.39-3.43 (m, 2H), 4.08-4.13 (m, 2H), 5.09 (s, 2H), 7.34-7.36 (m, 5H), 8.22 (s, 2H); chemical formula: $C_{15}H_{16}BrN_3O_3$; Molecular Weight: 366.21

Step 6: Preparation of tert-butyl (S)-(1-(4-(5-(3-(((benzyloxy)carbonyl)amino)propoxy)pyrimidin-2-yl)phenyl)ethyl)carbamate

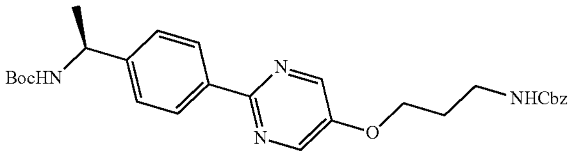 [SMILES: C[C@H](NC(=O)OC(C)(C)C)c1ccc(-c2ncc(OCCCNC(=O)OCc3ccccc3)cn2)cc1]

To a stirred solution of benzyl 3-(2-bromopyrimidin-5-yloxy)propylcarbamate (2.4 g, 6.6 mmol), (S)-tert-butyl 1-(4-(4,4,5,5-tetramethyl-1,3,2-dioxaborolan-2-yl)phenyl) ethylcarbamate (2.3 g, 6.6 mmol) and potassium phosphate tribasic trihydrate (3.5 g, 13.3 mmol) in N,N-dimethylformamide (30 mL) and water (5 mL) was added bis(triphenylphosphine)palladium(II) chloride (766 mg, 0.66 mmol) at room temperature under nitrogen atmosphere. The mixture was degassed and refilled with nitrogen three times. The resulting mixture was stirred at 80° C. for 4 hours. The reaction mixture was partitioned between ethyl acetate (70 mL) and water (30 mL). The organic layer was collected, washed with brine (30 mL), dried over anhydrous sodium sulfate, and concentrated under reduced pressure to give a crude residue which was purified by silica gel flash column chromatography (eluted with 10-50% ethyl acetate in hexane) to afford tert-butyl (S)-(1-(4-(5-(3-(((benzyloxy) carbonyl)amino)propoxy)pyrimidin-2-yl)phenyl) ethyl)carbamate (2.2 g, yield 67%) as a white solid. LC/MS ($ES^+$): m/z 507.5 [$M+H^+$]; $t_R$=2.841 min; chemical formula: $C_{28}H_{34}N_4O_5$; molecular weight: 506.59

Step 7: Preparation of tert-butyl (1S)-1-(4-(5-(3-(2-(2,6-dioxopiperidin-3-yl)-1,3-dioxoisoindolin-4-ylamino)propoxy)pyrimidin-2-yl)phenyl)ethylcarbamate

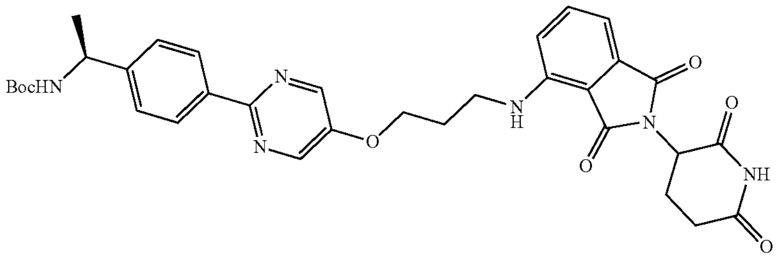 [SMILES: C[C@H](NC(=O)OC(C)(C)C)c1ccc(-c2ncc(OCCCNc3cccc4c3C(=O)N(C3CCC(=O)NC3=O)C4=O)cn2)cc1]

A mixture of tert-butyl (S)-(1-(4-(5-(3-(((benzyloxy)carbonyl)amino)propoxy)pyrimidin-2-yl)phenyl)ethyl)carbamate (2.2 g, 4.4 mmol) and palladium hydroxide on carbon (10%, 200 mg) in methanol (5 mL) was stirred at room temperature overnight under hydrogen atmosphere (hydrogen balloon). The catalyst was removed through filtration and washed with methanol (50 mL), and the combined filtrate was concentrated under reduced pressure. The residue was re-dissolved in 1-methyl-2-pyrrolidinone (20 mL), followed by sequential addition of 2-(2,6-dioxopiperidin-3-yl)-4-fluoroisoindoline-1,3-dione (1.2 g, 4.3 mmol) and N-ethyl-N-isopropylpropan-2-amine (2.3 g, 17.4 mmol). The resulting mixture was stirred at 80° C. for 2 hours. The reaction mixture was partitioned between ethyl acetate (30 mL) and water (15 mL). The aqueous layer was separated and extracted with ethyl acetate (25 mL×2). The combined organic layer was washed with brine (30 mL), dried over anhydrous sodium sulfate, and concentrated under reduced pressure to give a crude residue which was purified by silica gel flash column chromatography (eluted with 1-2% methanol in dichloromethane) to afford tert-butyl (1S)-1-(4-(5-(3-(2-(2,6-dioxopiperidin-3-yl)-1,3-dioxoisoindolin-4-ylamino)propoxy)pyrimidin-2-yl)phenyl)ethylcarbamate (710 mg, yield 26%) as a yellow oil. LC/MS ($ES^+$): m/z 629.3 $[M+H^+]$; $t_R$=2.660 min; $^1$HNMR (400 MHz, $CDCl_3$): δ1.42-1.48 (m, 12H), 2.04-2.07 (m, 2H), 2.11-2.26 (m, 4H), 3.54-3.59 (m, 2H), 4.24-4.26 (m, 2H), 4.90-4.94 (m, 1H), 6.50-6.53 (m, 1H), 6.93-6.95 (m, 1H), 7.11-7.12 (m, 1H), 7.39-7.41 (m, 2H), 7.43-7.48 (m, 3H), 8.08 (br, 1H), 8.28-8.32 (m, 2H), 8.51 (s, 2H); chemical formula: $C_{33}H_{36}N_6O_7$; molecular weight: 628.67;

Step 8: Preparation of 2-((S)-4-(4-chlorophenyl)-2,3,9-trimethyl-6H-thieno[3,2-f][1,2,4]triazolo[4,3-a][1,4]diazepin-6-yl)-N-((1S)-1-(4-(5-(3-(2-(2,6-dioxopiperidin-3-yl)-1,3-dioxoisoindolin-4-ylamino)propoxy)pyrimidin-2-yl)phenyl)ethyl)acetamide a.k.a. 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-[(1S)-1-{4-[5-(3-{[2-(2,6-dioxopiperidin-3-yl)-1,3-dioxo-2,3-dihydro-1H-isoindol-4-yl]amino}propoxy)pyrimidin-2-yl]phenyl}ethyl]acetamide

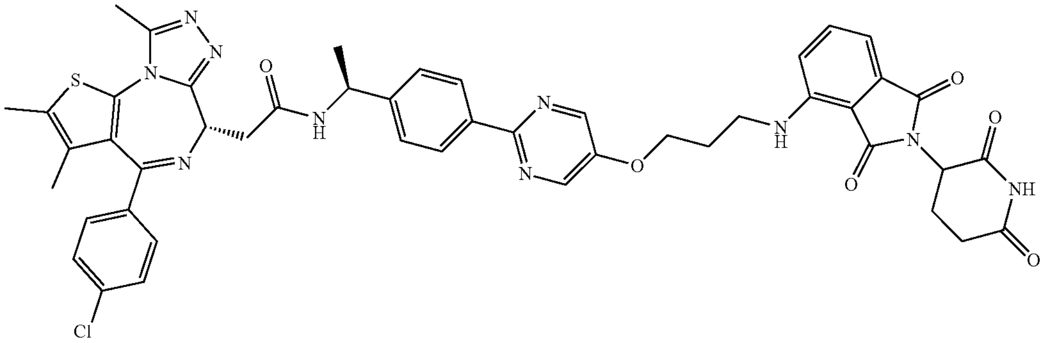 [SMILES: Cc1sc2c(c1C)C(c1ccc(Cl)cc1)=N[C@@H](CC(=O)N[C@@H](C)c1ccc(-c3ncc(OCCCNc4cccc5c4C(=O)N(C4CCC(=O)NC4=O)C5=O)cn3)cc1)c1nnc(C)n1-2]

A mixture of tert-butyl (1S)-1-(4-(5-(3-(2-(2,6-dioxopiperidin-3-yl)-1,3-dioxoisoindolin-4-ylamino)propoxy)pyrimidin-2-yl)phenyl)ethylcarbamate (710 mg, 1.1 mmol) and 2,2,2-trifluoroacetic acid (7 mL) in dichloromethane (7 mL) was stirred at room temperature for 1 hour. The volatiles were evaporated under reduced pressure. The residue was re-dissolved in dry N,N-dimethylformamide (10 mL), followed by sequential addition of (S)-2-(4-(4-chlorophenyl)-2,3,9-trimethyl-6H-thieno[3,2-f][1,2,4]triazolo[4,3-a][1,4]diazepin-6-yl)acetic acid (407 mg, 1.0 mmol), N-ethyl-N-isopropylpropan-2-amine (730 mg, 5.6 mmol), and HATU (2-(7-aza-1H-benzotriazole-1-yl)-1,1,3,3-tetramethyluronium hexafluorophosphate) (1.3 g, 3.3 mmol) at 0° C. The resulting mixture was allowed to warm up to room temperature and stirred at room temperature for 30 min. The reaction mixture was partitioned between ethyl acetate (40 mL) and water (20 mL). The aqueous layer was separated and extracted with ethyl acetate (25 mL×2). The combined organic layers were washed with brine (30 mL), dried over anhydrous sodium sulfate, and concentrated under reduced pressure to give a crude residue which was purified by preparative TLC (eluted with 7% methanol in dichloromethane) to afford 2-((S)-4-(4-chlorophenyl)-2,3,9-trimethyl-6H-thieno[3,2-f][1,2,4]triazolo[4,3-a][1,4]diazepin-6-yl)-N-((1S)-1-(4-(5-(3-(2-(2,6-dioxopiperidin-3-yl)-1,3-dioxoisoindolin-4-ylamino)propoxy)pyrimidin-2-yl)phenyl)ethyl)acetamide (160 mg, 15.5% yield after two steps) as a yellow solid. LC/MS ($ES^+$): m/z 911.3 [$M+H^+$]; $t_R$=2.666 min; $^1$HNMR (400 MHz, $CDCl_3$): δ 1.58 (d, J=6.8 Hz, 3H), 1.66 (s, 3H), 1.94-2.01 (m, 1H), 2.11-2.14 (m, 1H), 2.22-2.23 (m, 2H), 2.38 (s, 3H), 2.66 (s, 3H), 2.75-2.90 (m, 2H), 3.38-3.43 (m, 1H), 3.55-3.62 (m, 3H), 4.24-4.26 (m, 2H), 4.58-4.61 (m, 1H), 4.89-4.93 (m, 1H), 5.18-5.22 (m, 1H), 6.48-6.55 (m, 1H), 6.89-6.94 (m, 2H), 7.10-7.12 (m, 1H), 7.32-7.41 (m, 6H), 7.50 (t, J=7.6 Hz, 1H), 8.26-8.28 (m, 3H), 8.51 (s, 2H); chemical formula: $C_{47}H_{43}ClN_{10}O_6S$; molecular weight: 911.43

C. Protein Degradation Bioassays:

The following bioassays were performed to evaluate the level of protein degradation observed in various cell types using representative compounds disclosed herein.

In each bioassay, cells were treated with varying amounts of compounds encompassed by the present disclosure, as shown in Table 1. The degradation of the following proteins were evaluated in this study: TANK-binding kinase 1 (TBK1), estrogen receptor α (ERα), bromodomain-containing protein 4 (BRD4), androgen receptor (AR), and c-Myc.

1. TBK1 Western Protocol

Panc02.13 cells were purchased from ATCC and cultured in RPMI-1640 (Gibco), supplemented with 15% FBS (ATCC) and 10 Units/mL human recombinant insulin (Gibco). DMSO control and compound treatments (0.1 μM, 0.3 μM, and 1 μM) were carried out in 12-well plates for 16 h. TLR3 agonist Poly I:C (Invivogen; tlrl-pic) was added for the final 3 h. Cells were harvested, and lysed in RIPA buffer (50 mM Tris pH8, 150 mM NaCl, 1% Tx-100, 0.1% SDS, 0.5% sodium deoxycholate) supplemented with protease and phosphatase inhibitors. Lysates were clarified at 16,000 g for 10 minutes, and supernatants were separated by SDS-PAGE. Immunoblotting was performed using standard protocols. The antibodies used were TBK1 (Cell Signaling #3504), pIRF3 (abcam #ab76493), and GAPDH (Cell Signaling #5174). Bands were quantified using a Biorad ChemiDoc MP imaging system.

2. ERRα Western Protocol

NAMALWA cells (ATCC) were cultured in RPMI-1640 (Life Technologies) supplemented with 15% FBS (Life Technologies). DMSO controls and compound incubations (0.1 μM, 0.3 μM, and 1 μM) were carried out in 24-well plates for 16 h. Cells were harvested and lysed with cell lysis buffer (Cell Signaling Technologies) containing protease inhibitors (Thermo Scientific). Lysates were clarified at 16,000 g for 10 minutes, and supernatants were separated by SDS-PAGE. Immunoblotting was performed using standard protocols. The antibodies used were ERRα (Cell Signaling #8644) and GAPDH (Cell Signaling #5174). Bands were quantified using a Bio-Rad ChemiDoc MP imaging system.

3. BRD4 Western Protocol

VCaP cells were purchased from ATCC and cultured in Dulbecco's Modified Eagle's Medium (ATCC), supplemented with 10% FBS (ATCC) and Penicillin/Streptomycin (Life Technologies). DMSO control and compound treatments (0.003 μM, 0.01 μM, 0.03 μM and 0.1 μM) were performed in 12-well plates for 16 h. Cells were harvested, and lysed in RIPA buffer (50 mM Tris pH8, 150 mM NaCl, 1% Tx-100, 0.1% SDS, 0.5% sodium deoxycholate) supplemented with protease and phosphatase inhibitors. Lysates were clarified at 16,000 g for 10 minutes, and protein concentration was determined. Equal amount of protein (20 μg) was subjected to SDS-PAGE analysis and followed by immunoblotting according to standard protocols. The antibodies used were BRD4 (Cell Signaling #13440), and Actin (Sigma #5441). Detection reagents were Clarity Western ECL substrate (Bio-rad #170-5060).

4. AR ELISA Protocol

VCaP cells were purchased from ATCC and cultured in Dulbecco's Modified Eagle's Medium (ATCC), supplemented with 10% FBS (ATCC) and Penicillin/Streptomycin (Life Technologies). DMSO control and compound treatments (0.0001 μM-1 μM) were performed in 96-well plates for 16 h. Cells were harvested, and lysed with Cell Lysis Buffer (Catalog #9803) (20 mM Tris-HCL (pH 7.5), 150 mM NaCl, 1 mM $Na_2EDTA$, 1 mM EGTA, 1% Triton, 2.5 mM sodium pyrophosphate, 1 mM B-glycerophosphate, 1 mM $Na_3VO_4$, 1 ug/ml leupeptin. Lysates were clarified at 16,000 g for 10 minutes, and loaded into the PathScan AR ELISA (Cell Signaling Catalog #12850). The PathScan® Total Androgen Receptor Sandwich ELISA Kit is a solid phase sandwich enzyme-linked immunosorbent assay (ELISA) that detects endogenous levels of total androgen receptor protein. An Androgen Receptor Rabbit mAb has been coated onto the microwells. After incubation with cell lysates, androgen receptor protein is captured by the coated antibody. Following extensive washing, an Androgen Receptor Mouse Detection mAb is added to detect the captured androgen receptor protein. Anti-mouse IgG, HRP-linked Antibody is then used to recognize the bound detection antibody. HRP substrate, TMB, is added to develop color. The magnitude of absorbance for the developed color is proportional to the quantity of total androgen receptor protein. Antibodies in kit are custom formulations specific to kit.

5. c-Myc ELISA Assay Protocol

22RV-1 cells were purchased from ATCC and and cultured in RPMI+10% FBS media. Cells were harvested using trypsin (Gibco #25200-114), counted and seeded at 30,000 cells/well at a volume of 75 μL/well in RPMI +10% FBS media in 96-well plates. The cells were dosed with compounds diluted in 0.1% DMSO, incubated for 18 h then washed and lysed in 50 uL RIPA buffer (50 mM Tris pH8, 150 mM NaCl, 1% Tx-100, 0.1% SDS, 0.5% sodium deoxycholate) supplemented with protease and phosphatase inhibitors. The lysates were clarified at 4000 rpm at 4° C. for 10 minutes then aliquots were added into a 96-well ELISA plate of Novex Human c-myc ELISA kit from Life Technologies Catalog #KHO2041. 50 ul of c-Myc Detection antibody was added into every well, the plates incubated at room temperature for 3 hrs, then washed with ELISA wash buffer. 100 uL of the anti-rabbit IgG-HRP secondary antibody was added to each well and incubated at room temperature for 30 minutes. The plates were washed with ELISA wash buffer, 100 μL TMB added to each well, and then monitored every 5 minutes for a color change. 100 μL of stop solution is added and the plates read at 450 nm.

D. Results

Table 1 provides the results of experimental data obtained from a representative number of compounds encompassed by the present disclosure. In particular, various cell types were treated with the Compounds listed in Table 1, which are identified by chemical structure, mass spectrometry characterization, and compound name.

Table 1 shows that (A) 10-30% degradation was achieved in cells treated with 1 uM of Compounds 1, 6-9, 12, and 17; (B) 31-50% degradation was achieved in cells treated with 1 uM of Compounds 2-5, 10, and 20; and (C) >50% degradation was achieved in cells treated with 1 uM of Compounds 11, 13-16, 18-19, 21 and 22. Table 1 also shows that (D) Compounds 24 and 26-35 have an $IC_{50}$<50 nM, while (E) Compounds 23 and 25 have an $IC_{50}$ of >50 nM.

Example 2

Small molecule inhibitors have been the cornerstone of oncology drug development and generally work by inhibiting enzyme activity (such as kinase inhibitors) or by interfering protein-protein interactions (such as BRD4 inhibitors). Given the reversible binding of most small molecule inhibitors, large systemic drug concentrations are often required to ensure sufficient functional inhibition. Additionally, achieving and maintaining a high systemic drug level that is required for in vivo efficacy has proven challenging for many targets.

BRD4, a member of the bromodomain and extraterminal domain (BET) family, is a protein characterized by two bromodomains (BD domain) at the N-terminus and an extraterminal domain (ET domain) at the C-terminus. The two BD domains recognize and interact with acetylated-lysine residues at the N-terminal tail of histone protein. The ET domain is considered to serve a scaffolding function in recruiting diverse transcriptional regulators, but has not yet been fully characterized. BRD4 has been shown to be located at super-enhancer regions, which often reside upstream of important oncogenes, such as c-MYC, Bcl-xL and BCL-6, and play a key role in regulating their expressions. Based on its role in regulating gene expression by recruiting relevant transcription modulators to specific genomic loci, BRD4 is a candidate drug target for treating and/or preventing a number of human cancers, such as midline carcinoma, acute myeloid leukemia (AML), multiple myeloma (MM), Burkitt lymphoma (BL), and prostate cancer.

Several small molecule BET bromodomain inhibitors have been developed, such as JQ1, iBET, and OTX15, which have shown therapeutic potential in certain preclinical models of various cancers, including BL. Almost all BL cases contain c-myc gene translocation that places it under control of a super-enhancer located upstream of IgH, thus driving an abnormally high level of c-MYC expression, tumor development and maintenance. Preclinical studies with BRD4 inhibitors demonstrate their ability to suppress c-MYC and proliferation in BL cell lines; however, the $IC_{50}$ values of these inhibitors is often in the range of 100 nM to 1 μM.

A. Materials and Methods

The details of the experimental design and procedures from this study are provided below:

1. Compounds

Compound No. 14 (Table 1) was synthesized according to the procedure discussed above in Example 1, Synthesis #8. This compound, referred as "A825" throughout this Example, has the following name and structure.

2-((S)-4-(4-chlorophenyl)-2,3,9-trimethyl-6H-thieno [3,2-f][1,2,4]triazolo[4,3-a][1,4]diazepin-6-yl)-N-(4-(2-(2-(2-(2-(2-(2,6-dioxopiperidin-3-yl)-1,3-dioxoisoindolin-4-ylamino)ethoxy)ethoxy)ethoxy)ethoxy) phenyl)acetamide

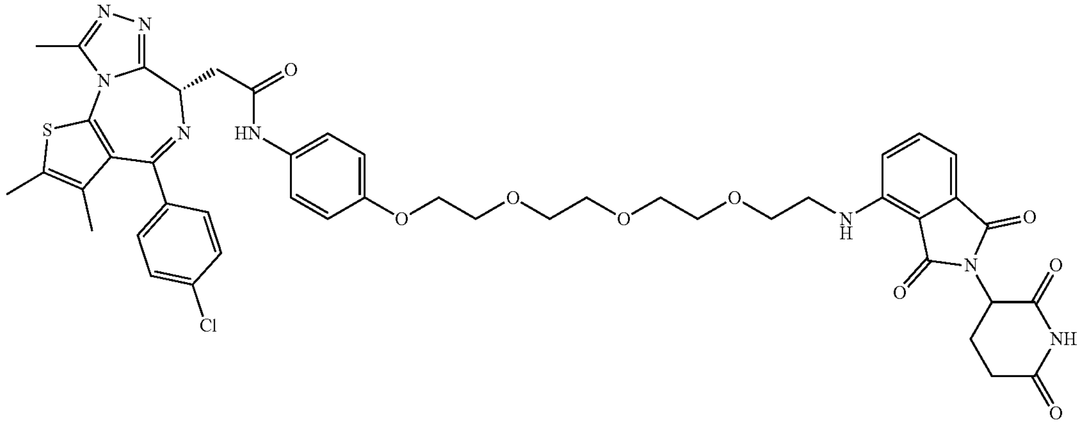 [SMILES: Cc1sc2c(c1C)C(c1ccc(Cl)cc1)=N[C@@H](CC(=O)Nc1ccc(OCCOCCOCCOCCNc3cccc4c3C(=O)N(C3CCC(=O)NC3=O)C4=O)cc1)c1nnc(C)n1-2]

Figure 2:
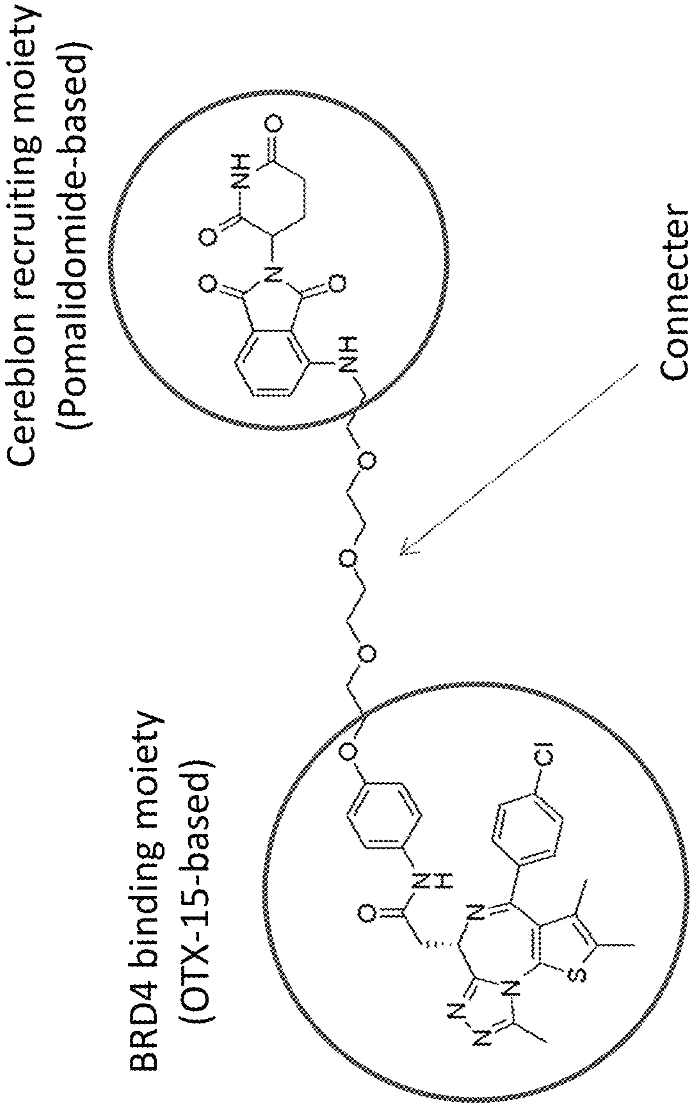
FIG. 2: Chimeric compound, A825, designed utilizing PROTAC technology. A825 contains a BRD4 binding moiety (a derivative of OTX-15) that is connected to an E3 ubiquitin ligase Cereblon recruiting moiety (a derivative of pomalidomide) through a tetraoxatetradecane linker.

As shown in FIG. 2, A825 contains a BRD4 binding moiety (a derivative of OTX-15) that is connected to an E3 ubiquitin ligase Cereblon recruiting moiety (a derivative of pomalidomide) through a tetraoxatetradecane linker.

The cellular effects of A825 were evaluated in various cell lines and these effects were compared to two known BET domain inhibitors, JQ1 and OTX-15. JQ1 is the most frequently used BET domain inhibitor in published studies, and OTX-15 is a BET domain inhibitor in advanced stages of clinical development.

The Cereblon recruiting moiety of A825 was also evaluated in various cell lines and compared with pomalidomide.

Inhibitors JQ1, OTX-15, and pomalidomide were synthesized according to methods published.

2. Cells and Reagents

NAMALWA, Ramos, CA-46 and DAUDI cells were purchased from ATCC and maintained as instructed. Antibodies against BRD4 (#E2A7X), c-MYC (#D84C12), PARP (#46D11) were purchased from Cell Signaling Technology. Actin (#A5441) antibody was purchased from SigmaAldrich. Secondary antibodies (#7074, #7076) were purchased from Cell Signaling Technology. MG132 (#M7449) was purchased from SigmaAldrich. Carfizomib (#S2853) was purchased from Selleck.

3. Western Blot Analysis

Cultured cells were collected in lysis buffer containing 40 mM HEPES (pH 7.4), 140 mM NaCl, 2.5 mM EDTA, 1%

NP-40, 0.1% SDS and protease inhibitor cocktail. After 10 minutes of centrifugation (14000 rpm), supernatant was collected for protein concentration determination by BCA method and subjected for immunoblotting by standard protocol. Western blot results were visualized using Bio-Rad Clarity ECL Western Blotting Substrate on Bio-Rad ChemiDoc™ MP imaging system.

4. RT-PCR

RNA extraction was performed with Aurum™ Total RNA Mini Kit (#732-6820) from Bio-Rad. First-strand cDNA from total RNA was synthesized with High-Capacity cDNA Reverse Transcription Kit (#4368813) from Life Technologies according to manufacturer's instruction. Quantitative PCR was performed using Bio-rad SsoAdvanced™ Universal SYBR® Green Supermix (#172-5271). The following primers were used:

5. Proliferation Assay

| Primer | Sequence |
|---|---|
| GAPDH-Forward | GAAGGTGAAGGTCGGAGTC (SEQ ID NO: 6) |
| GAPDH-Reverse | GAAGATGGTGATGGGATTTC (SEQ ID NO: 7) |
| SLC19A1-Forward | ATGGCCCCCAAGAAGTAGAT (SEQ ID NO: 8) |
| SLC19A1-Reverse | GTCAACACGTTCTTTGCCAC (SEQ ID NO: 9) |

To assess the effect of the inhibitors on proliferation, cells (50,000/100 μl) were seeded in 96-well tissue culture plates followed by addition of compound at the indicated concentration. After 72 hours, 100 μL per well of reconstituted CellTiter-Glo (CTG) reagent (#G7572 from Promega) was added and read on Cytation 3 imaging reader from BioTek. Relative cell growth was determined by comparing assay readings of treated cells with control DMSO treated cells.

6. Kd Determination

Affinity of compounds with Bromodomain 1&2 of BRD4 was determined with BROMOscan™ by DiscoverX.

B. Results

The cellular effects of JQ1, OTX-15, and A825 were evaluated and compared in the following experiments.

1. Small Molecule BET Domain Inhibitors Lead to Significant BRD4 Protein Accumulation and Inefficient c-MYC Suppression a. Dose-Dependent Accumulation of BRD4 with JQ1 and OTX-15 Treatment Studies have shown that Burkitt's lymphoma (BL) cell lines respond to BRD4 inhibitors due to the cell lines' dependence on c-myc oncogene that is translocated and brought under the control of IgH super-enhancers downstream of BRD4.

In an initial experiment, various BL cell lines (NAMALWA, Ramos, CA-46 and Daudi cells) were treated with two known BET domain inhibitors (JQ1 and OTX-15) at various concentrations to confirm that these inhibitors were effective in reducing and/or preventing the degradation of BRD4. Specifically, NAMALWA and Ramos cells were treated with various concentrations of JQ1 and OTX-15 (3 nM, 10 nM, 100 nM, 300 nM, 1000 nM, and 3000 nM); and CA-46 and Daudi cells were treated with 100 nM and 300 nM of JQ1 and OTX-15. A separate set of cells were treated in the same manner, except that DMSO was used in place of the inhibitor. All of the cells were treated overnight with increasing doses of JQ1 and OTX15. Following treatment, cell lysates were collected and analyzed by immunoblot for BRD4 and Actin.

The effects from these treatments were determined by evaluating the amount of BRD4 present in the cells by Western blot analysis following treatment (FIGS. 3A, 3B, 3C, and 3D).

FIGS. 3A-3D show that both JQ1 and OTX-15 lead to significant accumulation of BRD4 protein in a dose-dependent manner in all cell lines tested. These results are consistent with previous observation that JQ1 treatment results in BRD4 up-regulation in some lung cancer cell lines Shimamura, T., Chen, Z., Soucheray, M., Carretero, J., Kikuchi, E., Tchaicha, J. H., Gao, Y., Cheng, K. A., Cohoon, T. J., Qi, J., et al. (2013). (J. A. Mertz, et al., *PNAS,* 108 (2011) 16669-16674; and K. Klapproth, et al., British journal of haematology, 149 (2010) 484-497).

b. Rate of Accumulation of BRD4 with JQ1 and OTX-15 Treatment

The rate in which BRD4 accumulates in BL cell lines after treatment with JQ1 and OTX-15 was also determined. Specifically, NAMALWA and Ramos cells were treated with 300 nM of each inhibitor for 0 hr, 0.5 hr, 1.0 hr, 2.0 hr, 4.0 hr, 7.0 hr, 24 hr, and 48.0 hr. Following treatment, cell lysates were collected and analyzed by immunoblot for BRD4 and Actin.

Figures 3A, 3B:
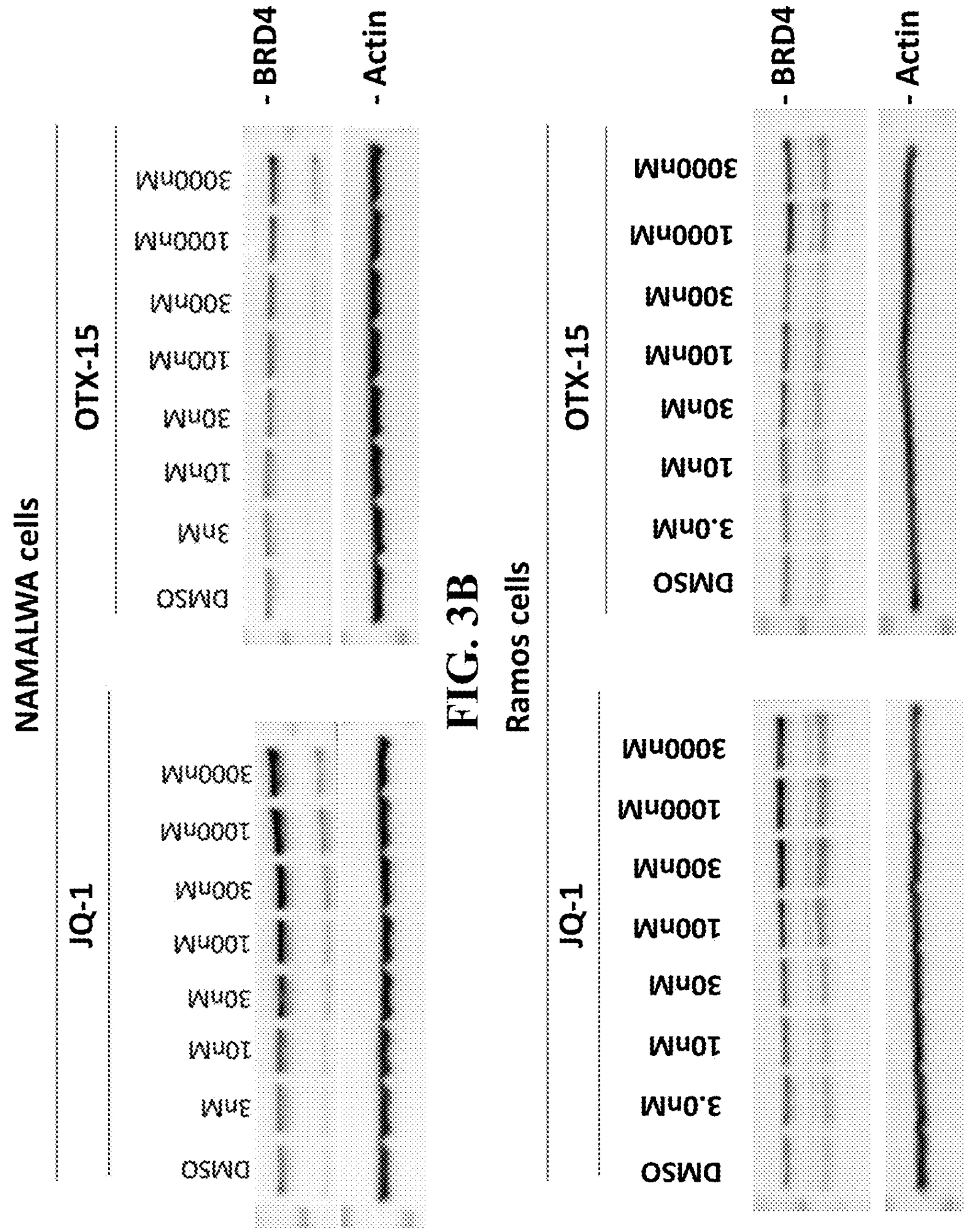
FIGS. 3A-3I: Western blot images showing the cellular effects of small molecule BRD4 inhibitors (JQ1 and OTX-15) on BL cell lines. JQ1 and OTX-15 lead to significant BRD4 accumulation in NAMALWA (FIG. 3A) and Ramos cells (FIG. 3B) in a dose-dependent manner (Namalwa and Ramos cells were treated overnight with increasing doses of JQ1 and OTX15; lysates were collected and subjected to immunoblot analysis with antibodies for BRD4 and Actin). OTX-15 leads to BRD4 accumulation in CA-46 cells (FIG. 3C) and DAUDI cells (FIG. 3D) in a dose-dependent manner (CA-46 and DAUDI cells were treated with OTX15 at 0.1 uM and 0.3 uM overnight; lysates were collected and analyzed by immunoblot with antibodies specific for BRD4 and Actin). JQ1 and OTX-15 lead to significant BRD4 accumulation in NAMALWA cells (FIG. 3E) and Ramos cells (FIG. 3F) (Namalwa and Ramos cells were treated with 0.3 uM of JQ1 or OTX15 for various time as indicated, lysates were collected and analyzed by immunoblot for BRD4 and Actin).
Figures 3C, 3D:
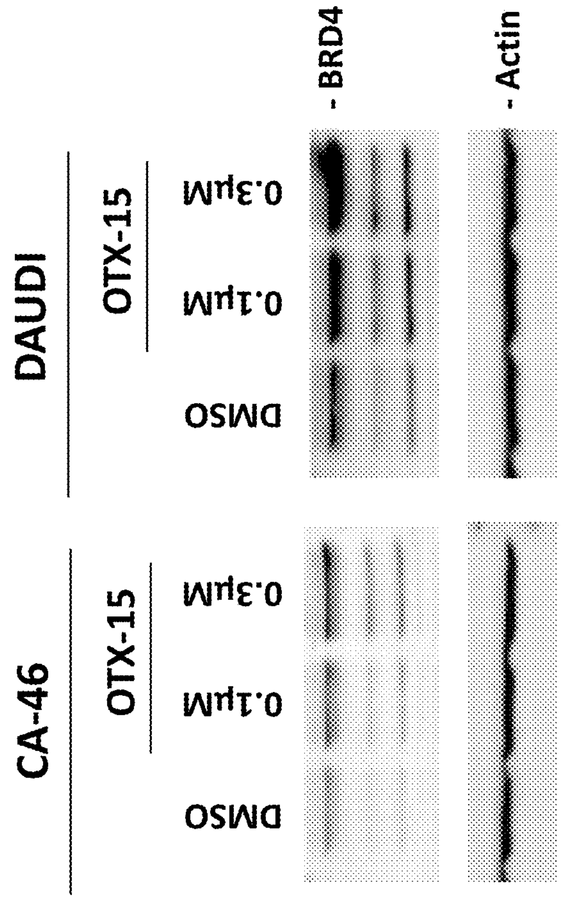
Figure 3F:
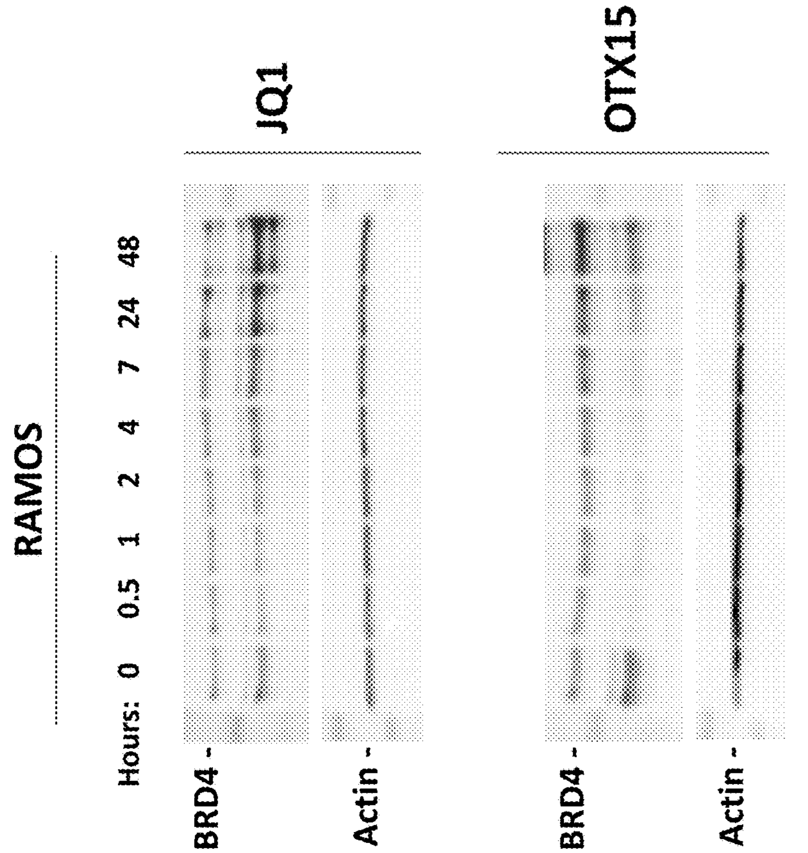
Figure 3E:
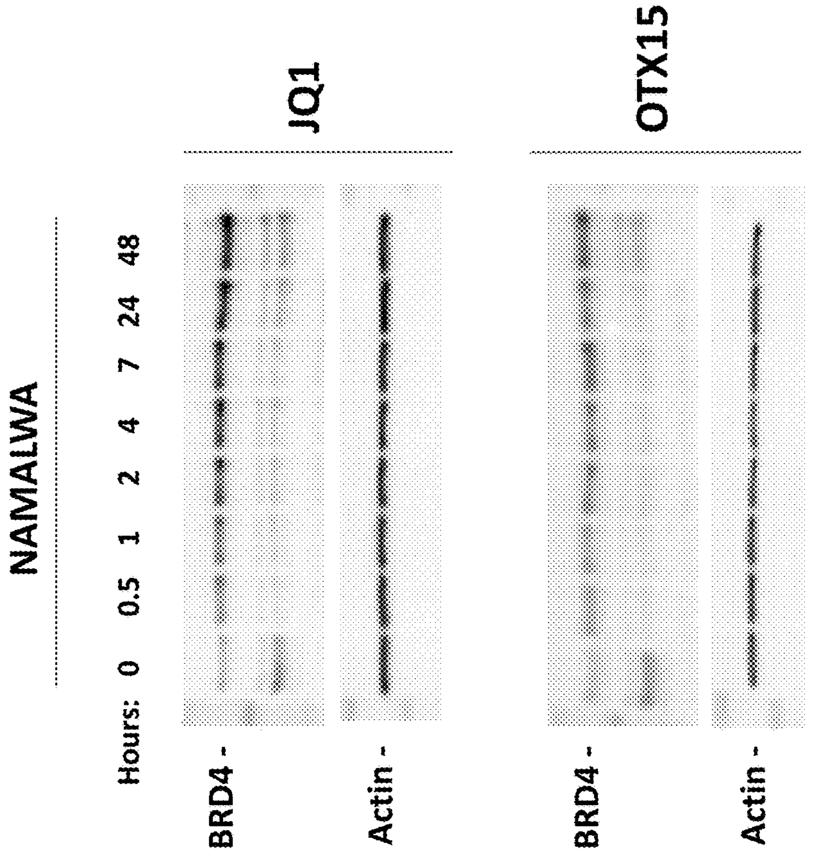

FIG. 3E shows that NAMALWA cells contain a detectable level of BRD4 prior to treatment with any inhibitor (0 hr). The amount of BRD4 present in NAMALWA cells increased noticeably within 30 minutes of treatment with either JQ1 or OTX-15 and the amount of BRD4 continued to increase with longer time treatment (0.5 hr to 48.0 hr).

FIG. 3F shows, similar to NAMALWA cells, Ramos cells also contain a detectable level of BRD4 prior to treatment with any inhibitor (0 hr). However, BRD4 accumulated at a slower rate in Ramos cells compared to NAMALWA cells. Specifically, a noticeable increase in the amount of BRD4 was observed between about 4.0 hours to about 7.0 hours of treatment with either JQ1 or OTX-15. A noticeable increase in the amount of BRD4 in Ramos cells was observed after 24.0 hours of treatment with both inhibitors.

Collectively, the results shown in FIGS. 3E and 3F demonstrate that small molecule BRD4 inhibitors lead to rapid BRD4 accumulation in various BL cell lines with 0.3 μm of JQ1 or OTX15.

c. JQ1 and OTX-15 Lead to Downstream c-Myc Suppression

As discussed above, BRD4 has been shown to be located at super-enhancer regions, which often reside upstream of important oncogenes, such as c-Myc, Bcl-xL and BCL-6. To determine whether BET domain inhibitors can impact the expression of downstream oncogenes, NAMALWA cells were treated with increasing concentrations (3 nM, 10 nM, 100 nM, 300 nM, 1000 nM, and 3000 nM) of either JQ1 or OTX-15 overnight. A separate set of cells were treated in the same manner, except that DMSO was used in place of the inhibitor. Following treatment, cell lysates were collected and analyzed by immunoblot for c-Myc and Actin.

Figure 3G:
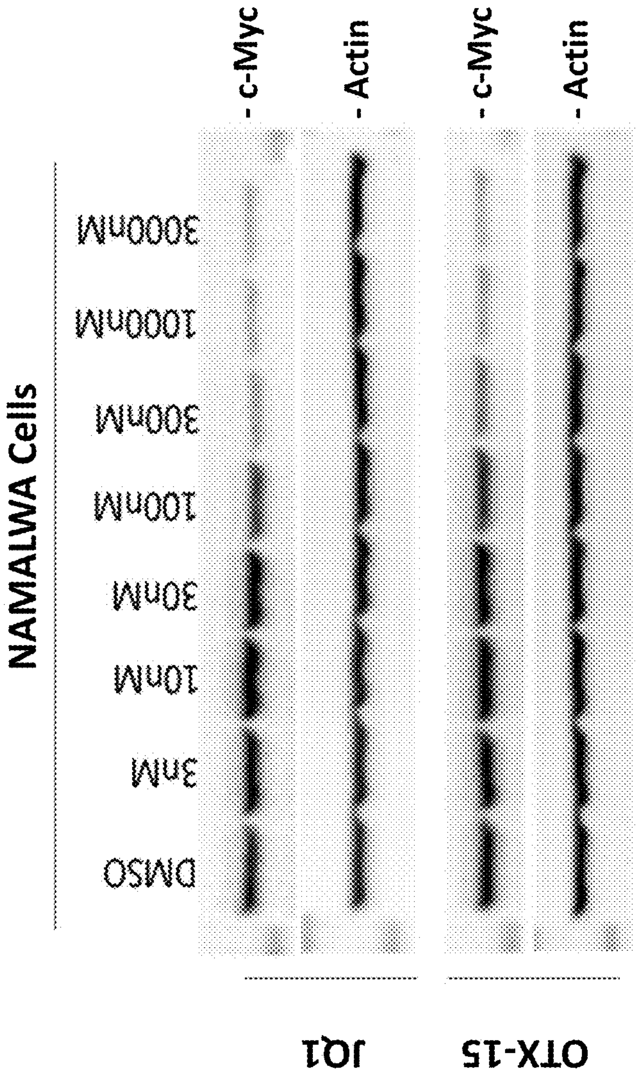

FIG. 3G shows that treating cells with BET domain inhibitors can lead to downstream suppression of c-Myc to a certain extent but, even at high concentrations, the inhibitors are not able to completely inhibit c-Myc expression. Specifically, the Figure shows that low concentrations (3 nM to 30 nM), the inhibitors did not have a noticeable impact on the level of c-Myc present in the cells. However, the amount of c-Myc was noticeably reduced in cells treated with 100 nM of either JQ1 or OTX-15 and was reduced even further in cells treated with 300 nM and 1000 nM of JQ1 or OTX-15. Although both JQ1 and OTX-15 repressed c-Myc level significantly at concentrations between 100 nM to 1000 nM, the results show that higher doses of either inhibitor did not appear to result in a further reduction of c-Myc (FIG. 3G, compare 1000 nM with 3000 nM).

Based on these results, the treatment of cells with the BET domain inhibitors JQ1 and OTX-15 leads a significant suppression of the BRD4 downstream protein c-Myc at concentrations between 100 nM and 1000 nM. However, higher concentrations of JQ1 and OTX-15 (above 1000 nM) did not lead to a further suppression of c-Myc protein beyond the effect seen with 1000 nM of inhibitor. Moreover, neither JQ1 nor OTX-15 was able to completely suppress c-Myc expression, even at concentrations of 3000 nM.

d. Suppression of c-Myc by JQ1 and OTX-15 is Reversible

The following study was performed to determine if the suppressive effect of c-Myc expression by JQ1 and OTX-15 was reversible.

In this study, NAMALWA cells were treated with JQ1 (1000 nM) for 24 hours, followed by three washes to remove the inhibitor. Cells were re-seeded and incubated without inhibitor for 0 hr, 0.5 hr, 1.0 hr, 2.0 hr, 3.0 hr, 4.0 hr, and 6.0 hr. Cell lysates were then collected at the various time points and analyzed by immunoblot for c-Myc and Actin. In a parallel control experiment, NAMALWA cells were treated in the same manner, except DMSO was used in place of JQ1.

Figure 3H:
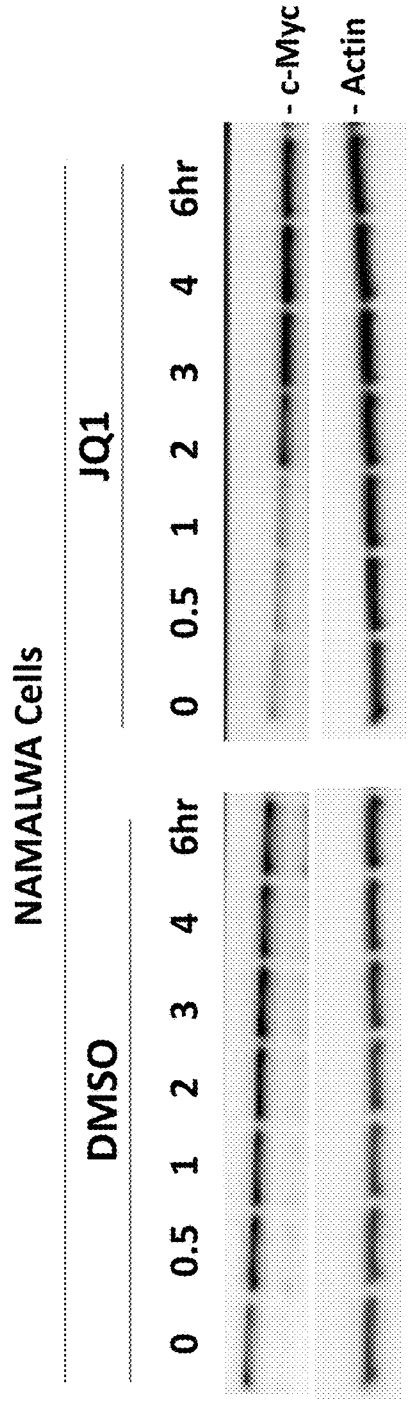

FIG. 3H shows that 1000 nM of JQ1 significantly suppressed c-Myc protein levels in NAMALWA cells (compare 0 hr lane of JQ1 treated cells with 0 hr lane of the DMSO control), which is consistent with the results shown in FIGS. 3A-3D. FIG. 3H also shows that the suppression of c-Myc by JQ1 was quickly reversible since c-Myc protein levels increased significantly between 1.0 to 2.0 hours post removal of inhibitor and, within 3.0 hours post removal of inhibitor, c-Myc protein returned to the level of the control sample.

In another experiment, Ramos cells were treated with either JQ1 (1000 nM), OTX-15 (1000 nM), or DMSO (control) for 24 hours. After treatment, the cells were either lysed (to evaluate the suppression of c-Myc by the inhibitors) or washed to remove the inhibitor, re-seeded, and incubated without inhibitor for 4.0 hours (to evaluate the reversibility of c-Myc suppression). Cell lysates were collected and analyzed by immunoblot for c-Myc and Actin.

Figure 3I:
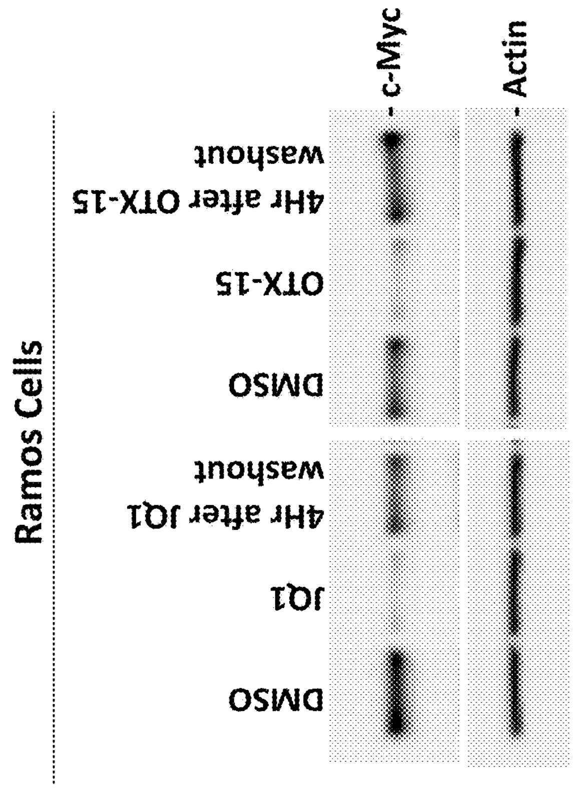

The results from the Ramos cells were consistent with those observed in the NAMALWA cells. Specifically, FIG. 3I (bottom panel) shows that JQ1 and OTX-15 suppressed c-Myc in Ramos cells ("JQ1" and "OTX15" lanes), but this suppressive effect was reversible, as c-Myc levels increased significantly within 4.0 hours after the inhibitors were removed ("4Hr after JQ1 washout" and "4Hr after OTX15 washout" lanes).

The results from this study demonstrate that small molecule BRD4 inhibitors (JQ1 and OTX-15) lead to downstream c-Myc suppression in BL cell lines. However, the inhibitors were unable to completely suppress the expression of c-Myc in the cells, even at high concentrations. Furthermore, the suppressive effect of c-Myc expression by these inhibitors was found to be quickly reversible, with c-Myc protein levels increasing about 2.0 to 4.0 hours after removal of the inhibitors. The results obtained in this study are consistent with previous findings in AML that c-MYC is repressed by JQ1 treatment, but bounds back quickly upon JQ1 removal (J. A. Mertz, et al., *PNAS,* 108 (2011) 16669-16674).

2. Hijacking the E3 Ubiquitin Ligase Cereblon to Create PROTAC to Efficiently Degrade BRD4

The rapid and robust accumulation of BRD4 by JQ1 and OTX-15 treatment, together with the reversible nature of inhibitor binding to BRD4 observed in the previous study, may account for the moderate effects on downstream c-Myc suppression and proliferation inhibition observed in BL and other cancers. To circumvent the limitations of small molecule BRD4 inhibitors, a chimera compound, A825, was designed utilizing PROTACs technology (discussed above and shown in FIG. 2).

a. Inhibitor Binding Affinity to Bromodomains of BRD4

The binding affinity of A825 to bromodomain 1 (BD1) and bromodomain 2 (BD2) of BRD4 was evaluated and compared to the binding affinities of JQ1 and OTX-15 the same domains. The binding affinities of each of these compounds is summarized in the table below.

| | Binding Affinity ($K_d$) | |
|---|---|---|
| Compound | BD1 | BD2 |
| A825 | 90 nM | 28 nM |
| JQ1 | 12 nM | 10 nM |
| OTX-15 | 14 nM | 3.5 nM |

The binding affinity studies showed that A825 has a slightly reduced binding affinity to BD1 and BD2 of BRD4 compared to those of JQ1 and OTX-15.

b. A825 Leads to Efficient Degradation of BRD4

The effect of A825 on BRD4 protein levels in BL cell lines was evaluated. Specifically, NAMALWA and CA-46 cells were treated overnight with increasing concentrations (0.3 nM, 1.0 nM, 3.0 nM, 10 mM, 30 nM, 100 nM, 300 nM, and 1000 nM) of A825. Following treatment, cell lysates were collected and analyzed by immunoblot for BRD4 and Actin.

Figure 4B:
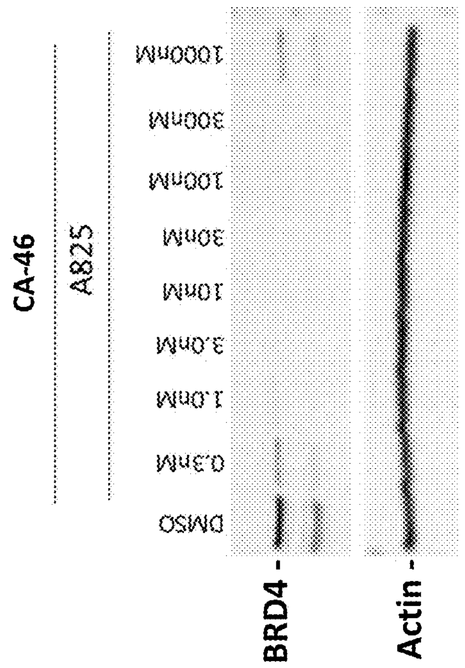
FIGS. 4A-4G. Western blot images showing the cellular effects of A825 on BL cell lines. BRD4 degradation by A825 occurs in a dose-dependent, bell-shaped manner in NAMALWA cells (FIG. 4A) and CA-46 cells (FIG. 4B) (Namalwa and CA-46 cells were treated overnight with increasing doses of A825, lysates were analyzed for BRD4 levels by immunoblot with Actin serving as loading control).
Figure 4A:
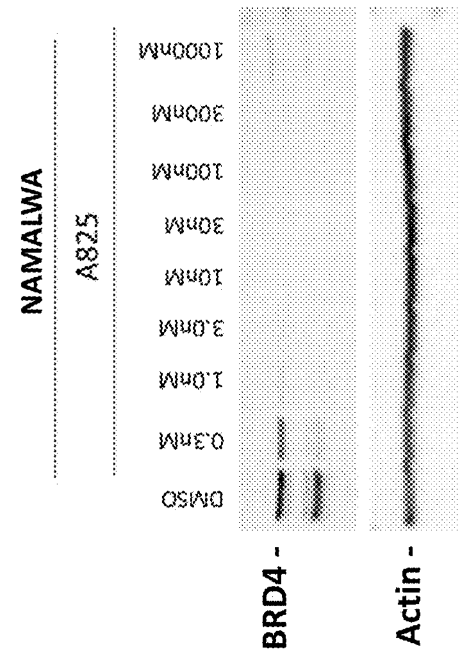

FIG. 4A and FIG. 4B show that treatment of BL cell lines with A825 induces complete BRD4 protein degradation at low concentrations of this compound. In particular, based on the data shown in this Figure, the $DC_{50}$ (50% of maximum degradation) of BRD4 in NAMALWA cells appears to be achieved by treating cells with 1.0 nM or less of A825 (4A). Similarly, the $DC_{50}$ of BRD4 in CA-46 cells appears to be achieved by treating cells with 0.3 nM to 1.0 nM or less of A825 (4B).

Also, BRD4 appears to be completely degraded in both BL cell lines treated with A825 in concentrations ranging between about 3.0 nM to about 300 nM, as evidenced by the lack of any noticeable protein band for BRD4 at these treatment concentrations. Interestingly, a small amount of BRD4 protein was observed in the lane containing the lysates of both BL cell lines treated with 1000 nM of A825, indicating that BRD4 degradation by A825 occurs in a dose-dependent, bell-shaped manner. That is, complete degradation of BRD4 occurs within a critical concentration range of A825, because incomplete BRD4 degradation is observed when A825 is present above or below this critical range.

Considering the fact that BRD4 and Cereblon binding moieties in A825 have Kd of 28-90 nM and 3 uM to their respective targets, this suggests that A825 acts catalytically in mediating BRD4 degradation.

c. A825 Leads to Rapid Degradation of BRD4

The degradation rate of BRD4 in BL cell lines after treatment with A825 was also determined. In this study NAMALWA and Ramos cells were treated with A825 (100 nM) for 0 hr, 0.5 hr, 1.0 hr, 2.0 hr, 4.0 hr, 7.0 hr, and 24 hr. Following treatment, cell lysates were collected and analyzed by immunoblot for BRD4 and Actin.

Figure 4D:
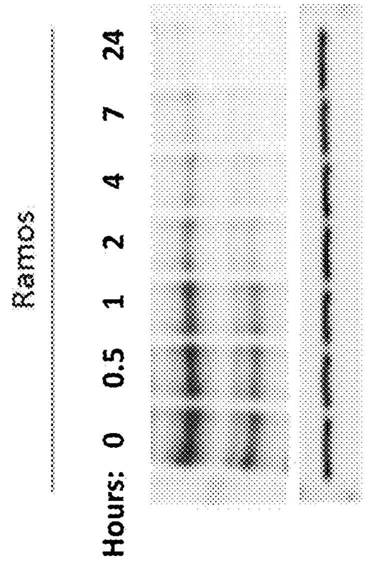
Figure 4C:
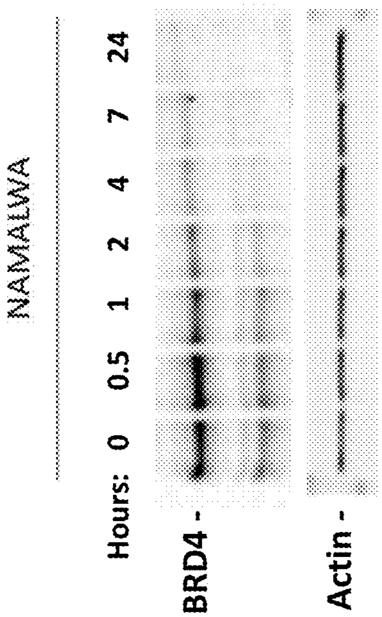

FIG. 4C and FIG. 4D show that BRD4 is present in both BL cell lines prior to treatment with A825 (0 hr). BRD4 protein levels noticeably decreased within 1 hour of treatment with A825 and the protein levels continued to decrease steadily over the course of the 24.0 hour treatment period. This Figure also shows that BRD4 degradation by A825 occurs rapidly, resulting in more than 50% of protein lost within 2 hours of A825 treatment.

d. BRD4 Degradation by A825 is Dependent on Cereblon

To confirm that BRD4 degradation induced by A825 treatment is dependent on Cereblon, a competitive inhibition experiment was performed in which BL cell lines were treated with either A825, pomalidomide, or a combination of the two compounds. As discussed above and shown in FIG. 2, A825 contains an E3 ubiquitin ligase Cereblon recruiting moiety, which is a derivative of pomalidomide and, as such, pomalidomide and A825 compete for Cereblon binding. Thus, if BRD4 degradation by A825 treatment is dependent on Cereblon, then cells treated with a combination of A825 and pomalidomide should show a reduction in BRD4 degradation compared to cells treated with A825 alone.

In this study, NAMALWA and Ramos cells were treated overnight with various concentrations of A825 alone (10 nM, 100 nM, and 1000 nM), pomalidomide (10 μM) alone, or a combination of A825 and pomalidomide. Following treatment, cell lysates were collected and analyzed by immunoblot for BRD4 and Actin.

Figure 4F:
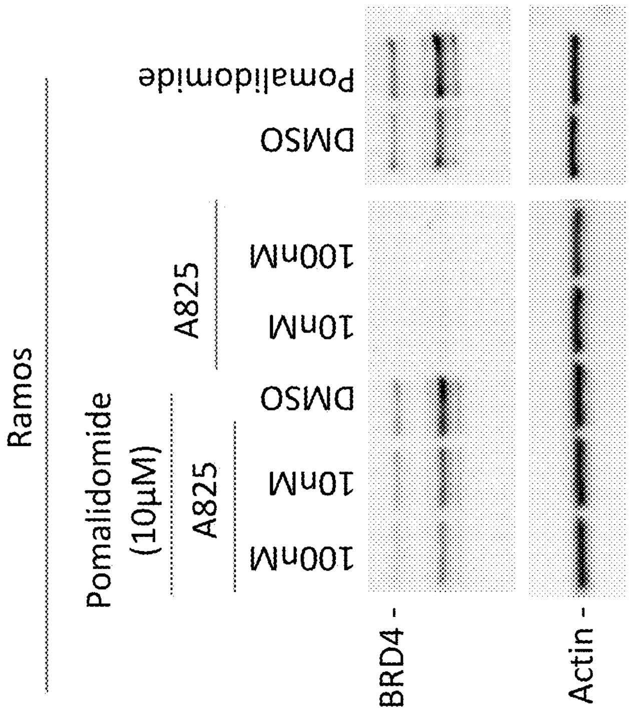
Figure 4E:
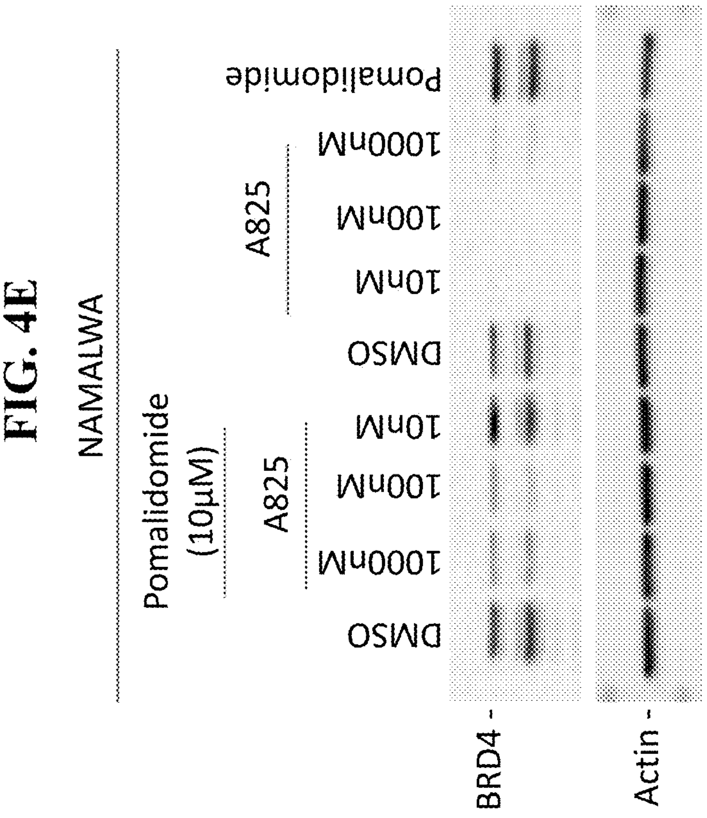

FIGS. 4E and 4F show complete BRD4 degradation in cells treated with 10 nM and 100 nM of A825, while a small amount of BRD4 is present in cells treated with 1000 nM of A825, which is consistent with the results shown in FIGS. 4A and 4B. FIGS. 4E and 4F also shows that BRD4 levels were not affected in cells treated with pomalidomide alone, which was expected since pomalidomide does not target BRD4 for degradation. Finally, FIGS. 4E and 4F shows that BRD4 protein levels were partially rescued from degradation in cells treated with a combination of A825 and pomalidomide.

The results from this study confirm that BRD4 degradation by A825 is mediated by Cereblon.

e. Proteasome Inhibitors Prevent BRD4 Degradation by A825

Cereblon is an E3 Ubiquitin Ligase protein that, alone or in combination with an E2 ubiquitin-conjugating enzyme, causes the attachment of ubiquitin to a lysine on a target protein, and subsequently targets the specific protein substrates for degradation by the proteasome. To confirm that BRD4 degradation by A825 occurs through the proteasome pathway, BL cell lines were treated with A825 with and without proteasome inhibitors.

Specifically, NAMALWA cells were treated overnight with A825 alone (10 nM and 100 nM); MG132 alone (5 μM); or Carfizomib alone (5 μM); or a combination of A825 with MG132 or with Carfizomib. Following treatment, cell lysates were collected and analyzed by immunoblot for BRD4 and Actin.

Figure 4G:
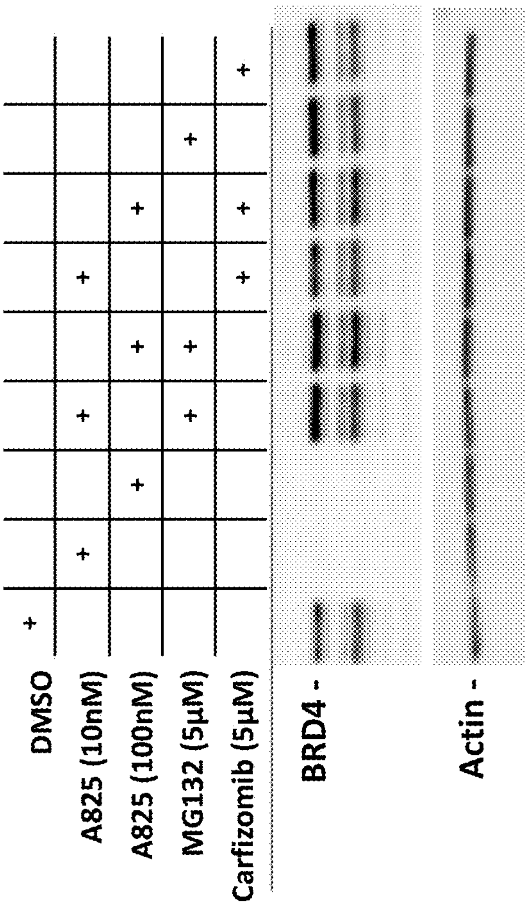

FIG. 4G shows that BRD4 was completely degraded in cells treated with either 10 nM or 100 nM of A825 alone, which is consistent with the results shown in FIGS. 4A and 4B. FIGS. 4E and 4F also shows that both MG132 and Carfizomib completely prevented BRD4 degradation induced by either 10 nM or 100 nM of A825. These results confirm that BRD4 degradation by A825 proceeds according to the normal Cereblon pathway, through the proteasome.

f. Summary and Discussion

Taken together, the data obtained from experiments (a) to (f) above demonstrate that A825 leads to fast and efficient BRD4 degradation in a Cereblon-mediated and proteasome-dependent mechanism.

Figure 8A:
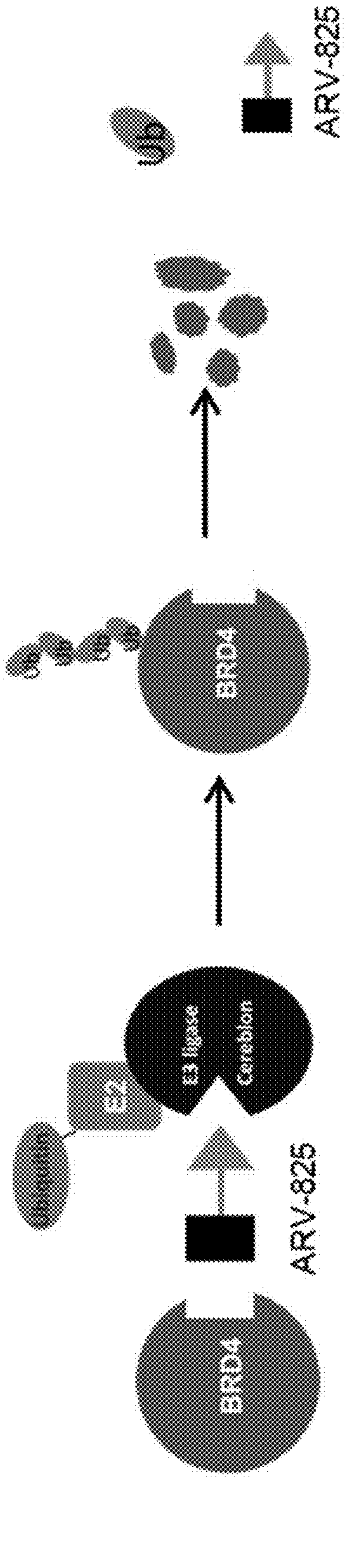
FIGS. 8A-8B. Schematic showing mechanism of action model for BRD4 degradation by A825 treatment.
Figure 8B:
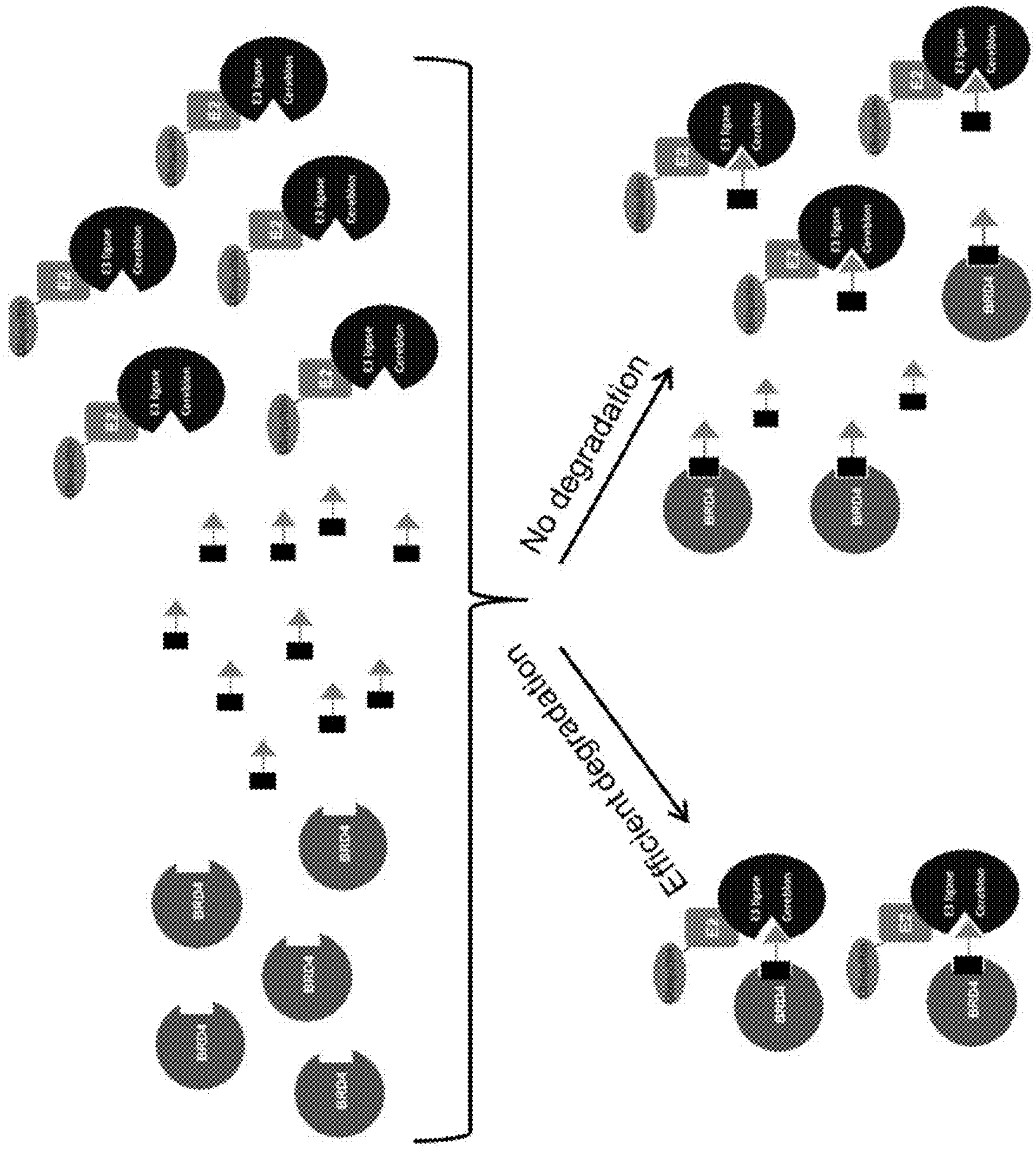

The BRD4 degradation profile observed in this study supports the following mechanism of action model, which is illustrated in FIG. 8. Specifically, in untreated cells, BRD4 expression is not inhibited and functions under regular cellular control. However, when cells are treated with low concentrations of A825, enough A825 is present in the cell to effectively bind to BRD4 on one end of the molecule and Cereblon at the other end to form a "BRD4-A825-Cereblon" trimer complex (FIG. 8A). This "BRD4-A825-Cereblon" trimer complex drives efficient BRD4 degradation in the cell. The trimer complex is able to form in cells treated with A825 within a particular concentration range and can lead to a complete depletion of BRD4 in the cell (FIG. 8A). However, when cells are treated with high concentrations of A825, "BRD4-A825" and "A825-Cereblon" dimers are formed that hinder optimal trimer formation, which results in less effective BRD4 degradation (FIG. 8B).

3. A825 Leads to More Significant and Longer Lasting c-MYC Suppression than Small Molecule Inhibitors As discussed above, treating cells with 100 nM or more of small molecule BET domain inhibitors JQ1 and OTX-15 resulted in a significant, but incomplete, suppression of the downstream protein c-Myc and that concentrations above 1000 nM did not result in a further suppression of c-Myc. In the following studies, the downstream effects of A825 on c-Myc expression were compared with the small molecule inhibitors, JQ1 and OTX15.

a. A825 Suppresses c-Myc to a Greater Extent than JQ1 and OTX-15

In this study, the suppression of c-Myc by A825 was compared to JQ1 and OTX-15. Specifically, NAMALWA and Ramos cells were treated overnight with various concentrations of A825 (100 nM, 300 nM, and 1000 nM), or JQ1 (100 nM, 300 nM, 1000 nM, 3000 nM, and 10000 nM), or OTX15 (100 nM, 300 nM, 1000 nM, 3000 nM, and 10000 nM). Following treatment, cell lysates were collected and analyzed by immunoblot for BRD4, c-Myc and Actin.

Figure 5A:
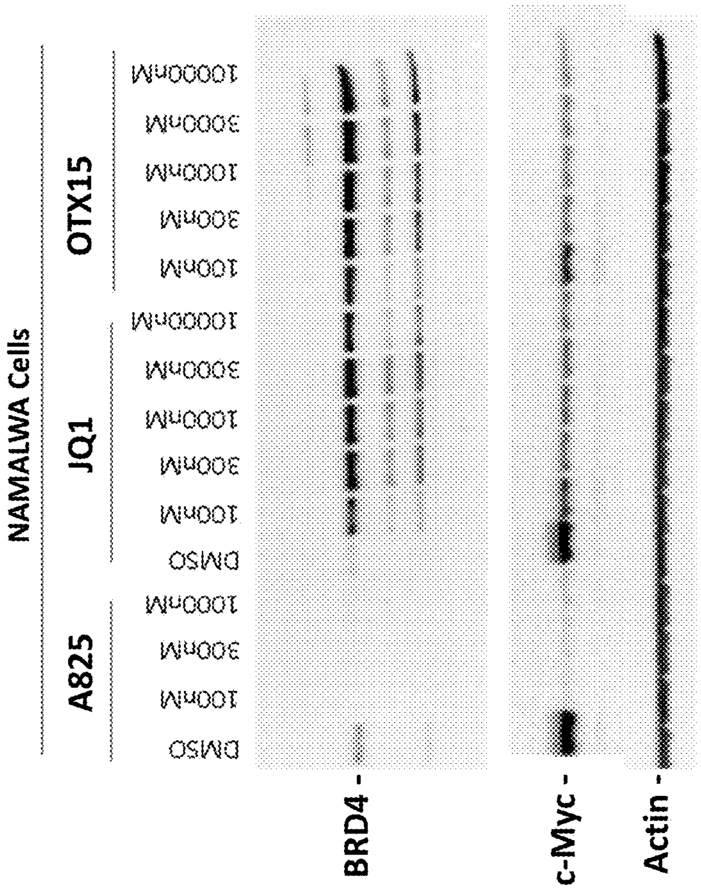
FIGS. 5A-5F. Comparison of the cellular effects by A825, JQ1, and OTX-15 treatment.
Figure 5B:
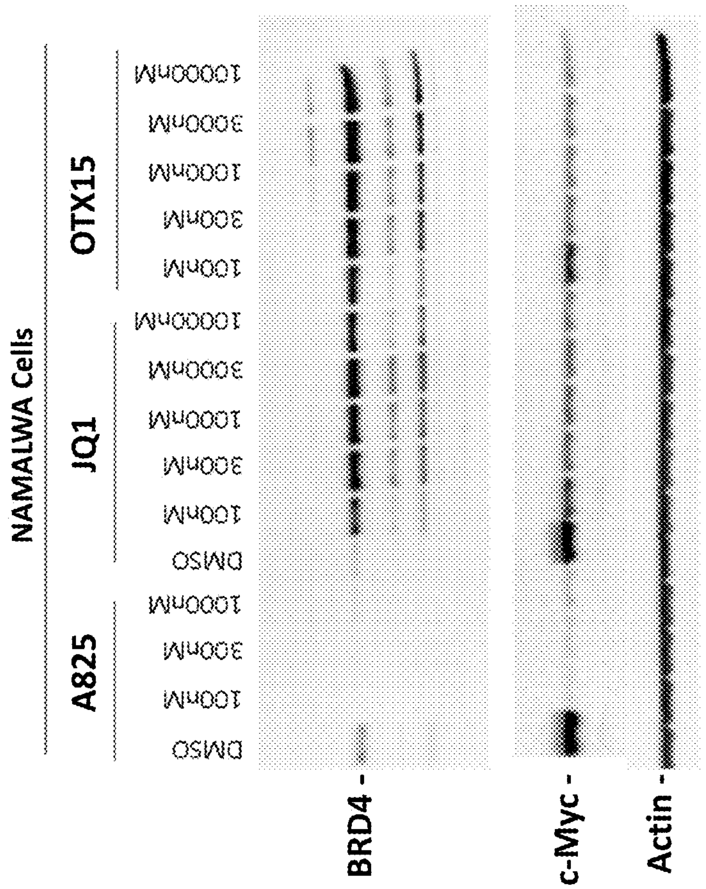

FIGS. 5A and 5B show that JQ1 and OTX-15 lead to robust BRD4 accumulation and significant, but incomplete, c-Myc suppression in both BL cell lines (consistent with FIG. 3G). FIGS. 5A and 5B also shows that A825 resulted in a significant BRD4 degradation (consistent with FIGS. 4A-4G) and a much more pronounced downregulation of c-Myc compared to JQ1 and OTX-15 in both BL cell lines. Notably, A825 was able to downregulate c-Myc expression to a much greater extent than JQ1 and OTX-15 with a much lower concentration of the compound.

b. A825 Suppresses c-Myc Expression Longer than JQ1 and OTX-15

The following study was performed to compare the duration of c-Myc suppression by A825, JQ1, and OTX-15.

Specifically, NAMALWA cells were treated for 24 hours with A825 (0.1 μM), JQ1 (1.0 μM) and OTX-15 (1.0 μM), followed by three washes to remove the compounds. Cells were re-seeded in fresh medium and incubated without any compound for 0 hr, 2.0 hr, 4.0 hr, 6.0 hr, and 24.0 hr. In a parallel control experiment, cells were treated in the same manner, except DMSO was used in place of inhibitor. Lysates were collected and analyzed by immunoblot for BRD4, c-Myc, and Actin.

Figure 5C:
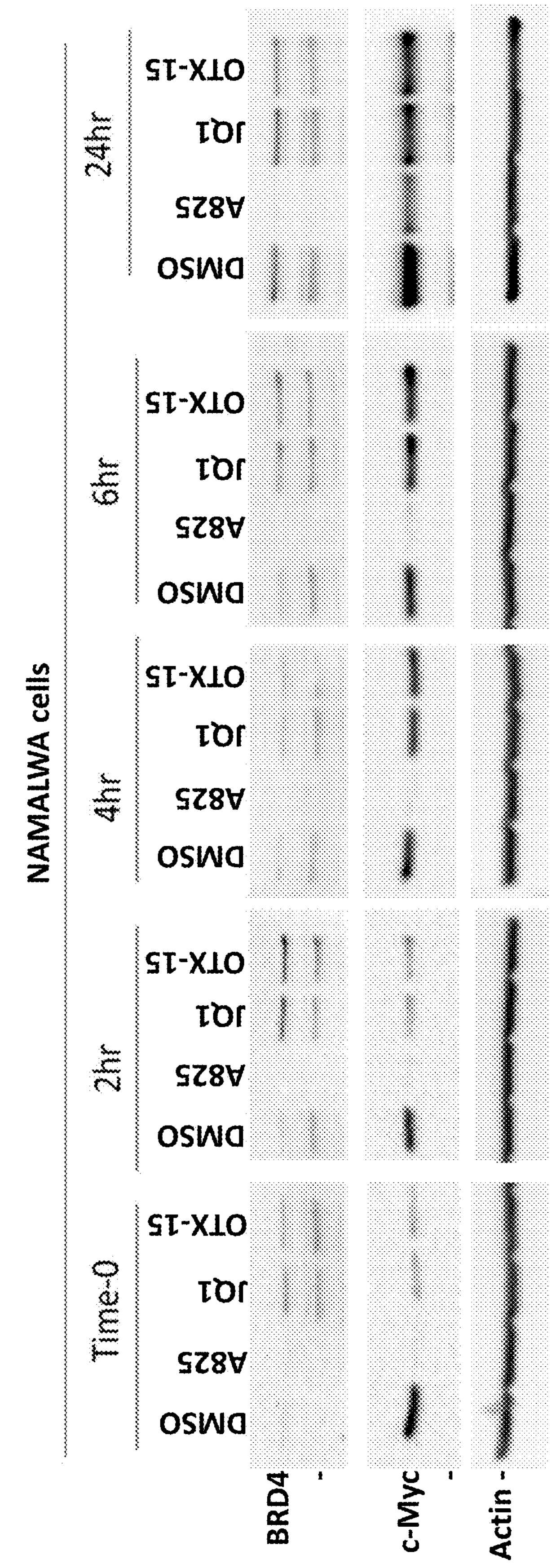

FIG. 5C shows that the post-treatment effect on BRD4 by A825 (BRD4 degradation) is maintained for much longer than the post-treatment effect by JQ1 and OTX-15 (BRD4 accumulation). Additionally, the post-treatment downstream suppression effect on c-Myc by A825 is also maintained much longer with A825 compared to JQ1 and OTX-15. In particular, the Figure shows that no detectible BRD4 protein was observed in the cells 6 hours post-treatment with A825.

Additionally, even after 24 hours post-treatment with A825, only a small amount of BRD4 was observed in the Western blot, which was well below the BRD4 level observed in the control sample. In contrast, the accumulation of BRD4 by JQ1 and OTX-15 was short-lived, with the protein level of BRD4 in these samples returning to the level of the control sample within about 4 hours post-treatment. The Figure also shows that only a small level of c-Myc protein was detected between 2 hours to 6 hours post-treatment with A825 and, even 24 hours post-treatment, the level of c-Myc was well below the control sample. In contrast, the Figure shows that c-Myc protein levels recover to the control level within about 4 hours after the removal of JQ1 and OTX15. Therefore, these results demonstrate that the post-treatment effects on BRD4 and c-Myc by A825 are maintained over a longer period of time compared to JQ1 and OTX-15.

c. A825 Suppresses c-Myc Function Longer than JQ1 and OTX-15.

c-Myc protein is a transcription factor that activates expression of many genes, including SLC19A1, which is a membrane protein that is a transporter of folate and is involved in the regulation of intracellular concentrations of folate. In the preceding experiments, it was shown that A825, JQ1, and OTX-15 suppress c-Myc expression, and the effect by A825 was stronger and longer lasting compared to JQ1 and OTX-15. To further investigate how A825, JQ1, and OTX-15 can impact pathways and events downstream of BRD4, cells were treated with each compound and the expression of the SLC19A1 gene was evaluated at various time times post-treatment.

Specifically, NAMALWA cells were treated for 24 hours with A825 (0.1 μM), JQ1 (1.0 μM) and OTX-15 (1.0 μM), followed by three washes to remove the compounds. Cells were re-seeded in fresh medium and incubated without any inhibitor for 0 hr, 6.0 hr, and 24.0 hr. In a parallel control experiment, cells were treated in the same manner, except DMSO was used in place of inhibitor. At each time point, RNA was extracted from the lysates, reverse-transcribed into cDNA, and quantified by QPCR with SLC19A1 specific primers. GAPDH was also quantified by QPCR as an internal control.

Figures 5D, 5E, 5F:
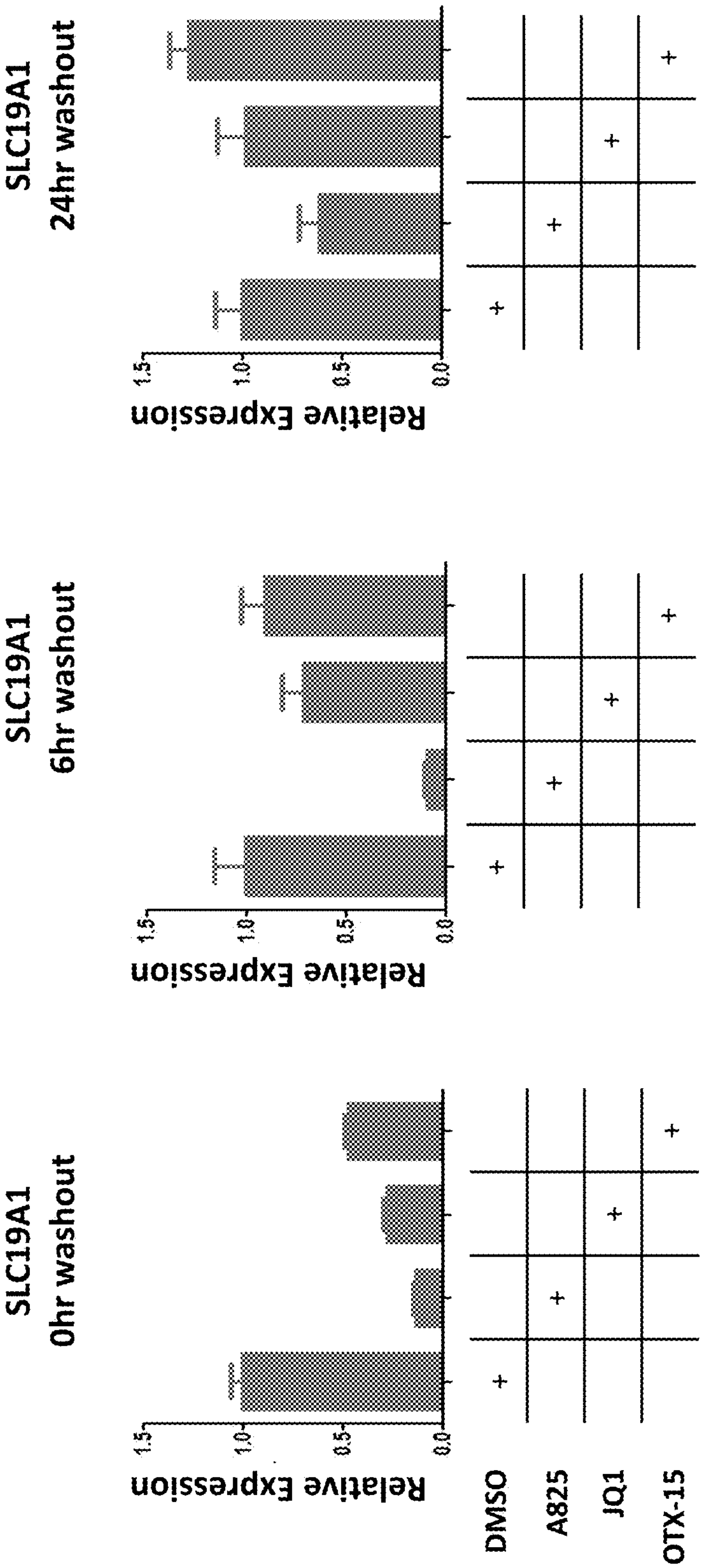

Consistent with the results for c-Myc protein suppression (shown in FIG. 5C), FIGS. 5D-5F show that A825 treatment results in a more substantial and longer-lasting suppression of c-Myc function, as determined by SLC19A1 gene expression, compared to JQ1 and OTX-15. In particular, the Figure shows that SLC19A1 gene expression is significantly reduced by A825 and that even after 24 hours post-treatment, SLC19A1 gene expression is greatly reduced compared to the control sample. In contrast, the Figure shows that SLC19A1 gene expression is reduced by JQ1 and OTX-15, but returns to the control treatment level within 6.0 to 24.0 hours.

4. A825 has Superior Cellular Proliferation Suppression Compared to Small Molecule Inhibitors BL cells are known to be sensitive to BRD4 inhibitors, which suppress c-Myc signaling and induce inhibition of cell proliferation (J. A. Mertz, et al., *PNAS,* 108 (2011) 16669-16674). The effects of A825, JQ1, and OTX-15 treatment on cell proliferation were evaluated in the following experiments.

a. A825 Suppresses Cellular Proliferation to a Greater Extent than JQ1 and OTX-15

In this study, the proliferation of various BL cell lines was evaluated following treatment with A825, JQ1, and OTX-15. Specifically, NAMALWA, Ramos, CA-46, and Daudi cell lines were seeded at 50,000 cells/100 μl in 96-well plates. The cells were treated with increasing concentrations of A825 (100 μM, 300 μM, 1 nM, 3 nM, 10 nM, 30 nM, 100 nM, 300 nM, 1 μM) JQ1 and OTX15 (1 nM, 3 nM, 10 nM, 30 nM, 100 nM, 300 nM, 1 μM, 3 μM; for NAMALWA, JQ1 and OTX-15 were used up to 10 uM) as shown in FIGS. 6A-6D). Following treatment, the relative proliferation of the samples was determined by CTG assay 72 hours following treatment.

FIGS. 6A-6D show that A825 treatment resulted in a more pronounced suppression of proliferation compared to JQ1 or OTX15 in all BL cell lines tested, and that this effect was achieved using significantly lower concentrations of the compound. Interestingly, the relative growth in Ramos and Daudi cell lines treated with the higher concentrations of A825 was close to 0.0.

b. A825 Suppresses Cellular Proliferation Longer than JQ1 and OTX-15

In this study, the duration of the anti-proliferation effect in NAMALWA cells was evaluated following treatment and removal with A825, JQ1, and OTX-15. Specifically, NAMALWA cells were treated for 24 hours with A825 (0.1 μM), JQ1 (1.0 μM) and OTX15 (1.0 μM), followed by three washes to remove the compounds. Cells were re-seeded in fresh medium and incubated without any compound for 0 hr, 24.0 hr, and 48.0 hr. In a parallel control experiment, cells were treated in the same manner, except DMSO was used in place of inhibitor. Following treatment, the relative proliferation of the samples was determined by CTG assay.

Figure 6A:
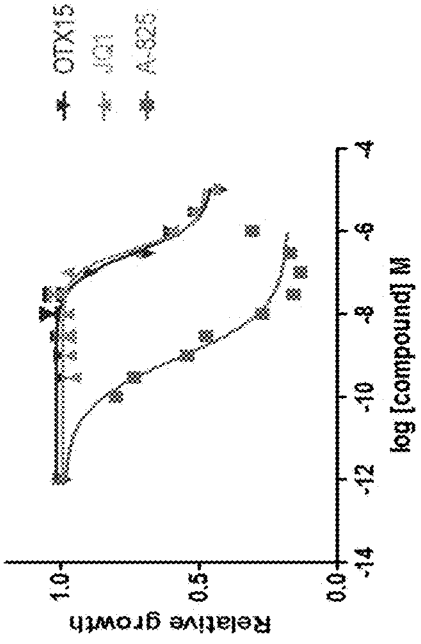
FIGS. 6A-6H. Comparison of the anti-proliferation effect on BL cell lines with A825, JQ1, and OTX-15.
Figure 6B:
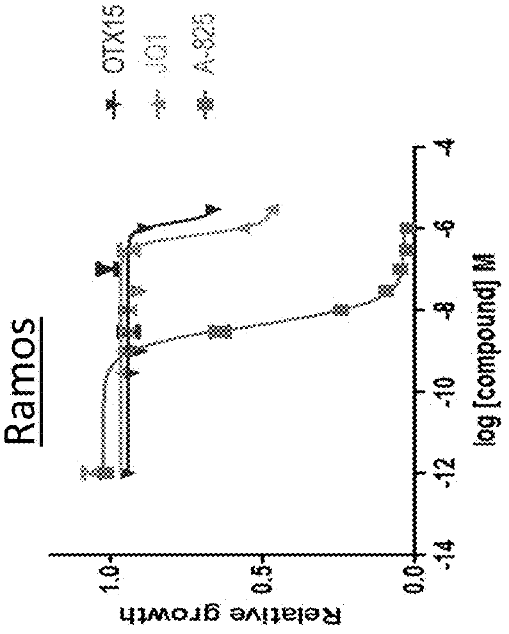
Figure 6C:
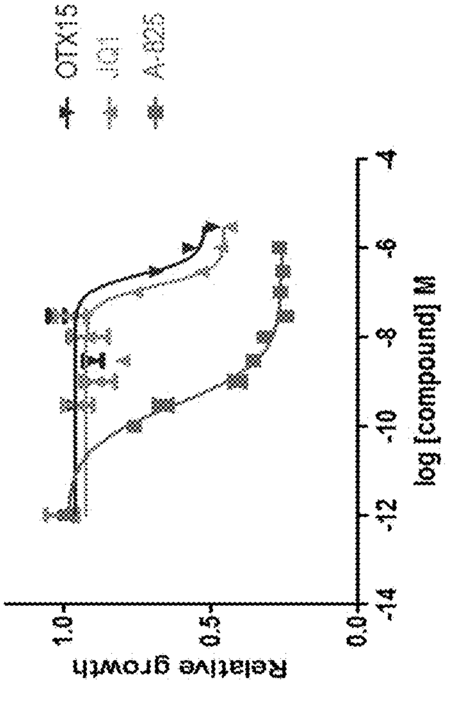
Figure 6D:
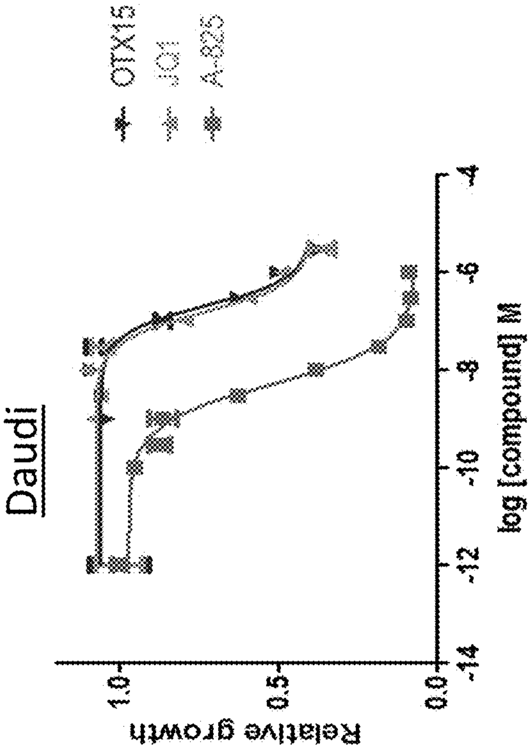
Figure 6E:
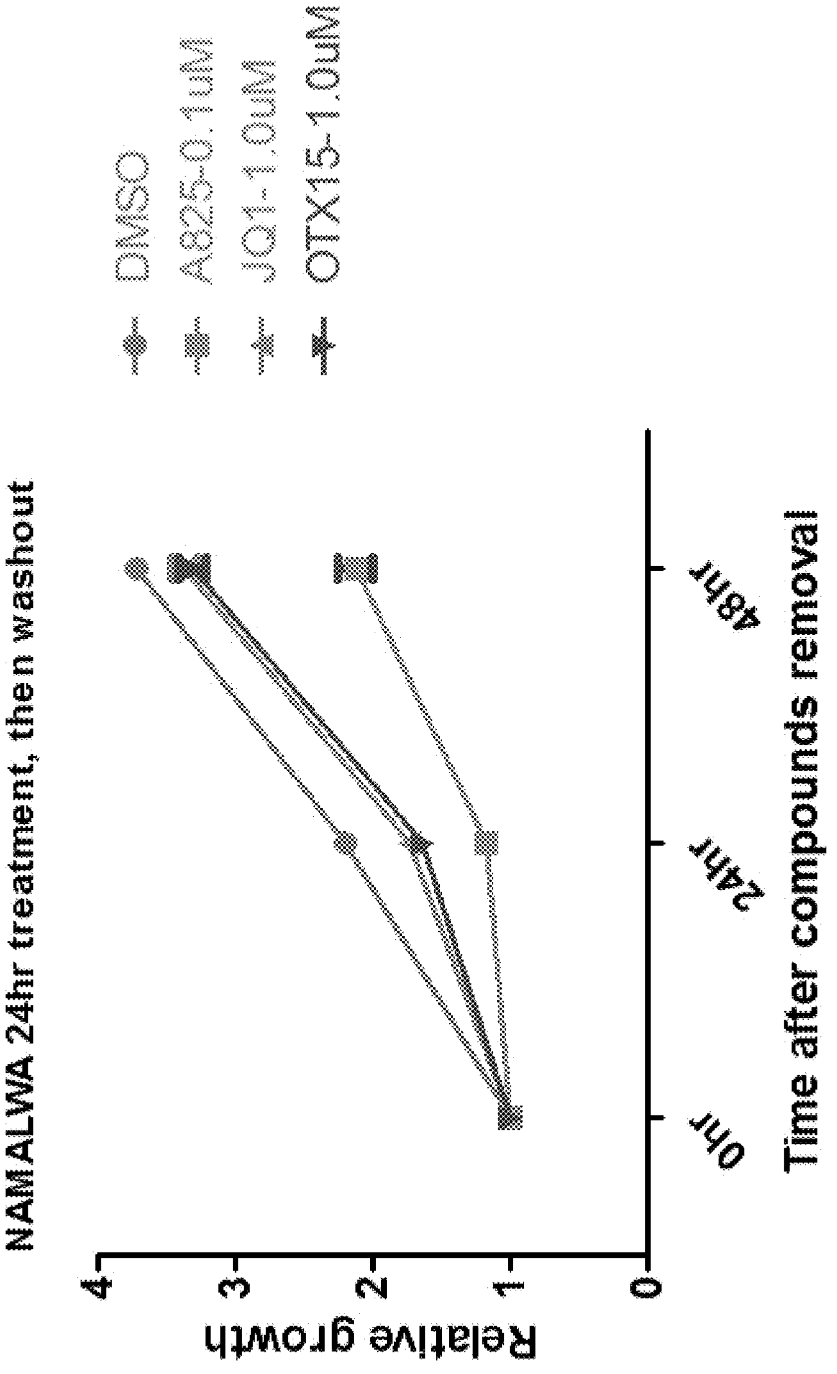

FIG. 6E shows that the proliferation suppression effect by A825 was sustained for more than 48 hours post-treatment compared to that of JQ1 or OTX15. This result is consistent with the experimental results discussed above, where A825 provides long-lasting effect on BRD4 degradation and downstream signaling repression (e.g., FIGS. 5A-5F).

c. Pomalidomide Reduces the Anti-Proliferative Effect Caused by A825

As discussed above, the results in FIG. 4C demonstrated that BRD4 protein levels were partially rescued from degradation when pomalidomide was present during A825 treatment, due to competitive inhibition of Cereblon binding. The following experiment was performed to determine whether pomalidomide can also prevent, or at least reduce, the anti-proliferative effect in various BL cell lines by A825.

Specifically, NAMALWA, CA-46, and Daudi cells were treated with A825 (10 nM or 100 nM) alone, or in combination with pomalidomide (1.0 μM or 10.0 μM) for 72 hours. In a parallel control experiment, cells were treated in the same manner, except DMSO was used in place of inhibitor. Following treatment, the relative proliferation of the samples was determined by CTG assay.

Figure 6F:
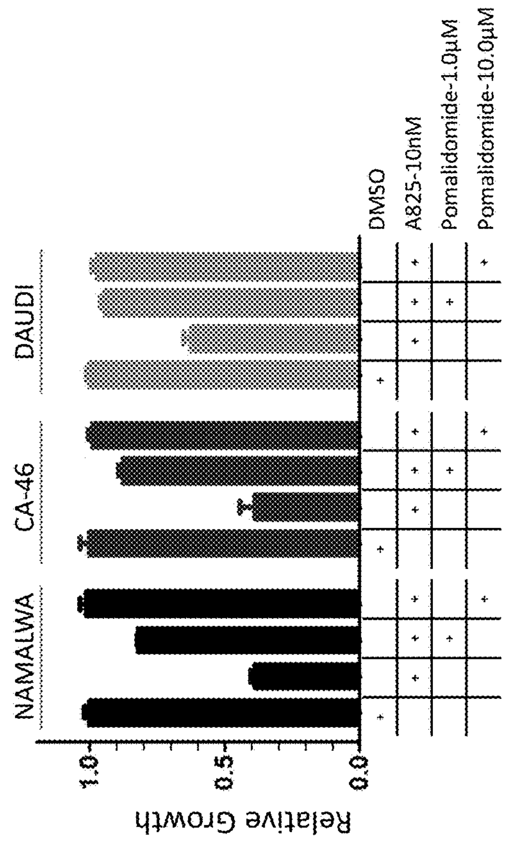

Treating cells with 10 nM of A825 alone resulted in significant proliferation suppression compared to control cells (FIG. 6F), which is consistent with the results shown in FIGS. 6A-6E. FIG. 6F shows that treatment with 10 nM of A825 alone reduced cell growth to approximately 40% in NAMALWA and CA-46 cells and to approximately 65% in Daudi cells, relative to the growth of the control cells. Pomalidomide reduced the anti-proliferation effect caused by 10 nM of A825 in a dose-dependent manner. In particular, treatment with 1.0 μM pomalidomide in combination with 10 nM of A825 resulted in a less dramatic reduction in cell growth relative to the control sample (about 80% in NAMALWA cells, about 90% in CA-46 cells, and about 95% in Daudi cells). Increasing the concentration of pomalidomide to 10.0 μM during treatment with 10 nM of A825 prevented the anti-proliferation effect in all cell lines tested in relation to the control sample.

Figure 6G:
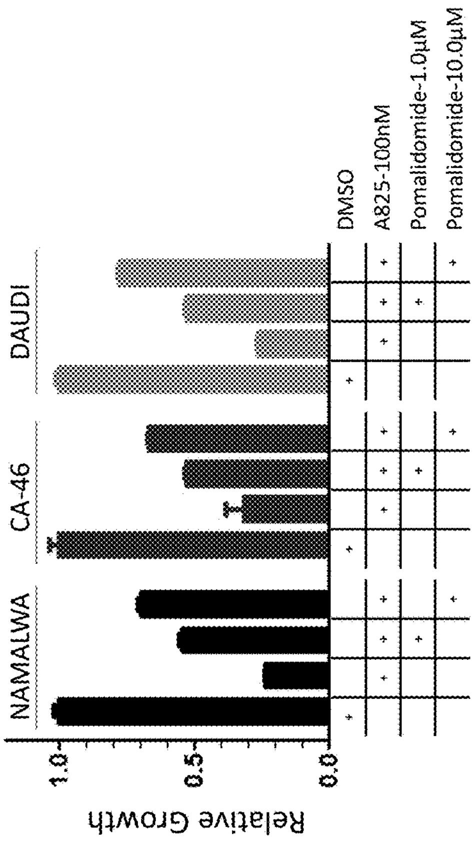

Treating cells with 100 nM of A825 alone suppressed proliferation of all cell types tested to a greater extent compared to treatment with 10 nM of A825 alone (compare FIG. 6G with FIG. 6F), which is consistent with the results shown in FIGS. 6A-66E. FIG. 6G shows that treatment with 100 nM of A825 alone reduced cell growth to approximately 25%-27% in NAMALWA and Daudi cells and to approximately 33% in Daudi cells, relative to the growth of the control cells. Pomalidomide reduced the anti-proliferation effect caused by 100 nM of A825 in a dose-dependent manner. In particular, treatment with 1.0 μM pomalidomide in combination with 100 nM of A825 resulted in a less dramatic reduction in cell growth (about 55% in all cell lines) relative to the control sample. Increasing the concentration of pomalidomide to 10.0 μM during treatment with 100 nM of A825 further reduced the anti-proliferation effect in all cell lines (between about 70% to about 80% in all cell lines relative to the control sample).

Figure 6H:
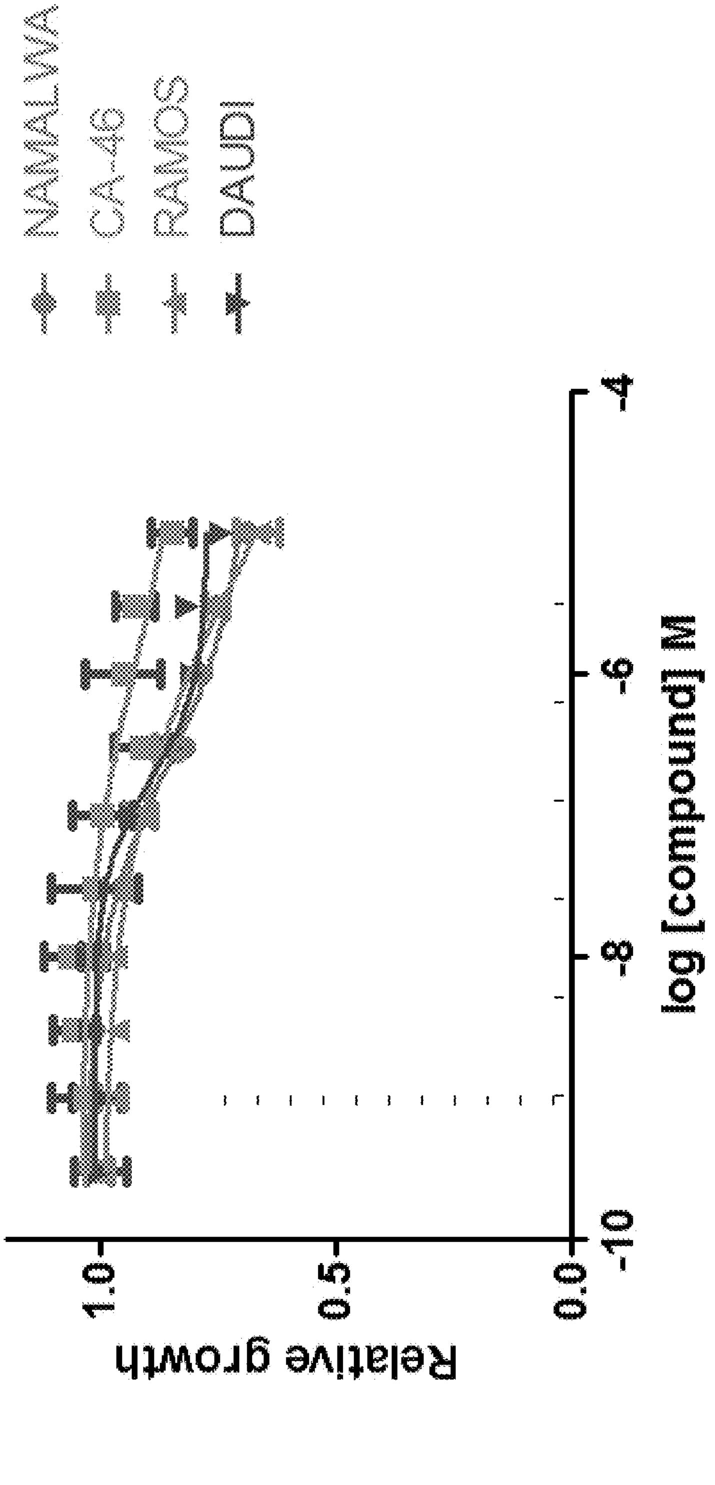

As an additional control, BL cells were treated with pomalidomide to determine if pomalidomide alone, without A825, has an effect on cell proliferation. Specifically, BL cells were treated with various concentrations of pomalidomide alone (0.001 uM, 0.003 uM, 0.01 uM 0.03 μM, 0.1 μM, 0.3 μM, 1 μM, 3 μM, 10 μM, as shown in FIG. 6H) for 72 hours. In a parallel experiment, cells were treated in the same manner, except DMSO was used in place of pomalidomide. Following treatment, the relative proliferation of the samples treated with pomalidomide was determined by CTG assay and compared with the DMSO control.

FIG. 6H shows that treating cells with pomalidomide alone did not result in a significant effect on the proliferation of these cell lines.

5. A825 has Superior Apoptosis Induction Compared to Small Molecule Inhibitors c-Myc is a pleiotropic oncoprotein involved in many hallmarks of cancer, including cell cycle, senescence, proliferation and apoptosis depending on different tumor entities (M. Gabay, et al., *Cold Spring Harb Perspect Med.* (2014) 4:a014241). The preceding experiments demonstrate a universal effect on proliferation suppression in all BL lines tested following treatment with small molecule BRD4 inhibitors (JQ1 and OTX-15) as well as A825. The following experiments evaluate the extent in which JQ1, OTX-15, and A825 can induce apoptosis in BL cell lines.

a. A825 Leads to a More Significant Increase in Caspase Activity Compared to JQ1 and OTX-15

Various BL cell lines were treated with ARV-825 (0.1 μM), or JQ1 (1.0 μM), or OTX015 (1.0 μM), or puromycin (10 mg/ml) as positive control of apoptosis induction, for 24 hours, caspase 3/7 activity was measured by Caspase 3/7-Glow assay.

Figure 7A:
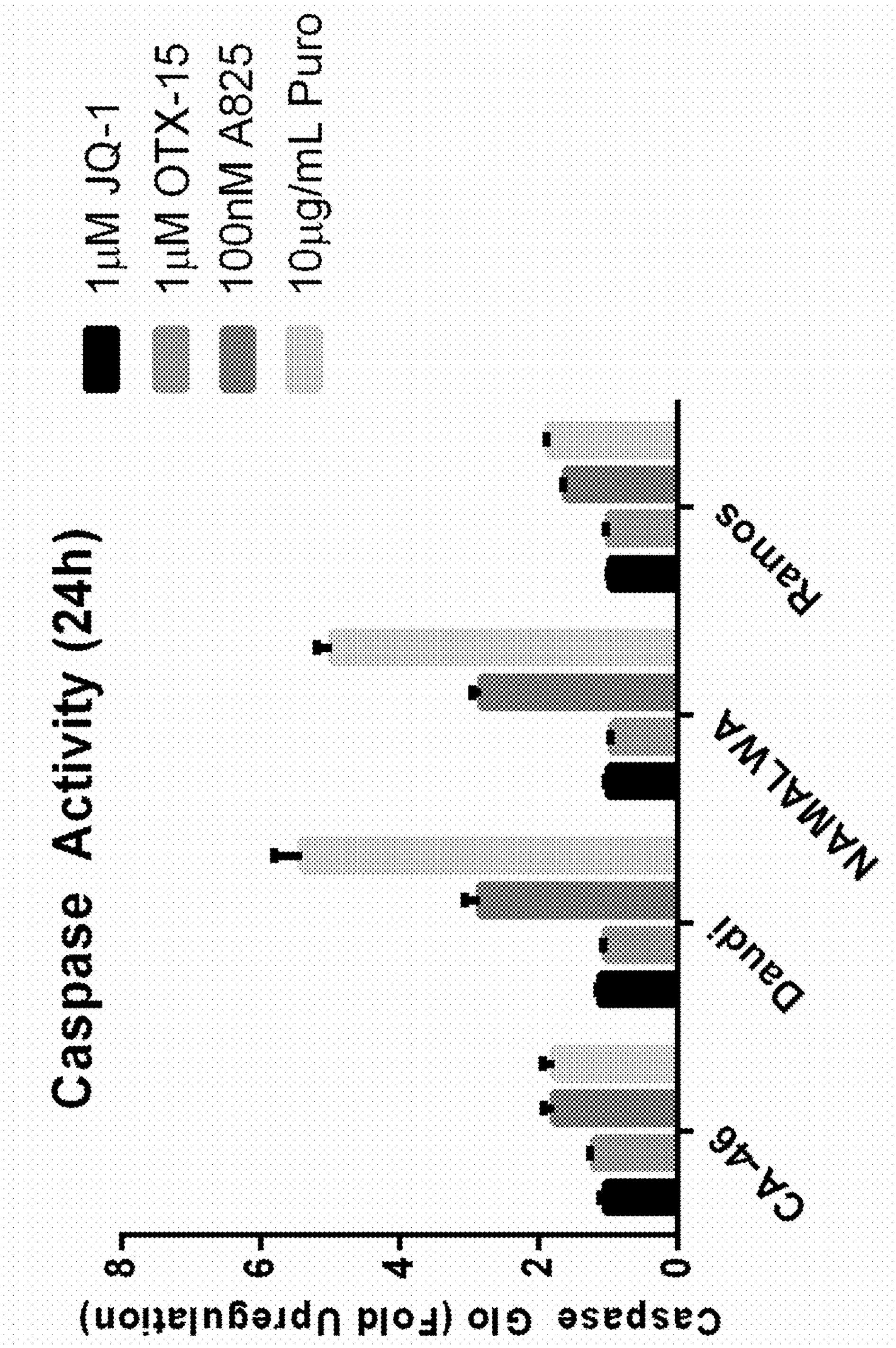
FIGS. 7A-7B. Comparison of the apoptosis effect on BL cells with A825, JQ1, and OTX-15 treatment.

FIG. 7A shows that caspase activity varies markedly depending on both the BL cell line tested and the inhibitor used in the treatment. Specifically, treatment of BL cells with 100 nM of A825 resulted in a statistically significant increase in caspase activity compared to BL cells treated with JQ1 and OTX-15. The increase in caspase activity was even more significant in Daudi and NAMALWA cells compared to Ramos and CA-56 cells.

Increased caspases 3/7 activity was observed after 24 hours treatment of all BL cell lines with A825, but not by higher dose of JQ1 and OTX15 (FIG. 5A).

b. A825 Leads to a More Significant Increase in PARP Cleavage Compared to JQ1 and OTX-15

Ramos and CA-46 cells were treated with increasing doses of ARV-825 (up to 1.0 μM), or JQ1 and OTX015 (up to 10.0 μM) for 48 hours. Lysates were collected and analyzed by immunoblot for PARP cleavage with actin as loading control.

Figure 7B:
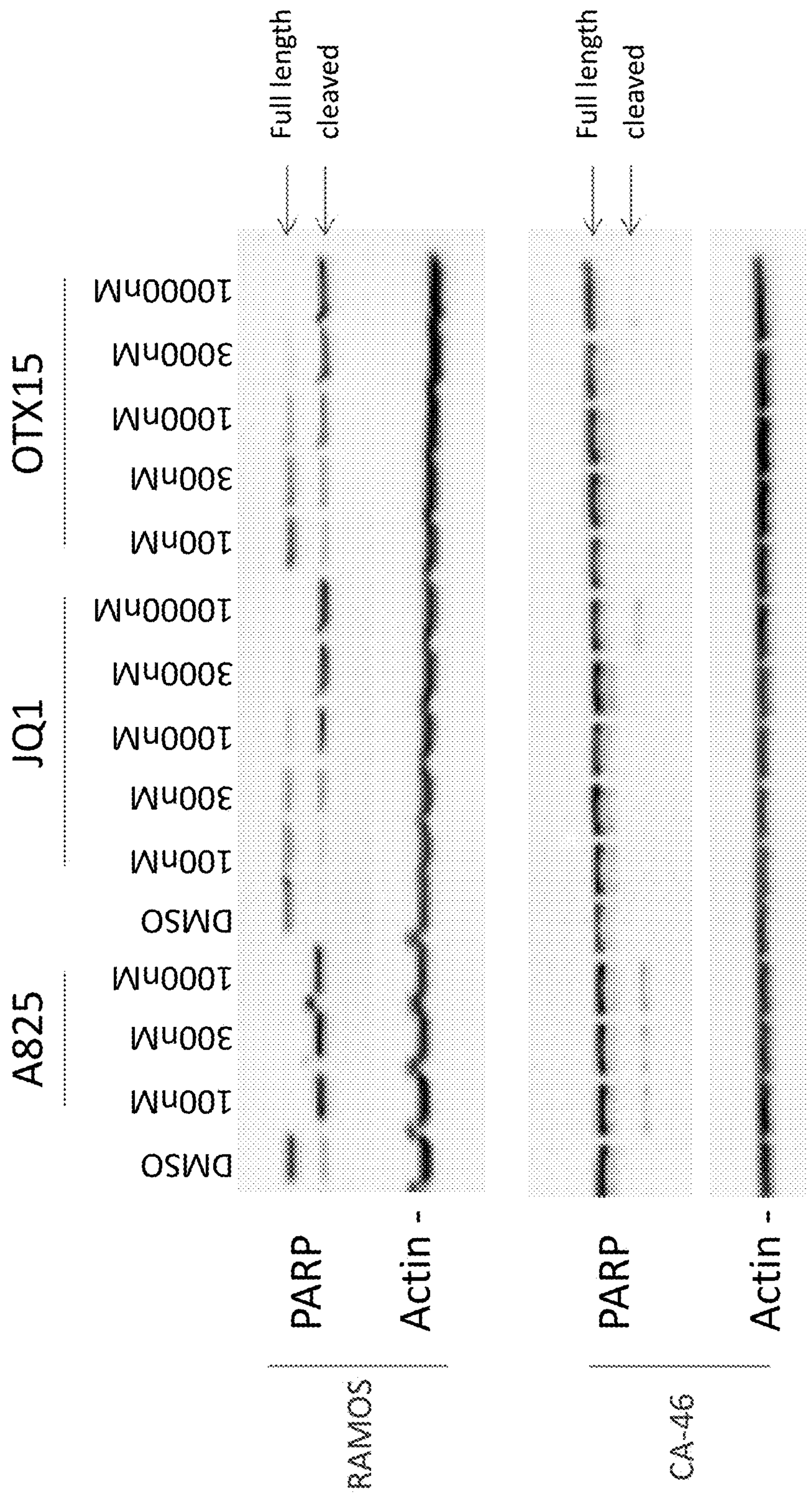

FIG. 7B shows that by 48 hours, Ramos cells demonstrated significant apoptosis with 0.1 uM of A825 treatment, as evidenced prominent PARP cleavage. In contrast, significantly higher dose of inhibitors, JQ1 and OTX15, are needed to elicit similar level of apoptosis in corresponding cell lines. The need for higher concentrations of JQ1 and OTX-15 is likely due to these inhibitors having an inefficient BRD4 inhibition and downstream c-Myc repression. Taken together, these findings provide strong evidence that PROTAC-mediated BRD4 degradation is a more effective strategy in targeting BRD4 in BLs compared to small molecule inhibitors.

6. Summary and Discussion

BL cells are known to be sensitive to BRD4 inhibitors, which suppress c-Myc signaling and induce inhibition of cell proliferation (J. A. Mertz, et al., *PNAS,* 108 (2011) 16669-16674). Recently, there has been significant progress in designing compounds that effectively inhibit BRD4 in cells. However, despite this recent progress, BRD4 inhibitors having significant functional and clinical benefits have yet to be discovered, which can partially be explained by the pronounced BRD4 accumulation observed during inhibitor treatment and reversible/transient nature of inhibition observed post-treatment, after the inhibitor is removed.

The experiments performed in this Example demonstrate that small molecule BRD4 inhibitors, JQ1 and OTX15, lead to significant BRD4 protein accumulation in all BL cell lines tested. Although both inhibitors suppressed downstream c-Myc level, the suppression required high concentration of the compounds. Moreover, even with high concentrations of these inhibitors, c-Myc suppression was not complete. The results observed in this Example for JQ1 and OTX-15 are consistent with results obtained by others in a panel of lung and prostate cancer cell lines (Shimamura, T., Chen, Z., Soucheray, M., Carretero, J., Kikuchi, E., Tchaicha, J. H., Gao, Y., Cheng, K. A., Cohoon, T. J., Qi, J., et al. (2013). and data not shown). The results obtained above suggest that robust accumulation of BRD4, together with the reversible nature of inhibitor binding to BRD4, may account for the moderate effect in downstream c-Myc suppression and associated limited proliferation inhibition with small molecule inhibitors. One possible explanation for the JQ1 and OTX-15 data is that the binding of inhibitor with BRD4 results in a conformational change which leads to increase in its stability or hinders its accessibility to its natural degradation machinery. Alternatively, the BRD4 inhibitors may be suppressing a BRD4-mediated negative feedback loop that regulates BRD4 protein levels. Nevertheless, the prominent increase of BRD4 level, together with the reversible nature of inhibitor binding, could partially account for the inefficiency of BRD4 inhibition and downstream MYC suppression.

Both preclinical and clinical studies have shown that the effects of BRD4 inhibitors were largely cytostatic, with apoptosis limited to a few cell lines and phase I patients.

This could significantly limit the potential benefit of future patients at clinically achievable concentrations of BRD4 inhibitors.

Another recurring phenomenon of small molecule inhibitor drug development is the emergence of mutations in target proteins to mediate resistance or even to convert from an antagonist to an agonist. For example, although enzalutamide is efficacious in treating prostate cancer by inhibiting androgen receptor, it becomes an agonist in tumor cells with androgen receptor containing F876L mutation. Thus, prostate cancer patients whose tumors contain pre-existing or treatment-induced ARF876L will not benefit from enzalutamide treatment. In contrast, PROTAC mediated target degradation will avoid these pitfalls and provide a powerful strategy of efficient targeting. To circumvent the limitations of small molecule BRD4 inhibitors, a chimera molecule, A825, was designed by connecting a small molecule BRD4 binding moiety to an E3 ligase Cereblon binding moiety through PROTAC technology.

The experiments above show that A825 induced rapid and efficient BRD4 degradation by actively recruiting E3 ligase Cereblon to BRD4, which directs BRD4 to the proteasome degradation machinery. These results also demonstrate that A825 leads to a more pronounced suppression on downstream c-Myc expression and function, cell proliferation, and apoptosis induction compared to the small molecule BRD4 inhibitors.

The improved functional effects of BRD4 degrader over inhibitors could be partially attributed to the more complete and sustained suppression on c-MYC, a driver oncoprotein in BLs. It is also possible that BRD4 possess "chaperon" functions as it is a large protein with many binding partners that remain to be further identified and elucidated. Understandably, eliminating BRD4 would elicit more profound effect than mere inhibition of its binding to acetyl-lysine containing partners. A comparison of phenotypes of BRD4 knockout or knockdown (such as by CRISPR and shRNAs) with that of BRD4 inhibition by inhibitors would address this question, however, is outside the scope of this study.

Binding affinity of OTX15 and Pomalidomide to their respective target, BRD4 and Cereblon, are ~10 nM and ~3 uM, respectively. A825, which is based on these two ligands, achieves a $DC_{50}$ for BRD4 below 1 nM. This strongly suggests that BRD4 PROTAC possesses catalytic feature and opens up enormous opportunities in developing functional degraders consisting of target ligands with sub-optimal affinity no known function. Therefore, many "difficult" targets, which typically lack natural ligand binding sites, may become "druggable" with PROTAC mediated degradation.

The present disclosure provides a novel strategy in efficiently targeting BRD4 by creating potent BRD4 degrader through PROTAC technology. Moreover, it breaks the ground for a new class of drug molecules which actively recruits E3 ligase to target specific pathological protein for degradation, thus renders many "difficult" targets by traditional small molecule approaches "druggable".

7. Industrial Applicability

A novel bifunctional molecule, which contains a BRD4 recruiting moiety and an E3 Ligase Cereblon recruiting moiety, through PROTAC technology is described. A825 actively degrades BRD4, leading to significant and persistent downstream MYC suppression and robust cellular proliferation suppression and apoptosis induction in BLs. A825 represents a new strategy for efficiently targeting BRD4, which emerges as a promising target in multiple cancers. A825 represents one example that PROTAC mediated protein degradation provides a promising strategy in targeting the "undruggable" pathological proteins by traditional approaches.

TABLE 1

| # | Structure | Degradation Activity AR[1] | BRD4[1] | TBK1[2] | ERRa[3] | cMyc[4] | MH+ | Chemical Name |
|---|---|---|---|---|---|---|---|---|
| 1 | 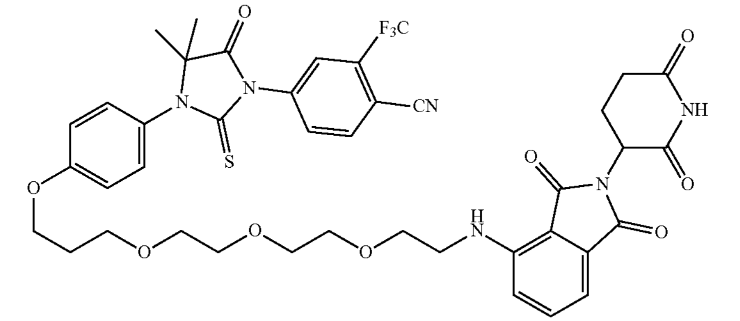 [SMILES: CC1(C)C(=O)N(c2ccc(C#N)c(C(F)(F)F)c2)C(=S)N1c1ccc(OCCCOCCOCCOCCNc2cccc3c2C(=O)N(C2CCC(=O)NC2=O)C3=O)cc1] | A | | | | | 851.25 | 4-(3-(4-(3-(2-(2-(2-((2-(2,6-dioxopiperidin-3-yl)-1,3-dioxoisoindolin-4-yl)amino)ethoxy)ethoxy)ethoxy)propoxy)phenyl)-4,4-dimethyl-5-oxo-2-thioxoimidazolidin-1-yl)-2-(trifluoromethyl)benzonitrile |
| 2 | 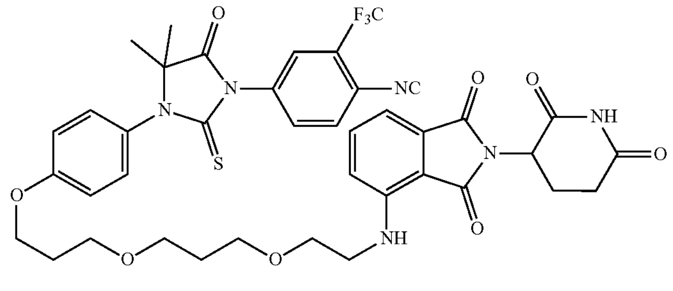 | B | | | | | 821.25 | 4-(3-(4-(3-(3-(2-((2-(2,6-dioxopiperidin-3-yl)-1,3-dioxoisoindolin-4-yl)amino)ethoxy)propoxy)propoxy)phenyl)-4,4-dimethyl-5-oxo-2-thioxoimidazolidin-1-yl)-2-(trifluoromethyl)benzonitrile |
| 3 | 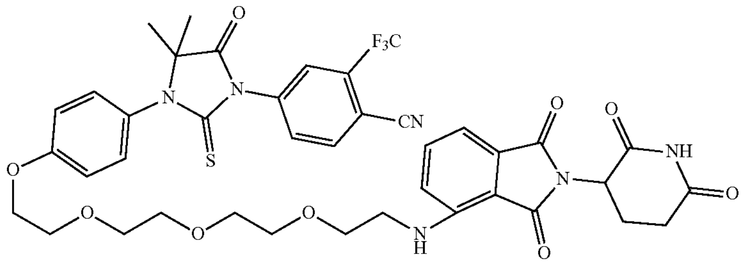 [SMILES: CC1(C)C(=O)N(c2ccc(C#N)c(C(F)(F)F)c2)C(=S)N1c1ccc(OCCOCCOCCOCCNc2cccc3c2C(=O)N([C@H]2CCC(=O)NC2=O)C3=O)cc1] | B | | | | | 837.23 | 4-(3-(4-(2-(2-(2-(2-((2-(2,6-dioxopiperidin-3-yl)-1,3-dioxoisoindolin-4-yl)amino)ethoxy)ethoxy)ethoxy)ethoxy)phenyl)-4,4-dimethyl-5-oxo-2-thioxoimidazolidin-1-yl)-2-(trifluoromethyl)benzonitrile |

TABLE 1-continued

| | | | | |
|---|---|---|---|---|
| 4 | 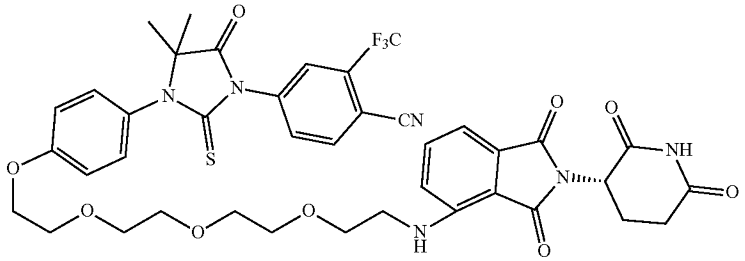 | B | 837.24 | (S)-4-(3-(4-(2-(2-(2-(2-((2-(2,6-dioxopiperidin-3-yl)-1,3-dioxoisoindolin-4-yl)amino)ethoxy)ethoxy)ethoxy)ethoxy)phenyl)-4,4-dimethyl-5-oxo-2-thioxoimidazolidin-1-yl)-2-(trifluoromethyl)benzonitrile |
| 5 | 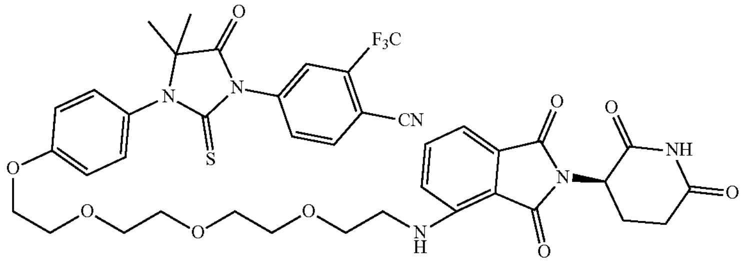 | B | 837.24 | (R)-4-(3-(4-(2-(2-(2-(2-((2-(2,6-dioxopiperidin-3-yl)-1,3-dioxoisoindolin-4-yl)amino)ethoxy)ethoxy)ethoxy)ethoxy)phenyl)-4,4-dimethyl-5-oxo-2-thioxoimidazolidin-1-yl)-2-(trifluoromethyl)benzonitrile |
| 6 | 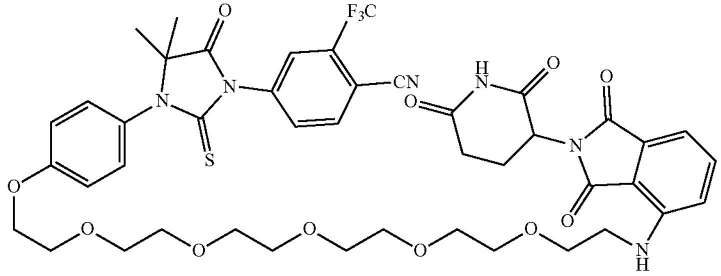 [SMILES: CC1(C)C(=O)N(c2ccc(C#N)c(C(F)(F)F)c2)C(=S)N1c1ccc(OCCOCCOCCOCCOCCOCCNc2cccc3c2C(=O)N(C2CCC(=O)NC2=O)C3=O)cc1] | A | 925.30 | 4-(3-(4-((17-((2-(2,6-dioxopiperidin-3-yl)-1,3-dioxoisoindolin-4-yl)amino)-3,6,9,12,15-pentaoxa-heptadecyl)oxy)phenyl)-4,4-dimethyl-5-oxo-2-thioxoimidazolidin-1-yl)-2-(trifluoromethyl)benzonitrile |

TABLE 1-continued

| | | | | |
|---|---|---|---|---|
| 7 | 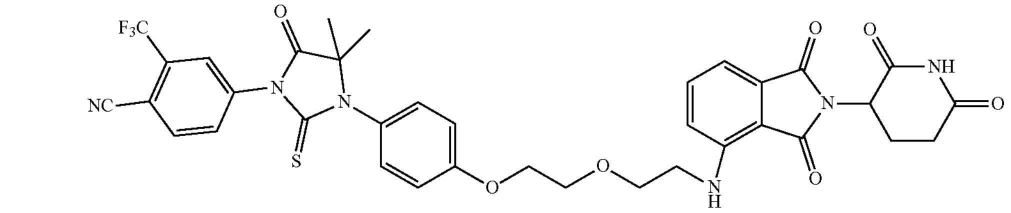 [SMILES: CC1(C)C(=O)N(c2ccc(C#N)c(C(F)(F)F)c2)C(=S)N1c1ccc(OCCOCCNc2cccc3c2C(=O)N(C2CCC(=O)NC2=O)C3=O)cc1] | A | 749.19 | 4-(3-(4-(2-(2-((2-(2,6-dioxopiperidin-3-yl)-1,3-dioxoisoindolin-4-yl)amino)ethoxy)ethoxy)phenyl)-4,4-dimethyl-5-oxo-2-thioxoimidazolidin-1-yl)-2-(trifluoromethyl)benzonitrile |
| 8 | 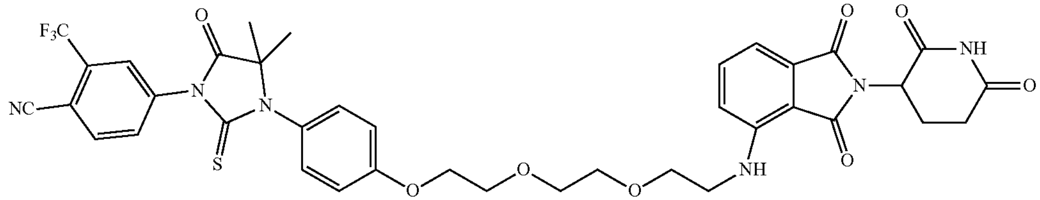 [SMILES: CC1(C)C(=O)N(c2ccc(C#N)c(C(F)(F)F)c2)C(=S)N1c1ccc(OCCOCCOCCNc2cccc3c2C(=O)N(C2CCC(=O)NC2=O)C3=O)cc1] | A | 79.28 | 4-(3-(4-(2-(2-(2-((2-(2,6-dioxopiperidin-3-yl)-1,3-dioxoisoindolin-4-yl)amino)ethoxy)ethoxy)ethoxy)phenyl)-4,4-dimethyl-5-oxo-2-thioxoimidazolidin-1-yl)-2-(trifluoromethyl)benzonitrile |
| 9 | 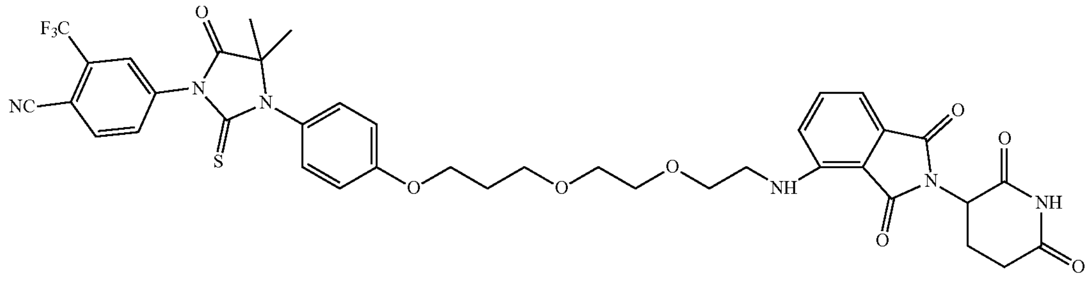 [SMILES: CC1(C)C(=O)N(c2ccc(C#N)c(C(F)(F)F)c2)C(=S)N1c1ccc(OCCCOCCOCCNc2cccc3c2C(=O)N(C2CCC(=O)NC2=O)C3=O)cc1] | A | 807.32 | 4-(3-(4-(3-(2-(2-((2-(2,6-dioxopiperidin-3-yl)-1,3-dioxoisoindolin-4-yl)amino)ethoxy)ethoxy)propoxy)phenyl)-4,4-dimethyl-5-oxo-2-thioxoimidazolidin-1-yl)-2-(trifluoromethyl)benzonitrile |

TABLE 1-continued

| | | | | |
|---|---|---|---|---|
| 10 | 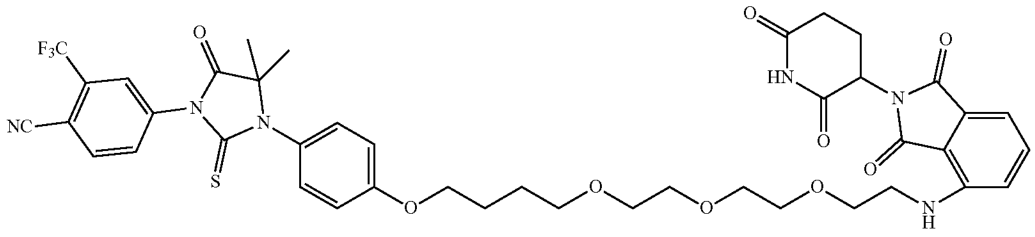 [SMILES: CC1(C)C(=O)N(c2ccc(C#N)c(C(F)(F)F)c2)C(=S)N1c1ccc(OCCCCOCCOCCOCCNc2cccc3c2C(=O)N(C2CCC(=O)NC2=O)C3=O)cc1] | B | 865.36 | 4-(3-(4-(4-(2-(2-((2-(2,6-dioxopiperidin-3-yl)-1,3-dioxoisoindolin-4-yl)amino)ethoxy)ethoxy)ethoxy)butoxy)phenyl)-4,4-dimethyl-5-oxo-2-thioxoimidazolidin-1-yl)-2-(trifluoromethyl)benzonitrile |
| 11 | 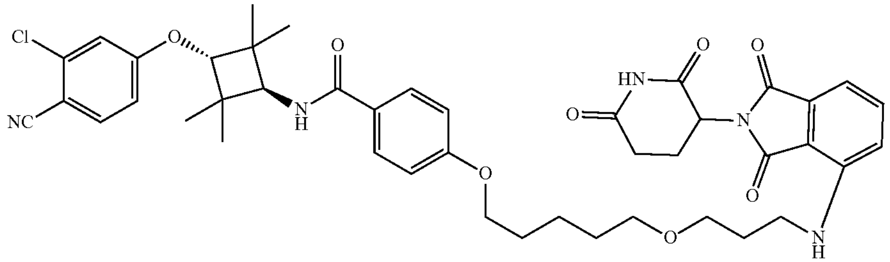 [SMILES: CC1(C)[C@H](NC(=O)c2ccc(OCCCCCOCCCNc3cccc4c3C(=O)N(C3CCC(=O)NC3=O)C4=O)cc2)C(C)(C)[C@H]1Oc1ccc(C#N)c(Cl)c1] | C | 799.31 | 4-((5-(3-((2-(2,6-dioxopiperidin-3-yl)-1,3-dioxo-2,3-dihydro-1H-isoindol-4-yl)amino)propoxy)pentyl)oxy)-N(trans-3-(3-chloro-4-cyanophenoxy)-2,2,4,4-tetramethyl-cyclobutyl)benzamide |
| 12 | 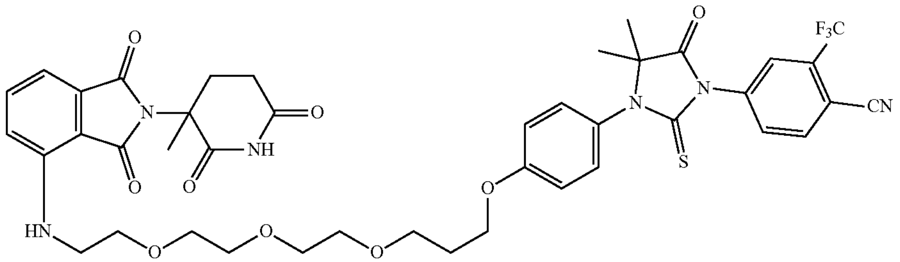 [SMILES: CC1(C)C(=O)N(c2ccc(C#N)c(C(F)(F)F)c2)C(=S)N1c1ccc(OCCCOCCOCCOCCNc2cccc3c2C(=O)N(C2(C)CCC(=O)NC2=O)C3=O)cc1] | A | 865.16 | 4-(4,4-dimethyl-3-(4-((1-(2-(3-methyl-2,6-dioxopiperidin-3-yl)-1,3-dioxo-2,3-dihydro-1H-isoindol-4-yl)-4,7,10-trioxa-1-azatridecan-13-yl)oxy)phenyl)-5-oxo-2-sulfanylidene-imidazolidin-1-yl)-2-(trifluoromethyl)benzonitrile |

TABLE 1-continued

| | | | | |
|---|---|---|---|---|
| 13 | 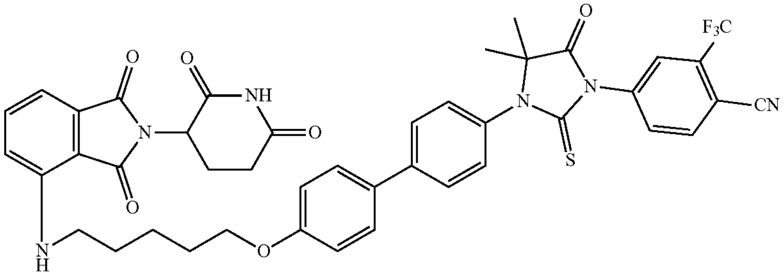 [SMILES: CC1(C)C(=O)N(c2ccc(C#N)c(C(F)(F)F)c2)C(=S)N1c1ccc(-c2ccc(OCCCCCNc3cccc4c3C(=O)N(C3CCC(=O)NC3=O)C4=O)cc2)cc1] | C | 923.12 | 4-(3-(4-(4-((5-((2-(2,6-dioxopiperidin-3-yl)-1,3-dioxo-2,3-dihydro-1H-isoindol-4-yl)amino)pentyl)oxy)phenyl)phenyl)-4,4-dimethyl-5-oxo-2-sulfanylidene-imidazolidin-1-yl)-2-(trifluoromethyl)benzonitrile |
| 14 | 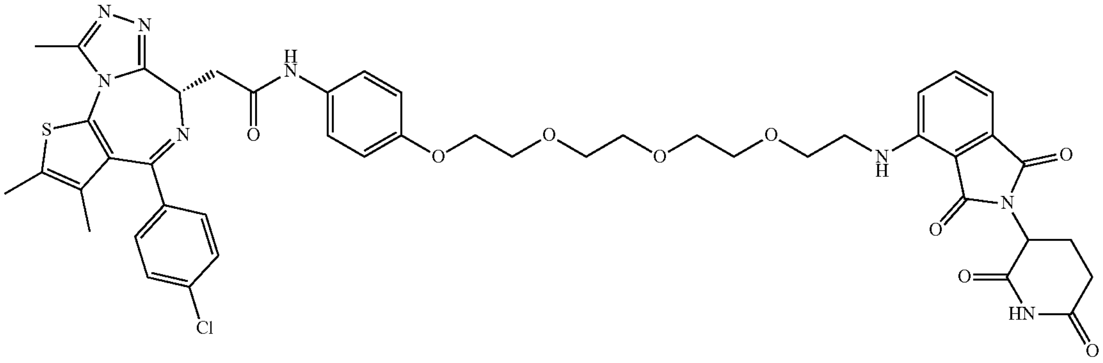 [SMILES: Cc1sc2c(c1C)C(c1ccc(Cl)cc1)=N[C@@H](CC(=O)Nc1ccc(OCCOCCOCCOCCNc3cccc4c3C(=O)N(C3CCC(=O)NC3=O)C4=O)cc1)c1nnc(C)n1-2] | C | 823.29 & 925.29 | 2-((9S)-7-(4-chlorophenyl)-4,5,13-trimethyl-3-thia-1,8,11,12-tetraazatricyclo[8.3.0.02,6]trideca-2(6),4,7,10,12-pentaen-9-yl)-N-(4-((1-(2-(2,6-dioxopiperidin-3-yl)-1,3-dioxo-2,3-dihydro-1H-isoindol-4-yl)-4,7,10-trioxa-1-azadodecan-12-yl)oxy)phenyl)acetamide |
| 15 | 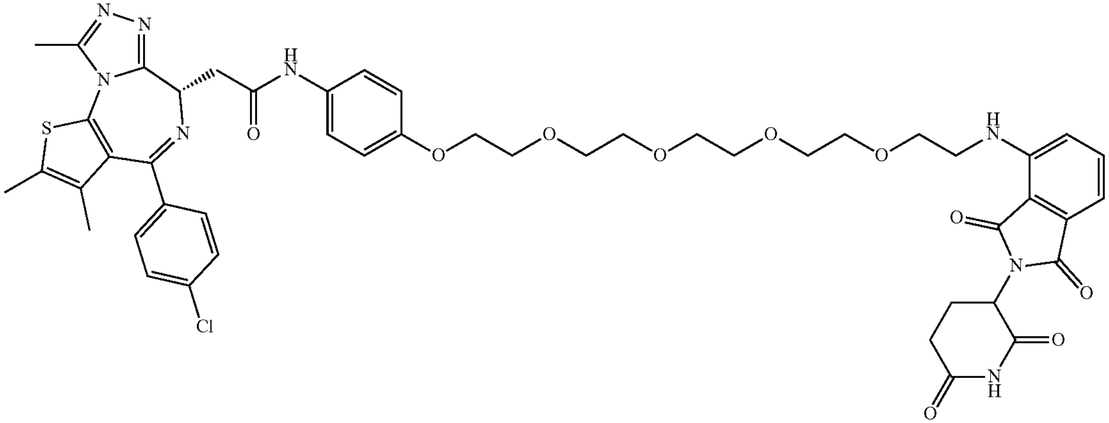 [SMILES: Cc1sc2c(c1C)C(c1ccc(Cl)cc1)=N[C@@H](CC(=O)Nc1ccc(OCCOCCOCCOCCOCCNc3cccc4c3C(=O)N(C3CCC(=O)NC3=O)C4=O)cc1)c1nnc(C)n1-2] | C | 967.31 & 969.31 | 2--((9S)-7-(4-chlorophenyl)-4,5,13-trimethyl-3-thia-1,8,11,12-tetraazatricyclo[8.3.0.02,6]trideca-2(6),4,7,10,12-pentaen-9-yl)-N-(4-((1-(2-(2,6-dioxopiperidin-3-yl)-1,3-dioxo-2,3-dihydro-1H-isoindol-4-yl)-4,7,10,13-tetraoxa-1-azapentadecan-15-yl)oxy)phenyl)acetamide |

TABLE 1-continued

| | | | | |
|---|---|---|---|---|
| 16 | 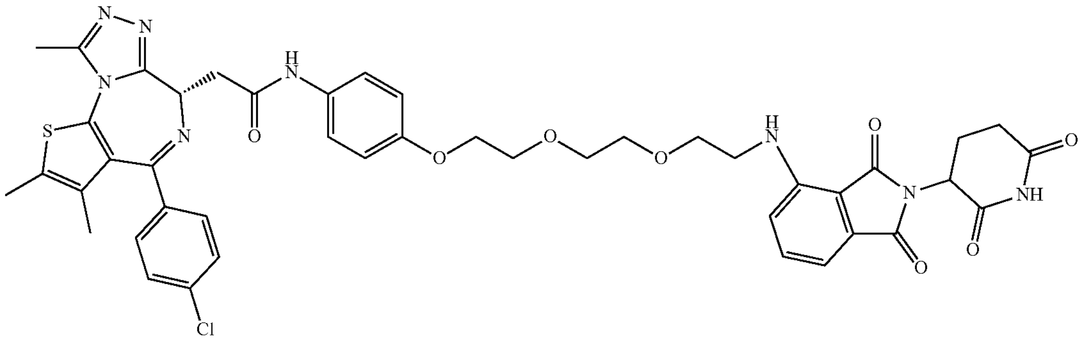 [SMILES: Cc1sc2c(c1C)C(c1ccc(Cl)cc1)=N[C@@H](CC(=O)Nc1ccc(OCCOCCOCCNc3cccc4c3C(=O)N(C3CCC(=O)NC3=O)C4=O)cc1)c1nnc(C)n1-2] | C | 879.26 & 881.26 | 2-((9S)-7-(4-chlorophenyl)-4,5,13-trimethyl-3-thia-1,8,11,12-tetraazatricyclo[8.3.0.02,6]trideca-2(6),4,7,10,12-pentaen-9-yl)-N-(4-(2-(2-(2-((2-(2,6-dioxopiperidin-3-yl)-1,3-dioxo-2,3-dihydro-1H-isoindol-4-yl)amino)ethoxy)ethoxy)ethoxy)phenyl)acetamide |
| 17 | 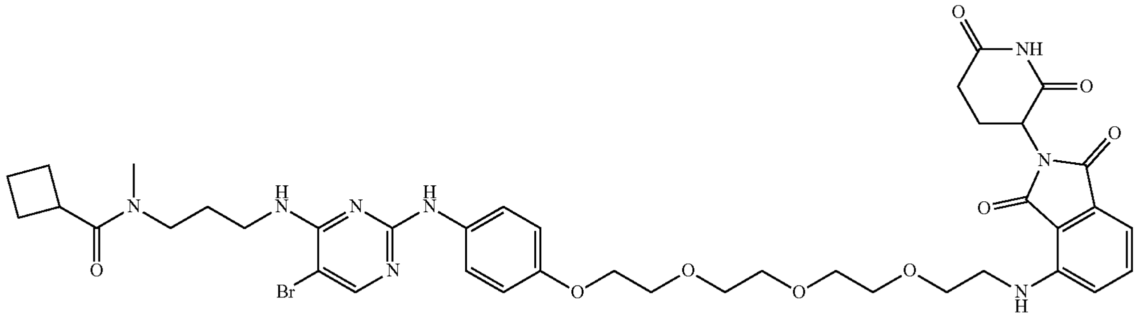 [SMILES: CN(CCCNc1nc(Nc2ccc(OCCOCCOCCOCCNc3cccc4c3C(=O)N(C3CCC(=O)NC3=O)C4=O)cc2)ncc1Br)C(=O)C1CCC1] | A | 865.27 & 867.27 | N-(3-((5-bromo-2-((4-(2-(2-(2-(2-((2-(2,6-dioxopiperidin-3-yl)-1,3-dioxoisoindolin-4-yl)amino)ethoxy)ethoxy)ethoxy)ethoxy)phenyl)amino)pyrimidin-4-yl)amino)propyl)-N-methylcyclobutane-carboxamide |
| 18 | 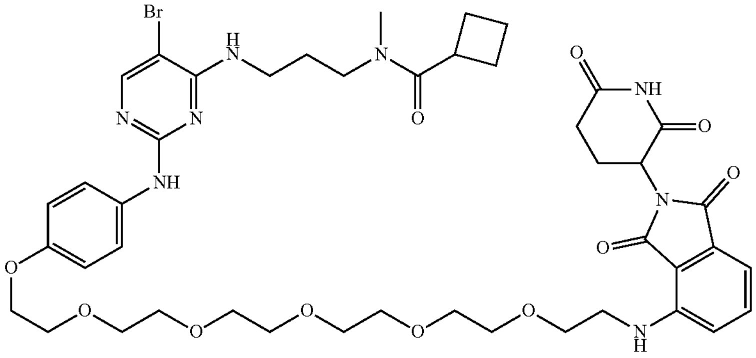 [SMILES: CN(CCCNc1nc(Nc2ccc(OCCOCCOCCOCCOCCOCCNc3cccc4c3C(=O)N(C3CCC(=O)NC3=O)C4=O)cc2)ncc1Br)C(=O)C1CCC1] | C | 953.32 & 955.32 | N-(3-((5-bromo-2-((4-((1-(2-(2,6-dioxopiperidin-3-yl)-1,3-dioxo-2,3-dihydro-1H-isoindol-4-yl)-4,7,10,13,16-pentaoxa-1-azaoctadecan-18-yl)oxy)phenyl)amino)pyrimidin-4-yl)amino)propyl)-N-methylcyclobutane-carboxamide |

TABLE 1-continued

| | | | | |
|---|---|---|---|---|
| 19 | 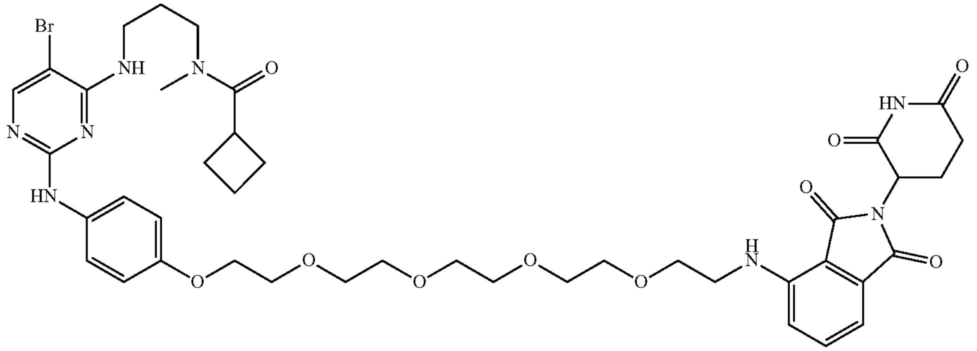 [SMILES: CN(CCCNc1nc(Nc2ccc(OCCOCCOCCOCCOCCNc3cccc4c3C(=O)N(C3CCC(=O)NC3=O)C4=O)cc2)ncc1Br)C(=O)C1CCC1] | C | 909.31 & 911.31 | N-(3-((5-bromo-2-((4-((1-(2-(2,6-dioxopiperidin-3-yl)-1,3-dioxo-2,3-dihydro-1h-isoindol-4-yl)-4,7,10,13-tetraoxa-1-azapentadecan-15-yl)oxy)phenyl)amino)pyrimidin-4-yl)amino)propyl)-N-methylcyclobutanecarboxamide |
| 20 | 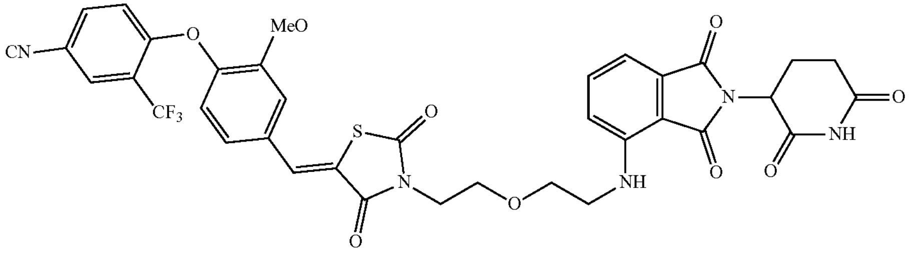 | B | 764.15 | 4-(4-(((5Z)-3-(2-(2-((2-(2,6-dioxopiperidin-3-yl)-1,3-dioxo-2,3-dihydro-1H-isoindol-4-yl)amino)ethoxy)ethyl)-2,4-dioxo-1,3-thiazolidin-5-ylidene)methyl)-2-methoxyphenoxy)-3-(trifluoromethyl)benzonitrile |
| 21 | 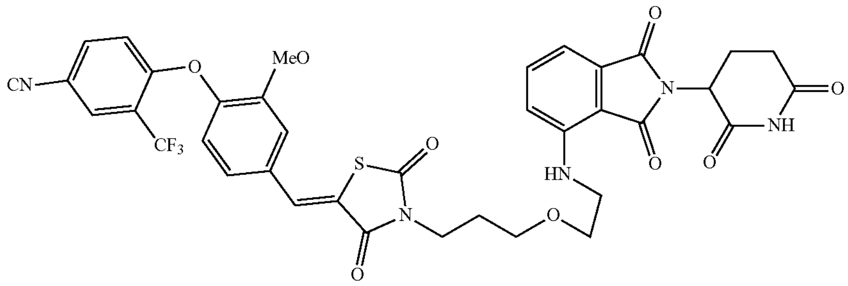 | C | 778.18 | 4-(4-(((5Z)-3-(3-(2-((2-(2,6-dioxopiperidin-3-yl)-1,3-dioxo-2,3-dihydro-1H-isoindol-4-yl)amino)ethoxy)propyl)-2,4-dioxo-1,3-thiazolidin-5-ylidene)methyl)-2-methoxyphenoxy)-3-(trifluoromethyl)benzonitrile |

TABLE 1-continued

| | | | | |
|---|---|---|---|---|
| 22 | 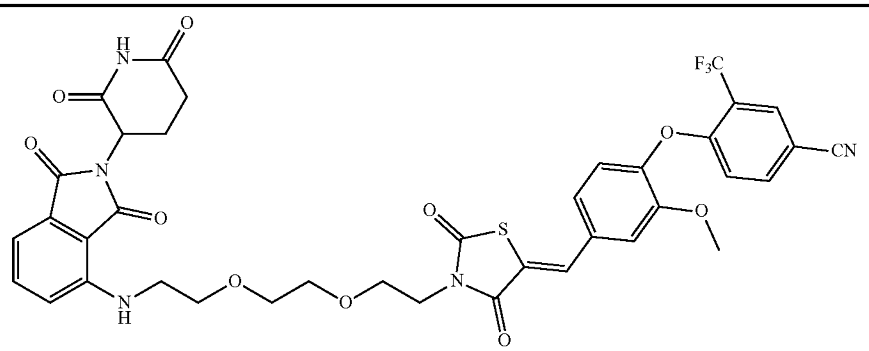 | C | 808.19 | 4-(4-(((5Z)-3-(2-(2-(2-((2-(2,6-dioxopiperidin-3-yl)-1,3-dioxo-23-dihydro-1H-isoindol-4-yl)amino)ethoxy)ethoxy)ethyl)-2,4-dioxo-1,3-thiazolidin-5-ylidene)methyl)-2-methoxyphenoxy)-3-(trifluoromethyl)benzonitrile |
| 23 | 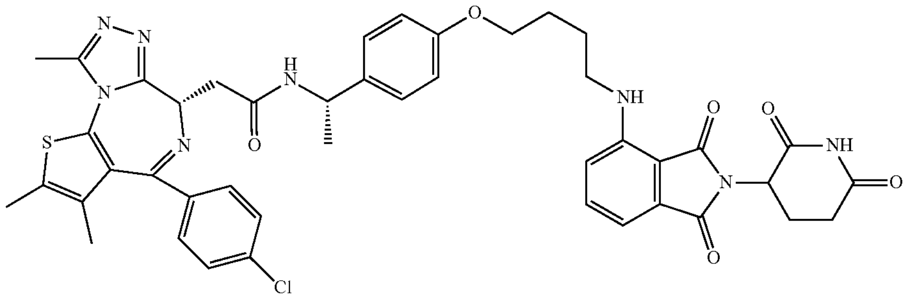 [SMILES: Cc1sc2c(c1C)C(c1ccc(Cl)cc1)=N[C@@H](CC(=O)N[C@@H](C)c1ccc(OCCCCNc3cccc4c3C(=O)N(C3CCC(=O)NC3=O)C4=O)cc1)c1nnc(C)n1-2] | E | 847.21 & 849.21 | 2-((9S)-7-(4-chlorophenyl)-4,5,13-trimethyl-3-thia-1,8,11,12-tetraazatricyclo[8.3.0.02,6]trideca-2(6),4,7,10,12-pentaen-9-yl)-N-((1S)-1-(4-(4-((2-(2,6-dioxopiperidin-3-yl)-1,3-dioxo-2,3-dihydro-1H-isoindol-4-yl)amino)butoxy)phenyl)ethyl)acetamide |
| 24 | 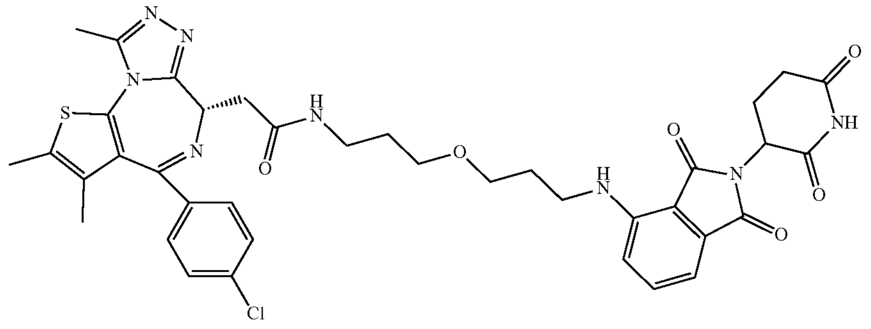 [SMILES: Cc1sc2c(c1C)C(c1ccc(Cl)cc1)=N[C@@H](CC(=O)NCCCOCCCNc1cccc3c1C(=O)N(C1CCC(=O)NC1=O)C3=O)c1nnc(C)n1-2] | D | 771.16 & 773.16 | 2-((9S)-7-(4-chlorophenyl)-4,5,13-trimethyl-3-thia-1,8,11,12-tetraazatricyclo[8.3.0.02,6]trideca-2(6),4,7,10,12-pentaen-9-yl)-N-(3-(3-((2-(2,6-dioxopiperidin-3-yl)-1,3-dioxo-2,3-dihydro-1H-isoindol-4-yl)amino)propoxy)propyl)acetamide |

TABLE 1-continued

| | | | | |
|---|---|---|---|---|
| 25 | 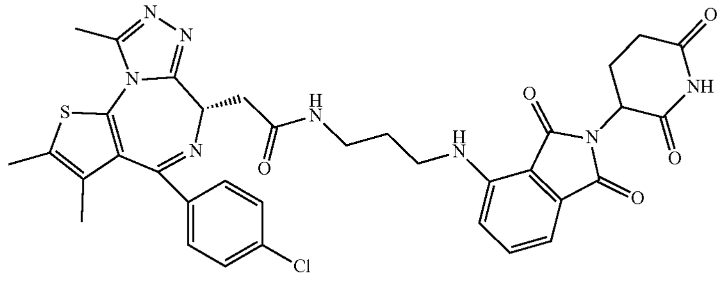 [SMILES: Cc1sc2c(c1C)C(c1ccc(Cl)cc1)=N[C@@H](CC(=O)NCCCNc1cccc3c1C(=O)N(C1CCC(=O)NC1=O)C3=O)c1nnc(C)n1-2] | E | 713.14 & 715.14 | 2-((9S)-7-(4-chlorophenyl)-4,5,13-trimethyl-3-thia-1,8,11,12-tetraazatricyclo[8.3.0.02,6]trideca-2(6),4,7,10,12-pentaen-9-yl)-N-(3-((2-(2,6-dioxopiperidin-3-yl)-1,3-dioxo-2,3-dihydro-1H-isoindol-4-yl)amino)propyl)acetamide |
| 26 | 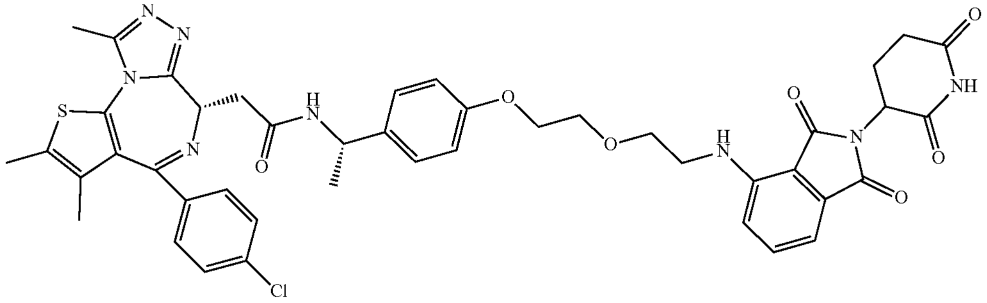 [SMILES: Cc1sc2c(c1C)C(c1ccc(Cl)cc1)=N[C@@H](CC(=O)N[C@@H](C)c1ccc(OCCOCCNc3cccc4c3C(=O)N(C3CCC(=O)NC3=O)C4=O)cc1)c1nnc(C)n1-2] | D | 863.26 & 865.26 | 2-((9S)-7-(4-chlorophenyl)-4,5,13-trimethyl-3-thia-1,8,11,12-tetraazatricyclo[8.3.0.02,6]trideca-2(6),4,7,10,12-pentaen-9-yl)-N-((1S)-1-(4-(2-(2-((2-(2,6-dioxopiperidin-3-yl)-1,3-dioxo-2,3-dihydro-1H-isoindol-4-yl)amino)ethoxy)ethoxy)phenyl)ethyl)acetamide |
| 27 | 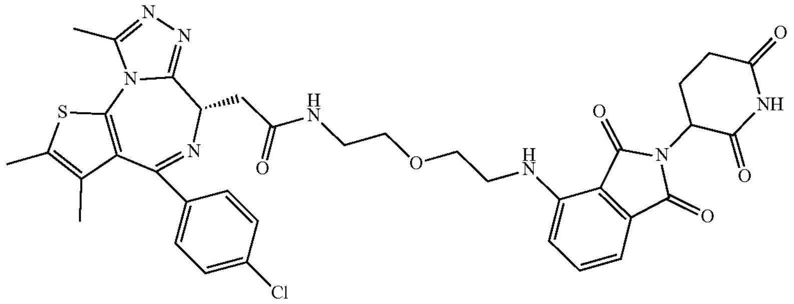 [SMILES: Cc1sc2c(c1C)C(c1ccc(Cl)cc1)=N[C@@H](CC(=O)NCCOCCNc1cccc3c1C(=O)N(C1CCC(=O)NC1=O)C3=O)c1nnc(C)n1-2] | D | 743.20 & 745.20 | 2-((9S)-7-(4-chlorophenyl)-4,5,13-trimethyl-3-thia-1,8,11,12-tetraazatricyclo[8.3.0.02,6]trideca-2(6),4,7,10,12-pentaen-9-yl)-N-(2-(2-((2-(2,6-dioxopiperidin-3-yl)-1,3-dioxo-2,3-dihydro-1H-isoindol-4-yl)amino)ethoxy)ethyl)acetamide |

TABLE 1-continued
| | | | | |
|---|---|---|---|---|
| 28 | 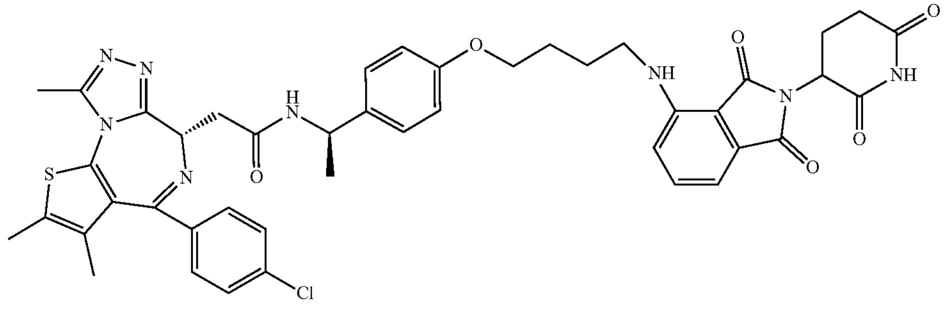 [SMILES: Cc1sc2c(c1C)C(c1ccc(Cl)cc1)=N[C@@H](CC(=O)N[C@H](C)c1ccc(OCCCCNc3cccc4c3C(=O)N(C3CCC(=O)NC3=O)C4=O)cc1)c1nnc(C)n1-2] | D | 847.42 & 849.42 | 2-((9S)-7-(4-chlorophenyl)-4,5,13-trimethyl-3-thia-1,8,11,12-tetraazacyclo[8.3.0.02,6]trideca-2(6),4,7,10,12-pentaen-9-yl)-N-((1R)-1-(4-(4-(2-(2,6-dioxopiperidin-3-yl)-1,3-dioxo-2,3-dihydro-1H-isoindol-4-yl)amino)butoxy)phenyl)ethyl)acetamide |
| 29 | 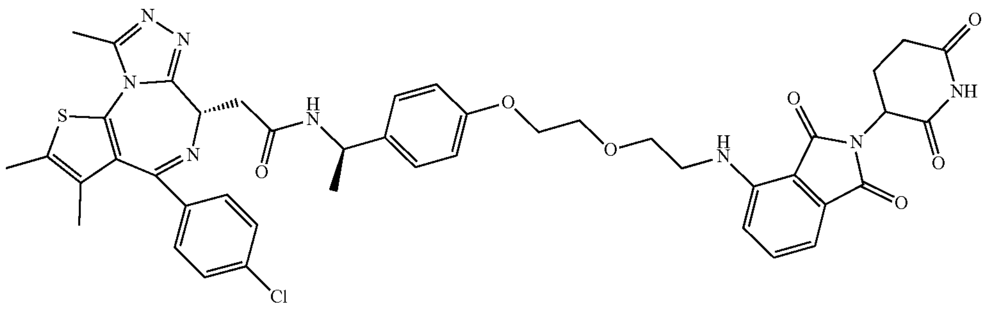 [SMILES: Cc1sc2c(c1C)C(c1ccc(Cl)cc1)=N[C@@H](CC(=O)N[C@H](C)c1ccc(OCCOCCNc3cccc4c3C(=O)N(C3CCC(=O)NC3=O)C4=O)cc1)c1nnc(C)n1-2] | D | 863.18 & 865.18 | 2-((9S)-7-(4-chlorophenyl)-4,5,13-trimethyl-3-thia-1,8,11,12-tetraazatricyclo[8.3.0.02,6]trideca-2(6),4,7,10,12-pentaen-9-yl)N-((1R)-1-(4-(2-(2-((2-(2,6-dioxopiperidin-3-yl)-1,3-dioxo-2,3-dihydro-1H-isoindol-4-yl)amino)ethoxy)ethoxy)phenyl)ethyl)acetamide |

TABLE 1-continued
| | | | | |
|---|---|---|---|---|
| 30 | 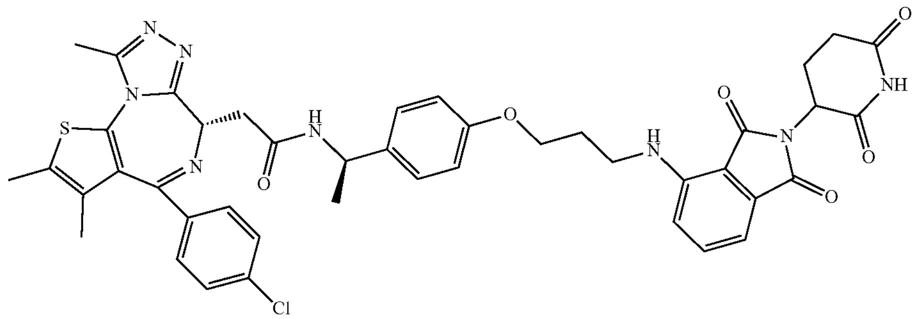 [SMILES: Cc1sc2c(c1C)C(c1ccc(Cl)cc1)=N[C@@H](CC(=O)N[C@H](C)c1ccc(OCCCNc3cccc4c3C(=O)N(C3CCC(=O)NC3=O)C4=O)cc1)c1nnc(C)n1-2] | D | 833.31 & 835.31 | 2-((9S)-7-(4-chlorophenyl)-4,5,13-trimethyl-3-thia-1,8,11,12-tetraazatricyclo[8.3.0.02,6]trideca-2(6),4,7,10,12-pentaen-9-yl)-N-((1R)-1-(4-(3-((2-(2,6-dioxopiperidin-3-yl)-1,3-dioxo-2,3-dihydro-1H-isoindol-4-yl)amino)propoxy)phenyl)ethyl)acetamide |
| 31 | 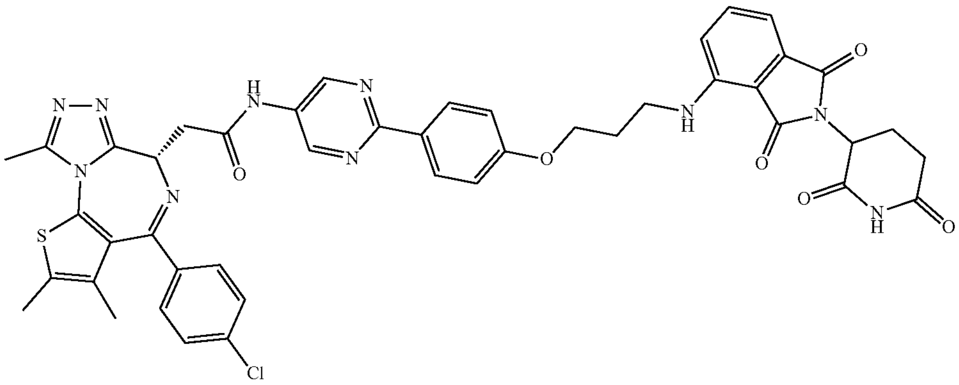 [SMILES: Cc1sc2c(c1C)C(c1ccc(Cl)cc1)=N[C@@H](CC(=O)Nc1cnc(-c3ccc(OCCCNc4cccc5c4C(=O)N(C4CCC(=O)NC4=O)C5=O)cc3)nc1)c1nnc(C)n1-2] | D | 883.24 & 885.24 | 2-((9S)-7-(4-chlorophenyl)-4,5,13-trimethyl-3-thia-1,8,11,12-tetraazatricyclo[8.3.0.02,6]trideca-2(6),4,7,10,12-pentaen-9-yl)-N-(2-(4-(3-((2-(2,6-dioxopiperidin-3-yl)-1,3-dioxo-2,3-dihydro-1H-isoindol-4-yl)amino)propoxy)phenyl)pyrimidin-5-yl)acetamide |

TABLE 1-continued

| | | | | |
|---|---|---|---|---|
| 32 | 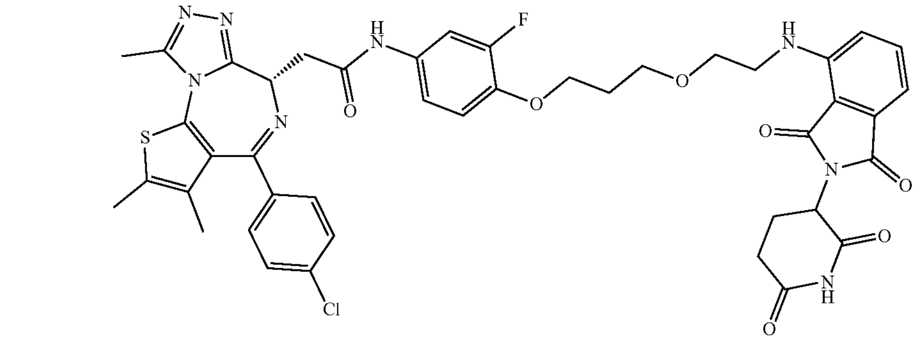 [SMILES: Cc1sc2c(c1C)C(c1ccc(Cl)cc1)=N[C@@H](CC(=O)Nc1ccc(OCCCOCCNc3cccc4c3C(=O)N(C3CCC(=O)NC3=O)C4=O)c(F)c1)c1nnc(C)n1-2] | D | 867.12 & 869.12 | 2-((9S)-7-(4-chlorophenyl)-4,5,13-trimethyl-3-thia-1,8,11,12-tetraazatricyclo [8.3.0.02,6]trideca-2(6),4,7,10,12-pentaen-9-yl)-N-(4-(3-(2-((2-(2,6-dioxopiperidin-3-yl)-1,3-dioxo-2,3-dihydro-1H-isoindol-4-yl)amino)ethoxy) propoxy)-3-fluorophenyl) acetamide |
| 33 | 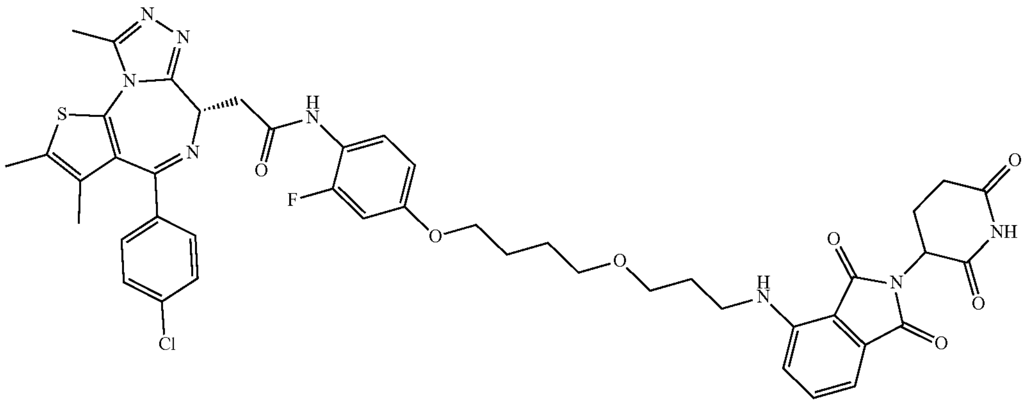 [SMILES: Cc1sc2c(c1C)C(c1ccc(Cl)cc1)=N[C@@H](CC(=O)Nc1ccc(OCCCCOCCCNc3cccc4c3C(=O)N(C3CCC(=O)NC3=O)C4=O)cc1F)c1nnc(C)n1-2] | D | 895.15 & 897.15 | 2-((9S)-7-(4-chlorophenyl)-4,5,13-trimethyl-3-thia-1,8,11,12-tetraazatricyclo [8.3.0.02,6]trideca-2(6),4,7,10,12-pentaen-9-yl)-n-(4-(4-(3-((2-(2,6-dioxopiperidin-3-yl)-1,3-dioxo-2,3-dihydro-1h-isoindol-4-yl) amino)propoxy) butoxy)-2-fluorophenyl) acetamide |
| 34 | 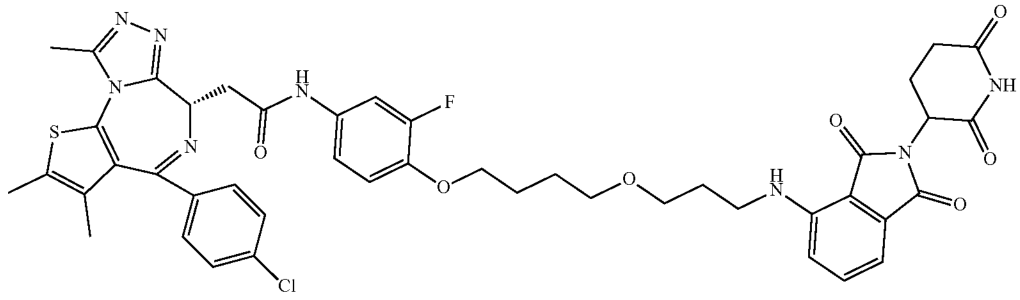 [SMILES: Cc1sc2c(c1C)C(c1ccc(Cl)cc1)=N[C@@H](CC(=O)Nc1ccc(OCCCCOCCCNc3cccc4c3C(=O)N(C3CCC(=O)NC3=O)C4=O)c(F)c1)c1nnc(C)n1-2] | D | 895.15 & 897.15 | 2-((9S)-7-(4-chlorophenyl)-4,5,13-trimethyl-3-thia-1,8,11,12-tetraazatricyclo [8.3.0.02,6]trideca-2(6),4,7,10,12-pentaen-9-yl)-N-(4-(4-(3-((2-(2,6-dioxopiperidin-3-yl)-1,3-dioxo-2,3-dihydro-1H-isoindol-4-yl) amino)propoxy) |

TABLE 1-continued

| # | Structure | cMyc $IC_{50}$ | $MH^+$ | chemical name |
|---|---|---|---|---|
| | | | | butoxy)-3-fluorphenyl)acetamide |
| 35 | 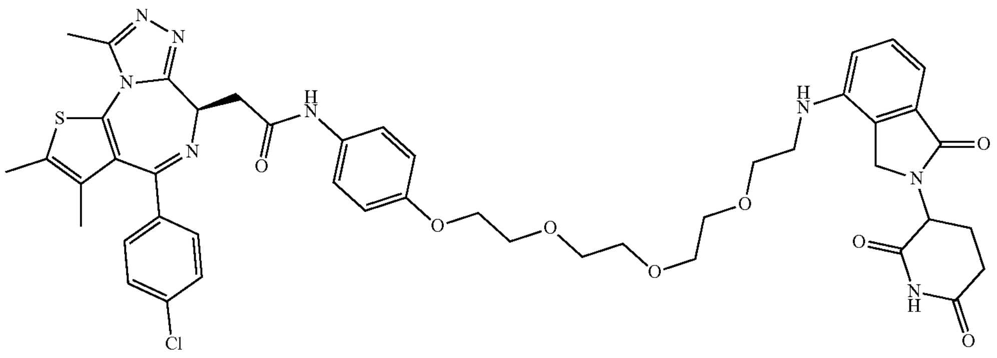 [SMILES: Cc1sc2c(c1C)C(c1ccc(Cl)cc1)=N[C@H](CC(=O)Nc1ccc(OCCOCCOCCOCCNc3cccc4c3CN(C3CCC(=O)NC3=O)C4=O)cc1)c1nnc(C)n1-2] | D | 910.21 & 912.21 | 2-((9R)-7-(4-chlorophenyl)-4,5,13-trimethyl-3-thia-1,8,11,12-tetraazatricyclo[8.3.0.02,6]trideca-2(6),4,7,10,12-pentaen-9-yl)-N-(4-((1-(2-(2,6-dioxopiperidin-3-yl)-1-oxo-2,3-dihydro-1H-isoindol-4-yl)-4,7,10-trioxa-1-azadodecan-12-yl)oxy)phenyl)acetamide |
| 36 | 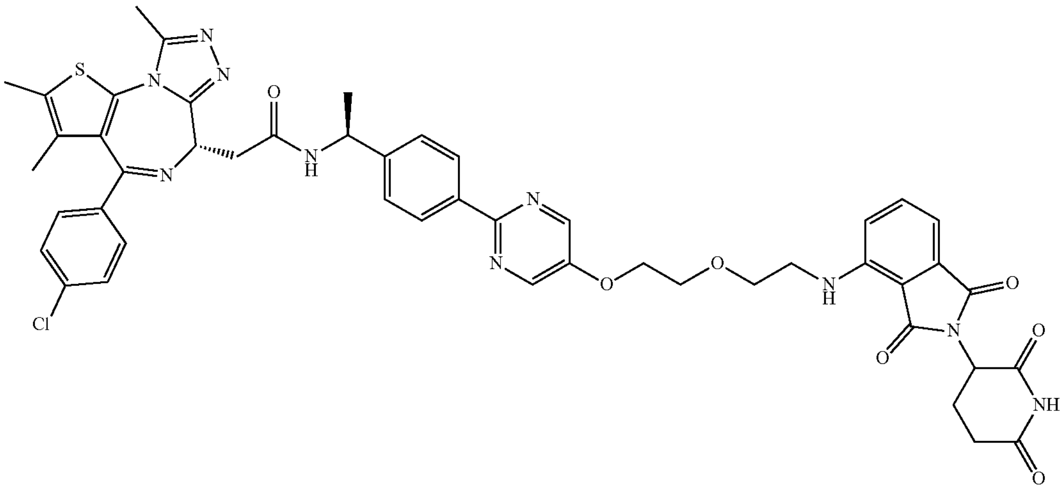 [SMILES: Cc1sc2c(c1C)C(c1ccc(Cl)cc1)=N[C@@H](CC(=O)N[C@@H](C)c1ccc(-c3ncc(OCCOCCNc4cccc5c4C(=O)N(C4CCC(=O)NC4=O)C5=O)cn3)cc1)c1nnc(C)n1-2] | D | 941.19 & 943.19 | 2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]-N-[(1S)-1-(4-{5-[2-(2-{[2-(2,6-dioxopiperidin-3-yl)-1,3-dioxo-2,3-dihydro-1H-isoindol-4-yl]amino}ethoxy)ethoxy]pyrimidin-2-yl}phenyl)ethyl]acetamide |

TABLE 1-continued
| | | | | |
|---|---|---|---|---|
| 37 | 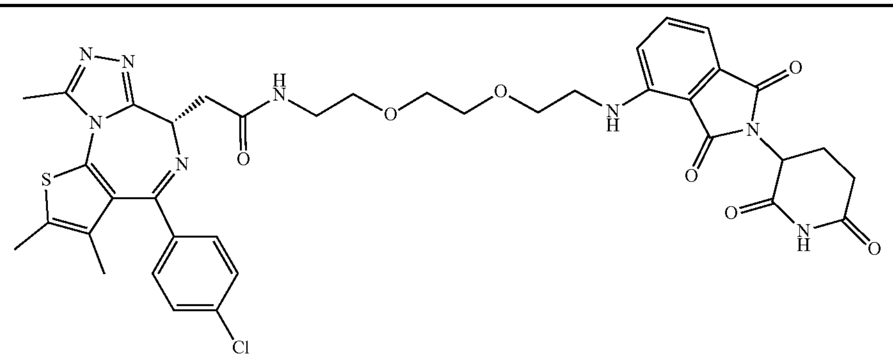 | D | 787.15 & 789.15 | 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-{2-[2-(2-{[2-(2,6-dioxopiperidin-3-yl)-1,3-dioxo-2,3-dihydro-1H-isoindol-4-yl]amino}ethoxy)ethoxy]ethyl}acetamide |
| 38 | 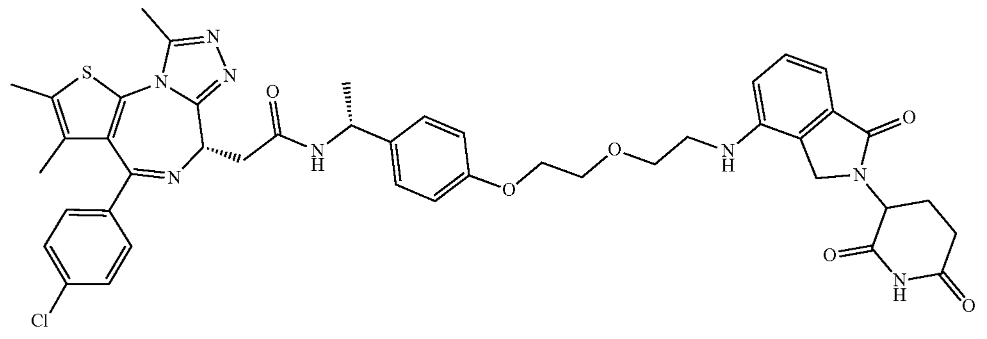 [SMILES: Cc1sc2c(c1C)C(c1ccc(Cl)cc1)=N[C@@H](CC(=O)N[C@H](C)c1ccc(OCCOCCNc3cccc4c3CN(C3CCC(=O)NC3=O)C4=O)cc1)c1nnc(C)n1-2] | D | 849.20 & 851.20 | 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-[(1R)-1-{4-[2-(2-{[2-(2,6-dioxopiperidin-3-yl)-1-oxo-2,3-dihydro-1H-isoindol-4-yl]amino}ethoxy)ethoxyphenyl}ethyl]acetamide |

TABLE 1-continued
| | | | | |
|---|---|---|---|---|
| 39 | 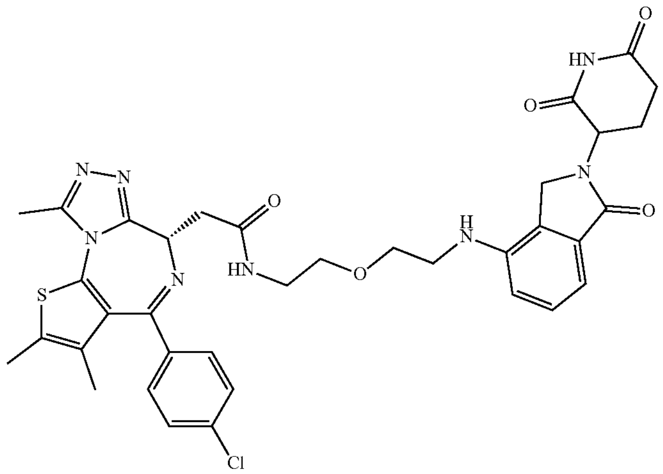 [SMILES: Cc1sc2c(c1C)C(c1ccc(Cl)cc1)=N[C@@H](CC(=O)NCCOCCNc1cccc3c1CN(C1CCC(=O)NC1=O)C3=O)c1nnc(C)n1-2] | E | 730.15 & 732.15 | 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-[2-(2-{[2-(2,6-dioxopiperidin-3-yl)-1-oxo-2,3-dihydro-1H-isoindol-4-yl]amino}ethoxy)ethyl]acetamide |
| 40 | 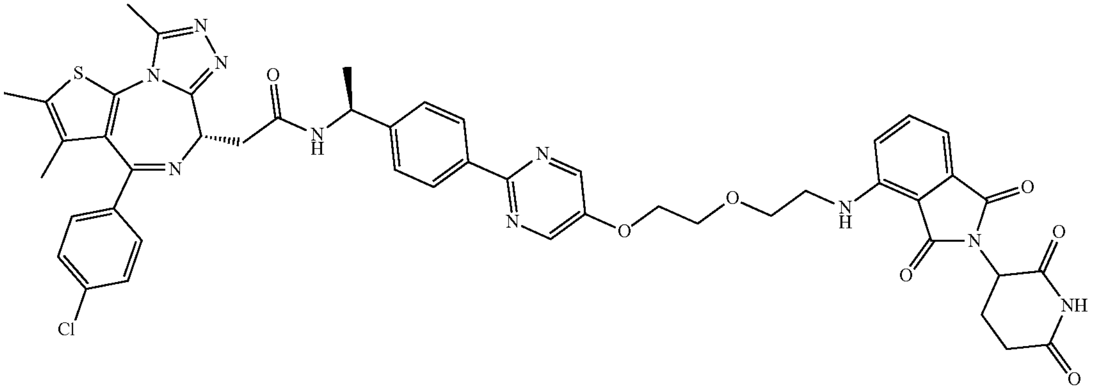 [SMILES: Cc1sc2c(c1C)C(c1ccc(Cl)cc1)=N[C@@H](CC(=O)N[C@@H](C)c1ccc(-c3ncc(OCCOCCNc4cccc5c4C(=O)N(C4CCC(=O)NC4=O)C5=O)cn3)cc1)c1nnc(C)n1-2] | D | 911.18 & 913.18 | 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-[(1S)-1-{4-[5-(3-{[2-(2,6-dioxopiperidin-3-yl)-1,3-dioxo-2,3-dihydro-1H-isoindol-4-yl]amino}propoxy)pyrimidin-2-yl]phenyl}ethyl]acetamide |

TABLE 1-continued

| | | | | |
|---|---|---|---|---|
| 41 | 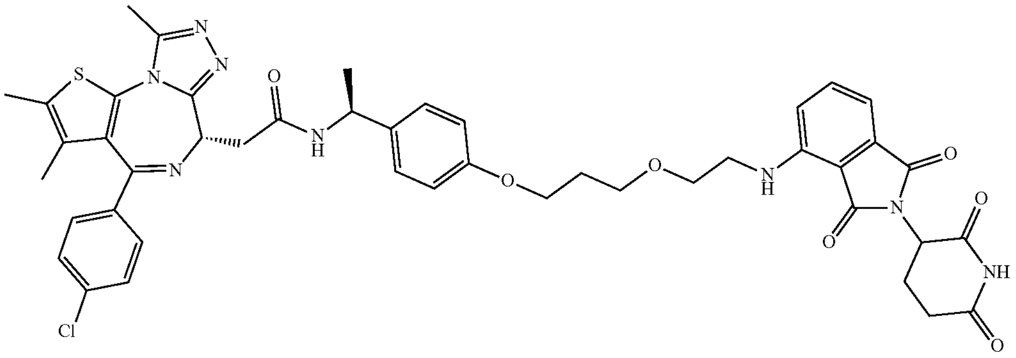 [SMILES: Cc1sc2c(c1C)C(c1ccc(Cl)cc1)=N[C@@H](CC(=O)N[C@@H](C)c1ccc(OCCCOCCNc3cccc4c3C(=O)N(C3CCC(=O)NC3=O)C4=O)cc1)c1nnc(C)n1-2] | D | 877.19 & 879.19 | 2-[9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-[(1S)-1-{4-[3-(2-{[2-(2,6-dioxopiperidin-3-yl)-1,3-dioxo-2,3-dihydro-1H-isoindol-4-yl]amino}ethoxy)propoxyphenyl}ethyl]acetamide |
| 42 | 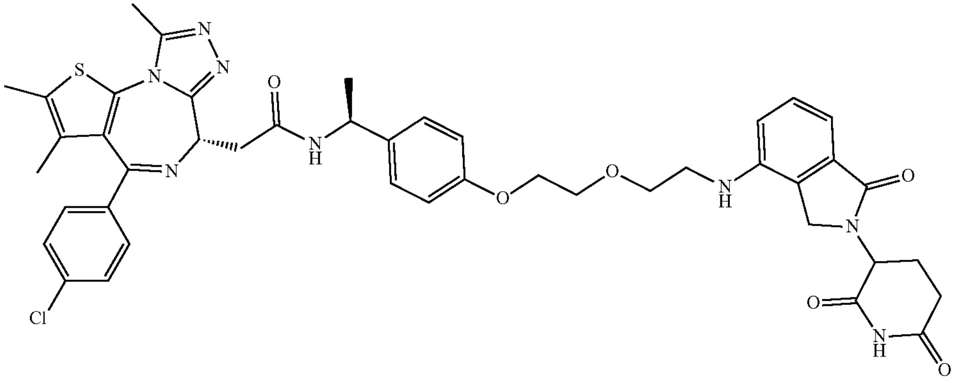 [SMILES: Cc1sc2c(c1C)C(c1ccc(Cl)cc1)=N[C@@H](CC(=O)N[C@@H](C)c1ccc(OCCOCCNc3cccc4c3CN(C3CCC(=O)NC3=O)C4=O)cc1)c1nnc(C)n1-2] | D | 849.19 & 851.19 | 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-[(1S)-1-{4-[2-(2-{[2-(2,6-dioxopiperidin-3-yl)-1-oxo-2,3-dihydro-1H-isoindol-4-yl]amino}ethoxy)ethoxyphenyl}ethyl]acetamide |
| 43 | 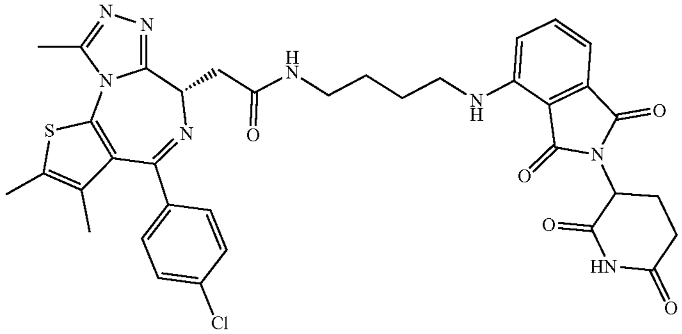 [SMILES: Cc1sc2c(c1C)C(c1ccc(Cl)cc1)=N[C@@H](CC(=O)NCCCCNc1cccc3c1C(=O)N(C1CCC(=O)NC1=O)C3=O)c1nnc(C)n1-2] | E | 727.13 & 729.13 | 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-(4-{[2-(2,6-dioxopiperidin-3-yl)-1,3-dioxo-2,3-dihydro-1H-isoindol-4-yl]amino}butyl)acetamide |

TABLE 1-continued
| | | | | |
|---|---|---|---|---|
| 44 | 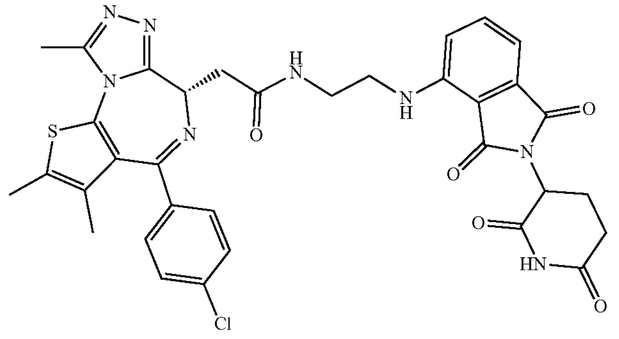 [SMILES: Cc1sc2c(c1C)C(c1ccc(Cl)cc1)=N[C@@H](CC(=O)NCCNc1cccc3c1C(=O)N(C1CCC(=O)NC1=O)C3=O)c1nnc(C)n1-2] | E | 699.10 & 701.10 | 2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]-N-(2-{[2-(2,6-dioxopiperidin-3-yl)-1,3-dioxo-2,3-dihydro-1H-isoindol-4-yl]amino}ethyl)acetamide |
| 45 | 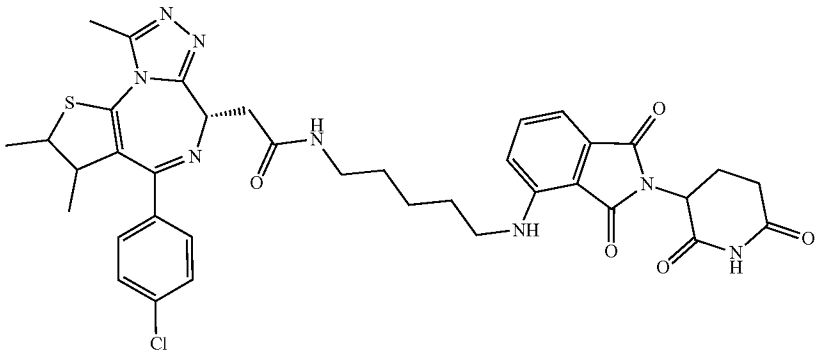 [SMILES: Cc1nnc2n1C1=C(C(c3ccc(Cl)cc3)=N[C@H]2CC(=O)NCCCCCNc2cccc3c2C(=O)N(C2CCC(=O)NC2=O)C3=O)C(C)C(C)S1] | D | 741.14 & 743.14 | 2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]-N-(5-{[2-(2,6-dioxopiperidin-3-yl)-1,3-dioxo-2,3-dihydro-1H-isoindol-4-yl]amino}pentyl)acetamide |

TABLE 1-continued

| | | | | |
|---|---|---|---|---|
| 46 | 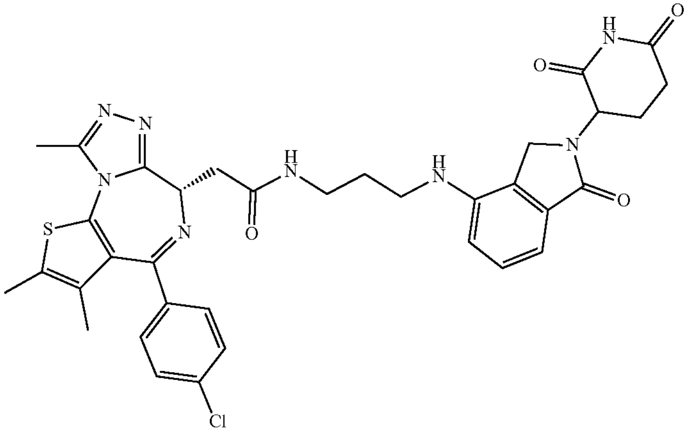 [SMILES: Cc1sc2c(c1C)C(c1ccc(Cl)cc1)=N[C@@H](CC(=O)NCCCNc1cccc3c1CN(C1CCC(=O)NC1=O)C3=O)c1nnc(C)n1-2] | E | 699.13 & 701.13 | 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-(3-{[2-(2,6-dioxopiperidin-3-yl)-1-oxo-2,3-dihydro-1H-isoindol-4-yl]amino}propyl)acetamide |
| 47 | 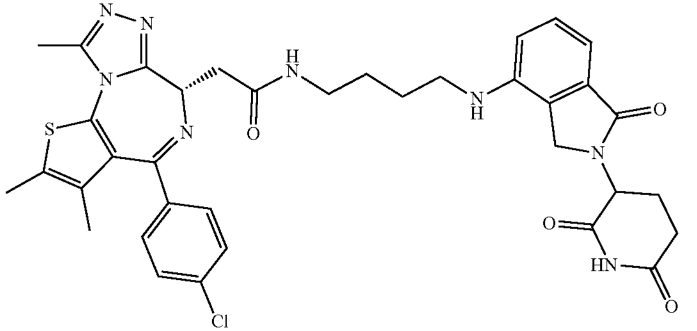 [SMILES: Cc1sc2c(c1C)C(c1ccc(Cl)cc1)=N[C@@H](CC(=O)NCCCCNc1cccc3c1CN(C1CCC(=O)NC1=O)C3=O)c1nnc(C)n1-2] | E | 713.15 & 715.15 | 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-(4-{[2-(2,6-dioxopiperidin-3-yl)-1-oxo-2,3-dihydro-1H-isoindol-4-yl]amino}butyl)acetamide |
| 48 | 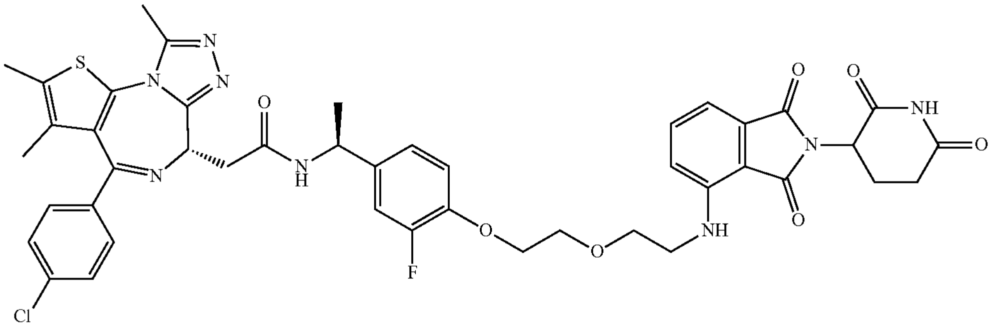 [SMILES: Cc1sc2c(c1C)C(c1ccc(Cl)cc1)=N[C@@H](CC(=O)N[C@@H](C)c1ccc(OCCOCCNc3cccc4c3C(=O)N(C3CCC(=O)NC3=O)C4=O)c(F)c1)c1nnc(C)n1-2] | D | 881.15 & 883.15 | 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-[(1S)-1-{4-[2-(2-{[2-(2,6-dioxopiperidin-3-yl)-1,3-dioxo-2,3-dihydro-1H-isoindol-4-yl]amino}ethoxy)

TABLE 1-continued

| | | | | |
|---|---|---|---|---|
| | | | | ethoxy]-3-fluorophenyl}ethyl]acetamide |
| 49 | 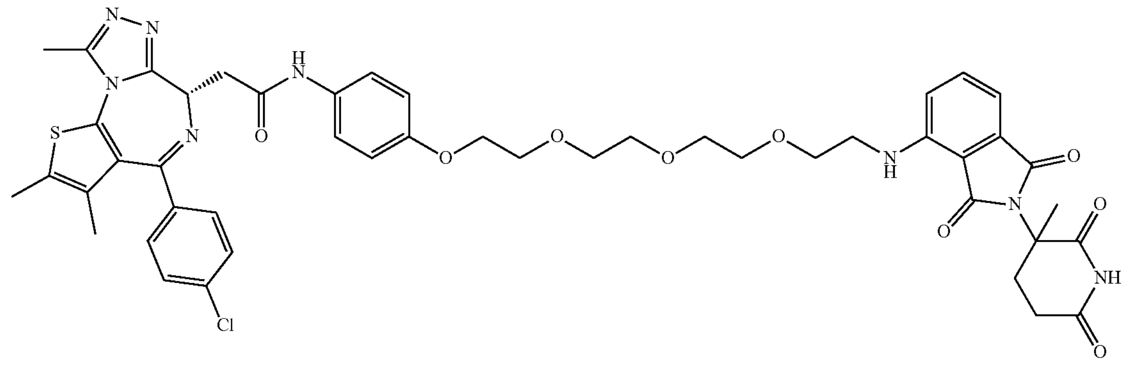 [SMILES: Cc1sc2c(c1C)C(c1ccc(Cl)cc1)=N[C@@H](CC(=O)Nc1ccc(OCCOCCOCCOCCNc3cccc4c3C(=O)N(C3(C)CCC(=O)NC3=O)C4=O)cc1)c1nnc(C)n1-2] | E | 937.20 & 939.20 | 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-[4-({1-[2-(3-methyl-2,6-dioxopiperidin-3-yl)-1,3-dioxo-2,3-dihydro-1H-isoindol-4-yl]-4,7,10-trioxa-1-azadodecan-12-yl}oxy)phenyl]acetamide |
| 50 | 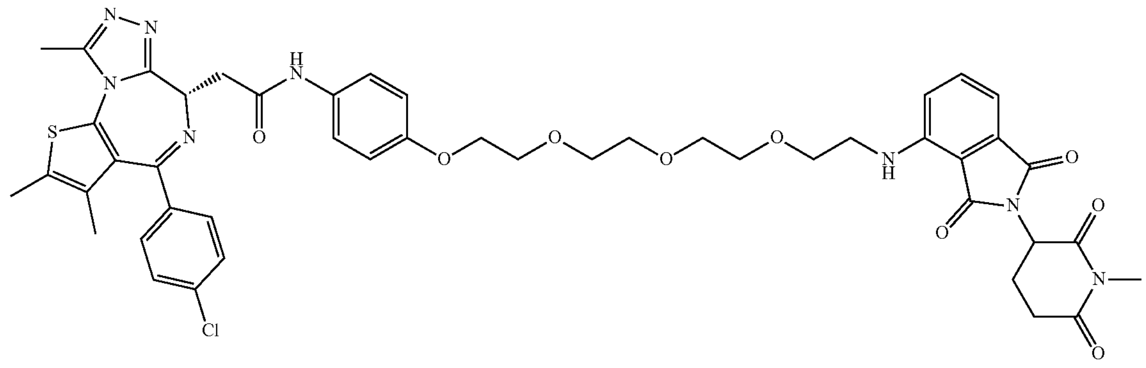 | E | 937.20 & 939.20 | 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-[4-({1-[2-(1-methyl-2,6-dioxopiperidin-3-yl)-1,3-dioxo-2,3-dihydro-1H-isoindol-4-yl]-4,7,10-trioxa-1-azadodecan-12-yl}oxy)phenyl]acetamide |

TABLE 1-continued

| | | | | |
|---|---|---|---|---|
| 51 | 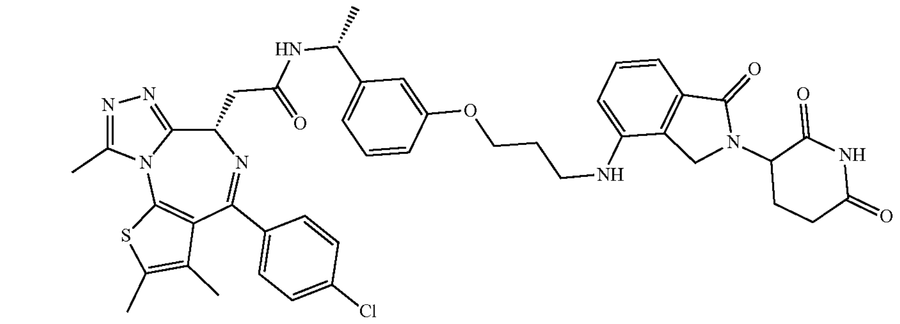 [SMILES: Cc1sc2c(c1C)C(c1ccc(Cl)cc1)=N[C@@H](CC(=O)N[C@H](C)c1cccc(OCCCNc3cccc4c3CN(C3CCC(=O)NC3=O)C4=O)c1)c1nnc(C)n1-2] | E | 819.18 & 821.18 | 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-[(1R)-1-[3-(3-{[2-(2,6-dioxopiperidin-3-yl)-1-oxo-2,3-dihydro-1H-isoindol-4-yl]amino}propoxy)phenyl]ethyl]acetamide |
| 52 | 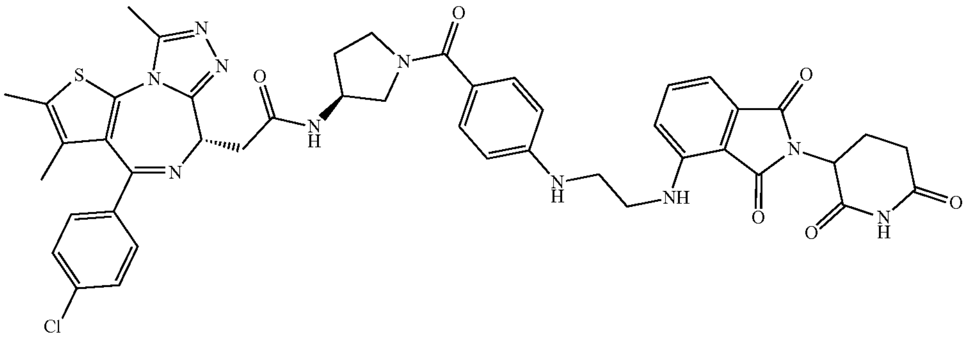 [SMILES: Cc1sc2c(c1C)C(c1ccc(Cl)cc1)=N[C@@H](CC(=O)N[C@H]1CCN(C(=O)c3ccc(NCCNc4cccc5c4C(=O)N(C4CCC(=O)NC4=O)C5=O)cc3)C1)c1nnc(C)n1-2] | E | 887.17 & 889.17 | 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-[(3S)-1-{4-[(2-{[2-(2,6-dioxopiperidin-3-yl)-1,3-dioxo-2,3-dihydro-1H-isoindol-4-yl]amino}ethyl)amino]benzoyl}pyrrolidin-3-yl]acetamide |
| 53 | 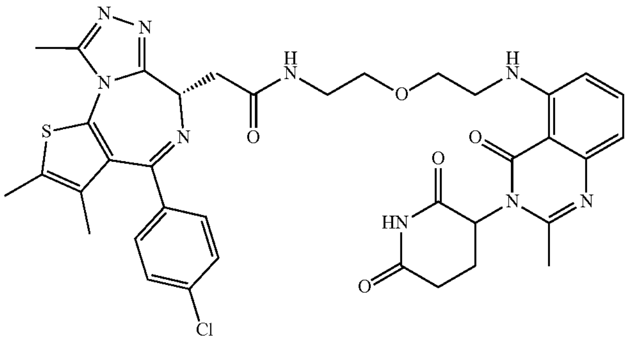 [SMILES: Cc1sc2c(c1C)C(c1ccc(Cl)cc1)=N[C@@H](CC(=O)NCCOCCNc1cccc3nc(C)n(C4CCC(=O)NC4=O)c(=O)c13)c1nnc(C)n1-2] | E | 756.15 & 758.15 | 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-[2-(2-{[3-(2,6-dioxopiperidin-3-yl)-2-methyl-4-oxo-3,4-dihydroquinazolin-5-yl]amino}ethoxy)ethyl]acetamide |

TABLE 1-continued

| | | | | |
|---|---|---|---|---|
| 54 | 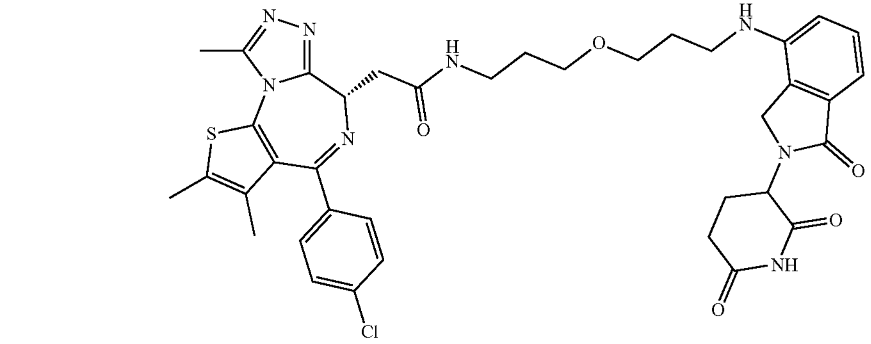 [SMILES: Cc1sc2c(c1C)C(c1ccc(Cl)cc1)=N[C@@H](CC(=O)NCCCOCCCNc1cccc3c1CN(C1CCC(=O)NC1=O)C3=O)c1nnc(C)n1-2] | D | 757.17 & 759.17 | 2-[(9S)-7-(4-chlorophenyl)-4,5,13-trimethyl-3-thia-1,8,11,12-tetraazatricyclo [8.3.0.0$^{2}$,$^{6}$]trideca-2(6),4,7,10,12-pentaen-9-yl]-N-[3-(3-{[2-(2,6-dioxopiperidin-3-yl)-1-oxo-2,3-dihydro-1H-isoindol-4-yl] amino}propoxy) propyl]acetamide |
| 55 | 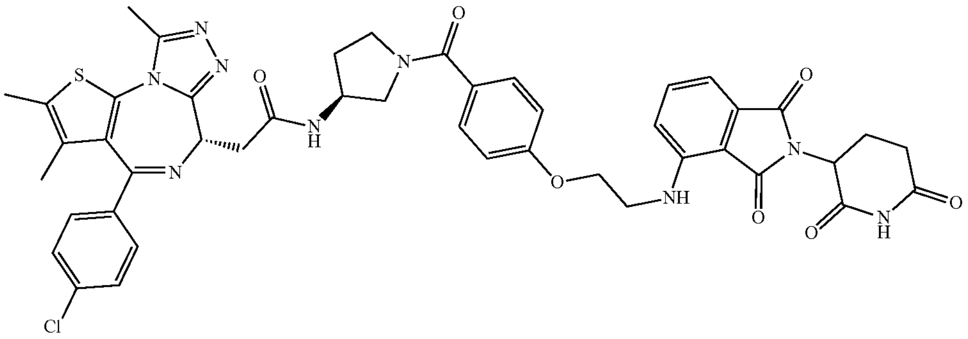 [SMILES: Cc1sc2c(c1C)C(c1ccc(Cl)cc1)=N[C@@H](CC(=O)N[C@H]1CCN(C(=O)c3ccc(OCCNc4cccc5c4C(=O)N(C4CCC(=O)NC4=O)C5=O)cc3)C1)c1nnc(C)n1-2] | D | 888.16 & 890.16 | 2-[(9S)-7-(4-chlorophenyl)-4,5,13-trimethyl-3-thia-1,8,11,12-tetraazatricyclo [8.3.0.0$^{2}$,$^{6}$]trideca-2(6),4,7,10,12-pentaen-9-yl]-N-[(3S)-1-[4-(2-{[2-(2,6-dioxopiperidin-3-yl)-1,3-dioxo-2,3-dihydro-1H-isoindol-4-yl]amino}ethoxy) benzoyl]pyrrolidin-3-yl]acetamide |
| 56 | 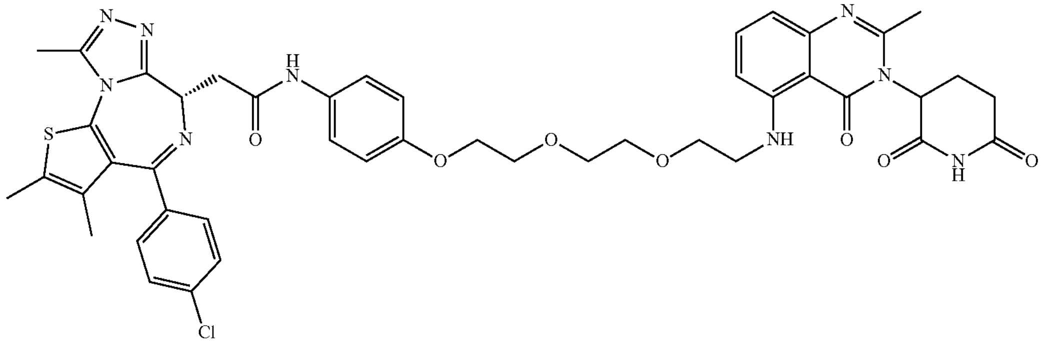 [SMILES: Cc1sc2c(c1C)C(c1ccc(Cl)cc1)=N[C@@H](CC(=O)Nc1ccc(OCCOCCOCCNc3cccc4nc(C)n(C5CCC(=O)NC5=O)c(=O)c34)cc1)c1nnc(C)n1-2] | D | 892.19 & 894.19 | 2-[(9S)-7-(4-chlorophenyl)-4,5,13-trimethyl-3-thia-1,8,11,12-tetraazatricyclo [8.3.0.0$^{2}$,$^{6}$]trideca-2(6),4,7,10,12-pentaen-9-yl]-N-(4-{2-[2-(2-{[3-(2,6-dioxopiperidin-3-yl)-2-methyl-4-oxo-3,4-dihydroquinazolin-5-yl]amino}ethoxy) ethoxy]ethoxy} phenyl)acetamide |

TABLE 1-continued

| | | | | |
|---|---|---|---|---|
| 57 | 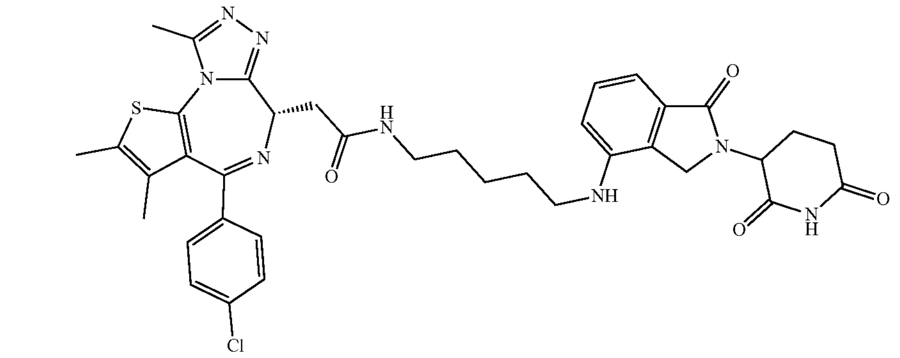 [SMILES: Cc1sc2c(c1C)C(c1ccc(Cl)cc1)=N[C@@H](CC(=O)NCCCCCNc1cccc3c1CN(C1CCC(=O)NC1=O)C3=O)c1nnc(C)n1-2] | D | 727.16 & 729.16 | 2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]-N-(5-{[2-(2,6-dioxopiperidin-3-yl)-1-oxo-2,3-dihydro-1H-isoindol-4-yl]amino}pentyl)acetamide |
| 58 | 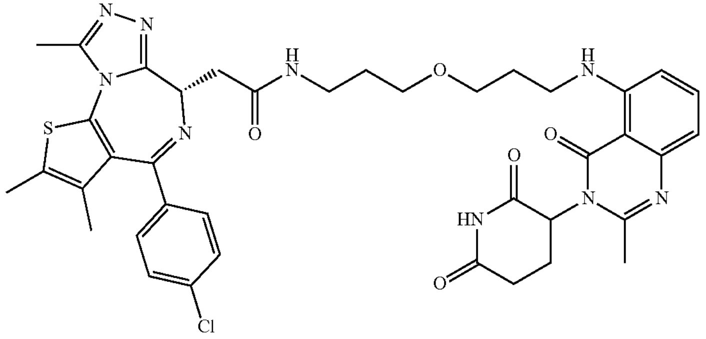 [SMILES: Cc1sc2c(c1C)C(c1ccc(Cl)cc1)=N[C@@H](CC(=O)NCCCOCCCNc1cccc3nc(C)n(C4CCC(=O)NC4=O)c(=O)c13)c1nnc(C)n1-2] | E | 784.18 & 786.18 | 2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]-N-[3-(3-{[3-(2,6-dioxopiperidin-3-yl)-2-methyl-4-oxo-3,4-dihydroquinazolin-5-yl]amino}propoxy)propyl]acetamide |
| 59 | 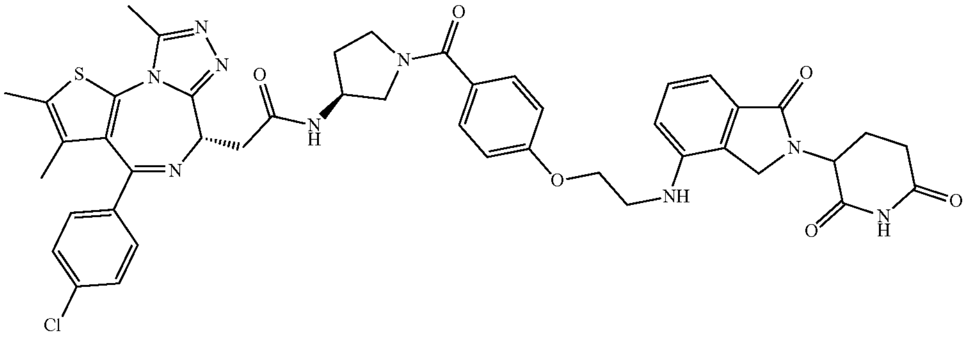 [SMILES: Cc1sc2c(c1C)C(c1ccc(Cl)cc1)=N[C@@H](CC(=O)N[C@H]1CCN(C(=O)c3ccc(OCCNc4cccc5c4CN(C4CCC(=O)NC4=O)C5=O)cc3)C1)c1nnc(C)n1-2] | E | 874.18 & 876.18 | 2-[(9S)-7-(4-chlorophenyl)-4,5,13-trimethyl-3-thia-1,8,11,12-tetraazatricyclo[8.3.0.$0^{2,6}$]trideca-2(6),4,7,10,12-pentaen-9-yl]-N-[(3S)-1-[4-(2-{[2-(2,6-dioxopiperidin-3-yl)-1-oxo-2,3-dihydro-1H-isoindol-4-yl]amino}ethoxy)benzoyl]pyrrolidin-3-yl]acetamide |

TABLE 1-continued

| | | | | |
|---|---|---|---|---|
| 60 | 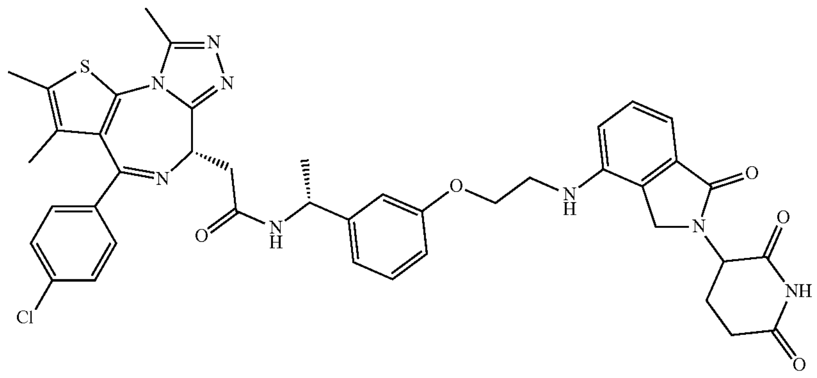 [SMILES: Cc1sc2c(c1C)C(c1ccc(Cl)cc1)=N[C@@H](CC(=O)N[C@H](C)c1cccc(OCCNc3cccc4c3CN(C3CCC(=O)NC3=O)C4=O)c1)c1nnc(C)n1-2] | E | 805.17 & 807.17 | 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-[(1R)-1-[3-(2-{[2-(2,6-dioxopiperidin-3-yl)-1-oxo-2,3-dihydro-1H-isoindol-4-yl]amino}ethoxy)phenyl]ethyl]acetamide |
| 61 | 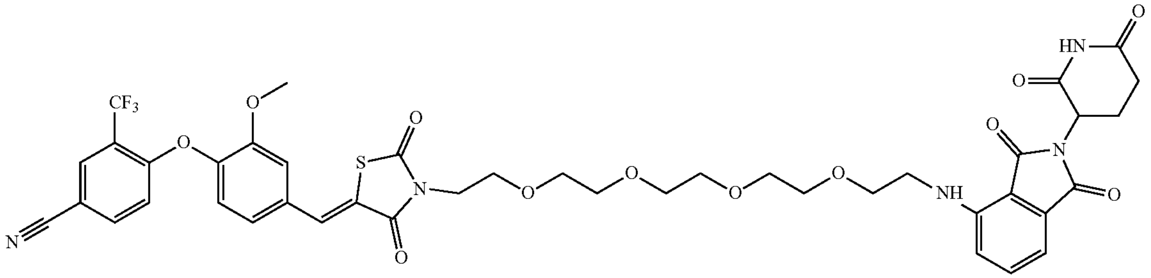 [SMILES: COc1cc(/C=C2\SC(=O)N(CCOCCOCCOCCOCCNc3cccc4c3C(=O)N(C3CCC(=O)NC3=O)C4=O)C2=O)ccc1Oc1ccc(C#N)cc1C(F)(F)F] | F | 918.2 (M + 23) | 4-(4-{[(5Z)-3-{1-[2-(2,6-dioxopiperidin-3-yl)-1,3-dioxo-2,3-dihydro-1H-isoindol-4-yl]-4,7,10,13-tetraoxa-1-azapentadecan-15-yl}-2,4-dioxo-1,3-thiazolidin-5-ylidene]methyl}-2-methoxyphenoxy)-3-(trifluoromethyl)benzonitrile |
| 62 | 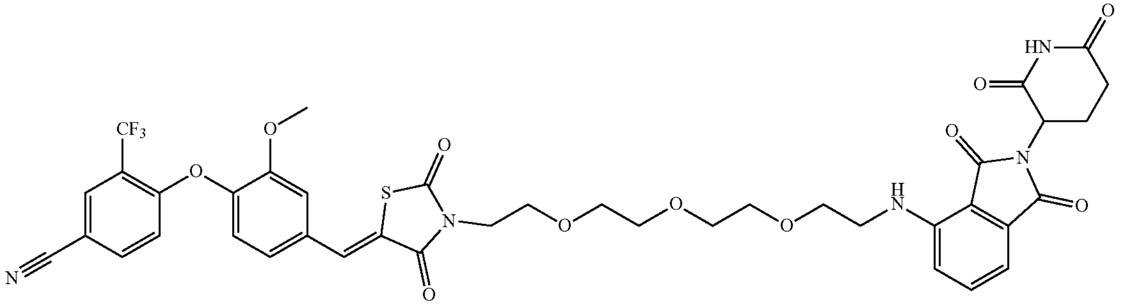 [SMILES: COc1cc(/C=C2\SC(=O)N(CCOCCOCCOCCNc3cccc4c3C(=O)N(C3CCC(=O)NC3=O)C4=O)C2=O)ccc1Oc1ccc(C#N)cc1C(F)(F)F] | F | 874.3 (M + 23) | 4-(4-{[(5Z)-3-{1-[2-(2,6-dioxopiperidin-3-yl)-1,3-dioxo-2,3-dihydro-1H-isoindol-4-yl]-4,7,10-trioxa-1-azadodecan-12-yl}-2,4-dioxo-1,3-thiazolidin-5-ylidene]methyl}-2-methoxyphenoxy)-3-(trifluoromethyl)benzonitrile |

TABLE 1-continued

| | | | | |
|---|---|---|---|---|
| 63 | 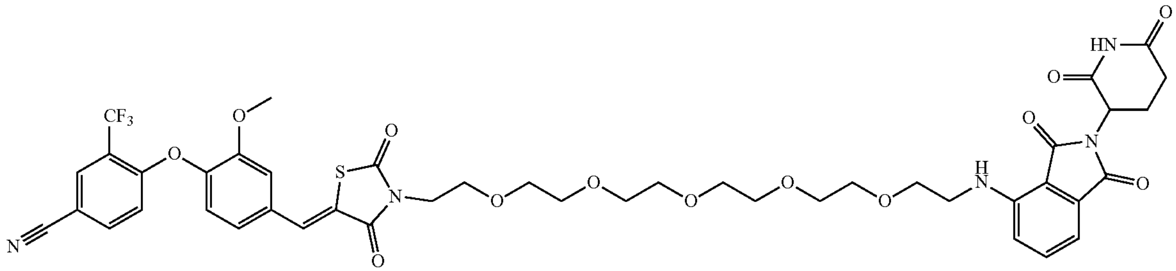 [SMILES: COc1cc(/C=C2\SC(=O)N(CCOCCOCCOCCOCCOCCNc3cccc4c3C(=O)N(C3CCC(=O)NC3=O)C4=O)C2=O)ccc1Oc1ccc(C#N)cc1C(F)(F)F] | F | 940.2 | 4-(4-{[(5Z)-3-{1-[2-(2,6-dioxopiperidin-3-yl)-1,3-dioxo-2,3-dihydro-1H-isoindol-4-yl]-4,7,10,13,16-pentaoxa-1-azaoctadecan-18-yl}-2,4-dioxo-1,3-thiazolidin-5-ylidene]methyl}-2-methoxyphenoxy)-3-(trifluoromethyl)benzonitrile |
| 64 | 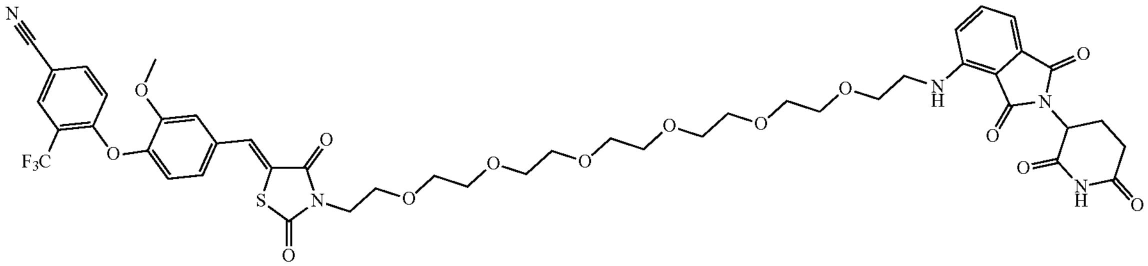 [SMILES: COc1cc(/C=C2\SC(=O)N(CCOCCOCCOCCOCCOCCOCCNc3cccc4c3C(=O)N(C3CCC(=O)NC3=O)C4=O)C2=O)ccc1Oc1ccc(C#N)cc1C(F)(F)F] | F | 984.3 | 4-(4-{[(5Z)-3-{1-[2-(2,6-dioxopiperidin-3-yl)-1,3-dioxo-2,3-dihydro-1H-isoindol-4-yl]-4,7,10,13,16,19-hexaoxa-1-azahenicosan-21-yl}-2,4-dioxo-1,3-thiazolidin-5-ylidenemethyl}-2-methoxyphenoxy)-3-(trifluoromethyl)benzonitrile |

For Table 1: A = 10-30% degradation at 1 uM, B = 31-50% degradation at 1 uM, C = >50% degradation at 1 uM, D = $IC_{50}$ <50 nM, E = $IC_{50}$ >50 nM, F = untested Cell used in bioassay: 1: VCaP cells, 2: Panc02.13 cells, 3: Namalwa cells, 4: 22RV-1 cells

Example 3: Exemplary ImiD Analogs

Thalidomide, Pomalidomide and Lenalidomide, collectively known as Immunomodulatory Drugs (IMiDs), have been employed to treat multiple myeloma for many years. For the majority of this time, the molecular mechanism of action was unknown rendering attempts to explore the structure activity relationships challenging. In recent years, the elucidation of the unique mechanism of action of these compounds has caused a resurgence of interest in IMiDs. These compounds function by inducing ectopic protein-protein interactions between the E3 ligase Cereblon and un-natural substrates (Ikaros, Aiolos and CK1α), resulting in ubiquitination and subsequent degradation of the neo-substrate. The fundamental understanding of the mechanism has enabled the discovery of analogues which induce degradation of additional proteins, namely the translation termination factor GSPT1. Recently, another family of molecules which function via a distinct but similar mechanism have also been reported. Molecules which bind to an E3 ubiquitin ligase are also of great interest to the field of targeted protein degradation, particularly as recruiting elements for proteolysis targeting chimera (PROTACs). Indeed ImiD drugs have been widely employed as E3 recruiting elements to enable the degradation of a wide variety of targets.

Intrigued by the "molecular glue" mechanism of these compounds, the structure degradation relationships of ImiD analogues was explored with an aim to elucidating the requirements for neo-substrate recruitment and the development of high affinity recruiting elements for use in proteolysis targeting chimera.

It was a challenge to develop a rapid and robust synthesis of IMiD analogues. The majority of routes employ the cyclisation of glutamine and condensation with an anhydride to yield the desired scaffold. Preparation of Boc-2-amino-glutarimide can be achieved by the treatment of Nα-(tert-butoxycarbonyl)-L-glutamine with CDI and catalytic DMAP in THE at reflux temperature as previously reported. Previous routes have employed step-wise deprotection and condensation reactions to yield the desired scaffold in moderate yields following purification. Alternatively, the condensation reaction can be performed before cyclisation of the glutarimide.

To expedite the process, a thermal BOC deprotection was combined with the condensation step. Since 2,2,2-trifluoroethanol (TFE) can afford t-butoxycarbamate (BOC) deprotection at high temperature, the one pot procedure shown in Scheme 1, entry 1, was attempted. The reaction proceeded to completion under these conditions and, upon cooling to room temperature, the product precipitated to provide analytically pure compound in high yield. Exploring the role of the reagent/solvent in this reaction exemplifies the advantage of employing TFE as a solvent in this reaction. Switching to ethanol results in a significantly reduced yield, as the deprotection step is considerably less efficient in the less acidic solvent. Addition of trifluoroacetic acid results in a complex mixture of unidentified products. Reflux of the reaction in TFE for 2 hours results in no deprotection of the BOC group and hence no subsequent condensation. Submersion of the reaction vessel in an oil bath at 150° C. rather than microwave irradiation results in a slightly reduced yield, which can likely be attributed to less efficient heating. The use of phthalic acid in place of the anhydride is tolerated due to in-situ formation of the anhydride.

Scheme 1: Synthesis of Thalidomide and screening of reaction conditions.

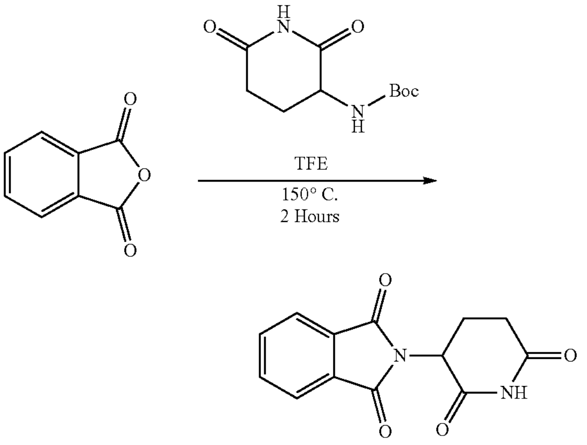

a: heated in an oil bath at 150° C. for 2 hours.
b: phthalic acid used in place of phthalic anhydride.

| | Solvent | Temperature/ ° C. | Isolated Yield |
|---|---|---|---|
| 1 | Trifluoroethanol | 150 | 91% |
| 2 | Ethanol | 150 | 24% |
| 3 | 10% TFA in Ethanol | 150 | Complex Mixture |
| 4 | Trifluoroethanol | Reflux | No reaction |
| 6 | Trifluoroethanol | 150 | 72%[a] |
| 7 | Trifluoroethanol | 150 | 62%[b] |

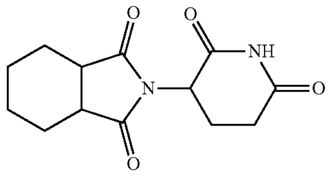
1

86%

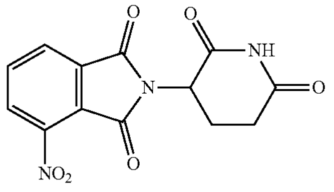
2

95%

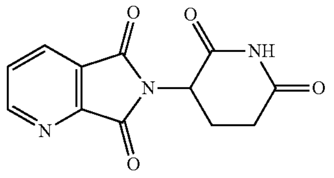
3

60%

-continued
4
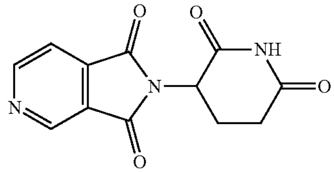
35%
5
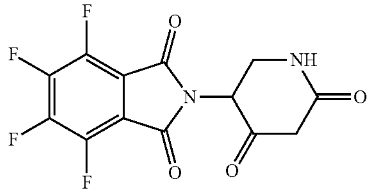
55%
6
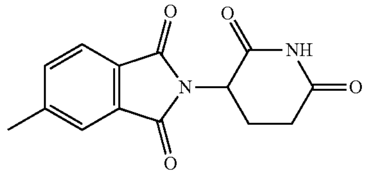
74%
7
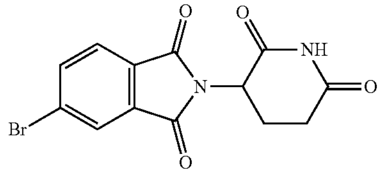
75%
8
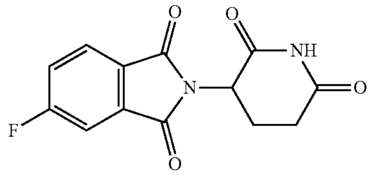
56%
9
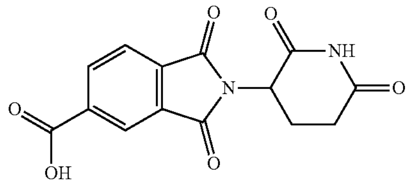
66%
10
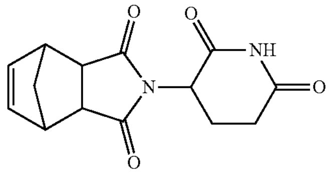
94%
-continued
11
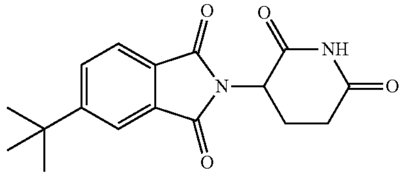
83%
12
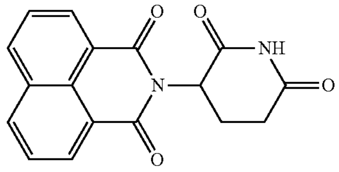
80%
13
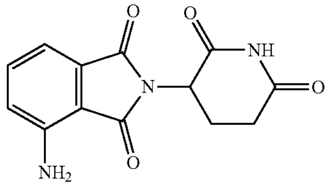
80%
14
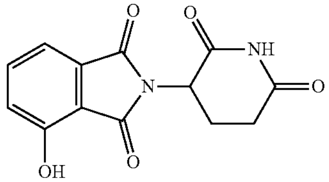
86%
15
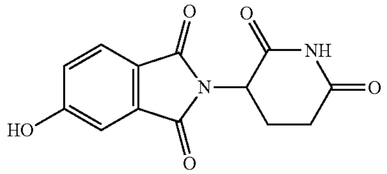
91%
16
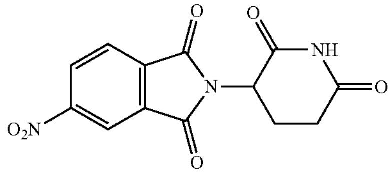
58%
17
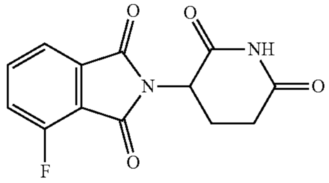
69%

-continued

18

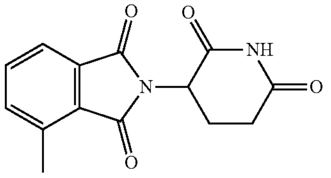

80%

19

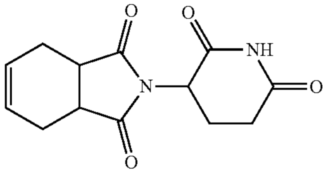

73%

20

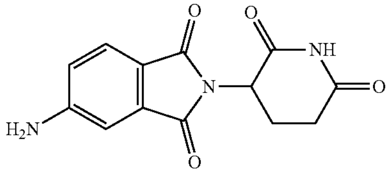

66%[a]

21

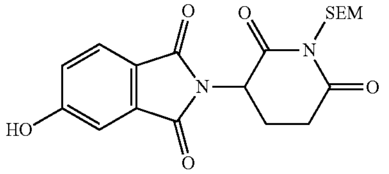

55%

22

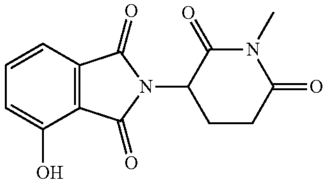

88%

After conditions for the synthesis of Thalidomide were explored, these optimized conditions were employed to prepare a library of analogues in a rapid and chromatography-free manner. These conditions proved to be relatively general and tolerate a variety of functional groups. Heteroaromatic anhydrides were well tolerated, as were substitutions in both the 3- and 4-positions. Bicyclic and fused ring systems as well as various degrees of saturation are also tolerated. Pomalidomide (compound 13) was prepared in one step from commercially available starting materials in an 80% yield with no purification step required. This is the first synthesis of Pomalidomide avoiding the use of nitro-group reduction as the aniline is tolerated under the present conditions. This approach can also be employed to prepare SEM protected 21 or N-methylated 22 analogues.

With unprecedented access to novel analogues of ImiDs, the structure-activity relationships with respect to Cereblon binding and the degradation of Aiolos (IKZF3) and CK1αwe were explored. To assess binding of ImiD analogues to Cereblon directly, an SPR assay with His-tagged Cereblon immobilized was employed. Dose-response curves were measured for each analogue and Kd values calculated. The results are summarized in Table 1. This direct binding analysis revealed that many of the newly synthesized ImiDs retain the ability to bind CRBN, indeed several of them have a higher affinity that the FDA approved compounds employed as positive controls. For example, the 1,8-Naphthalic anhydride derived compound 12 has an increased affinity presumably due to increased hydrophobic interactions with the protein surface. Molecular modelling revealed this compound is able to adopt the same binding conformation as pomalidomide.

TABLE 1

Binding constants for compounds to CRBN measured by surface plasmon resonance and their ability to induce degradation of neo-substrates Aiolos and CK1α at 10 uM.

| | Compound | CRBN Kd/ nM[1] | Degradation Aiolos | Degradation CK1α |
|---|---|---|---|---|
| 1 | Lenalidomide | 445 ± 19 | + | + |
| 2 | Pomalidomide | 264 ± 18 | + | − |
| 3 | 1 | >11000 | − | − |
| 4 | 2 | N.B. | − | − |
| 5 | 3 | N.D. | − | − |
| 6 | 4 | N.D. | − | − |
| 7 | 5 | N.D. | − | − |
| 8 | 6 | 1450 ± 49 | − | − |
| 9 | 7 | 1400 ± 375 | − | − |
| 10 | 8 | 55 ± 18 | − | − |
| 11 | 9 | N.B. | − | − |
| 12 | 10 | N.D. | − | − |
| 13 | 11 | 221 ± 52 | − | − |
| 14 | 12 | 111 ± 6 | − | − |
| 15 | 13 | 271 ± 110 | + | − |
| 16 | 14 | N.D. | − | − |
| 17 | 15 | N.D. | − | − |
| 18 | 16 | >11000 | − | − |
| 19 | 17 | 558 ± 51 | + | − |
| 20 | 18 | 2100 ± 400 | − | − |
| 21 | 19 | 325 ± 24 | + | − |
| 22 | 20 | 549 ± 66 | − | − |

N.B - no binding observed, N.D. - Not determined due to reference cell binding
[1]Average of at least 2 experiments In addition to measuring the binding to CRBN, the ability of these new analogues to induce degradation of the neo-substrates Aiolos and CK1α was explored. To this end MM-1S cells were treated with 10 μM of each compound for 24 hours before immunoblotting for the target proteins. Pomalidomide, Lenolidomide and Thalidomide were included as positive controls while DMSO served as a negative control.

Figure 9A:
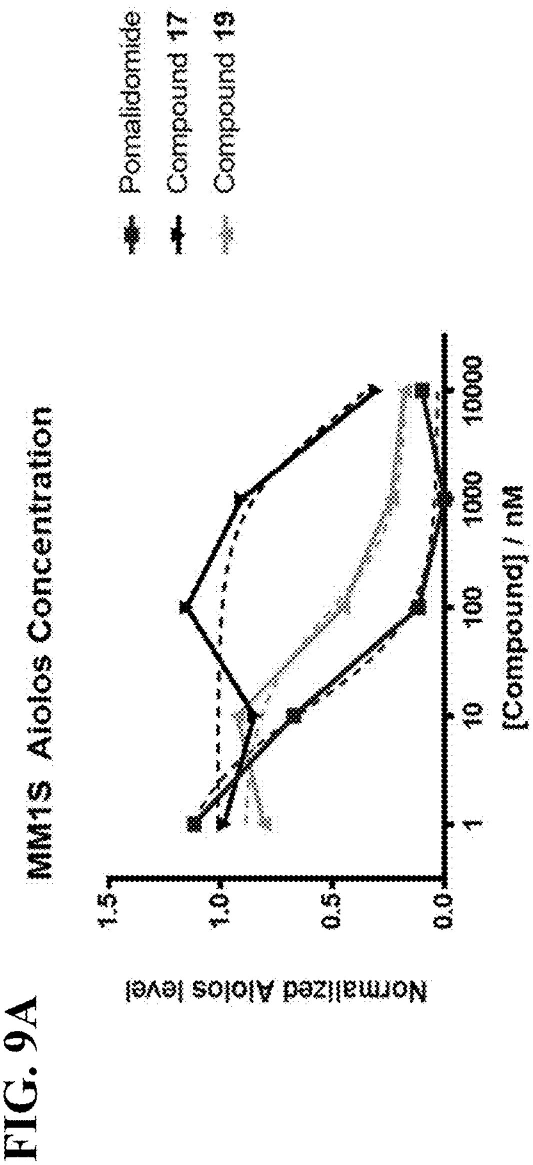
(FIG. 9A)—Normalized Aiolos levels in MM1S cells after 24 hours treatment with the indicated dose as assessed by Western Blotting and normalized to Tubulin.
Figure 9B:
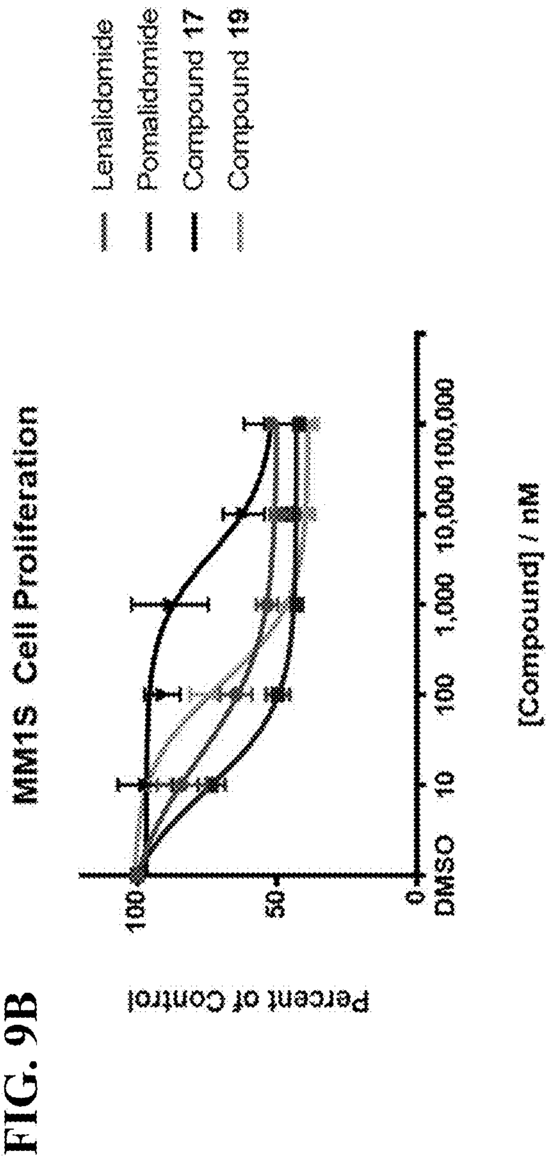
(FIG. 9B)—Inhibition of cell proliferation of selected compounds after 72 hours as measured by MTS assay.

Compounds 17 and 19, which were capable of inducing degradation of Aiolos at 10 μM, were further evaluated in dose-response experiments via immunoblotting. Quantification of the bands and normalization to tubulin loading controls allows the calculation of $DC_{50}$ values (the concentration at which half maximal degradation is observed) (FIG. 9A). Replacement of the aniline moiety in Pomalidomide ($DC_{50}$-11 nM) results in a modest loss of activity in the case of the methyl derivative compound 19 ($DC_{50}$-81 nM) and a more pronounced loss of activity in the fluoride compound 17 ($DC_{50}$-5300 nM). These compounds 17 and 19, which displayed interesting degradation characteristics, were progressed to cell proliferation assays in MM1S cells and compared to Lenalidomide and Pomalidomide. Both the new compounds were able to inhibit cell proliferation at similar doses to their corresponding $DC_{50}$ values (Compound 19 $IC_{50}$-128 nM, Compound 17 $IC_{50}$-3568 nM).

This small analogue library reveals the exquisite requirements of compounds which induce of interactions between CRBN and the neo-substrates, Aiolos and CK1α. Without wishing to be limited by any theory, this appears to be irrespective of affinity for CRBN, as some molecules binds to CRBN with an increased affinity yet fail to induce degradation. However even amongst the compounds which do induce degradation, CRBN affinity appears not to be predictive of cellular activity—Compound 17 binds with roughly 2-fold less affinity than Pomalidomide and Compound 19 however has >20-fold reduced effect on protein degradation and proliferation. More important are structural changes which, even when subtle, can completely abrogate the recruitment of the neo-substrate. This is due to perturbation of the required protein-protein interaction as even subtle changes, such as fluorination in the 5 position (Compound 8), drastically affect the combined protein/ligand surface preventing trimer formation.

The present report relates to a rapid, chromatography free synthesis of 2 FDA approved drugs as well as more than 20 additional analogues, along with the SAR for these new compounds. This includes the identification of previously unreported thalidomide analogues with anti-proliferative activity in a cellular multiple myeloma model. Furthermore, several compounds with improved pharmacological properties and/or increased CRBN binding affinity have been identified and may be useful as recruiting elements for Proteolysis Targeting Chimera (PROTACs). In certain embodiments, these new molecules are able to induce the degradation of additional neo-substrates or indeed inhibit the binding of natural substrates to CRBN, providing a useful tool to discover currently unknown substrates of CRBN.

Surface Plasmon Resonance

The surface plasmon resonance (SPR) experiments were conducted on a S200 Biacore (GE Healthcare). His-tagged cereblon protein was immobilized on a carboxymethylated dextran surface with nitriloacetic acid (NTA), taking advantage of NTA/Ni2+ chelation. The prepared surface equilibrated overnight in running buffer (10 mM HEPES buffer @ pH 7.4, 150 mM NaCl, 0.4 mg/mL BSA, 0.005% P20, 2% DMSO).

All compounds were prepared in 100% DMSO stock plates with a top concentration of 5 mM in a 3× serial dilution. Compounds were transferred from the stock plate to the assay plate and diluted into running buffer containing no DMSO. All compounds were run as a six point-concentration series with a final assay top concentration of 33 uM.

Data analysis was performed in S200 Bia-evaluation software (GE Healthcare). Blanks were subtracted and data was corrected for DMSO using a standard DMSO curve. All reported KD values represent an average of at least N=2 and were obtained by fitting to a minimum of five concentrations using a 1:1 fitting algorithm.

Cellular Evaluation of Compounds

MM.1 S cells were treated for 24 hours with 10 μM of each compound then harvested in lysis buffer (25 mM Tris-HCl pH 7.5 with 1% NP-40 and 0.25% deoxycholate, supplemented with protease and phosphatase inhibitors). Following centrifugation at 16,000×g for 10 min at 4° C. to pellet insoluble materials, the protein concentrations of the supernatants were quantitated by BCA assay (Thermo Fisher Scientific). Protein samples were resolved by SDS-PAGE, electrophoretically transferred to nitrocellulose and probed with antibodies for Aiolos, CK1α and Tubulin. Immunoblots were developed using enhanced chemiluminescence and visualized using a Bio-Rad Chemi-Doc MP Imaging System and quantitated with Image Lab v.5.2.1 software (Bio-Rad Laboratories).

Compounds showing reduced levels of Aiolos were further subjected to dose response experiments in a similar fashion.

Cell Proliferation Assays

Following 72 hour treatment of cells as indicated, culture medium was supplemented with 20 μl/well MTS Aqueous One (Promega Corp., Madison, WI) and incubated at 37° C. for 2 hours. Mitochondrial reduction of MTS to the formazan derivative was monitored by measuring the medium's absorbance at 490 nm using a Wallac Victor2 plate reader (Perkin-Elmer Life Sciences, Waltham, MA). Data analysis and statistics performed using Prism v7.0 software (GraphPad Software).

Synthesis

Tert-butyl (2,6-dioxopiperidin-3-yl)carbamate

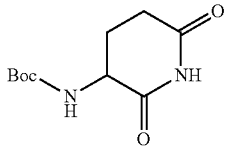 [SMILES: CC(C)(C)OC(=O)NC1CCC(=O)NC1=O]

5-amino-2-(tert-butoxycarbonylamino)-5-oxo-pentanoic acid (Boc-Gln-OH; 7 g, 28.42 mmol), 1,1'-Carbonyldiimidazole (4.61 g, 28.42 mmol), and DMAP (0.02 g, 0.14 mmol) were dissolved in anhydrous THE (20 mL) and heated to reflux for 16 h. The reaction slurry was cooled to r.t. and kept at −20° C. for 2 h. The product was filtered off, washed with THE and dried to constant weight to yield 5.69 g (88%) of tert-butyl N-(2,6-dioxo-3-piperidyl)carbamate as a white solid. $^1$H NMR (400 MHz, DMSO-$d_6$) δ=10.74 (s, 1H), 7.12 (d, J=8.7 Hz, 1H), 4.29-4.15 (m, 1H), 2.79-2.60 (m, 1H), 2.45 (t, J=3.7 Hz, 1H), 2.01-1.82 (m, 2H), 1.39 (s, 9H). $^{13}$C NMR (101 MHz, DMSO-$d_6$) δ=172.96, 172.51, 155.39, 78.14, 50.38, 30.97, 28.17, 24.42. HRMS: calc. [M−Boc+H]+ for $C_5H_9N_2O_2$=129.0659; found=129.0676 [M−Boc+H]+.

General Procedure 1: Deprotection Condensation Reaction

A suspension of tert-butyl N-(2,6-dioxo-3-piperidyl)carbamate (1 eq.) and the corresponding anhydride (1 eq.) in Trifluoroethanol was heated for 2 h at 150° C. under microwave conditions. After cooling to r.t. the reaction mixture was cooled to −20° C. for 4 h. If the desired product did not precipitate after cooling to −20° C., ethyl acetate (3 drops) was added and the mixture kept at −20° C. for additional 4 h. The precipitated product was filtered off, washed with ethyl acetate (3×2 ml) and dried to constant weight.

2-(2,6-dioxopiperidin-3-yl)hexahydro-1H-isoindole-1,3(2H)-dione, 1

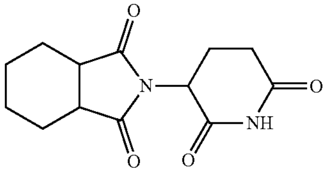 [SMILES: O=C1CCC(N2C(=O)C3CCCCC3C2=O)C(=O)N1]

Compound 1 was prepared according to GP1 using 400 mg of tert-butyl N-(2,6-dioxo-3-piperidyl)carbamate to yield 399 mg (86%) of 2-(2,6-dioxopiperidin-3-yl)hexahydro-1H-isoindole-1,3(2H)-dione. $^{1}$H NMR (500 MHz, DMSO-d6) δ 11.00 (s, 1H), 4.88 (dd, J=12.8, 5.5 Hz, 1H), 3.05-2.93 (m, 2H), 2.81 (ddd, J=17.1, 14.0, 5.5 Hz, 1H), 2.52 (ddd, J=17.0, 4.4, 2.5 Hz, 1H), 2.40 (qd, J=13.1, 4.4 Hz, 1H), 1.86 (dtd, J=13.1, 5.4, 2.4 Hz, 1H), 1.78-1.57 (m, 4H), 1.47-1.19 (m, 4H). $^{13}$C NMR (126 MHz, DMSO-$d_6$) δ 179.30, 179.21, 173.14, 169.85, 49.22, 31.17, 23.58, 23.39, 21.58, 21.53, 21.48. HRMS: calc. [M−H]− for $C_{13}H_{16}N_2O_4$=263.1110; found=263.1165 [M−H]−.

2-(2,6-dioxopiperidin-3-yl)-4-nitroisoindoline-1,3-dione, 2

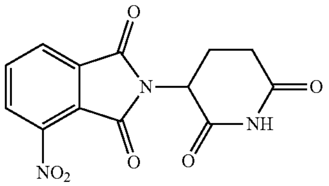 [SMILES: O=C1CCC(N2C(=O)c3cccc([N+](=O)[O-])c3C2=O)C(=O)N1]

Compound 2 was prepared according to GP1 using 200 mg of tert-butyl N-(2,6-dioxo-3-piperidyl)carbamate to yield 252 mg (95%) of 2-(2,6-dioxo-3-piperidyl)-4-nitro-isoindoline-1,3-dione. $^{1}$H NMR (400 MHz, DMSO-$d_6$) δ=11.17 (s, 1H), 8.36 (dd, J=8.1, 0.9 Hz, 1H), 8.24 (dd, J=7.5, 0.9 Hz, 1H), 8.12 (t, J=7.8 Hz, 1H), 5.20 (dd, J=12.9, 5.4 Hz, 1H), 2.95-2.82 (m, 1H), 2.66-2.52 (m, 2H), 2.12-2.03 (m, 1H). $^{13}$C NMR (101 MHz, DMSO-$d_6$) δ=172.67, 169.46, 165.15, 162.50, 144.41, 136.78, 132.98, 128.84, 127.27, 122.53, 49.41, 30.85, 21.71. HRMS: calc. [M+H]+ for $C_{13}H_{10}N_3O_6$=304.0564; found=304.0572 [M+H]+.

6-(2,6-dioxopiperidin-3-yl)-5H-pyrrolo[3,4-b]pyridine-5,7(6H)-dione, 3

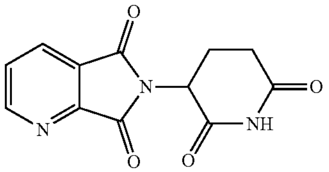 [SMILES: O=C1CCC(N2C(=O)c3cccnc3C2=O)C(=O)N1]

Compound 3 was prepared according to GP1 using 200 mg of tert-butyl N-(2,6-dioxo-3-piperidyl)carbamate to yield 137 mg (60%) of 6-(2,6-dioxo-3-piperidyl)pyrrolo[3,4-b]pyridine-5,7-dione. $^{1}$H NMR (400 MHz, DMSO-$d_6$) δ=9.03 (s, 1H), 8.68 (d, J=3.1 Hz, 1H), 8.21 (d, J=7.9 Hz, 1H), 7.46 (dd, J=7.8, 4.8 Hz, 1H), 3.72 (dd, J=12.1, 5.1 Hz, 1H), 2.71-2.51 (m, 2H), 2.12-2.01 (m, 1H), 1.90-1.76 (m, 1H). $^{13}$C NMR (101 MHz, DMSO-$d_6$) δ=174.18, 173.03, 166.85, 151.97, 150.28, 136.65, 129.41, 123.40, 50.33, 30.64, 24.87. HRMS: calc. [M+H]+ for $C_{12}H_{10}N_3O_4$=260.0666; found=260.0664 [M+H]+.

2-(2,6-dioxopiperidin-3-yl)-1H-pyrrolo[3,4-c]pyridine-1,3(2H)-dione, 4

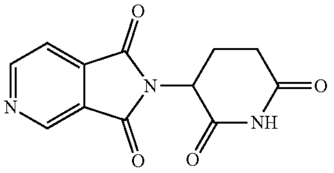 [SMILES: O=C1CCC(N2C(=O)c3ccncc3C2=O)C(=O)N1]

Compound 4 was prepared according to GP1 using 200 mg of tert-butyl N-(2,6-dioxo-3-piperidyl)carbamate to yield 79 mg (35%) of 2-(2,6-dioxopiperidin-3-yl)-1H-pyrrolo[3,4-c]pyridine-1,3(2H)-dione. $^{1}$H NMR (400 MHz, DMSO-$d_6$) δ=11.17 (s, 1H), 9.20 (d, J=1.1 Hz, 1H), 9.16 (d, J=4.8 Hz, 1H), 7.96 (dd, J=4.9, 1.1 Hz, 1H), 5.22 (dd, J=12.9, 5.4 Hz, 1H), 2.96-2.83 (m, 1H), 2.67-2.56 (m, 1H), 2.55-2.44 (m, 1H), 2.12-2.02 (m, 1H). $^{13}$C NMR (101 MHz, DMSO-$d_6$) δ=172.67, 169.51, 166.39, 166.05, 156.30, 144.34, 138.77, 125.30, 117.12, 49.21, 30.86, 21.78. HRMS: calc. [M+H]+ for $C_{12}H_{10}N_3O_4$=260.0666; found=260.0687 [M+H]+.

2-(2,6-dioxopiperidin-3-yl)-4,5,6,7-tetrafluoroisoindoline-1,3-dione, 5

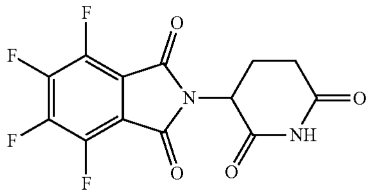 [SMILES: O=C1CCC(N2C(=O)c3c(F)c(F)c(F)c(F)c3C2=O)C(=O)N1]

Compound 5 was prepared according to GP1 using 200 mg of tert-butyl N-(2,6-dioxo-3-piperidyl)carbamate to yield 159.4 mg (55%) of 2-(2,6-dioxo-3-piperidyl)-4,5,6,7-tetrafluoro-isoindoline-1,3-dione. $^{1}$H NMR (400 MHz, DMSO-$d_6$) δ=11.18 (s, 1H), 5.19 (dd, J=13.0, 5.4 Hz, 1H), 2.97-2.77 (m, 1H), 2.67-2.55 (m, 1H), 2.49-2.38 (m, 1H), 2.18-1.95 (m, 1H). $^{13}$C NMR (101 MHz, DMSO-$d_6$) δ=172.99, 169.62, 162.27, 146.22, 144.48, 143.58, 141.92, 113.83, 49.97, 31.24, 22.07.

$^{19}$F NMR (376 MHz, DMSO-$d_6$) δ=−138.31, −138.35, −143.84, −143.87. HRMS: calc. [M+H]+ for $C_{13}H_7F_4N_2O_4$=331,0337; found=331.0356 [M+H]+.

2-(2,6-dioxopiperidin-3-yl)-5-methylisoindoline-1,3-dione, 6

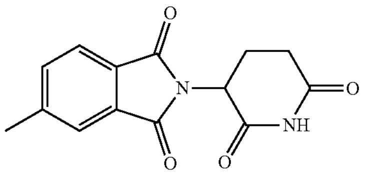 [SMILES: Cc1ccc2c(c1)C(=O)N(C1CCC(=O)NC1=O)C2=O]

Compound 6 was prepared according to GP1 using 2000 mg of tert-butyl N-(2,6-dioxo-3-piperidyl)carbamate to yield 1750 mg (74%) of 2-(2,6-dioxopiperidin-3-yl)-5-methylisoindoline-1,3-dione. $^{1}$H NMR (400 MHz, DMSO-$d_6$) δ 11.09 (s, 1H), 7.77 (d, J=7.6 Hz, 1H), 7.72 (s, 1H), 7.66 (d, J=7.7 Hz, 1H), 5.10 (dd, J=13.0, 5.3 Hz, 1H), 2.95-2.77 (m, 1H), 2.61-2.40 (m, 5H), 2.08-1.94 (m, 1H). $^{13}$C NMR (101 MHz, DMSO-$d_6$) δ 172.50, 169.63, 167.03, 166.91, 145.68, 134.95, 131.38, 128.41, 123.58, 123.08, 48.72, 30.72, 21.81, 21.16. HRMS: calc. [M−H]− for $C_{14}H_{12}N_2O_4$=271.0724; found=271.1587 [M−H]−.

5-bromo-2-(2,6-dioxopiperidin-3-yl)isoindoline-1,3-dione, 7

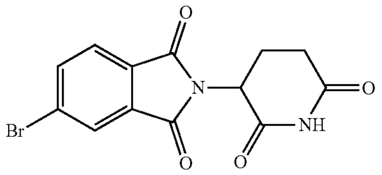 [SMILES: O=C1CCC(N2C(=O)c3ccc(Br)cc3C2=O)C(=O)N1]

Compound 7 was prepared according to GP1 using 500 mg of tert-butyl N-(2,6-dioxo-3-piperidyl)carbamate to yield 555 mg (75%) of 5-bromo-2-(2,6-dioxopiperidin-3-yl) isoindoline-1,3-dione. $^{1}$H NMR (400 MHz, DMSO-$d_6$) δ 11.11 (s, 1H), 8.12 (d, J=1.6 Hz, 1H), 8.06 (dd, J=7.9, 1.7 Hz, 1H), 7.83 (d, J=7.9 Hz, 1H), 5.13 (dd, J=12.8, 5.4 Hz, 1H), 2.86 (ddd, J=17.0, 13.8, 5.4 Hz, 1H), 2.65-2.48 (m, 2H), 2.03 (dtd, J=12.9, 5.2, 2.1 Hz, 1H). $^{13}$C NMR (101 MHz, DMSO-$d_6$) δ 173.13, 170.09, 166.86, 166.30, 138.05, 133.58, 130.58, 128.95, 126.82, 125.70, 55.34, 49.60, 31.33, 22.33. HRMS: calc. [M+H]+ for $C_{13}H_9BrN_2O_4$=338.9798; found=338.9832 [M+H]+.

5-fluoro-2-(2,6-dioxopiperidin-3-yl)isoindoline-1,3-dione, 8

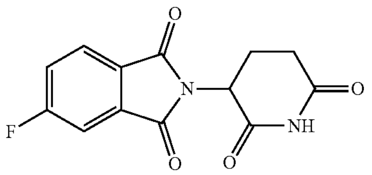 [SMILES: O=C1CCC(N2C(=O)c3ccc(F)cc3C2=O)C(=O)N1]

Compound 8 was prepared according to GP1 using 500 mg of tert-butyl N-(2,6-dioxo-3-piperidyl)carbamate to yield 342 mg (56%) of 5-fluoro-2-(2,6-dioxopiperidin-3-yl) isoindoline-1,3-dione. $^{1}$H NMR (400 MHz, DMSO-$d_6$) δ 11.11 (s, 1H), 7.98 (dd, J=8.3, 4.5 Hz, 1H), 7.82 (dd, J=7.4, 2.3 Hz, 1H), 7.69 (ddd, J=10.5, 8.3, 2.4 Hz, 1H), 5.13 (dd, J=12.8, 5.4 Hz, 1H), 2.86 (ddd, J=16.9, 13.7, 5.4 Hz, 1H), 2.66-2.52 (m, 2H), 2.03 (dtd, J=13.0, 5.2, 2.1 Hz, 1H). $^{13}$C NMR (101 MHz, DMSO-$d_6$) δ 173.16, 170.17, 167.67, 166.60, 166.33, 166.30, 165.14, 134.67, 134.58, 127.86, 127.84, 126.75, 126.65, 122.30, 122.06, 112.00, 111.74, 49.60, 31.34, 22.36. HRMS: calc. [M−H]− for $C_{13}H_9FN_2O_4$=275.0474; found=275.0462 [M−H]−.

2-(2,6-dioxopiperidin-3-yl)-1,3-dioxoisoindoline-5-carboxylic acid, 9

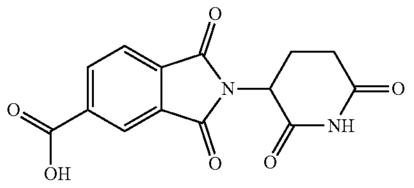 [SMILES: O=C1CCC(N2C(=O)c3ccc(C(=O)O)cc3C2=O)C(=O)N1]

Compound 9 was prepared according to GP1 using 2000 mg of tert-butyl N-(2,6-dioxo-3-piperidyl)carbamate to yield 1760 mg (66%) of 2-(2,6-dioxopiperidin-3-yl)-1,3-dioxoisoindoline-5-carboxylic acid. $^{1}$H NMR (400 MHz, DMSO-$d_6$) δ 11.12 (s, 1H), 8.37 (dd, J=7.7, 1.4 Hz, 1H), 8.24 (d, J=1.3 Hz, 1H), 8.01 (d, J=7.8 Hz, 1H), 5.17 (dd, J=12.8, 5.4 Hz, 1H), 2.87 (ddd, J=16.6, 13.6, 5.2 Hz, 1H), 2.62-2.48 (m, 2H), 2.10-1.86 (m, 1H). $^{13}$C NMR (101 MHz, DMSO-$d_6$) δ 173.15, 170.12, 166.84, 166.80, 166.16, 137.33, 136.11, 134.82, 132.07, 124.27, 123.83, 49.63, 31.34, 22.34. HRMS: calc. [M−H]− for $C_{14}H_{10}N_2O_4$=301.0466; found=301.0252 [M−H]−.

2-(2,6-dioxopiperidin-3-yl)-3a,4,7,7a-tetrahydro-1H-4,7-methanoisoindole-1,3(2H)-dione, 10

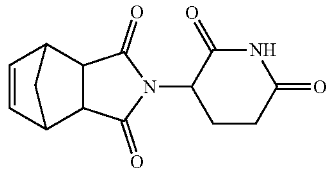 [SMILES: O=C1CCC(N2C(=O)C3C4C=CC(C4)C3C2=O)C(=O)N1]

Compound 10 was prepared according to GP1 using 1500 mg of tert-butyl N-(2,6-dioxo-3-piperidyl)carbamate to yield 1690 mg (94%) of 2-(2,6-dioxopiperidin-3-yl)-1,3-dioxoisoindoline-5-carboxylic acid. $^{1}$H NMR (400 MHz, DMSO-$d_6$) δ 10.93 (s, 1H), 6.03 (dd, J=6.9, 2.8 Hz, 2H), 4.72 (dd, J=12.6, 5.5 Hz, 1H), 3.44-3.34 (m, 2H), 3.30-3.20 (m, 3H), 2.72 (ddd, J=18.4, 14.0, 5.4 Hz, 1H), 2.47-2.37 (m, 1H), 2.17 (qd, J=13.0, 4.4 Hz, 1H), 1.69-1.57 (m, 1H), 1.56-1.44 (m, 2H). $^{13}$C NMR (101 MHz, DMSO-$d_6$) δ 176.98, 176.92, 173.02, 169.27, 134.72, 134.62, 51.95, 49.09, 45.58, 45.49, 45.06, 44.86, 30.93, 21.80. HRMS: calc. [M−H]− for $C_{14}H_{14}N_2O_4$=273.0881; found=273.0917 [M−H]−.

5-(tert-butyl)-2-(2,6-dioxopiperidin-3-yl)isoindoline-1,3-dione, 11

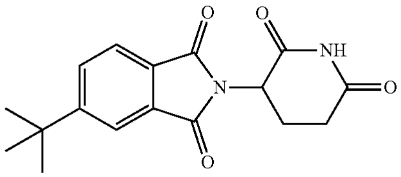 [SMILES: CC(C)(C)c1ccc2c(c1)C(=O)N(C1CCC(=O)NC1=O)C2=O]

Compound 11 was prepared according to GP1 using 300 mg of tert-butyl N-(2,6-dioxo-3-piperidyl)carbamate to yield 342 mg (83%) of 5-(tert-butyl)-2-(2,6-dioxopiperidin-3-yl)isoindoline-1,3-dione. $^{1}H$ NMR (400 MHz, DMSO-$d_6$) δ 11.08 (s, 1H), 7.93-7.85 (m, 2H), 7.82 (dd, J=7.6, 1.0 Hz, 1H), 5.11 (dd, J=13.0, 5.4 Hz, 1H), 3.84 (qd, J=9.6, 6.6 Hz, 2H), 2.86 (ddd, J=17.4, 14.0, 5.4 Hz, 1H), 2.62-2.46 (m, 4H), 2.02 (dtd, J=12.9, 5.9, 2.8 Hz, 1H), 1.33 (s, 9H). $^{13}C$ NMR (101 MHz, DMSO-$d_6$) δ 173.19, 170.32, 167.77, 167.46, 159.10, 132.10, 131.99, 129.16, 123.76, 120.73, 49.39, 35.97, 31.38, 31.17, 22.45. HRMS: calc. [M−H]− for $C_{17}H_{18}N_2O_4$=313.1267; found=313.1291 [M−H]−.

2-(2,6-dioxopiperidin-3-yl)-1H-benzo[de]isoquinoline-1,3(2H)-dione, 12

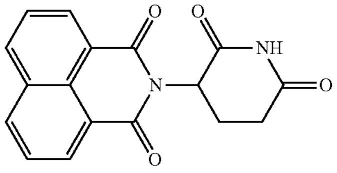 [SMILES: O=C1CCC(N2C(=O)c3cccc4cccc(c34)C2=O)C(=O)N1]

Compound 12 was prepared according to GP1 except the heating was extended to 6 hours, using 68 mg of tert-butyl N-(2,6-dioxo-3-piperidyl)carbamate to yield 82 mg (80%) of 2-(2,6-dioxopiperidin-3-yl)-1H-benzo[de]isoquinoline-1,3(2H)-dione. $^{1}H$ NMR (500 MHz, DMSO-$d_6$) δ 11.01 (bs, 1H), 8.70-8.33 (m, 4H), 7.90 (dd, J=8.0 Hz, 2H), 5.85 (dd, J=11.5, 5.7 Hz, 1H), 2.95 (ddd, J=18.2, 15.3, 5.4 Hz, 1H), 2.70-2.54 (m, 2H), 2.11-2.00 (m, 1H). $^{13}C$ NMR (151 MHz, DMSO-$d_6$) δ 172.86, 170.24, 163.44, 162.62, 134.90, 134.85, 131.55, 131.31, 130.96, 127.43, 127.37, 121.83, 121.48, 50.51, 30.86, 21.42. HRMS: (ESI); m/z [M+H]+: Calcd. for $C_{17}H_{13}N_2O_4$, 309.0875; found 309.0858.

4-amino-2-(2,6-dioxopiperidin-3-yl)isoindoline-1,3-dione, 13-Pomalidomide

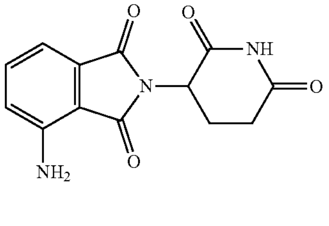 [SMILES: Nc1cccc2c1C(=O)N(C1CCC(=O)NC1=O)C2=O]

Compound 13 was prepared according to GP1 using 97 mg of tert-butyl N-(2,6-dioxo-3-piperidyl)carbamate to yield 93 mg (80%) of 4-amino-2-(2,6-dioxopiperidin-3-yl) isoindoline-1,3-dione. $^{1}H$ NMR (500 MHz, DMSO-$d_6$) δ 11.07 (s, 1H), 7.58-7.38 (m, 1H), 7.20-6.81 (m, 2H), 6.51 (bs, 2H), 5.04 (dd, J=12.7, 5.4 Hz, 1H), 2.88 (ddd, J=16.6, 13.7, 5.3 Hz, 1H), 2.69-2.46 (m, 2H), 2.13-1.91 (m, 1H). $^{13}C$ NMR (151 MHz, DMSO-$d_6$) δ 172.83, 170.14, 168.57, 167.38, 146.73, 135.48, 132.01, 121.71, 110.98, 108.52, 48.49, 30.99, 22.17. HRMS (ESI); m/z [M+H]+: Calcd. for $C_{13}H_{12}N_3O_4$, 274.0827; found 274.0837.

2-(2,6-dioxopiperidin-3-yl)-4-hydroxyisoindoline-1,3-dione, 14

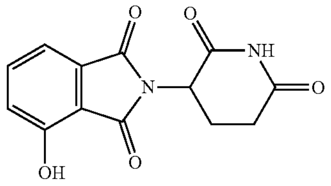 [SMILES: O=C1CCC(N2C(=O)c3cccc(O)c3C2=O)C(=O)N1]

Compound 14 was prepared according to GP1 using 265 mg of tert-butyl N-(2,6-dioxo-3-piperidyl)carbamate to yield 276 mg (86%) of 2-(2,6-dioxopiperidin-3-yl)-4-hydroxyisoindoline-1,3-dione. $^{1}H$ NMR (500 MHz, DMSO-$d_6$) δ 11.17 (s, 1H), 11.08 (s, 1H), 7.65 (t, J=7.8 Hz, 1H), 7.32 (d, J=7.1 Hz, 1H), 7.25 (d, J=8.4 Hz, 1H), 5.07 (dd, J=12.8, 5.4 Hz, 1H), 2.88 (ddd, J=16.8, 13.8, 5.4 Hz, 1H), 2.66-2.45 (m, 2H), 2.12-1.94 (m, 1H). $^{13}C$ NMR (151 MHz, DMSO-$d_6$) δ 172.83, 170.04, 167.04, 165.83, 155.48, 136.41, 133.16, 123.57, 114.37, 114.31, 48.65, 30.98, 22.05. HRMS (ESI); m/z: [M+H]+ Calcd. for $C_{13}H_{11}N_2O_5$, 275.1080; found 275.0667.

2-(2,6-dioxopiperidin-3-yl)-5-hydroxyisoindoline-1,3-dione, 15

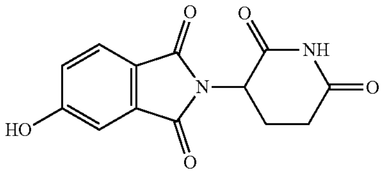 [SMILES: O=C1CCC(N2C(=O)c3ccc(O)cc3C2=O)C(=O)N1]

Compound 15 was prepared according to GP1 using 156 mg of tert-butyl N-(2,6-dioxo-3-piperidyl)carbamate to yield 170 mg (91%) of 2-(2,6-dioxopiperidin-3-yl)-4-hydroxyisoindoline-1,3-dione. $^{1}H$ NMR (400 MHz, DMSO-$d_6$) δ 11.08 (s, 1H), 11.03 (s, 1H), 7.74 (d, J=8.2 Hz, 1H), 7.24-7.10 (m, 2H), 5.08 (dd, J=12.8, 5.4 Hz, 1H), 2.98-2.76 (m, 1H), 2.66-2.39 (m, 2H), 2.13-1.94 (m, 1H). $^{13}C$ NMR (101 MHz, DMSO-$d_6$) δ 172.74, 169.95, 167.01, 166.90, 163.53, 134.05, 125.59, 121.39, 120.74, 109.95, 48.85, 30.94, 22.09. HRMS (ESI); m/z: [M+H]+ Calcd. for $C_{13}H_{11}N_2O_5$, 275.1080. Found 275.0580.

2-(2,6-dioxopiperidin-3-yl)-5-nitroisoindoline-1,3-dione, 16

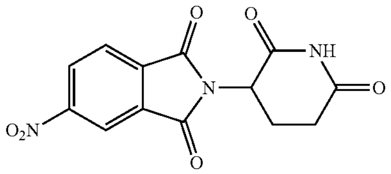

Compound 16 was prepared according to GP1 using 500 mg of tert-butyl N-(2,6-dioxo-3-piperidyl)carbamate to yield 389 mg (58%) of 2-(2,6-dioxopiperidin-3-yl)-5-nitroisoindoline-1,3-dione. $^{1}$H NMR (400 MHz, DMSO-$d_6$) δ 11.15 (s, 1H), 8.64 (dd, J=8.2, 2.0 Hz, 1H), 8.53 (d, J=1.9 Hz, 1H), 8.16 (d, J=8.1 Hz, 1H), 5.21 (dd, J=12.8, 5.4 Hz, 1H), 2.87 (ddd, J=17.0, 13.8, 5.4 Hz, 1H), 2.66-2.49 (m, 2H), 2.06 (dtd, J=12.9, 5.2, 2.1 Hz, 1H). $^{13}$C NMR (101 MHz, DMSO-$d_6$) δ 173.11, 169.92, 165.95, 152.14, 136.15, 132.95, 130.50, 125.41, 118.79, 49.91, 31.31, 22.25.

2-(2,6-dioxopiperidin-3-yl)-4-fluoroisoindoline-1,3-dione, 17

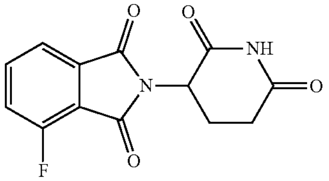 [SMILES: O=C1CCC(N2C(=O)c3cccc(F)c3C2=O)C(=O)N1]

Compound 17 was prepared according to GP1 using 2000 mg of tert-butyl N-(2,6-dioxo-3-piperidyl)carbamate to yield 1673 mg (69%) of 2-(2,6-dioxopiperidin-3-yl)-4-fluoroisoindoline-1,3-dione.

2-(2,6-dioxopiperidin-3-yl)-3a,4,7,7a-tetrahydro-1H-isoindole-1,3(2H)-dione, 18

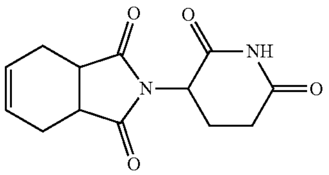 [SMILES: O=C1CCC(N2C(=O)C3CC=CCC3C2=O)C(=O)N1]

Compound 18 was prepared according to GP1 using 2000 mg of tert-butyl N-(2,6-dioxo-3-piperidyl)carbamate to yield 1678 mg (73%) of 2-(2,6-dioxopiperidin-3-yl)-3a,4,7,7a-tetrahydro-1H-isoindole-1,3(2H)-dione. $^{1}$H NMR (400 MHz, DMSO-$d_6$) δ 10.98 (s, 1H), 5.83 (dt, J=3.4, 1.5 Hz, 2H), 4.86 (dd, J=12.7, 5.5 Hz, 1H), 3.22-3.13 (m, 2H), 2.77 (ddd, J=17.1, 13.9, 5.5 Hz, 1H), 2.50 (dd, J=4.5, 2.6 Hz, 1H), 2.32 (dtd, J=15.3, 8.0, 3.7 Hz, 3H), 2.26-2.01 (m, 2H), 1.75 (dtd, J=13.2, 5.5, 2.4 Hz, 1H). $^{13}$C NMR (101 MHz, DMSO-$d_6$) δ 179.61, 173.08, 169.29, 127.76, 127.63, 49.60, 38.85, 38.67, 31.04, 23.45, 23.32, 21.70. HRMS: calc. [M−H]− for $C_{13}H_{14}N_2O_4$=261.0954; found=261.0947 [M−H]−.

2-(2,6-dioxopiperidin-3-yl)-4-methylisoindoline-1,3-dione, 19

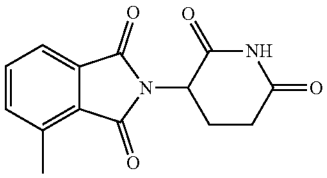 [SMILES: Cc1cccc2c1C(=O)N(C1CCC(=O)NC1=O)C2=O]

Compound 19 was prepared according to GP1 using 200 mg of tert-butyl N-(2,6-dioxo-3-piperidyl)carbamate to yield 174 mg (72%) of 2-(2,6-dioxopiperidin-3-yl)-4-methylisoindoline-1,3-dione. $^{1}$H NMR (400 MHz, DMSO-$d_6$) δ 11.08 (s, 1H), 7.71 (d, J=6.3 Hz, 2H), 7.64 (dd, J=5.9, 2.9 Hz, 1H), 5.10 (dd, J=13.0, 5.4 Hz, 1H), 2.87 (ddd, J=17.2, 13.9, 5.3 Hz, 1H), 2.60 (s, 3H), 2.58-2.44 (m, 2H), 2.02 (ddt, J=10.6, 5.6, 3.3 Hz, 1H). $^{13}$C NMR (101 MHz, DMSO-$d_6$) δ 173.20, 170.32, 168.25, 167.47, 138.03, 137.33, 134.79, 132.06, 128.33, 121.47, 49.22, 31.39, 22.44, 17.48. HRMS: calc. [M−H]− for $C_{14}H_{12}N_2O_4$=271.0797; found=271.1587 [M−H]−.

5-amino-2-(2,6-dioxopiperidin-3-yl)isoindoline-1,3-dione, 20

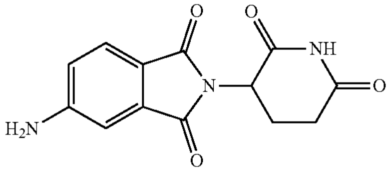

Following a literature procedure, a catalytic amount of Pd/C (50 mg, 10%) was assed to a solution of 16 (500 mg/1.65 mmol) in 30 mL of acetone. The mixture was stirred at ambient temperature for 20 hours under an atmosphere of $H_2$ (g). The mixture was then filtered through a pad of celite and the celite was washed with copious amounts of acetone. The solvent was evaporated in vacuo to yield 451 mg (66%) of 5-amino-2-(2,6-dioxopiperidin-3-yl)isoindoline-1,3-dione.

Tert-butyl(2,6-dioxo-1-((2-(trimethylsilyl)ethoxy)methyl)piperidin-3-yl)carbamate

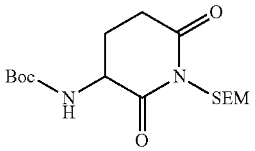 [SMILES: CC(C)(C)OC(=O)NC1CCC(=O)N(COCC[Si](C)(C)C)C1=O]

To a solution of tert-butyl N-(2,6-dioxo-3-piperidyl)carbamate (69 mg, 0.3 mmol) in DMF (1 mL) was added NaH (60%, 12.09 mg, 0.3 mmol) at 0° C., then the reaction was stirred for 15 min at the same temperature. Then 2-(Trimethylsilyl)ethoxymethyl chloride (60.48 mg, 0.36 mmol) was added and the reaction mixture was stirred at room temperature for an additional 1 h. Reaction mixture was poured into an aqueous solution of HCl (1N, 30 mL) and product was extracted with AcOEt (30 mL), organic layer was washed with aqueous HCl (1N, 3×20 mL), water (20 mL), dried $Na_2SO_4$ and evaporated under vacuum. Crude product was purified by flash chromatography (SiO2-12 g, Hex-AcOEt, 100% to 4:6 in 15 min), to give 70 mg of product as a white solid (65% yield). $^1H$ NMR (400 MHz, $CDCl_3$) δ 5.42 (s, 1H), 5.23 (d, J=9.5 Hz, 1H), 5.14 (d, J=9.5 Hz, 1H), 4.37-4.18 (m, 1H), 3.66-3.48 (m, 2H), 2.88 (dd, J=20.5, 2.4 Hz, 1H), 2.73 (ddd, J=18.4, 13.6, 5.5 Hz, 1H), 2.56-2.38 (m, 1H), 1.82 (qd, J=13.3, 4.8 Hz, 1H), 1.45 (s, 9H), 0.98-0.82 (m, 2H), −0.02 (s, 9H). $^{13}C$ NMR (101 MHz, $CDCl_3$) δ 172.04, 171.31, 155.62, 80.52, 69.29, 67.54, 52.59, 31.89, 28.40, 24.72, 18.20 , −1.32. HRMS: Calcd. for $C_{16}H_{30}N_2O_5SiNa$, 381.1821. Found 381.1870.

2-(2,6-dioxo-1-((2-(trimethylsilyl)ethoxy)methyl) piperidin-3-yl)-5-hydroxyisoindoline-1,3-dione, 21

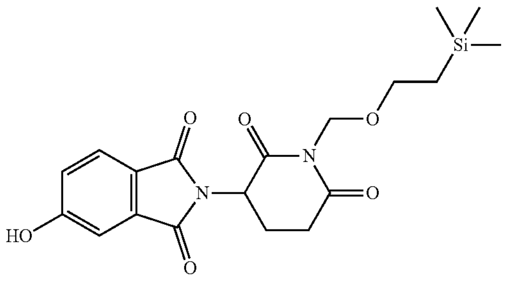 [SMILES: C[Si](C)(C)CCOCN1C(=O)CCC(N2C(=O)c3ccc(O)cc3C2=O)C1=O]

Compound 21 was prepared according to GP1 followed by concentration in vacuo and purification by preparative-TLC (1:1 Hexane/Ethyl Acetate) using 37 mg of tert-butyl (2,6-dioxo-1-((2-(trimethylsilyl)ethoxy)methyl)piperidin-3-yl)carb to yield 23 mg (55%) of 4-hydroxy-2-(1-methyl-2,6-dioxopiperidin-3-yl)isoindoline-1,3-dione. $^1H$ NMR (500 MHz, $CDCl_3$) δ 7.83 (bs, 1H), 7.62 (d, J=8.2 Hz, 1H), 7.13 (d, J=2.2 Hz, 1H), 7.05 (dd, J=8.2, 2.3 Hz, 1H), 5.36-5.21 (m, 2H), 5.05-4.93 (m, 1H), 3.75-3.54 (m, 2H), 3.08-2.95 (m, 1H), 2.91-2.66 (m, 2H), 2.17-2.09 (m, 1H), 0.96 (dd, J=9.1, 7.7 Hz, 2H), 0.00 (s, 9H). $^{13}C$ NMR (126 MHz, DMSO-$d_6$) δ 172.10, 170.40, 167.42, 167.30, 164.04, 134.50, 126.08, 121.81, 121.26, 110.41, 68.73, 66.39, 49.88, 31.64, 21.54, 17.89, −0.90. HRMS (ESI); m/z [M+Na]+: Calcd. for $C_{19}H_{24}N_2O_6SiNa$, 427.1301. Found 427.1344.

Tert-butyl (1-methyl-2,6-dioxopiperidin-3-yl)carbamate

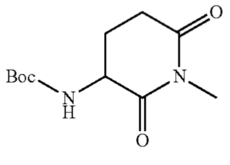 [SMILES: CN1C(=O)CCC(NC(=O)OC(C)(C)C)C1=O]

To a solution of tert-butyl N-(2,6-dioxo-3-piperidyl)carbamate (371 mg, 1.63 mmol) in DMF (5 mL) was added NaH (60%, 65.01 mg, 1.63 mmol) at 0° C., then the reaction was stirred for 15 min at the same temperature. Then the reaction mixture was stirred at room temperature for an additional 20 min. Then CH3I (0.12 ml, 1.95 mmol) was added into the reaction mixture at room temperature, and stirred for 2 h at the same temperature. Reaction mixture was poured into an aqueous solution of HCl (1N, 30 mL) and product was extracted with AcOEt (30 mL), organic layer was washed with aqueous HCl (1N, 3×20 mL), water (20 mL), dried $Na_2SO_4$ and evaporated under vacuum. Crude product was purified by flash chromatography (SiO2-25 g, Hex-AcOEt, 100% to 4:6 in 15 min), to give 260 mg of product (66%) as a white solid. $^1H$ NMR (400 MHz, DMSO-$d_6$) δ 7.19 (d, J=8.7 Hz, 1H), 4.39-4.21 (m, 1H), 2.97 (s, 3H), 2.85-2.73 (m, 1H), 2.71-2.53 (m, 1H), 2.09-1.75 (m, 2H), 1.40 (s, 9H). $^{13}C$ NMR (151 MHz, DMSO-$d_6$) δ 172.28, 172.01, 155.43, 78.18, 50.93, 31.14, 28.18, 26.46, 23.48. HRMS (ESI); m/z [M+H]+: Calcd. for $C_{11}H_{18}N_2O_4Na$, 265.1164. Found 265.1165.

4-hydroxy-2-(1-methyl-2,6-dioxopiperidin-3-yl) isoindoline-1,3-dione, 22

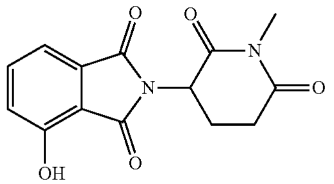 [SMILES: CN1C(=O)CCC(N2C(=O)c3cccc(O)c3C2=O)C1=O]

Compound 22 was prepared according to GP1 using 143 mg of tert-butyl (1-methyl-2,6-dioxopiperidin-3-yl)carbamate to yield 147 mg (88%) of 4-hydroxy-2-(1-methyl-2,6-dioxopiperidin-3-yl)isoindoline-1,3-dione. $^1H$ NMR (400 MHz, DMSO-$d_6$) δ 11.17 (s, 1H), 7.66 (dd, J=8.4, 7.2 Hz, 1H), 7.32 (d, J=7.2 Hz, 1H), 7.25 (d, J=8.4 Hz, 1H), 5.14 (dd, J=13.0, 5.4 Hz, 1H), 3.01 (s, 3H), 3.00-2.87 (m, 1H), 2.82-2.69 (m, 1H), 2.61-2.49 (m, 1H), 2.09-1.96 (m, 1H). $^{13}C$ NMR (151 MHz, DMSO-$d_6$) δ 171.79, 169.76, 167.00, 165.79, 155.49, 136.42, 133.13, 123.58, 114.34, 114.30, 49.20, 31.11, 26.60, 21.23. HRMS (ESI); m/z [M+H]+: Calcd. for $C_{14}H_{13}N_2O_5$, 289.0824. Found 289.0789.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the invention described herein. Such equivalents are intended to be encompassed by the following claims. It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

What is claimed is:

1. A compound according to the chemical structure:

PTM-L-CLM, wherein:

L is a chemical linker coupling the PTM to the CLM;

PTM is a protein targeting moiety that binds to a target protein;

CLM is a cereblon E3 ubiquitin ligase binding moiety with the structure:

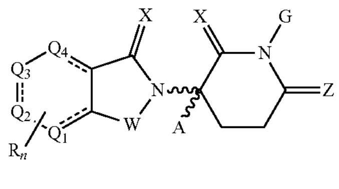

wherein:

each occurrence of X is O;

Z is O;

G is H;

each of $Q_1$-$Q_4$ is independently selected from the group consisting of N and a carbon substituted with at least one member independently selected from the group consisting of R', $NH_2$, OH, halogen, $C_1$-$C_6$ alkyl, acetyl, and carbonyl, with the proviso that (a) 0-2 $Q_1$-$Q_4$ is N;

(b) at least one $Q_1$-$Q_4$ is a carbon atom substituted with a $C_1$-$C_6$ alkyl that is bound to a non-contiguous $Q_1$-$Q_4$ and the ring has 0-2 unsaturated bonds;

W is independently selected from the group consisting of $CH_2$, CHR, CO═O, $S(═O)_2$, NH, and N-alkyl;

A is H;

each occurrence of R is independently selected from the group consisting of —C(═O)NR'R", —OR', —NR'R", —SR', —$S(═O)_2$R', —$S(═O)_2$NR'R", —CR'R", —CR'NR'R", aryl, heteroaryl, alkyl, cycloalkyl, heterocyclyl, —Cl, —F, —Br, —I, —$CF_3$, —CN, —$NO_2$, —$CO_2$R', —CR'═CR'R", —C≡CR', —$SF_5$, and —$OCF_3$;

wherein one R is covalently linked to the L;

each occurrence of R' and R" is independently selected from the group consisting of a bond, H, alkyl, cycloalkyl, aryl, heteroaryl, and heterocyclyl;

n is independently selected from the group consisting of 1, 2, 3, and 4;

∿∿∿ represents a bond that is stereospecific [(R) or (S)] or non-stereospecific;

or a salt thereof.

2. The compound of claim 1, wherein W is C═O.

3. The compound of claim 1, wherein each of $Q_1$-$Q_4$ is carbon.

4. The compound of claim 1, wherein the ring comprising $Q_1$-$Q_4$ is mono-unsaturated.

5. The compound of claim 1, wherein the CLM has the structure:

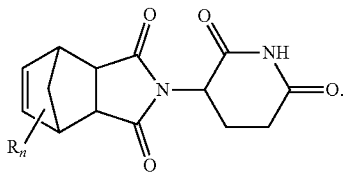

6. The compound of claim 1, wherein the target protein is selected from the group consisting of androgen receptor, estrogen receptor, bromodomain and extra-terminal domain (BET) protein.

7. The compound of claim 1, wherein the L is $-(A^L)_q-$, wherein:

q is an integer greater than or equal to 1;

each $A^L$ is independently selected from the group consisting of $CR^{L1}R^{L2}$, O, S, S(=O), $S(=O)_2$, $NR^{L3}$, $S(=O)_2NR^{L3}$, $S(=O)NR^{L3}$, $C(=O)NR^{L3}$, $NR^{L3}C(=O)NR^{L4}$, $NR^{L3}S(=O)_2NR^{L4}$, C(=O), $CR^{L1}=CR^{L2}$, C≡C, $C_{3-11}$ cycloalkyl optionally substituted with 0-6 $R^{L1}$ or $R^{L2}$ groups, $C_{5-13}$ spirocycloalkyl optionally substituted with 0-9 $R^{L1}$ or $R^{L2}$ groups, $C_{3-11}$ heterocyclyl optionally substituted with 0-6 $R^{L1}$ or $R^{L2}$ groups, $C_{5-13}$ spiroheterocycloalkyl optionally substituted with 0-8 $R^{L1}$ or $R^{L2}$ groups, aryl optionally substituted with 0-6 $R^{L1}$ or $R^{L2}$ groups, and heteroaryl optionally substituted with 0-6 $R^{L1}$ or $R^{L2}$ groups, wherein $R^{L1}$ and $R^{L2}$ each independently are optionally linked to other groups to form cycloalkyl or heterocyclyl moiety, optionally substituted with 0-4 $R^{L5}$ groups; and $R^{L1}$, $R^{L2}$, $R^{L3}$, $R^{L4}$, and $R^{L5}$ are each independently selected from the group consisting of H, halogen, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{3-8}$cycloalkyl, $SC_{3-8}$cycloalkyl, $NHC_{3-8}$cycloalkyl, $N(C_{3-8}cycloalkyl)_2$, $N(C_{3-8}cycloalkyl)(C_{1-8}alkyl)$, OH, $NH_2$, SH, $S(=O)_2C_{1-8}$alkyl, C≡C—$C_{1-8}$alkyl, C≡CH, CH=CH($C_{1-8}$alkyl), $C(C_{1-8}alkyl)=CH(C_{1-8}alkyl)$, $C(C_{1-8}alkyl)=C(C_{1-8}alkyl)_2$, $C(=O)C_{1-8}$alkyl, $CO_2H$, CN, $CF_3$, $CHF_2$, $CH_2F$, $NO_2$, $SF_5$, $SO_2NHC_{1-8}$alkyl, $S(=O)_2N(C_{1-8}alkyl)_2$, $S(=O)NHC_{1-8}$alkyl, $S(=O)N(C_{1-8}alkyl)_2$, $C(=O)NHC_{1-8}$alkyl, and $C(=O)N(C_{1-8}alkyl)_2$.

8. The compound of claim 1, wherein the L is selected from the group consisting of:

$N(R)—(CH_2)_m—O(CH_2)_n—O(CH_2)_o—O(CH_2)_p—O(CH_2)_q—O(CH_2)_r—OCH_2—$, $O—(CH_2)_m—O(CH_2)_n—O(CH_2)_o—O(CH_2)_p—O(CH_2)_qO(CH_2)_r—OCH_2—$, $O—(CH_2)_m—O(CH_2)_n—O(CH_2)_o—O(CH_2)_p—O(CH_2)_q—O(CH_2)_r—O—$;

$N(R)(CH_2)_m—O(CH_2)_n—O(CH_2)_o—O(CH_2)_p—O(CH_2)_q—O(CH_2)_r—O$;

$(CH_2)_m—O(CH_2)_n—O(CH_2)_o—O(CH_2)_p—O(CH_2)_q—O(CH_2)_r—O$;

$(CH_2)_m—O(CH_2)_n—O(CH_2)_o—O(CH_2)_p—O(CH_2)_q—O(CH_2)_r—OCH_2—$;

$—O—(CH_2)_m—O(CH_2)_n—O(CH_2)_o—O(CH_2)_p—O(CH_2)_qO(CH_2)_r—OCH_2—NH—C(O)CH_2—$,

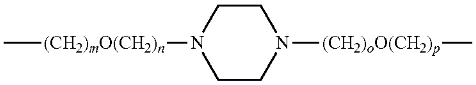
;

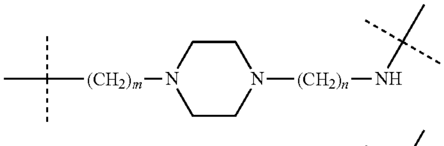
;

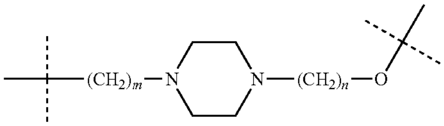
;

-continued

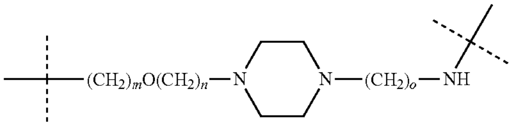
;

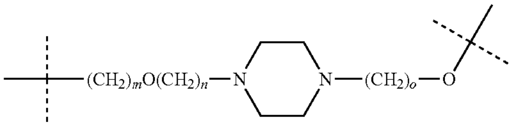
;

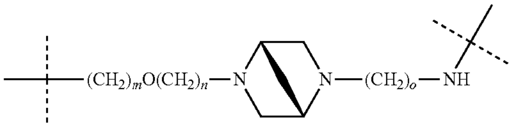
;

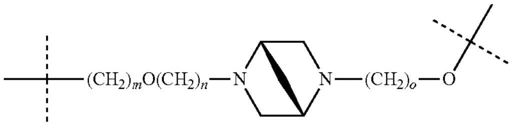
;

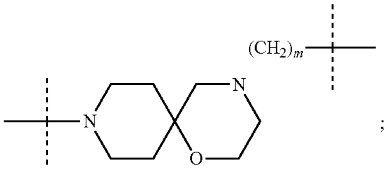
;

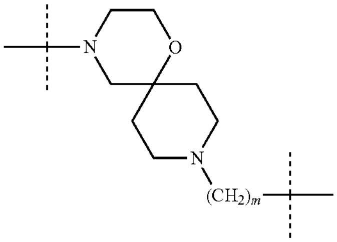
;

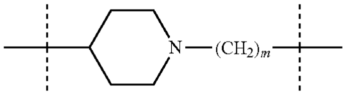
;

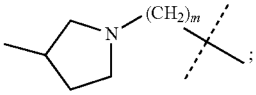
;

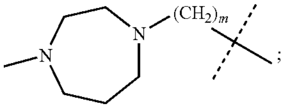
;

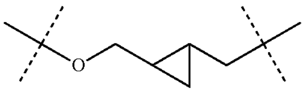
;

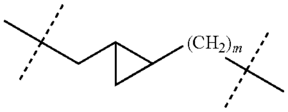
;

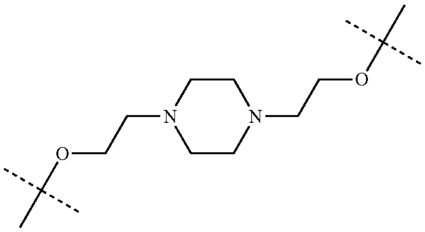
;

-continued

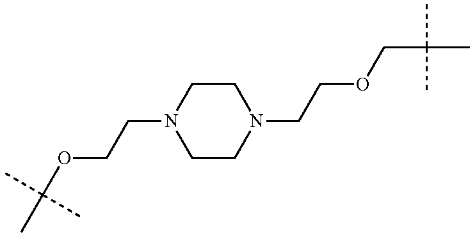

;

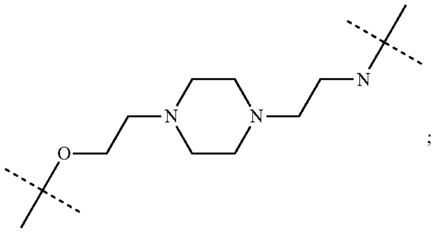

;

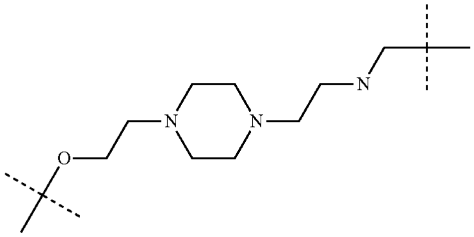

;

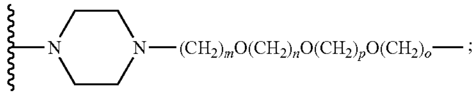

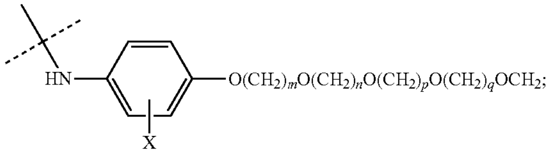

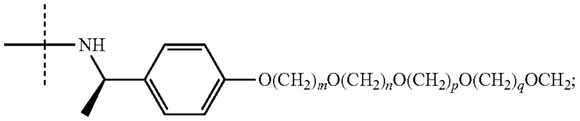

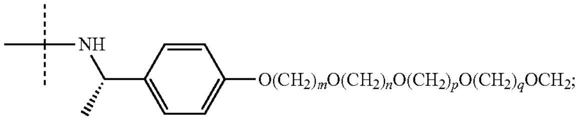

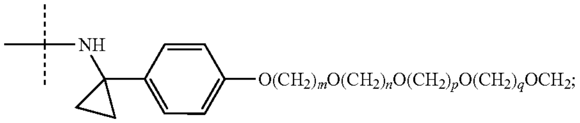

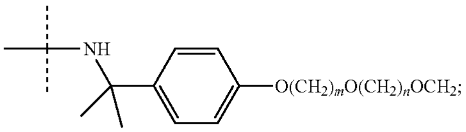

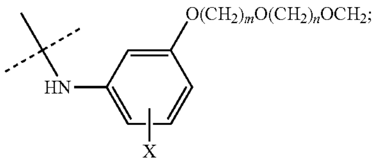

and

-continued

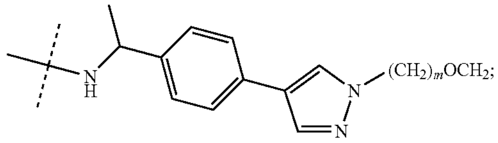

wherein each m, n, o, p, q, and r of each L is independently 0, 1, 2, 3, 4, 5, 6, 7, 8, 9, 10, 11, 12, 13, 14, 15, 16, 17, 18, 19, or 20, with the proviso that, if n=0, there is no N—O or O—O bond;

each R of each L is independently H, methyl, or ethyl; and each X of each L is independently H or F.

9. A pharmaceutical composition comprising the compound of claim 1, and at least one pharmaceutically acceptable carrier or excipient.

10. The compound of claim 1, wherein the L is selected from the group consisting of:

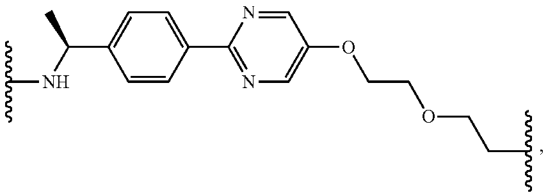

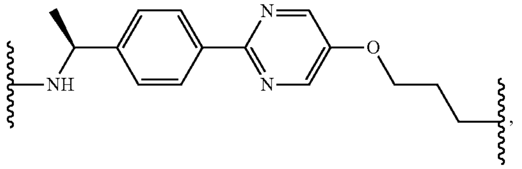

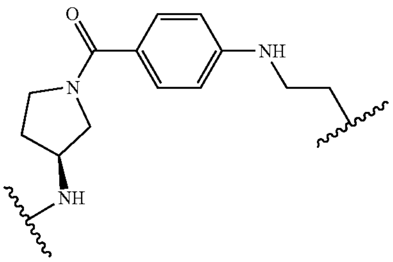

, and

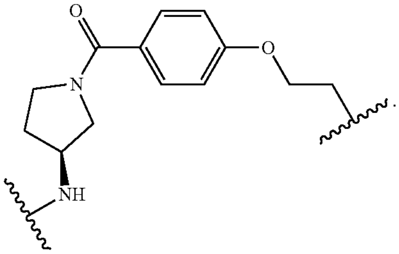

11. A method for inducing degradation of a target protein in a cell, the method comprising contacting the cell with an effective amount of a compound according to the chemical structure:

PTM-L-CLM, wherein:

L is a chemical linker coupling the PTM to the CLM;

PTM is a protein targeting moiety that binds to a target protein;

CLM is a cereblon E3 ubiquitin ligase binding moiety with the structure:

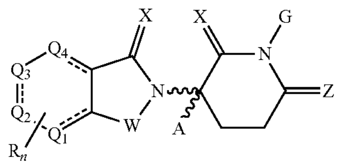

wherein:

each occurrence of X is O;

Z is O;

G is H;

each of $Q_1$-$Q_4$ is independently selected from the group consisting of N and a carbon substituted with at least one member independently selected from the group consisting of R', $NH_2$, OH, halogen, $C_1$-$C_6$ alkyl, acetyl, and carbonyl, with the proviso that (a) 0-2 $Q_1$-$Q_4$ is selected from the group consisting of N and N-oxide;

(b) at least one $Q_1$-$Q_4$ is a carbon atom substituted with a $C_1$-$C_6$ alkyl that is bound to a non-contiguous $Q_1$-$Q_4$ and the ring has 0-2 unsaturated bonds;

W is independently selected from the group consisting of $CH_2$, CHR, C═O, $S(═O)_2$, NH, and N-alkyl;

A is H;

each occurrence of R is independently selected from the group consisting of —C(═O)NR'R", —OR', —NR'R", —SR', —$S(═O)_2$R', —$S(═O)_2$NR'R", —CR'R", —CR'NR'R", aryl, heteroaryl, alkyl, cycloalkyl, heterocyclyl, —Cl, —F, —Br, —I, —$CF_3$, —CN, —$NO_2$, —$CO_2$R', —CR'═CR'R", —C≡CR', —$SF_5$, and —$OCF_3$;

wherein one R is covalently linked to the L;

each occurrence of R' and R" is independently selected from the group consisting of a bond, H, alkyl, cycloalkyl, aryl, heteroaryl, and heterocyclyl;

n is independently selected from the group consisting of 1, 2, 3, and 4;

∿∿∿ represents a bond that is stereospecific [(R) or (S)] or non-stereospecific;

or a salt thereof, wherein the compound is effective in degrading the target protein in the cell.

12. The method of claim 11, wherein the target protein is selected from the group consisting of androgen receptor, estrogen receptor, and bromodomain and extra-terminal domain (BET) protein.

13. A method for treating a disease state or condition in a subject in need thereof, wherein dysregulated protein activity is responsible for the disease state or condition, the method comprising administering to the subject a therapeutically effective amount of a compound according to the chemical structure:

PTM-L-CLM, wherein:

L is a chemical linker coupling the PTM to the CLM;

PTM is a protein targeting moiety that binds to a target protein;

CLM is a cereblon E3 ubiquitin ligase binding moiety with the structure:

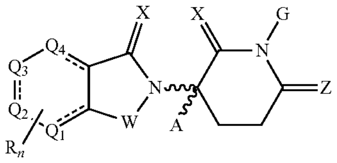

wherein:

each occurrence of X is O;

Z is O;

G is H;

each of $Q_1$-$Q_4$ is independently selected from the group consisting of N and a carbon substituted with at least one member independently selected from the group consisting of R', $NH_2$, OH, halogen, $C_1$-$C_6$ alkyl, acetyl, and carbonyl, with the proviso that (a) 0-2 $Q_1$-$Q_4$ is selected from the group consisting of N and N-oxide;

(b) at least one $Q_1$-$Q_4$ is a carbon atom substituted with a $C_1$-$C_6$ alkyl that is bound to a non-contiguous $Q_1$-$Q_4$ and the ring has 0-2 unsaturated bonds;

W is independently selected from the group consisting of $CH_2$, CHR, C═O, $S(═O)_2$, NH, and N-alkyl;

A is H;

each occurrence of R is independently selected from the group consisting of —C(═O)NR'R", —OR', —NR'R", —SR', —$S(═O)_2$R', —$S(═O)_2$NR'R", —CR'R", —CR'NR'R", aryl, heteroaryl, alkyl, cycloalkyl, heterocyclyl, —Cl, —F, —Br, —I, —$CF_3$, —CN, —$NO_2$, —$CO_2$R', —CR'═CR'R", —C≡CR', —$SF_5$, and —$OCF_3$;

wherein one R is covalently linked to the L;

each occurrence of R' and R" is independently selected from the group consisting of a bond, H, alkyl, cycloalkyl, aryl, heteroaryl, and heterocyclyl;

n is independently selected from the group consisting of 1, 2, 3, and 4;

∿∿∿ represents a bond that is stereospecific [(R) or (S)] or non-stereospecific;

or a salt thereof, whereby the compound promotes protein degradation or inhibition.

14. The method of claim 13, wherein the disease state or condition is cancer.

15. The method of claim 14, wherein the cancer is at least one selected from the group consisting of squamous-cell carcinoma, basal cell carcinoma, adenocarcinoma, hepatocellular carcinomas, renal cell carcinomas, cancer of the head and neck, leukemia, benign and malignant lymphoma, benign and malignant melanoma, myeloproliferative disease, multiple myeloma, sarcoma, Ewing's sarcoma, hemangiosarcoma, Kaposi's sarcoma, liposarcoma, myosarcoma, peripheral neuroepithelioma, synovial sarcoma, glioma, astrocytoma, oligodendroglioma, ependymoma, glioblastoma, neuroblastoma, ganglioneuroma, ganglioglioma, medulloblastoma, pineal cell tumor, meningioma, meningeal sarcoma, neurofibroma, Schwannoma, bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, kidney cancer, liver cancer, colon cancer, bladder cancer, melanoma, carcinosarcoma, Hodgkin's disease, Wilms' tumor, and teratocarcinoma.

16. The method of claim 15, wherein the cancer is Burkitt's lymphoma or Non-Hodgkin's lymphoma.

17. The method of claim 14, wherein the cancer is at least one selected from the group consisting of T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitt's Lymphoma, B-cell ALL, Philadelphia chromosome positive ALL, and Philadelphia chromosome positive CIVIL.

18. The method of claim 14, wherein the cancer is at least one selected from the group consisting of breast cancer, prostate cancer, glioma, and ovarian cancer.

19. The method of claim 13, wherein the disease state or condition is Kennedy's Disease.

20. The method of claim 13, wherein the target protein is selected from the group consisting of androgen receptor, estrogen receptor, and bromodomain and extra-terminal domain (BET) protein.

* * * * *

SEQUENCE LISTING

<160> NUMBER OF SEQ ID NOS: 9

<210> SEQ ID NO 1
<211> LENGTH: 41
<212> TYPE: DNA
<213> ORGANISM: Artificial Sequence
<220> FEATURE:
<223> OTHER INFORMATION: Chemically synthesized

<400> SEQUENCE: 1
gtgccgcgtg gctccatggc cggcgaagga gatcagcagg a 41

<210> SEQ ID NO 2
<211> LENGTH: 41
<212> TYPE: DNA
<213> ORGANISM: Artificial Sequence
<220> FEATURE:
<223> OTHER INFORMATION: Chemically synthesized

<400> SEQUENCE: 2
gcttcctttc gggcttatta caagcaaagt attactttgt c 41

<210> SEQ ID NO 3
<211> LENGTH: 50
<212> TYPE: DNA
<213> ORGANISM: Artificial Sequence
<220> FEATURE:
<223> OTHER INFORMATION: Cemically synthesized

<400> SEQUENCE: 3
tcgggcgcgg ctctcggtcc gaaaaggatg tcgtacaact acgtggtaac 50

<210> SEQ ID NO 4
<211> LENGTH: 61
<212> TYPE: DNA
<213> ORGANISM: Artificial Sequence
<220> FEATURE:
<223> OTHER INFORMATION: Chemically synthesized

<400> SEQUENCE: 4
gcttcctttc gggcttattt ttcgaactgc gggtggctcc aatggatccg agttagctcc 60
t 61

<210> SEQ ID NO 5
<211> LENGTH: 61
<212> TYPE: DNA
<213> ORGANISM: Artificial Sequence
<220> FEATURE:
<223> OTHER INFORMATION: Chemically synthesized

<400> SEQUENCE: 5
gcttcctttc gggcttactt atcgtcatcg tccttgtagt ccaagcaaag tattactttg 60
t 61

<210> SEQ ID NO 6
<211> LENGTH: 19
<212> TYPE: DNA
<213> ORGANISM: Artificial Sequence
<220> FEATURE:
<223> OTHER INFORMATION: Chemically synthesized

<400> SEQUENCE: 6
gaaggtgaag gtcggagtc 19

-continued

```
<210> SEQ ID NO 7
<211> LENGTH: 20
<212> TYPE: DNA
<213> ORGANISM: Artificial Sequence
<220> FEATURE:
<223> OTHER INFORMATION: Chemically synthesized

<400> SEQUENCE: 7

gaagatggtg atgggatttc                                          20


<210> SEQ ID NO 8
<211> LENGTH: 20
<212> TYPE: DNA
<213> ORGANISM: Artificial Sequence
<220> FEATURE:
<223> OTHER INFORMATION: Chemically synthesized

<400> SEQUENCE: 8

atggccccca agaagtagat                                          20


<210> SEQ ID NO 9
<211> LENGTH: 20
<212> TYPE: DNA
<213> ORGANISM: Artificial Sequence
<220> FEATURE:
<223> OTHER INFORMATION: Chemically synthesized

<400> SEQUENCE: 9

gtcaacacgt tctttgccac                                          20
```